US011469379B2

(12) United States Patent
Mun et al.

(10) Patent No.: US 11,469,379 B2
(45) **Date of Patent: *Oct. 11, 2022**

(54) COMPOUND FOR ORGANIC ELECTRONIC ELEMENT, ORGANIC ELECTRONIC ELEMENT USING THE SAME, AND ELECTRONIC DEVICE THEREOF

(71) Applicant: DUK SAN NEOLUX CO., LTD., Cheonan-si (KR)

(72) Inventors: Soung Yun Mun, Cheonan-si (KR); Sun-Hee Lee, Cheonan-si (KR); Jung Cheol Park, Suwon-si (KR); DaeSung Kim, Yongin-si (KR); Bum Sung Lee, Cheonan-si (KR); Seong Je Park, Busan (KR)

(73) Assignee: DUK SAN NEOLUX CO., LTD., Cheonan-si (KR)

( * ) Notice: Subject to any disclaimer, the term of this patent is extended or adjusted under 35 U.S.C. 154(b) by 390 days.

This patent is subject to a terminal disclaimer.

(21) Appl. No.: 16/530,449

(22) Filed: Aug. 2, 2019

(65) Prior Publication Data

US 2020/0243771 A1 Jul. 30, 2020

Related U.S. Application Data

(62) Division of application No. 15/121,472, filed as application No. PCT/KR2015/001801 on Feb. 25, 2015, now Pat. No. 10,396,291.

(30) Foreign Application Priority Data

Feb. 27, 2014 (KR) ........................ 10-2014-0023356
May 28, 2014 (KR) ........................ 10-2014-0064727
Oct. 24, 2015 (KR) ........................ 10-2015-0025588

(51) Int. Cl.

| | |
|---|---|
| ***H01L 51/00*** | (2006.01) |
| ***H01L 51/50*** | (2006.01) |
| ***C07D 209/86*** | (2006.01) |
| ***C07D 409/04*** | (2006.01) |
| ***C07D 409/12*** | (2006.01) |
| ***C09K 11/06*** | (2006.01) |

(52) U.S. Cl.

CPC ........ *H01L 51/0061* (2013.01); *C07D 209/86* (2013.01); *C07D 409/04* (2013.01); *C07D 409/12* (2013.01); *C09K 11/06* (2013.01); *H01L 51/006* (2013.01); *H01L 51/0059* (2013.01); *H01L 51/0067* (2013.01); *H01L 51/0072* (2013.01); *H01L 51/0073* (2013.01); *H01L 51/0074* (2013.01); *H01L 51/5064* (2013.01); *H01L 51/5096* (2013.01); *C09K 2211/1029* (2013.01); *C09K 2211/1088* (2013.01); *C09K 2211/1092* (2013.01); *C09K 2211/185* (2013.01); *H01L 51/0052* (2013.01); *H01L 51/0081* (2013.01); *H01L 51/0085* (2013.01); *H01L 51/5012* (2013.01); *H01L 51/5056* (2013.01); *H01L 51/5088* (2013.01); *Y02E 10/549* (2013.01)

(58) Field of Classification Search

CPC .. C07D 209/86; C07D 409/04; C07D 409/12; C09K 11/06; C09K 2211/185; H01L 51/0052; H01L 51/0059; H01L 51/006; H01L 51/0061; H01L 51/0067; H01L 51/0072; H01L 51/0073; H01L 51/0074; H01L 51/0081; H01L 51/0085; H01L 51/5012; H01L 51/5056; H01L 51/5088; Y02E 10/549

See application file for complete search history.

(56) References Cited

U.S. PATENT DOCUMENTS

| | | | | |
|---|---|---|---|---|
| 9,917,257 B2* | 3/2018 | Lee | H01L 51/0059 | |
| 10,249,825 B2* | 4/2019 | Lee | C07D 209/86 | |
| 2005/0221124 A1* | 10/2005 | Hwang | C07D 403/12 | 428/690 |
| 2012/0217492 A1* | 8/2012 | Kim | H01L 51/0052 | 548/440 |
| 2013/0087776 A1* | 4/2013 | Lee | C07D 403/12 | 548/440 |
| 2013/0105771 A1* | 5/2013 | Ryu | H05B 33/14 | 548/440 |
| 2013/0321375 A1* | 12/2013 | Ka | G09G 3/3233 | 345/212 |
| 2015/0221874 A1* | 8/2015 | Kim | H01L 51/0072 | 257/40 |
| 2015/0325795 A1* | 11/2015 | Lee | C07D 401/12 | 257/40 |
| 2016/0133850 A1* | 5/2016 | Matsuura | C09K 11/025 | 257/40 |

FOREIGN PATENT DOCUMENTS

| | | | |
|---|---|---|---|
| KR | 10-2009-0035729 A | | 4/2009 |
| KR | 20100131629 A | * | 12/2010 |
| WO | WO 2015/080404 A1 | * | 6/2015 |

OTHER PUBLICATIONS

Machine translation for WO 2015/080404 A1 (publication date Jun. 2015). (Year: 2015).*

(Continued)

*Primary Examiner* — Dawn L Garrett

(74) *Attorney, Agent, or Firm* — Vorys, Sater, Seymour and Pease LLP; Mih Suhn Koh

(57) ABSTRACT

Provided are a compound of Formula 1 and an organic electric element including a first electrode, a second electrode, and an organic material layer between the first electrode and the second electrode and comprising the compound, the element showing improved luminescence efficiency, stability, and life span.

18 Claims, 1 Drawing Sheet

OTHER PUBLICATIONS

Machine translation for KR 20100131629 A (publication date Dec. 2010). (Year: 2010).*
The Korean Office Action for corresponding KR Patent Application No. 2005-0025588, dated May 7, 2021, 7 pages.

* cited by examiner

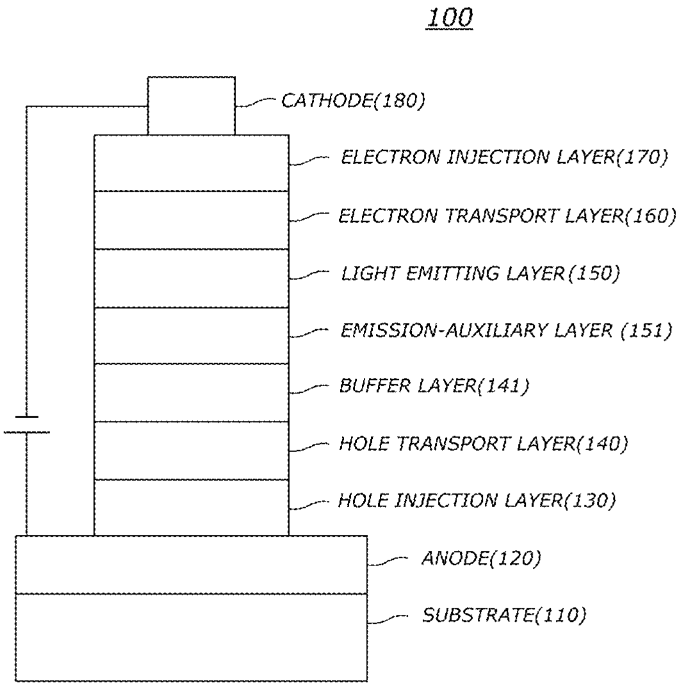
100
CATHODE(180)
ELECTRON INJECTION LAYER(170)
ELECTRON TRANSPORT LAYER(160)
LIGHT EMITTING LAYER(150)
EMISSION-AUXILIARY LAYER (151)
BUFFER LAYER(141)
HOLE TRANSPORT LAYER(140)
HOLE INJECTION LAYER(130)
ANODE(120)
SUBSTRATE(110)

COMPOUND FOR ORGANIC ELECTRONIC ELEMENT, ORGANIC ELECTRONIC ELEMENT USING THE SAME, AND ELECTRONIC DEVICE THEREOF

CROSS-REFERENCE TO RELATED APPLICATION

This patent application is a Divisional of U.S. patent application Ser. No. 15/121,472 filed Aug. 25, 2016, which is a National Stage entry from International Application No. PCT/KR2015/001801 filed on Feb. 25, 2015, which claims priority to Korean Patent Application No. 10-2014-0023356 filed on Feb. 27, 2014, Korean Patent Application No. 10-2014-0064727 filed on May 28, 2014, and Korean Patent Application No. 10-2015-0025588 filed on Feb. 24, 2015, the contents of which are hereby incorporated by reference for all purposes as if fully set forth herein.

BACKGROUND

Technical Field

The present invention relates to compounds for organic electric elements, organic electric elements using the same, and electronic devices thereof.

Background Art

In general, an organic light emitting phenomenon refers to a phenomenon in which electric energy is converted into light energy of an organic material. An organic electric element utilizing the organic light emitting phenomenon usually has a structure including an anode, a cathode, and an organic material layer interposed therebetween. In many cases, the organic material layer may have a multilayered structure including multiple layers made of different materials in order to improve the efficiency and stability of an organic electric element, and for example, may include a hole injection layer, a hole transport layer, a light emitting layer, an electron transport layer, an electron injection layer, or the like.

A material used as an organic material layer in an organic electric element may be classified into a light emitting material and a charge transport material, for example, a hole injection material, a hole transport material, an electron transport material, an electron injection material, and the like according to its function.

Currently, the power consumption is required more and more as size of display becomes larger and larger in the portable display market. Therefore, the power consumption is a very important factor in the portable display with a limited power source of the battery, and efficiency and life span issue also must be solved.

Efficiency, life span, driving voltage, and the like are correlated with each other. For example, if efficiency is increased, then driving voltage is relatively lowered, and the crystallization of an organic material due to Joule heating generated during operation is reduced as driving voltage is lowered, as a result of which life span shows a tendency to increase.

However, efficiency cannot be maximized only by simply improving the organic material layer. This is because long life span and high efficiency can be simultaneously achieved when an optimal combination of energy levels and T1 values, inherent material properties (mobility, interfacial properties, etc.), and the like among the respective layers included in the organic material layer is given. Therefore it is required to develop a light emitting material that has high thermal stability and can achieve efficiently a charge balance in the light-emitting layer.

Further, in order to solve the emission problem with a hole transport layer in a recent organic electric element, an emission-auxiliary layer is present between the hole transport layer and a light emitting layer, and it is time to develop different emission-auxiliary layers according to respective light emitting layers (R, G, B).

In general, an electron transferred from an electron transport layer to a light emitting layer and a hole transferred from a hole transport layer to the light emitting layer are recombined to form an exciton.

However, since a material used in a hole transporting layer should have a low HOMO value, it mainly has a low T1 value. Due to this, excitons generated from a light emitting layer are transported to the hole transporting layer, resulting in a charge unbalance in the light emitting layer. Thus, light emission occurs in the hole transporting layer or at an interface of the hole transporting layer so that the organic electroluminescent device is reduced in color purity, efficiency, and lifespan.

Also, when using a material having rapid hole mobility for reducing a driving voltage, this is tend to decrease the efficiency. In an OLEDs, a charge unbalance in the light emitting layer is caused because of that hole mobility is faster than electron mobility, and reduced efficiency and lifespan is happened.

Therefore, an emitting auxiliary layer must be formed by a material what can solve the problems of an hole transport layer, having hole mobility (within the driving voltage range of the blue element of full device) to give the suitable driving voltage, high T1 energy value (electron block) and wide band gap. These requirements are not satisfied only by structural characteristics about a core of the emitting auxiliary layer's material. Therefore, it is necessary to develop of the material for the emitting auxiliary layer having high T1 energy value and wide band gap, to improve efficiency and lifespan of the organic electric element as combined core of material and characteristics of sub substituents appropriately.

In order to allow an organic electric element to fully exhibit the above-mentioned excellent features, it should be prerequisite to support a material constituting an organic material layer in the element, for example, a hole injection material, a hole transport material, a light emitting material, an electron transport material, an electron injection material, or the like, by a stable and efficient material. However, such a stable and efficient organic material layer material for an organic electric element has not yet been fully developed. Accordingly, there is a continuous need to develop new materials for an organic material layer.

SUMMARY

In order to solve one or more of the above-mentioned problems occurring in the prior art, an aspect of the present invention is to provide a compound which allows an organic electric element to improve luminescence efficiency, stability and lifespan, an organic electric element containing the same, and an electronic device including the organic electric element.

In accordance with an aspect of the present invention, the compound represented by the following Formula is provided.

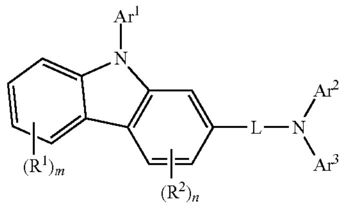

In another aspect of the present invention, organic electric elements containing the compound represented by the formula above and electronic devices including the organic electric element are provided.

By employing the compound of the present invention that has wide band gap and high T1 energy value due to the non-linear linker (L) attached to the carbazole core, the organic electric element according to one or more embodiments of the present invention can have not only high luminescence efficiency and high heat-resistance, but also significantly improved color purity and lifespan.

BRIEF DESCRIPTION OF THE DRAWINGS

The FIG. illustrates an example of an organic light emitting diode according to an embodiment of the present invention.

DETAILED DESCRIPTION

Hereinafter, some embodiments of the present invention will be described in detail with reference to the accompanying illustrative drawings.

In designation of reference numerals to components in respective drawings, it should be noted that the same elements will be designated by the same reference numerals although they are shown in different drawings. Further, in the following description of the present invention, a detailed description of known functions and configurations incorporated herein will be omitted when it may make the subject matter of the present invention rather unclear.

In addition, terms, such as first, second, A, B, (a), (b) or the like may be used herein when describing components of the present invention. Each of these terminologies is not used to define an essence, order or sequence of a corresponding component but used merely to distinguish the corresponding component from other component(s). It should be noted that if it is described in the specification that one component is “connected,” “coupled” or “joined” to another component, a third component may be “connected,” “coupled,” and “joined” between the first and second components, although the first component may be directly connected, coupled or joined to the second component. In addition, it will be understood that when an element such as a layer, film, region or substrate is referred to as being “on” or “over” another element, it can be directly on the other element or intervening elements may also be present. In contrast, when an element is referred to as being “directly on” another element, there are no intervening elements present.

As used in the specification and the accompanying claims, unless otherwise stated, the following is the meaning of the term as follows.

Unless otherwise stated, the term “halo” or “halogen” as used herein includes fluorine (F), chlorine (Cl), bromine (Br), or iodine (I).

Unless otherwise stated, the term “alkyl” or “alkyl group” as used herein has a single bond of 1 to 60 carbon atoms, and means aliphatic functional radicals including a linear alkyl group, a branched chain alkyl group, a cyclo alkyl group (alicyclic), or an alkyl group substituted with a cyclo alkyl.

Unless otherwise stated, the term “halo alkyl” or “halogen alkyl” as used herein includes an alkyl group substituted with a halogen.

Unless otherwise stated, the term “alkenyl” or “alkynyl” as used herein has, but not limited to, double or triple bonds of 2 to 60 carbon atoms, and includes a linear alkyl group, or a branched chain alkyl group.

Unless otherwise stated, the term “cyclo alkyl” as used herein means, but not limited to, alkyl forming a ring having 3 to 60 carbon atoms.

The term “alkoxyl group”, “alkoxy group” or “alkyloxy group” as used herein means an oxygen radical attached to an alkyl group, but not limited to, and has 1 to 60 carbon atoms.

The term “alkenoxyl group”, “alkenoxy group”, “alkenyloxyl group” or “alkenyloxy group” as used herein means an oxygen radical attached to an alkyl group, but not limited to, and has 2 to 60 carbon atoms.

The term “aryloxyl group” or “aryloxy group” as used herein means an oxygen radical attached to an aryl group, but not limited to, and has 6 to 60 carbon atoms.

Unless otherwise stated, the term “aryl group” or “arylene group” as used herein has, but not limited to, 6 to 60 carbon atoms. Herein, the aryl group or arylene group means a monocyclic or polycyclic aromatic group, and may also be formed in conjunction with an adjacent group. Examples of “aryl group” or “arylene group” may include a phenyl group, a biphenyl group, a fluorene group, or a spirofluorene group or a spirobifluorene group.

Also, when prefixes are named subsequently, it means that substituents are listed in the order described first. For example, an aryl alkoxy means an alkoxy substituted with an aryl, an alkoxyl carbonyl means a carbonyl substituted with an alkoxyl, and an aryl carbonyl alkenyl also means an alkenyl substitutes with an aryl carbonyl, wherein the aryl carbonyl may be a carbonyl substituted with an aryl.

Unless otherwise stated, the “hetero aryl group” or “hetero arylene group” as used herein means, but not limited to, a ring containing one or more hetero atoms, and having 2 to 60 carbon atoms. They include at least one monocyclic or polycyclic ring, and may be linked together to form a fused ring.

Unless otherwise stated, the term “heterocyclic group” as used herein means, but not limited to, a ring containing one or more hetero atoms, and having 2 to 60 carbon atoms. They include at least one monocyclic or polycyclic ring, and hetero aliphatic or hetero aromatic ring, and may be linked together to form a fused ring.

Unless otherwise stated, the term “heteroatom” as used herein represents at least one of N, O, S, P, and Si.

Also, the term “heterocyclic group” may include $SO_2$ instead of carbon consisting of cycle. For example, “heterocyclic group” includes compound below.

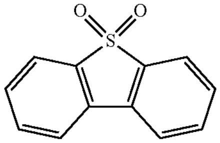 [SMILES: O=S1(=O)c2ccccc2-c2ccccc21]

Unless otherwise stated, the term "aliphatic" as used herein means aliphatic hydrocarbon, having 1 to 60 carbon atoms. The term "aliphatic ring" means aliphatic hydrocarbon ring, having 1 to 60 carbon.

Unless otherwise stated, the term "ring" as used herein means aliphatic ring having 3 to 60 carbon or aromatic ring having 6 to 60 carbon, or heterocyclic ring having 2 to 60 carbon or a fused ring formed by combinations thereof, includes saturated or unsaturated ring.

The other hetero cyclic compounds or hetero radicals may include, but not limited to, at least one hetero atom, except to the described hetero cyclic compound above.

Unless otherwise stated, the term "substituted or unsubstituted" as used herein means that substitution is carried out by at least one substituent selected from the group consisting of, but not limited to, deuterium, halogen, an amino group, a nitrile group, a nitro group, a $C_1$-$C_{20}$ alkyl group, a $C_1$-$C_{20}$ alkoxy group, a $C_1$-$C_{20}$ alkylamine group, a $C_1$-$C_{20}$ alkylthio group, a $C_6$-$C_{20}$ arylthio group, a $C_2$-$C_{20}$ alkenyl group, a $C_2$-$C_{20}$ alkynyl group, a $C_3$-$C_{20}$ cycloalkyl group, a $C_6$-$C_{60}$ aryl group, a $C_6$-$C_{20}$ aryl group substituted by deuterium, a $C_8$-$C_{20}$ arylalkenyl group, a silane group, a boron group, a germanium group, and a $C_2$-$C_{20}$ heterocyclic group.

Otherwise specified, the Formulas used in the present invention are as defined in the index definition of the substituent of the following Formula.

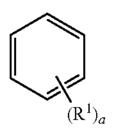

Wherein, when a is an integer of zero, the substituent $R^1$ is absent, when a is an integer of 1, the sole $R^1$ is linked to any one of the carbon atoms constituting the benzene ring, when a is an integer of 2 or 3, the substituent $R^1$'s may be the same and different, and are linked to the benzene ring as follows. when a is an integer of 4 to 6, the substituents $R^1$'s may be the same and different, and are linked to the benzene ring in a similar manner to that when a is an integer of 2 or 3, hydrogen atoms linked to carbon constituents of the benzene ring being not represented as usual.

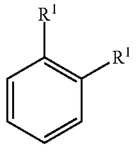

(a = 2)

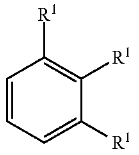

(a = 3)

The FIGURE illustrates an organic electric element according to an embodiment of the present invention.

Referring to the FIGURE, an organic electric element 100 according to an embodiment of the present invention includes a first electrode 120 formed on a substrate 110, a second electrode 180, and an organic material layer between the first electrode 110 and the second electrode 180, which contains the inventive compound. Here, the first electrode 120 may be an anode (positive electrode), and the second electrode 180 may be a cathode (negative electrode). In the case of an inverted organic electric element, the first electrode may be a cathode, and the second electrode may be an anode.

The organic material layer includes a hole injection layer 130, a hole transport layer 140, a light emitting layer 150, an electron transport layer 160, and an electron injection layer 170 formed in sequence on the first electrode 120. Here, the layers included in the organic material layer, except the light emitting layer 150, may not be formed. The organic material layer may further include a hole blocking layer, an electron blocking layer, an emission-auxiliary layer 151, a buffer layer 141, etc., and the electron transport layer 160 and the like may serve as the hole blocking layer.

Although not shown, the organic electric element according to an embodiment of the present invention may further include at least one protective layer or one capping layer formed on at least one of the sides the first and second electrodes, which is a side opposite to the organic material layer.

The inventive compound employed in the organic material layer may be used as a host material, a dopant material, or a capping layer material in the hole injection layer 130, the hole transport layer 140, the electron transport layer 160, the electron injection layer 170, or the light emitting layer 150. For example, the inventive compound may be used as materials of the light emitting layer 150, the hole transport layer 140, and/or the emission-auxiliary layer 151.

Since depending on the type and position of a substituent to be attached, a band gap, electrical properties, interfacial properties, and the like may vary even in the same core, it is very important what the types of core and a combination of substituent attached to the core are. Specially, long life span and high efficiency can be simultaneously achieved when an optimal combination of energy levels and T1 values, inherent material properties (mobility, interfacial properties, etc.), and the like among the respective layers included in the organic material layer is given.

As already described above, in order to solve the emission problem with a hole transport layer in a conventional organic electric element, an emission-auxiliary layer is preferably formed between the hole transport layer and a light emitting layer, and it is time to develop different emission-auxiliary layers according to respective light emitting layers (R, G, B). However, even when a similar core is used, it is very difficult to infer the characteristics of an emission-auxiliary layer if a used organic material layer varies because the correlation between the emission-auxiliary layer and a hole transport layer and the correlation between the emission-auxiliary layer and a light emitting layer (host) mused be discovered.

Accordingly, in the present invention, a combination of energy levels and T1 values, inherent material properties (mobility, interfacial properties, etc.), and the like among the respective layers included in the organic material layer is optimized by forming a light emitting layer and/or an emission-auxiliary layer by using the compound represented by Formula 1, and thus the life span and efficiency of the organic electric element can be improved at the same time.

The organic electric element according to an embodiment of the present invention may be manufactured using various deposition methods. The organic electric element according to an embodiment of the present invention may be manufactured using a PVD (physical vapor deposition) method or CVD (chemical vapor deposition) method. For example, the organic electric element may be manufactured by depositing a metal, a conductive metal oxide, or a mixture thereof on the substrate to form the anode 120, forming the organic material layer including the hole injection layer 130, the hole transport layer 140, the light emitting layer 150, the electron transport layer 160, and the electron injection layer 170 thereon, and then depositing a material, which can be used as the cathode 180, thereon. Also, an emitting auxiliary layer 151 may be comprised between the hole transport layer 140 and the light emitting layer 150.

And also, the organic material layer may be manufactured in such a manner that a smaller number of layers are formed using various polymer materials by a soluble process or solvent process, for example, spin coating, dip coating, doctor blading, screen printing, inkjet printing, or thermal transfer, instead of deposition. Since the organic material layer according to the present invention may be formed in various ways, the scope of protection of the present invention is not limited by a method of forming the organic material layer.

According to used materials, the organic electric element according to an embodiment of the present invention may be of a top emission type, a bottom emission type, or a dual emission type.

A WOLED (White Organic Light Emitting Device) readily allows for the formation of ultra-high definition images, and is of excellent processability as well as enjoying the advantage of being produced using conventional color filter technologies for LCDs. In this regard, various structures for WOLEDs, used as back light units, have been, in the most part, suggested and patented. Representative among the structures are a parallel side-by-side arrangement of R (Red), G (Green), B (Blue) light-emitting units, a vertical stack arrangement of RGB light-emitting units, and a CCM (color conversion material) structure in which electroluminescence from a blue (B) organic light emitting layer, and photoluminescence from an inorganic luminescent using the electroluminescence are combined. The present invention is applicable to these WOLEDs.

Further, the organic electric element according to an embodiment of the present invention may be any one of an organic light emitting diode (OLED), an organic solar cell, an organic photo conductor (OPC), an organic transistor (organic TFT), and an element for monochromatic or white illumination.

Another embodiment of the present invention provides an electronic device including a display device, which includes the above described organic electric element, and a control unit for controlling the display device. Here, the electronic device may be a wired/wireless communication terminal which is currently used or will be used in the future, and covers all kinds of electronic devices including a mobile communication terminal such as a cellular phone, a personal digital assistant (PDA), an electronic dictionary, a point-to-multipoint (PMP), a remote controller, a navigation unit, a game player, various kinds of TVs, and various kinds of computers.

Hereinafter, an organic electric element according to an aspect of the present invention will be described.

The compound according to an aspect of the present invention is represented by the following Formula 1.

[Formula 1]

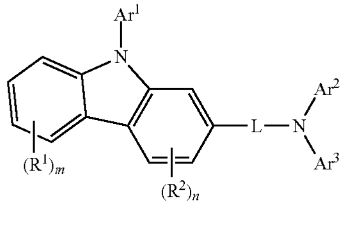

In Formula 1 above, $Ar^1$ to $Ar^3$ may be each independently selected from the group consisting of a $C_6$-$C_{60}$ aryl group; a fluorenyl group; a $C_2$-$C_{60}$ heterocyclic group containing at least one heteroatom selected from the group consisting of O, N, S, Si, and P, a fused ring formed by a $C_3$-$C_{60}$ aliphatic ring and a $C_6$-$C_{60}$ aromatic ring; a $C_1$-$C_{50}$ alkyl group; a $C_2$-$C_{20}$ alkenyl group; a $C_2$-$C_{20}$ alkynyl group; a $C_1$-$C_{30}$ alkoxy group; and a $C_6$-$C_{30}$ aryloxy group. For example, $Ar^1$ to $Ar^3$ may be each independently phenyl, naphthyl, biphenyl, terphenyl, phenyl substituted with deuterium, methyl phenyl, t-butyl phenyl, methoxy phenyl, terphenyl substituted with deuterium, 9,9-dimethyl-9H-fluorenyl, 9,9-diphenyl-9H-fluorenyl, 7,7-diphenyl-7H-benzo[c]fluorenyl, spirobifluorenyl, 9-phenyl-9H-carbazolyl, 9-naphthyl-9H-carbazolyl, 9-biphenyl-9H-carbazolyl, 9-triazinyl-9H-carbazolyl, 9-dibenzothienyl-9H-carbazolyl, 7-phenyl-7H-benzo[c]carbazolyl, 5-phenyl-5H-benzo[b]carbazolyl, 11-phenyl-11H-benzo[a]carbazolyl, dibenzothienyl, dibenzofuryl, naphto[2,1-b]benzothienyl, naphto[2,1-b]benzofuryl or phenylpyrimidinyl.

L may be

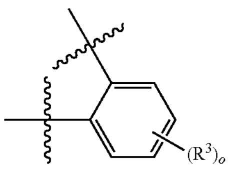

or

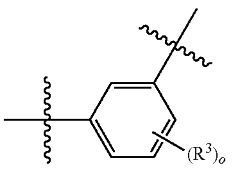

wherein, $R^3$ may be selected from the group consisting of i) deuterium; halogen; a $C_6$-$C_{60}$ aryl group; a fluorenyl group; a $C_2$-$C_{60}$ heterocyclic group containing at least one heteroatom selected from the group consisting of O, N, S, Si, and P, a fused ring formed by a $C_3$-$C_{60}$ aliphatic ring and a $C_6$-$C_{60}$ aromatic ring; a $C_1$-$C_{50}$ alkyl group; a $C_2$-$C_{20}$ alkenyl group; a $C_2$-$C_{20}$ alkynyl group; a $C_1$-$C_{30}$ alkoxy group; a $C_6$-$C_{30}$ aryloxy group; -L'-N($R^a$)($R^b$); and combinations thereof, or ii) two adjacent groups, may be optionally linked together to form at least one ring, and the group(s) of $R^3$s not forming a ring may be the same as defined in the above i). For example, $R^3$ may be phenyl, biphenyl, naphthyl, pyridyl, pyrimidyl, quinolyl, isoquinolyl, quinazolyl, or adjacent $R^3$s may be linked together to form at least one aromatic ring such as naphthalene or phenanthrene, or hetero cyclic ring such as isoquinoline, quinoline, quinazoline or quinoxaline with the benzene ring to which $R^3$s are attached.

o may be an integer of 0 to 4, plural $R^3$s may be same or different each other when o is 2 or more. And all of or some of the adjacent groups, $R^3$s, may be linked together to form a ring, and the group(s) of $R^3$s not forming a ring may be any one of substituents as defined in the above i).

In Formula 1 above, m may be an integer of 0 to 4, and n may be an integer of 0 to 3.

$R^1$ and $R^2$ may be each independently selected from the group consisting of i) deuterium; halogen; a $C_6$-$C_{60}$ aryl group; a fluorenyl group; a $C_2$-$C_{60}$ heterocyclic group containing at least one heteroatom selected from the group consisting of O, N, S, Si, and P; a fused ring formed by a $C_3$-$C_{60}$ aliphatic ring and a $C_6$-$C_{60}$ aromatic ring; a $C_1$-$C_{50}$ alkyl group; a $C_2$-$C_{20}$ alkenyl group; a $C_2$-$C_{20}$ alkynyl group; a $C_1$-$C_{30}$ alkoxy group; a $C_6$-$C_{30}$ aryloxy group; and -L'-N($R^a$)($R^b$), or ii) any two adjacent groups may be optionally linked together to form at least one ring, and the group(s) of $R^1$ and $R^2$ not forming a ring may be the same as defined in the above i). For example, $R^1$ and $R^2$ may be each independently propenyl, phenyl, dibenzothienyl, triazinyl, quinolyl or quinazolyl, adjacent $R^1$s and/or $R^2$s may be linked together to form an aromatic ring such as naphthalene or phenanthrene, or hetero cyclic ring such as isoquinoline, quinoline, quinazoline or quinoxaline, with the benzene ring to which they are attached.

Plural $R^1$s may be same or different each other when m is 2 or more, and all of some of the adjacent groups, $R^1$s, may be linked together to form a ring. The same applies to plural $R^2$s where n is 2 or more, and all of or some of the adjacent groups, $R^2$s, may be linked together to form a ring.

Meanwhile, a fused ring formed by adjacent groups may be a $C_3$-$C_{60}$ aliphatic ring or a $C_6$-$C_{60}$ aromatic ring, a $C_2$-$C_{60}$ hetero cyclic ring, a $C_3$-$C_{60}$ alicyclic ring, or a fused ring formed y combinations thereof, and it may be a monocyclic or polycyclic ring, and/or a saturated or unsaturated ring.

L' may be selected from the group consisting of single bond; a $C_6$-$C_{60}$ arylene group; a fluorenylene group; a fused ring formed by a $C_3$-$C_{60}$ aliphatic ring and a $C_6$-$C_{60}$ aromatic ring; and a $C_2$-$C_{60}$ heterocyclic group containing at least one heteroatom selected from the group consisting of O, N, S, Si, and P, $R^a$ and $R^b$ may be each independently selected from the group consisting of $C_6$-$C_{60}$ aryl group; a fluorenyl group; a fused ring formed by a $C_3$-$C_{60}$ aliphatic ring and a $C_6$-$C_{60}$ aromatic ring; and a $C_2$-$C_{60}$ heterocyclic group containing at least one heteroatom selected from the group consisting of O, N, S, Si, and P.

For example, in Formula 1 above, $Ar^1$ may be selected from the following structures:

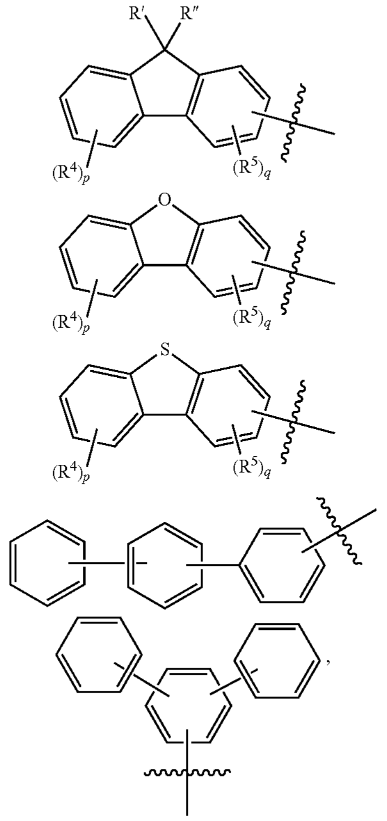

wherein R' and R" may be each independently selected from the group consisting of hydrogen; deuterium; tritium; a $C_6$-$C_{20}$ aryl group; a $C_1$-$C_{20}$ alkyl group; and a $C_2$-$C_{20}$ alkenyl group. For example, R' and R" may be each independently methyl or phenyl, and R' and R" may be linked together to form a spiro compound with the carbon to which they are attached.

$R^4$ and $R^5$ may be each independently selected from the group consisting of deuterium; tritium; halogen; a $C_6$-$C_{60}$ aryl group; a fluorenyl group; a $C_2$-$C_{60}$ heterocyclic group containing at least one heteroatom selected from the group consisting of O, N, S, Si, and P; a fused ring formed by a $C_3$-$C_{60}$ aliphatic ring and a $C_6$-$C_{60}$ aromatic ring; a $C_1$-$C_{50}$ alkyl group; a $C_2$-$C_{20}$ alkenyl group; a $C_2$-$C_{20}$ alkynyl group; a $C_1$-$C_{30}$ alkoxyl group; and a $C_6$-$C_{30}$ aryloxy group, and any two adjacent groups may be optionally linked together to form at least one ring. Herein, the groups of $R^4$s and $R^5$s not forming a ring may be the same as defined in the above.

p may be an integer of 0 to 4, q may be an integer of 0 to 3. When p and/or q are 2 or more, plural $R^4$s may be same or different each other, and plural $R^5$s may be same or different each other. Further, all of or some of adjacent $R^4$s may be linked together to form one or more ring, and all of or some of adjacent $R^5$s may be linked together to form one or more ring. Furthermore, for example, adjacent $R^4$s may be linked together to form a ring, and adjacent $R^5$s may be each independently aryl group or hetero cyclic ring.

The ring formed by linking between adjacent groups may be a $C_3$-$C_{60}$ aliphatic ring or a $C_6$-$C_{60}$ aromatic ring, a $C_2$-$C_{60}$ hetero ring, a $C_3$-$C_{60}$ alicyclic ring, or a fused ring formed by combinations thereof, and the ring may be a mono cyclic or poly cyclic ring, and/or saturated or unsaturated ring.

Also, $Ar^2$ and $Ar^3$ in Formula 1 above may be selected from the following structures:

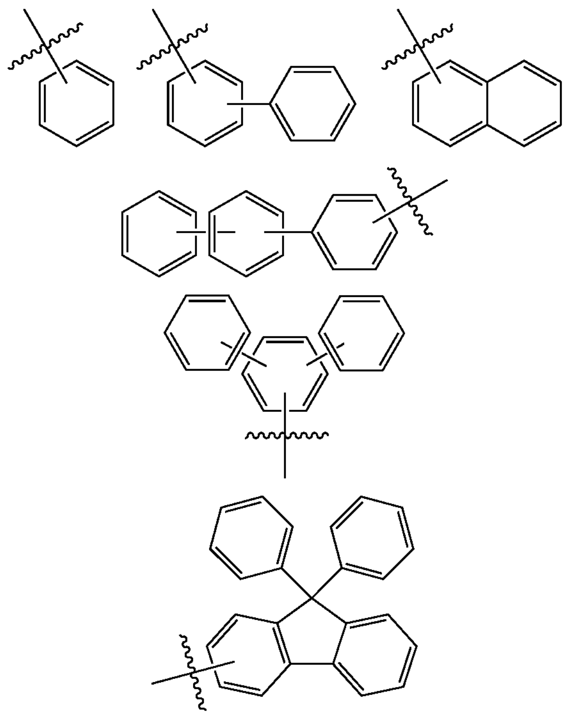

-continued

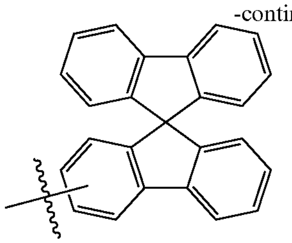

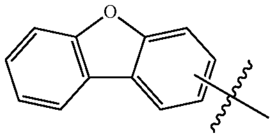

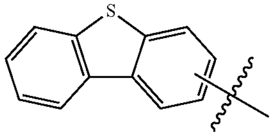

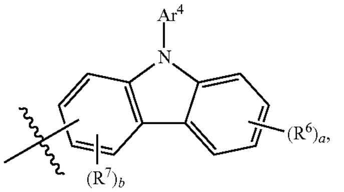

wherein, $Ar^4$ may be selected from the group consisting of a $C_6$-$C_{60}$ aryl group; a fluorenyl group; and a $C_2$-$C_{60}$ heterocyclic group containing at least one heteroatom selected from the group consisting of O, N, S, Si, and P. For example, $Ar^4$ may be phenyl, biphenyl, naphthyl, pyridyl, 9,9-dimethyl-9H-fluorenyl, triazinyl, phenyl substituted with deuterium, or dibenzothienyl.

$R^6$ and $R^7$ may be each independently selected from the group consisting of deuterium; halogen; a $C_6$-$C_{60}$ aryl group; a fluorenyl group; a $C_2$-$C_{60}$ heterocyclic group containing at least one heteroatom selected from the group consisting of O, N, S, Si, and P; a fused ring formed by a $C_3$-$C_{60}$ aliphatic ring and a $C_6$-$C_{60}$ aromatic ring; a $C_1$-$C_{50}$ alkyl group; a $C_2$-$C_{20}$ alkenyl group; a $C_2$-$C_{20}$ alkynyl group; a $C_1$-$C_{30}$ alkoxy group; a $C_6$-$C_{30}$ aryloxy group; and -L'-N($R^a$)($R^b$). Herein L', $R^a$ and $R^b$ may be the same as defined in above $R^1$ to $R^3$.

Further, any two adjacent $R^6$s and $R^7$s may be independently linked together to form at least one ring, and the groups of $R^6$s and $R^7$s not forming a ring may be the same as defined in the above. For example, adjacent $R^6$s and/or $R^7$s may be optionally linked together to form an aromatic ring such as naphthalene or phenanthrene, or hetero cyclic ring such as isoquinoline, quinoline, quinazoline or quinoxaline, with the benzene ring to which they are attached.

Further, a may be an integer of 0 to 4, b may be an integer of 0 to 3, wherein each of plural $R^6$s and plural $R^7$s may be same or different each other when a and b are each 2 or more. All of or some of adjacent $R^6$s may be linked together to form at least one ring, all of or some of adjacent $R^7$s may be linked together to form at least one ring, and even though adjacent $R^6$s may be linked together to form a ring, adjacent $R^7$s may be each independently aryl group or hetero cyclic ring.

The ring formed by adjacent groups may be a $C_3$-$C_{60}$ aliphatic ring or a $C_6$-$C_{60}$ aromatic ring, a $C_2$-$C_{60}$ hetero ring, a $C_3$-$C_{60}$ alicyclic ring, or a fused ring formed by combinations thereof, and it may be a mono cyclic or poly cyclic ring, and/or saturated or unsaturated ring.

Each of the above aryl group, fluorenyl group, heterocyclic group, fused ring group, alkyl group, alkenyl group, alkynyl group, alkoxy group, aryloxy group, arylene group and fluorenylene group may be substituted with one or more substituents selected from the group consisting of deuterium; halogen; a silane group; a siloxane group; a boron group; a germanium group; a cyano group; a nitro group; a $C_1$-$C_{20}$ alkylthio group; a $C_1$-$C_{20}$ alkoxy group; a $C_1$-$C_{20}$ alkyl group; a $C_2$-$C_{20}$ alkenyl group; a $C_2$-$C_{20}$ alkynyl group; a $C_6$-$C_{20}$ aryl group; a $C_6$-$C_{20}$ aryl group substituted with deuterium; a fluorenyl group; a $C_2$-$C_{20}$ heterocyclic group containing at least one heteroatom selected from the group consisting of O, N, S, Si, and a $C_3$-$C_{20}$ cycloalkyl group; a $C_7$-$C_{20}$ arylalkyl group; and a $C_8$-$C_{20}$ arylalkenyl group.

Specifically, the compounds represented by Formula 1 above may be represented any one of the following Formulas, and the following Formulas represent the cases when adjacent $R^1$s and/or adjacent $R^2$s may be linked together to form a ring.

[Formula 2]

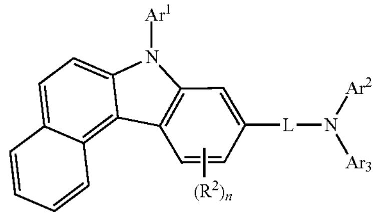

[Formula 3]

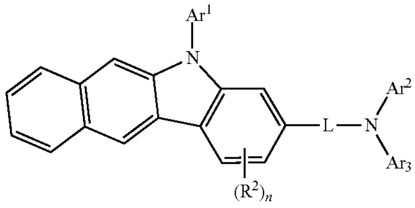

[Formula 4]

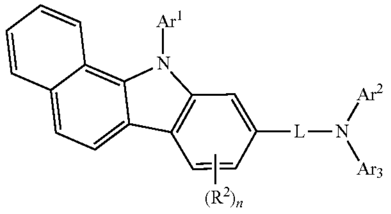

[Formula 5]

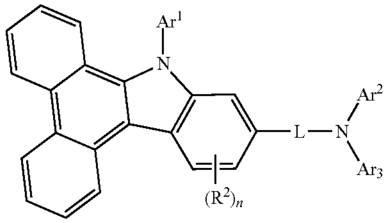

[Formula 6]

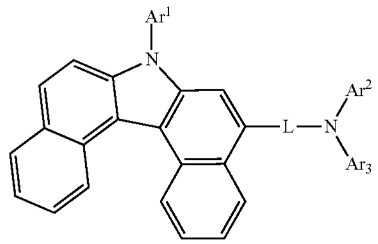

-continued
[Formula 7]
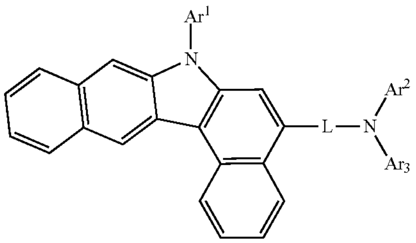
[Formula 8]
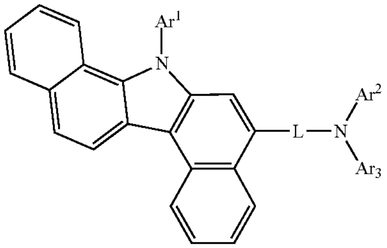
[Formula 9]
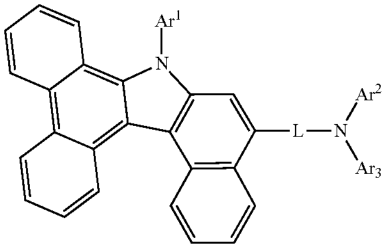
[Formula 10]
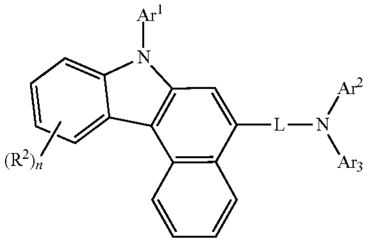
In Formulas 2 to 10 above, each symbols of $Ar^1$ to $Ar^3$, L, $R^1$, m and n may be the same as defined in Formula 1 above.
Specifically, the compounds represented by Formula 1 above may be represented any one of the following Formulas:
[Formula 11]
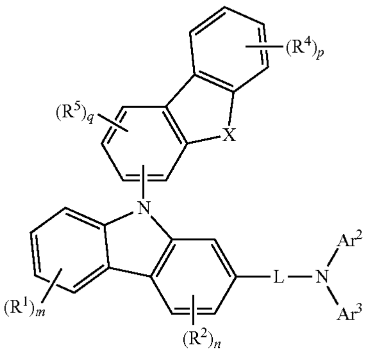
[Formula 12]
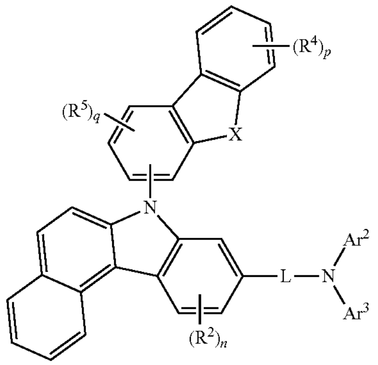
[Formula 13]
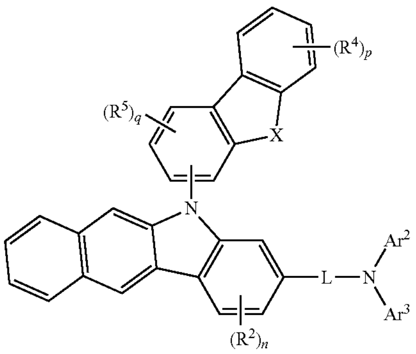
[Formula 14]
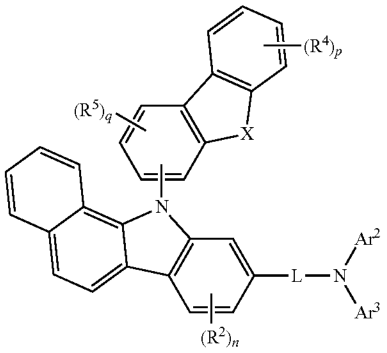

-continued

[Formula 15]

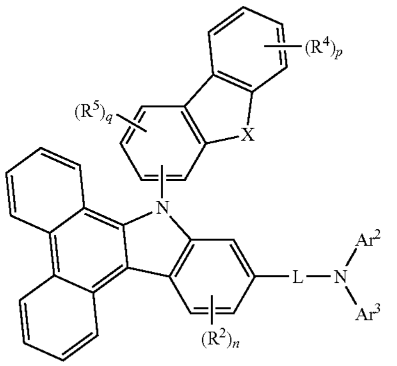

[Formula 16]

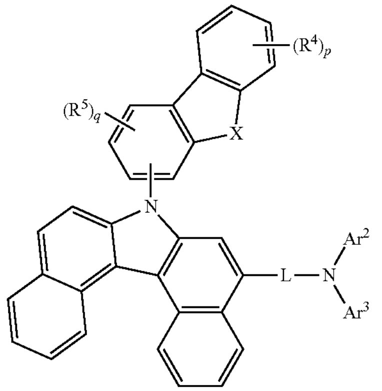

[Formula 17]

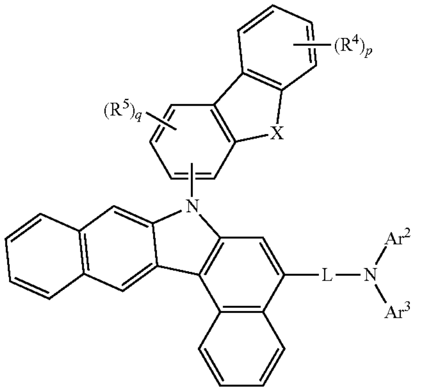

[Formula 18]

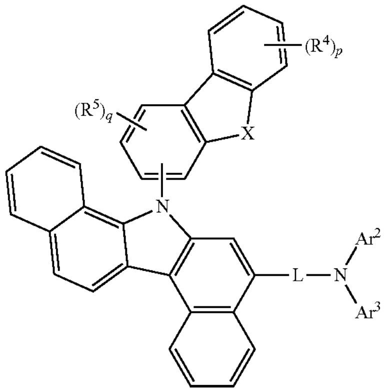

-continued

[Formula 19]

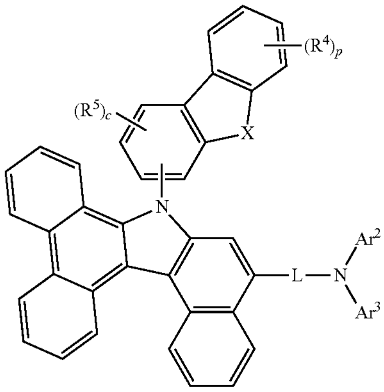

[Formula 20]

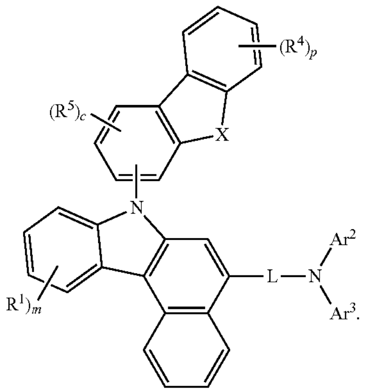

In Formulas 11 to 20, each symbol of $Ar^2$, $Ar^3$, L, $R^1$, $R^2$, m, and n may be the same as defined in Formula 1 above.

$R^4$ and $R^5$ may be each independently selected from the group consisting of hydrogen; deuterium; tritium; halogen; a $C_6$-$C_{60}$ aryl group; a fluorenyl group; a $C_2$-$C_{60}$ heterocyclic group containing at least one heteroatom selected from the group consisting of O, N, S, Si, and F; a fused ring formed by a $C_3$-$C_{60}$ aliphatic ring and a $C_6$-$C_{60}$ aromatic ring; a $C_1$-$C_{50}$ alkyl group; a $C_2$-$C_{20}$ alkenyl group; a $C_2$-$C_{20}$ alkynyl group; a $C_1$-$C_{30}$ alkoxy group; and a $C_6$-$C_{30}$ aryloxy group, or the adjacent groups may be optionally linked together to form at least one ring. Herein, the group(s) not forming a ring may be the same as defined in the above.

X may be O, S or C(R')(R"), and R' and R" may be the same as defined in the structural formula of $Ar^1$ above. That is, R' and R" may be each independently selected from the group consisting of hydrogen; deuterium; tritium; a $C_6$-$C_{20}$ aryl group; a $C_1$-$C_{20}$ alkyl group; and a $C_2$-$C_{20}$ alkenyl group. Further, R' and R" may be optionally linked together to form a spiro compound with the carbon to which they are attached.

The Formula 1 may be represented by the following formula:

[Formula 21]

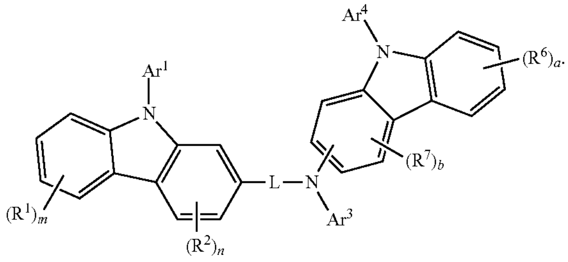

In Formula 21 above, the symbols are defined as the same in Formula 1 above. For example, $R^1$, $R^2$, m, n, $Ar^1$, $Ar^3$, L and the like may be the same as defined in Formula 1 above. $Ar^4$ may be the same as defined in the structural formula of $Ar^2$ above. That is, $Ar^4$ may be selected from the group consisting of a $C_6$-$C_{60}$ aryl group; a fluorenyl group; and a $C_2$-$C_{60}$ heterocyclic group containing at least one heteroatom selected from the group consisting of O, N, S, Si, and P.

$R^6$, $R^7$, a, and b may be the same as defined in the structure of $Ar^2$ above. That is, $R^6$ and $R^7$ may be each independently selected from the group consisting of i) deuterium; halogen; a $C_6$-$C_{60}$ aryl group; a fluorenyl group; a $C_2$-$C_{60}$ heterocyclic group containing at least one heteroatom selected from the group consisting of O, N, S, Si, and P, a fused ring formed by a $C_3$-$C_{60}$ aliphatic ring and a $C_6$-$C_{60}$ aromatic ring; a $C_1$-$C_{50}$ alkyl group; a $C_2$-$C_{20}$ alkenyl group; a $C_2$-$C_{20}$ alkynyl group; a $C_1$-$C_{30}$ alkoxy group; a $C_6$-$C_{30}$ aryloxy group; and -L'-N($R^a$)($R^b$), herein, L' may be selected from the group consisting of single bond; a $C_6$-$C_{60}$ arylene group; a fluorenylene group; a fused ring formed by a $C_3$-$C_{60}$ aliphatic ring and a $C_6$-$C_{60}$ aromatic ring; and a $C_2$-$C_{60}$ heterocyclic group containing at least one heteroatom selected from the group consisting of O, N, S, Si, and P, and $R^a$ and $R^b$ may be each independently selected from the group consisting of a $C_6$-$C_{60}$ aryl group; a fluorenyl group; a fused ring formed by a $C_3$-$C_{60}$ aliphatic ring and a $C_6$-$C_{60}$ aromatic ring; and a $C_2$-$C_{60}$ heterocyclic group containing at least one heteroatom selected from the group consisting of O, N, S, Si, and P. ii) adjacent groups of $R^6$ and $R^7$ may be optionally linked together to form at least one ring, and the group of $R^6$s and $R^7$s not forming a ring may be the same as defined in above i).

Further, a may be an integer of 0 to 4, and $R^6$ may be same or different each other when a is 2 or more, b may be an integer of 0 to 3, and $R^7$ may be same or different each other when b is 2 or more.

More specifically, the above Formula 21 may represent any one of the following formulas:

[Formula 22]

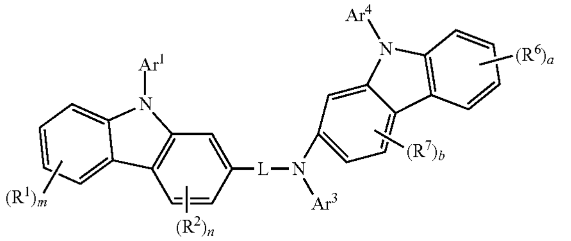

[Formula 23]

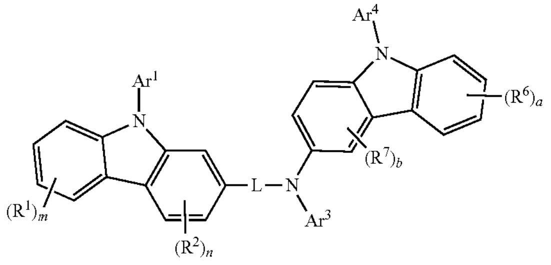

In Formulas 22 and 23, the symbols are defined as the same in Formula 1 or 21 above.

More specifically, the compounds represented by Formulas 1 to 21 may be any one of the following compounds.

P1-1

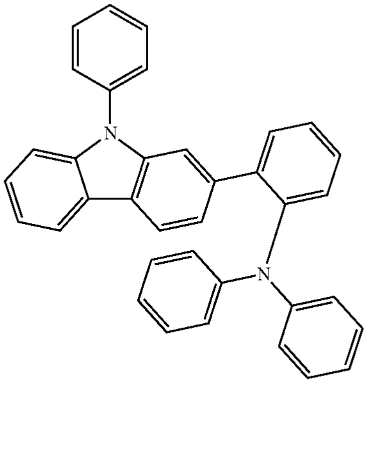

P1-2

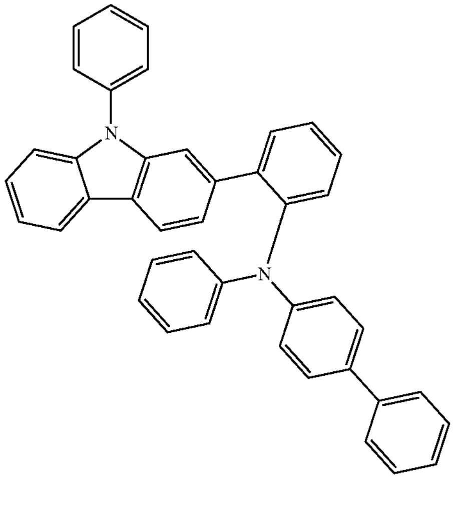

-continued
P1-3
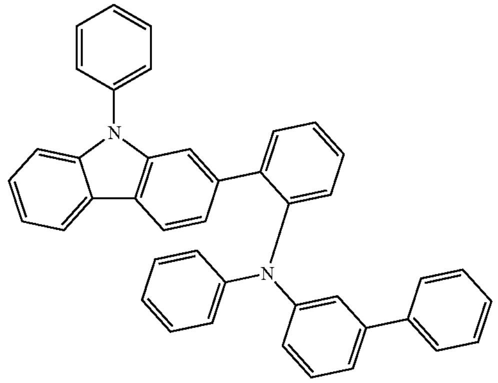
P1-4
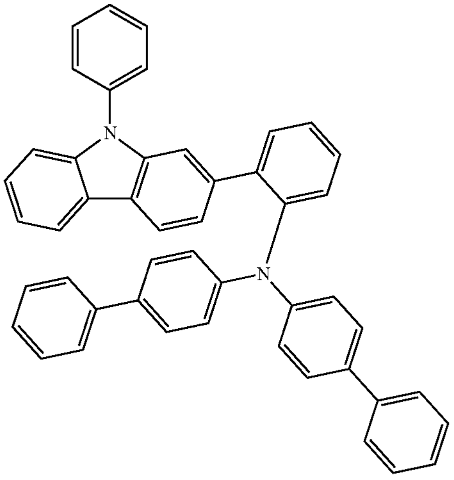
P1-5
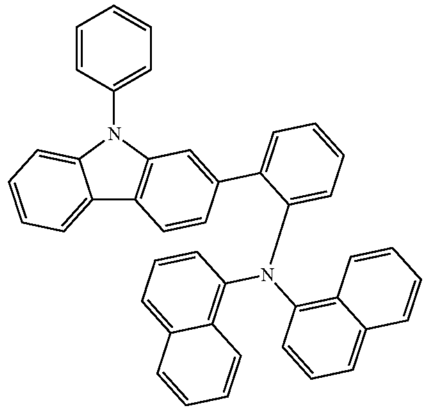
P1-6
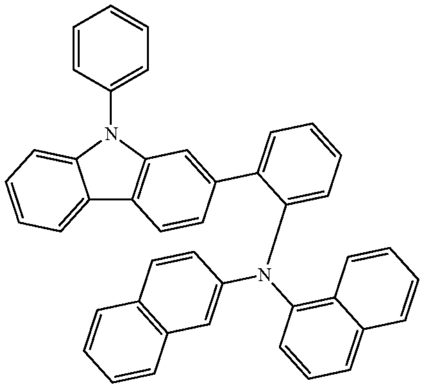
P1-7
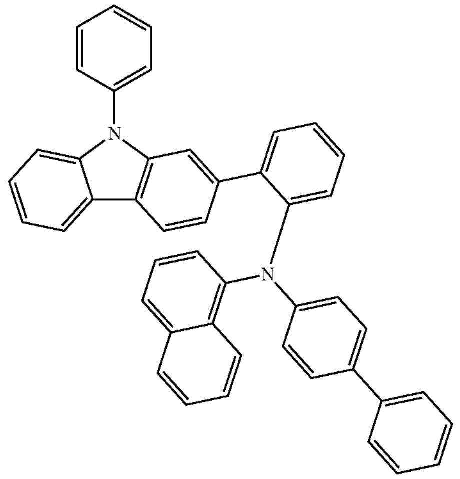
P1-8
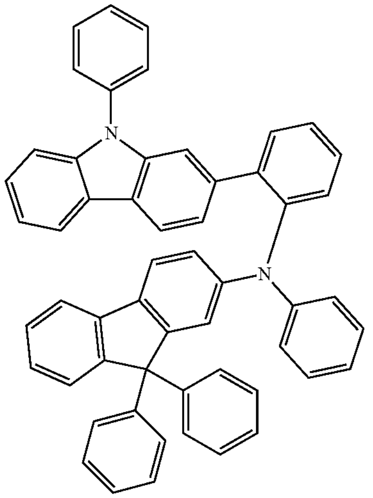

-continued
P1-9
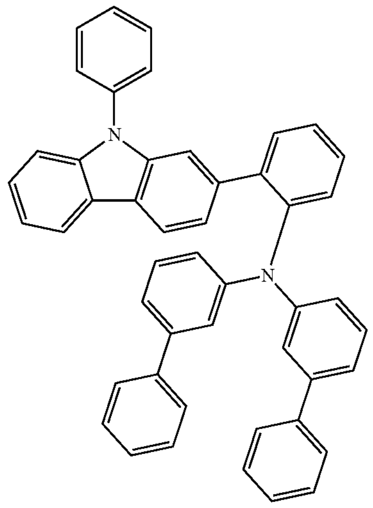
P1-10
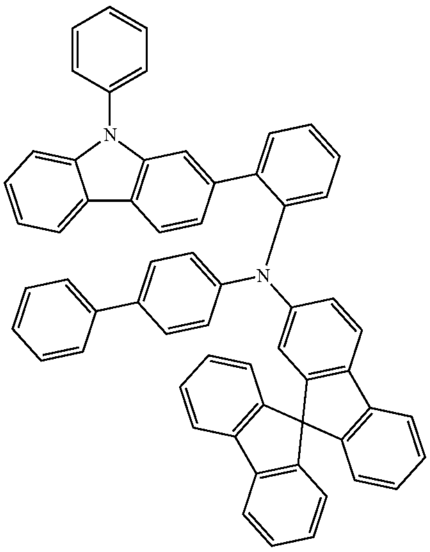
P1-11
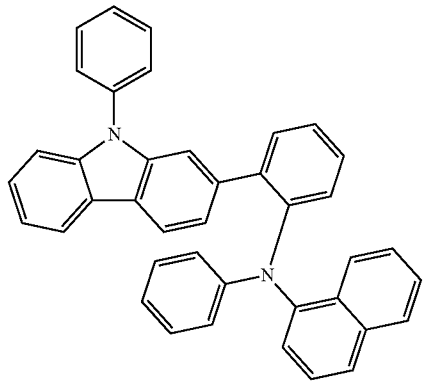
P1-12
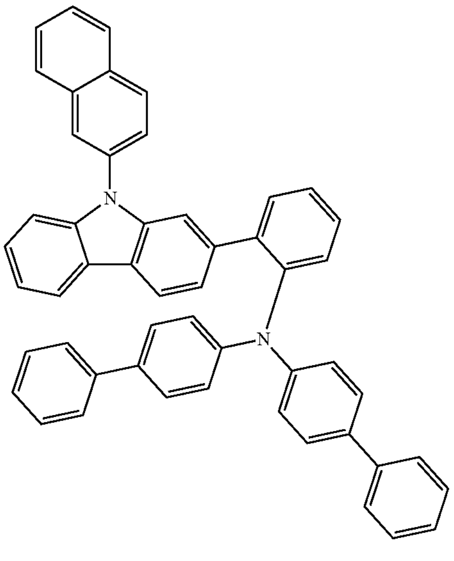

-continued
P1-13
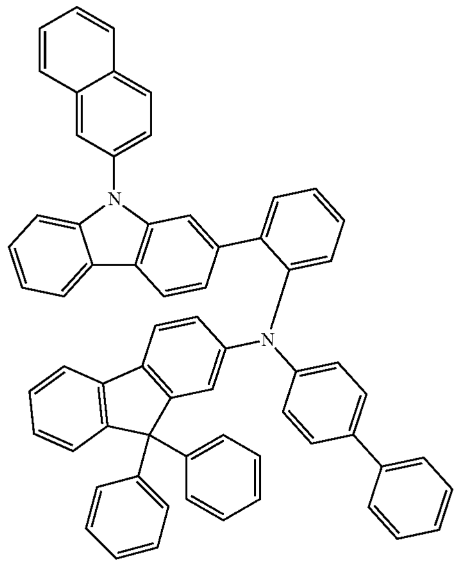
P1-14
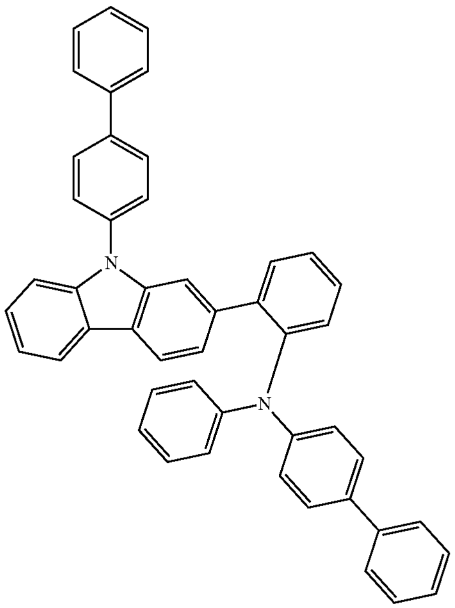
P1-15
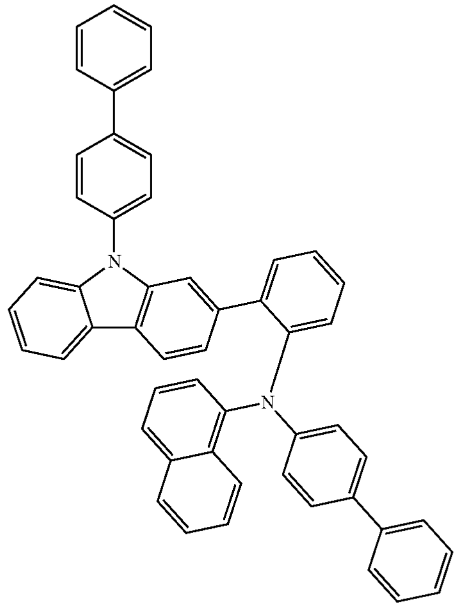
P1-16
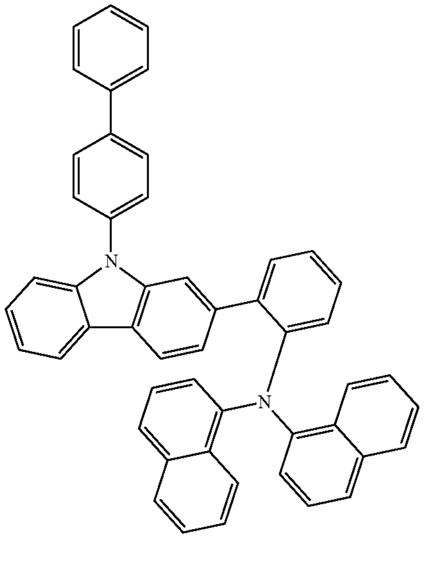
P1-17
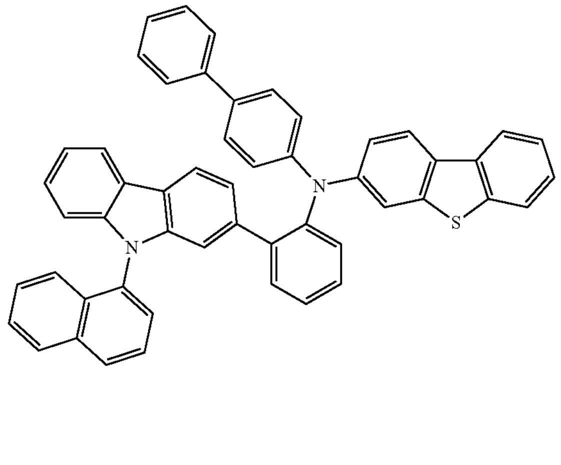
P1-18
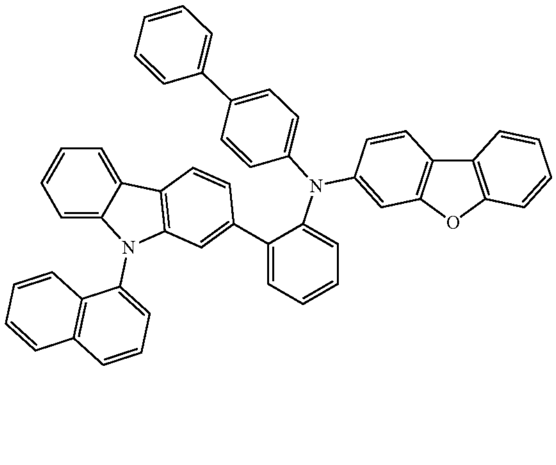

-continued
P1-19
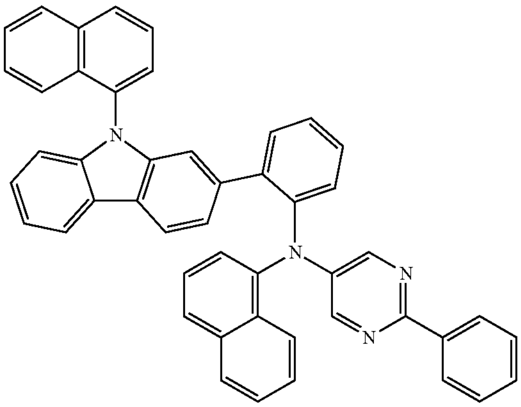
P1-20
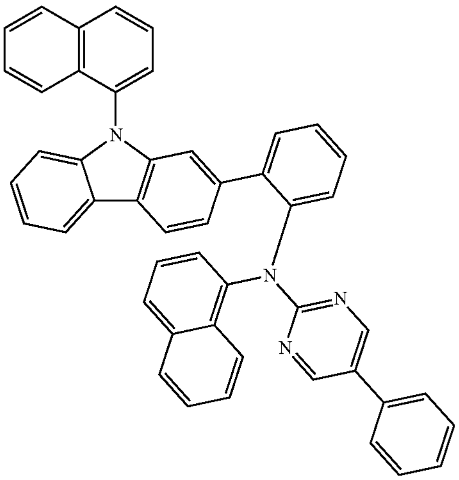
P1-21
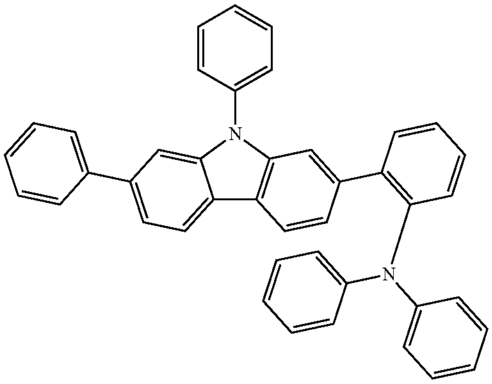
P1-22
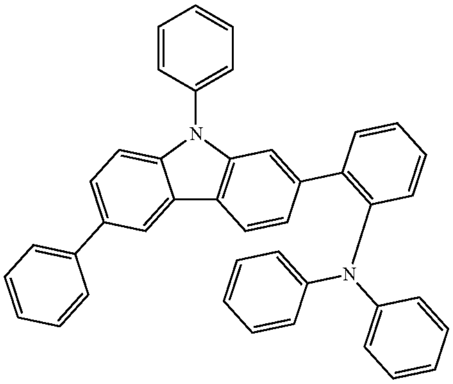
P1-23
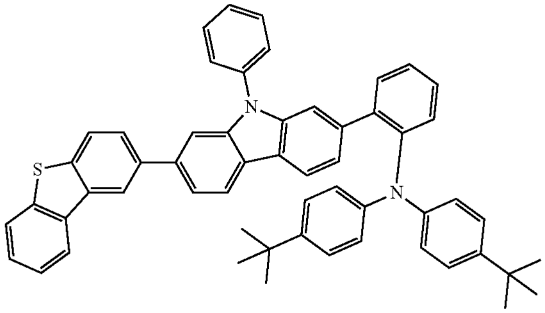
P1-24
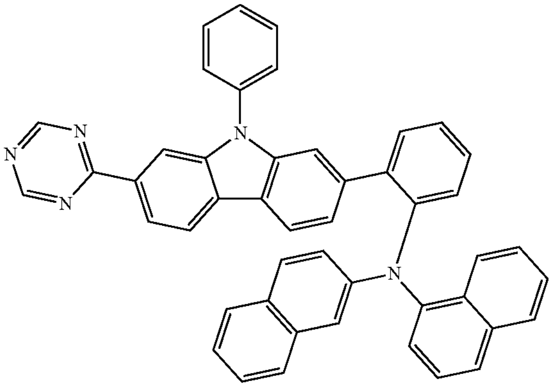

-continued
P1-25
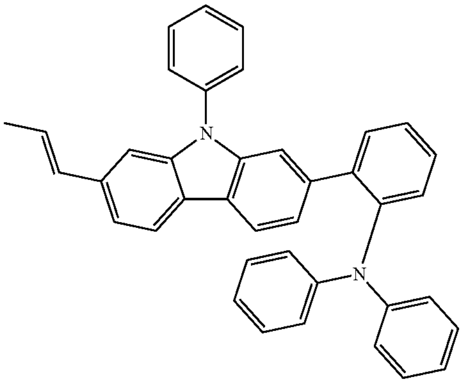
P1-26
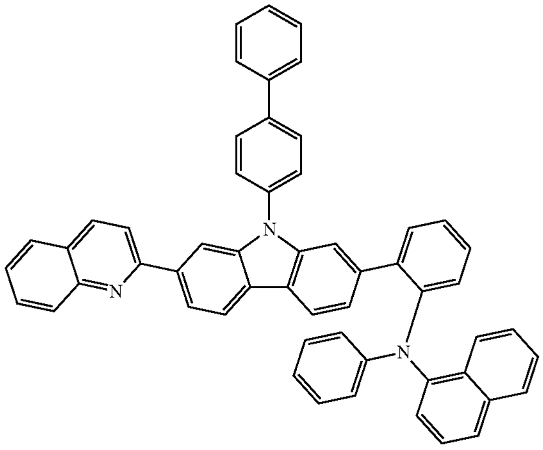
P1-27
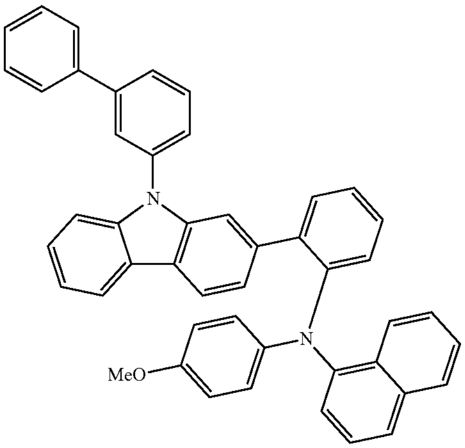
P1-28
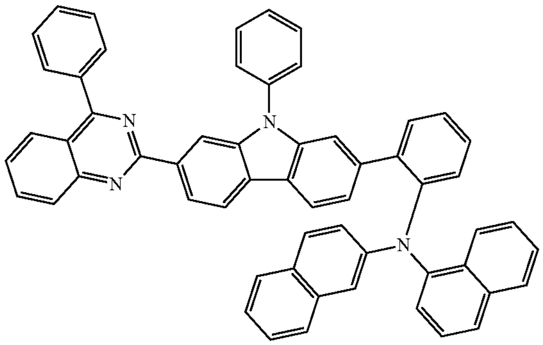
P1-29
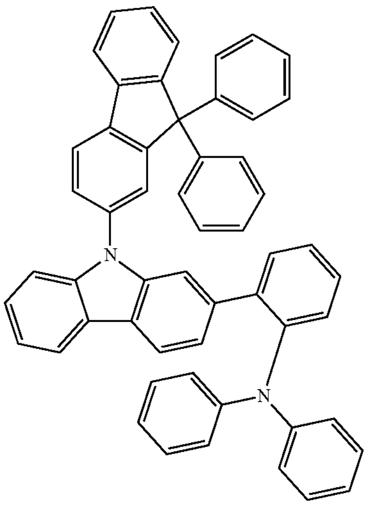
P1-30
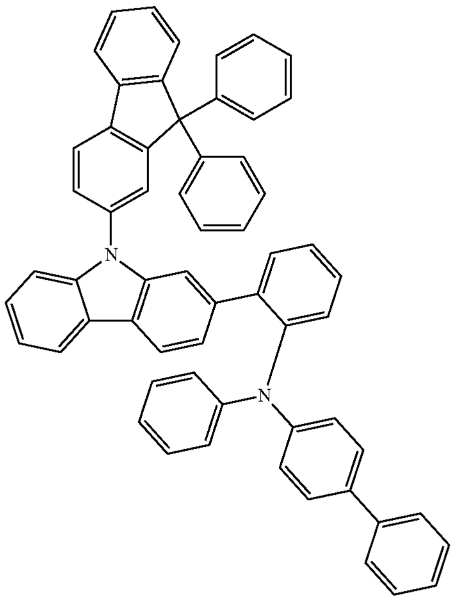

-continued
P1-31
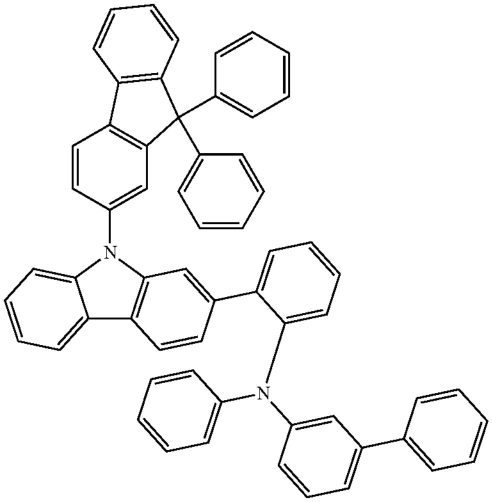
P1-32
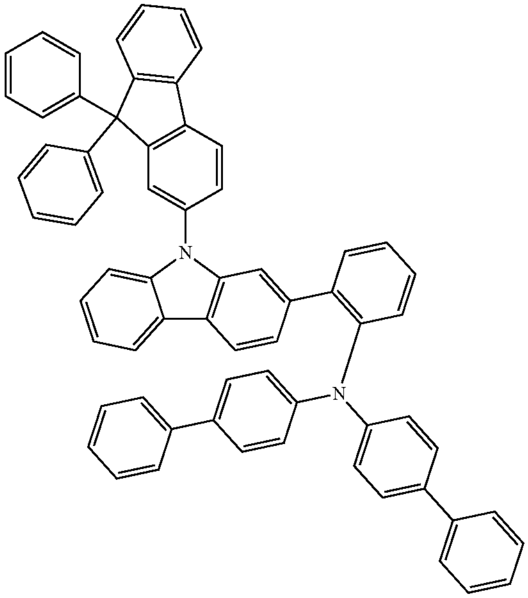
P1-33
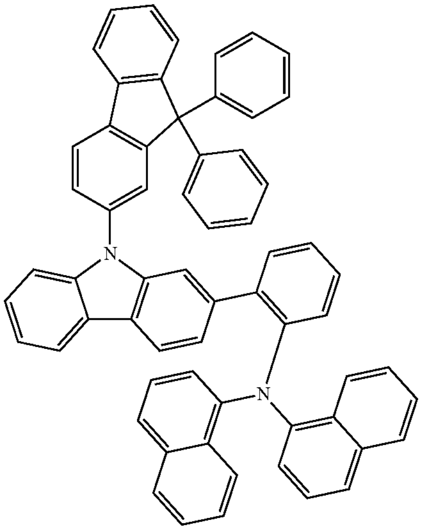
P1-34
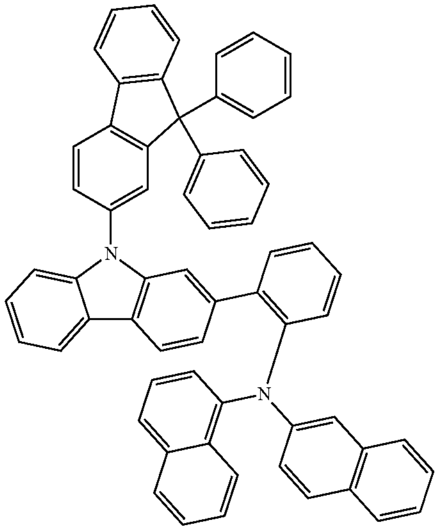

-continued
P1-35
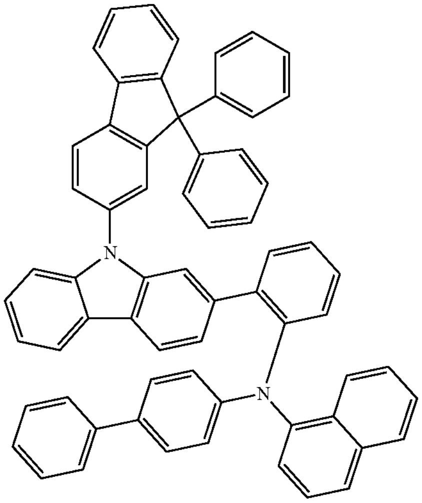
P1-36
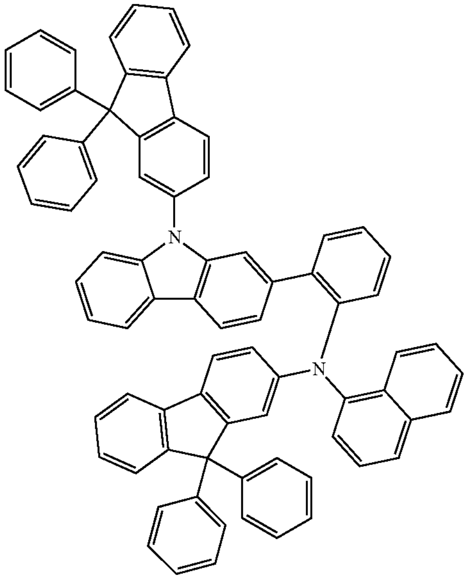
P1-37
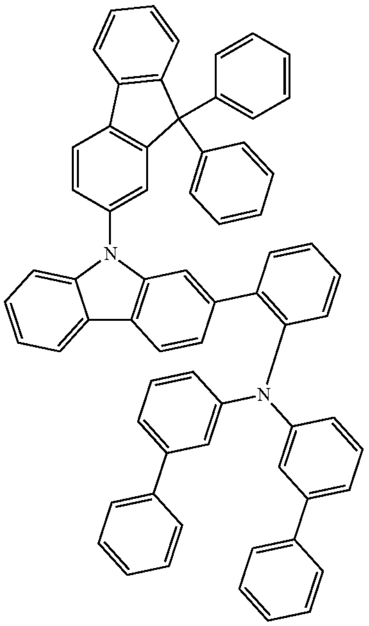
P1-38
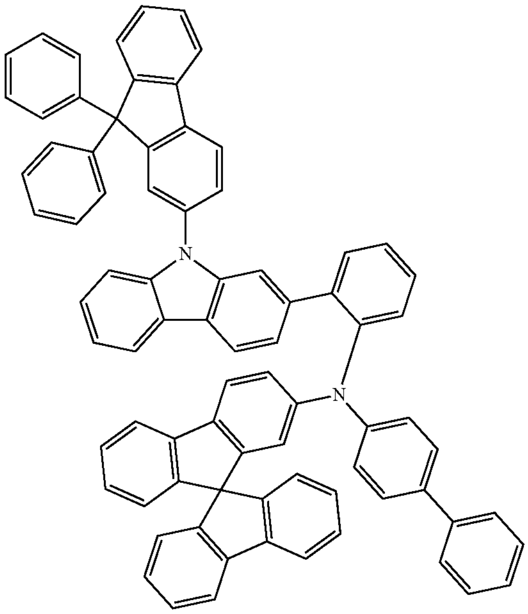

-continued
P1-39
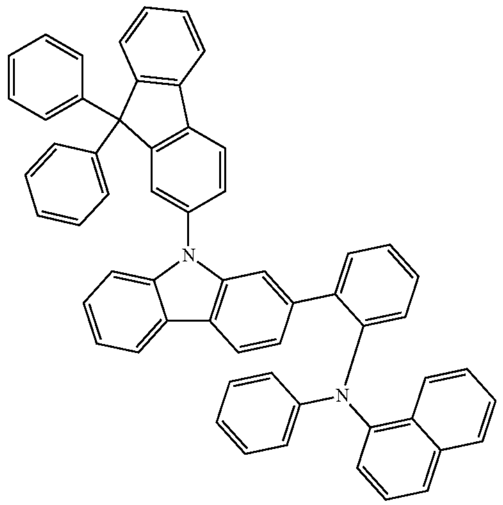
P1-40
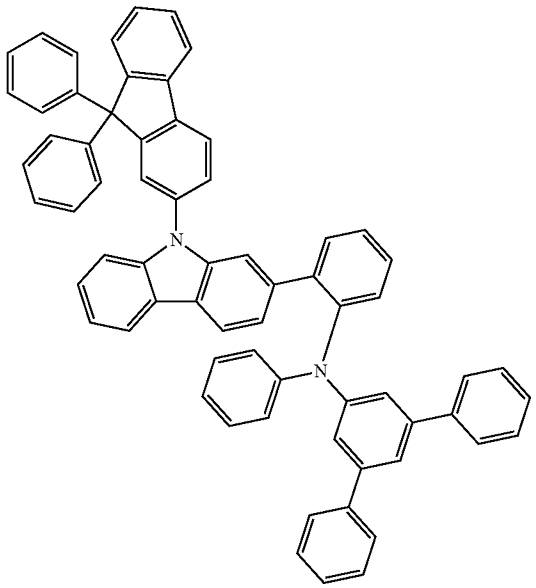
P1-41
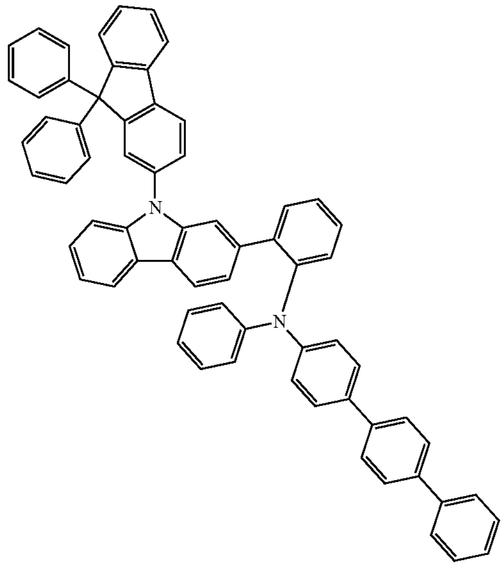
P1-42
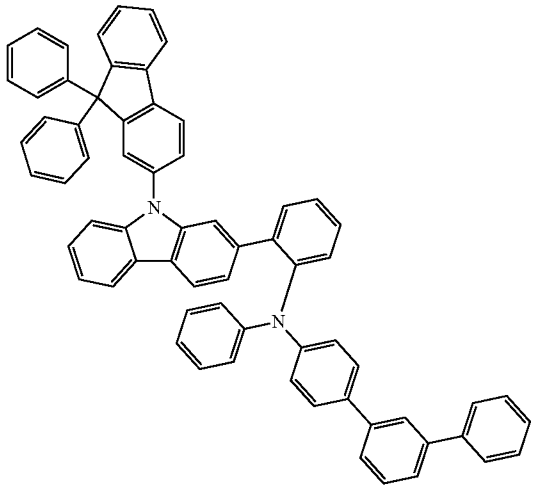

-continued
P1-43
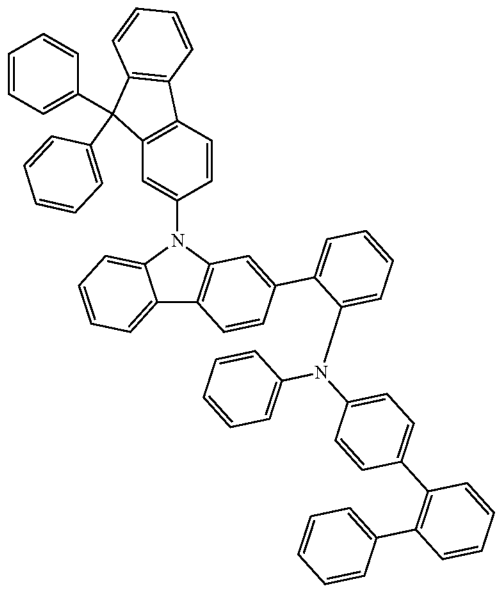
P1-44
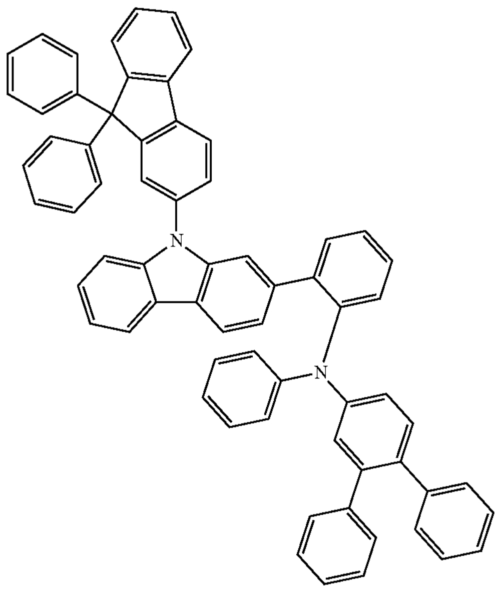
P1-45
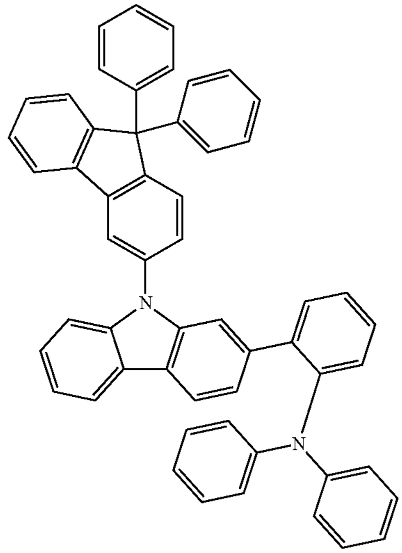
P1-46
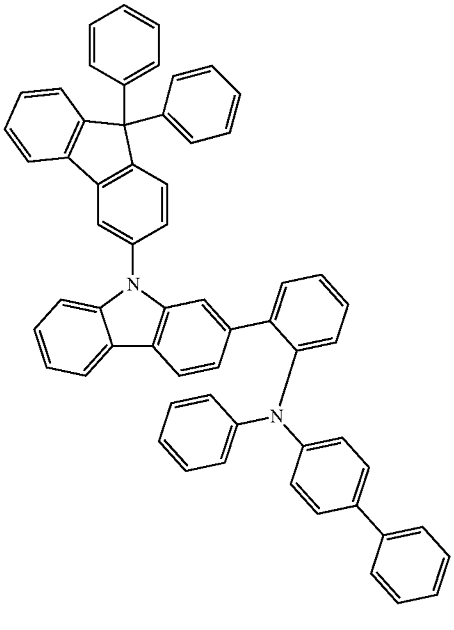

-continued
P1-47
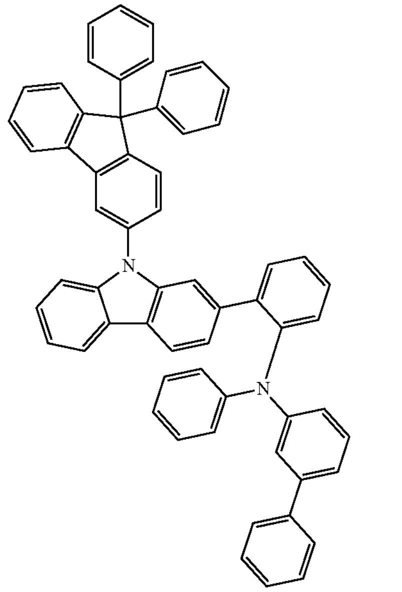
P1-48
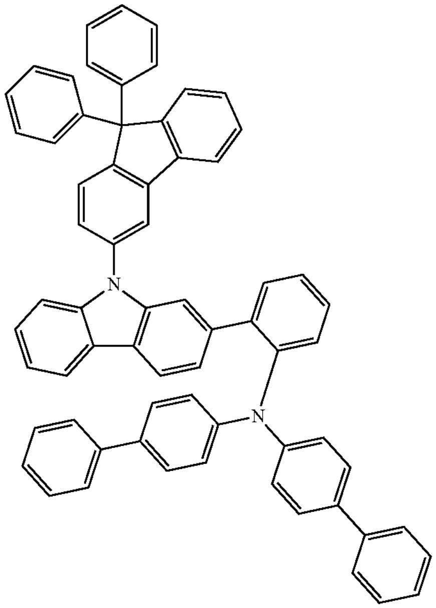
P1-49
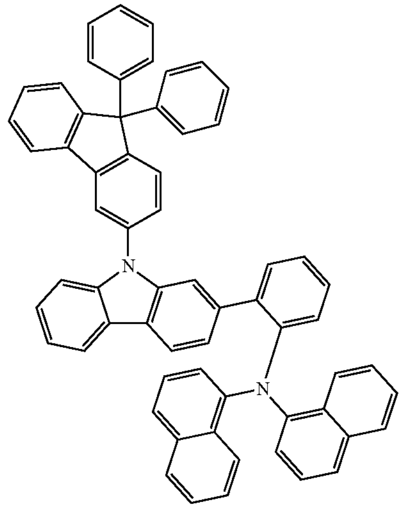
P1-50
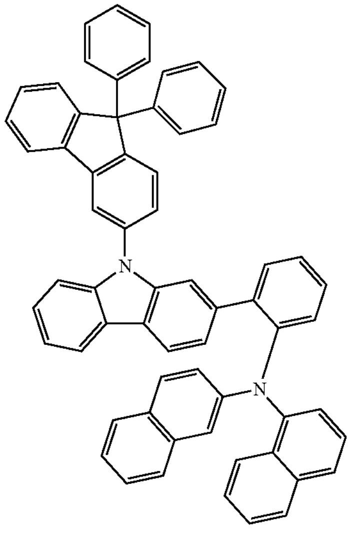

-continued
P1-51
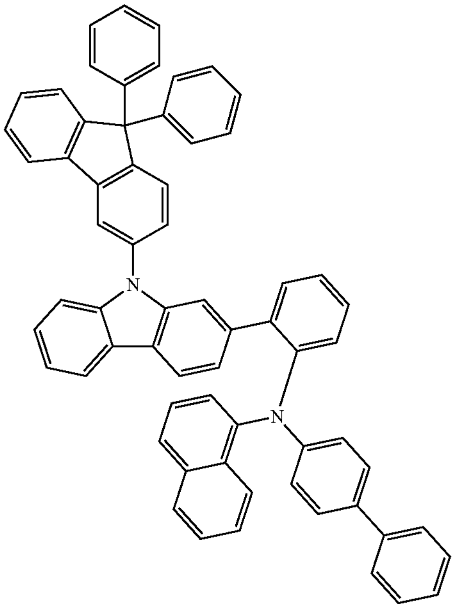
P1-52
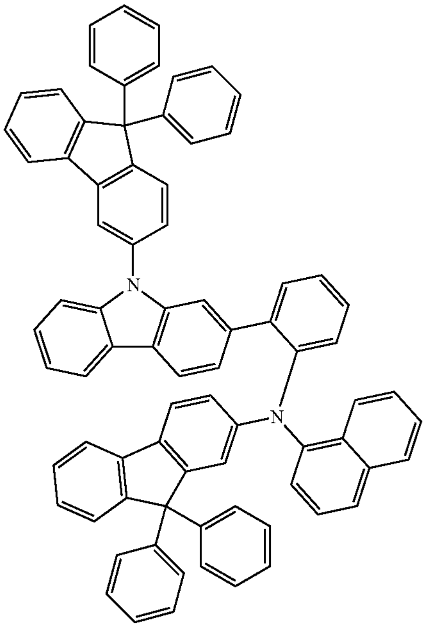
P1-53
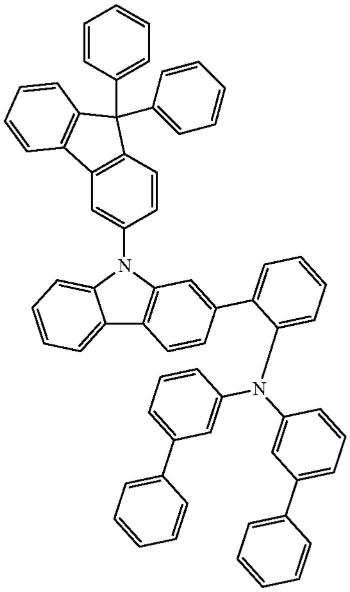
P1-54
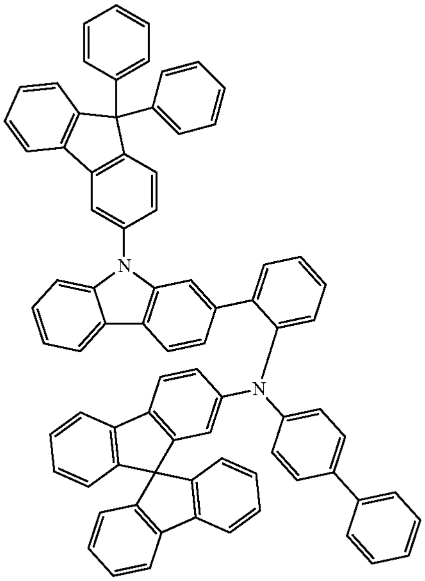

-continued
P1-55
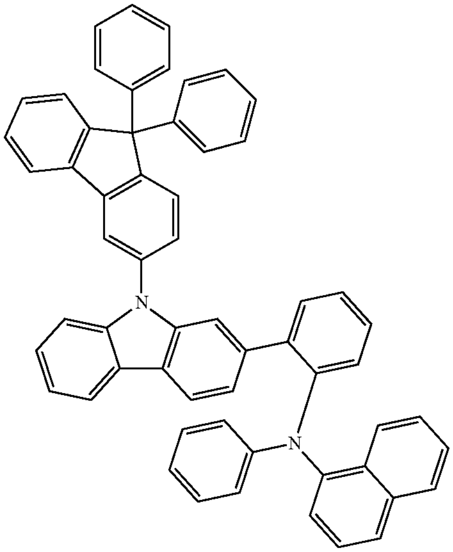
P1-56
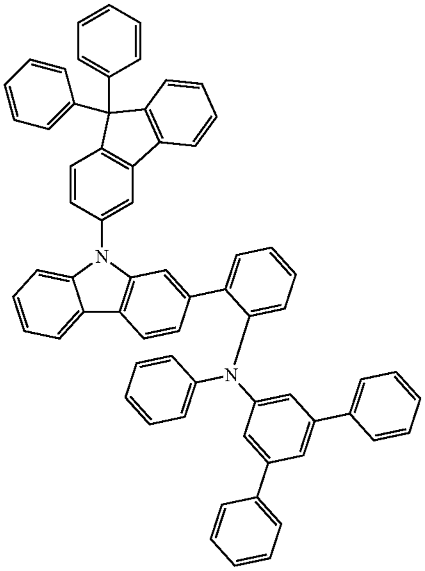
P1-57
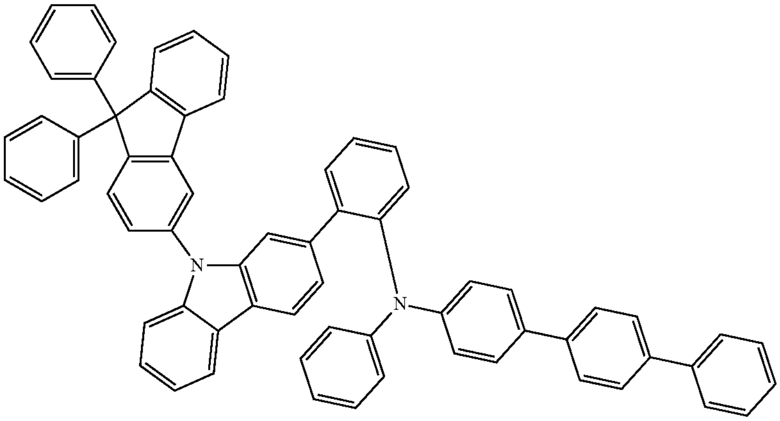
P1-58
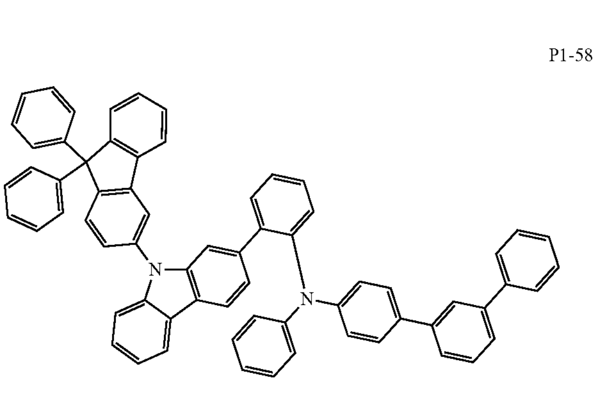
P1-59
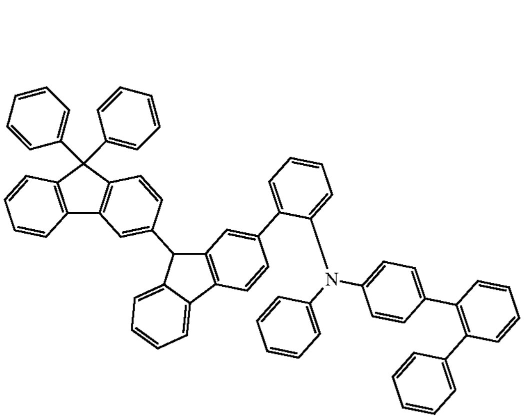

-continued
P1-60
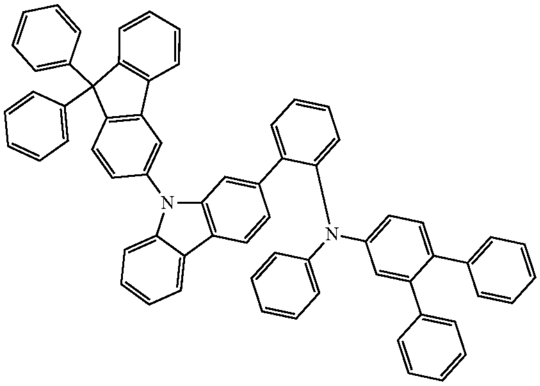
P1-61
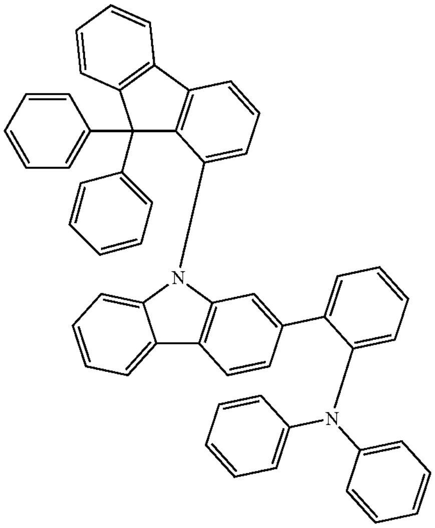
P1-62
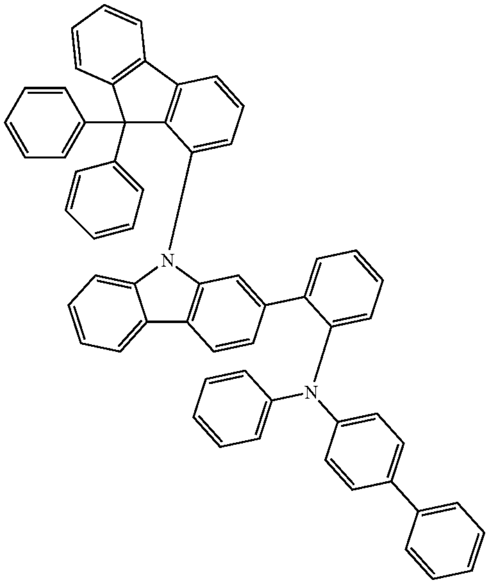
P1-63
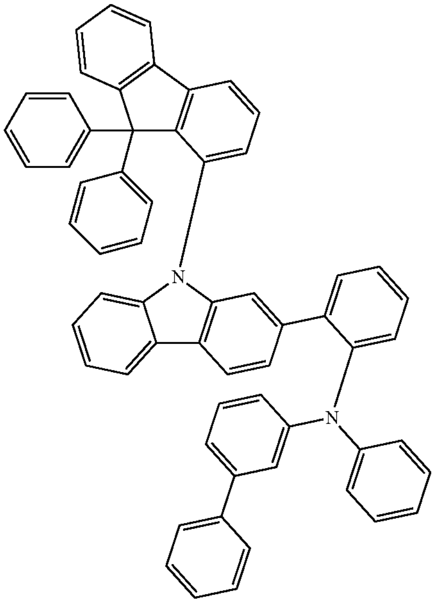

-continued
P1-64
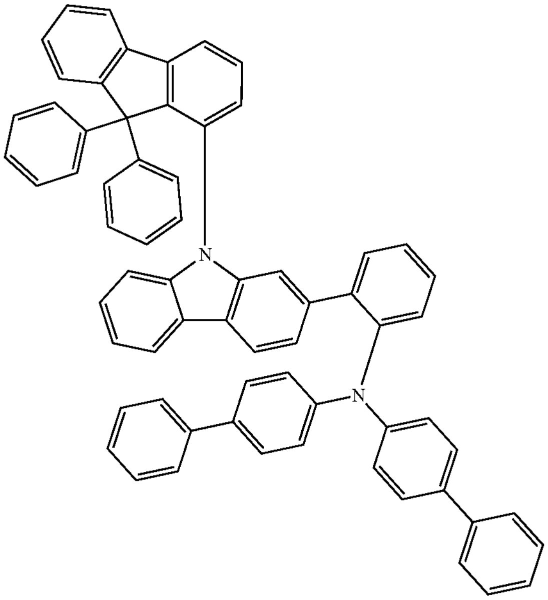
P1-65
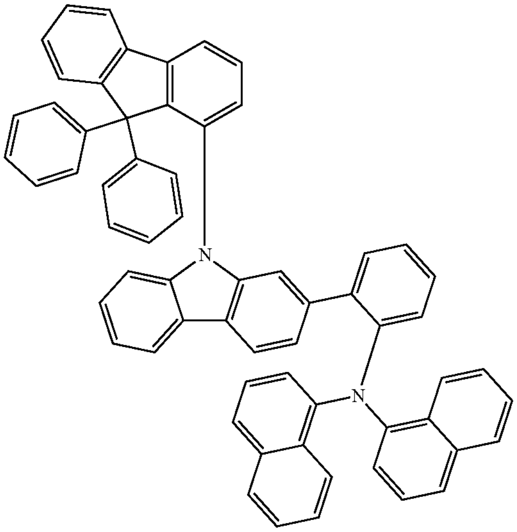
P1-66
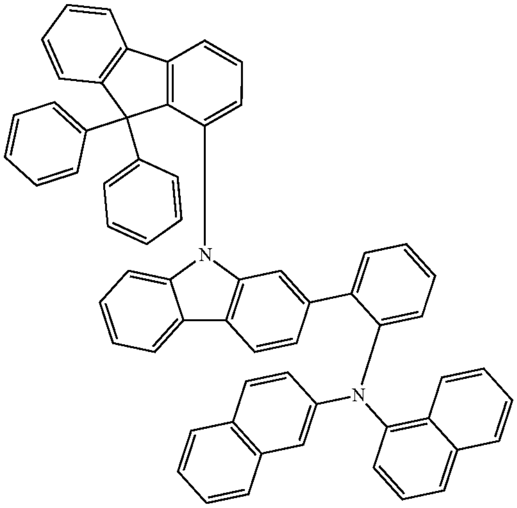
P1-67
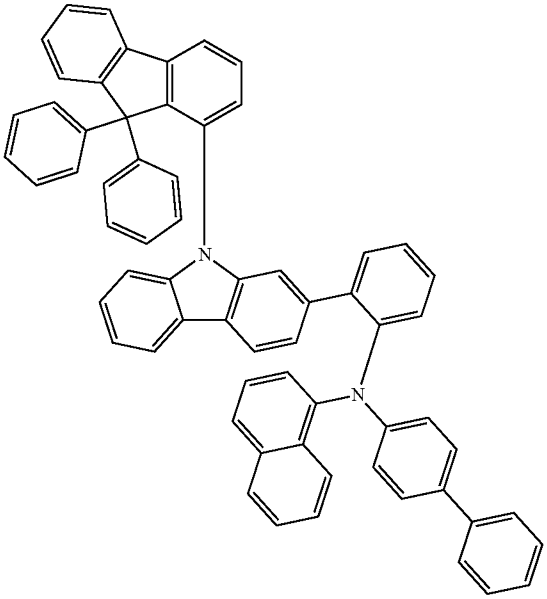

-continued
P1-68
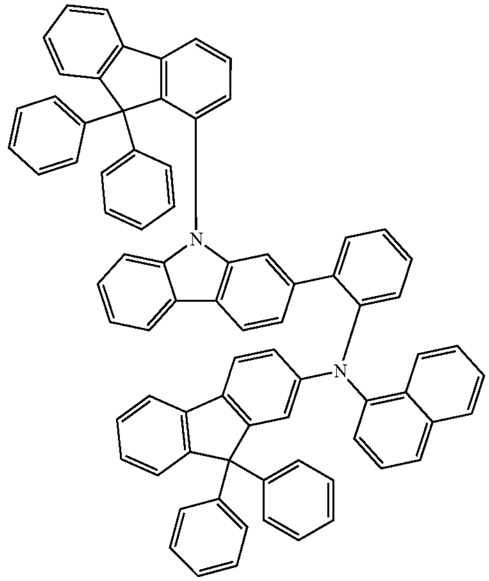
P1-69
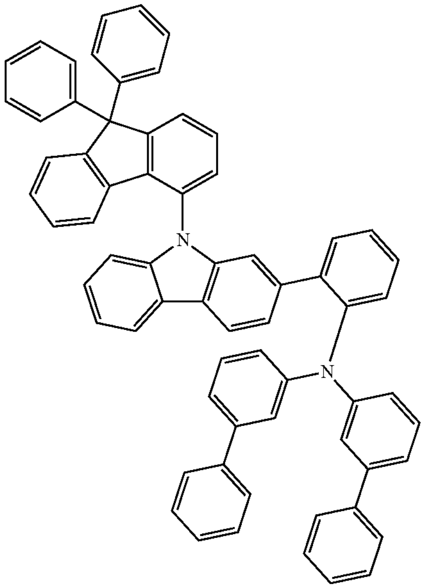
P1-70
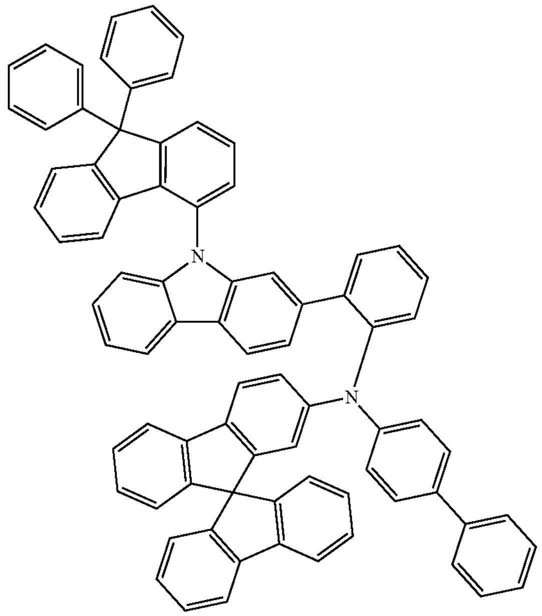
P1-71
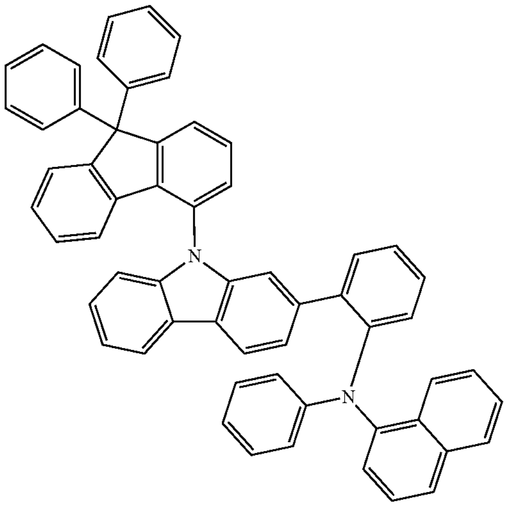

-continued
P1-72
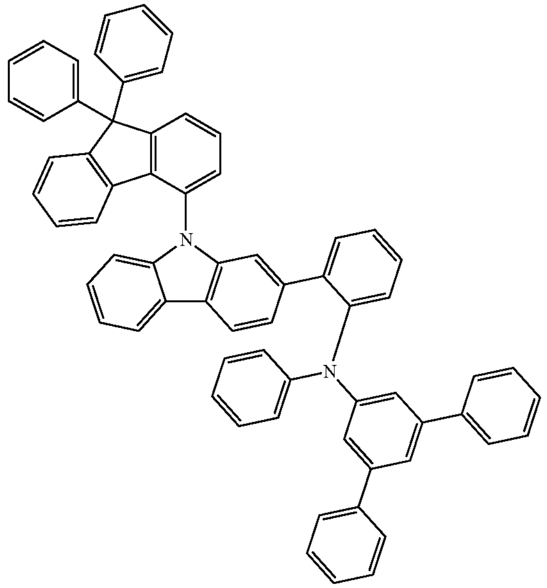
P1-73
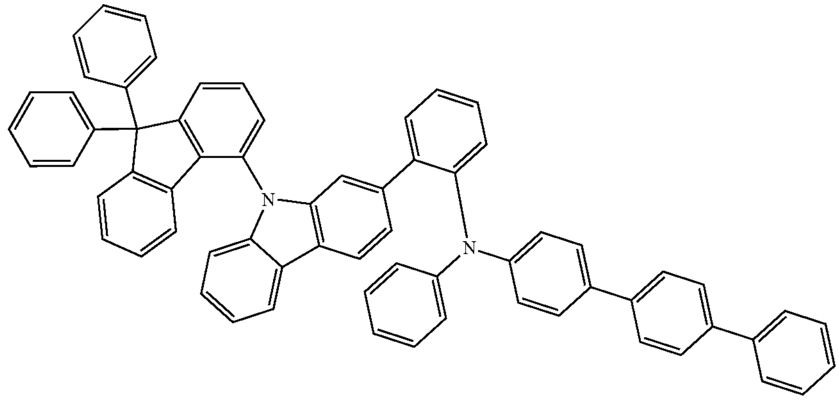
P1-74
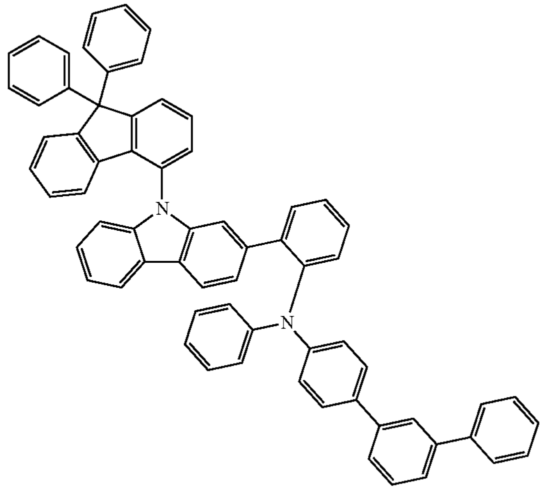
P1-75
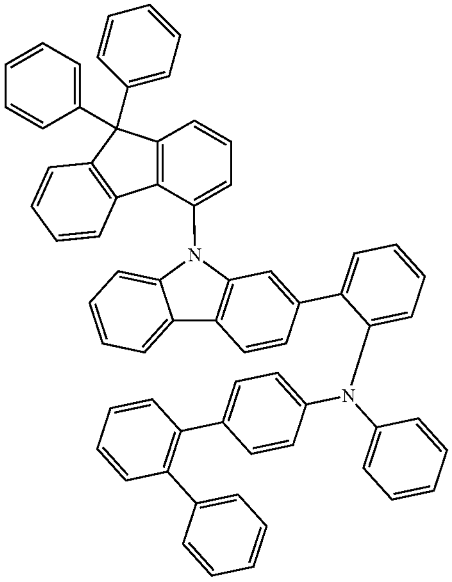

-continued
P1-76
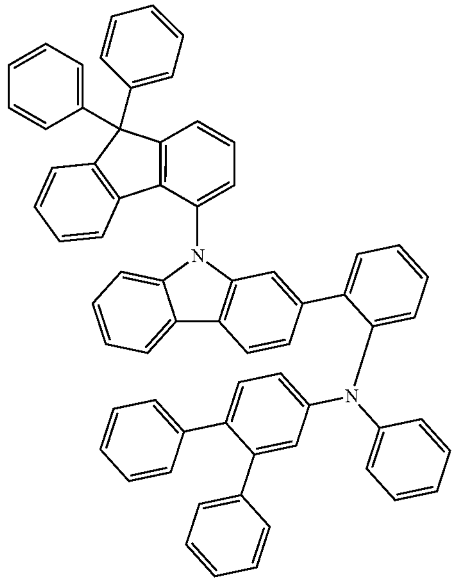
P1-77
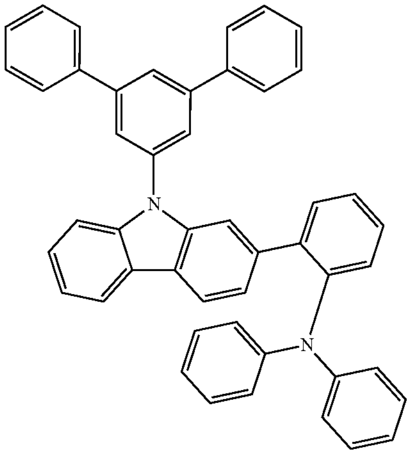
P1-78
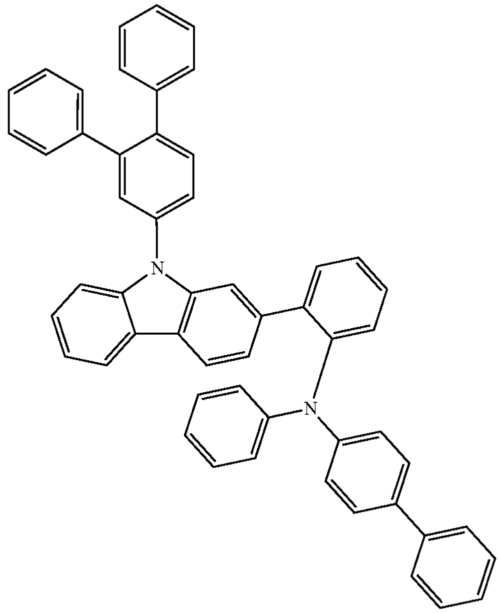
P1-79
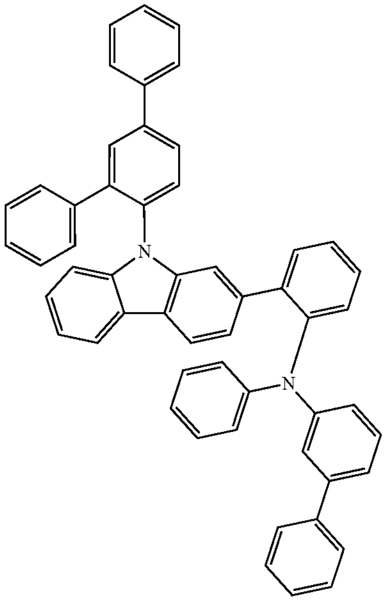

-continued
P1-80
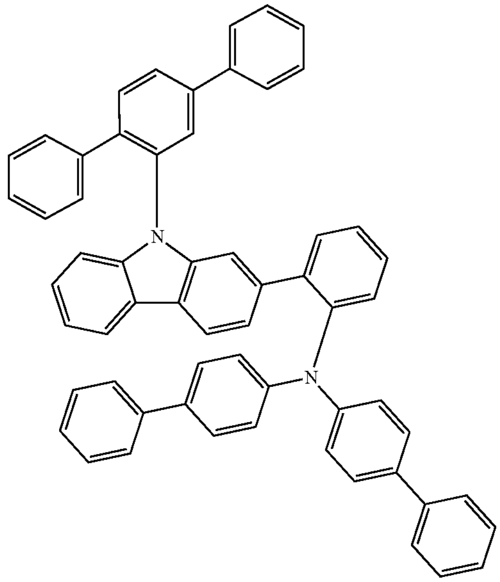
P1-81
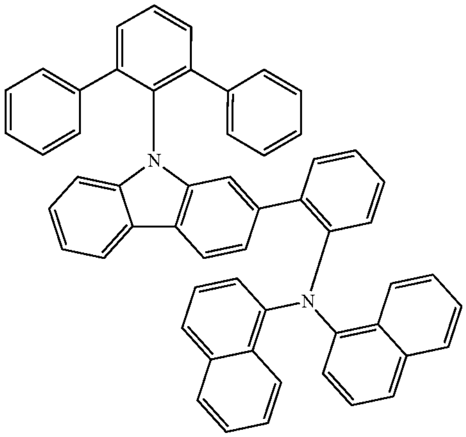
P1-82
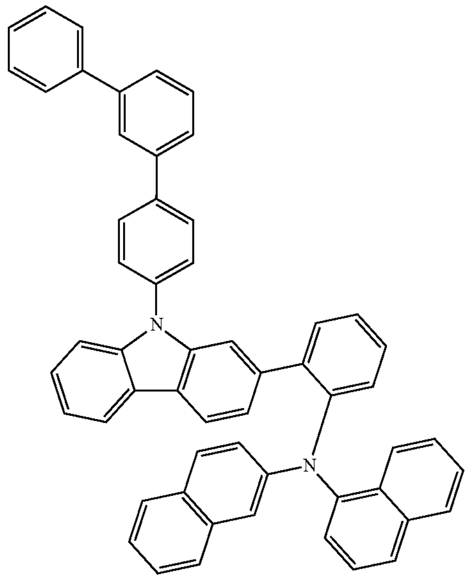
P1-83
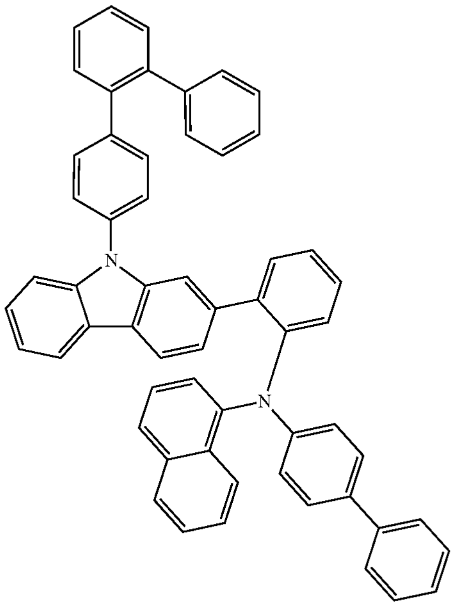

-continued
P1-84
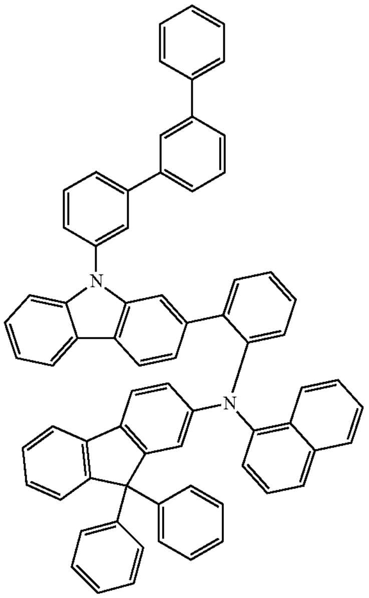
P1-85
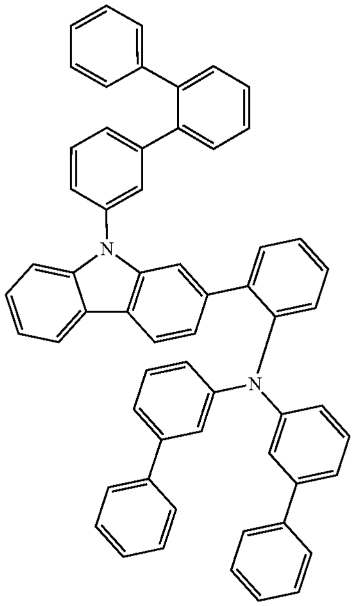
P1-86
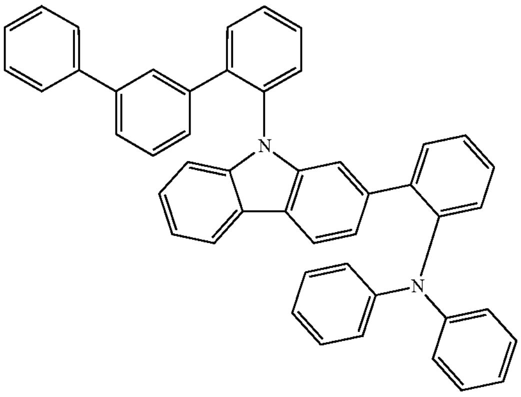
P1-87
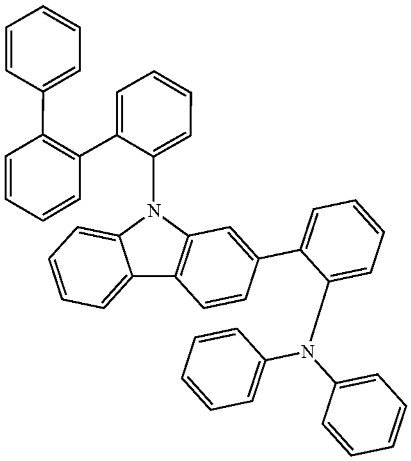
P1-88
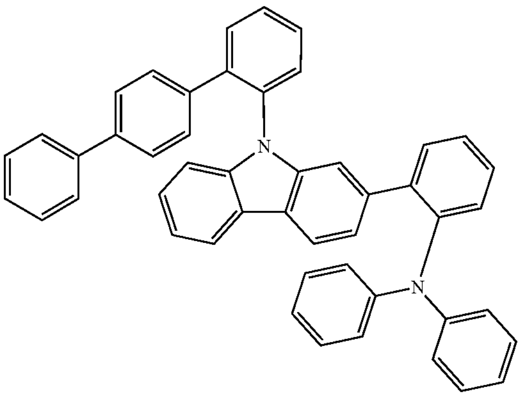
P1-89
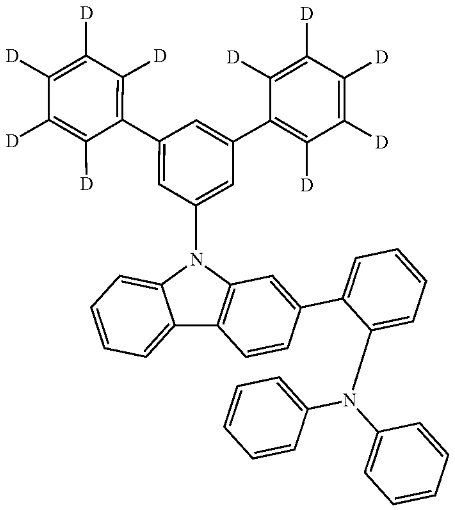

-continued
P1-90
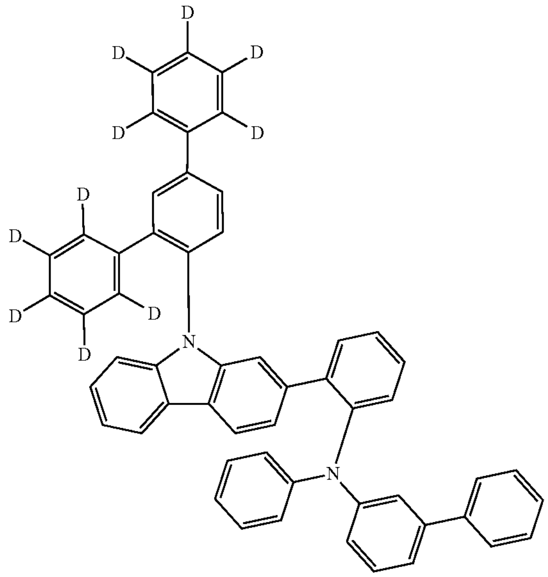
P1-91
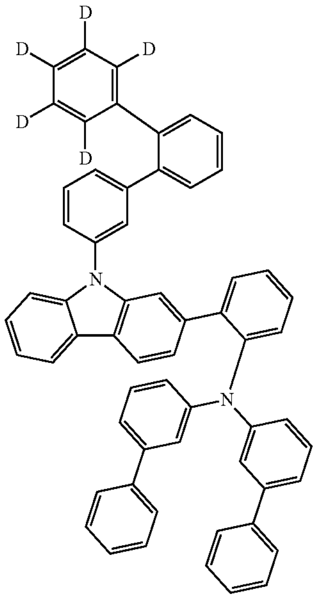
P1-92
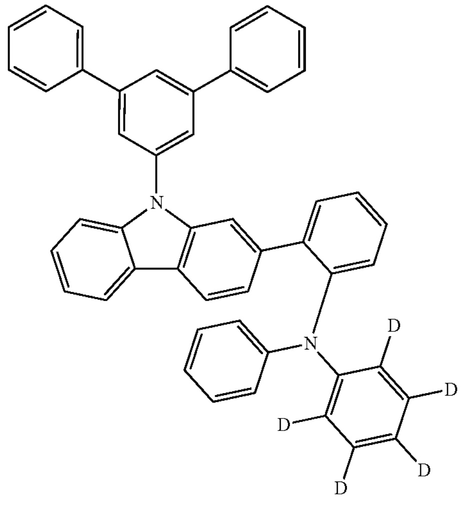
P1-93
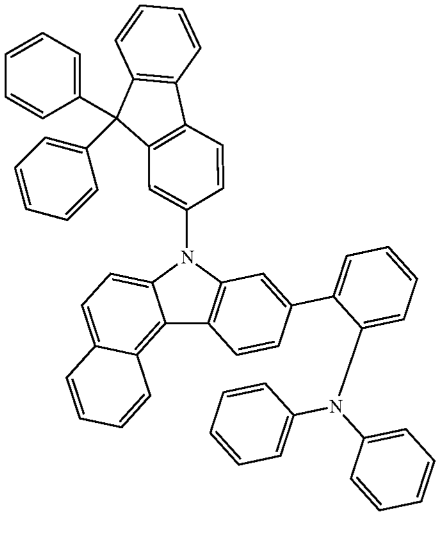

-continued
P1-94
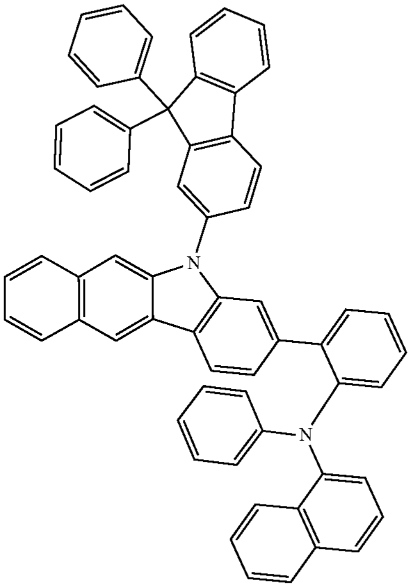
P1-95
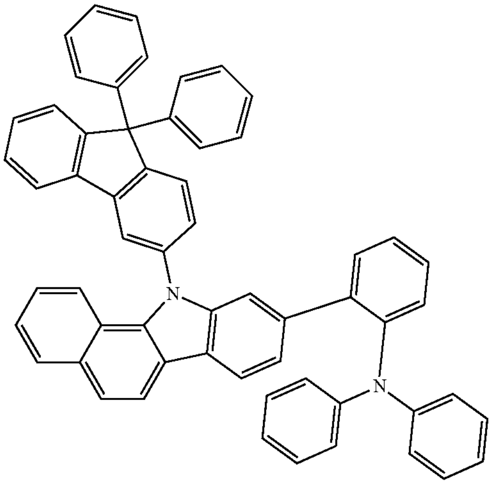
P1-96
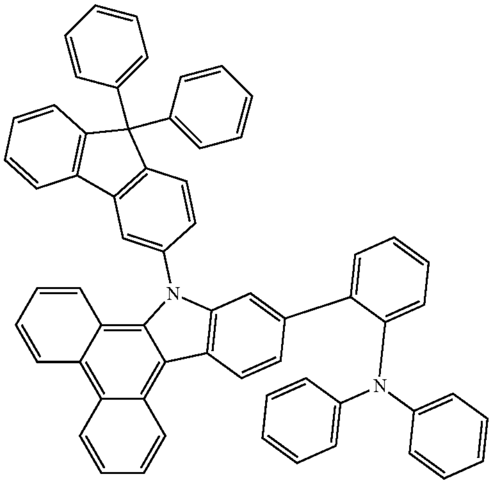
P1-97
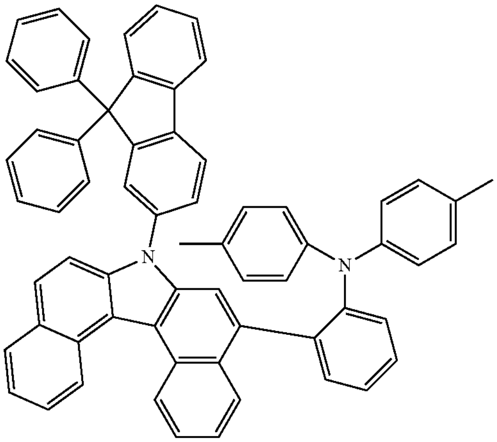
P1-98
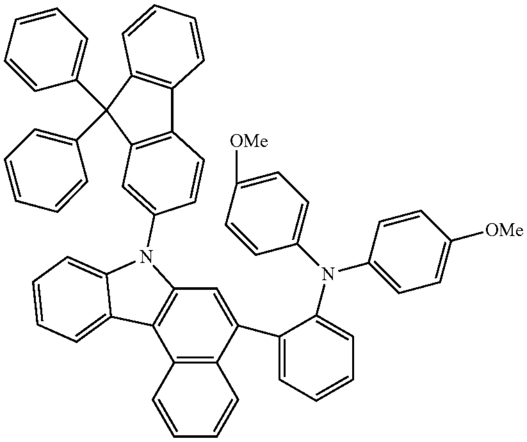
P1-99
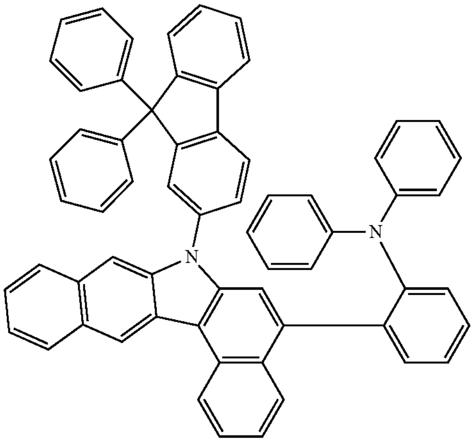

-continued
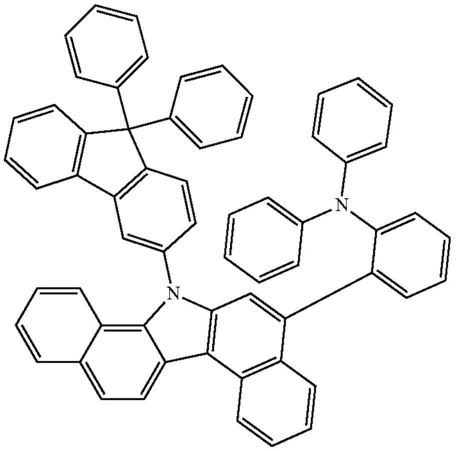
P1-100
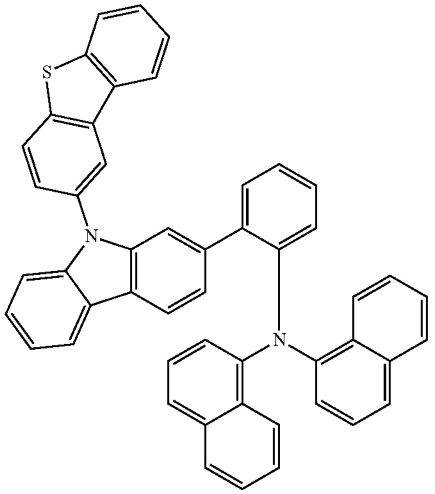
P1-101
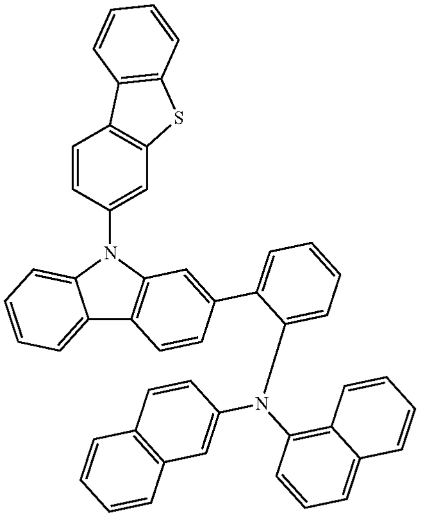
P1-102
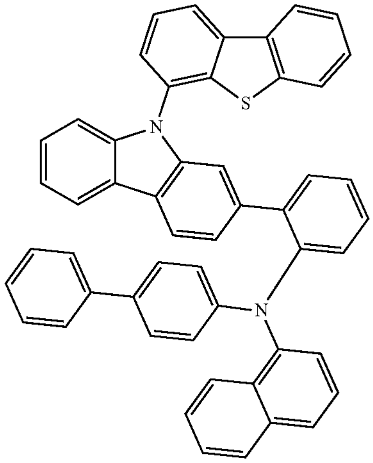
P1-103
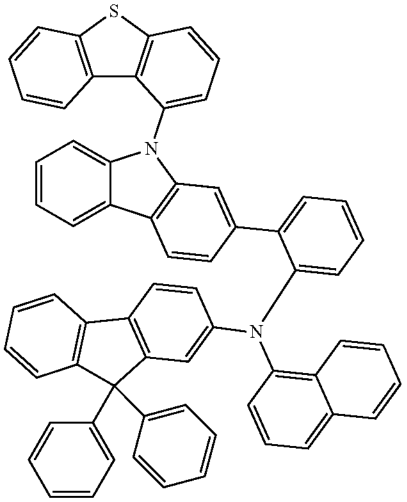
P1-104
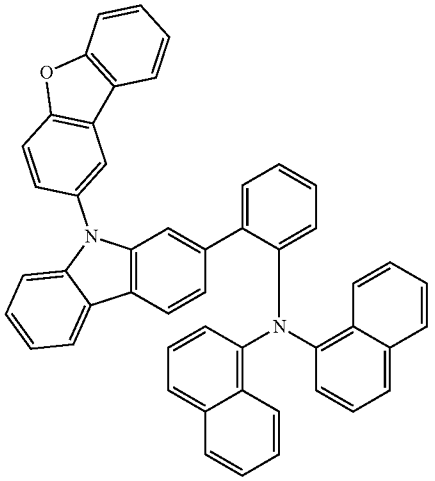
P1-105

-continued
P1-106
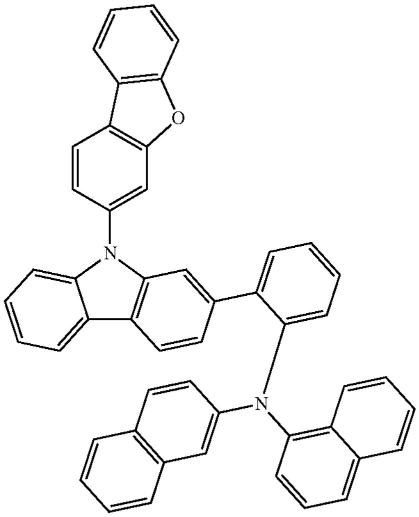
P1-107
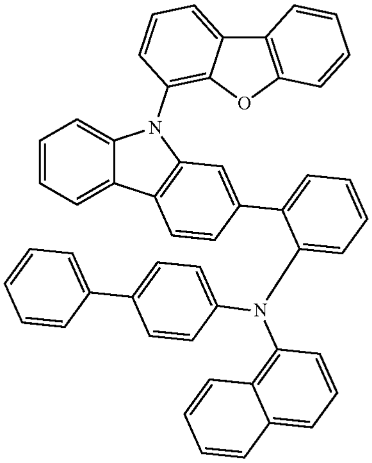
P1-108
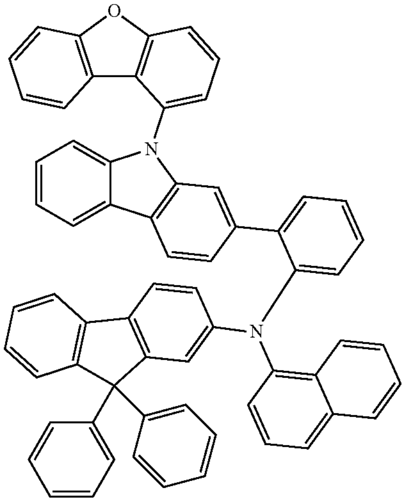
P1-109
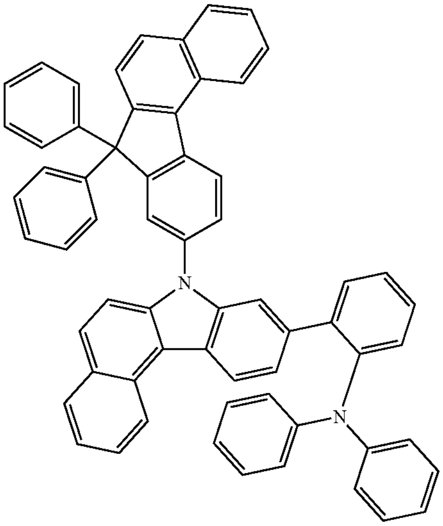
P1-110
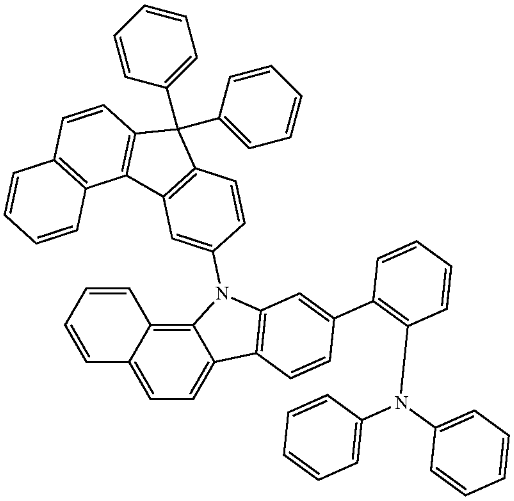
P1-111
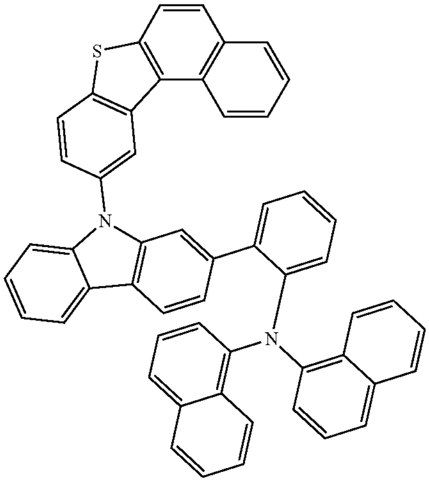

-continued
P1-112
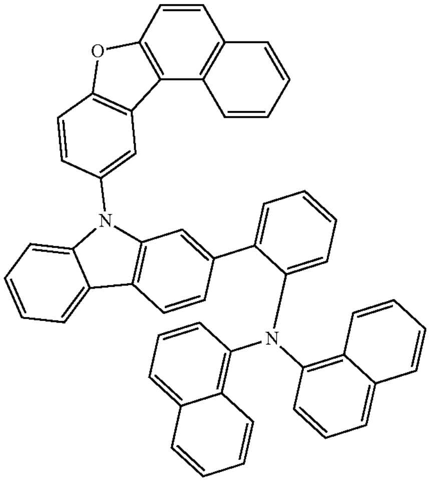
P2-1
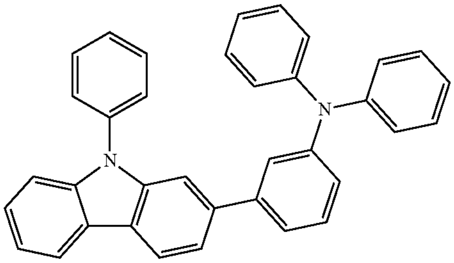
P2-2
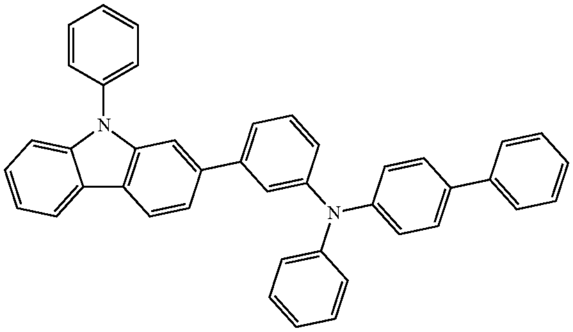
P2-3
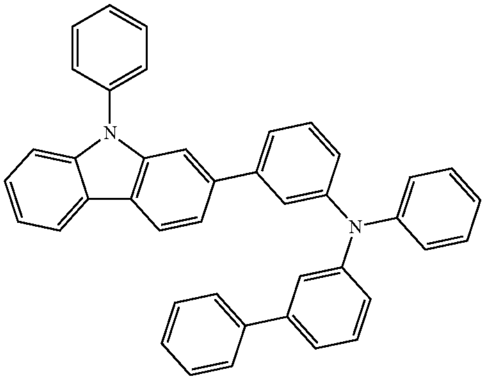
P2-4
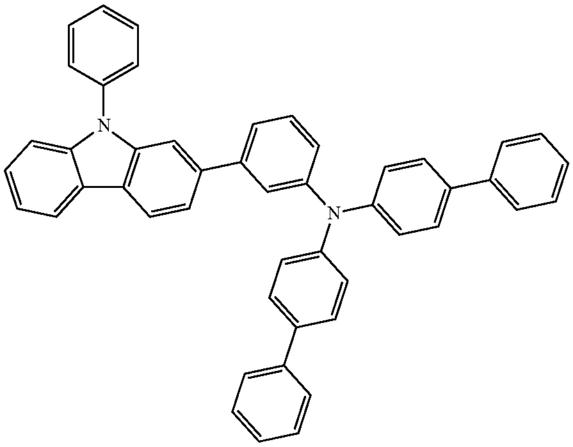
P2-5
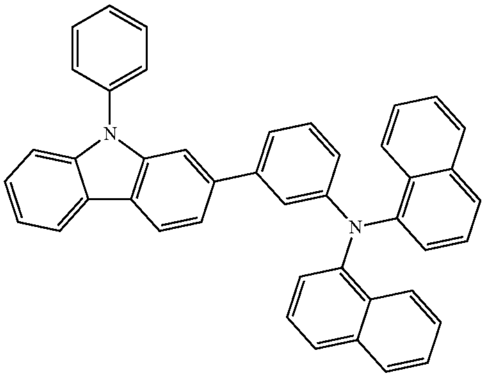

-continued
P2-6
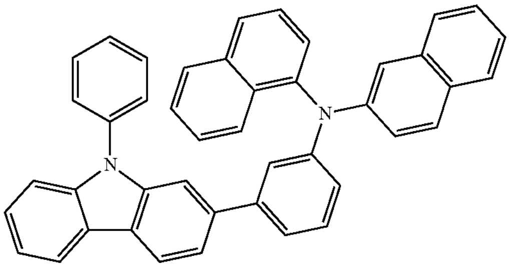
P2-7
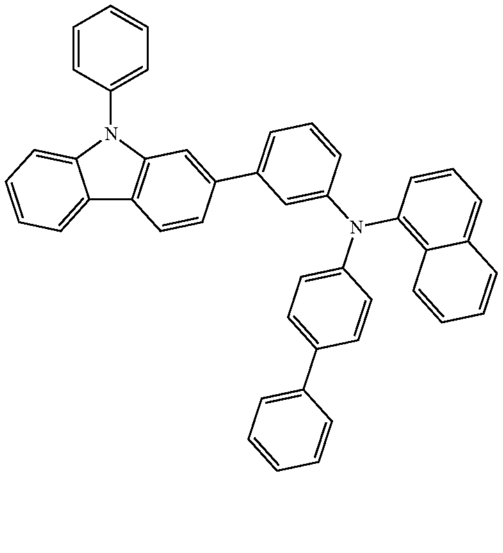
P2-8
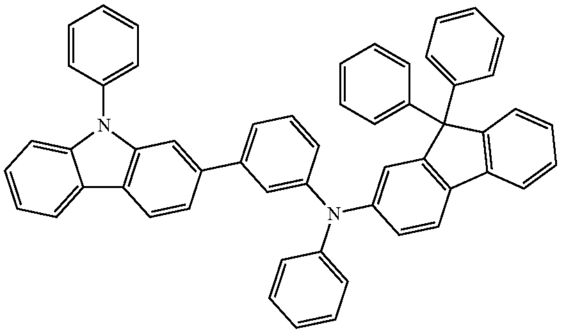
P2-9
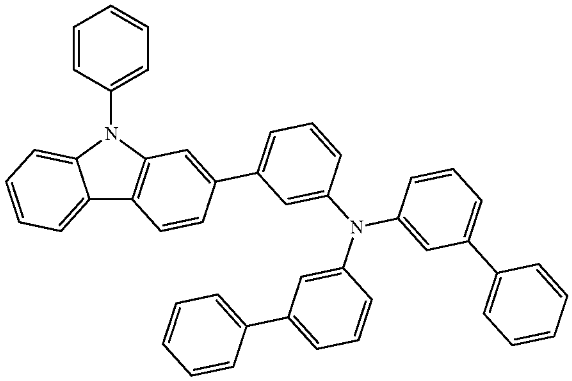
P2-10
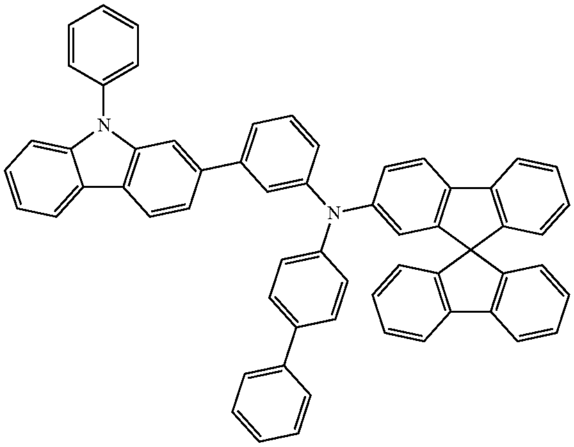
P2-11
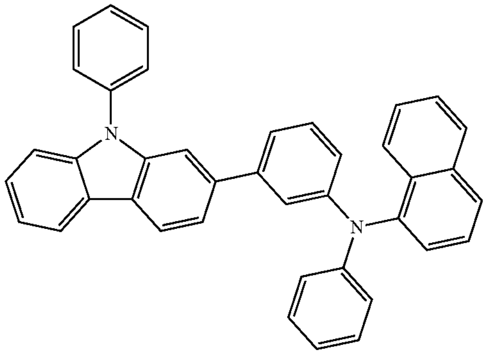

-continued
P2-12
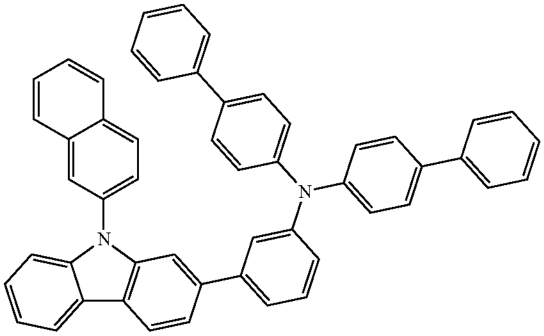
P2-13
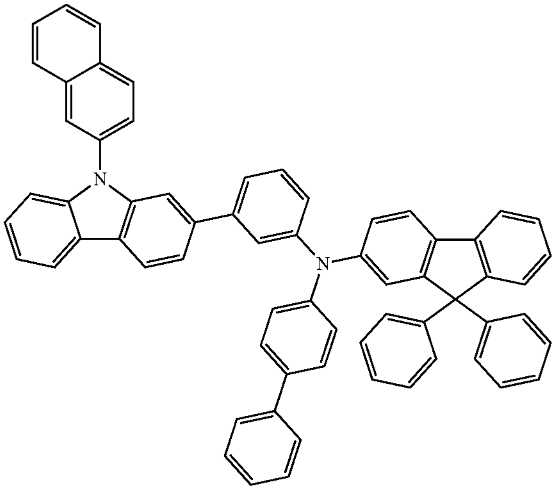
P2-14
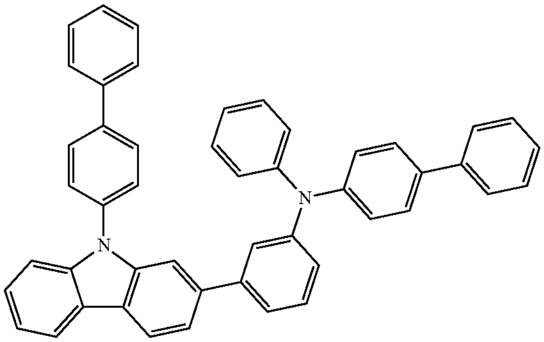
P2-15
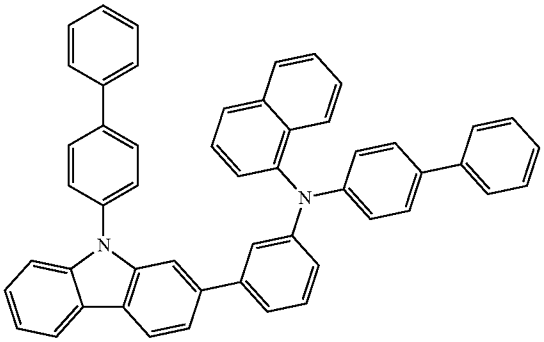
P2-16
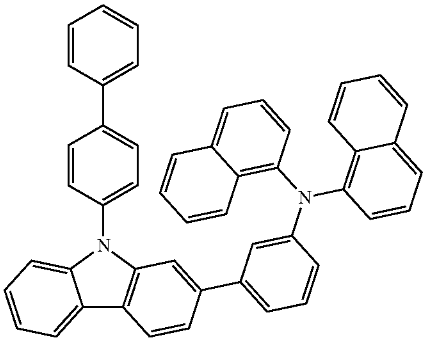
P2-17
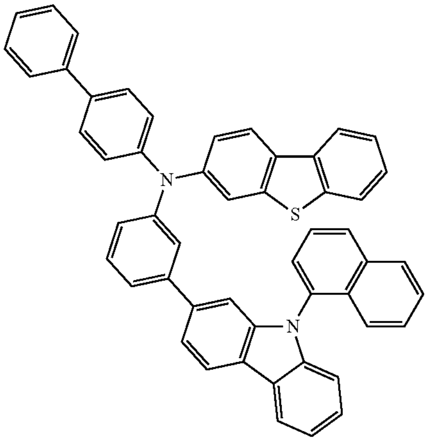

-continued
P2-18
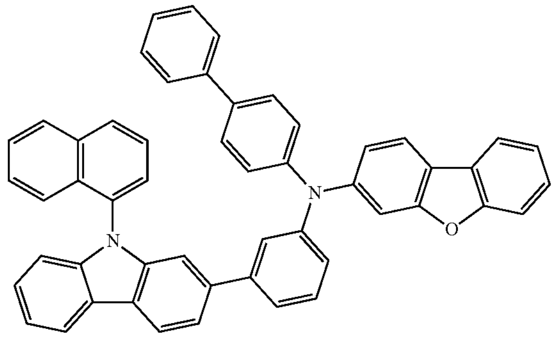
P2-19
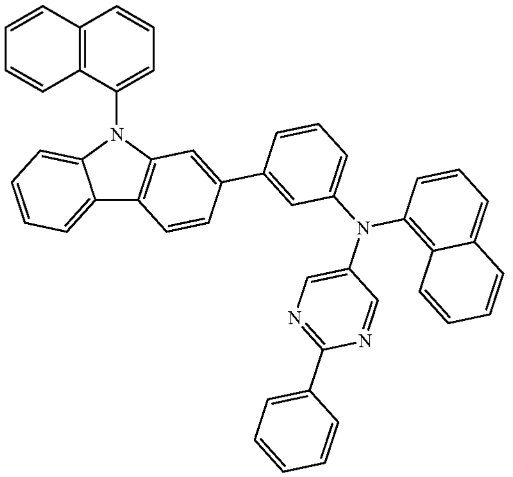
P2-20
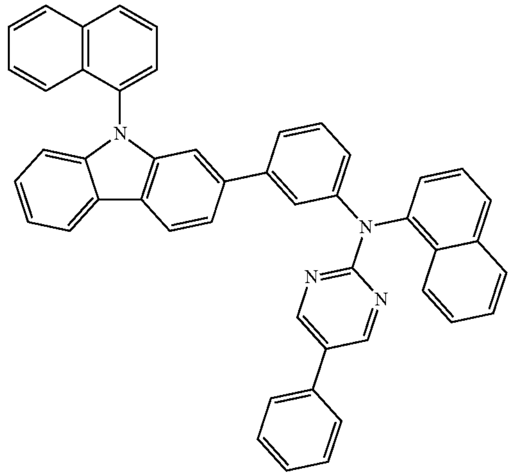
P2-21
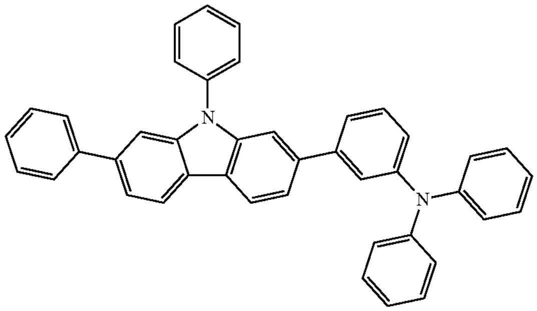
P2-22
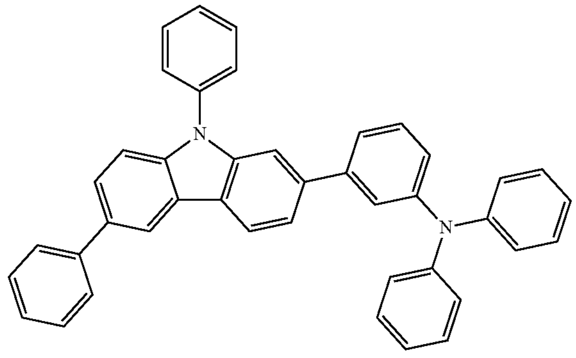
P2-23
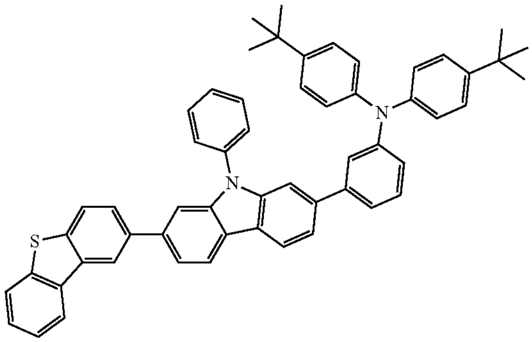
P2-24
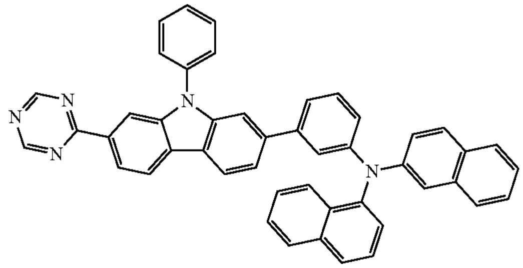
P2-25
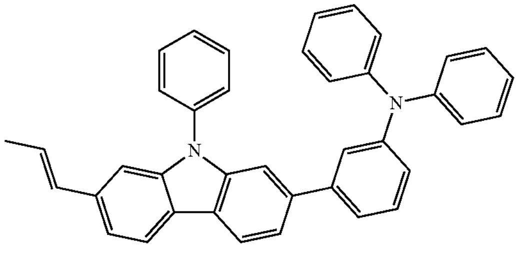

-continued
P2-26
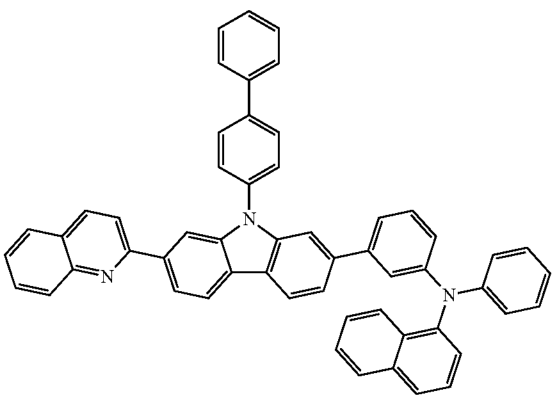
P2-27
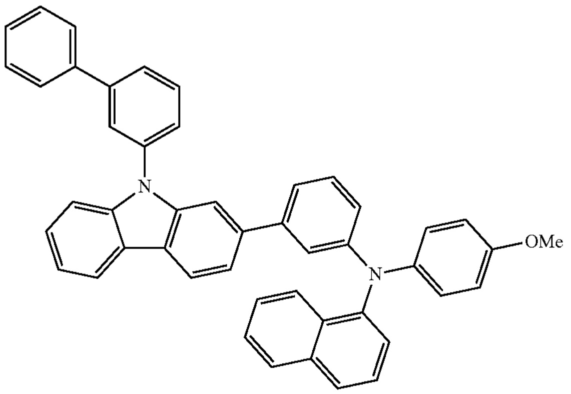
P2-28
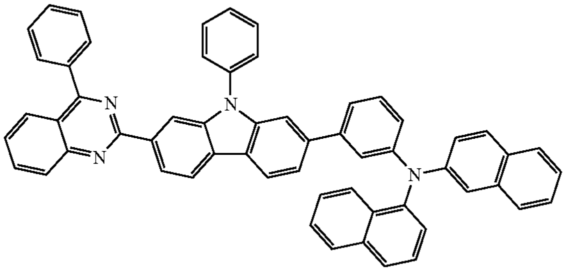
P2-29
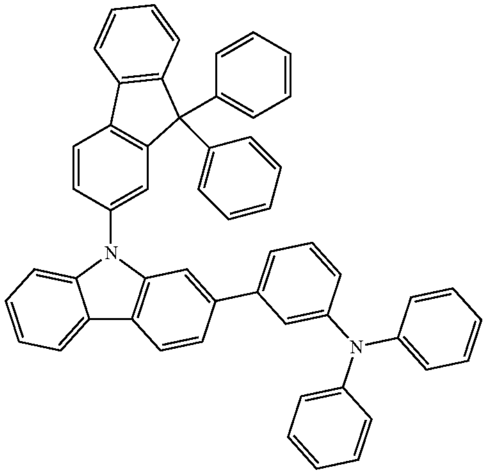
P2-30
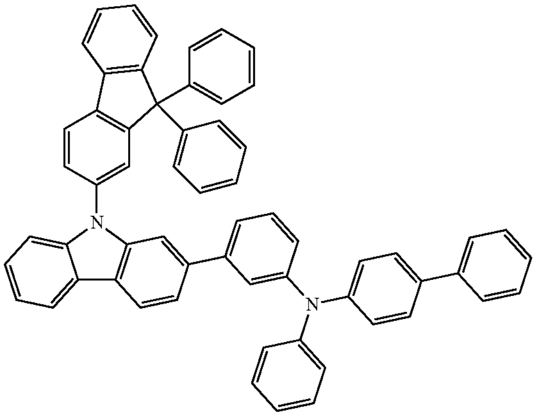
P2-31
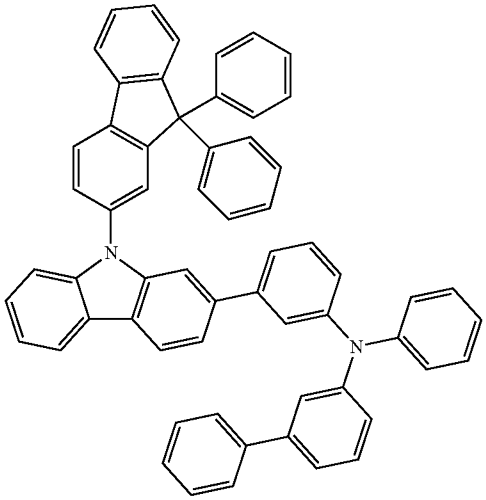

-continued
P2-32
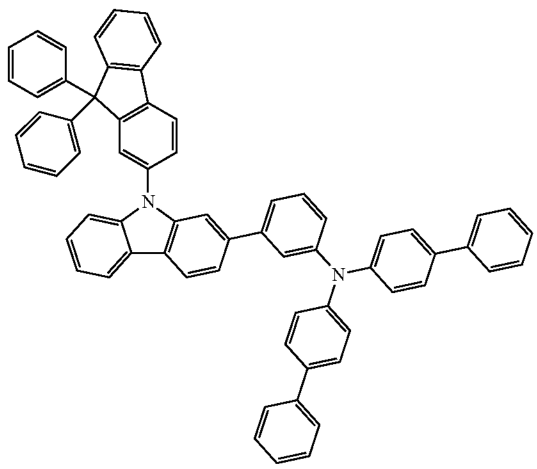
P2-33
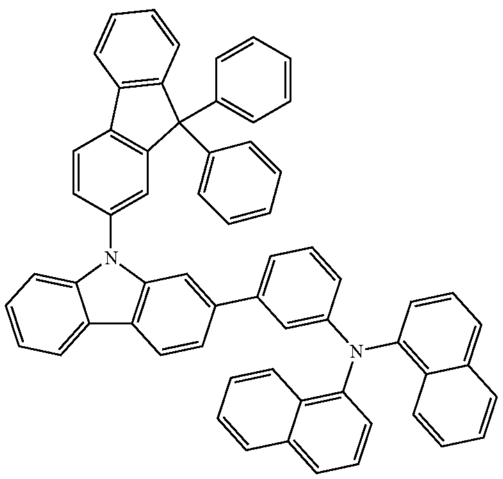
P2-34
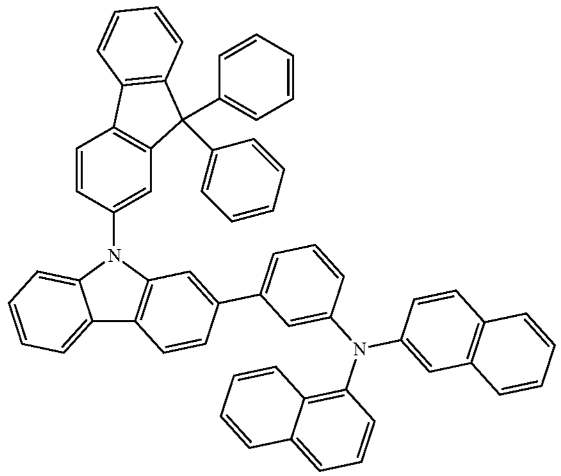
P2-35
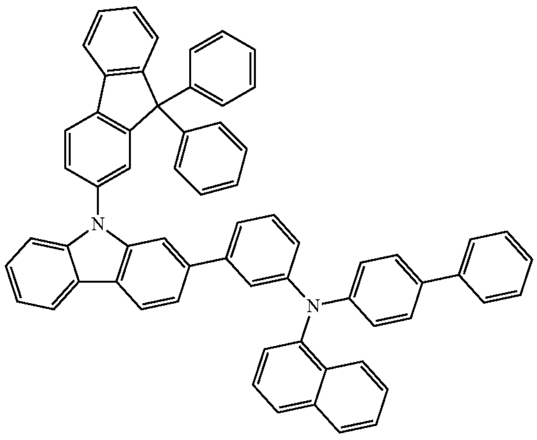
P2-36
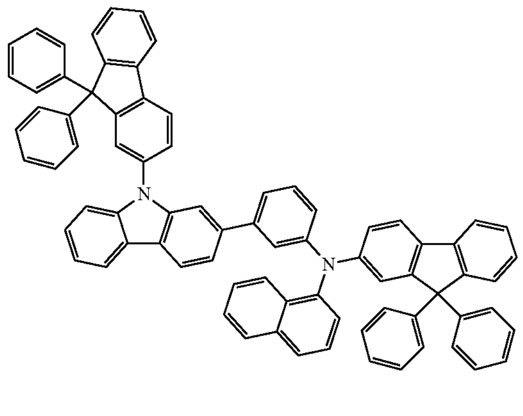
P2-37
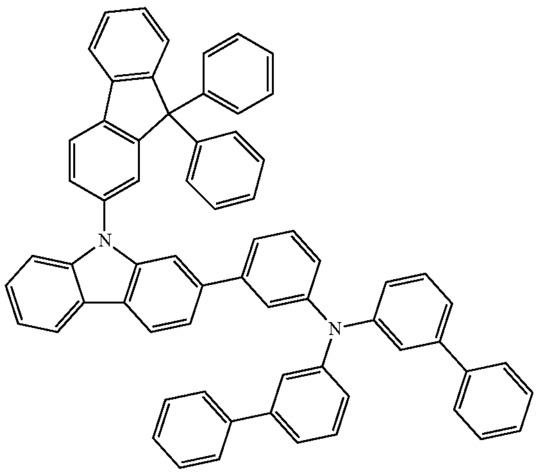

-continued
P2-38
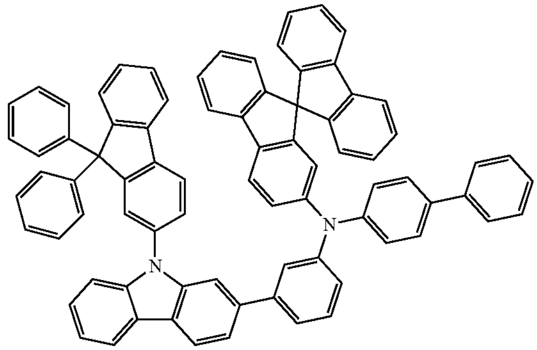
P2-39
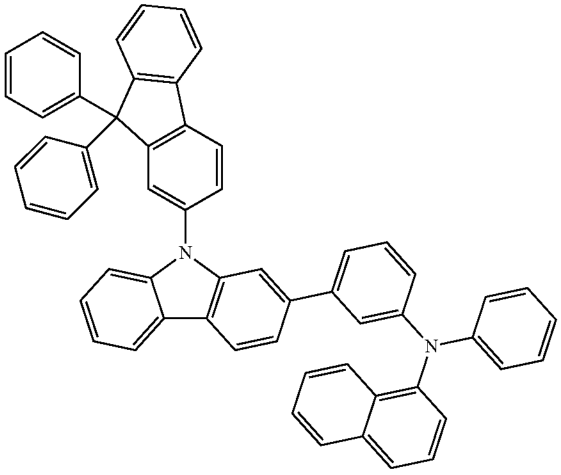
P2-40
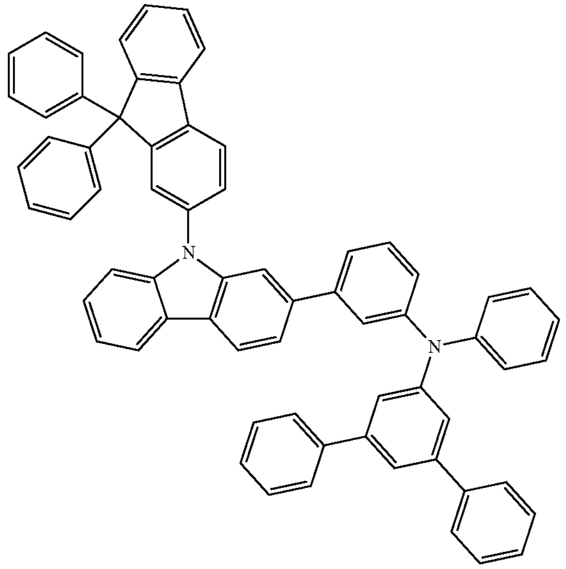
P2-41
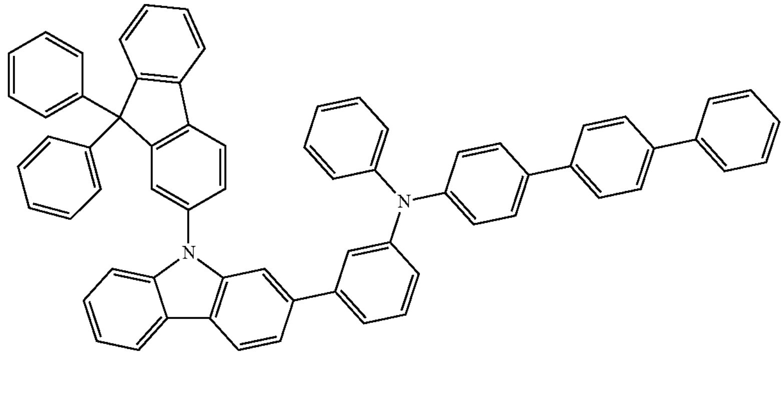

-continued
P2-42
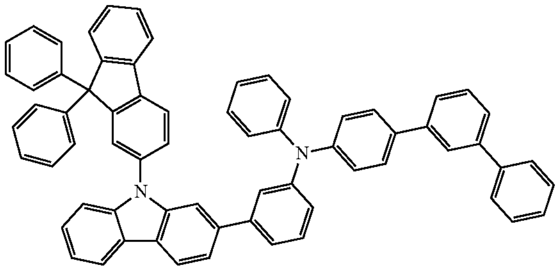
P2-43
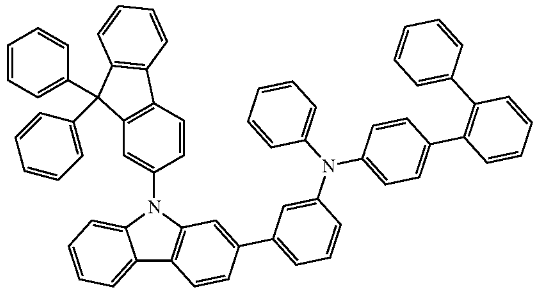
P2-44
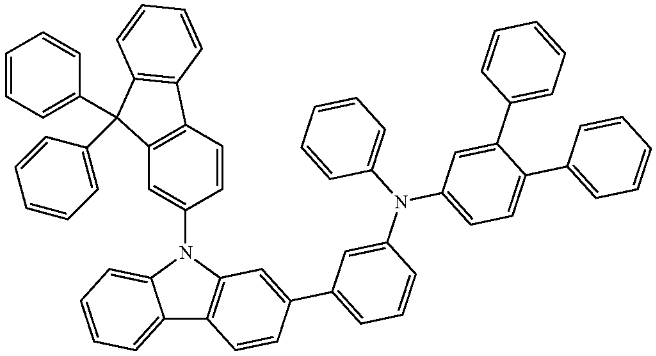
P2-45
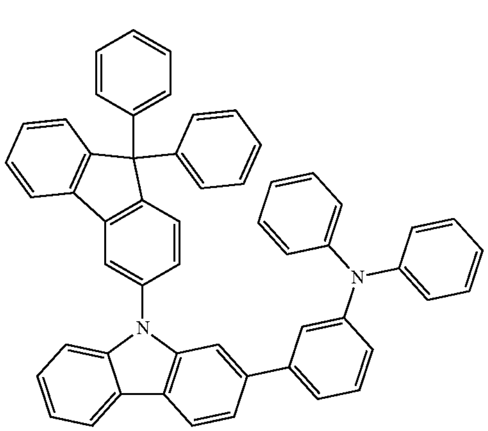
P2-46
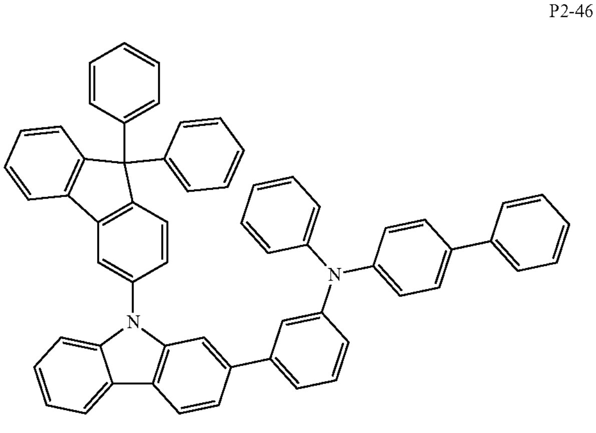

-continued
P2-47
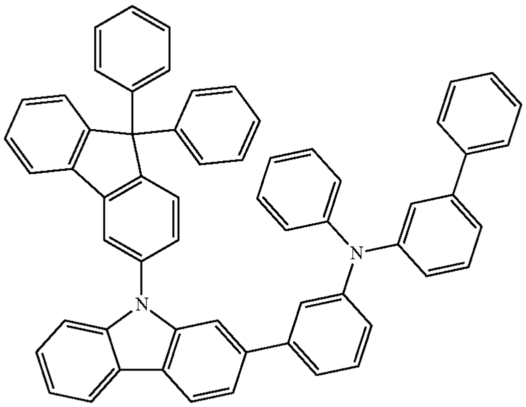
P2-48
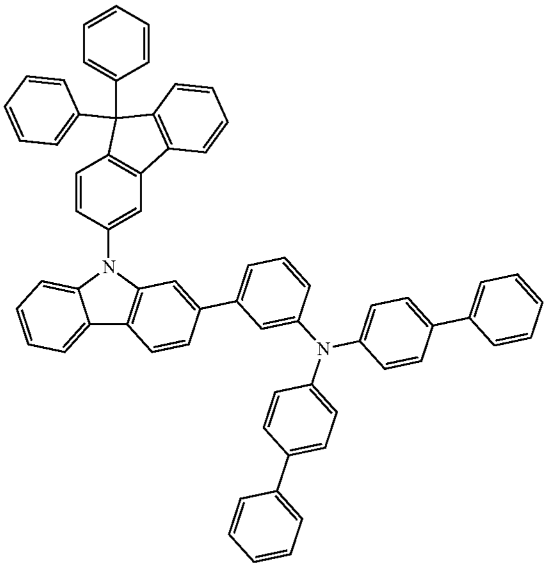
P2-49
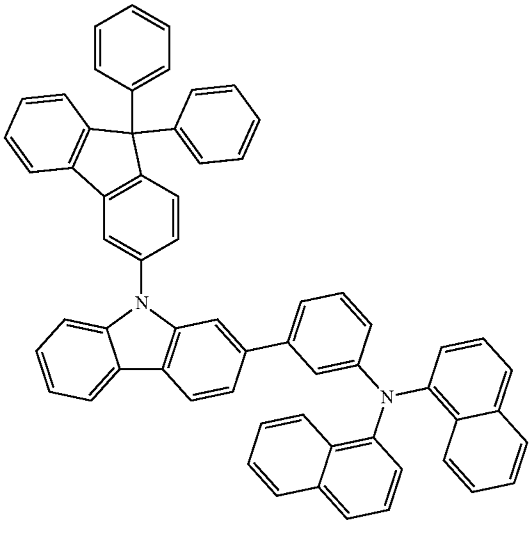
P2-50
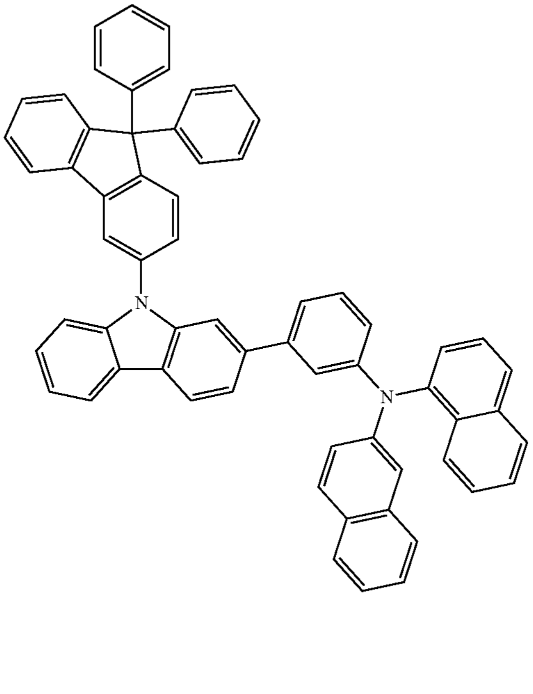

-continued
P2-51
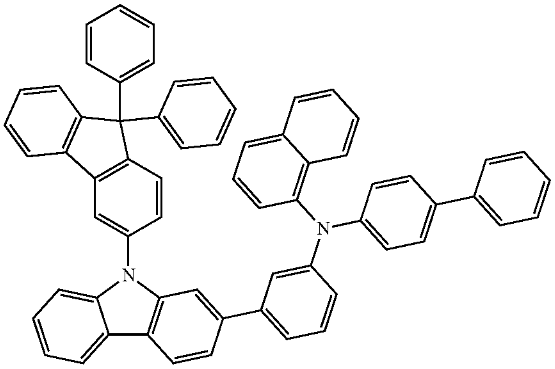
P2-52
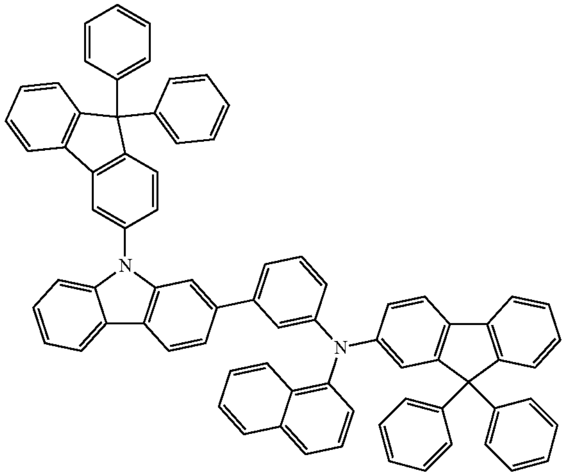
P2-53
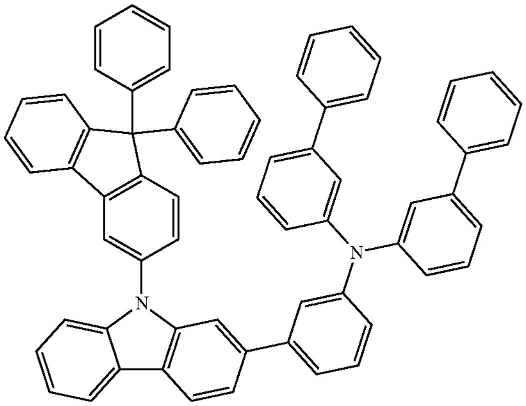
P2-54
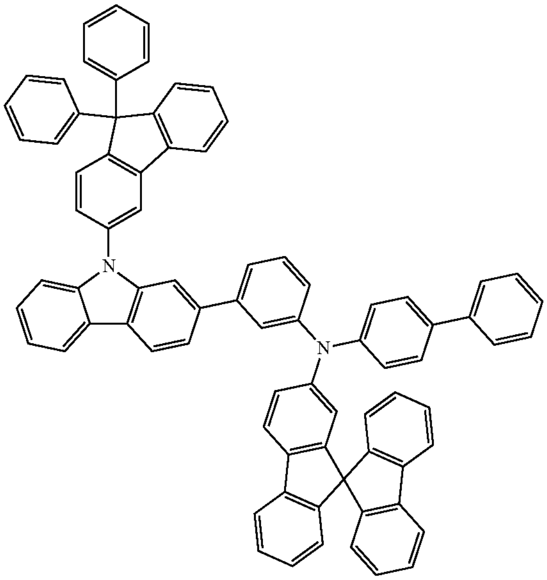
P2-55
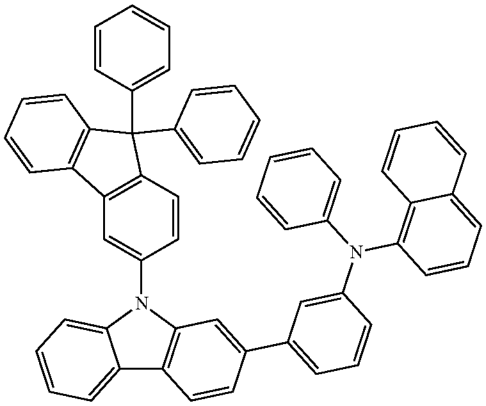
P2-56
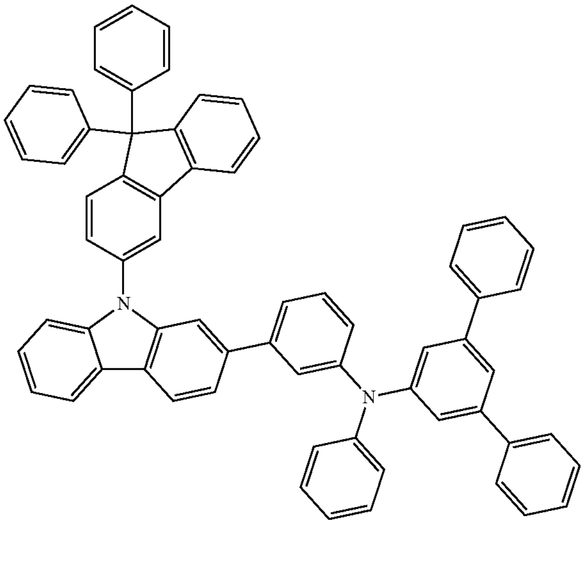

-continued
P2-57
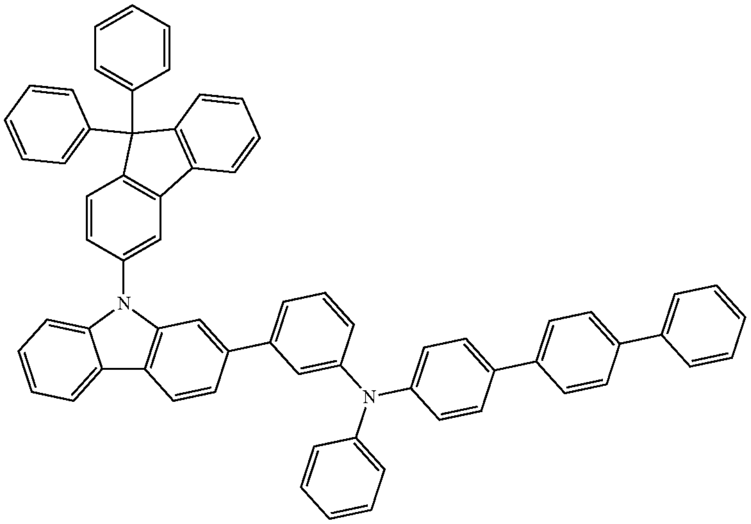
P2-58
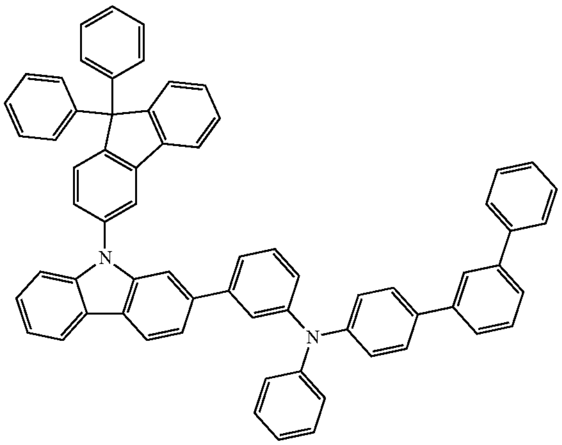
P2-59
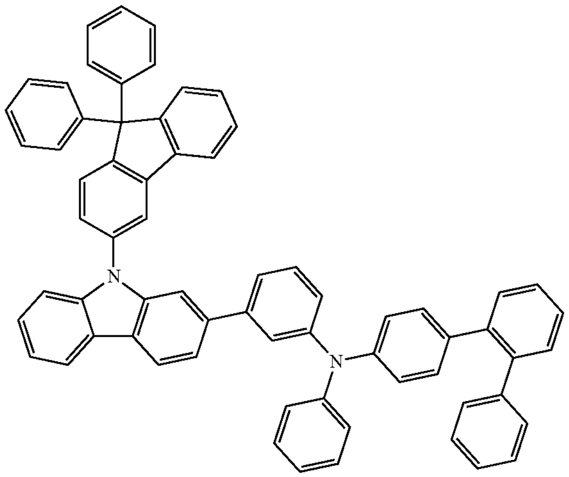
P2-60
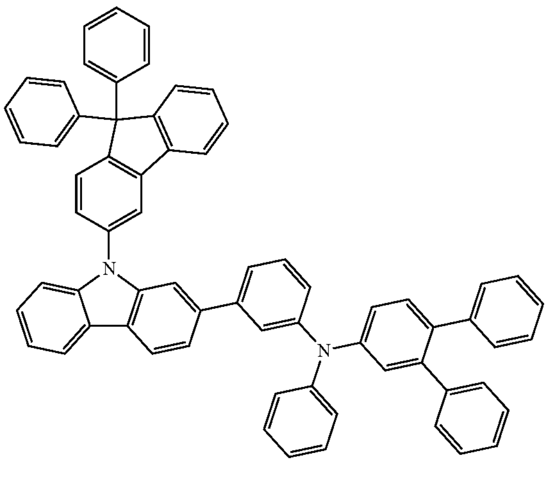
P2-61
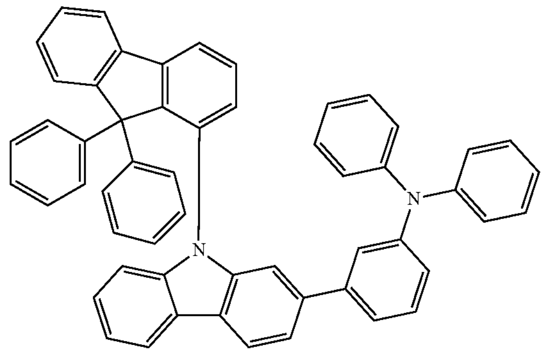

-continued
P2-62
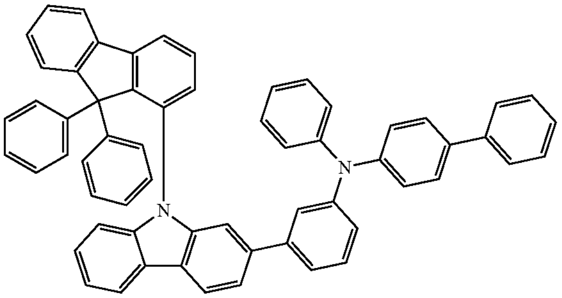
P2-63
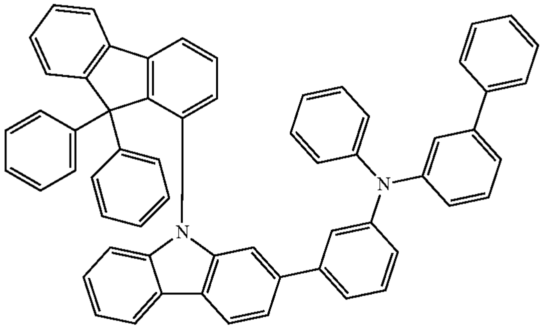
P2-64
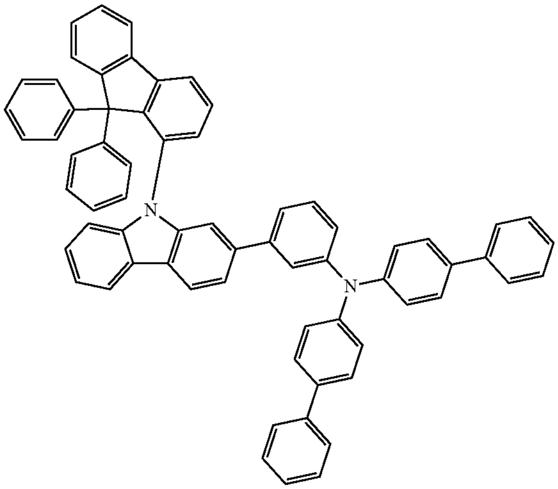
P2-65
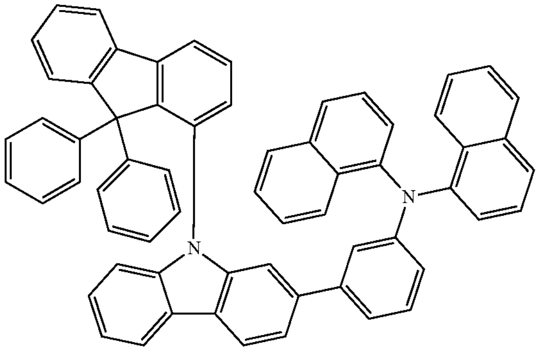
P2-66
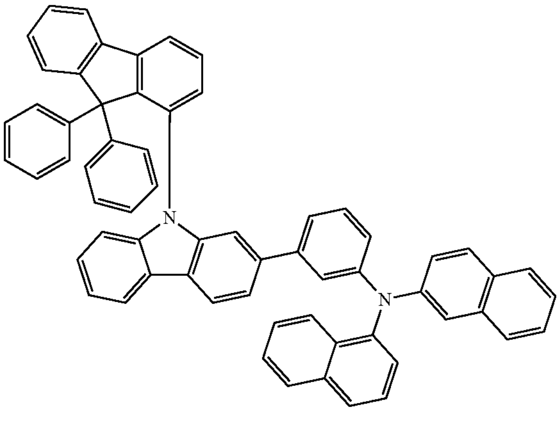
P2-67
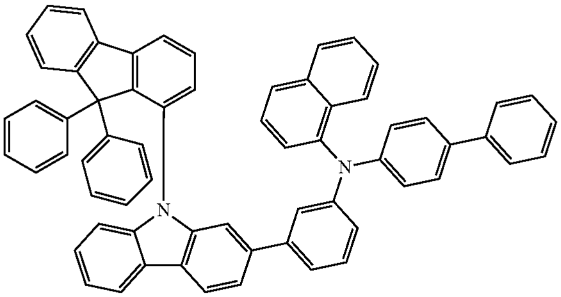

-continued
P2-68
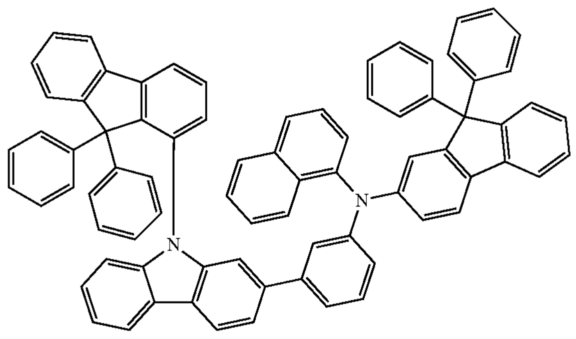
P2-69
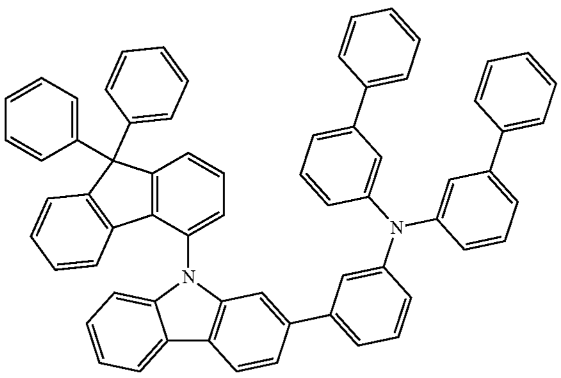
P2-70
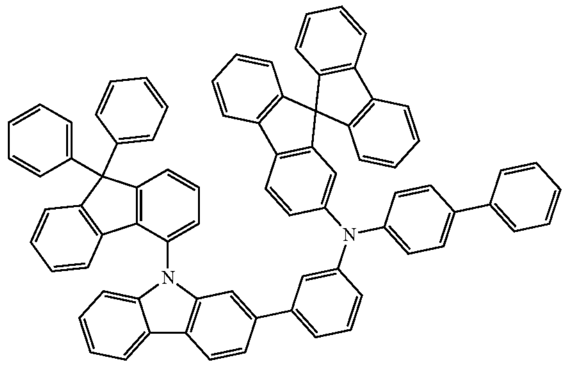
P2-71
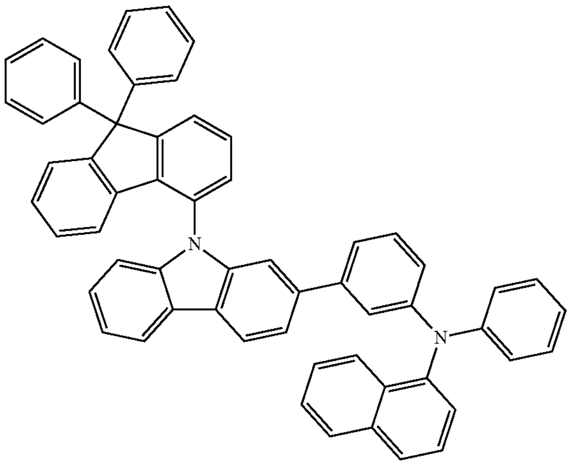
P2-72
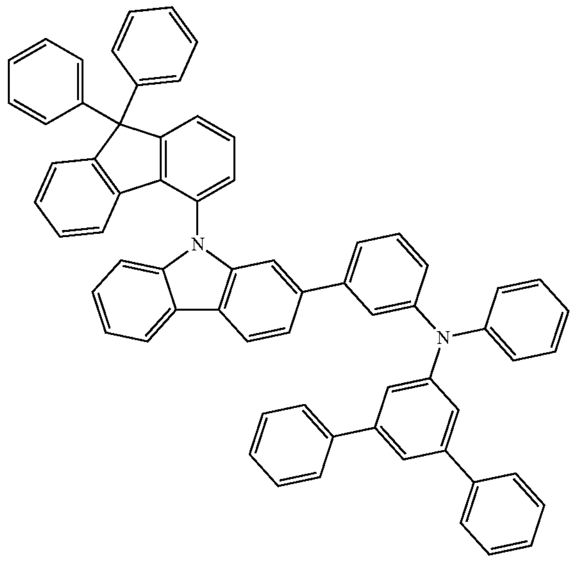

-continued
P2-73
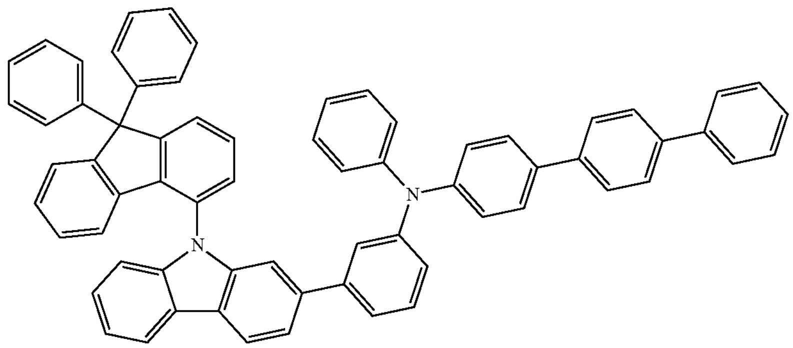
P2-74
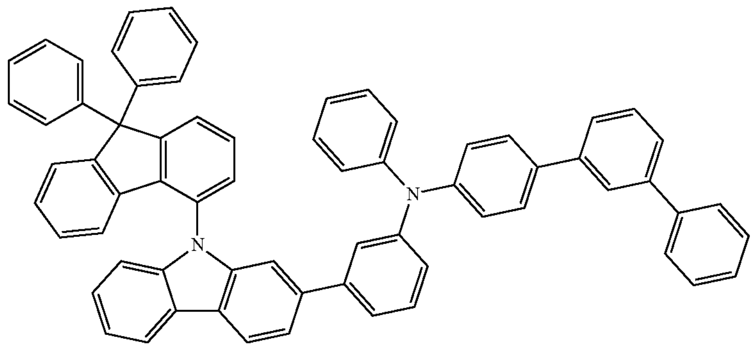
P2-75
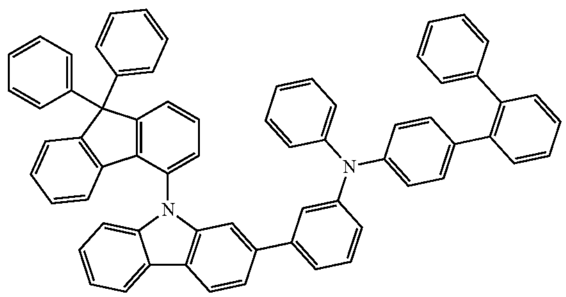
P2-76
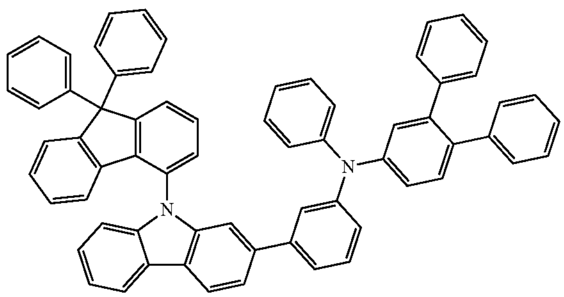
P2-77
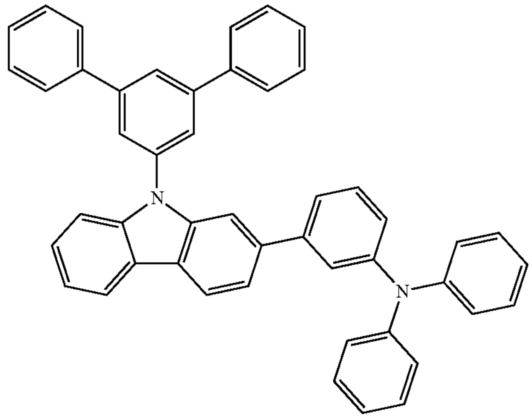
P2-78
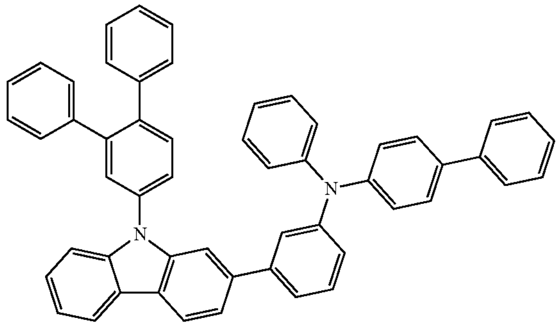

-continued
P2-79
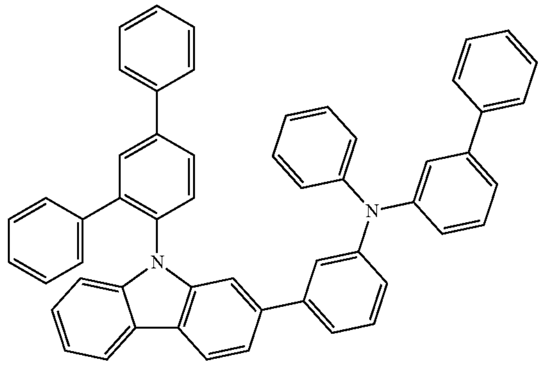
P2-80
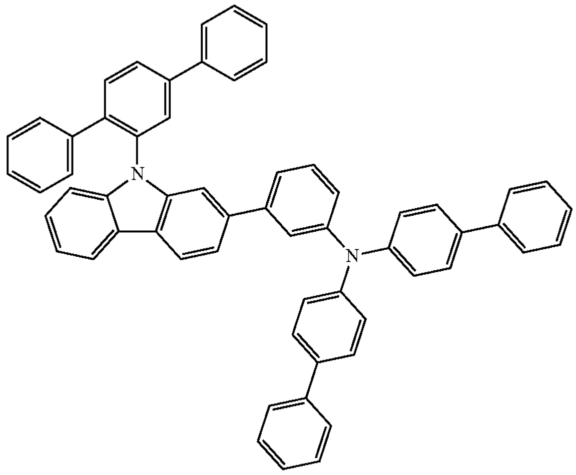
P2-81
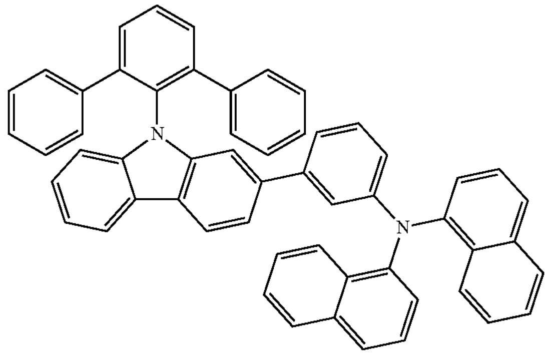
P2-82
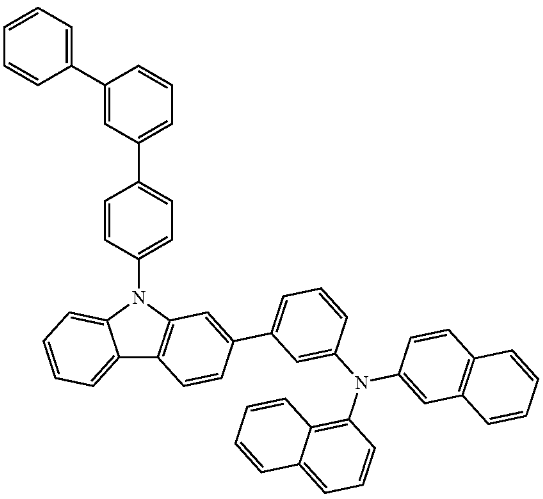
P2-83
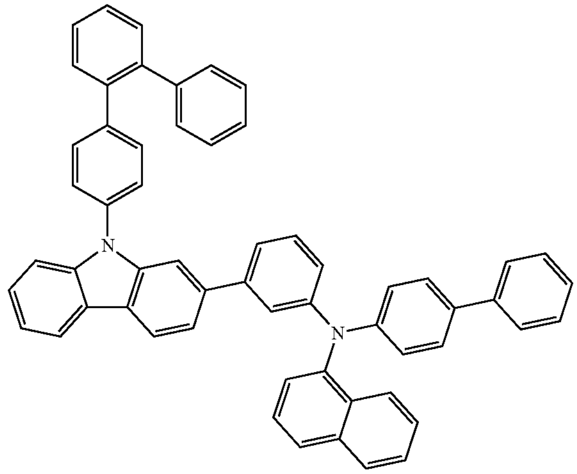
P2-84
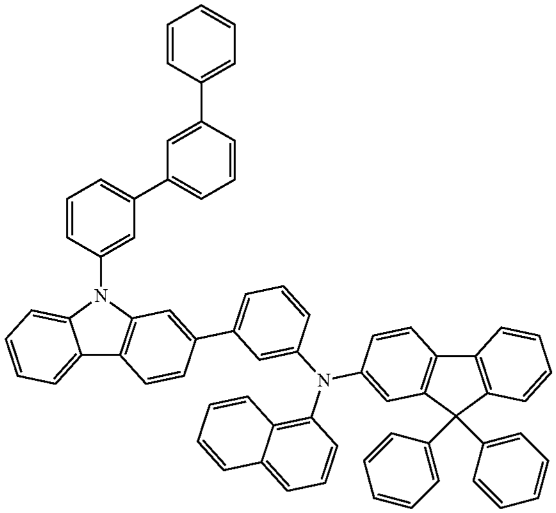

-continued
P2-85
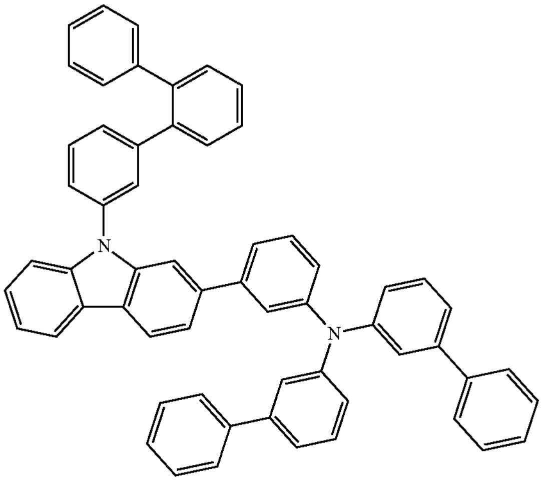
P2-86
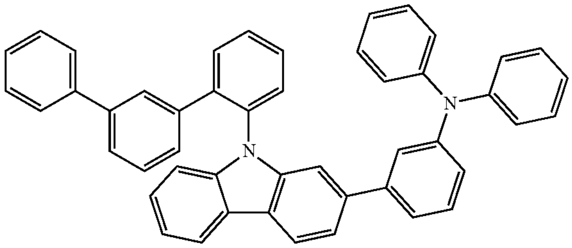
P2-87
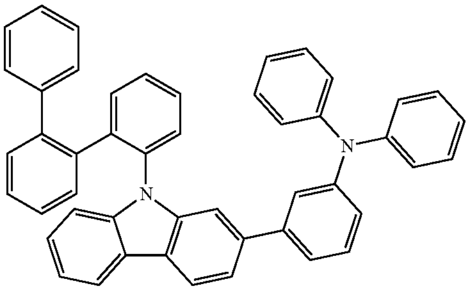
P2-88
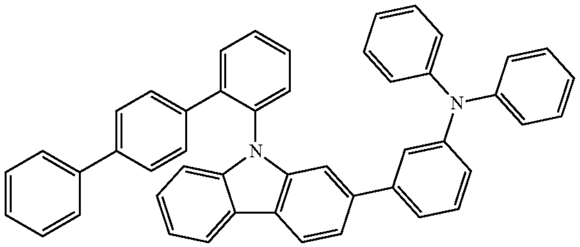
P2-89
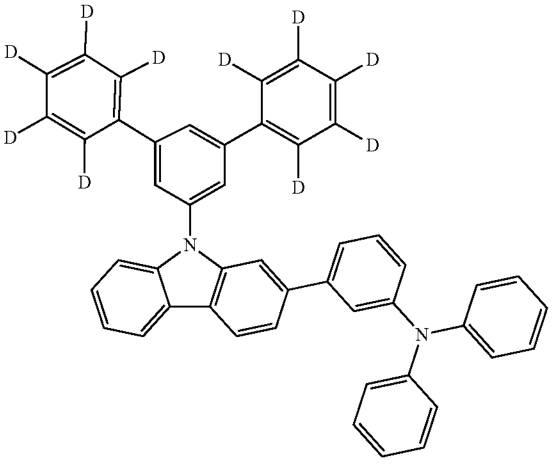
P2-90
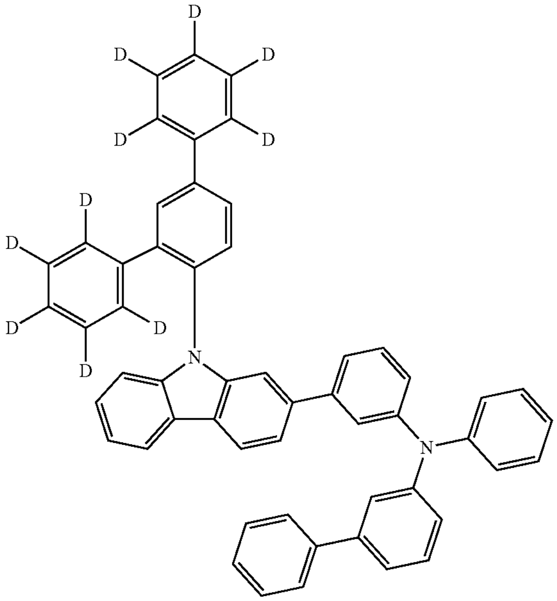

-continued
P2-91
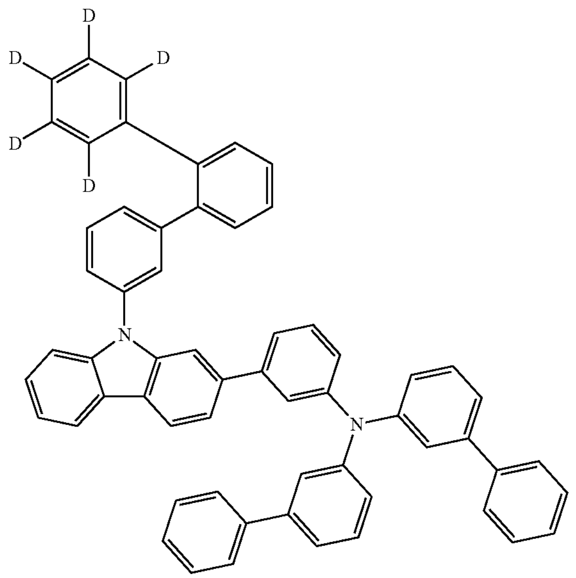
P2-92
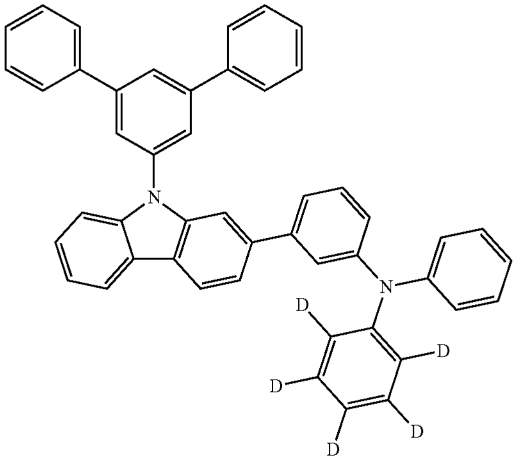
P2-93
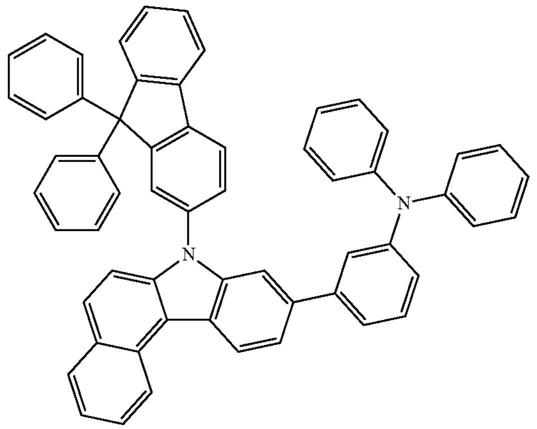
P2-94
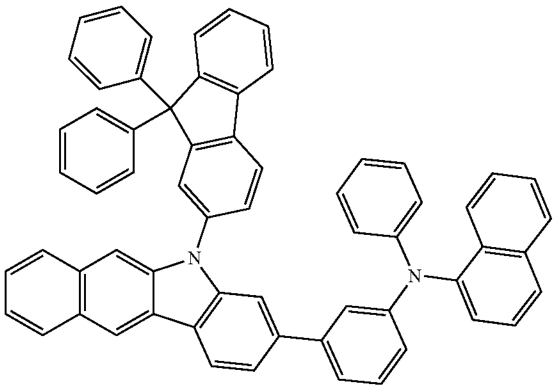
P2-95
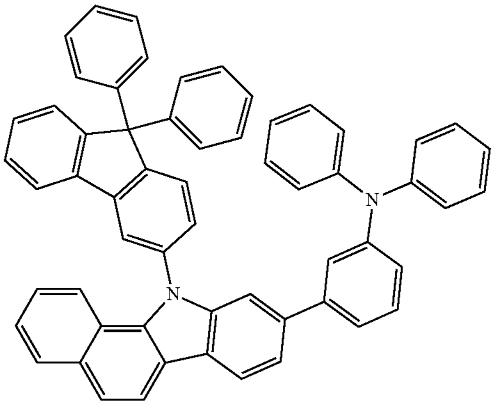
P2-96
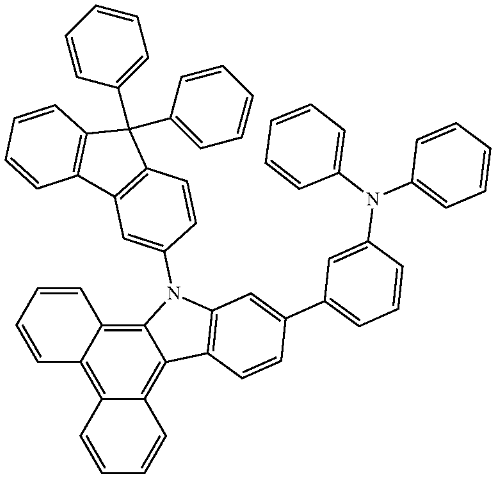

-continued
P2-97
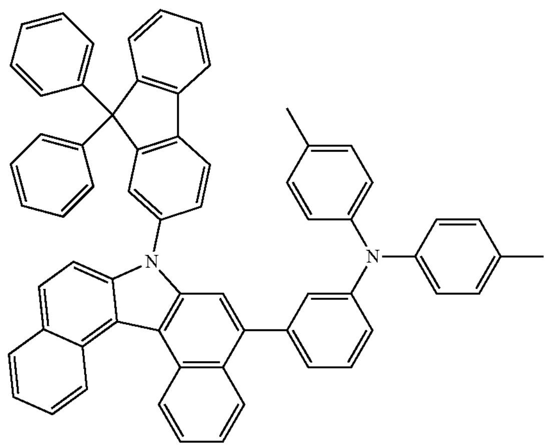
P2-98
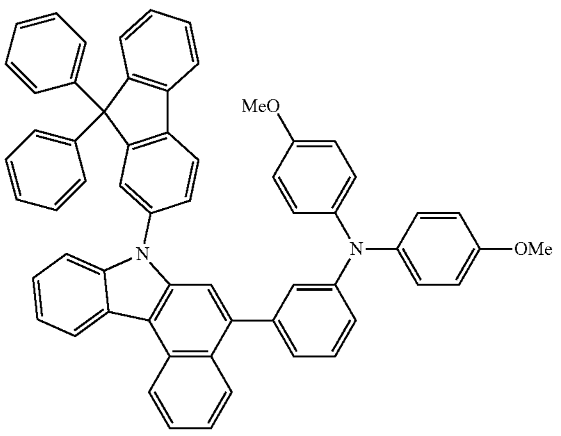
P2-99
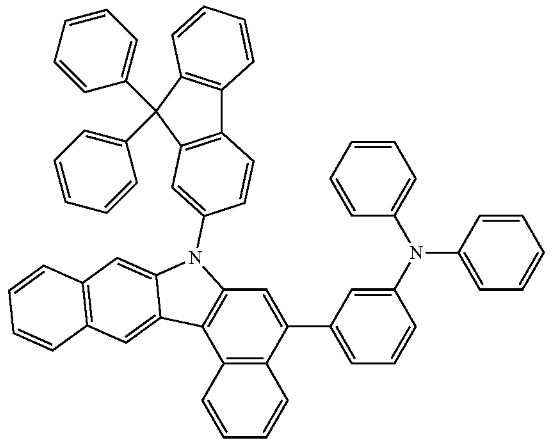
P2-100
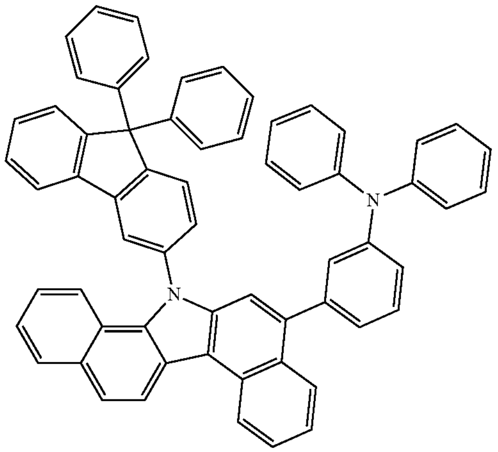
P2-101
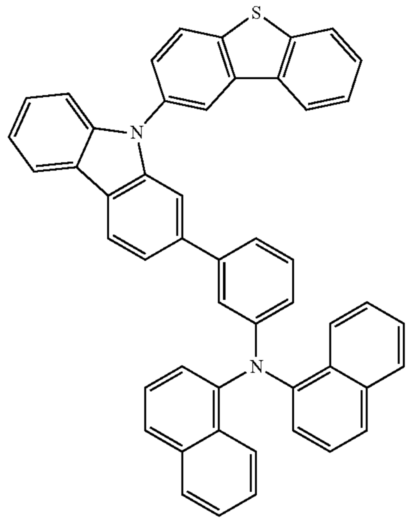
P2-102
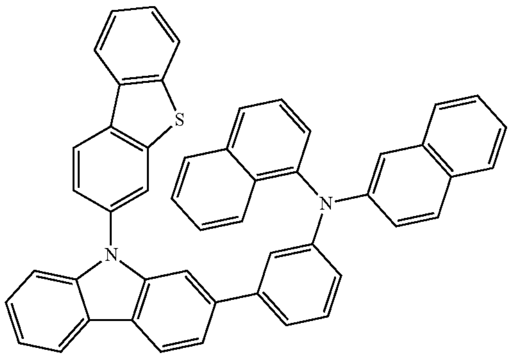

-continued
P2-103
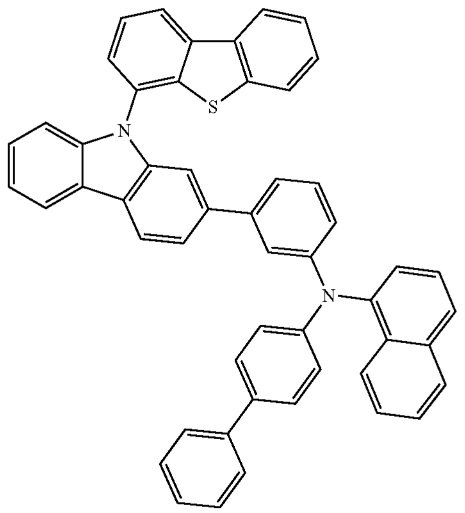
P2-104
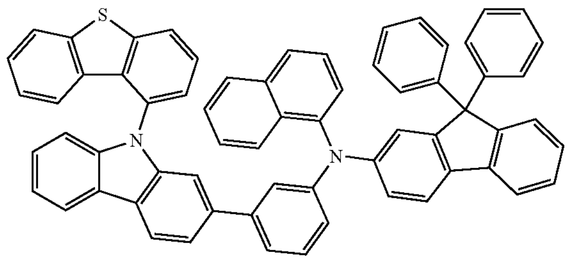
P2-105
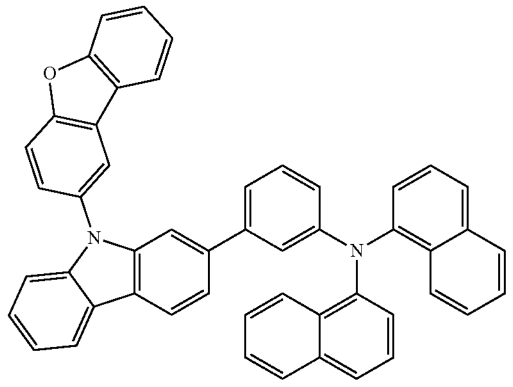
P2-106
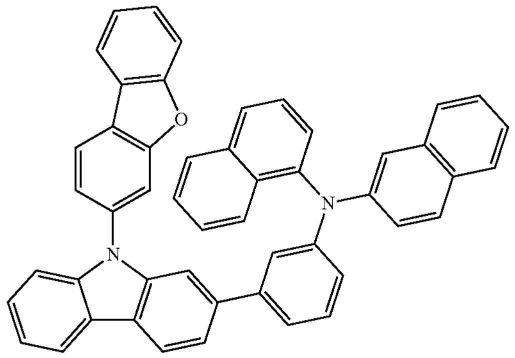
P2-107
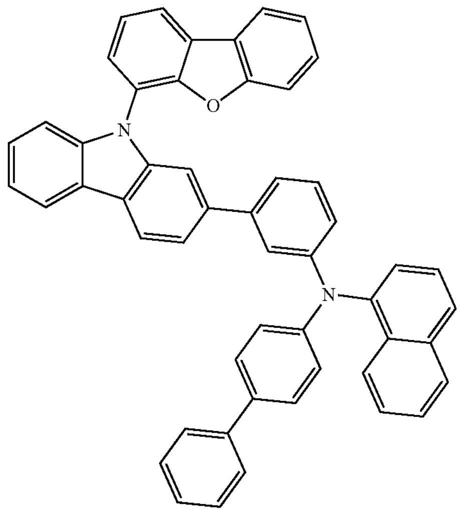
P2-108
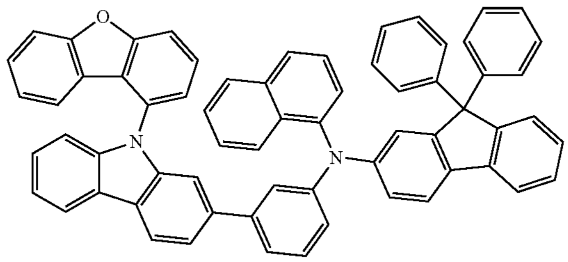

-continued
P2-109
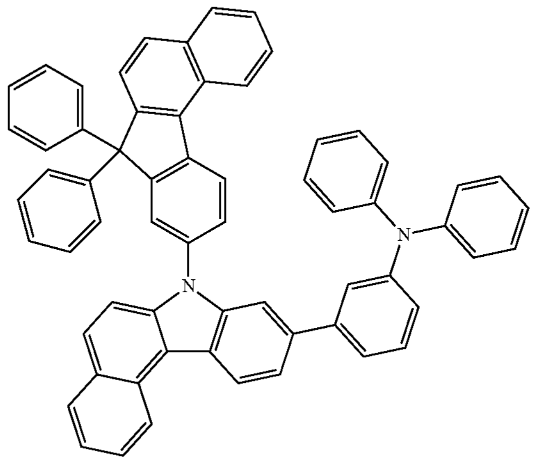
P2-110
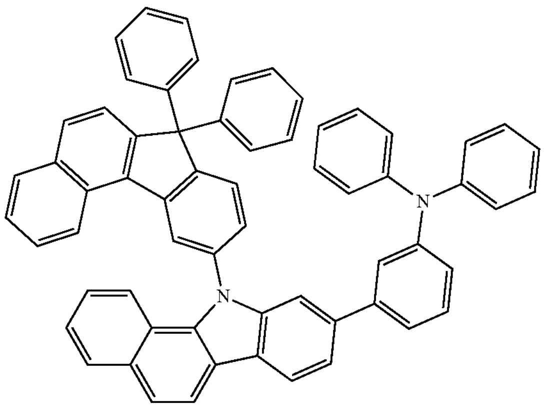
P2-111
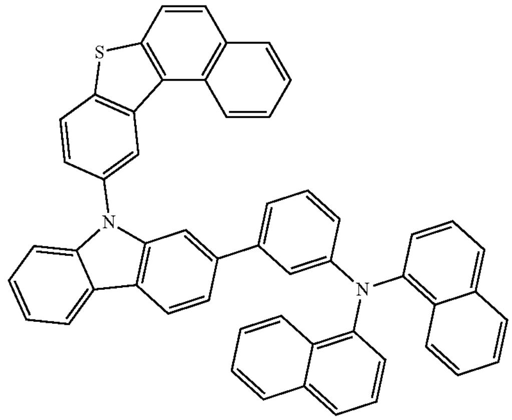
P2-112
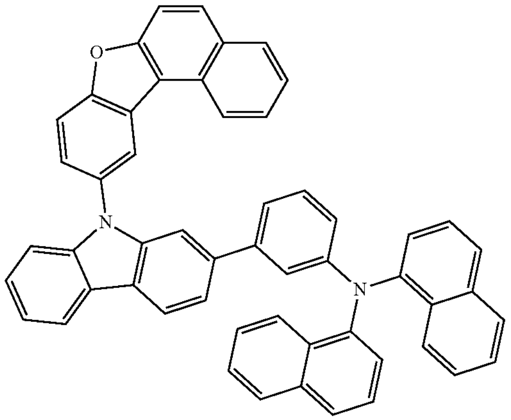
P3-1
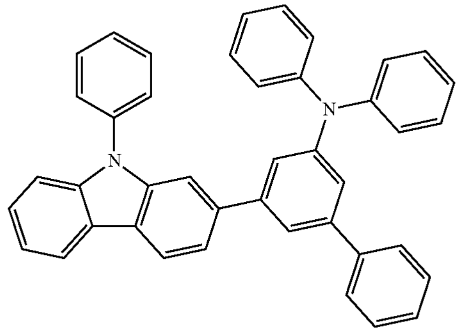
P3-2
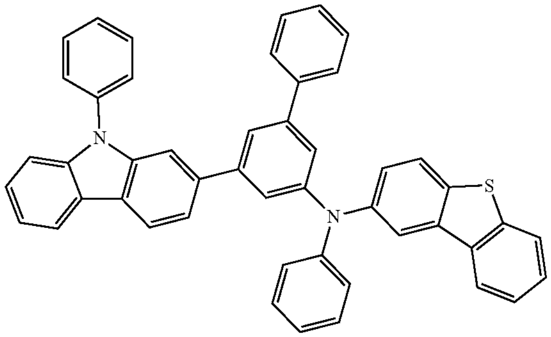

-continued
P3-3
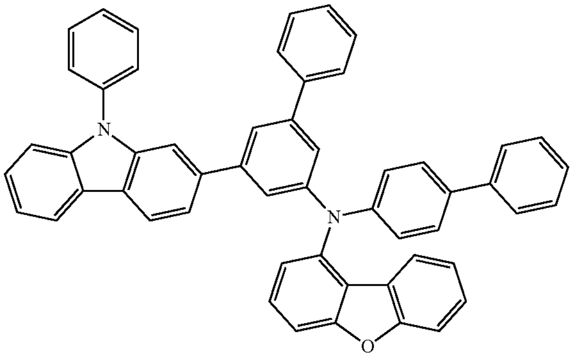
P3-4
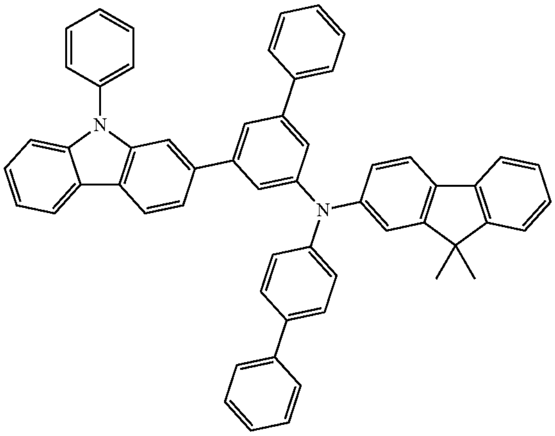
P3-5
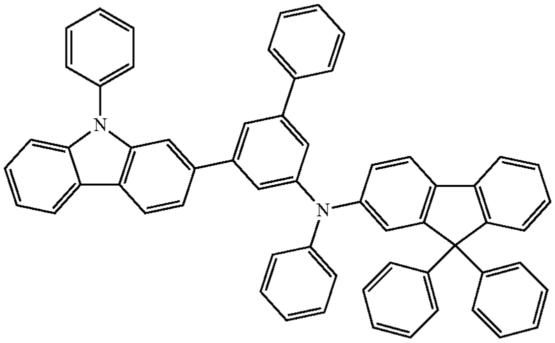
P3-6
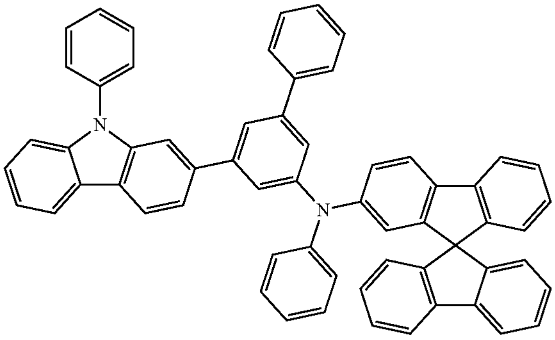
P3-7
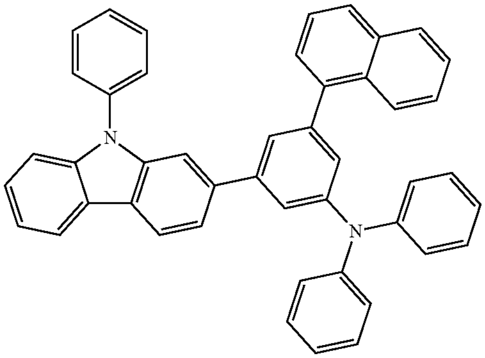
P3-8
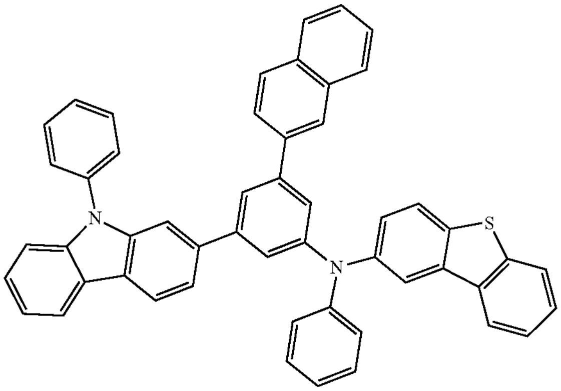

-continued
P3-9
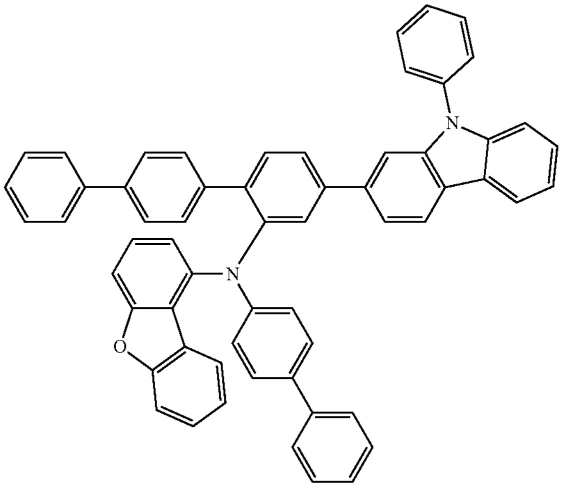
P3-10
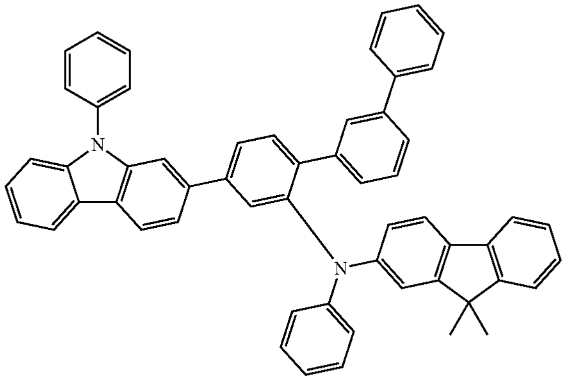
P3-11
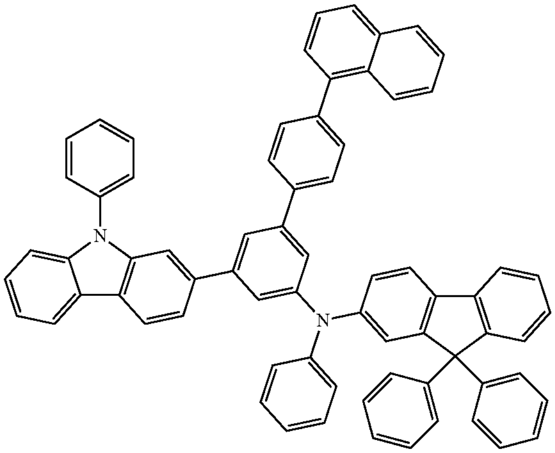
P3-12
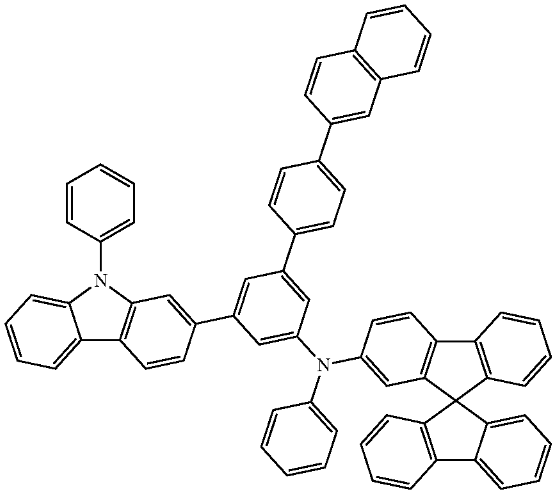
P3-13
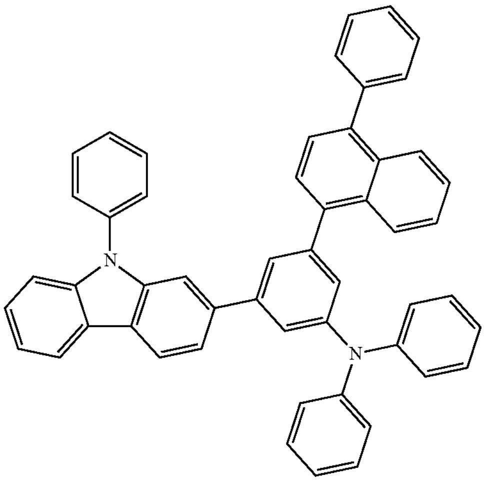
P3-14
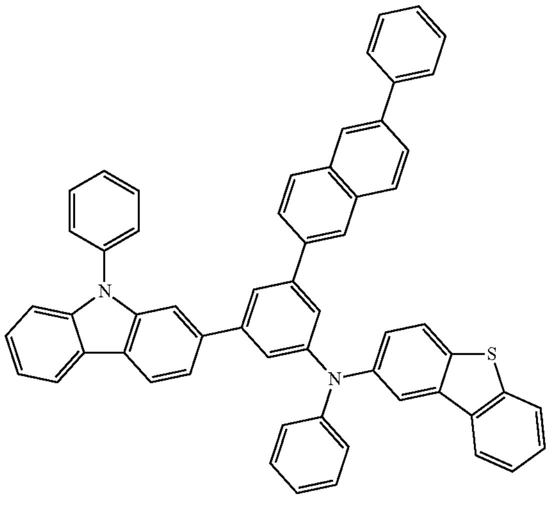

-continued
P3-15
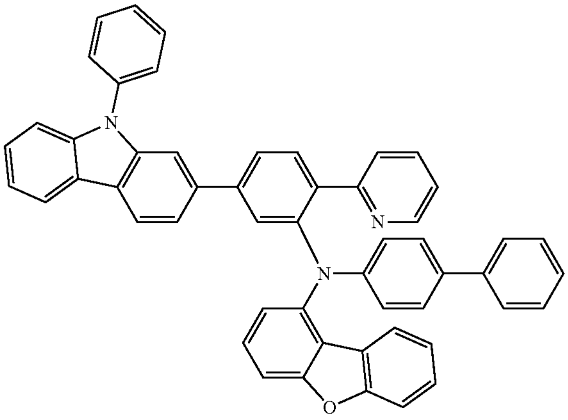
P3-16
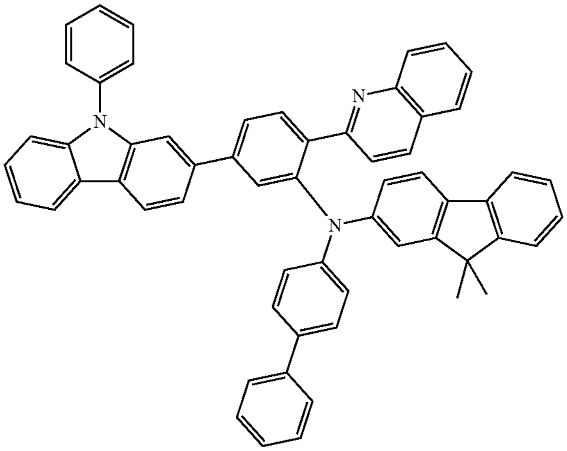
P3-17
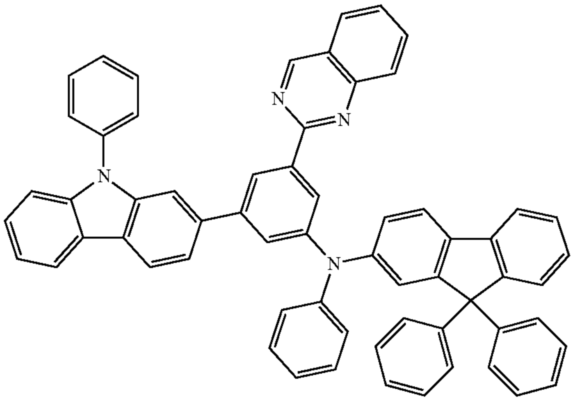
P3-18
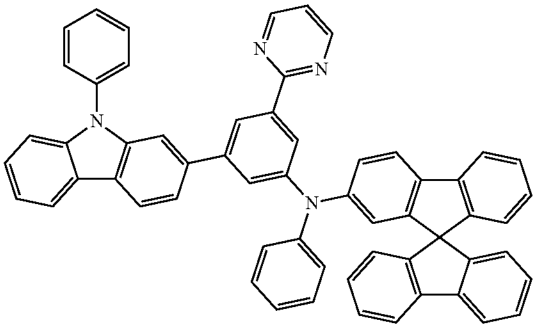
P3-19
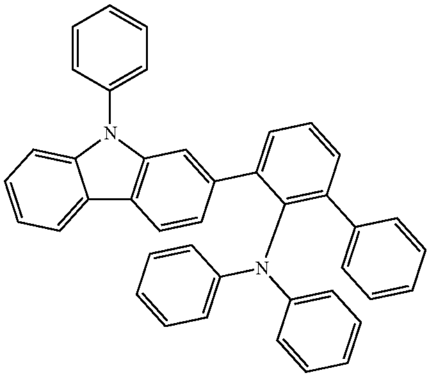
P3-20
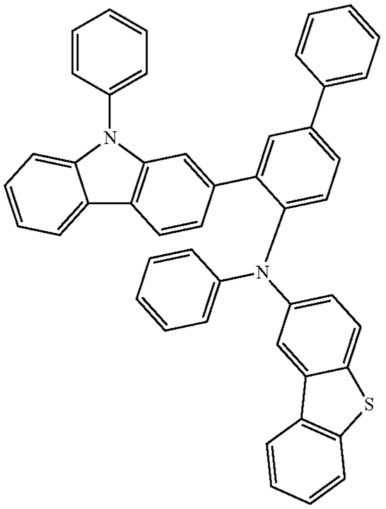

-continued
P3-21
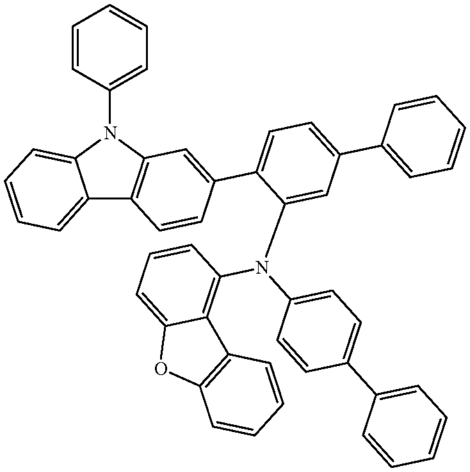
P3-22
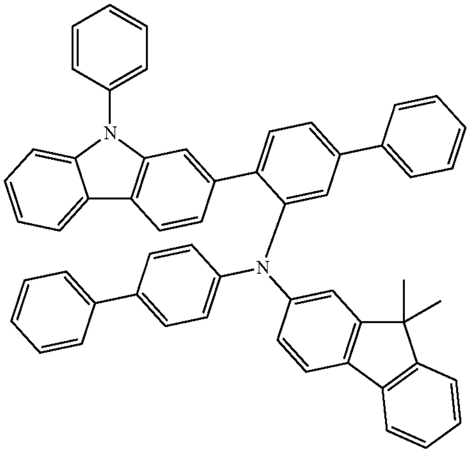
P3-23
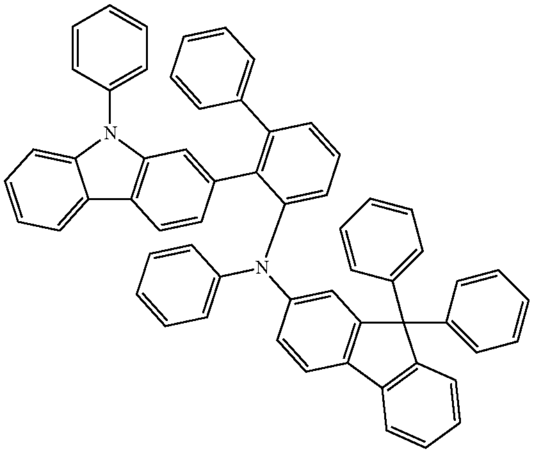
P3-24
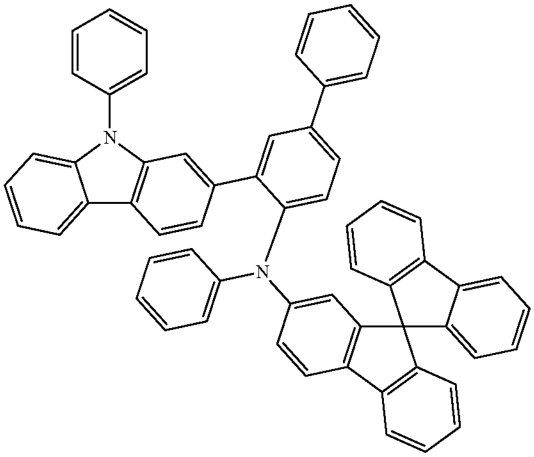
P3-25
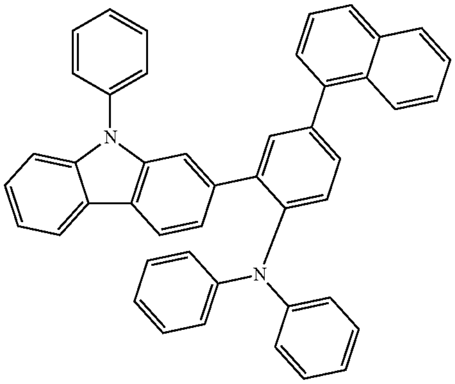
P3-26
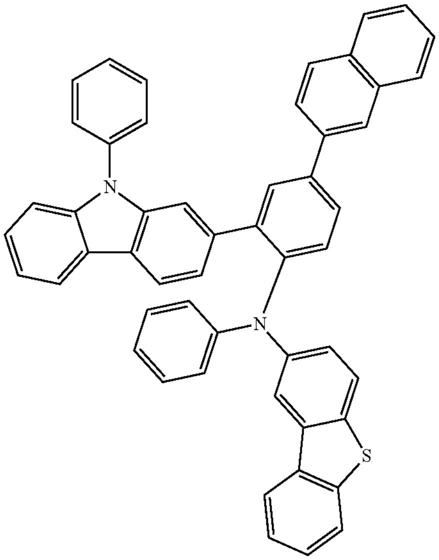

-continued
P3-27
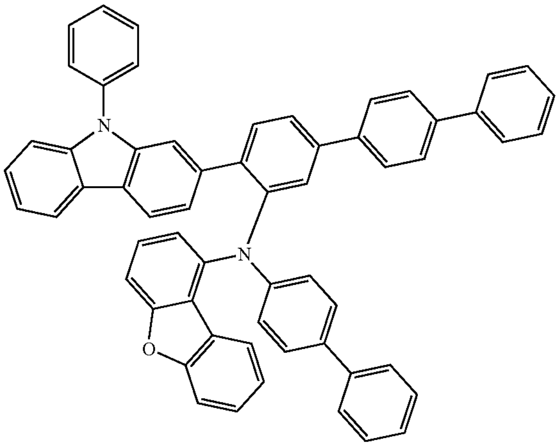
P3-28
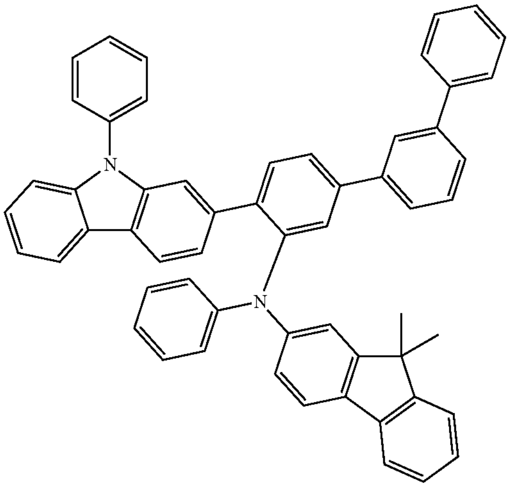
P3-29
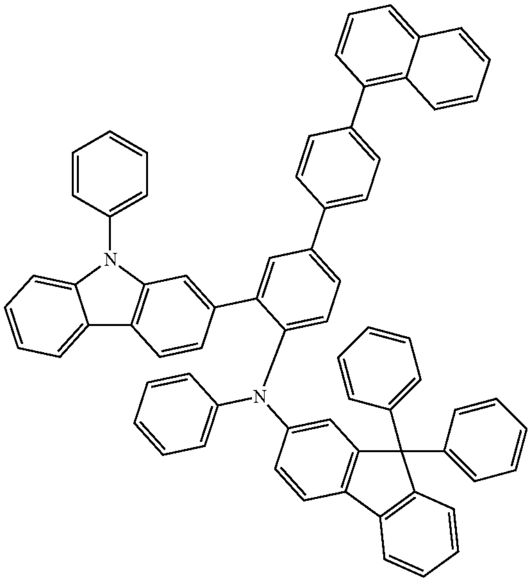
P3-30
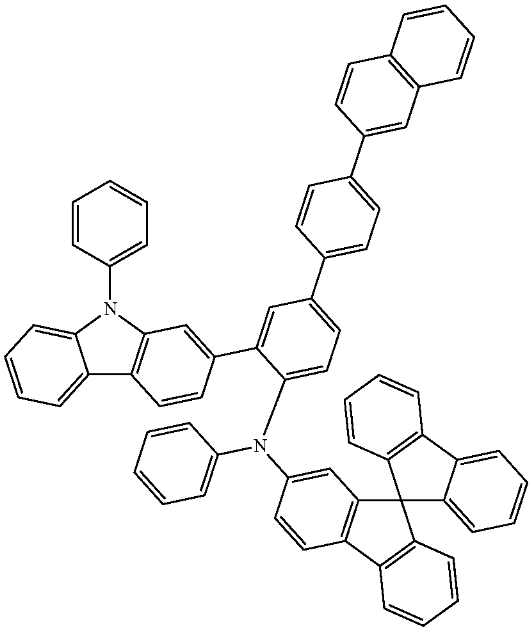

-continued
P3-31
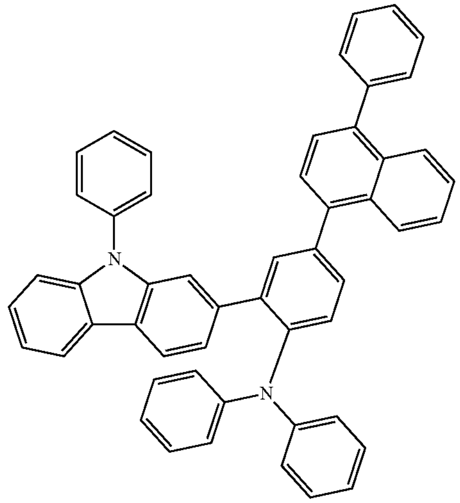
P3-32
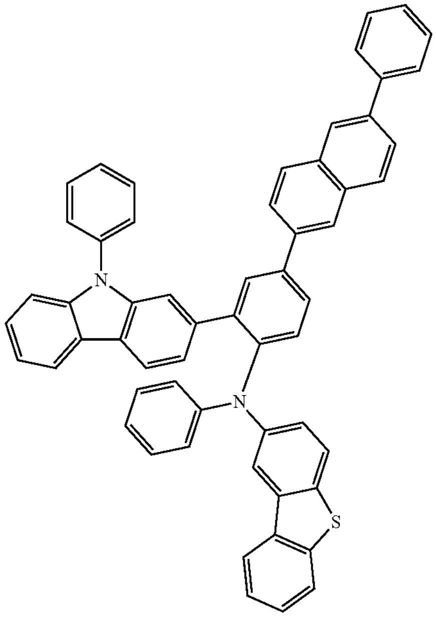
P3-33
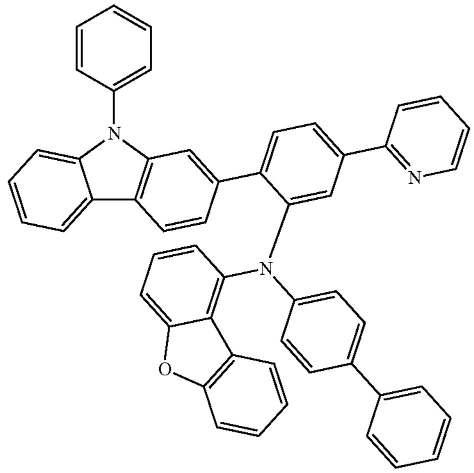
P3-34
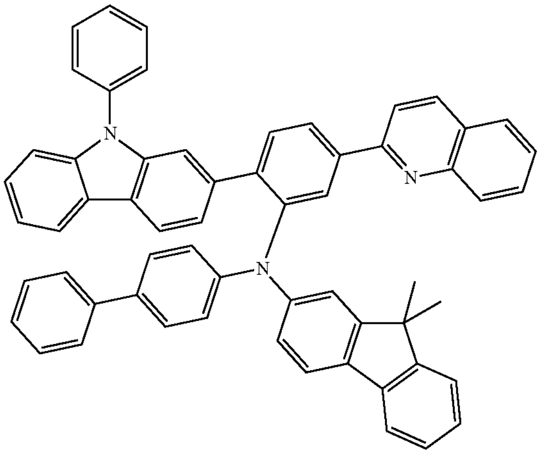
P3-35
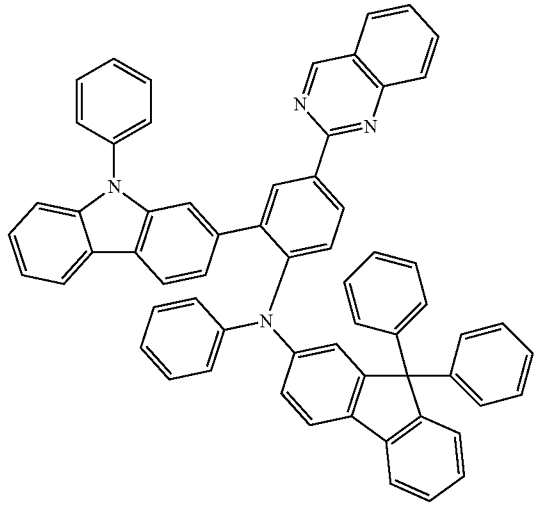
P3-36
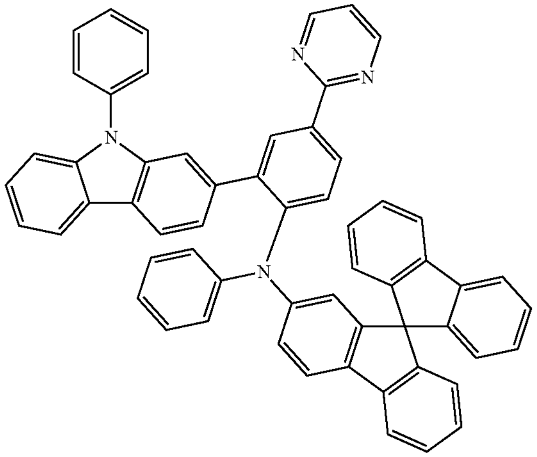

-continued
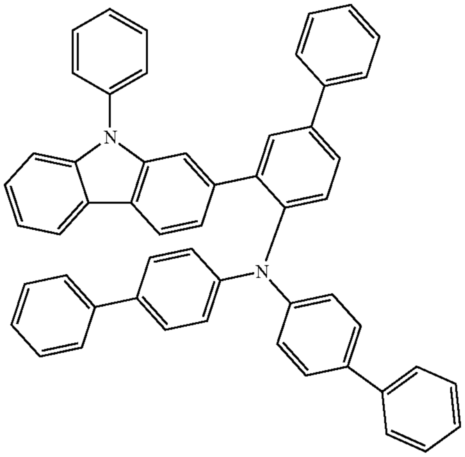
P3-37
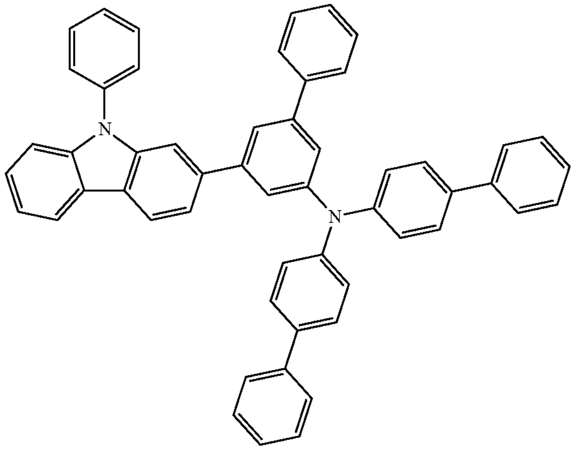
P3-38
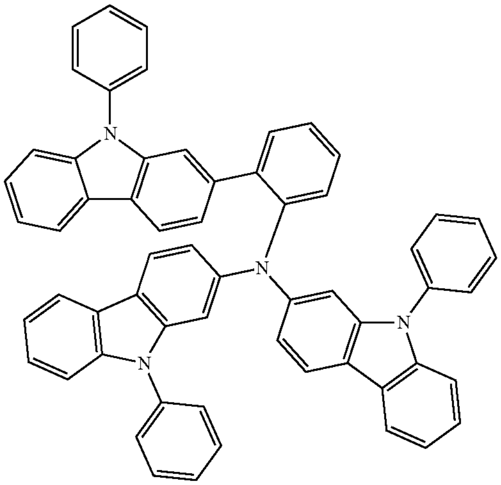
P4-1
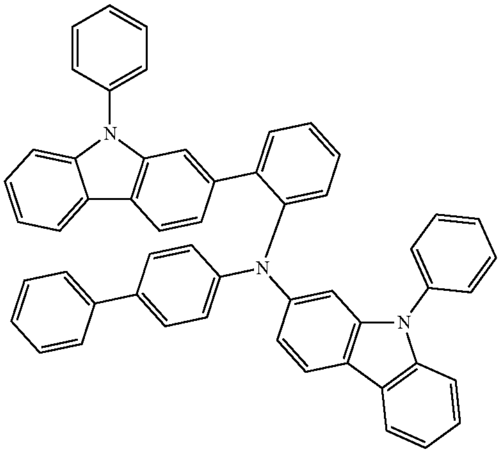
P4-2
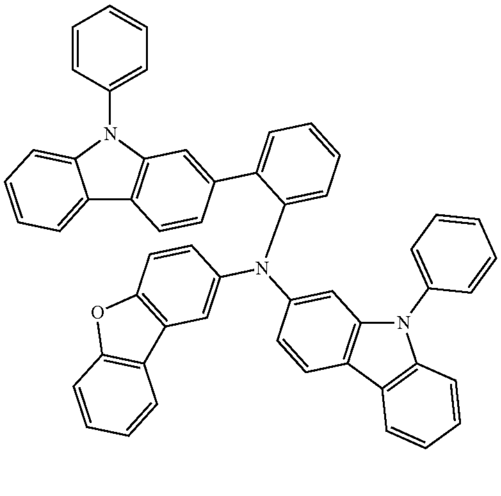
P4-3
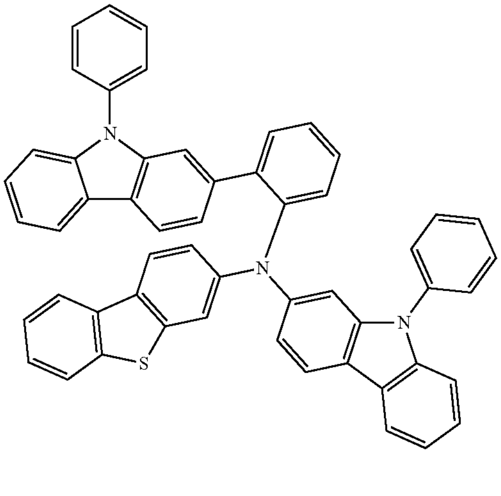
P4-4

-continued
P4-5
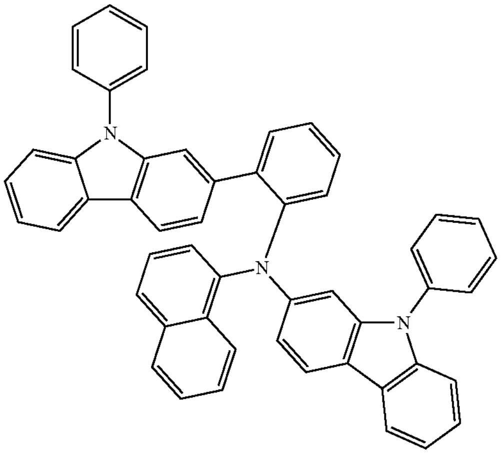
P4-6
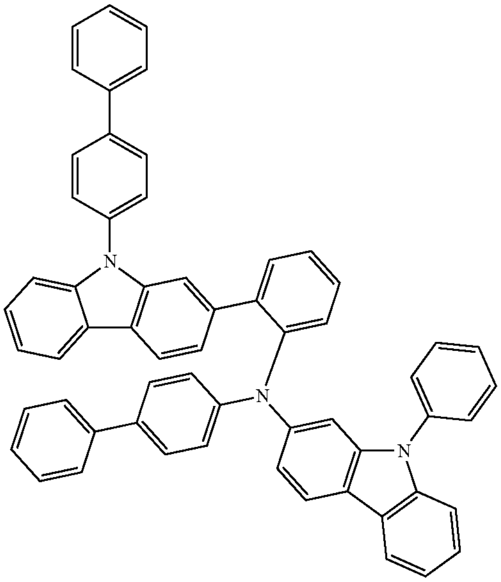
P4-7
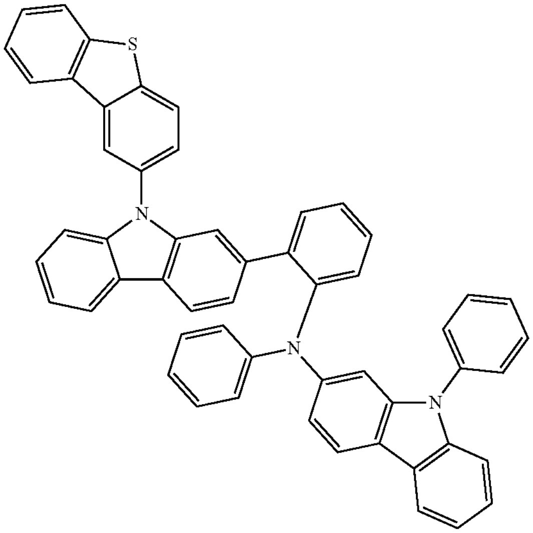
P4-8
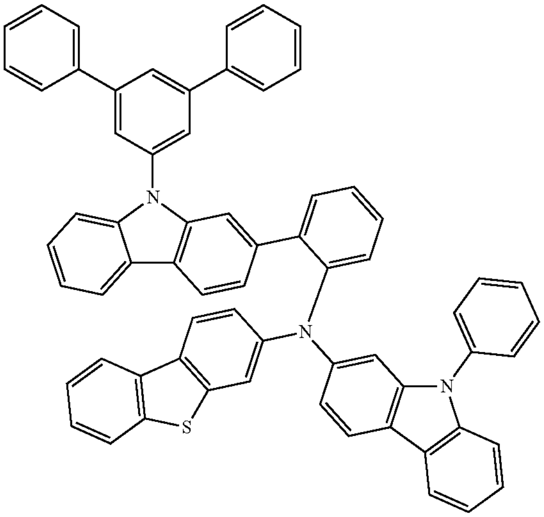
P4-9
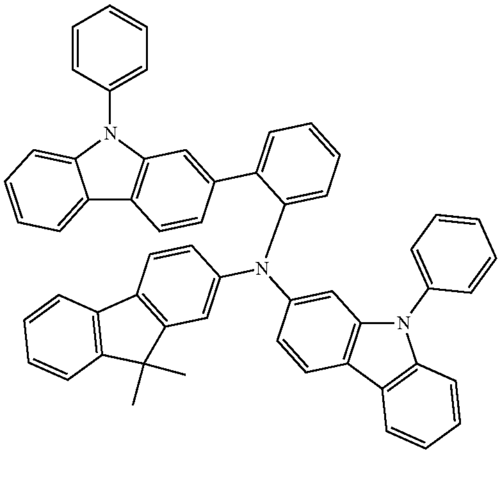
P4-10
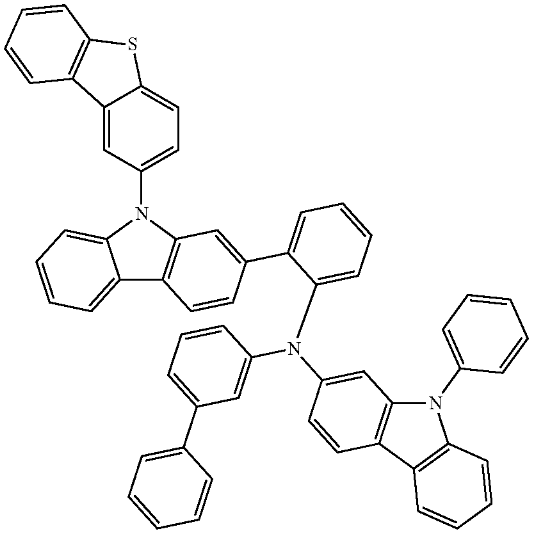

-continued
P4-11
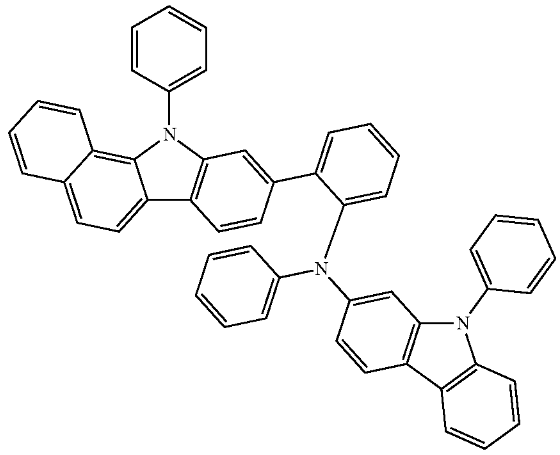
P4-12
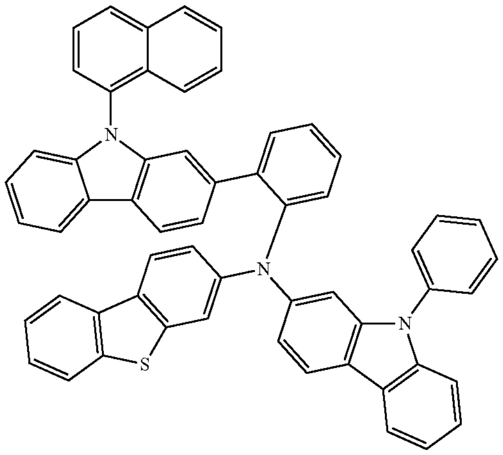
P4-13
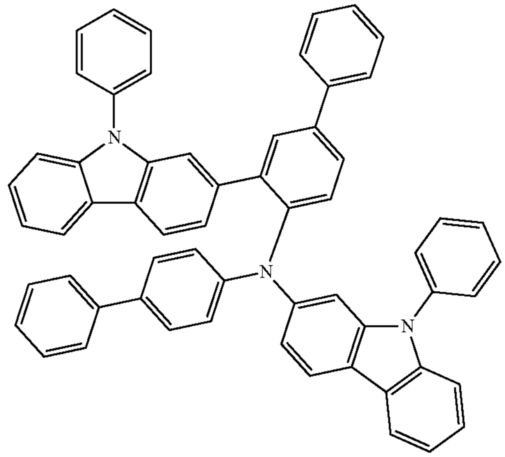
P4-14
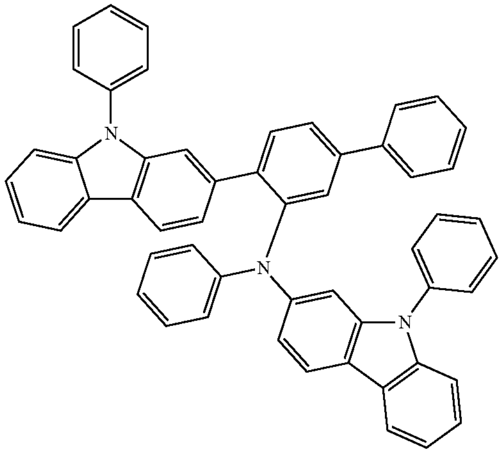
P4-15
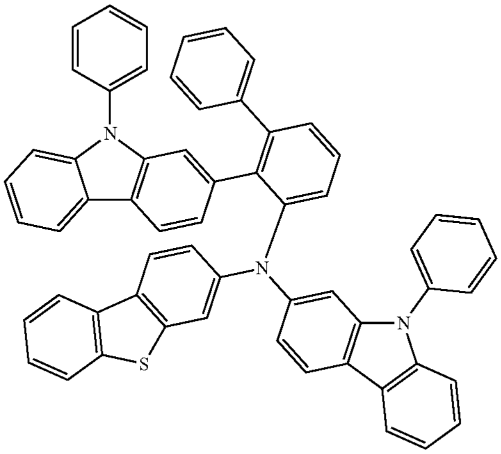
P4-16
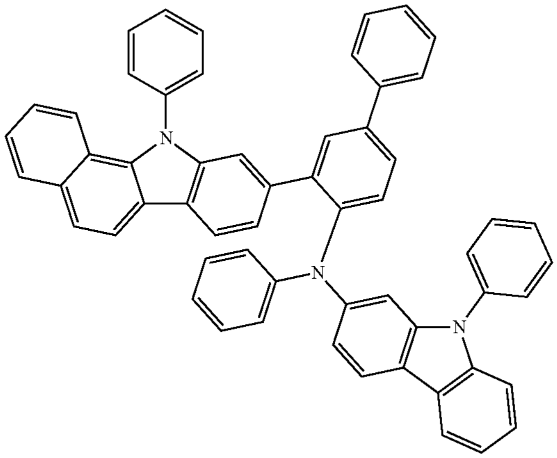

-continued
P4-17
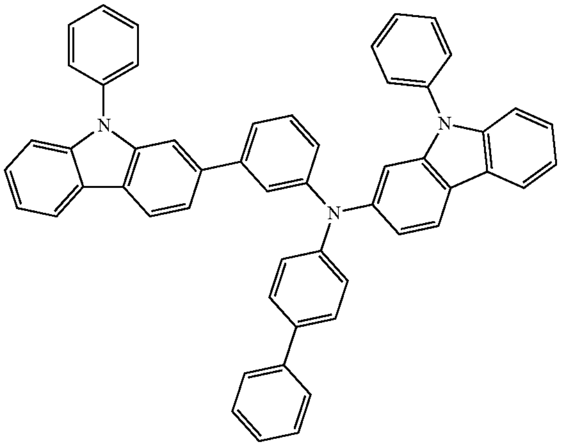
P4-18
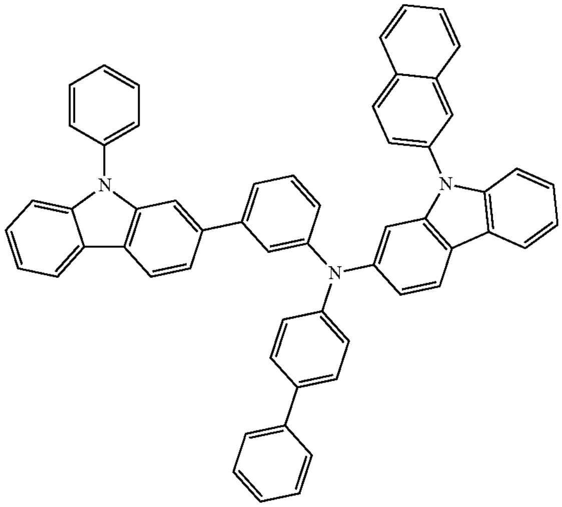
P4-19
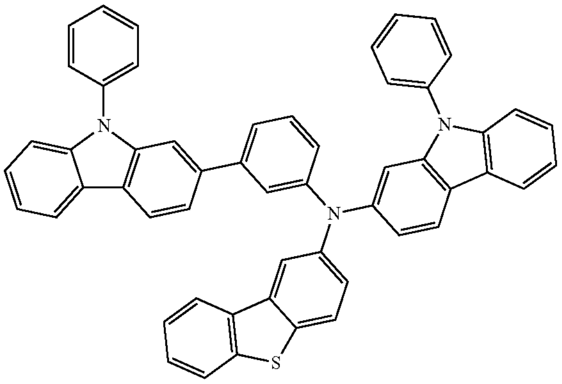
P4-20
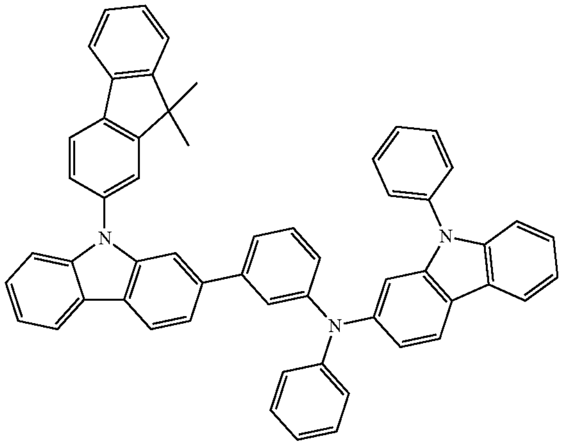
P4-21
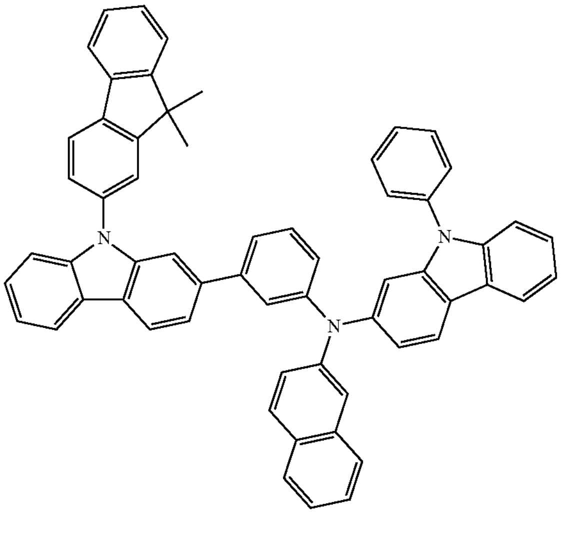
P4-22
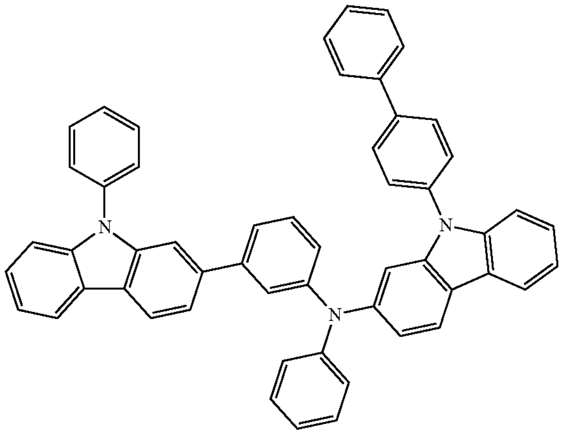

-continued
P4-23
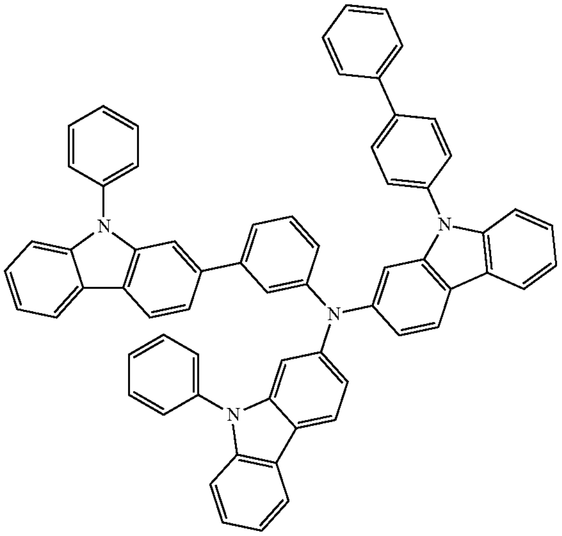
P4-24
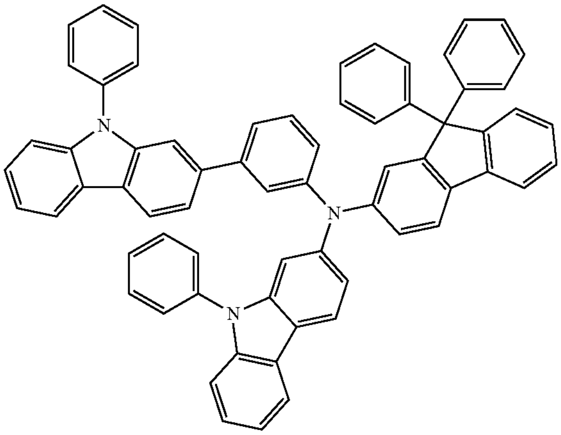
P4-25
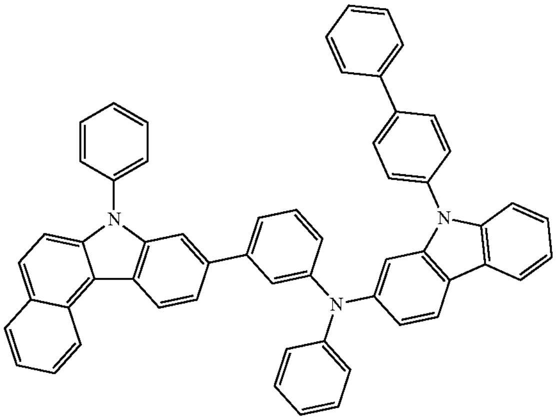
P4-26
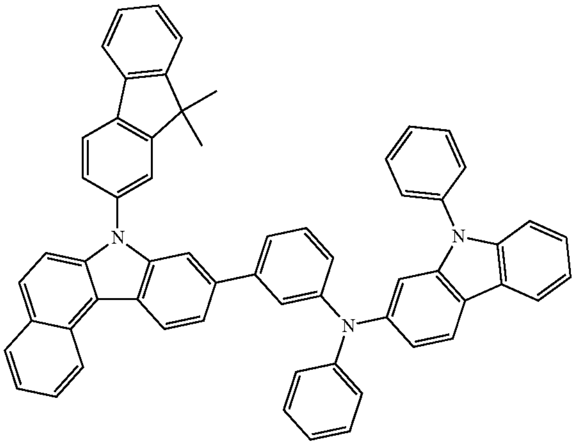
P4-27
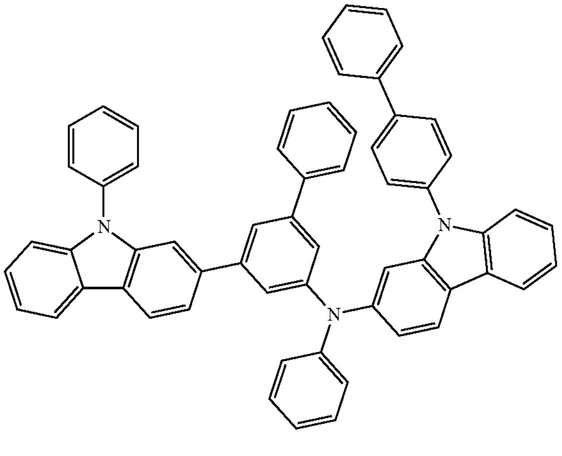
P4-28
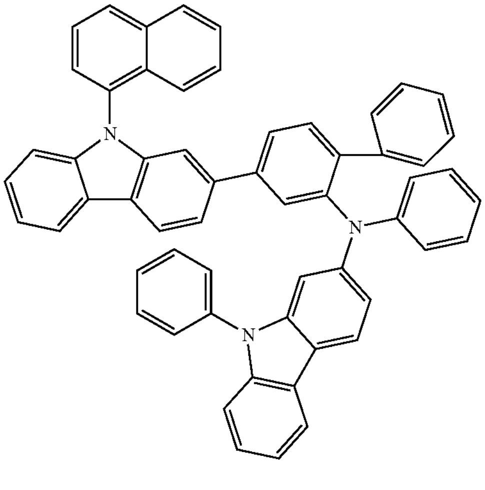

-continued
P4-29
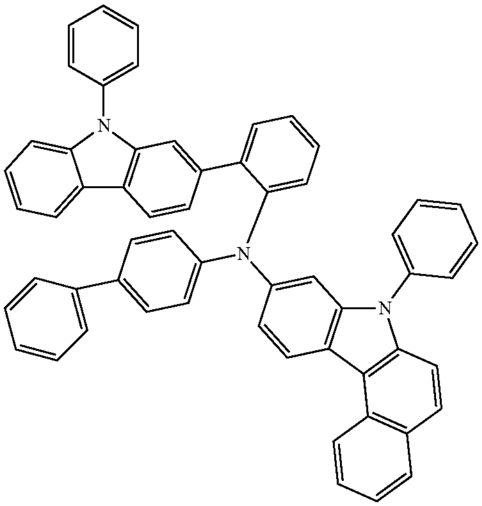
P4-30
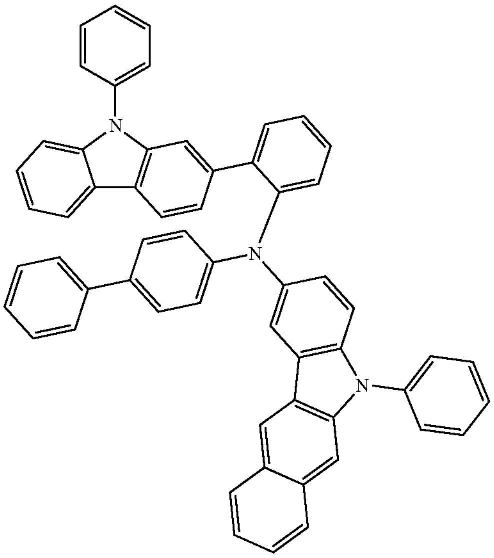
P4-31
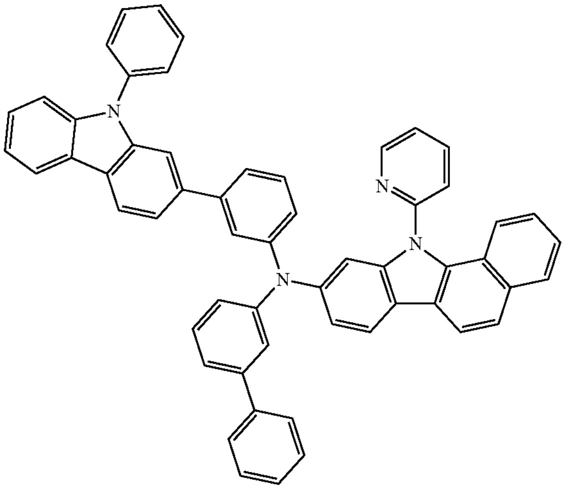
P4-32
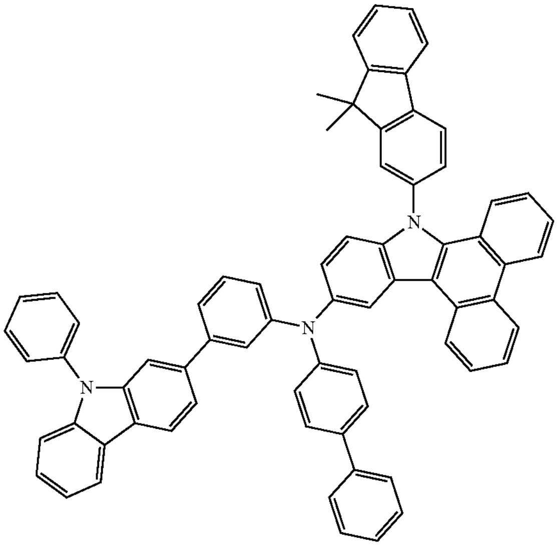

-continued

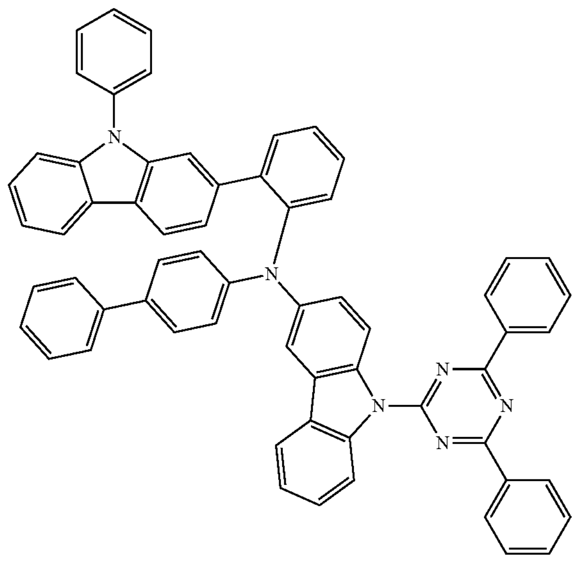

P4-33

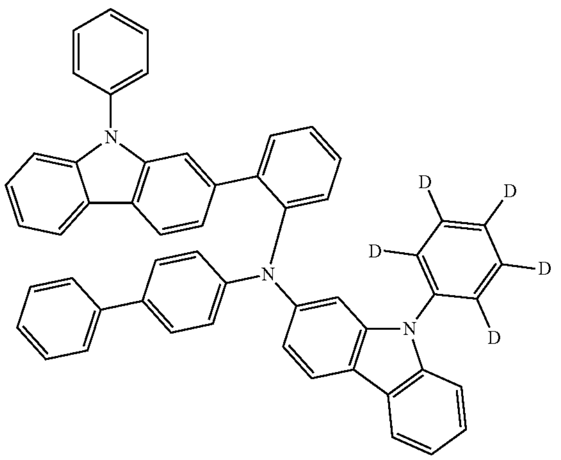

P4-34

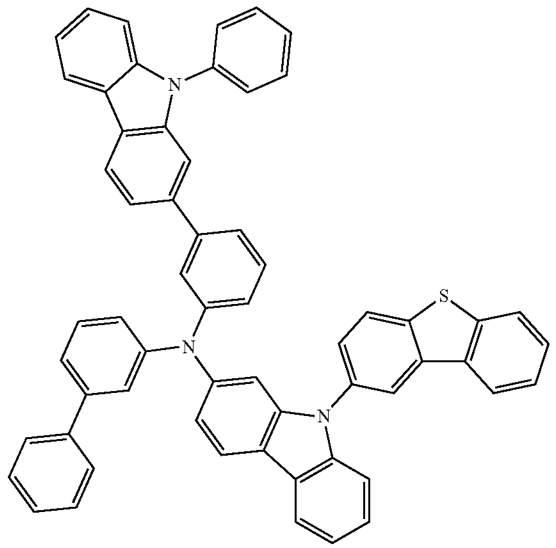

P4-35

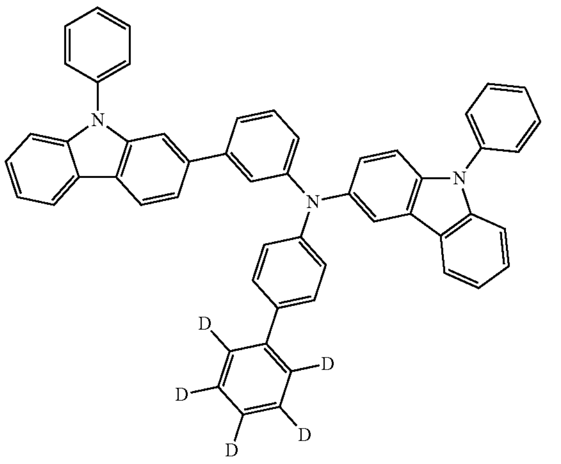

P4-36

In another aspect of the present invention, a compound for an organic electric element represented by Formula 1 above is provided.

In another aspect of the present invention, an organic electric element comprising the compound represented by Formula 1 above is provided.

The organic electric element can comprise a first electrode, a second electrode, and an organic material layer disposed between the first electrode and the second electrode. The organic material layer can comprise the compound represented by Formula 1. The compound represented Formula 1 can be contained in at least one layer of a hole injection layer, a hole transport layer, an emission-auxiliary layer and a light emitting layer of the organic material layer. That is, the compound represented by Formula 1 may be used as a material in the hole injection layer, a material in the hole transport layer, a material in the emission-auxiliary layer, or a material in the light emitting layer, preferably, as a material a hole transport layer and/or an emission-auxiliary layer.

Specifically, the organic electric element comprising the organic material layer comprising at least one of the compounds represented by Formula 2 to 23 is provided, and more specifically, the organic electric element comprising the organic material layer comprising at least one of the compounds P1-1 to P1-112, P2-1 to P2-112, P3-1 to P3-39 and P4-1 to P4-36 is provided.

Furthermore, the compounds comprising of an organic material layer can be one kind or two or more different kinds of the compounds represented by Formula 1 above. For example, a hole transport layer and/or an emission-auxiliary layer of an organic material layer may be formed as a single kind, 2 or more different kinds of individual compounds P1-1 or P1-2, or 3 or more different kinds of compound P1-1, P1-2 and P1-3.

In another aspect of the present invention, the present invention provides an organic electric element further including at least a layer to improve luminescence efficiency which is formed on at least one of the sides the first and second electrodes, which is opposite to the organic material layer.

Hereinafter, Synthesis Examples of the inventive compound represented by Formula 1 above and Preparation Examples of an organic electric element will be described in detail by way of example. However, the following examples are only for illustrative purposes and are not intended to limit the scope of the invention.

SYNTHESIS EXAMPLE

The final product of the present invention can be synthesized by reaction of Sub 1 and Sub 2 as illustrated in the following Reaction Scheme 1, but the present invention is not limited to the following examples.

<Reaction Scheme 1>

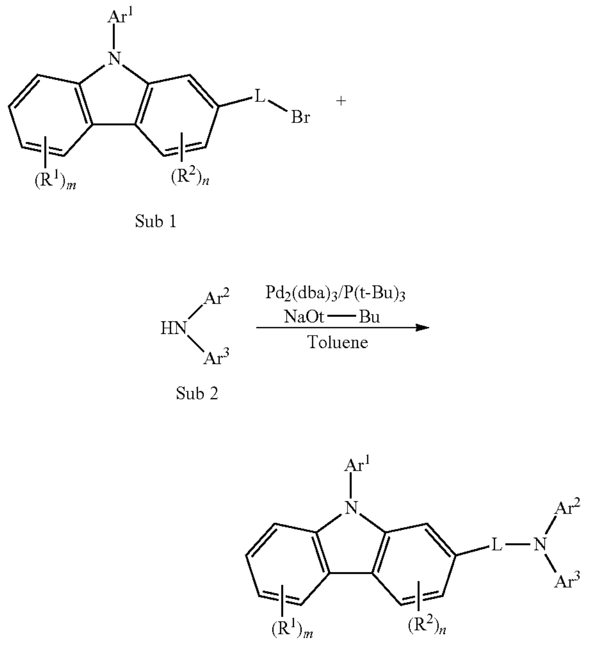

Sub 1

Sub 2

Final Products

I. Synthesis Example of Sub 1

Sub 1 of the Reaction Scheme 1 can be synthesized according to, but not limited to, the following Reaction Scheme 2.

<Reaction Scheme 2>

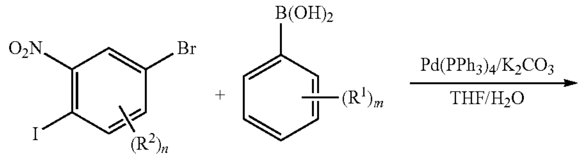

-continued

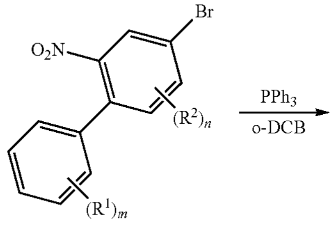

Sub 1-I

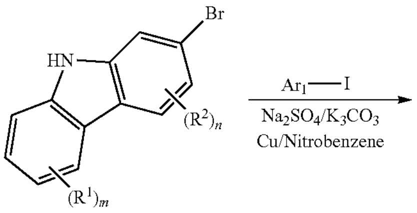

Sub 1-II

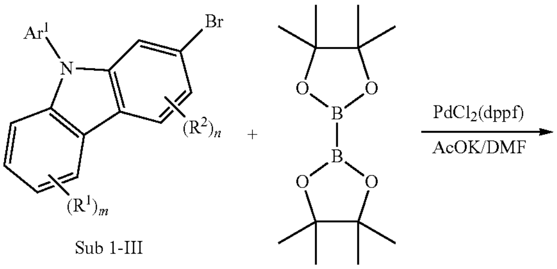

Sub 1-III

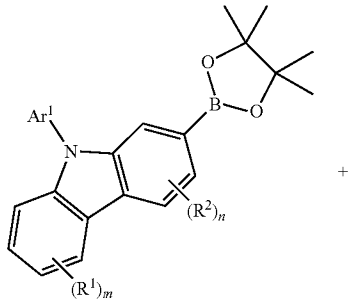

Sub 1-IV

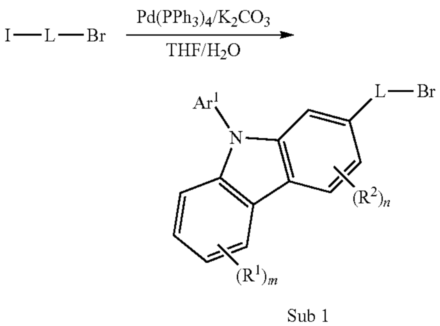

Sub 1

1. Synthesis Example of Sub 1-1

(1) Synthesis of Sub 1-I-1

<Reaction Scheme 3>

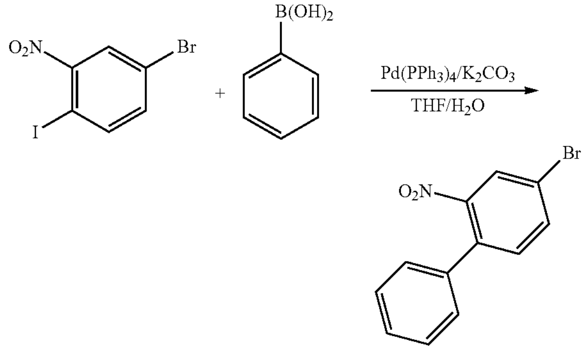

Sub 1-I-1

Phenylboronic acid (76.84 g, 630.2 mmol) was dissolved in THF (2780 ml) in a round bottom flask. Then, 4-bromo-1-iodo-2-nitrobenzene (309.96 g, 945.3 mmol), $Pd(PPh_3)_4$ (36.41 g, 31.5 mmol), $K_2CO_3$ (261.3 g, 1890.6 mmol) and water (1390 ml) were added into the round bottom flask, and the mixture was stirred at 80° C. After the completion of the reaction, the reaction product was extracted with $CH_2Cl_2$ and water. The extracted organic layer was dried over $MgSO_4$ and concentrated. The concentrated resultant was separated by silica gel column chromatography, and was then recrystallized, whereby a compound Sub 1-I-1 was obtained in an amount of 122.68 g in 70% yield.

(2) Synthesis of Sub 1-II-1

<Reaction Scheme 4>

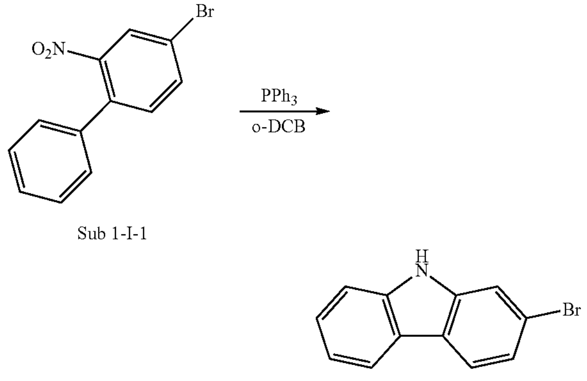

Sub 1-I-1

Sub 1-II-1

The compound Sub 1-I-1 (122.68 g, 441.1 mmol) obtained above was dissolved in o-dichlorobenzene (1810 ml) in a round bottom flask. Then, triphenylphosphine (289.26 g, 1102.8 mmol) was added into the round bottom flask, and the mixture was stirred at 200° C. After the completion of the reaction, o-dichlorobenzene from the reaction product was removed by distillation and the reaction product was extracted with $CH_2Cl_2$ and water. The extracted organic layer was dried over $MgSO_4$ and concentrated. The concentrated resultant was separated by silica gel column chromatography, and was then recrystallized, whereby a compound Sub 1-II-1 was obtained in an amount of 80.34 g in 74% yield.

(3) Synthesis of Sub 1-III-1

<Reaction Scheme 5>

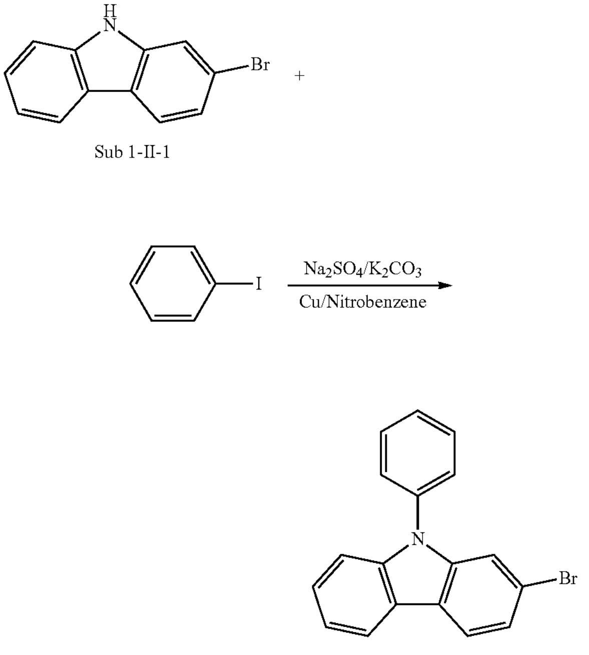

Sub 1-II-1

Sub 1-III-1

The compound Sub 1-II-1 (80.34 g, 326.5 mmol) obtained above was dissolved in nitrobenzene (653 ml) in a round bottom flask. Then, iodobenzene (99.9 g, 489.7 mmol), $Na_2SO_4$ (46.37 g, 326.5 mmol), $K_2CO_3$ (45.12 g, 326.5 mmol) and Cu (6.22 g, 97.9 mmol) were added into the round bottom flask, and the mixture was stirred at 200° C. After the completion of the reaction, nitrobenzene from the reaction product was removed by distillation and the reaction product was extracted with $CH_2Cl_2$ and water. The extracted organic layer was dried over $MgSO_4$ and concentrated. The concentrated resultant was separated by silica gel column chromatography, and was then recrystallized, whereby a compound Sub 1-III-1 was obtained in an amount of 76.78 g in 73% yield.

(4) Synthesis of Sub 1-IV-1

<Reaction Scheme 6>

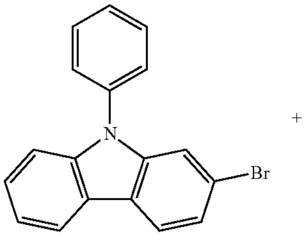

Sub 1-III-1

-continued

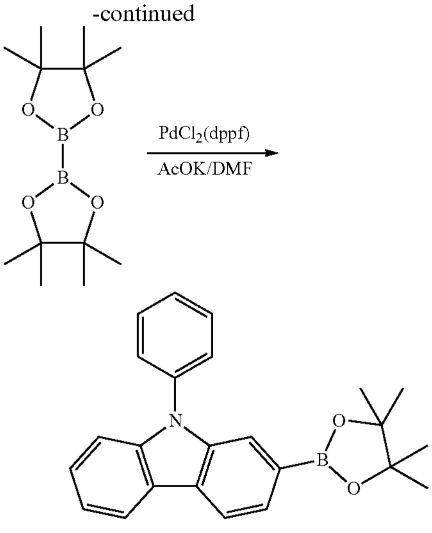

Sub 1-IV-1

The compound Sub 11-III-1 (76.78 g, 238.3 mmol) obtained above was dissolved in DMF in a round bottom flask. Then, bis(pinacolato)diboron (66.57 g, 262.1 mmol), $Pd(dppf)Cl_2$ (5.84 g, 7.1 mmol) and KOAc (70.16 g, 714.9 mmol) were added into the round bottom flask, and the mixture was stirred at 90° C. After the completion of the reaction, DMF from the reaction product was removed by distillation and the reaction product was extracted with $CH_2Cl_2$ and water. The extracted organic layer was dried over $MgSO_4$ and concentrated. The concentrated resultant was separated by silica gel column chromatography, and was then recrystallized, whereby a compound Sub 1-IV-1 was obtained in an amount of 73.92 g in 84% yield.

(5) Synthesis of Sub 1-1

<Reaction Scheme 7>

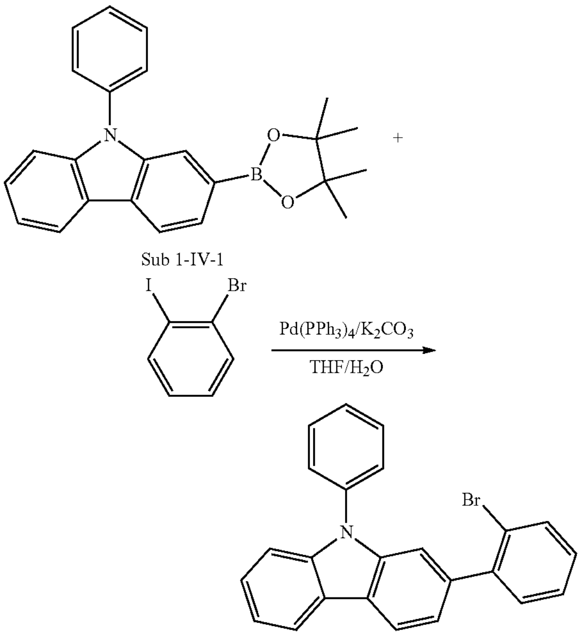

Sub 1-1

The compound Sub 1-IV-1 (73.92 g, 200.2 mmol) obtained above was dissolved in THF (880 ml) in a round bottom flask. Then, 1-bromo-2-iodobenzene (85.0 g, 300.3 mmol), $Pd(PPh_3)_4$ (11.6 g, 10 mmol), $K_2CO_3$ (83 g, 600.6 mmol) and water (440 mL) were added into the round bottom flask, and the mixture was stirred at 80° C. After the completion of the reaction, the reaction product was extracted with $CH_2Cl_2$ and water. The extracted organic layer was dried over $MgSO_4$ and concentrated. The concentrated resultant was separated by silica gel column chromatography, and was then recrystallized, whereby a compound Sub 1-1 was obtained in an amount of 55.8 g in 70% yield.

2. Synthesis Examples of Sub 1-7

(1) Synthesis of Sub 1-I-7

<Reaction Scheme 8>

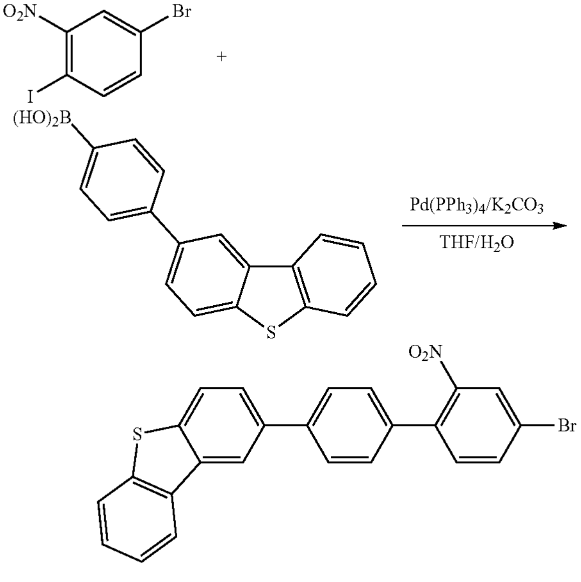

Sub 1-I-7

The compound Sub 1-I-7 was synthesized by using (4-(dibenzo[b,d]thiophen-2-yl)phenyl)boronic acid (95.8 g, 315.1 mmol), THF (1390 ml), 4-bromo-1-iodo-2-nitrobenzene (155 g, 472.7 mmol), $Pd(PPh_3)_4$ (18.2 g, 15.8 mmol), $K_2CO_3$ (130.7 g, 945.3 mmol) and water (695 ml) in the same manner as described in the synthesis method of the compound Sub 1-I-1 above, whereby a compound Sub 1-I-7 was obtained in an amount of 103 g in 71% yield.

(2) Synthesis of Sub 1-II-7

<Reaction Scheme 9>

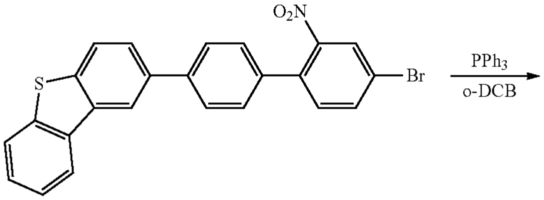

Sub 1-I-7

-continued

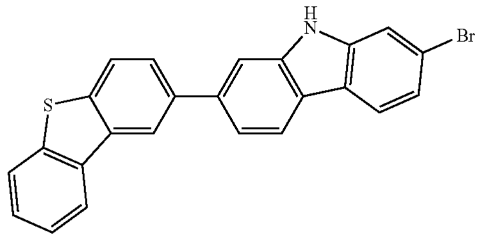

Sub 1-II-7

The compound Sub 1-II-7 was synthesized by using Sub 1-I-7 (103 g, 223.7 mmol), o-dichlorobenzene (917 ml), and triphenylphosphine (146.7 g, 559.3 mmol) in the same manner as described in the synthesis method of the compound Sub 1-II-1 above, whereby a compound Sub 1-II-7 was obtained in an amount of 69 g in 72% yield.

(3) Synthesis of Sub 1-III-7

<Reaction Scheme 10>

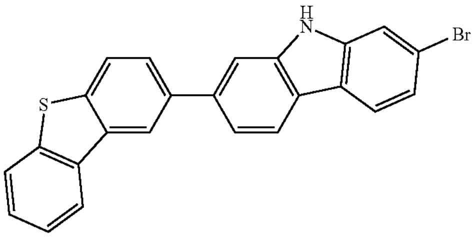

+

Sub 1-II-7

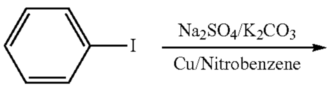

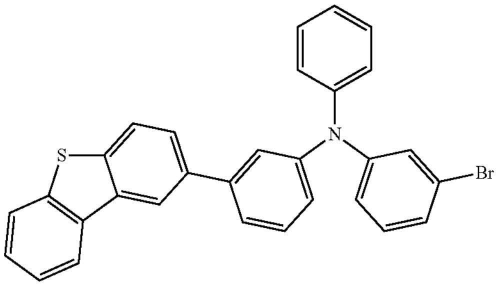

Sub 1-III-7

The compound Sub 1-III-7 was synthesized by using Sub 1-II-7 (69 g, 161.1 mmol), nitrobenzene (322 ml), iodobenzene (49.4 g, 242 mmol), $Na_2SO_4$ (22.9 g, 161.1 mmol), $K_2CO_3$ (22.3 g, 161.1 mmol) and Cu (3.1 g, 48.3 mmol) in the same manner as described in the synthesis method of the compound Sub 1-III-1 above, whereby a compound Sub 1-III-7 was obtained in an amount of 57 g in 70% yield.

(4) Synthesis of Sub 1-IV-7

<Reaction Scheme 11>

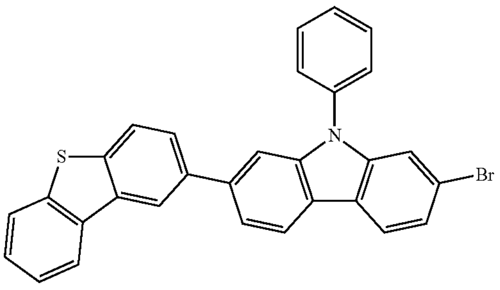

+

Sub 1-III-7

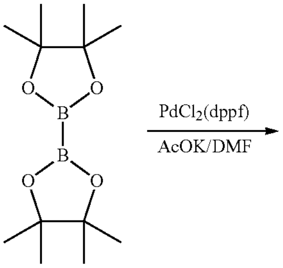

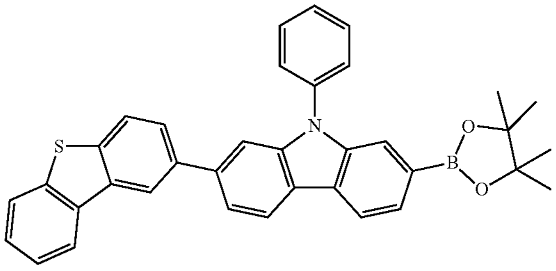

Sub 1-IV-7

The compound Sub 1-IV-7 was synthesized by using Sub 1-III-7 (57 g, 113 mmol), DMF (712 ml), Bis(pinacolato) diboron (31.6 g, 124.3 mmol), $Pd(dppf)Cl_2$ (2.8 g, 3.4 mmol) and KOAc (33.3 g, 339 mmol) in the same manner as described in the synthesis method of the compound Sub 1-IV-1 above, whereby a compound Sub 1-IV-7 was obtained in an amount of 49.2 g in 79% yield.

(5) Synthesis of Sub 1-7

<Reaction Scheme 12>

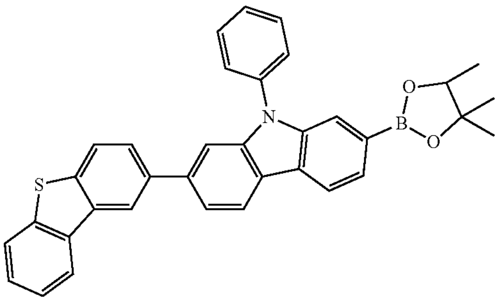

+

Sub 1-IV-7

-continued

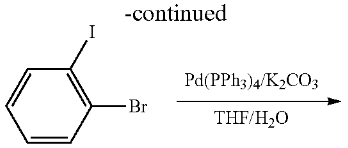

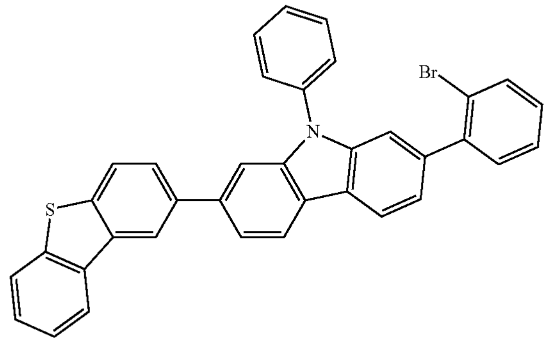

Sub 1-7

The compound Sub 1-7 was synthesized by using Sub 1-IV-7 (49.2 g, 89.2 mmol), 1-bromo-2-iodobenzene (39.9 g, 134 mmol), $Pd(PPh_3)_4$ (5.2 g, 4.5 mmol), $K_2CO_3$ (37 g, 268 mmol), THF (392 ml) and water (196 ml) in the same manner as described in the synthesis method of the compound Sub 1-1 above, whereby a compound Sub 1-7 was obtained in an amount of 35.7 g in 69% yield.

3. Synthesis Examples of Sub 1-13

(1) Synthesis of Sub 1-III-13

<Reaction Scheme 13>

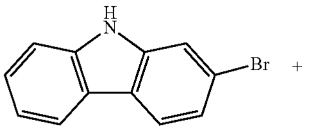

Sub 1-II-1

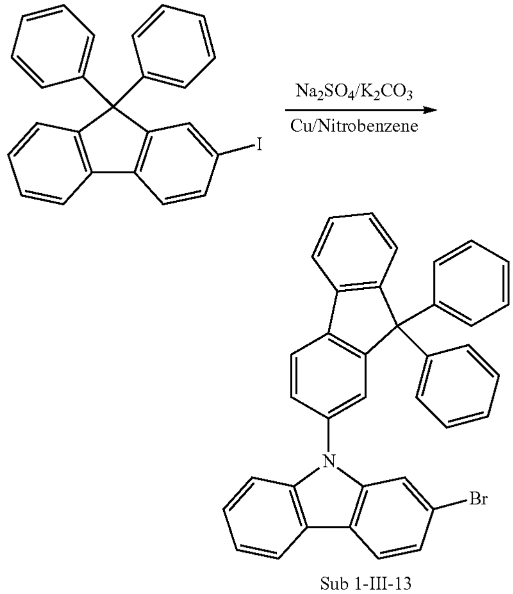

Sub 1-III-13

The compound Sub 1-III-13 was synthesized by using Sub 1-II-1 (70 g, 284.4 mmol), nitrobenzene (570 ml), 2-iodo-9,9-diphenyl-9H-fluorene (189.6 g, 426.7 mmol), $Na_2SO_4$ (40.4 g, 284.4 mmol), $K_2CO_3$ (39.3 g, 284.4 mmol) and Cu (5.42 g, 85.3 mmol) in the same manner as described in the synthesis method of the compound Sub 1-III-1 above, whereby a compound Sub 1-III-13 was obtained in an amount of 108.8 g in 68% yield.

(2) Synthesis of Sub 1-IV-13

<Reaction Scheme 14>

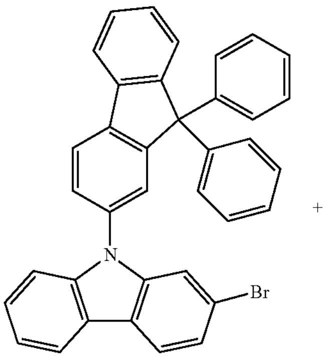

Sub 1-III-13

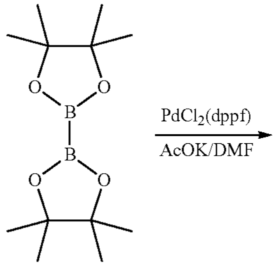

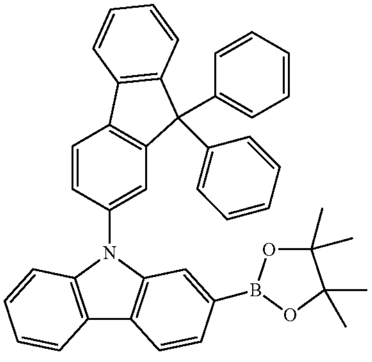

Sub 1-IV-13

The compound Sub 1-IV-13 was synthesized by using (108.8 g, 193.4 mmol), DMF (1220 ml), Bis(pinacolato) diboron (54.0 g, 212.76 mmol), $Pd(dppf)Cl_2$ (4.73 g, 5.8 mmol) and KOAc (56.94 g, 580.3 mmol) in the same manner as described in the synthesis method of the compound Sub 1-IV-1 above, whereby a compound Sub 1-IV-13 was obtained in an amount of 86.1 g in 73% yield.

(3) Synthesis of Sub 1-13

<Reaction Scheme 15>

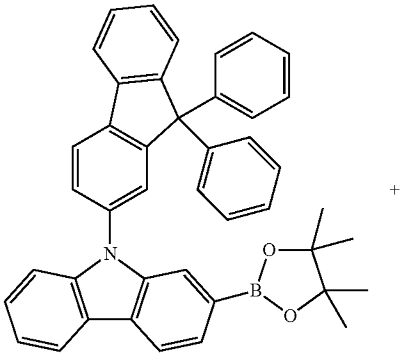

Sub 1-IV-13

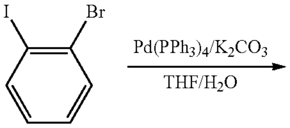

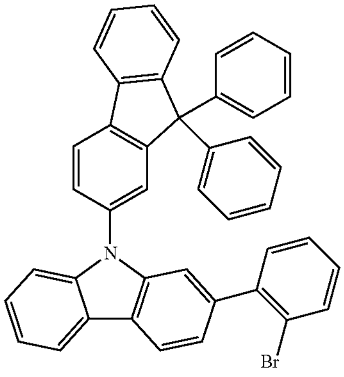

Sub 1-13

The compound Sub 1-13 was synthesized by using Sub 1-IV-13 (86.1 g, 141.2 mmol), THF (620 ml), 1-bromo-2-iodobenzene (59.9 g, 211.9 mmol), $Pd(PPh_3)_4$ (8.2 g, 7.06 mmol), $K_2CO_3$ (58.6 g, 423.7 mmol) and water (310 ml) in the same manner as described in the synthesis method of the compound Sub 1-1 above, whereby a compound Sub 1-13 was obtained in an amount of 58.6 g in 65% yield.

4. Synthesis of Sub 1-14

(1) Synthesis of Sub 1-III-14

<Reaction Scheme 16>

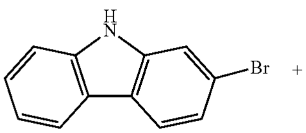

Sub 1-II-1

-continued

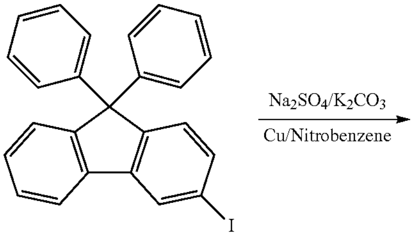

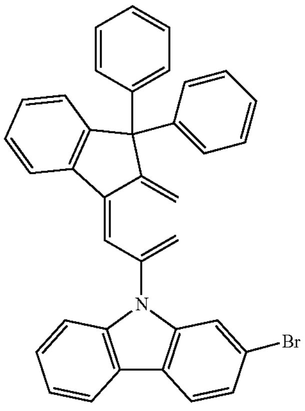

Sub 1-III-14

The compound Sub 1-III-14 was synthesized by using Sub 1-II-1 (63 g, 255.9 mmol), nitrobenzene (512 ml), 3-iodo-9,9-diphenyl-9H-fluorene (170.6 g, 383.9 mmol), $Na_2SO_4$ (36.4 g, 256 mmol), $K_2CO_3$ (35.4 g, 256 mmol) and Cu (4.88 g, 76.8 mmol) in the same manner as described in the synthesis method of the compound Sub 1-III-1 above, whereby a compound Sub 1-III-14 was obtained in an amount of 99.3 g in 69% yield.

(2) Synthesis of Sub 1-IV-14

<Reaction Scheme 17>

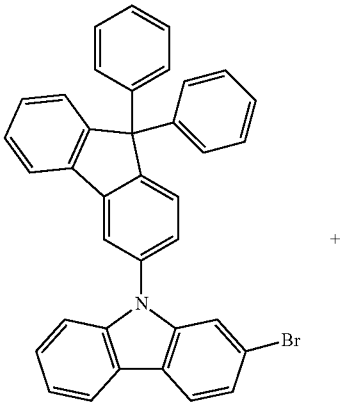

Sub 1-III-14

-continued

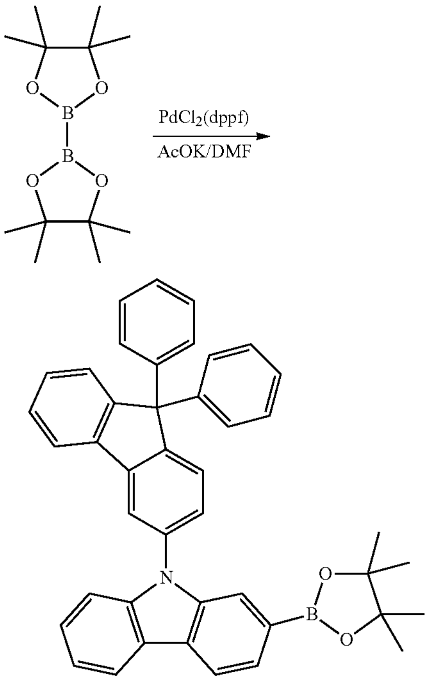

Sub 1-IV-14

The compound Sub 1-IV-14 was synthesized by using Sub 1-III-14 (99.3 g, 193.4 mmol), DMF (1110 ml), Bis(pinacolato)diboron (49.3 g, 194.2 mmol), Pd(dppf)$Cl_2$ (4.32 g, 5.3 mmol) and KOAc (52 g, 529.6 mmol) in the same manner as described in the synthesis method of the compound Sub 1-IV-1 above, whereby a compound Sub 1-IV-14 was obtained in an amount of 80.7 g in 75% yield.

(3) Synthesis of Sub 1-14

<Reaction Scheme 18>

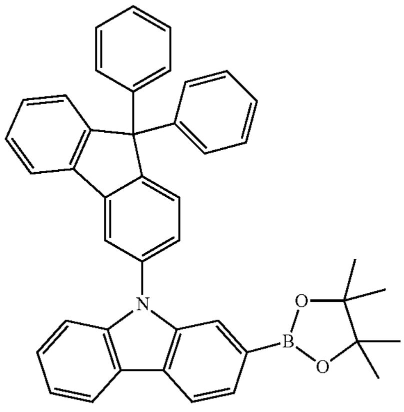

+

Sub 1-IV-14

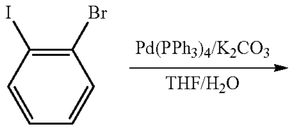

-continued

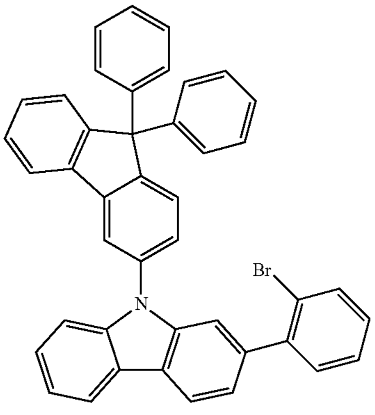

Sub 1-14

The compound Sub 1-14 was synthesized by using Sub 1-IV-14 (80.7 g, 132.3 mmol), THF (582 ml), 1-bromo-2-iodobenzene (56.2 g, 198.6 mmol), $Pd(PPh_3)_4$ (7.65 g, 6.62 mmol), $K_2CO_3$ (54.9 g, 397.2 mmol) and water (291 ml) in the same manner as described in the synthesis method of the compound Sub 1-1 above, whereby a compound Sub 1-14 was obtained in an amount of 52.4 g in 62% yield.

5. Synthesis of Sub 1-17

(1) Synthesis of Sub 1-III-17

<Reaction Scheme 19>

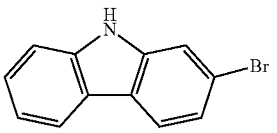

+

Sub 1-II-1

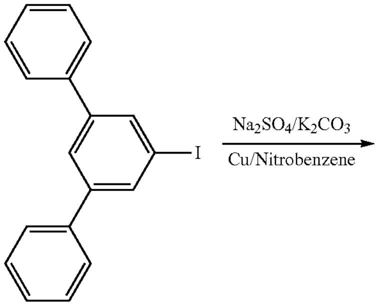

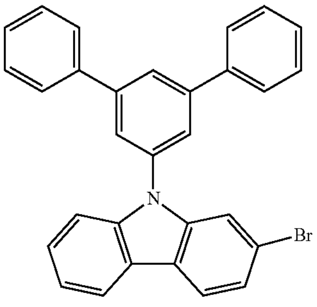

Sub 1-III-17

The compound Sub 1-III-17 was synthesized by using Sub 1-II-1 (60 g, 244 mmol), nitrobenzene (487 ml), 5'-iodo- 1,1':3',1"-terphenyl (130.3 g, 365.7 mmol), $Na_2SO_4$ (34.6 g, 244 mmol), $K_2CO_3$ (33.7 g, 244 mmol) and Cu (4.65 g, 73.1 mmol) in the same manner as described in the synthesis method of the compound Sub 1-III-1 above, whereby a compound Sub 1-III-17 was obtained in an amount of 82.1 g in 71% yield.

(2) Synthesis of Sub 1-IV-17

<u><Reaction Scheme 20></u>

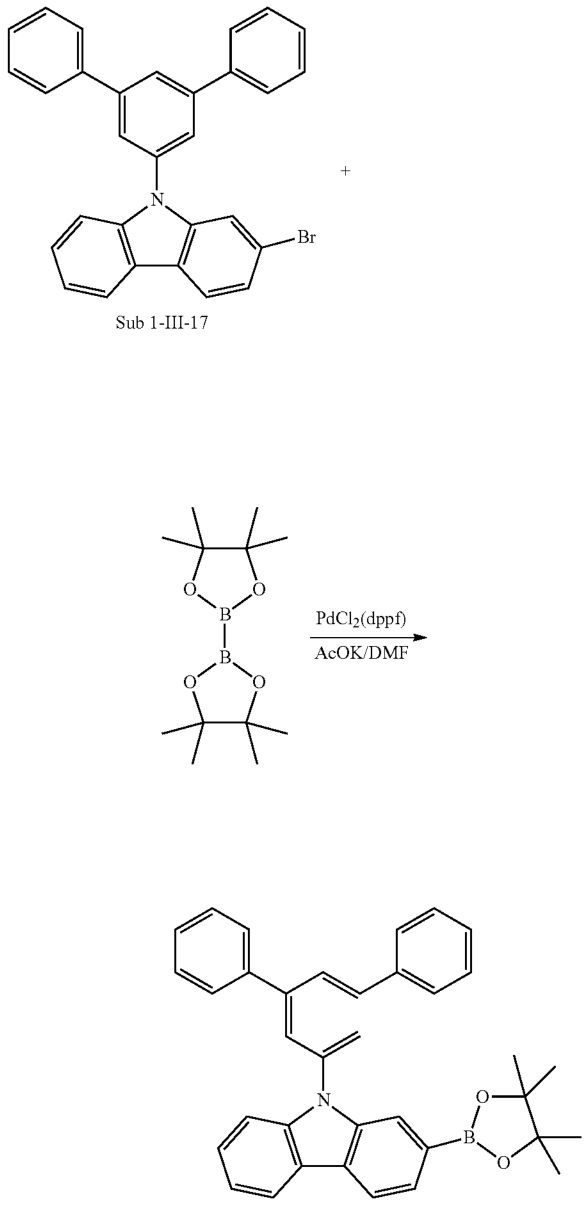

Sub 1-III-17

Sub 1-IV-17

The compound Sub 1-IV-17 was synthesized by using Sub 1-III-17 (82.1 g, 173.1 mmol), DMF (1090 ml), Bis(pinacolato)diboron (48.3 g, 190.4 mmol), $Pd(dppf)Cl_2$ (4.24 g, 5.2 mmol) and KOAc (51 g, 519.2 mmol) in the same manner as described in the synthesis method of the compound Sub 1-IV-1 above, whereby a compound Sub 1-IV-17 was obtained in an amount of 65.9 g in 73% yield.

(3) Synthesis of Sub 1-17

<u><Reaction Scheme 21></u>

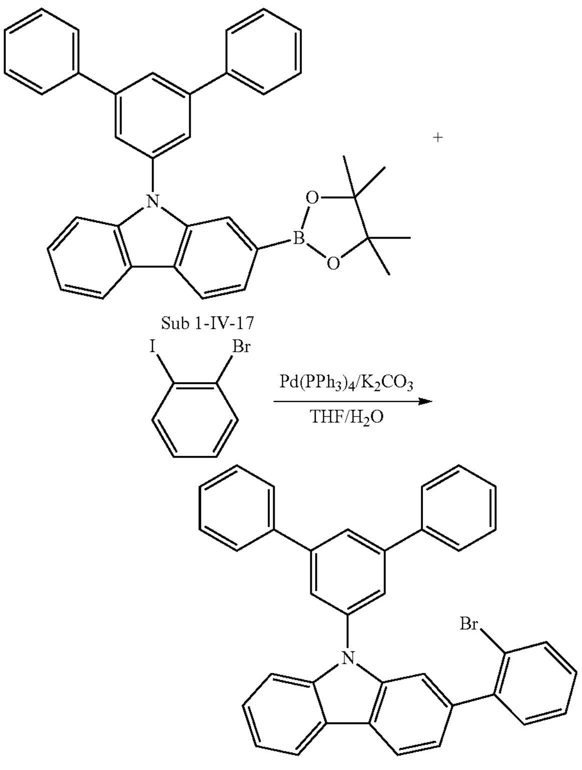

Sub 1-IV-17

Sub 1-17

The compound Sub 1-17 was synthesized by using Sub 1-IV-17 (65.9 g, 126.4 mmol), THF (556 ml), 1-bromo-2-iodobenzene (53.8 g, 190 mmol), $Pd(PPh_3)_4$ (7.3 g, 6.32 mmol), $K_2CO_3$ (52.4 g, 319.1 mmol) and water (278 ml) in the same manner as described in the synthesis method of the compound Sub 1-1 above, whereby a compound Sub 1-17 was obtained in an amount of 45.2 g in 65% yield.

6. Synthesis of Sub 1-32

(1) Synthesis of Sub 1-I-32

<u><Reaction Scheme 22></u>

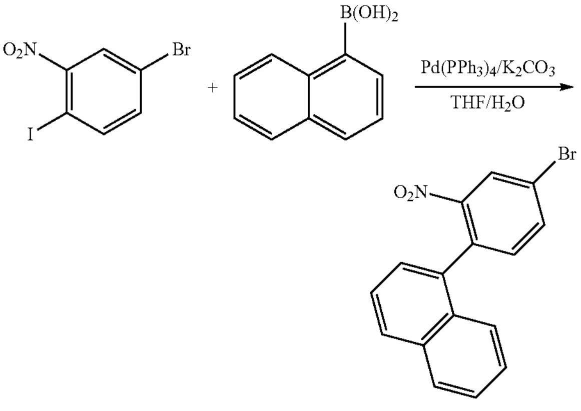

Sub 1-I-32

The compound Sub 1-I-32 was synthesized by using naphthalen-1-ylboronic acid (70 g, 407 mmol), THF (1790 ml), 4-bromo-1-iodo-2-nitrobenzene (200 g, 610.5 mmol), $Pd(PPh_3)_4$ (23.5 g, 20.35 mmol), $K_2CO_3$ (168.8 g, 1221 mmol) and water (895 ml) in the same manner as described in the synthesis method of the compound Sub 1-I-1 above, whereby a compound Sub 1-I-32 was obtained in an amount of 94.8 g in 71% yield.

(2) Synthesis of Sub 1-II-32

<Reaction Scheme 23>

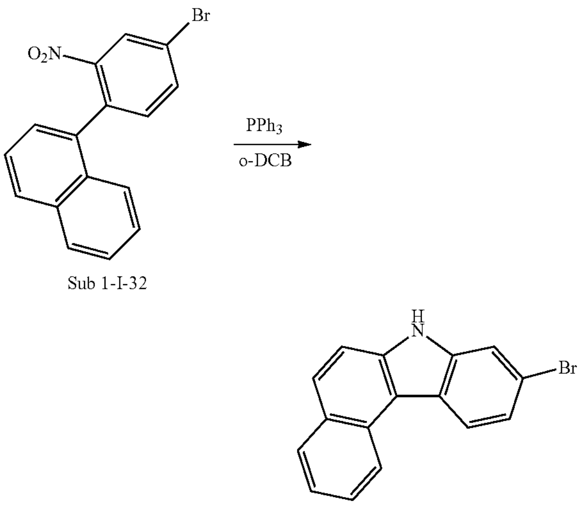

Sub 1-I-32

Sub 1-II-32

The compound Sub 1-II-32 was synthesized by using Sub 1-I -32 (94.8 g, 288.9 mmol), o-dichlorobenzene (1184 ml) and triphenylphosphine (189.4 g, 722.2 mmol) in the same manner as described in the synthesis method of the compound Sub 1-II-1 above, whereby a compound Sub 1-II-32 was obtained in an amount of 61.2 g in 75% yield.

(3) Synthesis of Sub 1-III-32

<Reaction Scheme 24>

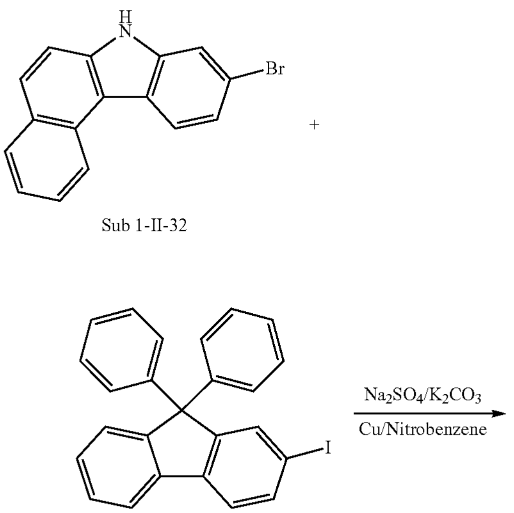

Sub 1-II-32

-continued

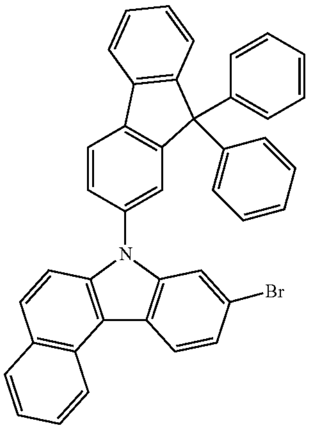

Sub 1-III-32

The compound Sub 1-III-32 was synthesized by using Sub 1-II-32 (61.2 g, 206.6 mmol), nitrobenzene (413 ml), 2-iodo-9,9-diphenyl-9H-fluorene (137.7 g, 310 mmol), $Na_2SO_4$ (29.35 g, 206.6 mmol), $K_2CO_3$ (28.6 g, 206.6 mmol) and Cu (3.9 g, 62 mmol) in the same manner as described in the synthesis method of the compound Sub 1-III-1 above, whereby a compound Sub 1-III-32 was obtained in an amount of 89.86 g in 71% yield.

(4) Synthesis of Sub 1-IV-32

<Reaction Scheme 25>

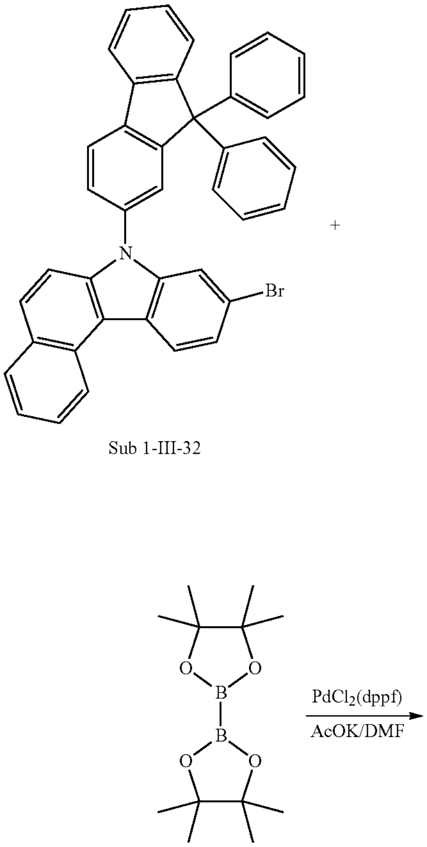

Sub 1-III-32

-continued

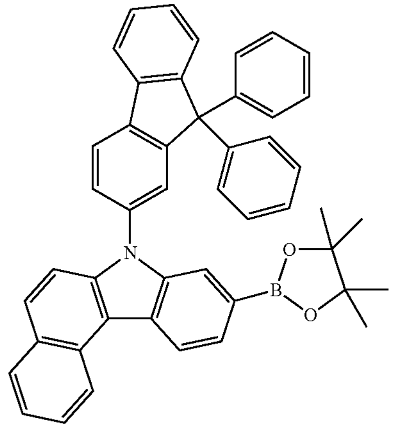

Sub 1-IV-32

The compound Sub 1-IV-32 was synthesized by using Sub 1-III-32 (89.86 g, 146.7 mmol), DMF (924 ml), Bis(pinacolato)diboron (41 g, 161.4 mmol), Pd(dppf)$Cl_2$ (3.59 g, 4.4 mmol) and KOAc (43.2 g, 440.1 mmol) in the same manner as described in the synthesis method of the compound Sub 1-IV-1 above, whereby a compound Sub 1-IV-32 was obtained in an amount of 74.5 g in 77% yield.

(5) Synthesis of Sub 1-32

<Reaction Scheme 26>

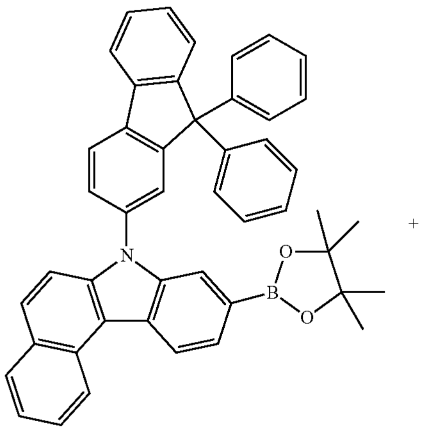

Sub 1-IV-32

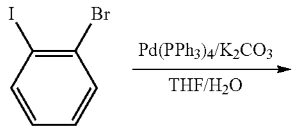

-continued

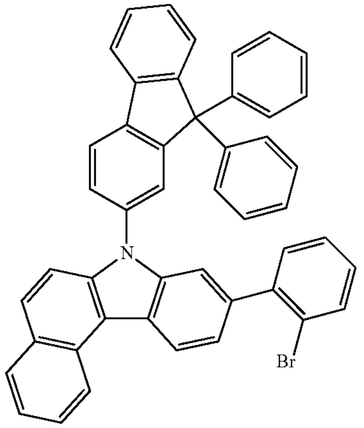

Sub 1-32

The compound Sub Sub 1-32 was synthesized by using Sub 1-IV-32 (74.5 g, 112.9 mmol), THF (496 ml), 2-iodobenzene (47.9 g, 169.4 mmol), $Pd(PPh_3)_4$ (6.53 g, 5.65 mmol), $K_2CO_3$ (46.8 g, 338.8 mmol) and water (248 ml) in the same manner as described in the synthesis method of the compound Sub 1-1 above, whereby a compound Sub Sub 1-32 was obtained in an amount of 47.4 g in 61% yield.

7. Synthesis of 1-34

(1) Synthesis of Sub 1-I-34

<Reaction Scheme 27>

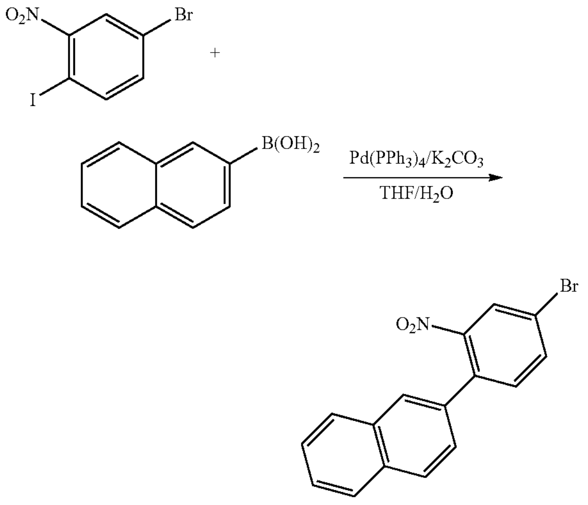

Sub 1-I-34

The compound Sub 1-I-34 was synthesized by using naphthalen-2-ylboronic acid (70 g, 407 mmol), THF (1790 ml), 4-bromo-1-iodo-2-nitrobenzene (200 g, 610.5 mmol), $Pd(PPh_3)_4$ (23.5 g, 20.35 mmol), $K_2CO_3$ (168.8 g, 1221 mmol) and water (895 ml) in the same manner as described in the synthesis method of the compound Sub 1-I-1 above, whereby a compound Sub 1-I-34 was obtained in an amount of 97.5 g in 73% yield.

(2) Synthesis of Sub 1-II-34

<Reaction Scheme 28>

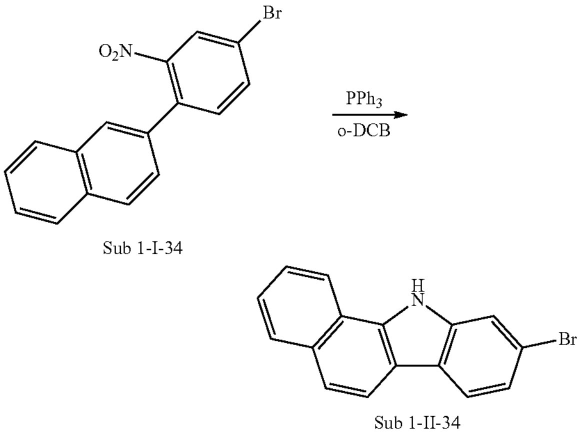

Sub 1-I-34

Sub 1-II-34

The compound Sub 1-II-34 was synthesized by using Sub 1-I-34 (97.5 g, 297.1 mmol), o-dichlorobenzene (1220 ml) and triphenylphosphine (194.8 g, 742.8 mmol) in the same manner as described in the synthesis method of the compound Sub 1-II-1 above, whereby a compound Sub 1-II-34 was obtained in an amount of 65.1 g in 74% yield.

(3) Synthesis of Sub 1-III-34

<Reaction Scheme 29>

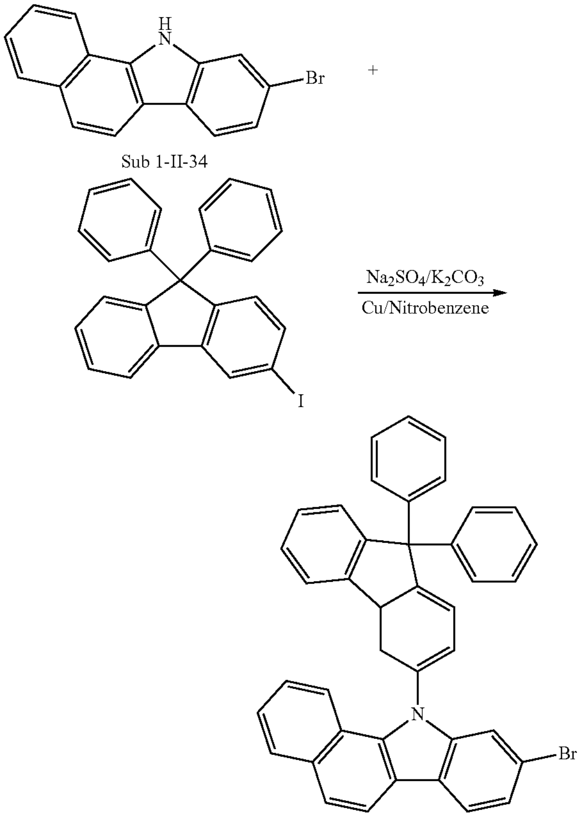

Sub 1-II-34

Sub 1-III-34

The compound Sub 1-III-34 was synthesized by using Sub 1-II-34 (65.1 g, 220 mmol), nitrobenzene (440 ml), 3-iodo-9,9-diphenyl-9H-fluorene (146.5 g, 330 mmol), $Na_2SO_4$ (31.2 g, 220 mmol), $K_2CO_3$ (30.4 g, 220 mmol) and Cu (4.2 g, 66 mmol) in the same manner as described in the synthesis method of the compound Sub 1-III-1 above, whereby a compound Sub 1-III-34 was obtained in an amount of 95.6 g in 71% yield.

(4) Synthesis of Sub 1-IV-34

<Reaction Scheme 30>

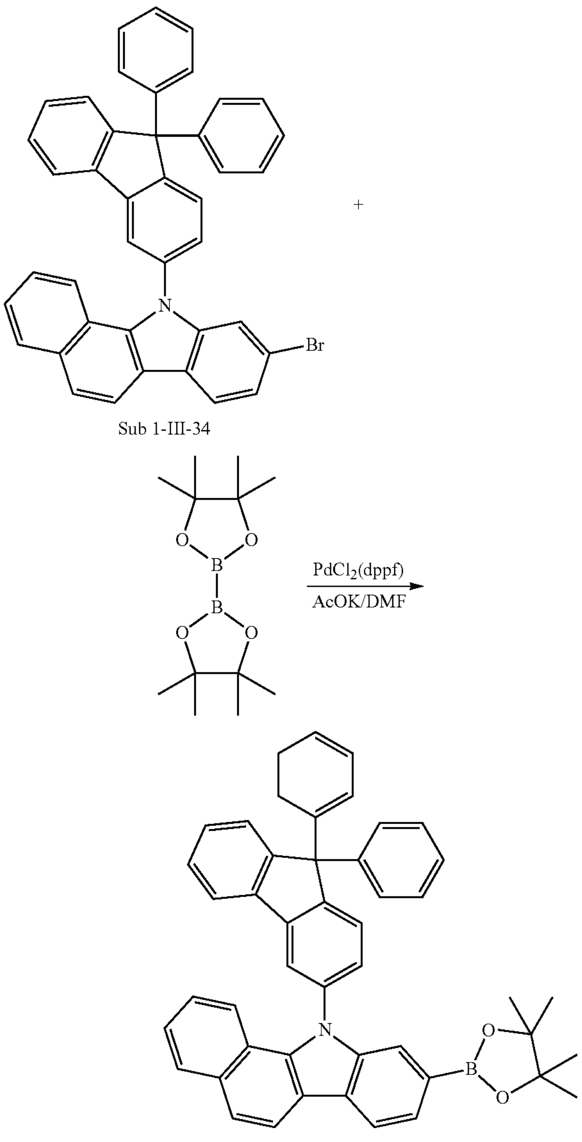

Sub 1-III-34

Sub 1-IV-34

The compound Sub 1-IV-34 was synthesized by using Sub 1-III-34 (95.6 g, 156.1 mmol), DMF (980 ml), Bis(pinacolato)diboron (43.6 g, 171.7 mmol), $Pd(dppf)Cl_2$ (3.82 g, 4.7 mmol) and KOAc (46 g, 468.2 mmol) in the same manner as described in the synthesis method of the compound Sub 1-IV-1 above, whereby a compound Sub 1-IV-34 was obtained in an amount of 77.2 g in 75% yield.

(5) Synthesis of Sub 1-34

<Reaction Scheme 31>

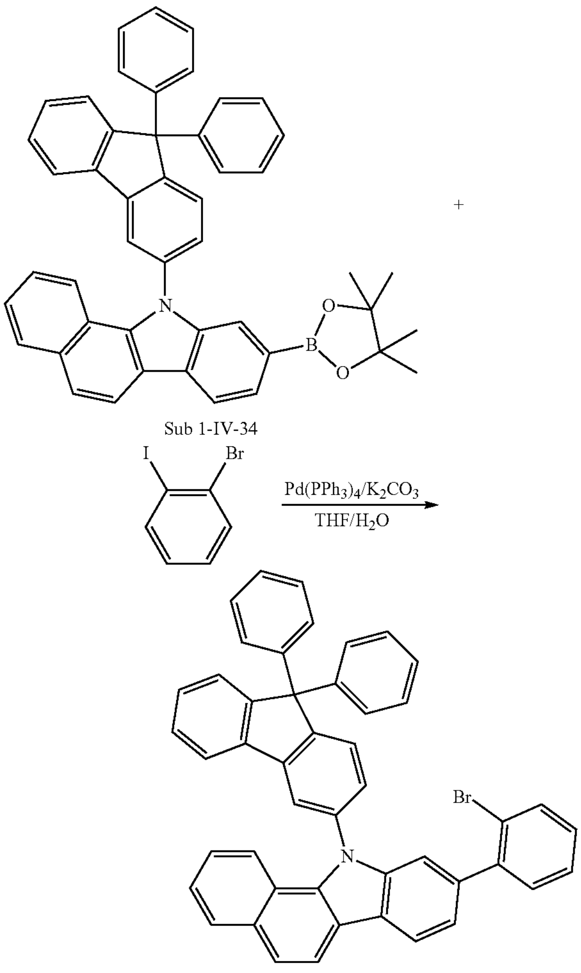

Sub 1-IV-34

Sub 1-34

The compound Sub 1-34 was synthesized by using Sub 1-IV-34 (77.2 g, 117 mmol), THF (510 ml), 1-bromo-2-(49.7 g, 175.6 mmol), $Pd(PPh_3)_4$ (6.76 g, 5.85 mmol), $K_2CO_3$ (48.5 g, 351 mmol) and water (255 ml) in the same manner as described in the synthesis method of the compound Sub 1-1 above, whereby a compound Sub 1-34 was obtained in an amount of 49.1 g in 63% yield.

8. Synthesis of 1-35

(1) Synthesis of Sub 1-I-35

<Reaction Scheme 32>

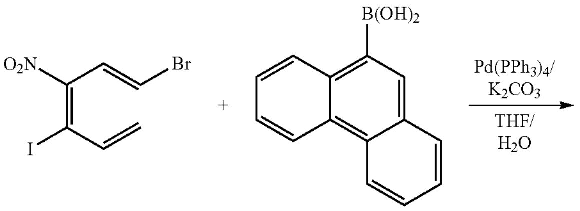

-continued

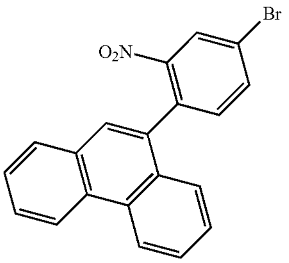

Sub 1-I-35

The compound Sub 1-I-35 was synthesized by using phenanthren-9-ylboronic acid (70 g, 315.2 mmol), THF (1388 ml), 4-bromo-1-iodo-2-nitrobenzene (155.1 g, 472.9 mmol), $Pd(PPh_3)_4$ (18.2 g, 15.8 mmol), $K_2CO_3$ (130.7 g, 945.7 mmol) and water (694 ml) in the same manner as described in the synthesis method of the compound Sub 1-I-1 above, whereby a compound Sub 1-I-35 was obtained in an amount of 85.8 g in 72% yield.

(2) Synthesis of Sub 1-II-35

<Reaction Scheme 33>

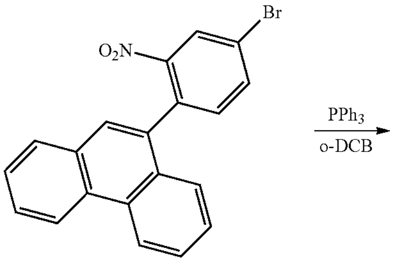

Sub 1-I-35

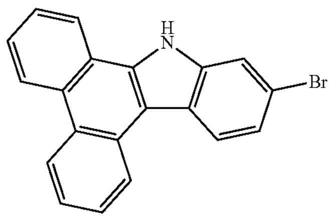

Sub 1-II-35

The compound Sub 1-II-35 was synthesized by using Sub 1-I-35 (85.8 g, 226.9 mmol), o-dichlorobenzene (930 ml) and triphenylphosphine (148.8 g, 567.1 mmol) in the same manner as described in the synthesis method of the compound Sub 1-II-1 above, whereby a compound Sub 1-II-35 was obtained in an amount of 60.5 g in 77% yield.

(3) Synthesis of Sub 1-III-35

<Reaction Scheme 34>

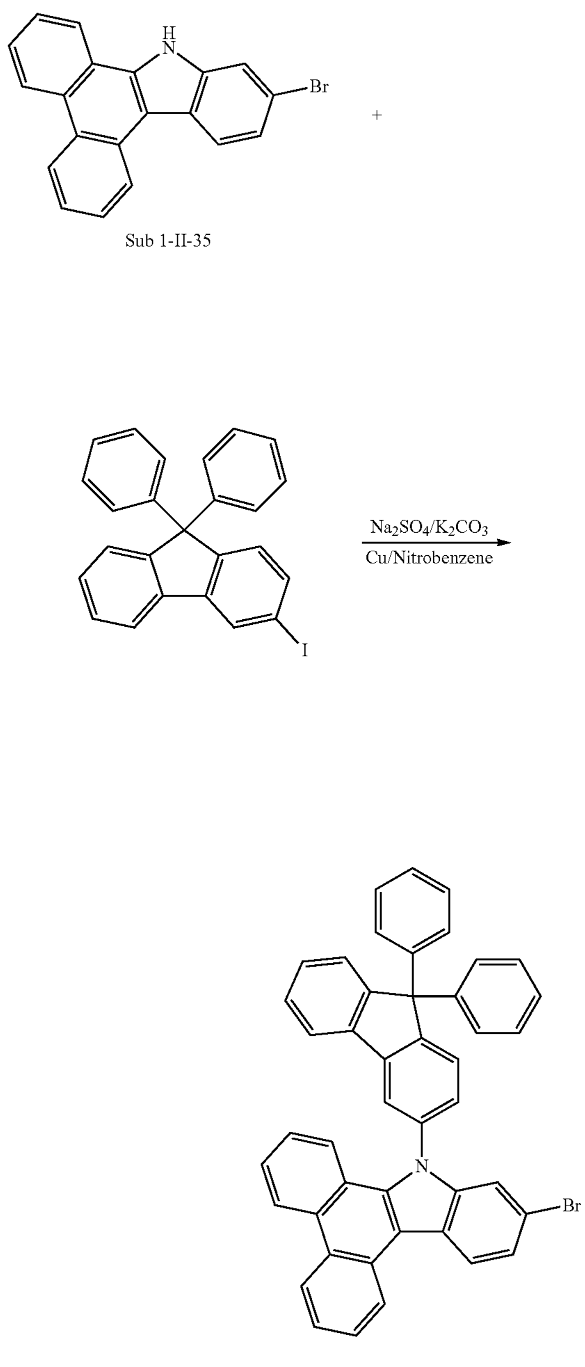

Sub 1-III-35

The compound Sub 1-III-35 was synthesized by using Sub 1-II-35 (60.5 g, 174.7 mmol), nitrobenzene (350 ml), 3-iodo-9,9-diphenyl-9H-fluorene (116.5 g, 262.1 mmol), $Na_2SO_4$ (24.8 g, 174.7 mmol), $K_2CO_3$ (24.2 g, 174.7 mmol) and Cu (3.33 g, 52.4 mmol) in the same manner as described in the synthesis method of the compound Sub 1-III-1 above, whereby a compound Sub 1-III-35 was obtained in an amount of 84.5 g in 73% yield.

(4) Synthesis of Sub 1-IV-35

<Reaction Scheme 35>

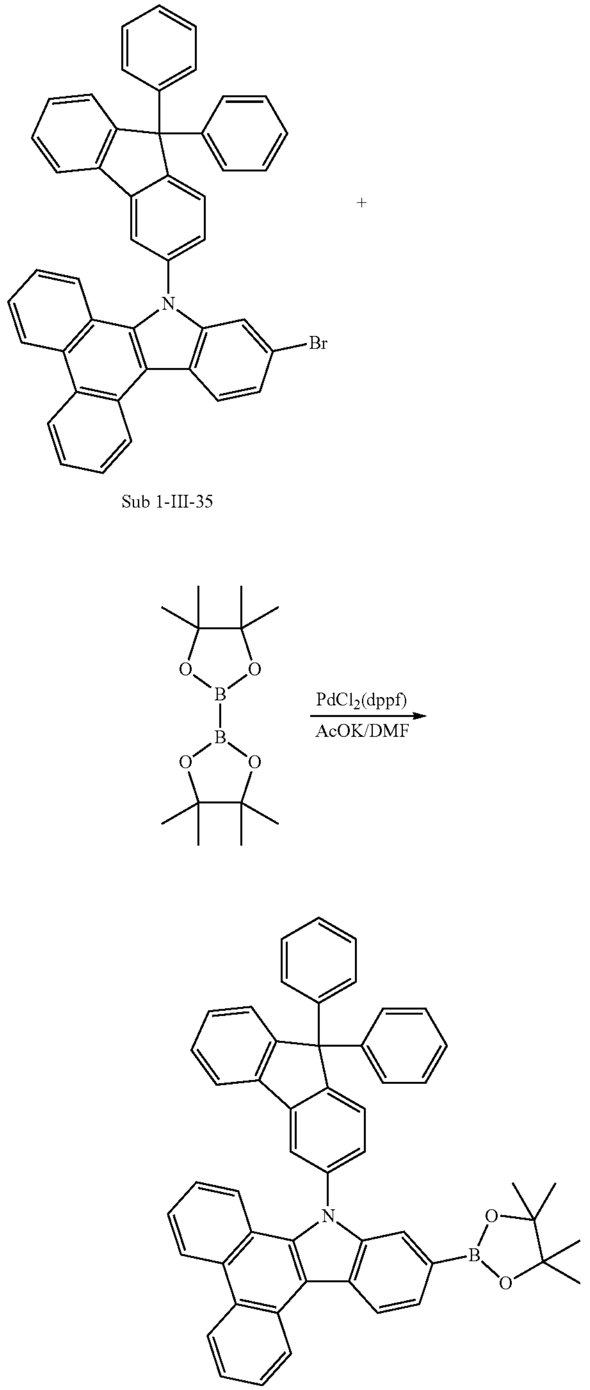

Sub 1-IV-35

The compound Sub 1-IV-35 was synthesized by using Sub 1-III-35 (84.5 g, 127.5 mmol), DMF (854 ml), Bis(pinacolato)diboron (35.6 g, 140.3 mmol), $Pd(dppf)Cl_2$ (3.12 g, 3.82 mmol) and KOAc (37.5 g, 382.5 mmol) in the same manner as described in the synthesis method of the compound Sub 1-IV-1 above, whereby a compound Sub 1-IV-35 was obtained in an amount of 70.6 g in 78% yield.

(5) Synthesis of Sub 1-35

<Reaction Scheme 36>

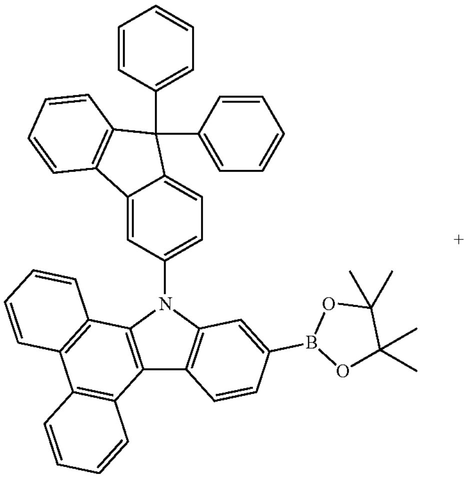

Sub 1-IV-35

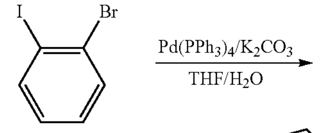

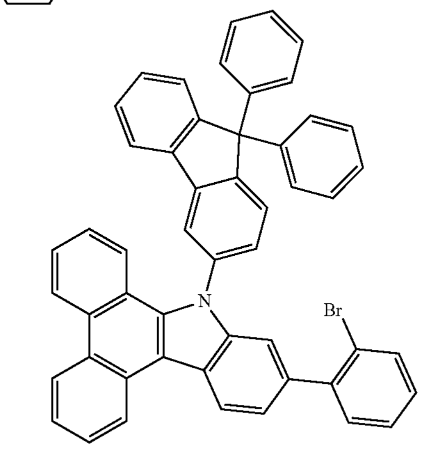

Sub 1-35

The compound Sub 1-IV-35 (70.6 g, 99.5 mmol), THF (438 ml), 1-bromo-2-iodobenzene (42.2 g, 149.2 mmol), $Pd(PPh_3)_4$ (5.75 g, 4.97 mmol), $K_2CO_3$ (41.2 g, 298.4 mmol) and water (219 ml) in the same manner as described in the synthesis method of the compound Sub 1-1 above, whereby a compound Sub 1-35 was obtained in an amount of 45.6 g in 62% yield.

9. Synthesis of Sub 1-44

(1) Synthesis of Sub 1-III-44

<Reaction Scheme 37>

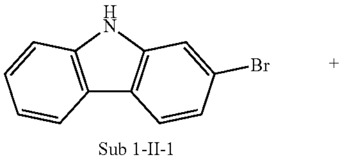

Sub 1-II-1

-continued

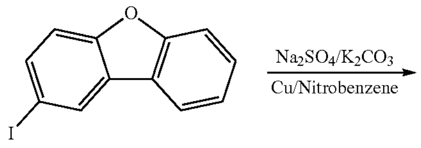

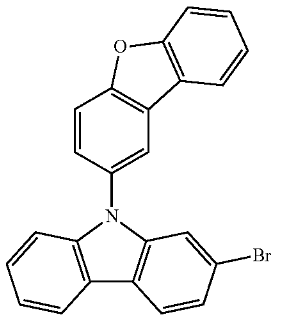

Sub 1-III-44

The compound Sub 1-III-44 was synthesized by using Sub 1-II-1 (60 g, 244 mmol), nitrobenzene (487 ml), 2-iododibenzo[b,d]furan (107.6 g, 365.7 mmol), $Na_2SO_4$ (34.6 g, 244 mmol), $K_2CO_3$ (33.7 g, 244 mmol) and Cu (4.65 g, 73.1 mmol) in the same manner as described in the synthesis method of the compound Sub 1-III-1 above, whereby a compound Sub 1-III-44 was obtained in an amount of 68.4 g in 68% yield.

(2) Synthesis of Sub 1-IV-44

<Reaction Scheme 38>

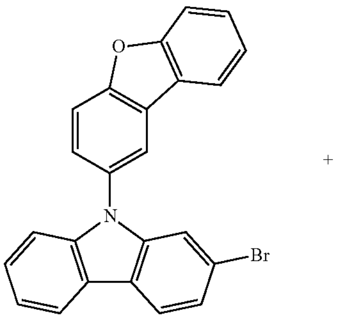

Sub 1-III-44

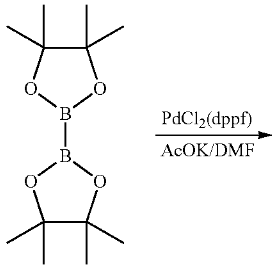

-continued

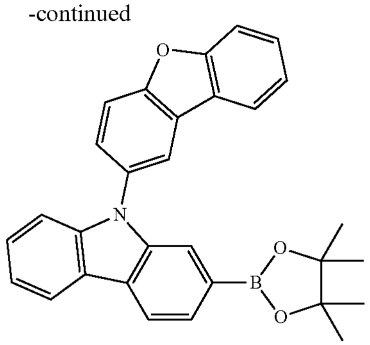

Sub 1-IV-44

The compound Sub 1-IV-44 was synthesized by using Sub 1-III-44 (68.4 g, 166 mmol), DMF (1045 ml), Bis(pinacolato)diboron (46.3 g, 182.5 mmol), $Pd(dppf)Cl_2$ (4.06 g, 5 mmol) and KOAc (48.8 g, 497.7 mmol) in the same manner as described in the synthesis method of the compound Sub 1-IV-1 above, whereby a compound Sub 1-IV-44 was obtained in an amount of 56.4 g in 74% yield.

(3) Synthesis of Sub 1-44

<Reaction Scheme 39>

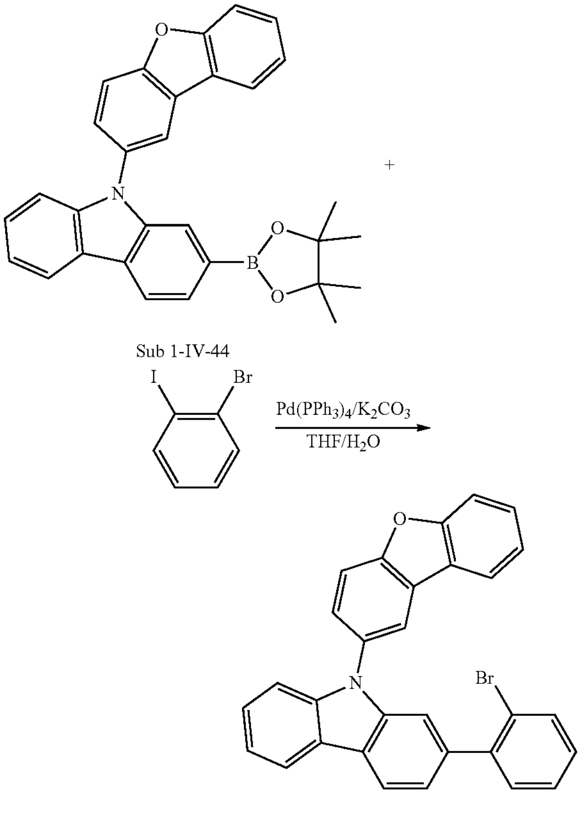

Sub 1-IV-44

Sub 1-44

The compound Sub 1-44 was synthesized by using Sub 1-IV-44 (56.4 g, 122.8 mmol), THF (540 ml), 1-bromo-2-iodobenzene (52.1 g, 184 mmol), $Pd(PPh_3)_4$ (7.1 g, 6.14 mmol), $K_2CO_3$ (50.9 g, 368.4 mmol) and water (270 ml) in the same manner as described in the synthesis method of the compound Sub 1-1 above, whereby a compound Sub 1-44 was obtained in an amount of 17.9 g in 65% yield.

10. Synthesis of Sub 1-54

(1) Synthesis of Sub 1-III-54

<Reaction Scheme 40>

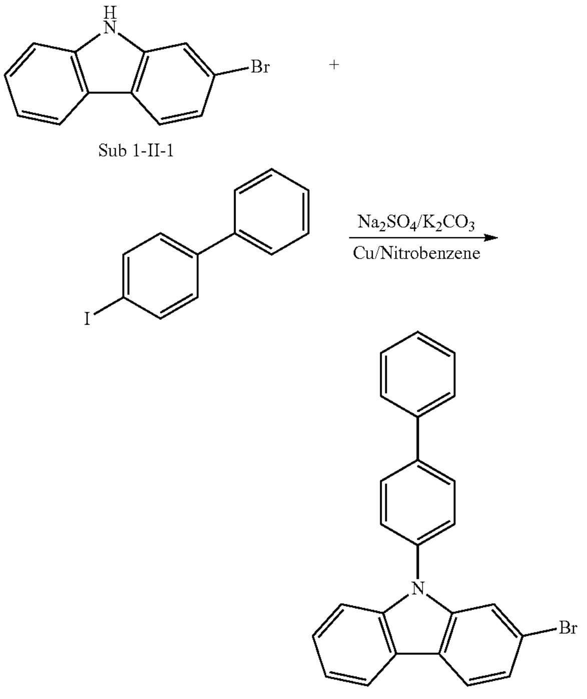

Sub 1-II-1

Sub 1-III-54

The compound Sub 1-III-54 was synthesized by using Sub 1-II-1 (50 g, 203.2 mmol), nitrobenzene (406 ml), 4-iodo-1,1'-biphenyl (85.4 g, 304.7 mmol), $Na_2SO_4$ (28.9 g, 203.2 mmol), $K_2CO_3$ (28.1 g, 203.2 mmol) and Cu (3.87 g, 61 mmol) in the same manner as described in the synthesis method of the compound Sub 1-III-1 above, whereby a compound Sub 1-III-54 was obtained in an amount of 54.2 g in 68% yield.

(2) Synthesis of Sub 1-IV-54

<Reaction Scheme 41>

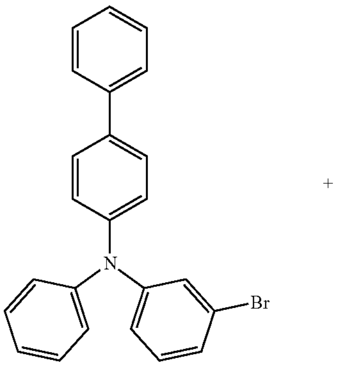

Sub 1-III-54

-continued

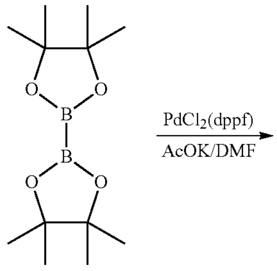

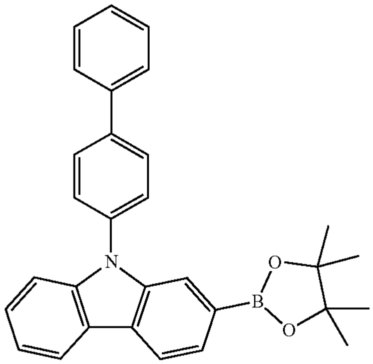

Sub 1-IV-54

The compound Sub 1-IV-54 was synthesized by using Sub 1-III-54 (54.2 g, 136.1 mmol), DMF (857 ml), Bis(pinacolato)diboron (38.0 g, 150 mmol), Pd(dppf)$Cl_2$ (3.33 g, 4.1 mmol) and KOAc (40.1 g, 408 mmol) in the same manner as described in the synthesis method of the compound Sub 1-IV-1 above, whereby a compound Sub 1-IV-54 was obtained in an amount of 42.4 g in 70% yield.

(3) Synthesis of Sub 1-54

<Reaction Scheme 42>

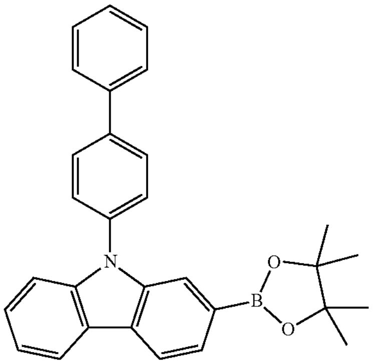

Sub 1-IV-54

+

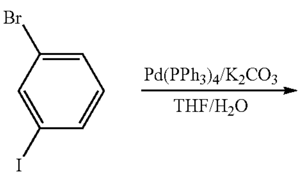

-continued

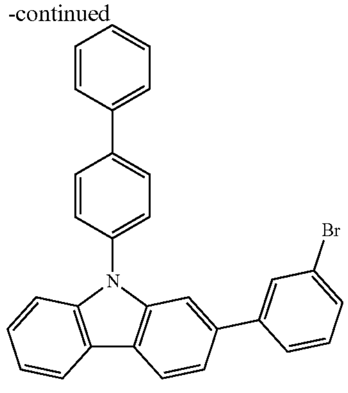

Sub 1-54

The compound Sub 1-54 was synthesized by using Sub 1-IV-54 (42.4 g, 95.2 mmol), THF (418 ml), 1-bromo-3-iodobenzene (40.4 g, 142.8 mmol), $Pd(PPh_3)_4$ (5.5 g, 4.76 mmol), $K_2CO_3$ (39.5 g, 285.6 mmol) and water (209 ml) in the same manner as described in the synthesis method of the compound Sub 1-1 above, whereby a compound Sub 1-54 was obtained in an amount of 30.7 g in 68% yield.

11. Synthesis of Sub 1-66

(1) Synthesis of Sub 1-III-66

<Reaction Scheme 43>

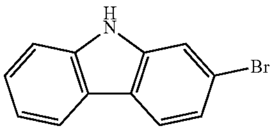

+

Sub 1-II-1

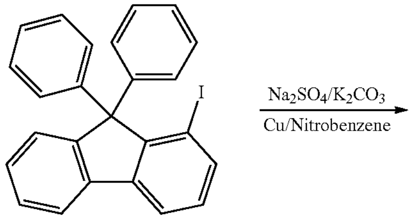

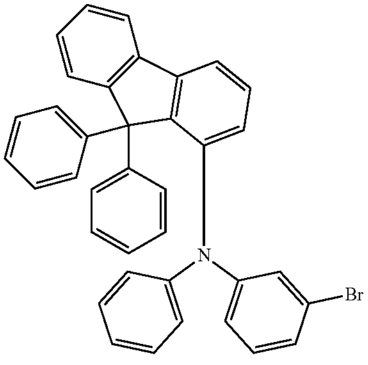

Sub 1-III-66

The compound Sub 1-III-66 was synthesized by using Sub 1-II-1 (50 g, 203.2 mmol), nitrobenzene (406 ml), 1-iodo-9,9-diphenyl-9H-fluorene (135.4 g, 305 mmol), $Na_2SO_4$ (28.9 g, 203.2 mmol), $K_2CO_3$ (28.1 g, 203.2 mmol) and Cu (3.87 g, 61 mmol) in the same manner as described in the synthesis method of the compound Sub 1-III-1 above, whereby a compound Sub 1-III-66 was obtained in an amount of 70.9 g in 62% yield.

(2) Synthesis of Sub 1-IV-66

<Reaction Scheme 44>

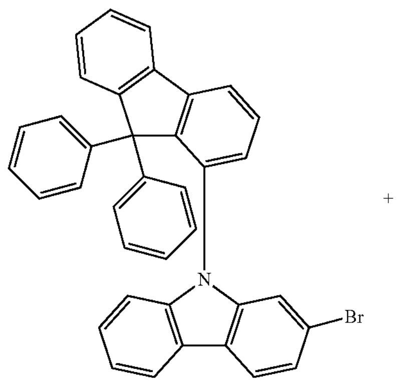

Sub 1-III-66

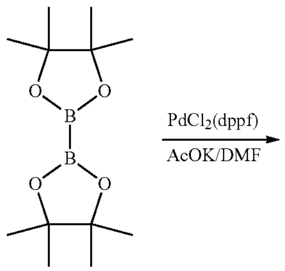

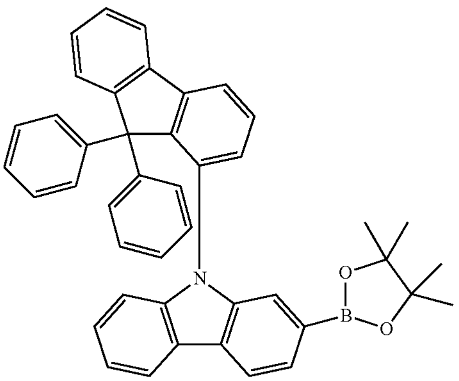

Sub 1-IV-66

The compound Sub 1-IV-66 was synthesized by using Sub 1-III-66 (70.9 g, 126 mmol), DMF (794 ml), Bis(pinacolato) diboron (35.2 g, 138.7 mmol), Pd(dppf)$Cl_2$ (3.09 g, 3.78 mmol) and KOAc (37.11 g, 378.1 mmol) in the same manner as described in the synthesis method of the compound Sub 1-IV-1 above, whereby a compound Sub 1-IV-66 was obtained in an amount of 51.5 g in 67% yield.

(3) Synthesis of Sub 1-66

<Reaction Scheme 45>

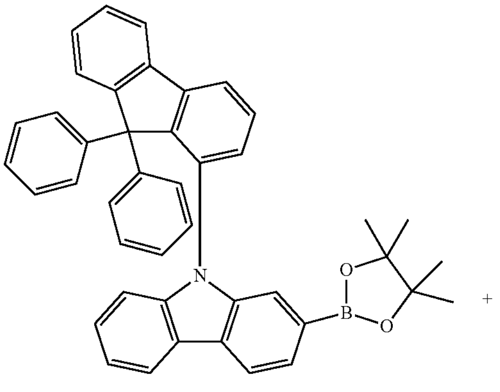

Sub 1-IV-66

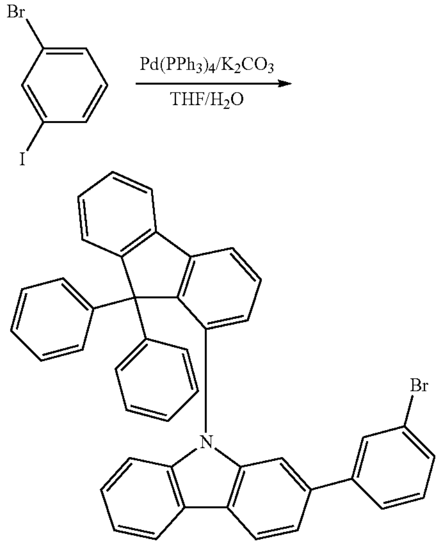

Sub 1-66

The compound Sub Sub 1-66 was synthesized by using Sub 1-IV-66 (51.5 g, 84.5 mmol), THF (370 ml), 1-bromo-3-iodobenzene (35.8 g, 126.7 mmol), $Pd(PPh_3)_4$ (4.88 g, 4.22 mmol), $K_2CO_3$ (35.03 g, 253.5 mmol) and water (185 ml) in the same manner as described in the synthesis method of the compound Sub 1-1 above, whereby a compound Sub Sub 1-66 was obtained in an amount of 33.5 g in 62% yield.

12. Synthesis of Sub 1-103

<Reaction Scheme 46>

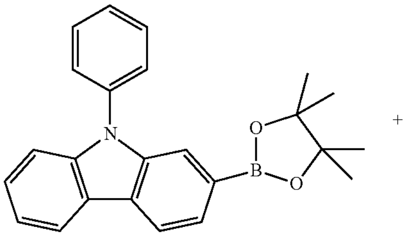

Sub 1-IV-1

-continued

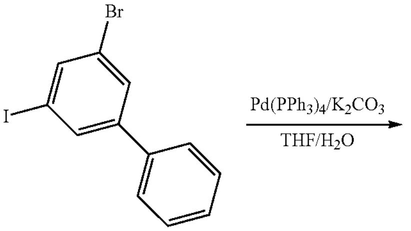

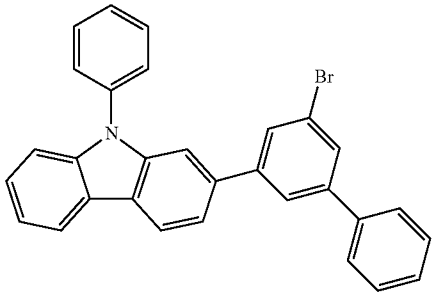

Sub 1-103

The compound Sub 1-103 was synthesized by Sub 1-IV-1 (31.2 g, 84.5 mmol), THF (370 mL), 3-bromo-5-iodo-1,1'-biphenyl (46.8 g, 126.7 mmol), $Pd(PPh_3)_4$ (4.88 g, 4.22 mmol), $K_2CO_3$ (35.03 g, 253.5 mmol) and water (185 mL) in the same manner as described in the synthesis method of the compound Sub 1-1 above, whereby a compound Sub 1-103 was obtained in an amount of 26.1 g in 65% yield.

13. Synthesis of Sub 1-115

<Reaction Scheme 47>

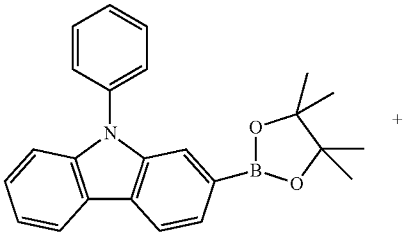

Sub 1-IV-1

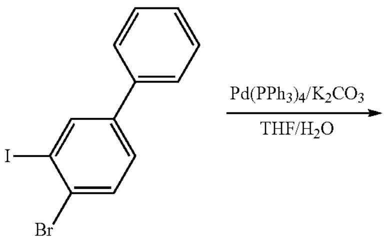

-continued

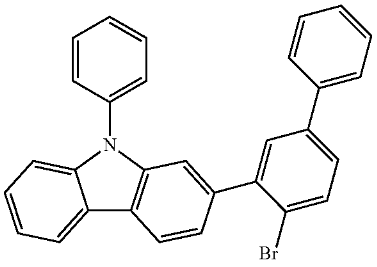

Sub 1-115

The compound Sub 1-115 was synthesized by Sub 1-IV-1 (31.2 g, 84.5 mmol), THF (370 mL), 3-bromo-5-iodo-1,1'-biphenyl (46.8 g, 126.7 mmol), $Pd(PPh_3)_4$ (4.88 g, 4.22 mmol), $K_2CO_3$ (35.03 g, 253.5 mmol) and water (185 mL) in the same manner as described in the synthesis method of the compound Sub 1-1 above, whereby a compound Sub 1-115 was obtained in an amount of 24.5 g in 61% yield.

Examples of Sub 1 compounds include, but are not limited to, the following compounds, and FD-MS (Field Desorption-Mass Spectrometry) data of the compounds are given in Table 1 below.

Sub 1-1

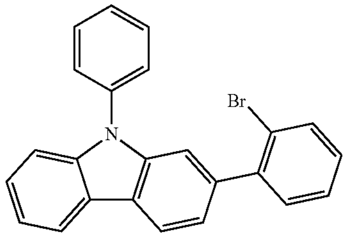

Sub 1-2

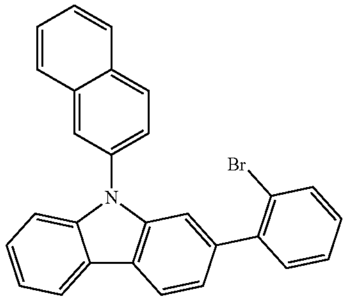

Sub 1-3

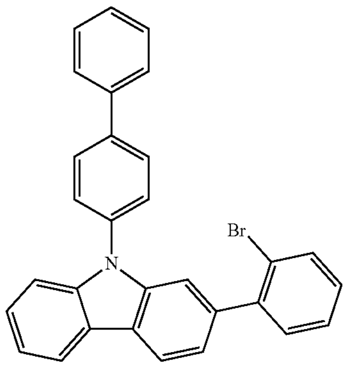

-continued
Sub 1-4
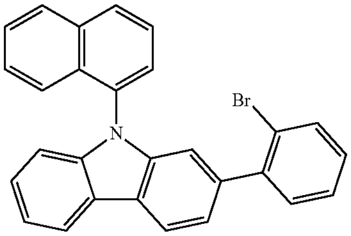
Sub 1-5
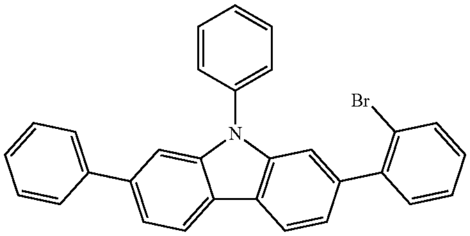
Sub 1-6
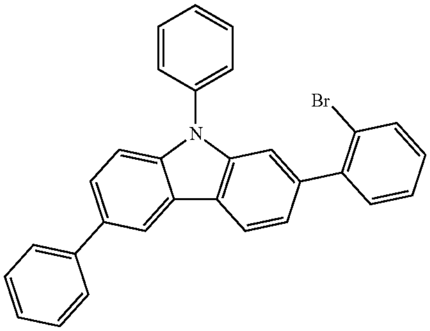
Sub 1-7
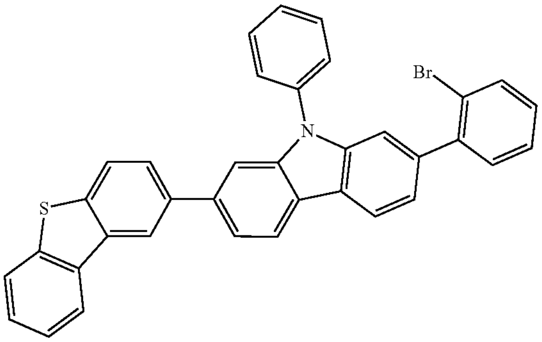
Sub 1-8
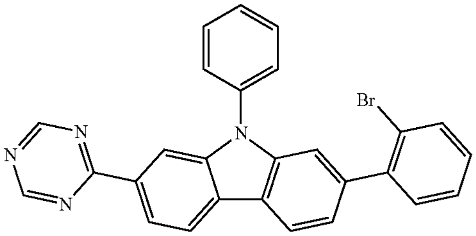
-continued
Sub 1-9
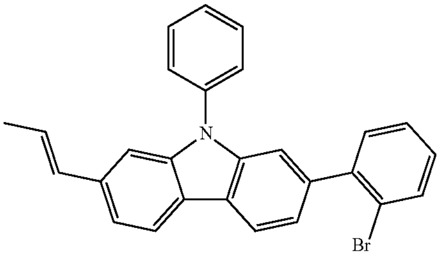
Sub 1-10
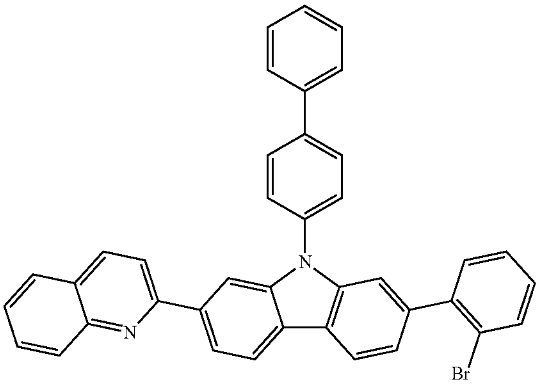
Sub 1-11
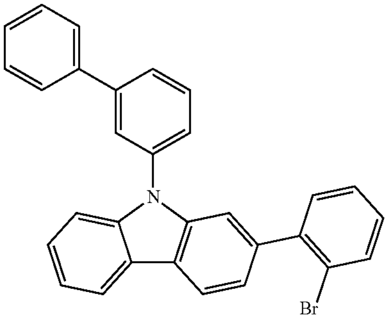
Sub 1-12
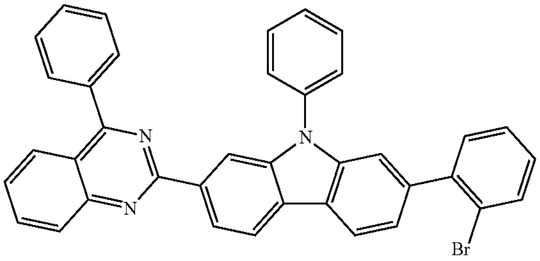

-continued
Sub 1-13
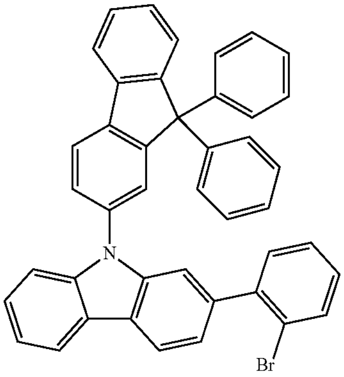
Sub 1-14
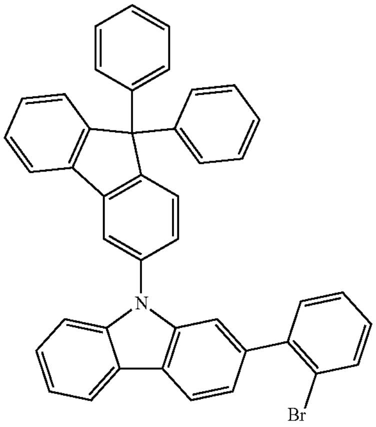
Sub 1-15
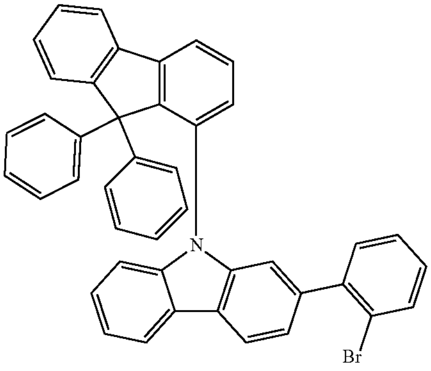
Sub 1-16
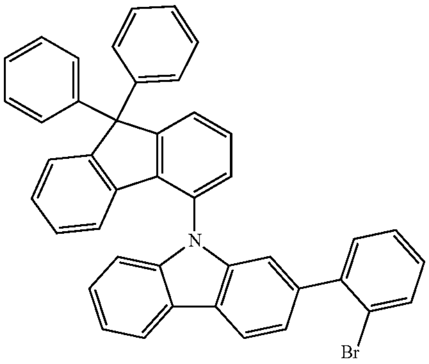
-continued
Sub 1-17
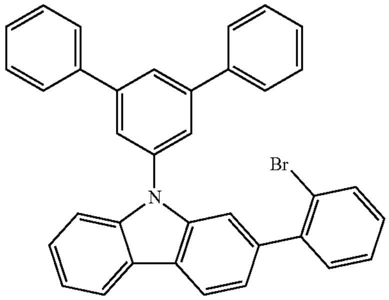
Sub 1-18
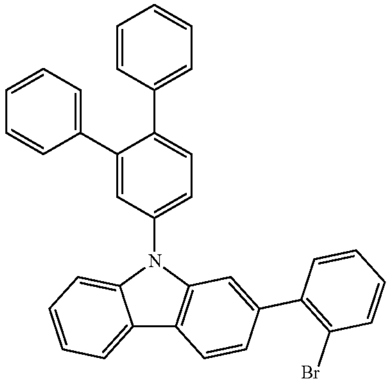
Sub 1-19
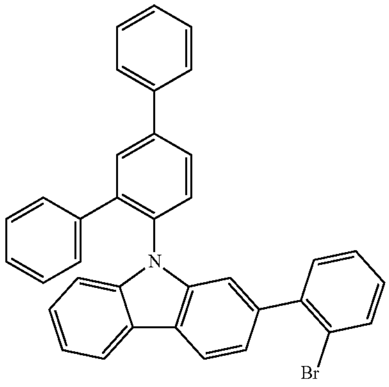
Sub 1-20
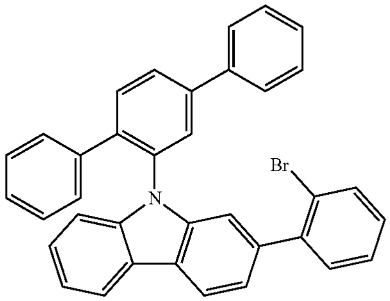

-continued
Sub 1-21
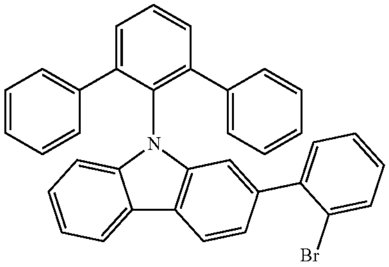
Sub 1-22
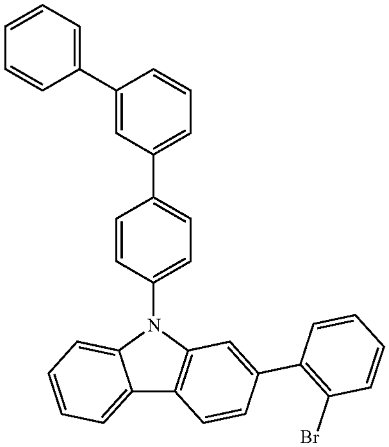
Sub 1-23
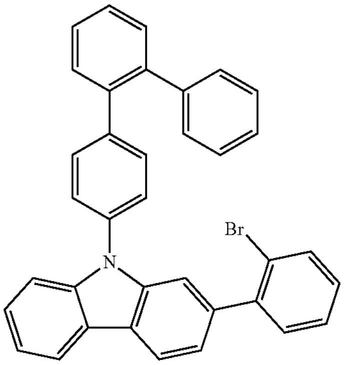
Sub 1-24
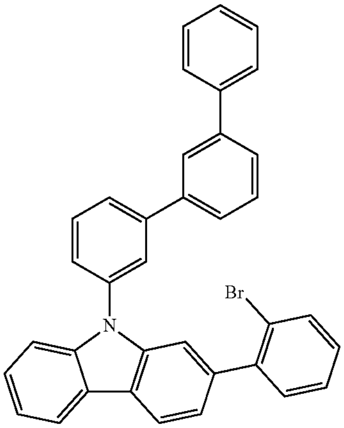
-continued
Sub 1-25
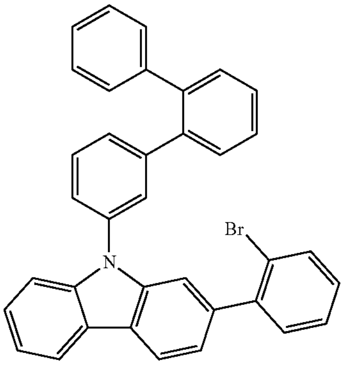
Sub 1-26
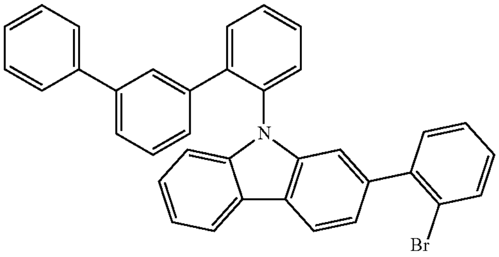
Sub 1-27
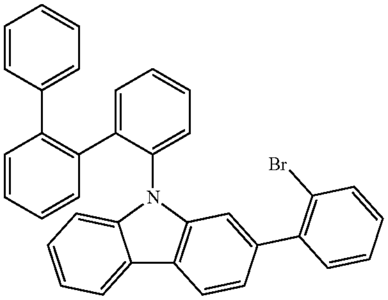
Sub 1-28
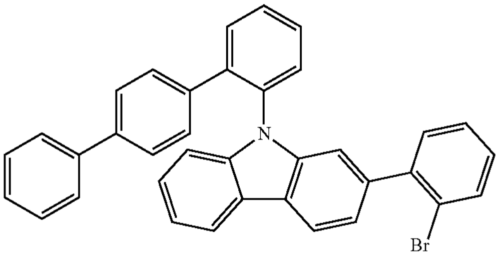
Sub 1-29
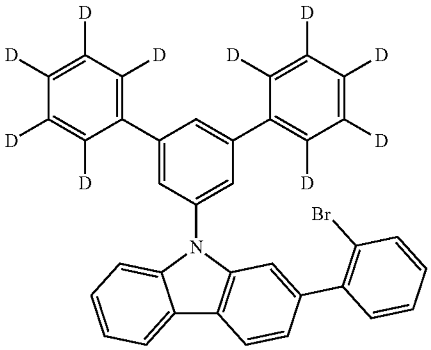

-continued
Sub 1-30
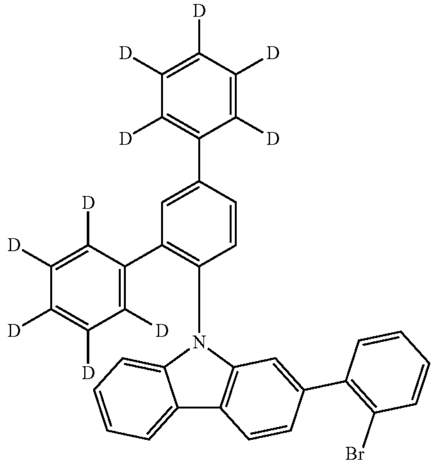
Sub 1-31
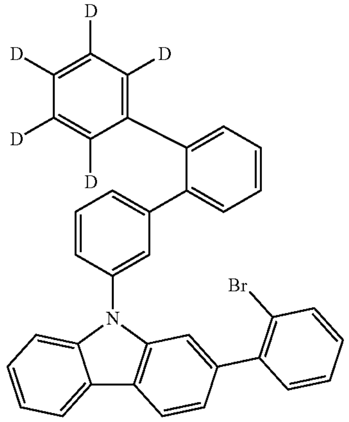
Sub 1-32
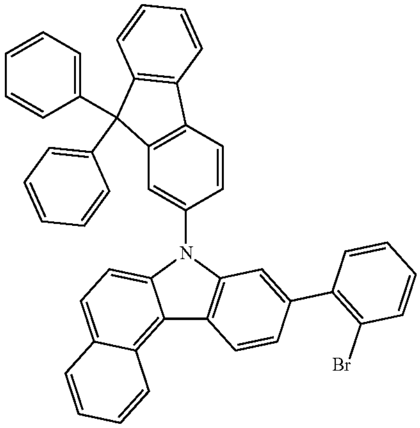
-continued
Sub 1-33
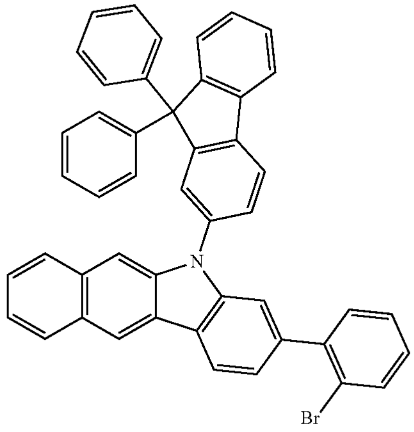
Sub 1-34
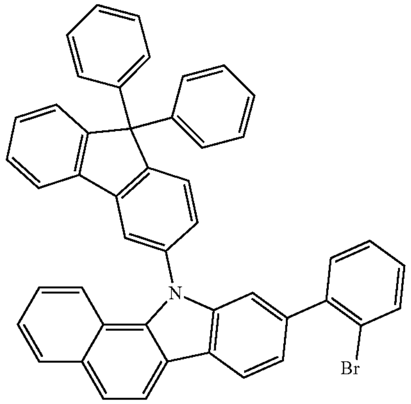
Sub 1-35
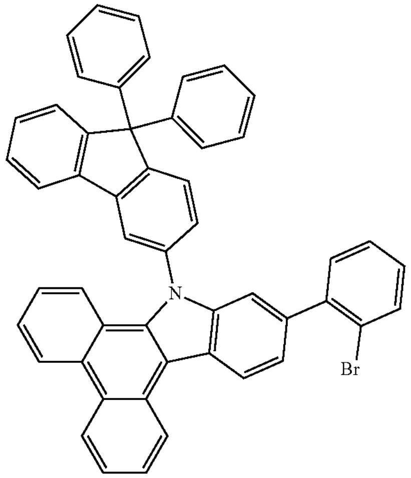

-continued
Sub 1-36
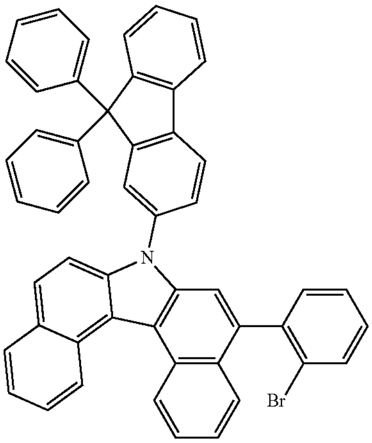
Sub 1-37
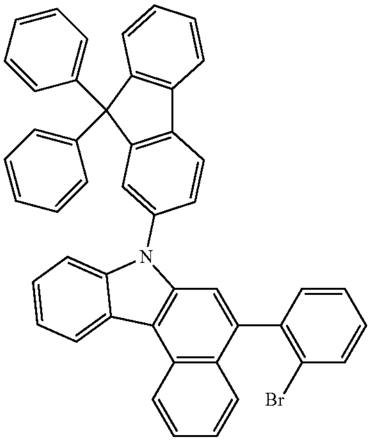
Sub 1-38
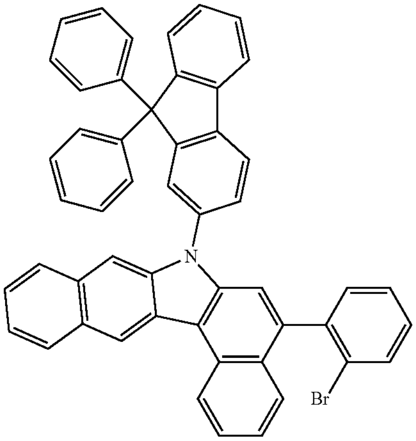
-continued
Sub 1-39
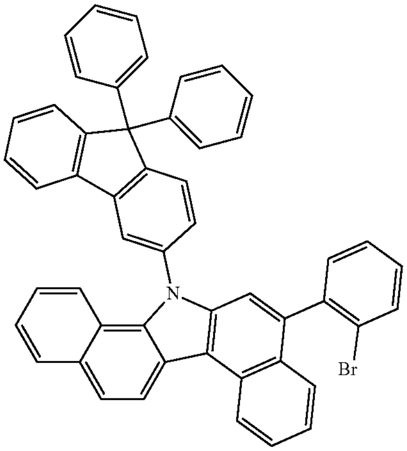
Sub 1-40
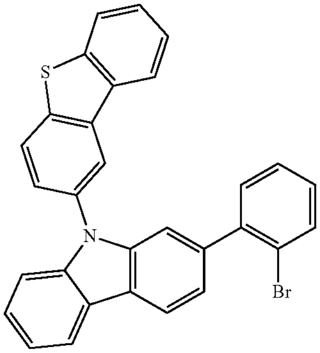
Sub 1-41
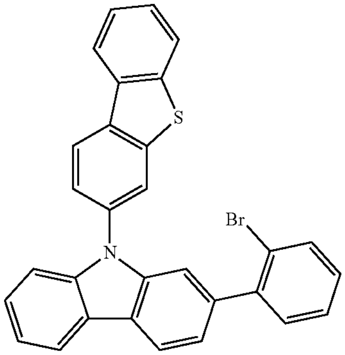
Sub 1-42
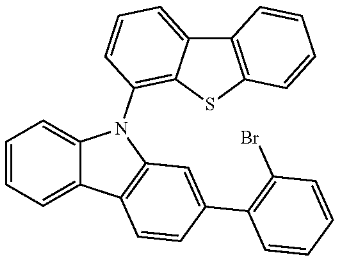

-continued
Sub 1-43
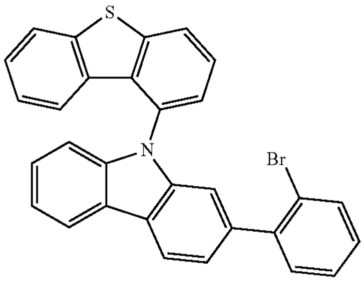
Sub 1-44
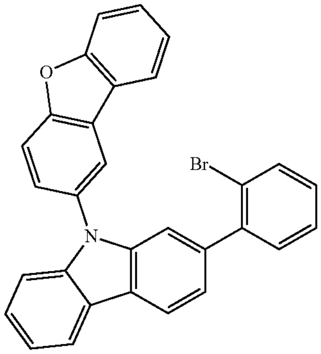
Sub 1-45
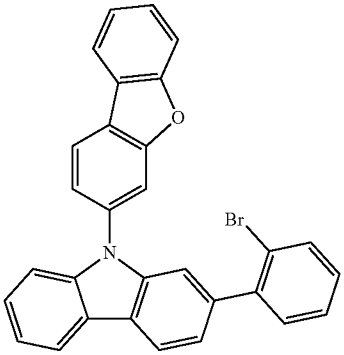
Sub 1-46
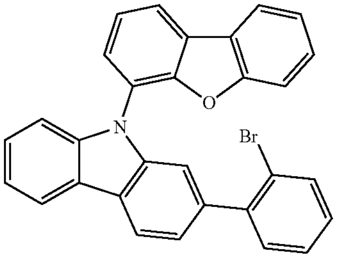
Sub 1-47
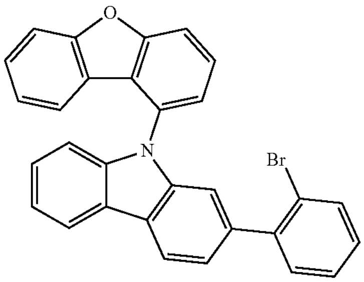
-continued
Sub 1-48
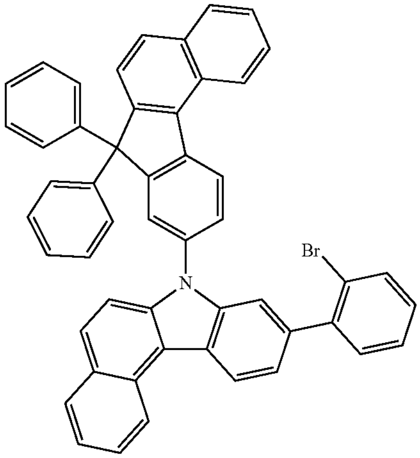
Sub 1-49
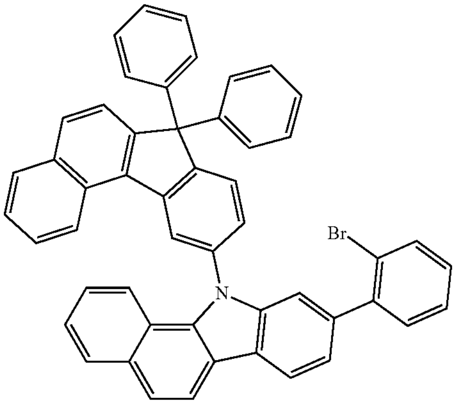
Sub 1-50
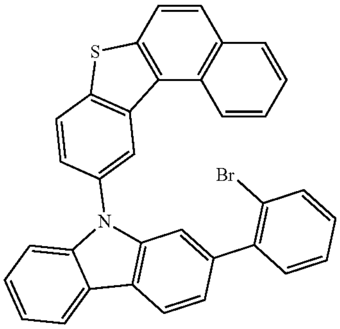
Sub 1-51
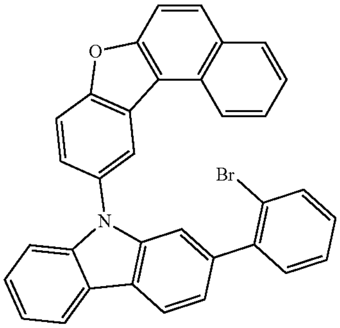

-continued
Sub 1-52
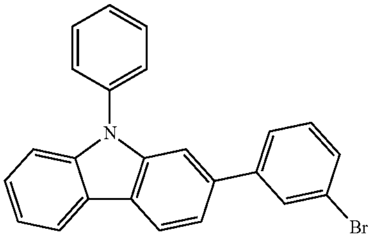
Sub 1-53
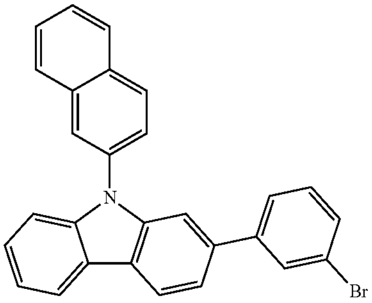
Sub 1-54
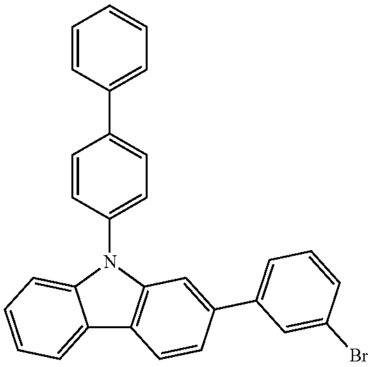
Sub 1-55
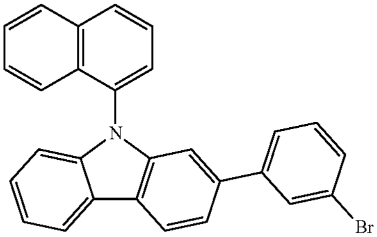
Sub 1-56
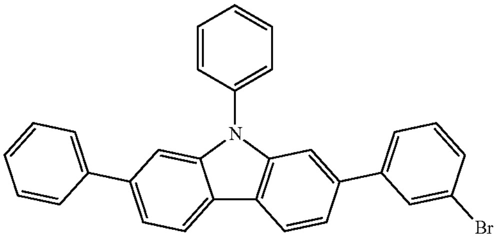
-continued
Sub 1-57
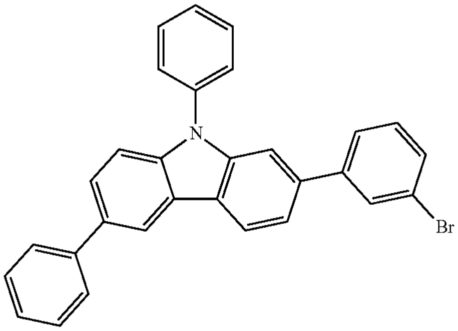
Sub 1-58
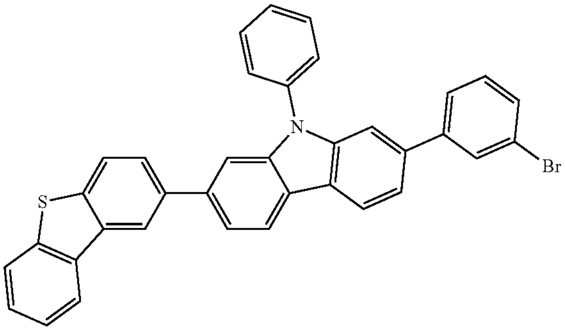
Sub 1-59
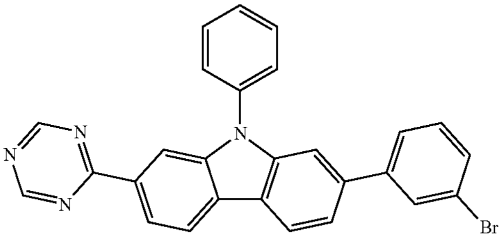
Sub 1-60
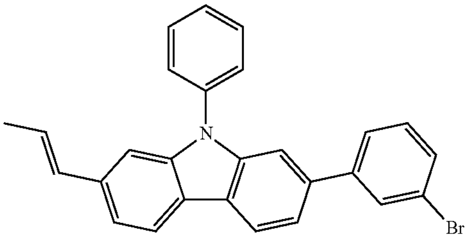
Sub 1-61
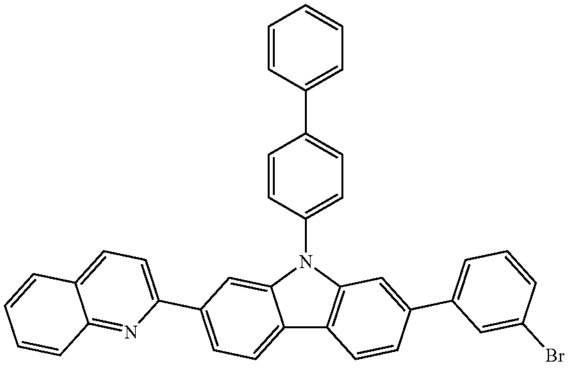

-continued
Sub 1-62
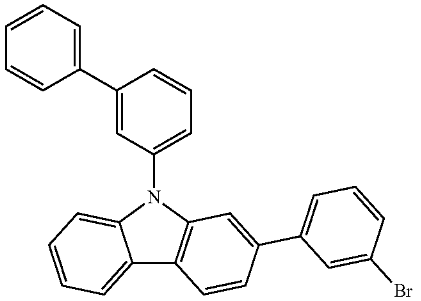
Sub 1-63
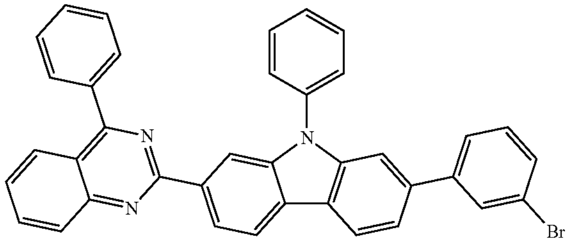
Sub 1-64
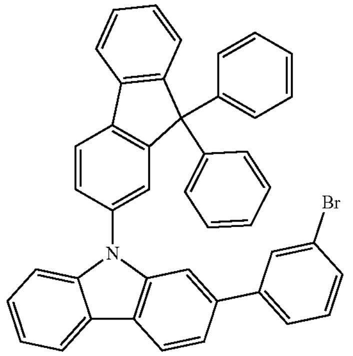
Sub 1-65
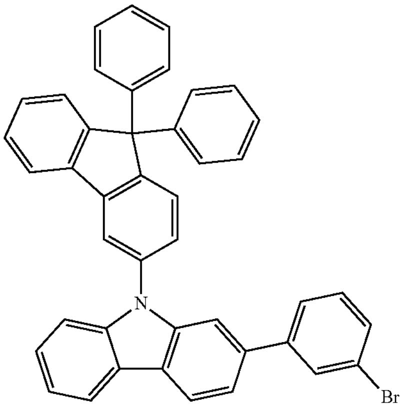
-continued
Sub 1-66
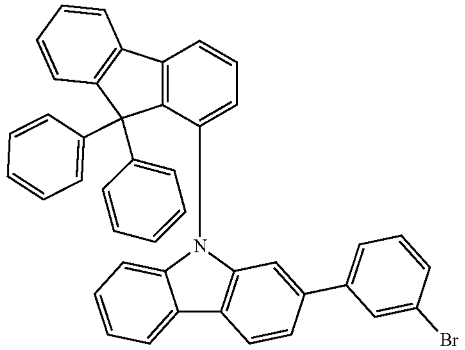
Sub 1-67
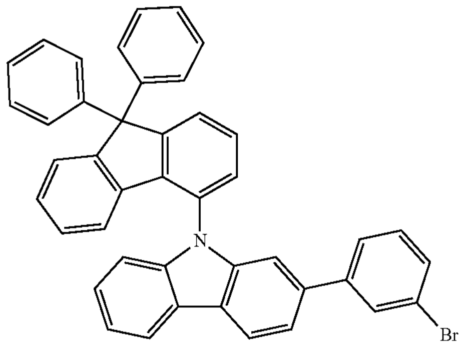
Sub 1-68
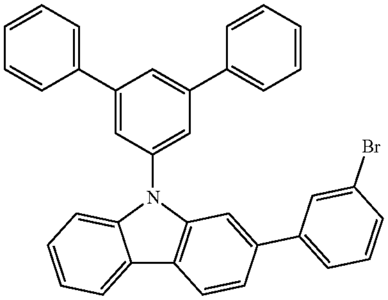
Sub 1-69
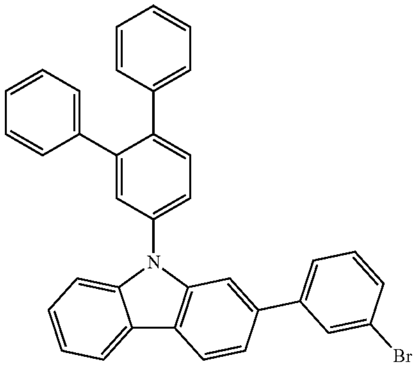

-continued
Sub 1-70
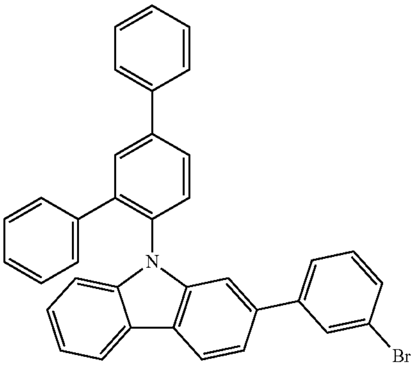
Sub 1-71
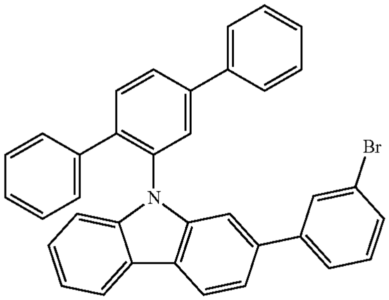
Sub 1-72
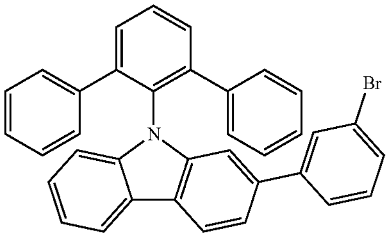
Sub 1-73
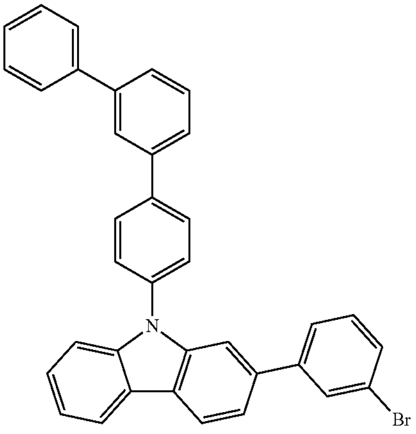
-continued
Sub 1-74
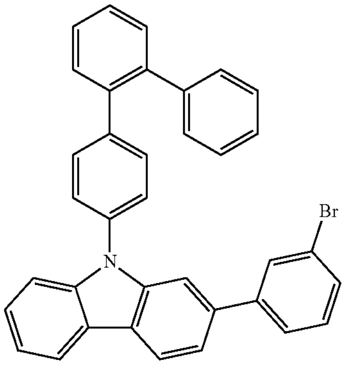
Sub 1-75
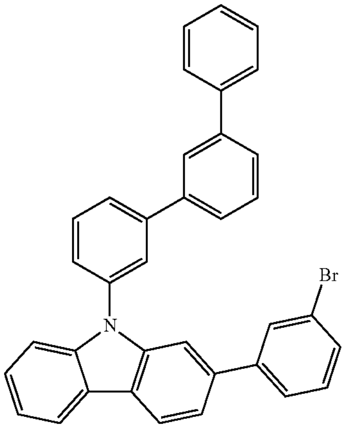
Sub 1-76
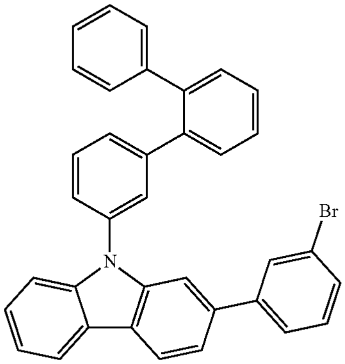
Sub 1-77
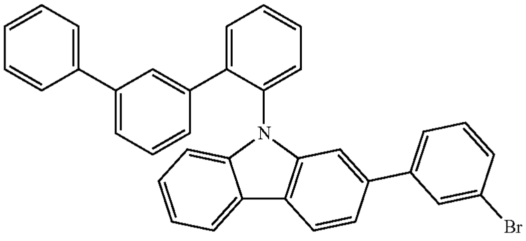

-continued
Sub 1-78
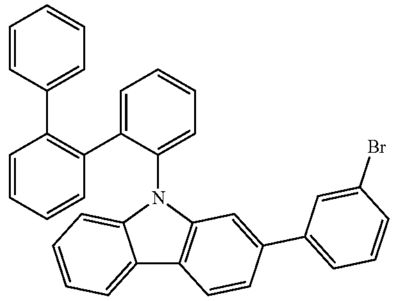
Sub 1-79
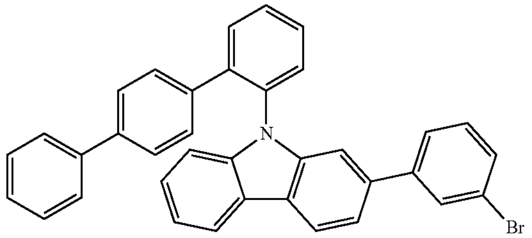
Sub 1-80
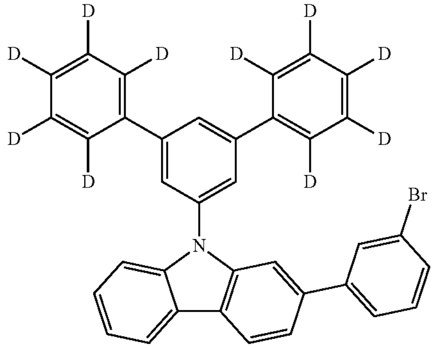
Sub 1-81
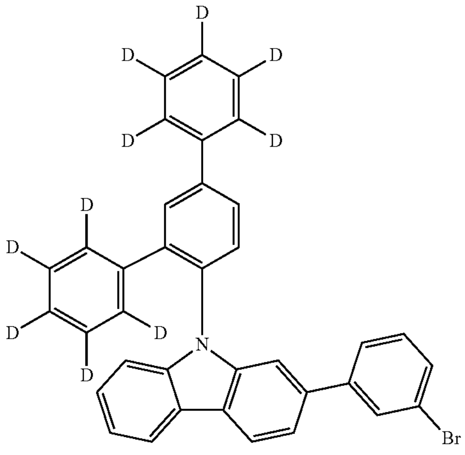
-continued
Sub 1-82
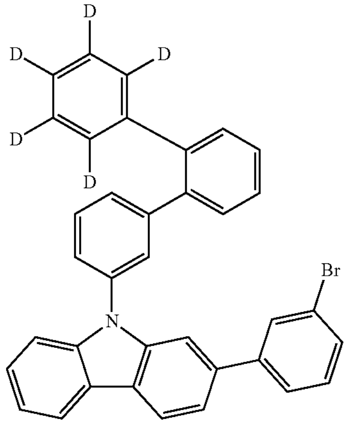
Sub 1-83
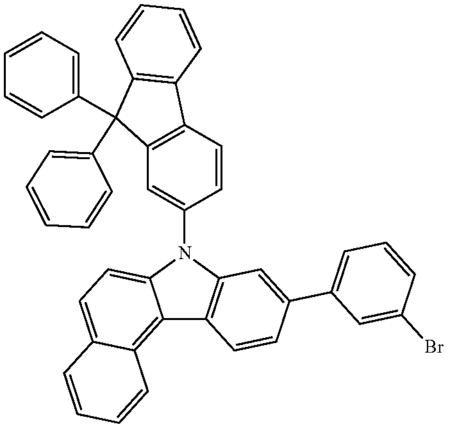
Sub 1-84
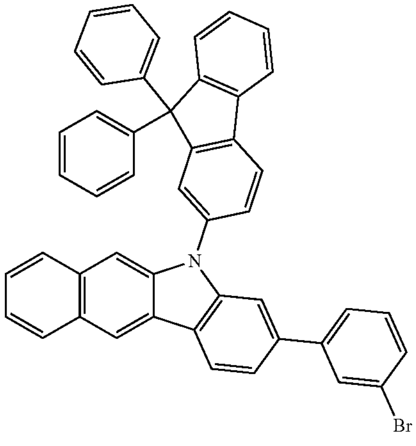

-continued
Sub 1-85
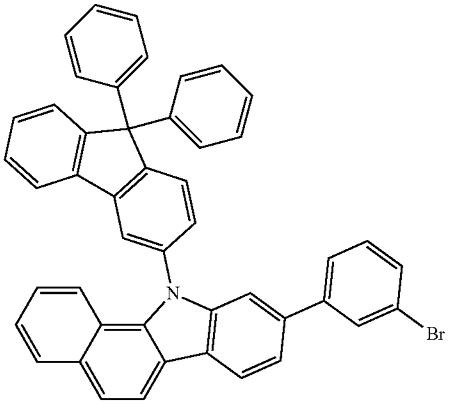
Sub 1-86
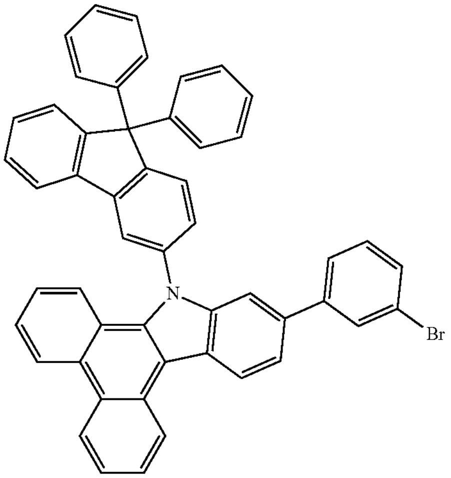
Sub 1-87
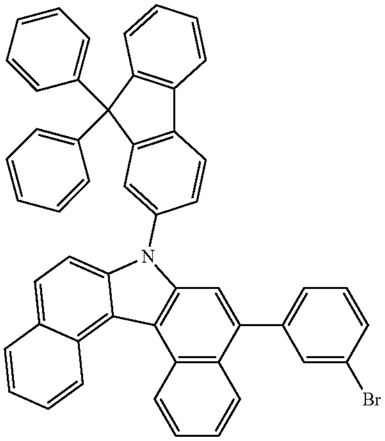
-continued
Sub 1-88
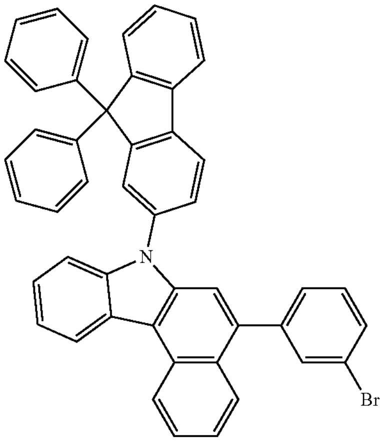
Sub 1-89
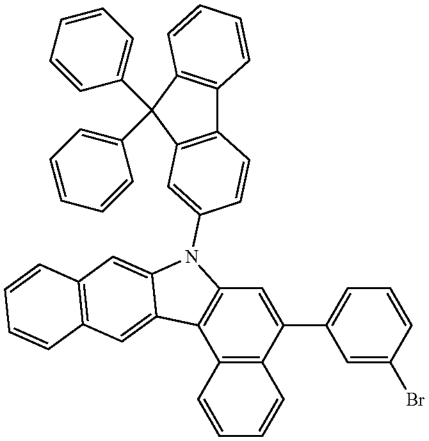
Sub 1-90
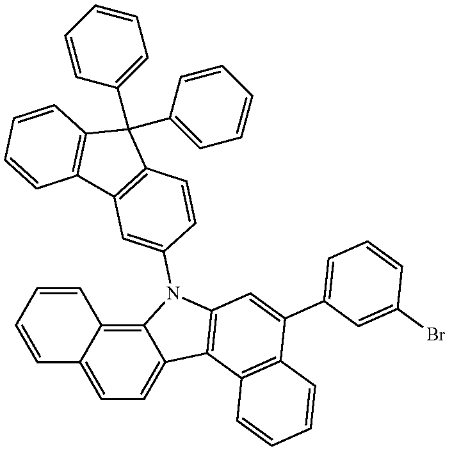

-continued
Sub 1-91
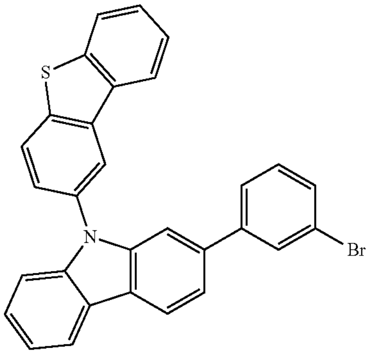
Sub 1-92
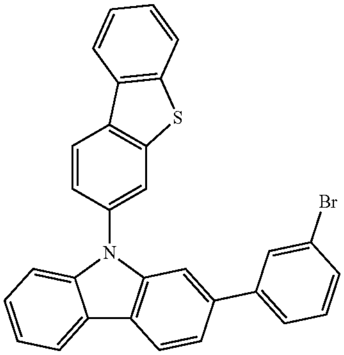
Sub 1-93
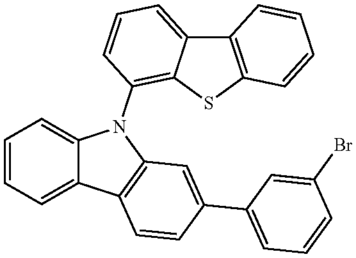
Sub 1-94
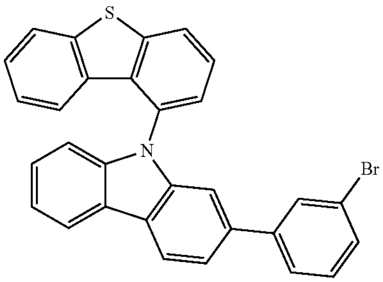
Sub 1-95
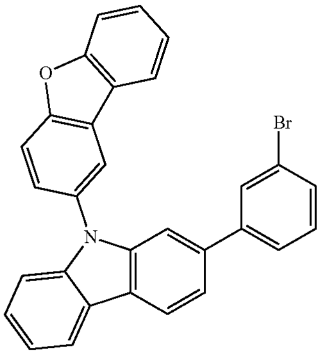
-continued
Sub 1-96
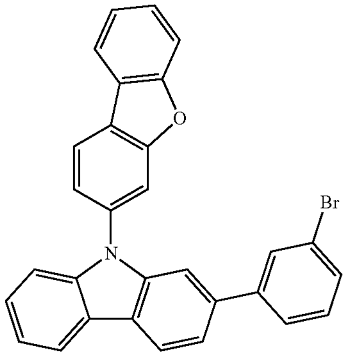
Sub 1-97
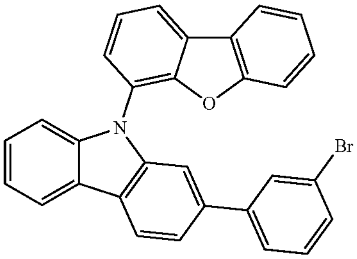
Sub 1-98
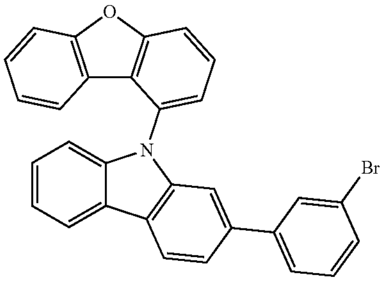
Sub 1-99
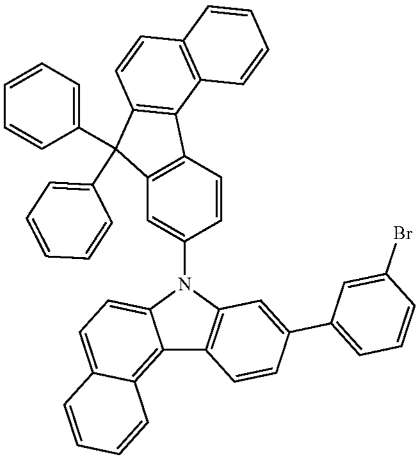

-continued
Sub 1-100
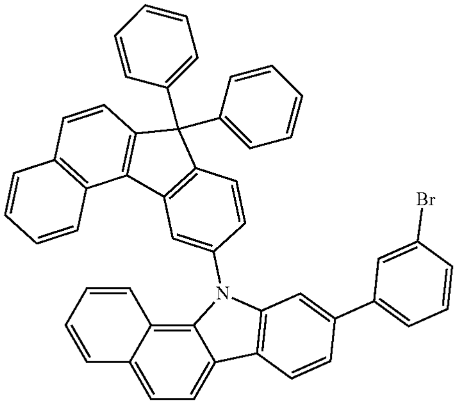
Sub 1-101
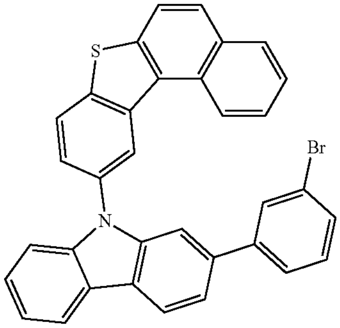
Sub 1-102
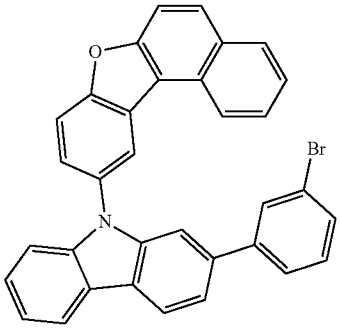
Sub 1-103
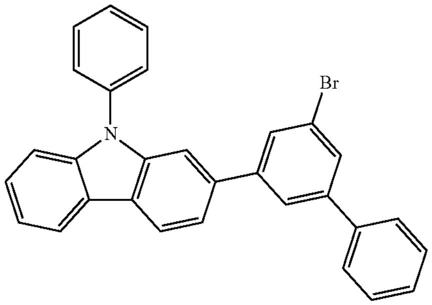
-continued
Sub 1-104
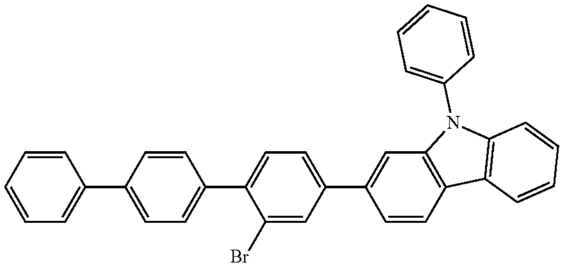
Sub 1-105
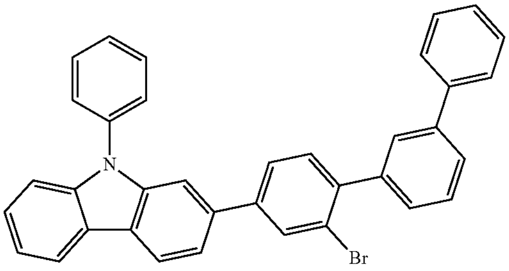
Sub 1-106
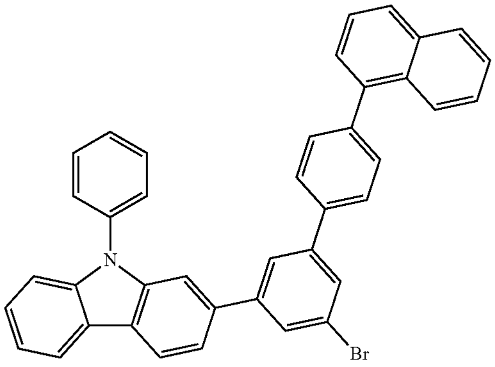
Sub 1-107
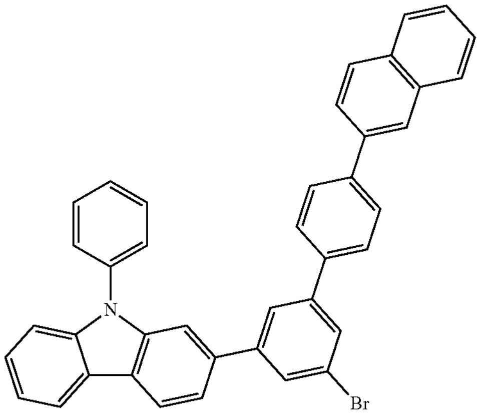

Sub 1-108
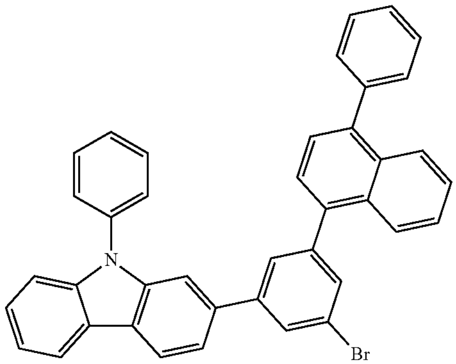
Sub 1-109
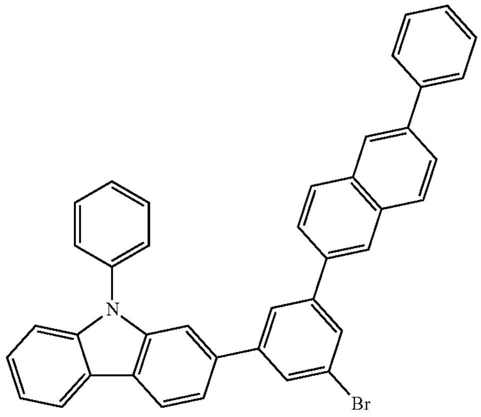
Sub 1-110
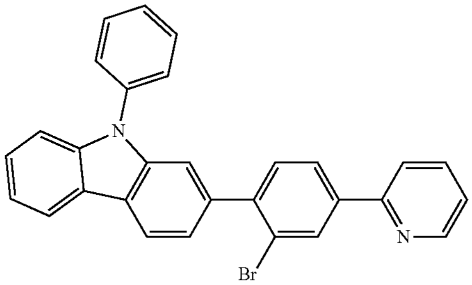
Sub 1-111
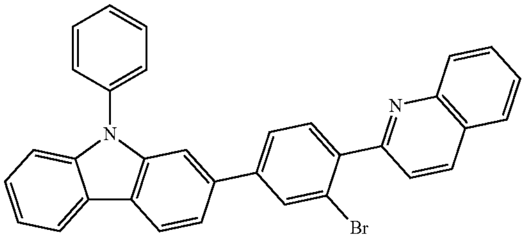
Sub 1-112
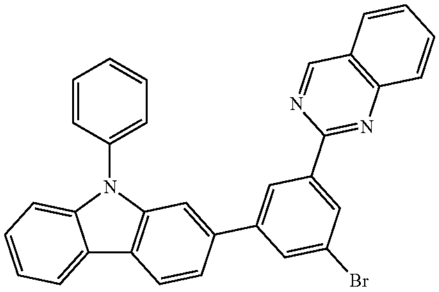
Sub 1-113
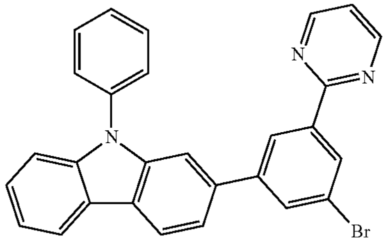
Sub 1-114
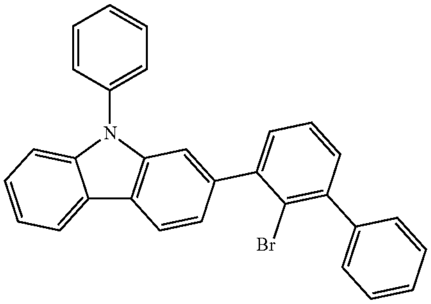
Sub 1-115
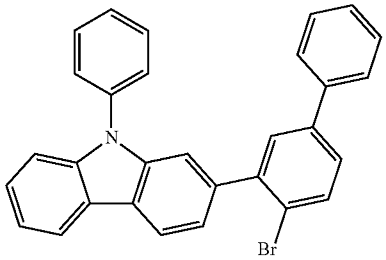
Sub 1-116
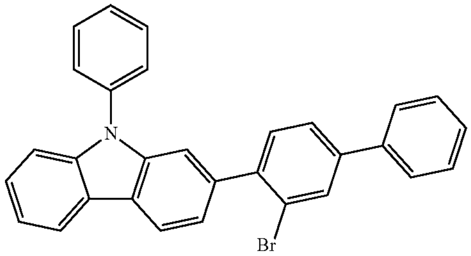

-continued
Sub 1-117
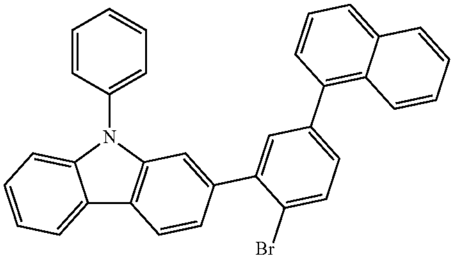
Sub 1-118
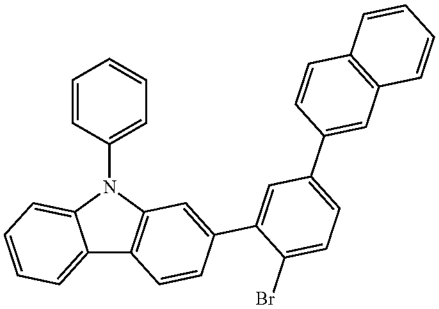
Sub 1-119
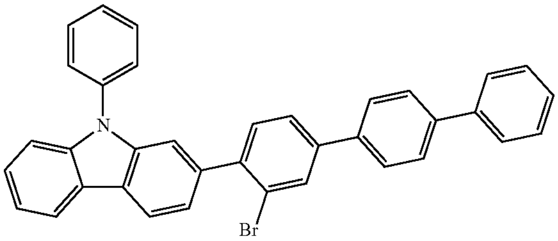
Sub 1-120
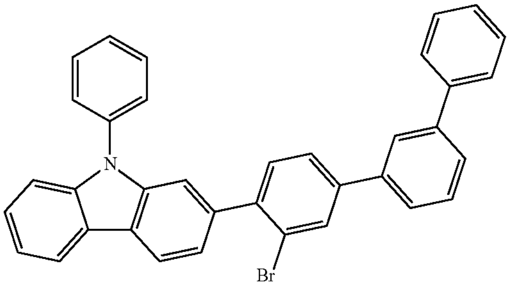
Sub 1-121
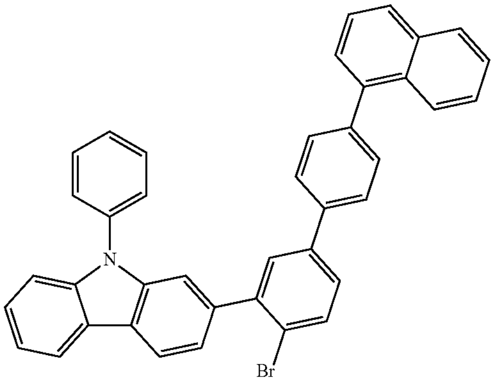
-continued
Sub 1-122
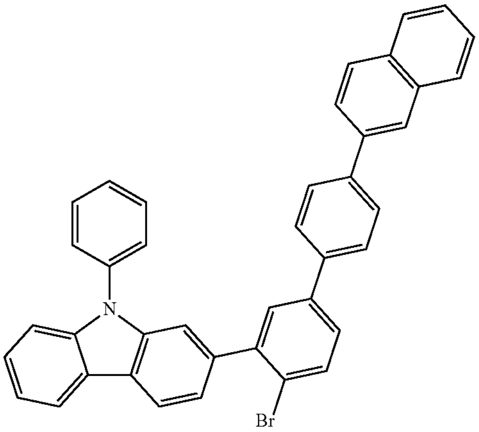
Sub 1-123
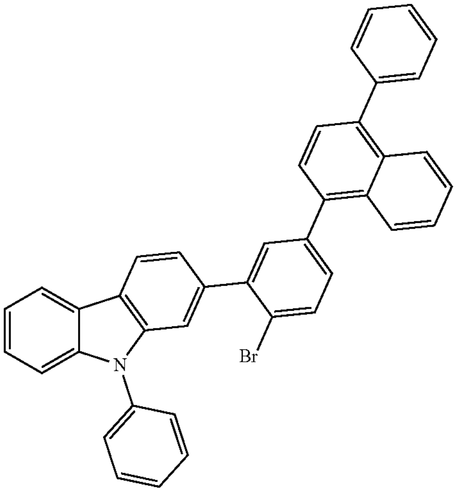
Sub 1-124
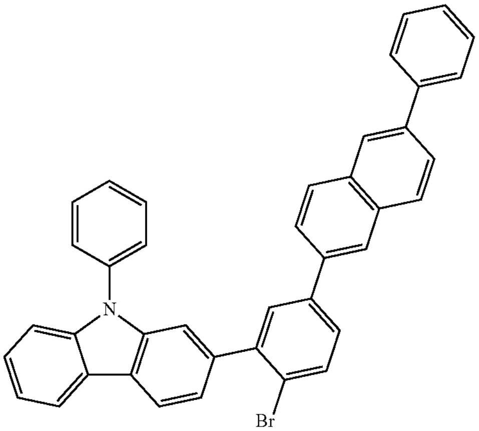

-continued

Sub 1-125

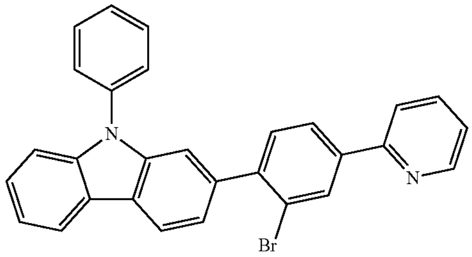

Sub 1-126

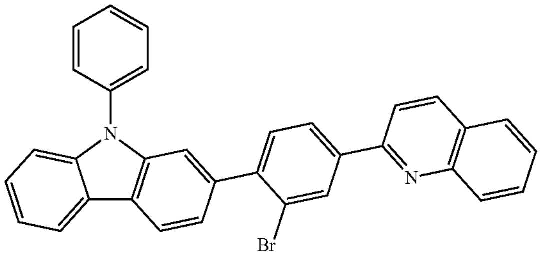

Sub 1-127

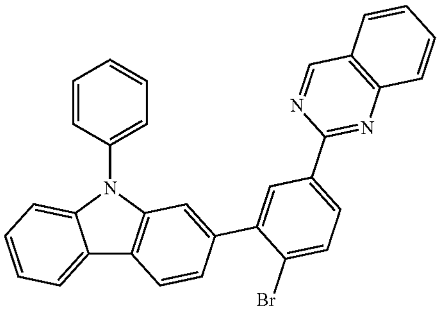

Sub 1-128

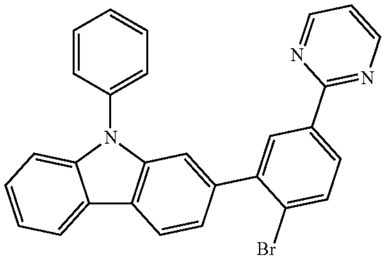

TABLE 1

| Compound | FD-MS |
|---|---|
| Sub 1-1 | m/z = 397.05($C_{24}H_{16}BrN$ = 398.29) |
| Sub 1-2 | m/z = 447.06($C_{28}H_{18}BrN$ = 448.35) |
| Sub 1-3 | m/z = 473.08($C_{30}H_{20}BrN$ = 474.39) |
| Sub 1-4 | m/z = 447.06($C_{28}H_{18}BrN$ = 448.35) |
| Sub 1-5 | m/z = 473.08($C_{30}H_{20}BrN$ = 474.39) |
| Sub 1-6 | m/z = 473.08($C_{30}H_{20}BrN$ = 474.39) |
| Sub 1-7 | m/z = 579.07($C_{36}H_{22}BrNS$ = 580.54) |
| Sub 1-8 | m/z = 476.06($C_{27}H_{17}BrN_4$ = 477.35) |
| Sub 1-9 | m/z = 437.08($C_{27}H_{20}BrN$ = 438.36) |
| Sub 1-10 | m/z = 600.12($C_{39}H_{25}BrN_2$ = 601.53) |
| Sub 1-11 | m/z = 473.08($C_{30}H_{20}BrN$ = 474.39) |
| Sub 1-12 | m/z = 601.12($C_{38}H_{24}BrN_3$ = 602.52) |
| Sub 1-13 | m/z = 637.14($C_{43}H_{28}BrN$ = 638.59) |
| Sub 1-14 | m/z = 637.14($C_{43}H_{28}BrN$ = 638.59) |
| Sub 1-15 | m/z = 637.14($C_{43}H_{28}BrN$ = 638.59) |
| Sub 1-16 | m/z = 637.14($C_{43}H_{28}BrN$ = 638.59) |

TABLE 1-continued

| Compound | FD-MS |
|---|---|
| Sub 1-17 | m/z = 549.11($C_{36}H_{24}BrN$ = 550.49) |
| Sub 1-18 | m/z = 549.11($C_{36}H_{24}BrN$ = 550.49) |
| Sub 1-19 | m/z = 549.11($C_{36}H_{24}BrN$ = 550.49) |
| Sub 1-20 | m/z = 549.11($C_{36}H_{24}BrN$ = 550.49) |
| Sub 1-21 | m/z = 549.11($C_{36}H_{24}BrN$ = 550.49) |
| Sub 1-22 | m/z = 549.11($C_{36}H_{24}BrN$ = 550.49) |
| Sub 1-23 | m/z = 549.11($C_{36}H_{24}BrN$ = 550.49) |
| Sub 1-24 | m/z = 549.11($C_{36}H_{24}BrN$ = 550.49) |
| Sub 1-25 | m/z = 549.11($C_{36}H_{24}BrN$ = 550.49) |
| Sub 1-26 | m/z = 549.11($C_{36}H_{24}BrN$ = 550.49) |
| Sub 1-27 | m/z = 549.11($C_{36}H_{24}BrN$ = 550.49) |
| Sub 1-28 | m/z = 549.11($C_{36}H_{24}BrN$ = 550.49) |
| Sub 1-29 | m/z = 559.2($C_{36}H_{14}D_{10}BrN$ = 560.6) |
| Sub 1-30 | m/z = 559.17($C_{36}H_{14}D_{10}BrN$ = 560.6) |
| Sub 1-31 | m/z = 554.1($C_{36}H_{19}D_5BrN$ = 555.52) |
| Sub 1-32 | m/z = 687.16($C_{47}H_{30}BrN$ = 688.65) |
| Sub 1-33 | m/z = 687.16($C_{47}H_{30}BrN$ = 688.65) |
| Sub 1-34 | m/z = 687.16($C_{47}H_{30}BrN$ = 688.65) |
| Sub 1-35 | m/z = 737.17($C_{51}H_{32}BrN$ = 738.71) |
| Sub 1-36 | m/z = 737.17($C_{51}H_{32}BrN$ = 738.71) |
| Sub 1-37 | m/z = 687.16($C_{47}H_{30}BrN$ = 688.65) |
| Sub 1-38 | m/z = 737.17($C_{51}H_{32}BrN$ = 738.71) |
| Sub 1-39 | m/z = 737.17($C_{51}H_{32}BrN$ = 738.71) |
| Sub 1-40 | m/z = 503.03($C_{30}H_{18}BrNS$ = 504.44) |
| Sub 1-41 | m/z = 503.03($C_{30}H_{18}BrNS$ = 504.44) |
| Sub 1-42 | m/z = 503.03($C_{30}H_{18}BrNS$ = 504.44) |
| Sub 1-43 | m/z = 503.03($C_{30}H_{18}BrNS$ = 504.44) |
| Sub 1-44 | m/z = 487.06($C_{30}H_{18}BrNO$ = 488.37) |
| Sub 1-45 | m/z = 487.1($C_{30}H_{18}BrNO$ = 488.37) |
| Sub 1-46 | m/z = 487.06($C_{30}H_{18}BrNO$ = 488.37) |
| Sub 1-47 | m/z = 487.1($C_{30}H_{18}BrNO$ = 488.37) |
| Sub 1-48 | m/z = 737.17($C_{51}H_{32}BrN$ = 738.71) |
| Sub 1-49 | m/z = 737.17($C_{51}H_{32}BrN$ = 738.71) |
| Sub 1-50 | m/z = 553.05($C_{34}H_{20}BrNS$ = 554.50) |
| Sub 1-51 | m/z = 537.07($C_{34}H_{20}BrNO$ = 538.43) |
| Sub 1-52 | m/z = 397.05($C_{24}H_{16}BrN$ = 398.29) |
| Sub 1-53 | m/z = 447.06($C_{28}H_{18}BrN$ = 448.35) |
| Sub 1-54 | m/z = 473.08($C_{30}H_{20}BrN$ = 474.39) |
| Sub 1-55 | m/z = 447.06($C_{28}H_{18}BrN$ = 448.35) |
| Sub 1-56 | m/z = 473.08($C_{30}H_{20}BrN$ = 474.39) |
| Sub 1-57 | m/z = 473.08($C_{30}H_{20}BrN$ = 474.39) |
| Sub 1-58 | m/z = 579.07($C_{36}H_{22}BrNS$ = 580.54) |
| Sub 1-59 | m/z = 476.06($C_{27}H_{17}BrN_4$ = 477.35) |
| Sub 1-60 | m/z = 437.08($C_{27}H_{20}BrN$ = 438.36) |
| Sub 1-61 | m/z = 600.12($C_{39}H_{25}BrN_2$ = 601.53) |
| Sub 1-62 | m/z = 473.08($C_{30}H_{20}BrN$ = 474.39) |
| Sub 1-63 | m/z = 601.12($C_{38}H_{24}BrN_3$ = 602.52) |
| Sub 1-64 | m/z = 637.14($C_{43}H_{28}BrN$ = 638.59) |
| Sub 1-65 | m/z = 637.14($C_{43}H_{28}BrN$ = 638.59) |
| Sub 1-66 | m/z = 637.14($C_{43}H_{28}BrN$ = 638.59) |
| Sub 1-67 | m/z = 637.14($C_{43}H_{28}BrN$ = 638.59) |
| Sub 1-68 | m/z = 549.11($C_{36}H_{24}BrN$ = 550.49) |
| Sub 1-69 | m/z = 549.11($C_{36}H_{24}BrN$ = 550.49) |
| Sub 1-70 | m/z = 549.11($C_{36}H_{24}BrN$ = 550.49) |
| Sub 1-71 | m/z = 549.11($C_{36}H_{24}BrN$ = 550.49) |
| Sub 1-72 | m/z = 549.11($C_{36}H_{24}BrN$ = 550.49) |
| Sub 1-73 | m/z = 549.11($C_{36}H_{24}BrN$ = 550.49) |
| Sub 1-74 | m/z = 549.11($C_{36}H_{24}BrN$ = 550.49) |
| Sub 1-75 | m/z = 549.11($C_{36}H_{24}BrN$ = 550.49) |
| Sub 1-76 | m/z = 549.11($C_{36}H_{24}BrN$ = 550.49) |
| Sub 1-77 | m/z = 549.11($C_{36}H_{24}BrN$ = 550.49) |
| Sub 1-78 | m/z = 549.11($C_{36}H_{24}BrN$ = 550.49) |
| Sub 1-79 | m/z = 549.11($C_{36}H_{24}BrN$ = 550.49) |
| Sub 1-80 | m/z = 559.17($C_{36}H_{14}D_{10}BrN$ = 560.6) |
| Sub 1-81 | m/z = 559.2($C_{36}H_{14}D_{10}BrN$ = 560.6) |
| Sub 1-82 | m/z = 554.14($C_{36}H_{19}D_5BrN$ = 555.52) |
| Sub 1-83 | m/z = 687.16($C_{47}H_{30}BrN$ = 688.65) |
| Sub 1-84 | m/z = 687.16($C_{47}H_{30}BrN$ = 688.65) |
| Sub 1-85 | m/z = 687.16($C_{47}H_{30}BrN$ = 688.65) |
| Sub 1-86 | m/z = 737.17($C_{51}H_{32}BrN$ = 738.71) |
| Sub 1-87 | m/z = 737.17($C_{51}H_{32}BrN$ = 738.71) |
| Sub 1-88 | m/z = 687.16($C_{47}H_{30}BrN$ = 688.65) |
| Sub 1-89 | m/z = 737.17($C_{51}H_{32}BrN$ = 738.71) |
| Sub 1-90 | m/z = 737.17($C_{51}H_{32}BrN$ = 738.71) |
| Sub 1-91 | m/z = 503.03($C_{30}H_{18}BrNS$ = 504.44) |
| Sub 1-92 | m/z = 503.03($C_{30}H_{18}BrNS$ = 504.44) |
| Sub 1-93 | m/z = 503.03($C_{30}H_{18}BrNS$ = 504.44) |
| Sub 1-94 | m/z = 503.03($C_{30}H_{18}BrNS$ = 504.44) |

TABLE 1-continued

| Compound | FD-MS |
|---|---|
| Sub 1-95 | m/z = 487.1($C_{30}H_{18}BrNO$ = 488.37) |
| Sub 1-96 | m/z = 487.06($C_{30}H_{18}BrNO$ = 488.37) |
| Sub 1-97 | m/z = 487.1($C_{30}H_{18}BrNO$ = 488.37) |
| Sub 1-98 | m/z = 487.06($C_{30}H_{18}BrNO$ = 488.37) |
| Sub 1-99 | m/z = 737.17($C_{51}H_{32}BrN$ = 738.71) |
| Sub 1-100 | m/z = 737.17($C_{51}H_{32}BrN$ = 738.71) |
| Sub 1-101 | m/z = 553.05($C_{34}H_{20}BrNS$ = 554.50) |
| Sub 1-102 | m/z = 537.07($C_{34}H_{20}BrNO$ = 538.43) |
| Sub 1-103 | m/z = 473.08(C30H20BrN = 474.39) |
| Sub 1-104 | m/z = 549.11(C36H24BrN = 550.49) |
| Sub 1-105 | m/z = 549.11(C36H24BrN = 550.49) |
| Sub 1-106 | m/z = 599.12(C40H26BrN = 600.55) |
| Sub 1-107 | m/z = 599.12(C40H26BrN = 600.55) |
| Sub 1-108 | m/z = 599.12(C40H26BrN = 600.55) |
| Sub 1-109 | m/z = 599.12(C40H26BrN = 600.55) |
| Sub 1-110 | m/z = 474.07(C29H19BrN2 = 475.38) |
| Sub 1-111 | m/z = 524.09(C33H21BrN2 = 525.44) |
| Sub 1-112 | m/z = 525.08(C32H20BrN3 = 526.43) |
| Sub 1-113 | m/z = 475.07(C28H18BrN3 = 476.37) |
| Sub 1-114 | m/z = 473.08(C30H20BrN = 474.39) |
| Sub 1-115 | m/z = 473.08(C30H20BrN = 474.39) |
| Sub 1-116 | m/z = 473.08(C30H20BrN = 474.39) |
| Sub 1-117 | m/z = 523.09(C34H22BrN = 524.45) |
| Sub 1-118 | m/z = 523.09(C34H22BrN = 524.45) |
| Sub 1-119 | m/z = 549.11(C36H24BrN = 550.49) |
| Sub 1-120 | m/z = 549.11(C36H24BrN = 550.49) |
| Sub 1-121 | m/z = 599.12(C40H26BrN = 600.55) |
| Sub 1-122 | m/z = 599.12(C40H26BrN = 600.55) |
| Sub 1-123 | m/z = 599.12(C40H26BrN = 600.55) |
| Sub 1-124 | m/z = 599.12(C40H26BrN = 600.55) |
| Sub 1-125 | m/z = 474.07(C29H19BrN2 = 475.38) |
| Sub 1-126 | m/z = 524.09(C33H21BrN2 = 525.44) |
| Sub 1-127 | m/z = 525.08(C32H20BrN3 = 526.43) |
| Sub 1-128 | m/z = 475.07(C28H18BrN3 = 476.37) |

II. Synthesis Examples of Sub 2

Sub 2 of the Reaction Scheme 1 can be synthesized according to, but not limited to, the following Reaction Scheme 48.

<Reaction Scheme 48>

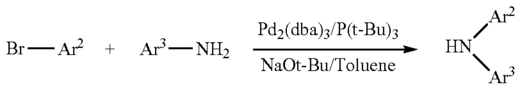

Sub 2

The synthesis examples of compounds included in Sub 2 are as below.

1. Synthesis of Sub 2-1

<Reaction Scheme 49>

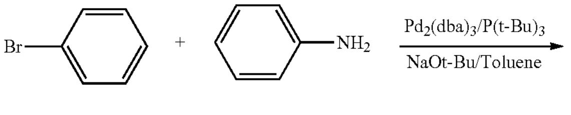

-continued

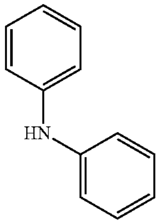

Sub 2-1

Bromobenzene (37.1 g, 236.2 mmol) was dissolved in toluene (2200 ml) in a round bottom flask. Then, aniline (20 g, 214.8 mmol), $Pd_2(dba)_3$ (9.83 g, 10.7 mmol), $P(t\text{-}Bu)_3$ (4.34 g, 21.5 mmol) and NaOt-Bu (62 g, 644.3 mmol) were added into the round bottom flask, and the mixture was stirred 100° C. After the completion of the reaction, the reaction product was extracted with ether and water. The extracted organic layer was dried over $MgSO_4$ and concentrated. The concentrated resultant was separated by silica gel column chromatography, and was then recrystallized, whereby a compound Sub 2-1 was obtained in an amount of 28 g in 77% yield.

2. Synthesis of Sub 2-3

<Reaction Scheme 50>

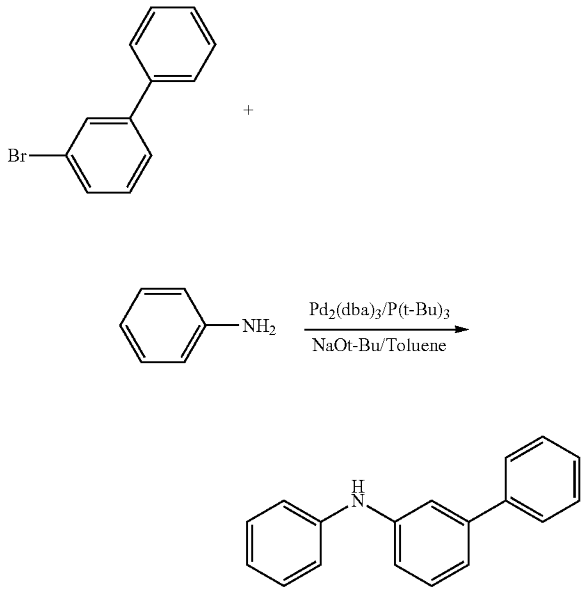

Sub 2-3

The compound Sub 2-3 was synthesized by using 3-bromo-1,1'-biphenyl (55.1 g, 236.2 mmol), aniline (20 g, 214.8 mmol), $Pd_2(dba)_3$ (9.83 g, 10.7 mmol), $P(t\text{-}Bu)_3$ (4.34 g, 21.5 mmol), NaOt-Bu (62 g, 644.3 mmol) and toluene (2200 ml) in the same manner as described in the synthesis method of the compound Sub 2-1 above, whereby a compound Sub 2-3 was obtained in an amount of 41.1 g in 78% yield.

3. Synthesis of Sub 2-4

<Reaction Scheme 51>

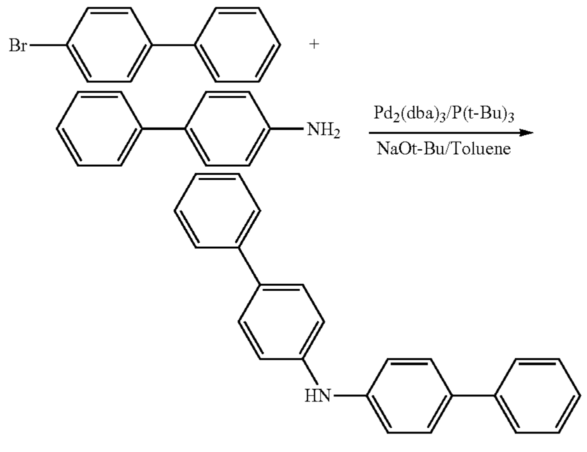

Sub 2-4

The compound Sub 2-4 was synthesized by using 4-bromo-1,1'-biphenyl (37.88 g, 162.5 mmol), [1,1'-biphenyl]-4-amine (25 g, 147.7 mmol), $Pd_2(dba)_3$ (6.76 g, 7.4 mmol), $P(t-Bu)_3$ (3 g, 14.8 mmol) and NaOt-Bu (66.62 g, 693.2 mmol) in the same manner as described in the synthesis method of the compound Sub 2-1 above, whereby a compound Sub 2-4 was obtained in an amount of 35.6 g in 75% yield.

4. Synthesis of Sub 2-7

<Reaction Scheme 52>

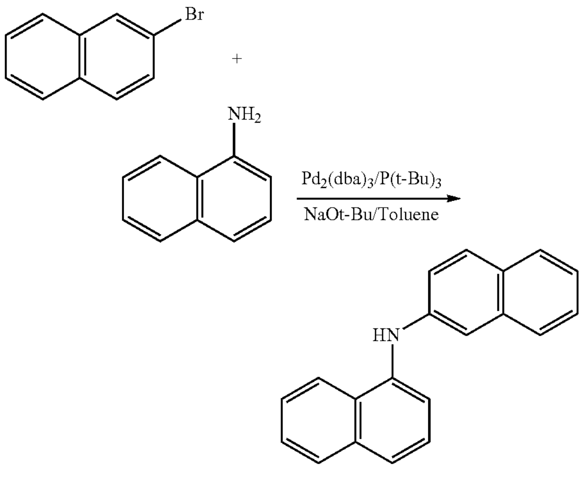

Sub 2-7

The compound Sub 2-7 was synthesized by using 2-bromonaphthalene (39.8 g, 192.1 mmol), naphthalen-1-amine (25 g, 174.6 mmol), $Pd_2(dba)_3$ (8.0 g, 8.73 mmol), $P(t-Bu)_3$ (3.53 g, 17.5 mmol), NaOt-Bu (50.3 g, 523.8 mmol) and toluene (1800 ml) in the same manner as described in the synthesis method of the compound Sub 2-1 above, whereby a compound Sub 2-7 was obtained in an amount of 36.2 g in 77% yield.

5. Synthesis of Sub 2-9

<Reaction Scheme 53>

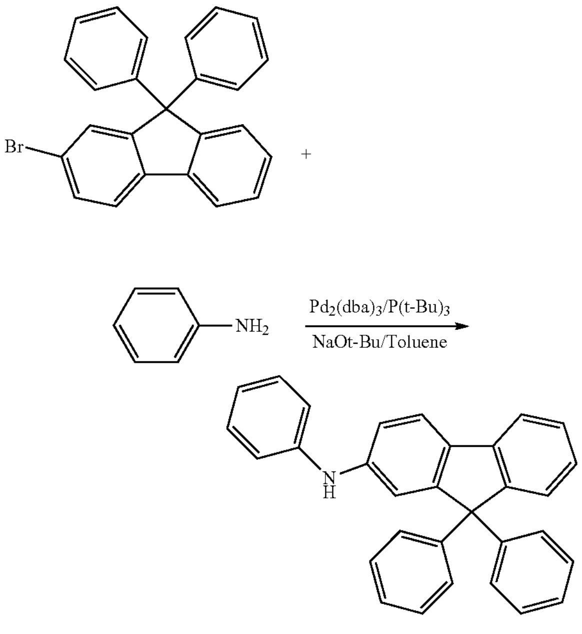

Sub 2-9

The compound Sub 2-9 was synthesized by using 2-bromo-9,9-diphenyl-9H-fluorene (93.9 g, 236.2 mmol), toluene (2250 ml), aniline (20 g, 214.8 mmol), $Pd_2(dba)_3$ (9.83 g, 10.7 mmol), $P(t-Bu)_3$ (4.34 g, 21.5 mmol) and NaOt-Bu (62 g, 644.3 mmol) in the same manner as described in the synthesis method of the compound Sub 2-1 above, whereby a compound Sub 2-9 was obtained in an amount of 63.3 g in 72% yield.

6. Synthesis of Sub 2-12

<Reaction Scheme 54>

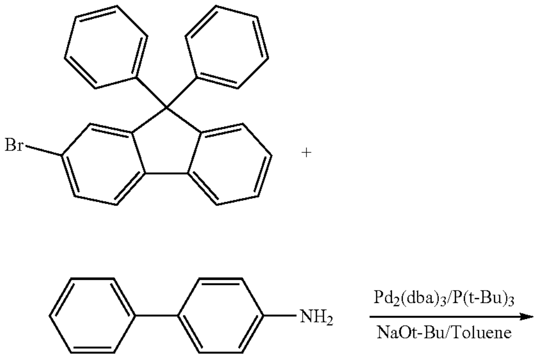

-continued

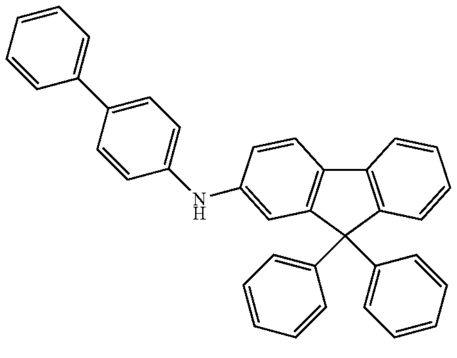

Sub 2-12

The compound Sub 2-12 was synthesized by using 2-bromo-9,9-diphenyl-9H-fluorene (64.6 g, 162.5 mmol), toluene (1550 ml), [1,1'-biphenyl]-4-amine (25 g, 147.7 mmol), $Pd_2(dba)_3$ (6.76 g, 162.5 mmol), $P(t-Bu)_3$ (3 g, 14.8 mmol) and NaOt-Bu (42.6 g, 443.2 mmol) in the same manner as described in the synthesis method of the compound Sub 2-1 above, whereby a compound Sub 2-12 was obtained in an amount of 53.8 g in 75% yield.

7. Synthesis of Sub 2-13

<Reaction Scheme 55>

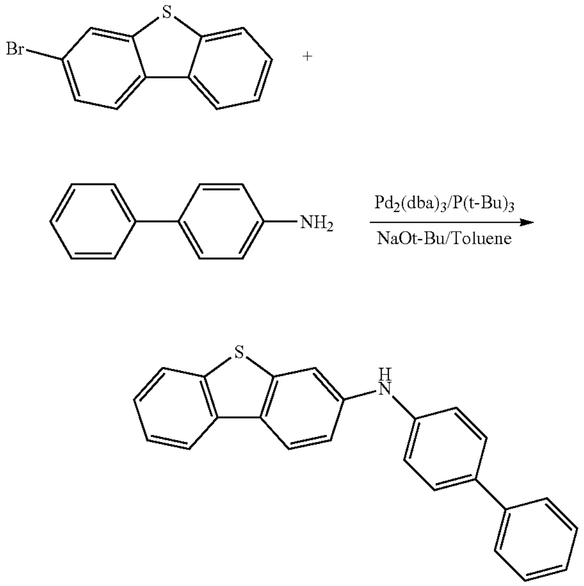

Sub 2-13

The compound Sub 2-13 was synthesized by using 3-bromodibenzo[b,d]thiophene (42.8 g, 162.5 mmol), toluene (1550 ml), [1,1'-biphenyl]-4-amine (25 g, 147.7 mmol), $Pd_2(dba)_3$ (6.76 g, 162.5 mmol), $P(t-Bu)_3$ (3 g, 14.8 mmol) and NaOt-Bu (42.6 g, 443.2 mmol) in the same manner as described in the synthesis method of the compound Sub 2-1 above, whereby a compound Sub 2-13 was obtained in an amount of 37.9 g in 73% yield.

8. Synthesis of Sub 2-17

<Reaction Scheme 56>

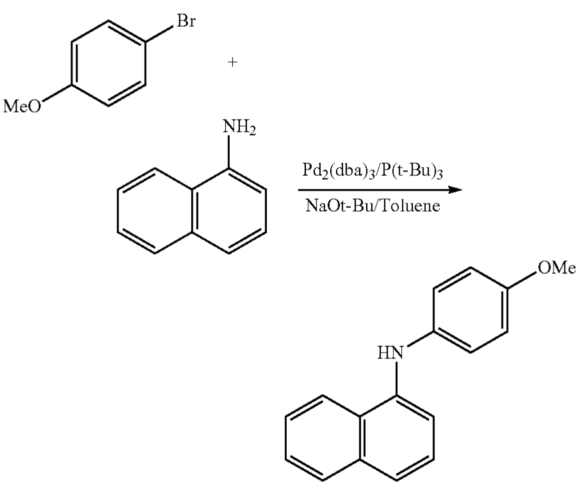

Sub 2-17

The compound Sub 2-17 was synthesized by using 1-bromo-4-methoxybenzene (36 g, 192.1 mmol), naphthalen-1-amine (25 g, 174.6 mmol), $Pd_2(dba)_3$ (8.0 g, 8.73 mmol), $P(t-Bu)_3$ (3.53 g, 17.5 mmol), NaOt-Bu (50.3 g, 523.8 mmol) and toluene (1800 ml) in the same manner as described in the synthesis method of the compound Sub 2-1 above, whereby a compound Sub 2-17 was obtained in an amount of 32.2 g in 74% yield.

9. Synthesis of Sub 2-26

<Reaction Scheme 57>

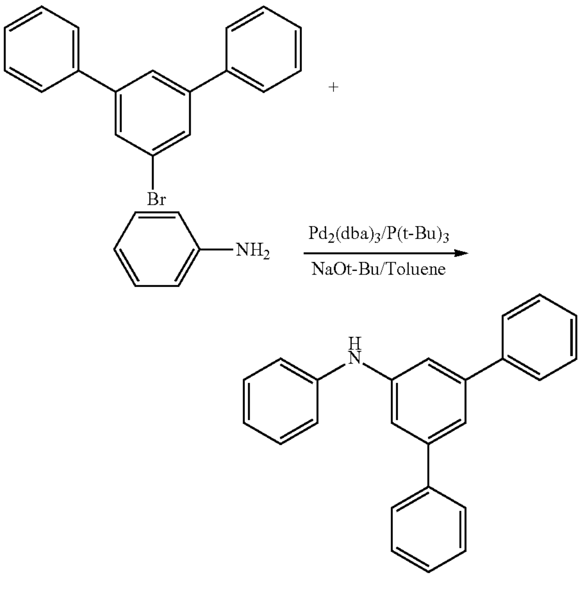

Sub 2-26

The compound Sub 2-26 was synthesized by using 5'-bromo-1,1':3',1"-terphenyl (73.04 g, 236.2 mmol), amine (20 g, 214.8 mmol), $Pd_2(dba)_3$ (9.83 g, 10.7 mmol), $P(t-Bu)_3$ (4.34 g, 21.5 mmol), NaOt-Bu (62 g, 644.3 mmol) and toluene (2250 ml) in the same manner as described in the synthesis method of the compound Sub 2-1 above, whereby a compound Sub 2-26 was obtained in an amount of 49 g in 71% yield.

10. Synthesis of Sub 2-31

<Reaction Scheme 58>

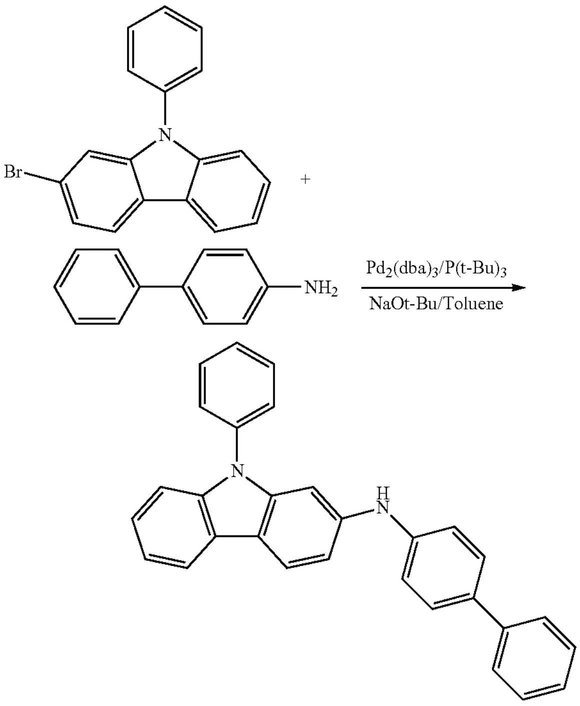

Sub 2-31

The compound Sub 2-31 was synthesized by 2-bromo-9-phenyl-9H-carbazole (52.4 g, 162.5 mmol), toluene (1550 mL), [1,1'-biphenyl]-4-amine (25 g, 147.7 mmol), $Pd_2(dba)_3$ (6.76 g, 162.5 mmol), $P(t-Bu)_3$ (3 g, 14.8 mmol) and NaOt-Bu (42.6 g, 443.2 mmol) in the same manner as described in the synthesis method of the compound Sub 2-1 above, whereby a compound Sub 2-26 was obtained in an amount of 45.4 g in 68% yield.

Examples of Sub 2 compounds include, but are not limited to, the following compounds, and FD-MS data of the compounds are given in Table 2 below.

Sub 2-1

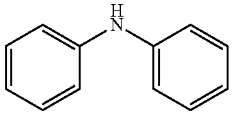

-continued

Sub 2-2

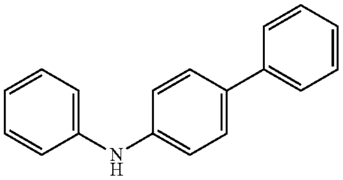

Sub 2-3

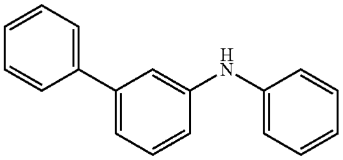

Sub 2-4

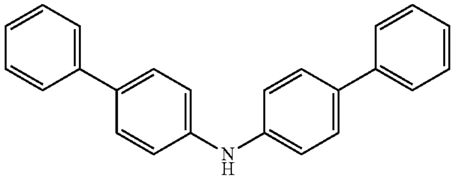

Sub 2-5

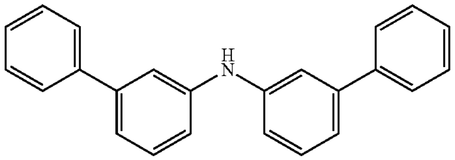

Sub 2-6

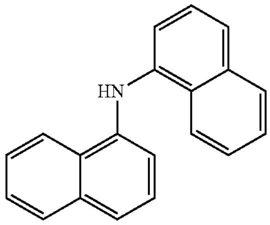

Sub 2-7

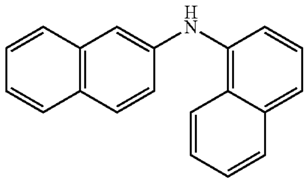

Sub 2-8

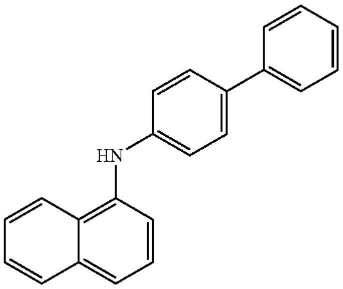

-continued
Sub 2-9
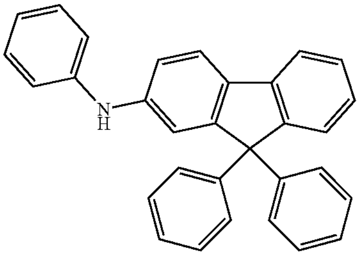
Sub 2-10
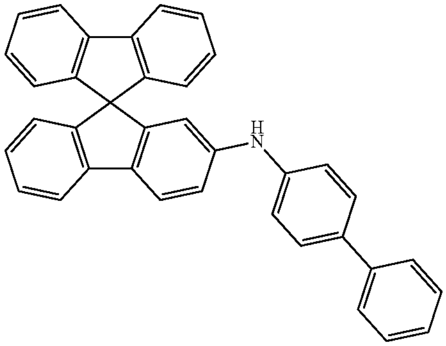
Sub 2-11
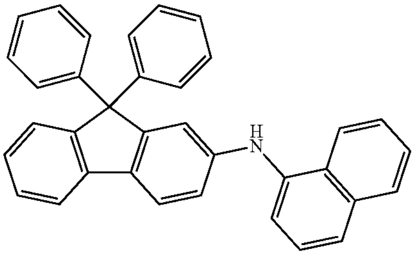
Sub 2-12
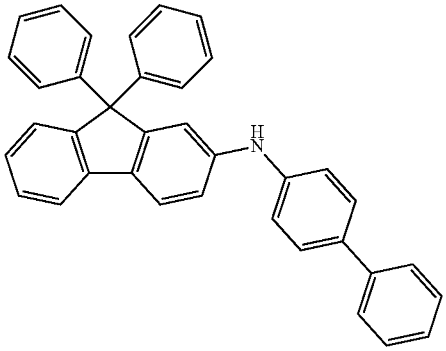
Sub 2-13
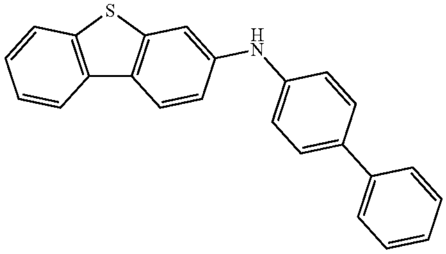
-continued
Sub 2-14
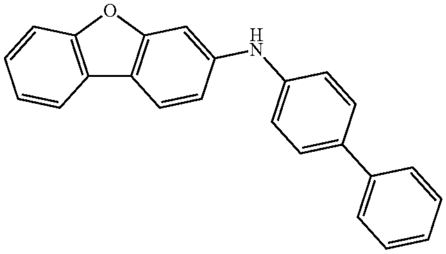
Sub 2-15
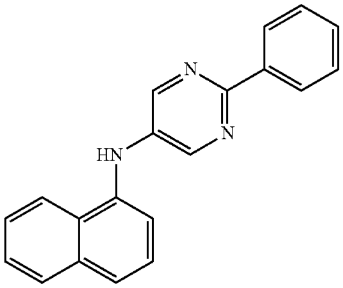
Sub 2-16
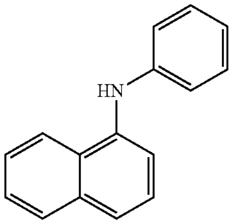
Sub 1-17
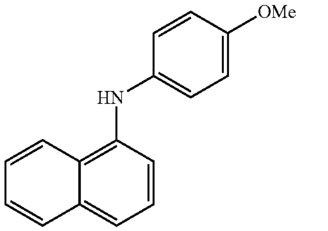
Sub 2-18
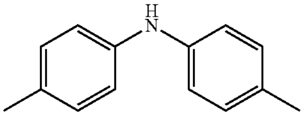
Sub 2-19
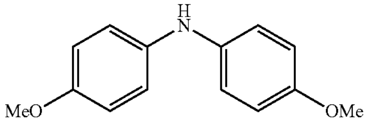
Sub 2-20
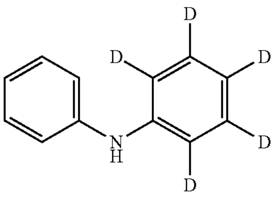

-continued
Sub 2-21
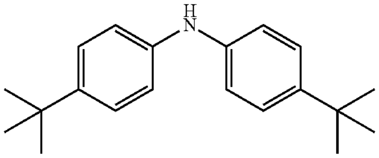
Sub 2-22
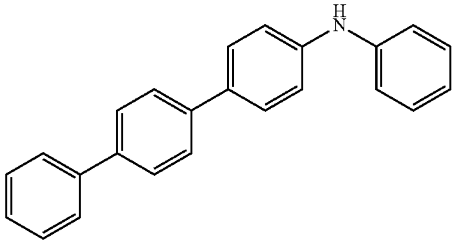
Sub 2-23
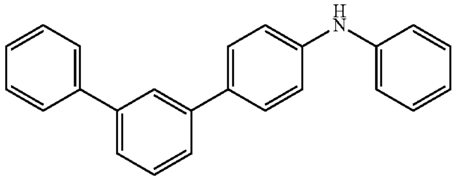
Sub 2-24
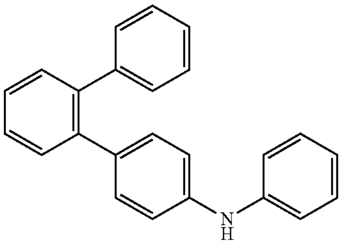
Sub 2-25
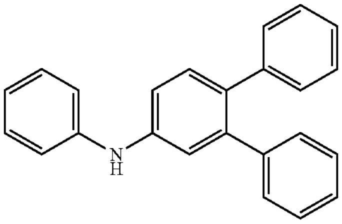
Sub 2-26
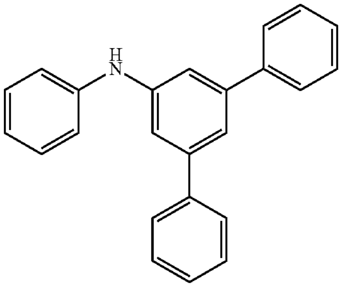
-continued
Sub 2-27
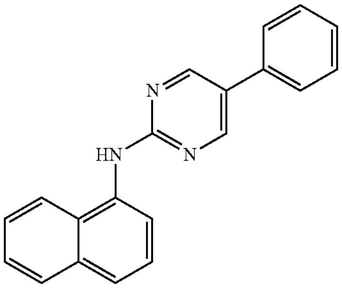
Sub 2-28
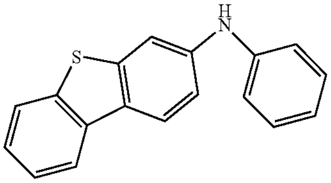
Sub 2-29
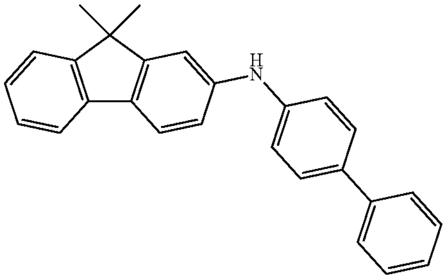
Sub 2-30
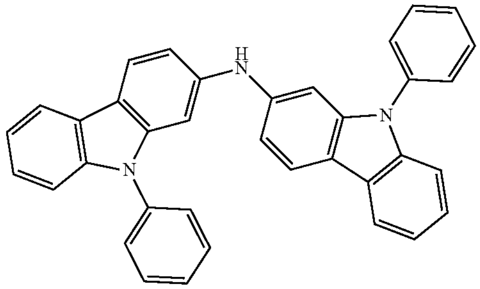
Sub 2-31
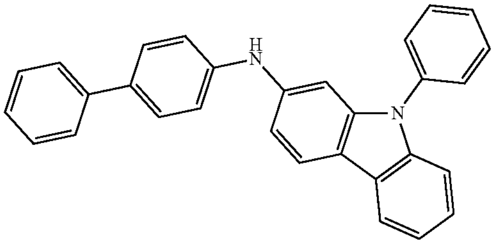
Sub 2-32
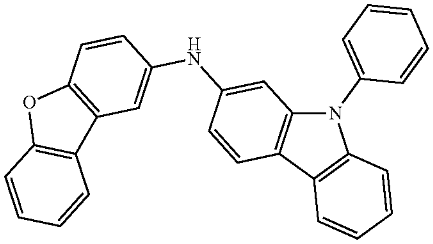

-continued
Sub 2-33
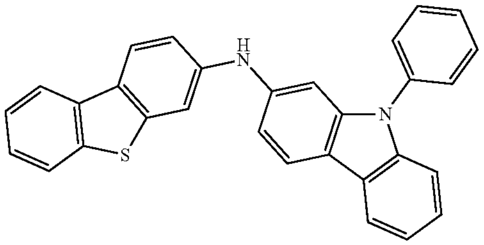
Sub 2-34
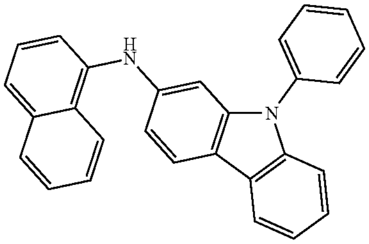
Sub 2-35
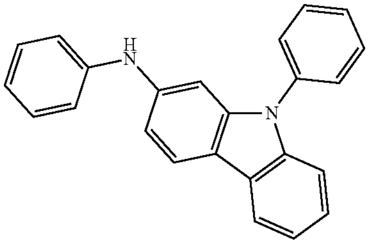
Sub 2-36
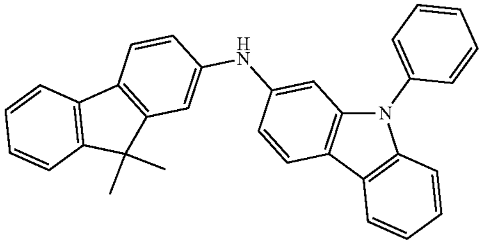
Sub 2-37
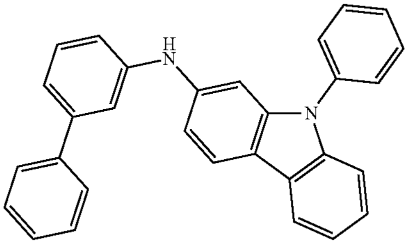
-continued
Sub 2-38
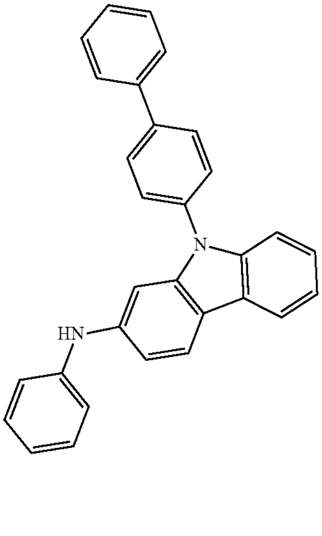
Sub 2-39
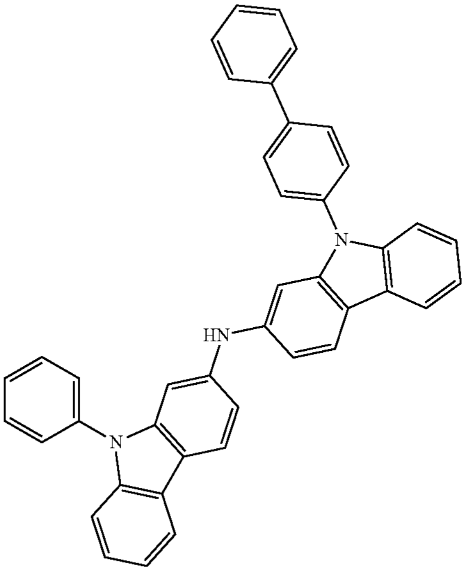
Sub 2-40
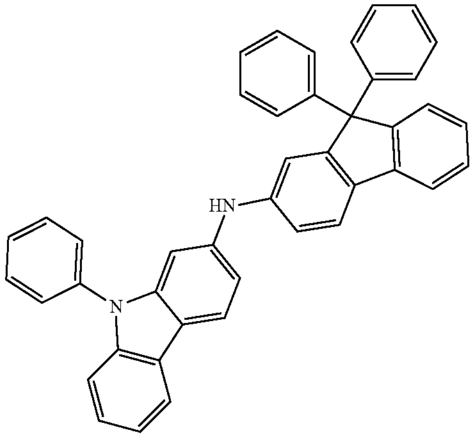

-continued
Sub 2-41
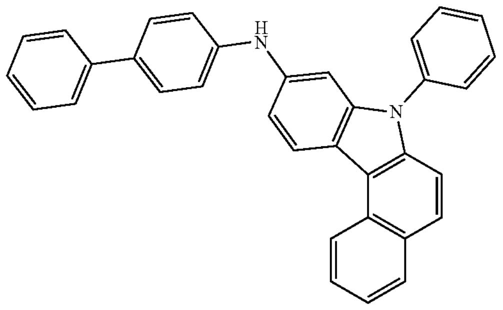
Sub 2-42
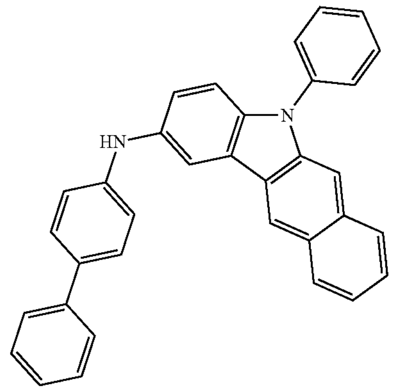
Sub 2-43
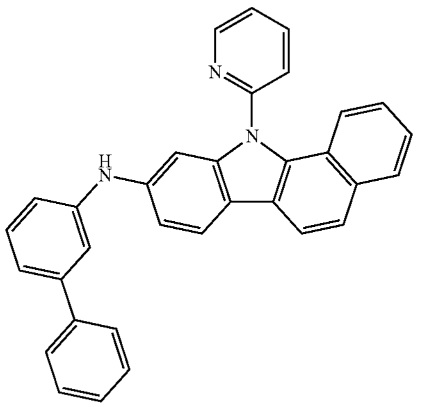
-continued
Sub 2-44
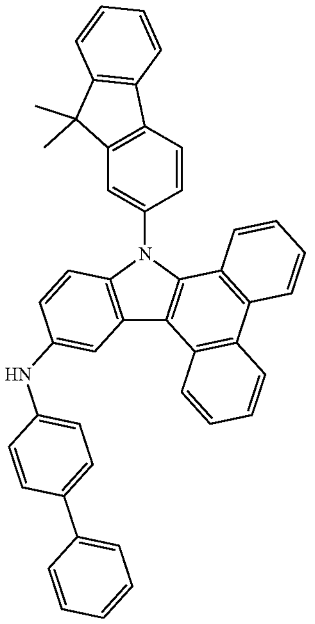
Sub 2-45
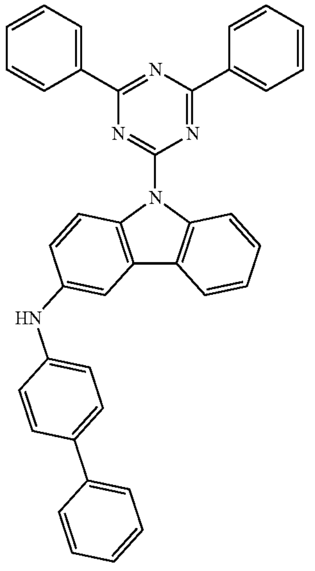

-continued

Sub 2-46

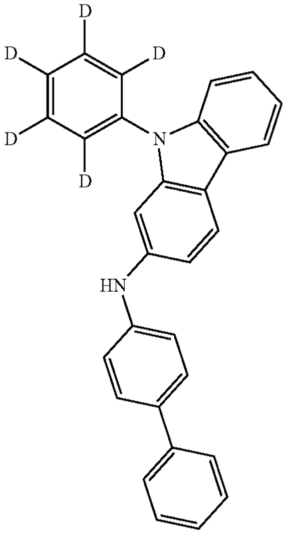

Sub 2-47

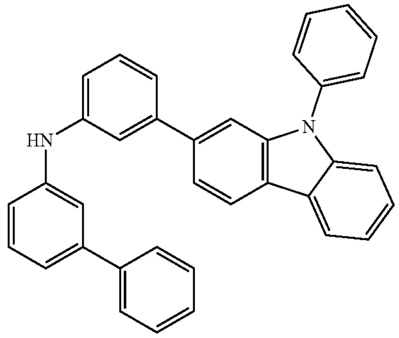

Sub 2-48

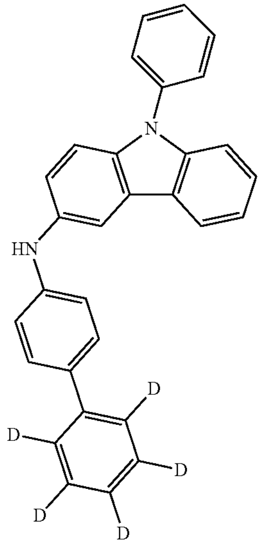

TABLE 2

| Compound | FD-MS |
| --- | --- |
| Sub 2-1 | m/z = 169.09($C_{12}H_{11}N$ = 169.22) |
| Sub 2-2 | m/z = 245.12($C_{18}H_{15}N$ = 245.32) |
| Sub 2-3 | m/z = 245.12($C_{18}H_{15}N$ = 245.32) |
| Sub 2-4 | m/z = 321.15($C_{24}H_{19}N$ = 321.41) |
| Sub 2-5 | m/z = 321.15($C_{24}H_{19}N$ = 321.41) |
| Sub 2-6 | m/z = 269.12($C_{20}H_{15}N$ = 269.34) |
| Sub 2-7 | m/z = 269.12($C_{20}H_{15}N$ = 269.34) |
| Sub 2-8 | m/z = 295.14($C_{22}H_{17}N$ = 295.38) |
| Sub 2-9 | m/z = 409.18($C_{31}H_{23}N$ = 409.52) |
| Sub 2-10 | m/z = 483.20($C_{37}H_{25}N$ = 483.60) |
| Sub 2-11 | m/z = 459.20($C_{35}H_{25}N$ = 459.58) |
| Sub 2-12 | m/z = 485.21($C_{37}H_{27}N$ = 485.62) |
| Sub 2-13 | m/z = 351.11($C_{34}H_{17}NS$ = 351.46) |
| Sub 2-14 | m/z = 335.13($C_{24}H_{17}NO$ = 335.40) |
| Sub 2-15 | m/z = 297.13($C_{20}H_{15}N_3$ = 297.35) |
| Sub 2-16 | m/z = 219.10($C_{16}H_{13}N$ = 219.28) |
| Sub 2-17 | m/z = 249.12($C_{17}H_{15}NO$ = 249.31) |
| Sub 2-18 | m/z = 197.12($C_{14}H_{15}N$ = 197.28) |
| Sub 2-19 | m/z = 229.11($C_{14}H_{15}NO_2$ = 229.27) |
| Sub 2-20 | m/z = 174.12($C_{12}H_6D_5N$ = 174.25) |
| Sub 2-21 | m/z = 281.21($C_{20}H_{27}N$ = 281.44) |
| Sub 2-22 | m/z = 321.15($C_{24}H_{19}N$ = 321.41) |
| Sub 2-23 | m/z = 321.15($C_{24}H_{19}N$ = 321.41) |
| Sub 2-24 | m/z = 321.15($C_{24}H_{19}N$ = 321.41) |
| Sub 2-25 | m/z = 321.15($C_{24}H_{19}N$ = 321.41) |
| Sub 2-26 | m/z = 321.15($C_{24}H_{19}N$ = 321.41) |
| Sub 2-27 | m/z = 297.13($C_{20}H_{15}N_3$ = 297.35) |
| Sub 2-28 | m/z = 275.08($C_{18}H_{13}NS$ = 275.37) |
| Sub 2-29 | m/z = 361.18($C_{27}H_{23}N$ = 361.48) |
| Sub 2-30 | m/z = 499.20($C_{36}H_{25}N_3$ = 499.60) |
| Sub 2-31 | m/z = 499.20($C_{36}H_{22}N_2$ = 410.51) |
| Sub 2-32 | m/z = 424.16($C_{30}H_{20}N_2O$ = 424.49) |
| Sub 2-33 | m/z = 440.13($C_{30}H_{20}N_2S$ = 440.56) |
| Sub 2-34 | m/z = 384.16($C_{28}H_{20}N_2$ = 384.47) |
| Sub 2-35 | m/z = 334.15($C_{24}H_{18}N_2$ = 334.41) |
| Sub 2-36 | m/z = 450.21($C_{33}H_{26}N_2$ = 450.57) |
| Sub 2-37 | m/z = 410.18($C_{30}H_{22}N_2$ = 410.51) |
| Sub 2-38 | m/z = 410.18($C_{30}H_{22}N_2$ = 410.51) |
| Sub 2-39 | m/z = 575.24($C_{42}H_{29}N_3$ = 575.70) |
| Sub 2-40 | m/z = 574.24($C_{43}H_{30}N_2$ = 574.71) |
| Sub 2-41 | m/z = 460.19($C_{34}H_{24}N_2$ = 460.57) |
| Sub 2-42 | m/z = 460.19($C_{34}H_{24}N_2$ = 460.57) |
| Sub 2-43 | m/z = 461.19($C_{33}H_{23}N_3$ = 461.56) |
| Sub 2-44 | m/z = 626.27($C_{47}H_{34}N_2$ = 626.79) |
| Sub 2-45 | m/z = 565.23($C_{39}H_{27}N_5$ = 565.67) |
| Sub 2-46 | m/z = 415.21($C_{30}H_{17}D_5N_2$ = 415.54) |
| Sub 2-47 | m/z = 486.21($C_{36}H_{26}N_2$ = 486.61) |
| Sub 2-48 | m/z = 415.21($C_{30}H_{17}D_5N_2$ = 415.54) |

III. Synthesis Examples of Final Products

Sub 2 (1 eq) was dissolved in toluene in a round bottom flask. Then, 1 (1.1 eq), $Pd_2(dba)_3$ (0.05 eq), $P(t\text{-}Bu)_3$ (0.1 eq) and NaOt-Bu (3 eq) were added into the round bottom flask, and the mixture was stirred 100° C. After the completion of the reaction, the reaction product was extracted with $CH_2Cl_2$ and water. The extracted organic layer was dried over $MgSO_4$ and concentrated. The concentrated resultant was separated by silica gel column chromatography, and was then recrystallized, whereby final products were obtained.

1. Synthesis of Product P1-1

<Reaction Scheme 59>

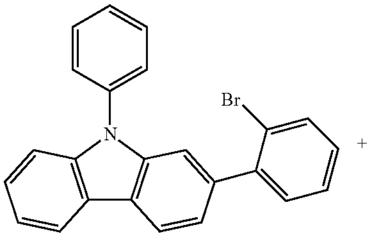

Sub 1-1

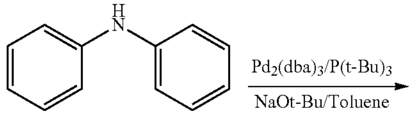

Sub 2-1

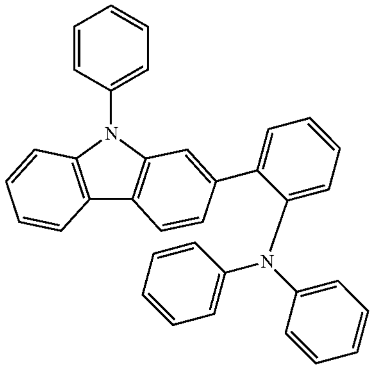

P1-1

Sub 2-1 (8 g, 47.3 mmol) was dissolved in toluene (500 ml) in a round bottom flask. Then, Sub 1-1 (20.7 g, 52.0 mmol), $Pd_2(dba)_3$ (2.2 g, 2.4 mmol), $P(t\text{-}Bu)_3$ (1 g, 4.73 mmol) and NaOt-Bu (13.6 g, 141.8 mmol) were added into the round bottom flask, and the mixture was stirred at 100° C. After the completion of the reaction, the reaction product was extracted with $CH_2C_2$ and water. The extracted organic layer was dried over $MgSO_4$ and concentrated. The concentrated resultant was separated by silica gel column chromatography, and was then recrystallized, whereby a compound P1-1 was obtained in an amount of 16.2 g in 70% yield.

2. Synthesis of Product P1-4

<Reaction Scheme 60>

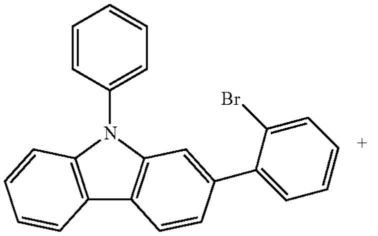

Sub 1-1

-continued

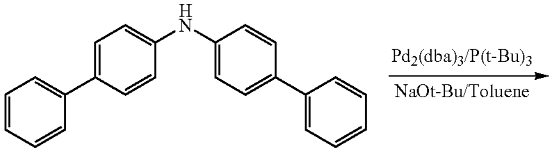

Sub 2-4

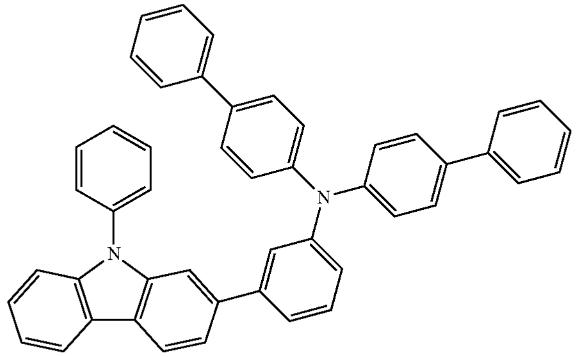

P1-4

The compound P1-4 was synthesized by using Sub 2-4 (7.8 g, 24.9 mmol), Sub 1-1 (10.7 g, 27.4 mmol), $Pd_2(dba)_3$ (1.14 g, 1.24 mmol), $P(t\text{-}Bu)_3$ (0.5 g, 2.49 mmol), NaOt-Bu (7.17 g, 74.7 mmol) and toluene (265 ml) in the same manner as described in the synthesis method of the compound Product P1-1 above, whereby a compound P1-4 was obtained in an amount of 10.6 g in 68% yield.

3. Synthesis of Product P1-8

<Reaction Scheme 61>

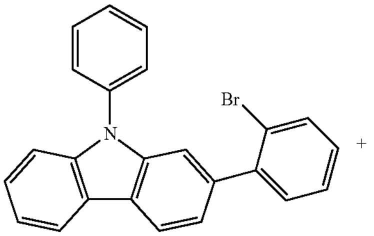

Sub 1-1

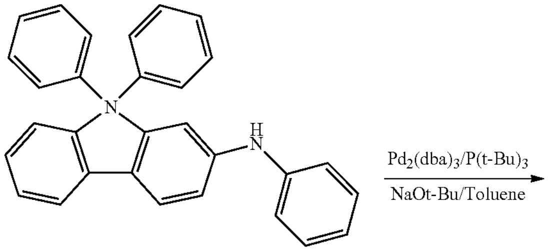

Sub 2-9

-continued

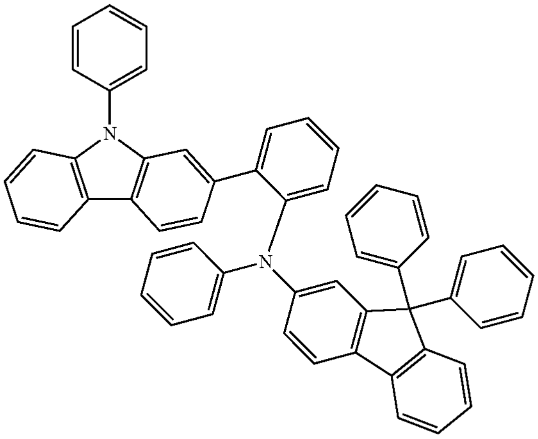

P1-8

The compound P1-8 was synthesized by using Sub 2-9 (10 g, 24.4 mmol), Sub 2-9 (10 g, 24.4 mmol), Sub 1-1 (10.7 g, 27.4 mmol), $Pd_2(dba)_3$ (1.14 g, 1.24 mmol), $P(t-Bu)_3$ (0.5 g, 2.49 mmol), NaOt-Bu (7.17 g, 74.7 mmol) and toluene (265 ml) in the same manner as described in the synthesis method of the compound Product P1-1 above, whereby a compound P1-8 was obtained in an amount of 11.5 g in 77% yield.

4. Synthesis of Product P1-17

<Reaction Scheme 62>

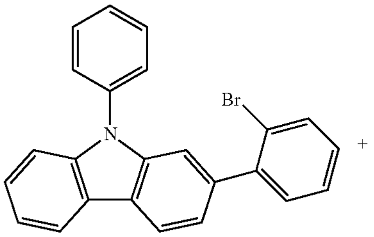

Sub 1-4

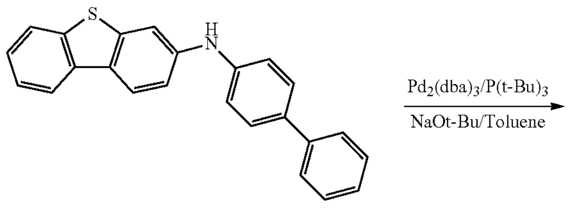

Sub 2-13

-continued

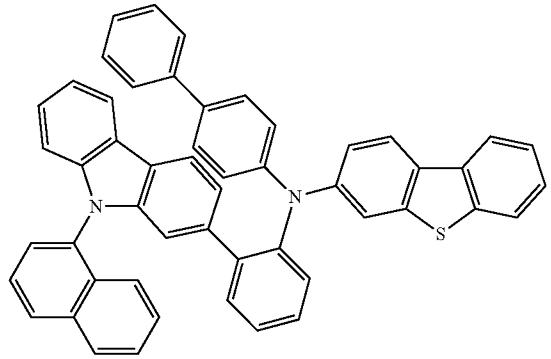

P1-17

The compound P1-17 was synthesized by using Sub 2-13 (10.0 g, 28.5 mmol), Sub 1-4 (14.0 g, 31.3 mmol), $Pd_2(dba)_3$ (1.3 g, 1.42 mmol), $P(t-Bu)_3$ (0.6 g, 2.85 mmol), NaOt-Bu (8.2 g, 85.4 mmol) and toluene (300 ml) in the same manner as described in the synthesis method of the compound Product P1-1 above, whereby a compound P1-17 was obtained in an amount of 13.5 g in 66% yield.

5. Synthesis of Product P1-49

<Reaction Scheme 63>

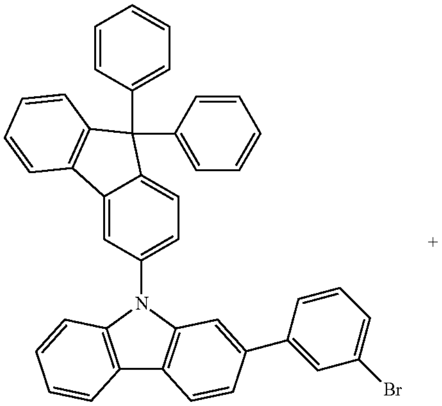

Sub 1-65

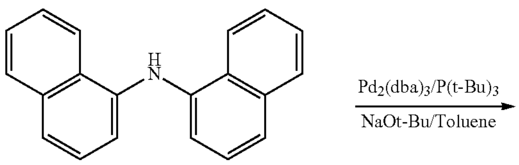

Sub 2-6

-continued

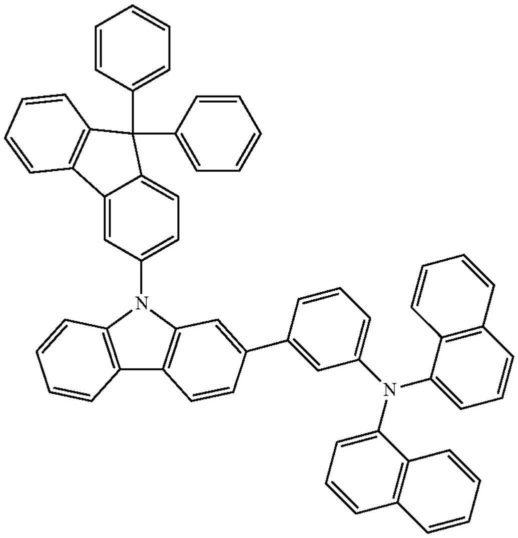

P2-49

The compound P2-49 was synthesized by using Sub 2-6 (11.0 g, 37.13 mmol), Sub 1-65 (23.7 g, 40.84 mmol), $Pd_2(dba)_3$ (1.7 g, 1.9 mmol), $P(t\text{-}Bu)_3$ (0.8 g, 3.7 mmol), NaOt-Bu (10.7 g, 111.4 mmol) and toluene (390 ml) in the same manner as described in the synthesis method of the compound Product P1-1 above, whereby a compound P2-49 was obtained in an amount of 24.7 g in 73% yield.

6. Synthesis of Product P2-77

<Reaction Scheme 64>

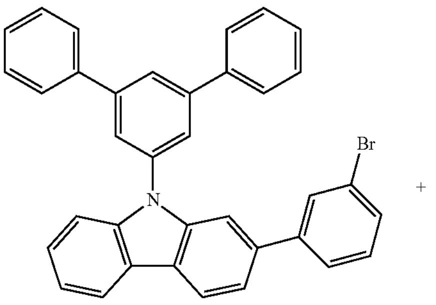

Sub 1-68

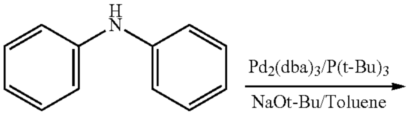

Sub 2-1

-continued

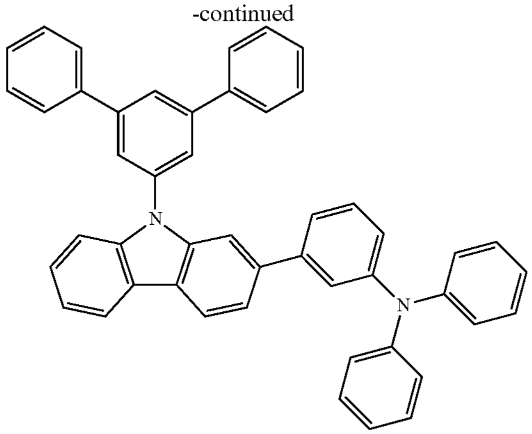

P2-77

The compound P2-77 was synthesized by using Sub 2-1 (8.0 g, 47.3 mmol), Sub 1-68 (28.6 g, 52 mmol), $Pd_2(dba)_3$ (2.2 g, 2.4 mmol), $P(t\text{-}Bu)_3$ (1 g, 4.73 mmol), NaOt-Bu (13.6 g, 141.8 mmol) and toluene (500 ml) in the same manner as described in the synthesis method of the compound Product P1-1 above, whereby a compound P2-77 was obtained in an amount of 22.7 g in 75% yield.

7. Synthesis of Product P3-2

<Reaction Scheme 65>

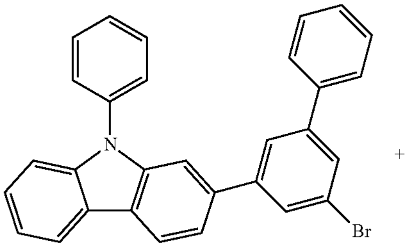

Sub 1-103

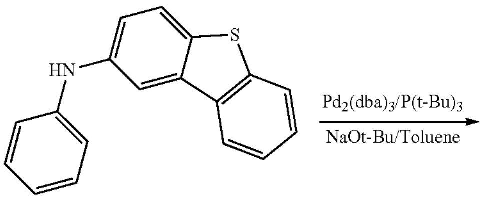

Sub 2-28

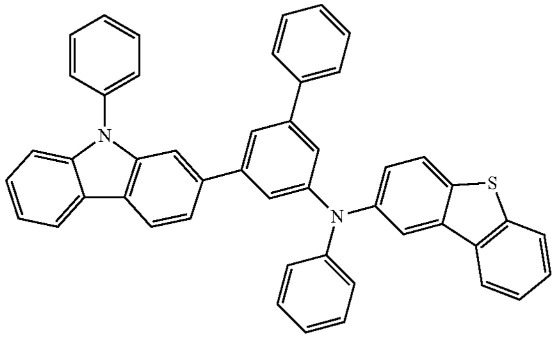

P3-2

The compound P3-4 was synthesized by Sub 2-28 (22.4 g, 47.3 mmol), Sub 1-103 (14.3 g, 52 mmol), $Pd_2(dba)_3$ (2.2 g, 2.4 mmol), $P(t\text{-}Bu)_3$ (1 g, 4.73 mmol), NaOt-Bu (13.6 g, 141.8 mmol) and toluene (500 mL) in the same manner as described in the synthesis method of the compound Product P1-1 above, whereby a compound P3-2 was obtained in an amount of 23.1 g in 73% yield.

8. Synthesis of Product P3-22

<Reaction Scheme 66>

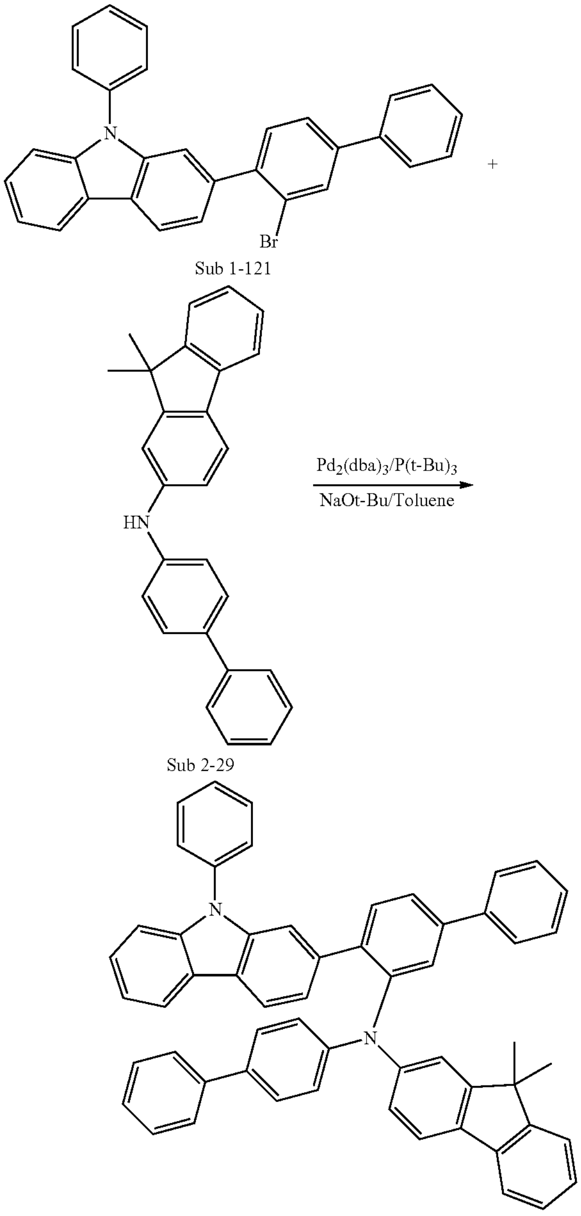

Sub 1-121

Sub 2-29

P3-22

The compound P3-22 was synthesized by using Sub 2-29 (22.4 g, 47.3 mmol), Sub 1-121 (18.8 g, 52 mmol), $Pd_2(dba)_3$ (2.2 g, 2.4 mmol), $P(t\text{-}Bu)_3$ (1 g, 4.73 mmol), NaOt-Bu (13.6 g, 141.8 mmol) and toluene (500 mL) in the same manner as described in the synthesis method of the compound Product P1-1 above, whereby a compound P3-22 was obtained in an amount of 24.3 g in 68% yield.

9. Synthesis of Product P4-2

<Reaction Scheme 67>

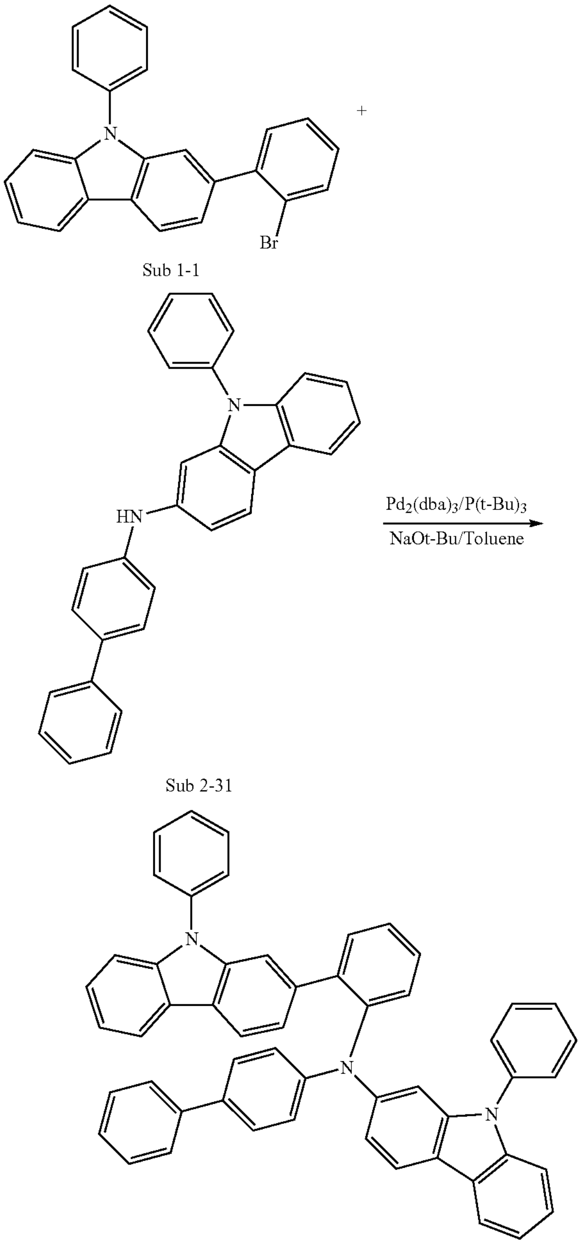

Sub 1-1

Sub 2-31

P4-2

The compound P4-2 was synthesized by using Sub 2-31 (19.4 g, 47.3 mmol), Sub 1-1 (20.7 g, 52 mmol), $Pd_2(dba)_3$ (2.2 g, 2.4 mmol), $P(t\text{-}Bu)_3$ (1 g, 4.73 mmol), NaOt-Bu (13.6 g, 141.8 mmol) and toluene (500 mL) in the same manner as described in the synthesis method of the compound Product P1-1 above, whereby a compound P4-2 was obtained in an amount of 30.3 g in 80% yield.

10. Synthesis of Product P4-9

<Reaction Scheme 68>

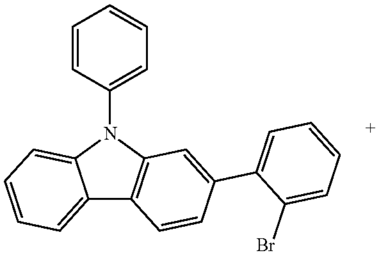

Sub 1-1

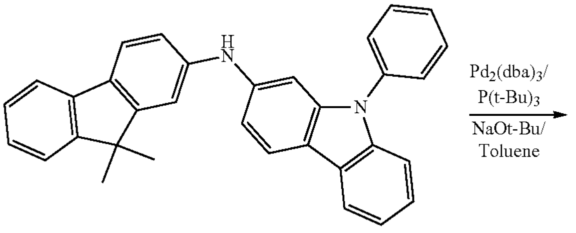

Sub 2-36

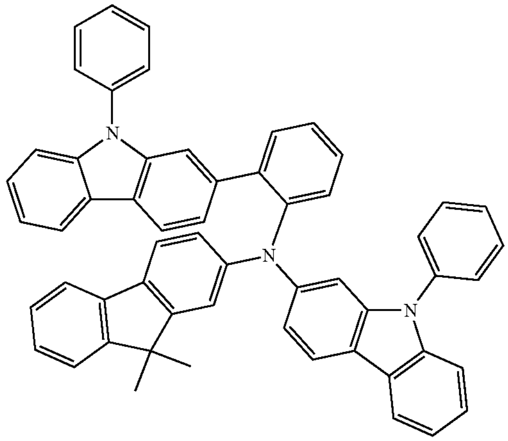

P4-9

The compound P4-9 was synthesized by using Sub 2-36 (21.3 g, 47.3 mmol), Sub 1-1 (20.7 g, 52 mmol), $Pd_2(dba)_3$ (2.2 g, 2.4 mmol), $P(t-Bu)_3$ (1 g, 4.73 mmol), NaOt-Bu (13.6 g, 141.8 mmol) and toluene (500 mL) in the same manner as described in the synthesis method of the compound Product P1-1 above, whereby a compound P4-9 was obtained in an amount of 32.7 g in 82% yield.

11. Synthesis of Product P4-15

<Reaction Scheme 69>

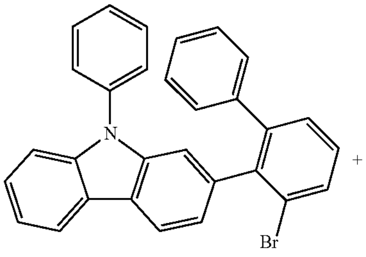

Sub 1-129

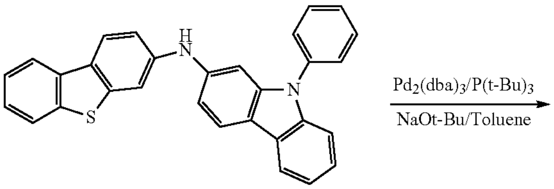

Sub 2-33

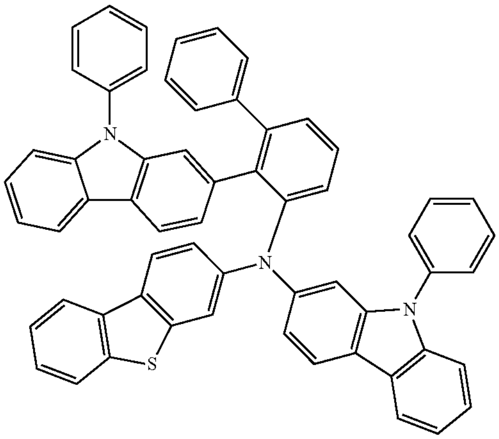

P4-15

The compound P4-15 was synthesized by using Sub 2-33 (20.8 g, 47.3 mmol), Sub 1-129 (24.7 g, 52 mmol), $Pd_2(dba)_3$ (2.2 g, 2.4 mmol), $P(t-Bu)_3$ (1 g, 4.73 mmol), NaOt-Bu (13.6 g, 141.8 mmol) and toluene (500 mL) in the same manner as described in the synthesis method of the compound Product P1-1 above, whereby a compound P4-15 was obtained in an amount of 33.8 g in 78% yield.

12. Synthesis of Product P4-20

<Reaction Scheme 70>

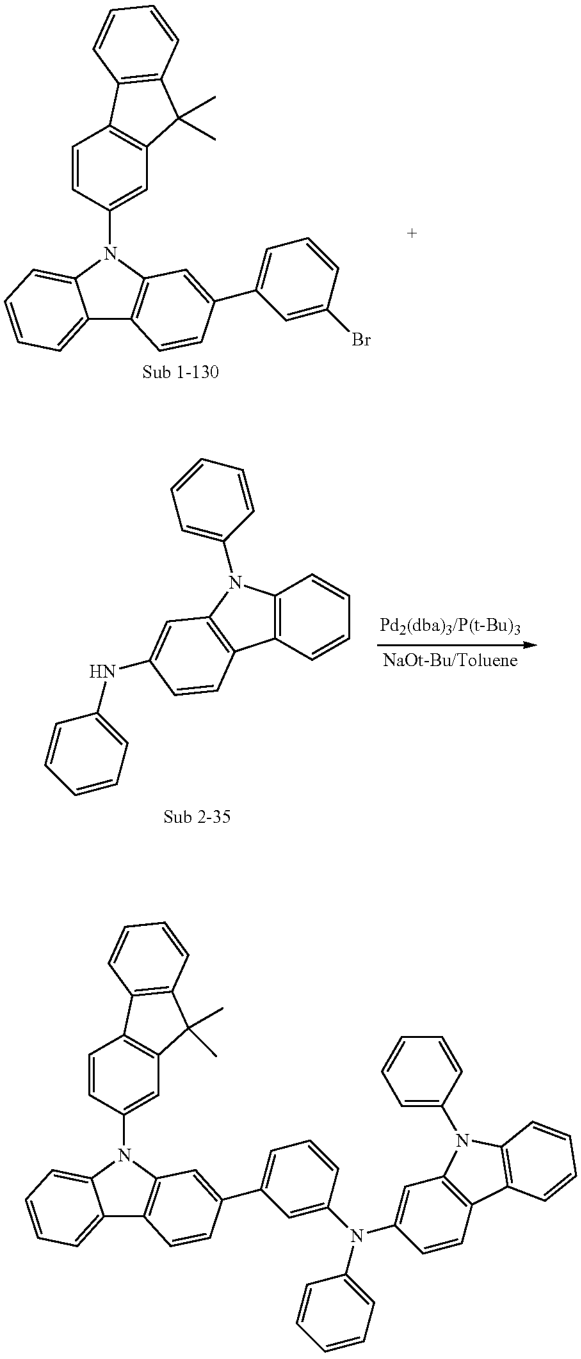

Sub 1-130

Sub 2-35

P4-20

The compound P4-20 was synthesized by using Sub 2-35 (15.8 g, 47.3 mmol), Sub 1-130 (26.8 g, 52 mmol), $Pd_2(dba)_3$ (2.2 g, 2.4 mmol), $P(t\text{-}Bu)_3$ (1 g, 4.73 mmol), NaOt-Bu (13.6 g, 141.8 mmol) and toluene (500 mL) in the same manner as described in the synthesis method of the compound Product P1-1 above, whereby a compound P4-20 was obtained in an amount of 32.3 g in 81% yield.

13. Synthesis of Product P4-29

<Reaction Scheme 71>

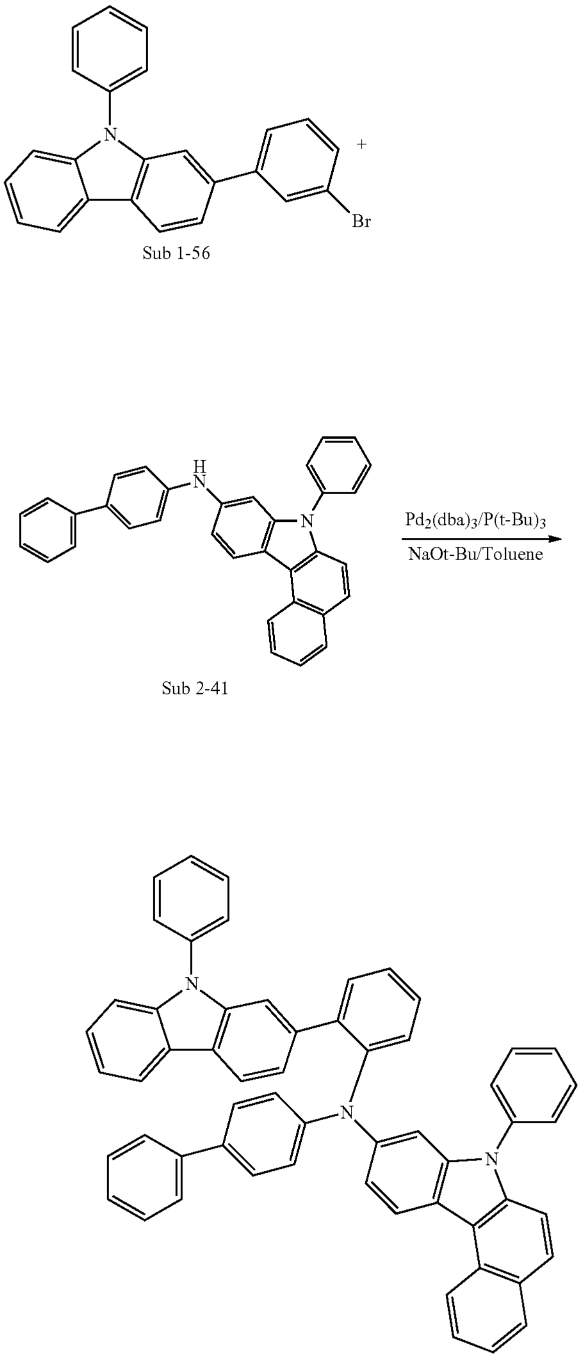

Sub 1-56

Sub 2-41

P4-29

The compound P4-29 was synthesized by using Sub 2-41 (21.8 g, 47.3 mmol), Sub 1-56 (20.7 g, 52 mmol), $Pd_2(dba)_3$ (2.2 g, 2.4 mmol), $P(t\text{-}Bu)_3$ (1 g, 4.73 mmol), NaOt-Bu (13.6 g, 141.8 mmol) and toluene (500 mL) in the same manner as described in the synthesis method of the compound Product P1-1 above, whereby a compound P4-29 was obtained in an amount of 32.0 g in 79% yield.

14. Synthesis of Product P4-33

<u><Reaction Scheme 72></u>

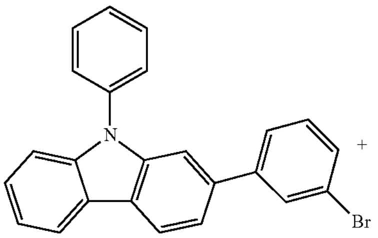

Sub 1-56

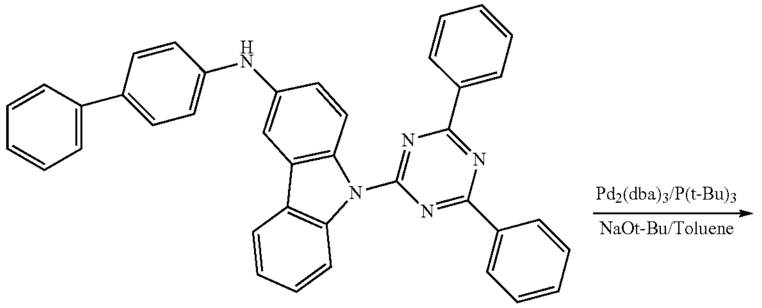

Sub 2-45

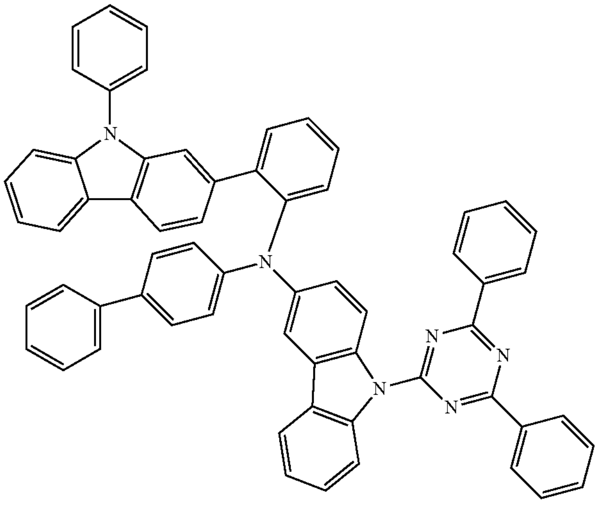

P4-33

The compound P4-33 was synthesized by using Sub 2-45 (26.8 g, 47.3 mmol), Sub 1-56 (20.7 g, 52 mmol), $Pd_2(dba)_3$ (2.2 g, 2.4 mmol), $P(t-Bu)_3$ (1 g, 4.73 mmol), NaOt-Bu (13.6 g, 141.8 mmol) and toluene (500 mL) in the same manner as described in the synthesis method of the compound Product P1-1 above, whereby a compound P4-33 was obtained in an amount of 36.7 g in 80% yield.

15. Synthesis of Product P4-36

<u><Reaction Scheme 73></u>

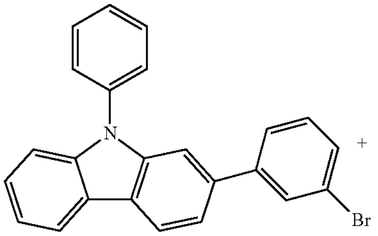

Sub 1-56

-continued

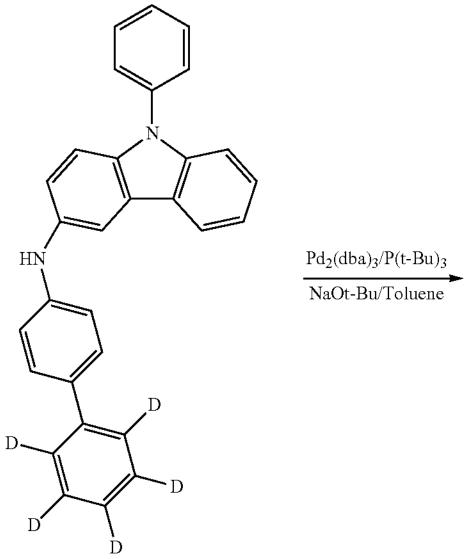

Sub 2-48

-continued

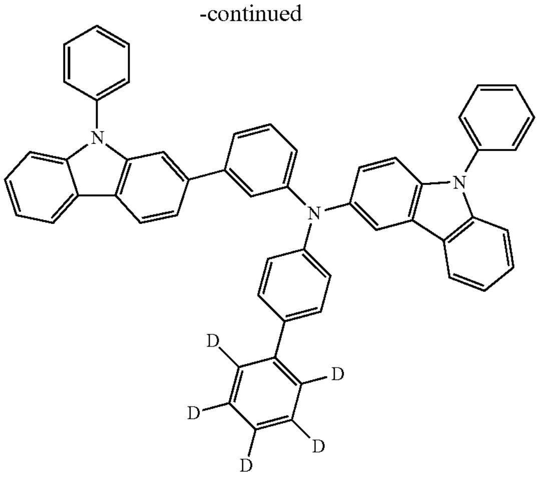

P4-36

The compound P4-36 was synthesized by using Sub 2-48 (19.7 g, 47.3 mmol), Sub 1-56 (20.7 g, 52 mmol), $Pd_2(dba)_3$ (2.2 g, 2.4 mmol), $P(t\text{-}Bu)_3$ (1 g, 4.73 mmol), NaOt-Bu (13.6 g, 141.8 mmol) and toluene (500 mL) in the same manner as described in the synthesis method of the compound Product P1-1 above, whereby a compound P4-36 was obtained in an amount of 29.0 g in 76% yield.

FD-MS data of the final products, P1-1 to P1-112, P2-1 to P2-112, P3-1 to P3-38, and P4-1 to P4-36, synthesized according to the above synthesis example are given in Table 3 below.

TABLE 3

| Compound | FD-MS |
|---|---|
| P1-1 | m/z = 486.21($C_{36}H_{26}N_2$ = 486.61) |
| P1-2 | m/z = 562.24($C_{42}H_{30}N_2$ = 562.70) |
| P1-3 | m/z = 562.24($C_{42}H_{30}N_2$ = 562.70) |
| P1-4 | m/z = 638.27($C_{48}H_{34}N_2$ = 638.80) |
| P1-5 | m/z = 586.24($C_{44}H_{30}N_2$ = 586.72) |
| P1-6 | m/z = 586.24($C_{44}H_{30}N_2$ = 586.72) |
| P1-7 | m/z = 612.26($C_{46}H_{32}N_2$ = 612.76) |
| P1-8 | m/z = 726.30($C_{55}H_{38}N_2$ = 726.90) |
| P1-9 | m/z = 638.27($C_{48}H_{34}N_2$ = 638.80) |
| P1-10 | m/z = 800.32($C_{61}H_{40}N_2$ = 800.98) |
| P1-11 | m/z = 536.23($C_{40}H_{28}N_2$ = 536.66) |
| P1-12 | m/z = 688.29($C_{52}H_{36}N_2$ = 688.86) |
| P1-13 | m/z = 852.35($C_{65}H_{44}N_2$ = 853.06) |
| P1-14 | m/z = 638.27($C_{48}H_{34}N_2$ = 638.80) |
| P1-15 | m/z = 688.29($C_{52}H_{36}N_2$ = 688.86) |
| P1-16 | m/z = 662.27($C_{50}H_{34}N_2$ = 662.82) |
| P1-17 | m/z = 718.24($C_{52}H_{34}N_2S$ = 718.90) |
| P1-18 | m/z = 702.27($C_{52}H_{34}N_2O$ = 702.84) |
| P1-19 | m/z = 664.26($C_{48}H_{32}N_4$ = 664.79) |
| P1-20 | m/z = 664.26($C_{48}H_{34}N_4$ = 664.79) |
| P1-21 | m/z = 562.24($C_{42}H_{30}N_2$ = 562.70) |
| P1-22 | m/z = 562.24($C_{42}H_{30}N_2$ = 562.70) |
| P1-23 | m/z = 780.35($C_{56}H_{48}N_2S$ = 781.06) |
| P1-24 | m/z = 665.26($C_{47}H_{31}N_5$ = 665.78) |
| P1-25 | m/z = 526.24($C_{39}H_{30}N_2$ = 526.67) |
| P1-26 | m/z = 739.30($C_{55}H_{37}N_3$ = 739.90) |
| P1-27 | m/z = 642.27($C_{47}H_{34}N_2O$ = 642.79) |
| P1-28 | m/z = 790.31($C_{58}H_{38}N_4$ = 790.95) |
| P1-29 | m/z = 726.30($C_{55}H_{38}N_2$ = 726.90) |
| P1-30 | m/z = 802.33($C_{61}H_{42}N_2$ = 803.00) |
| P1-31 | m/z = 802.33($C_{61}H_{42}N_2$ = 803.00) |
| P1-32 | m/z = 878.37($C_{67}H_{46}N_2$ = 879.10) |
| P1-33 | m/z = 726.30($C_{55}H_{38}N_2$ = 726.90) |
| P1-34 | m/z = 726.30($C_{55}H_{38}N_2$ = 726.90) |
| P1-35 | m/z = 852.35($C_{65}H_{44}N_2$ = 853.06) |
| P1-36 | m/z = 1016.41($C_{78}H_{52}N_2$ = 1017.26) |
| P1-37 | m/z = 878.37($C_{67}H_{46}N_2$ = 879.10) |

TABLE 3-continued

| Compound | FD-MS |
|---|---|
| P1-38 | m/z = 1040.41($C_{80}H_{52}N_2$ = 1041.28) |
| P1-39 | m/z = 776.32($C_{59}H_{40}N_2$ = 776.95) |
| P1-40 | m/z = 878.37($C_{67}H_{46}N_2$ = 879.10) |
| P1-41 | m/z = 878.37($C_{67}H_{46}N_2$ = 879.10) |
| P1-42 | m/z = 878.37($C_{67}H_{46}N_2$ = 879.10) |
| P1-43 | m/z = 878.37($C_{67}H_{46}N_2$ = 879.10) |
| P1-44 | m/z = 878.37($C_{67}H_{46}N_2$ = 879.10) |
| P1-45 | m/z = 726.30($C_{55}H_{38}N_2$ = 726.90) |
| P1-46 | m/z = 802.33($C_{61}H_{42}N_2$ = 803.00) |
| P1-47 | m/z = 802.33($C_{61}H_{42}N_2$ = 803.00) |
| P1-48 | m/z = 878.37($C_{67}H_{46}N_2$ = 879.10) |
| P1-49 | m/z = 826.33($C_{63}H_{42}N_2$ = 827.02) |
| P1-50 | m/z = 826.33($C_{63}H_{42}N_2$ = 827.02) |
| P1-51 | m/z = 852.35($C_{65}H_{44}N_2$ = 853.06) |
| P1-52 | m/z = 1016.41($C_{78}H_{52}N_2$ = 1017.26) |
| P1-53 | m/z = 878.37($C_{67}H_{46}N_2$ = 879.10) |
| P1-54 | m/z = 1040.41($C_{80}H_{52}N_2$ = 1041.28) |
| P1-55 | m/z = 776.32($C_{59}H_{40}N_2$ = 776.96) |
| P1-56 | m/z = 878.37($C_{67}H_{46}N_2$ =879.10) |
| P1-57 | m/z = 878.37($C_{67}H_{46}N_2$ = 879.10) |
| P1-58 | m/z = 878.37($C_{67}H_{46}N_2$ = 879.10) |
| P1-59 | m/z = 878.37($C_{67}H_{46}N_2$ = 879.10) |
| P1-60 | m/z = 878.37($C_{67}H_{46}N_2$ = 879.10) |
| P1-61 | m/z = 726.30($C_{55}H_{38}N_2$ = 726.90) |
| P1-62 | m/z = 802.33($C_{61}H_{42}N_2$ = 803.00) |
| P1-63 | m/z = 802.33($C_{61}H_{42}N_2$ = 803.00) |
| P1-64 | m/z = 878.37($C_{67}H_{46}N_2$ = 879.10) |
| P1-65 | m/z = 826.33($C_{63}H_{42}N_2$ = 827.02) |
| P1-66 | m/z = 826.33($C_{63}H_{42}N_2$ = 827.02) |
| P1-67 | m/z = 852.35($C_{65}H_{44}N_2$ = 853.06) |
| P1-68 | m/z = 1016.41($C_{78}H_{52}N_2$ = 1017.26) |
| P1-69 | m/z = 878.37($C_{67}H_{46}N_2$ = 879.10) |
| P1-70 | m/z = 1040.41($C_{80}H_{52}N_2$ = 1041.28) |
| P1-71 | m/z = 776.32($C_{59}H_{40}N_2$ = 776.96) |
| P1-72 | m/z = 878.37($C_{67}H_{46}N_2$ = 879.10) |
| P1-73 | m/z = 878.37($C_{67}H_{46}N_2$ = 879.10) |
| P1-74 | m/z = 878.37($C_{67}H_{46}N_2$ = 879.10) |
| P1-75 | m/z = 878.37($C_{67}H_{46}N_2$ = 879.10) |
| P1-76 | m/z = 878.37($C_{67}H_{46}N_2$ = 879.10) |
| P1-77 | m/z = 638.27($C_{48}H_{34}N_2$ = 638.80) |
| P1-78 | m/z = 714.30($C_{54}H_{38}N_2$ = 714.89) |
| P1-79 | m/z = 714.30($C_{54}H_{38}N_2$ = 714.89) |
| P1-80 | m/z = 790.33($C_{60}H_{42}N_2$ = 790.99) |
| P1-81 | m/z = 738.30($C_{56}H_{38}N_2$ = 738.91) |
| P1-82 | m/z = 738.30($C_{56}H_{38}N_2$ = 738.91) |
| P1-83 | m/z = 764.32($C_{58}H_{40}N_2$ = 764.95) |
| P1-84 | m/z = 928.38($C_{71}H_{48}N_2$ = 929.15) |
| P1-85 | m/z = 790.33($C_{60}H_{42}N_2$ = 790.99) |
| P1-86 | m/z = 638.27($C_{48}H_{34}N_2$ = 638.80) |
| P1-87 | m/z = 638.27($C_{48}H_{34}N_2$ = 638.80) |
| P1-88 | m/z = 638.27($C_{48}H_{34}N_2$ = 638.80) |
| P1-89 | m/z = 648.33($C_{48}H_{24}D_{10}N_2$ =648.86) |
| P1-90 | m/z = 724.37($C_{54}H_{28}D_{10}N_2$ = 724.95) |
| P1-91 | m/z = 795.37($C_{60}H_{37}D_5N_2$ = 796.02) |
| P1-92 | m/z = 643.30($C_{48}H_{29}D_5N_2$ = 643.83) |
| P1-93 | m/z = 776.32($C_{59}H_{40}N_2$ = 776.96) |
| P1-94 | m/z = 826.33($C_{63}H_{42}N_2$ = 827.02) |
| P1-95 | m/z = 776.32($C_{59}H_{40}N_2$ = 776.96) |
| P1-96 | m/z = 826.33($C_{63}H_{42}N_2$ = 827.02) |
| P1-97 | m/z = 854.37($C_{65}H_{46}N_2$ = 855.07) |
| P1-98 | m/z = 836.34($C_{61}H_{44}N_2O_2$ = 837.01) |
| P1-99 | m/z = 826.33($C_{63}H_{42}N_2$ = 827.02) |
| P1-100 | m/z = 826.33($C_{63}H_{42}N_2$ = 827.02) |
| P1-101 | m/z = 692.23($C_{50}H_{32}N_2S$ = 692.87) |
| P1-102 | m/z = 692.23($C_{50}H_{32}N_2S$ = 692.87) |
| P1-103 | m/z = 718.24($C_{52}H_{34}N_2S$ = 718.90) |
| P1-104 | m/z = 882.31($C_{65}H_{42}N_2S$ = 883.11) |
| P1-105 | m/z = 676.25($C_{50}H_{32}N_2O$ = 676.80) |
| P1-106 | m/z = 676.25($C_{50}H_{32}N_2O$ = 676.80) |
| P1-107 | m/z = 702.27($C_{52}H_{34}N_2O$ = 702.84) |
| P1-108 | m/z = 866.33($C_{65}H_{42}N_2O$ = 867.04) |
| P1-109 | m/z = 826.33($C_{63}H_{42}N_2$ = 827.02) |
| P1-110 | m/z = 826.33($C_{63}H_{42}N_2$ = 827.02) |
| P1-111 | m/z = 742.24($C_{54}H_{34}N_2S$ = 742.93) |
| P1-112 | m/z = 726.27($C_{54}H_{34}N_2O$ = 726.86) |
| P2-1 | m/z = 486.21($C_{36}H_{26}N_2$ = 486.61) |
| P2-2 | m/z = 562.24($C_{42}H_{30}N_2$ = 562.70) |
| P2-3 | m/z = 562.24($C_{42}H_{30}N_2$ = 562.70) |

TABLE 3-continued

| Compound | FD-MS |
|---|---|
| P2-4 | m/z = 638.27($C_{48}H_{34}N_2$ = 638.80) |
| P2-5 | m/z = 586.24($C_{44}H_{30}N_2$ = 586.72) |
| P2-6 | m/z = 586.24($C_{44}H_{30}N_2$ = 586.72) |
| P2-7 | m/z = 612.26($C_{46}H_{32}N_2$ = 612.76) |
| P2-8 | m/z = 726.30($C_{55}H_{38}N_2$ = 726.90) |
| P2-9 | m/z = 638.27($C_{48}H_{34}N_2$ = 638.80) |
| P2-10 | m/z = 800.32($C_{61}H_{40}N_2$ = 800.98) |
| P2-11 | m/z = 536.23($C_{40}H_{28}N_2$ = 536.66) |
| P2-12 | m/z = 688.29($C_{52}H_{36}N_2$ = 688.86) |
| P2-13 | m/z = 852.35($C_{65}H_{44}N_2$ = 853.06) |
| P2-14 | m/z = 638.27($C_{48}H_{34}N_2$ = 638.80) |
| P2-15 | m/z = 688.29($C_{52}H_{36}N_2$ = 688.86) |
| P2-16 | m/z = 662.27($C_{50}H_{34}N_2$ = 662.82) |
| P2-17 | m/z = 718.24($C_{52}H_{34}N_2S$ = 718.90) |
| P2-18 | m/z = 702.27($C_{52}H_{34}N_2O$ = 702.84) |
| P2-19 | m/z = 664.26($C_{48}H_{32}N_4$ = 664.79) |
| P2-20 | m/z = 664.26($C_{48}H_{32}N_4$ = 664.79) |
| P2-21 | m/z = 562.24($C_{42}H_{30}N_2$ = 562.70) |
| P2-22 | m/z = 562.24($C_{42}H_{30}N_2$ = 562.70) |
| P2-23 | m/z = 780.35($C_{56}H_{48}N_2S$ = 781.06) |
| P2-24 | m/z = 665.26($C_{47}H_{31}N_5$ = 665.78) |
| P2-25 | m/z = 526.24($C_{39}H_{30}N_2$ = 526.67) |
| P2-26 | m/z = 739.30($C_{55}H_{37}N_3$ = 739.90) |
| P2-27 | m/z = 642.27($C_{47}H_{34}N_2O$ = 642.79) |
| P2-28 | m/z = 790.31($C_{58}H_{38}N_4$ = 790.95) |
| P2-29 | m/z = 726.30($C_{55}H_{38}N_2$ = 726.90) |
| P2-30 | m/z = 802.33($C_{61}H_{42}N_2$ = 803.00) |
| P2-31 | m/z = 802.33($C_{61}H_{42}N_2$ = 803.00) |
| P2-32 | m/z = 878.37($C_{67}H_{46}N_2$ = 879.10) |
| P2-33 | m/z = 726.30($C_{55}H_{38}N_2$ = 726.90) |
| P2-34 | m/z = 726.30($C_{55}H_{38}N_2$ = 726.90) |
| P2-35 | m/z = 852.35($C_{65}H_{44}N_2$ = 853.06) |
| P2-36 | m/z = 1016.41($C_{78}H_{52}N_2$ = 1017.26) |
| P2-37 | m/z = 878.37($C_{67}H_{46}N_2$ = 879.10) |
| P2-38 | m/z = 1040.41($C_{80}H_{52}N_2$ = 1041.28) |
| P2-39 | m/z = 776.32($C_{59}H_{40}N_2$ = 776.96) |
| P2-40 | m/z = 878.37($C_{67}H_{46}N_2$ = 879.10) |
| P2-41 | m/z = 878.37($C_{67}H_{46}N_2$ = 879.10) |
| P2-42 | m/z = 878.37($C_{67}H_{46}N_2$ = 879.10) |
| P2-43 | m/z = 878.37($C_{67}H_{46}N_2$ = 879.10) |
| P2-44 | m/z = 878.37($C_{67}H_{46}N_2$ = 879.10) |
| P2-45 | m/z = 726.30($C_{55}H_{38}N_2$ = 726.90) |
| P2-46 | m/z = 802.33($C_{61}H_{42}N_2$ = 803.00) |
| P2-47 | m/z = 802.33($C_{61}H_{42}N_2$ = 803.00) |
| P2-48 | m/z = 878.37($C_{67}H_{46}N_2$ = 879.10) |
| P2-49 | m/z = 826.33($C_{63}H_{42}N_2$ = 827.02) |
| P2-50 | m/z = 826.33($C_{63}H_{42}N_2$ = 827.02) |
| P2-51 | m/z = 852.35($C_{65}H_{44}N_2$ = 853.06) |
| P2-52 | m/z = 1016.41($C_{78}H_{52}N_2$ = 1017.26) |
| P2-53 | m/z = 878.37($C_{67}H_{46}N_2$ = 879.10) |
| P2-54 | m/z = 1040.41($C_{80}H_{52}N_2$ = 1041.28) |
| P2-55 | m/z = 776.32($C_{59}H_{40}N_2$ = 776.96) |
| P2-56 | m/z = 878.37($C_{67}H_{46}N_2$ = 879.10) |
| P2-57 | m/z = 878.37($C_{67}H_{46}N_2$ = 879.10) |
| P2-58 | m/z = 878.37($C_{67}H_{46}N_2$ = 879.10) |
| P2-59 | m/z = 878.37($C_{67}H_{46}N_2$ = 879.10) |
| P2-60 | m/z = 878.37($C_{67}H_{46}N_2$ = 879.10) |
| P2-61 | m/z = 726.30($C_{55}H_{38}N_2$ = 726.90) |
| P2-62 | m/z = 802.33($C_{61}H_{42}N_2$ = 803.00) |
| P2-63 | m/z = 802.33($C_{61}H_{42}N_2$ = 803.00) |
| P2-64 | m/z = 878.37($C_{67}H_{46}N_2$ = 879.10) |
| P2-65 | m/z = 826.33($C_{63}H_{42}N_2$ = 827.02) |
| P2-66 | m/z = 826.33($C_{63}H_{42}N_2$ = 827.02) |
| P2-67 | m/z = 852.35($C_{65}H_{44}N_2$ = 853.06) |
| P2-68 | m/z = 1016.41($C_{78}H_{52}N_2$ = 1017.26) |
| P2-69 | m/z = 878.37($C_{67}H_{46}N_2$ = 879.10) |
| P2-70 | m/z = 1040.41($C_{80}H_{52}N_2$ = 1041.28) |
| P2-71 | m/z = 776.32($C_{59}H_{40}N_2$ = 776.96) |
| P2-72 | m/z = 878.37($C_{67}H_{46}N_2$ = 879.10) |
| P2-73 | m/z = 878.37($C_{67}H_{46}N_2$ = 879.10) |
| P2-74 | m/z = 878.37($C_{67}H_{46}N_2$ = 879.10) |
| P2-75 | m/z = 878.37($C_{67}H_{46}N_2$ = 879.10) |
| P2-76 | m/z = 878.37($C_{67}H_{46}N_2$ = 879.10) |
| P2-77 | m/z = 638.27($C_{48}H_{34}N_2$ = 638.80) |
| P2-78 | m/z = 714.30($C_{54}H_{38}N_2$ = 714.89) |
| P2-79 | m/z = 714.30($C_{54}H_{38}N_2$ = 714.89) |
| P2-80 | m/z = 790.33($C_{60}H_{42}N_2$ = 790.99 |
| P2-81 | m/z = 738.30($C_{56}H_{38}N_2$ = 738.91) |

TABLE 3-continued

| Compound | FD-MS |
|---|---|
| P2-82 | m/z = 738.30($C_{56}H_{38}N_2$ = 738.91) |
| P2-83 | m/z = 764.32($C_{58}H_{40}N_2$ = 764.95) |
| P2-84 | m/z = 928.38($C_{71}H_{48}N_2$ = 929.16) |
| P2-85 | m/z = 790.33($C_{60}H_{42}N_2$ = 790.99) |
| P2-86 | m/z = 638.27($C_{48}H_{34}N_2$ = 638.80) |
| P2-87 | m/z = 638.27($C_{48}H_{34}N_2$ = 638.80) |
| P2-88 | m/z = 638.27($C_{48}H_{34}N_2$ = 638.80) |
| P2-89 | m/z = 648.33($C_{48}H_{24}D_{10}N_2$ = 648.86 |
| P2-90 | m/z = 724.37($C_{54}H_{28}D_{10}N_2$ = 724.95) |
| P2-91 | m/z = 795.37($C_{60}H_{37}D_5N_2$ = 796.02) |
| P2-92 | m/z = 643.30($C_{48}H_{29}O_5N_2$ = 643.83) |
| P2-93 | m/z = 776.32($C_{59}H_{40}N_2$ = 776.96) |
| P2-94 | m/z = 826.33($C_{63}H_{42}N_2$ = 827.02) |
| P2-95 | m/z = 776.32($C_{59}H_{40}N_2$ = 776.96) |
| P2-96 | m/z = 826.33($C_{63}H_{42}N_2$ = 827.02) |
| P2-97 | m/z = 854.37($C_{65}H_{46}N_2$ = 855.07) |
| P2-98 | m/z = 836.34($C_{61}H_{44}N_2O_2$ = 837.01) |
| P2-99 | m/z = 826.33($C_{63}H_{42}N_2$ = 827.02) |
| P2-100 | m/z = 826.33($C_{63}H_{42}N_2$ = 827.02) |
| P2-101 | m/z = 692.23($C_{50}H_{32}N_2S$ = 692.87) |
| P2-102 | m/z = 692.23($C_{50}H_{32}N_2S$ = 692.87) |
| P2-103 | m/z = 718.24($C_{52}H_{34}N_2S$ = 718.90) |
| P2-104 | m/z = 882.31($C_{65}H_{42}N_2S$ = 883.11) |
| P2-105 | m/z = 676.25($C_{50}H_{32}N_2O$ = 676.80) |
| P2-106 | m/z = 676.25($C_{50}H_{32}N_2O$ = 676.80) |
| P2-107 | m/z = 702.27($C_{52}H_{34}N_2O$ = 702.84) |
| P2-108 | m/z = 866.33($C_{65}H_{42}N_2O$ = 867.04) |
| P2-109 | m/z = 826.33($C_{63}H_{42}N_2$ = 827.02) |
| P2-110 | m/z = 826.33($C_{63}H_{42}N_2$ = 827.02) |
| P2-111 | m/z = 742.24($C_{54}H_{34}N_2S$ = 742.93) |
| P2-112 | m/z = 726.27($C_{54}H_{34}N_2O$ = 726.86) |
| P3-1 | m/z = 562.24($C_{42}H_{30}N_2$ = 562.70) |
| P3-2 | m/z = 668.23($C_{48}H_{32}N_2S$ = 668.85) |
| P3-3 | m/z = 728.28($C_{54}H_{36}N_2O$ = 728.88) |
| P3-4 | m/z = 754.33($C_{57}H_{42}N_2$ = 754.96) |
| P3-5 | m/z = 802.33($C_{61}H_{42}N_2$ = 803.00) |
| P3-6 | m/z = 800.32($C_{61}H_{40}N_2$ = 800.98) |
| P3-7 | m/z = 612.26($C_{46}H_{32}N_2$ = 612.76) |
| P3-8 | m/z = 718.24($C_{52}H_{34}N_2S$ = 718.90) |
| P3-9 | m/z = 804.31($C_{60}H_{40}N_2O$ = 804.97) |
| P3-10 | m/z = 754.33($C_{57}H_{42}N_2$ = 754.96) |
| P3-11 | m/z = 928.38($C_{71}H_{48}N_2$ = 929.15) |
| P3-12 | m/z = 926.37($C_{71}H_{46}N_2$ = 927.14) |
| P3-13 | m/z = 688.29($C_{52}H_{36}N_2$ = 688.86) |
| P3-14 | m/z = 794.28($C_{58}H_{38}N_2S$ = 795.00) |
| P3-15 | m/z = 729.28($C_{53}H_{35}N_3O$ = 729.86) |
| P3-16 | m/z = 805.35($C_{60}H_{43}N_3$ = 806.00) |
| P3-17 | m/z = 854.34($C_{63}H_{42}N_4$ = 855.03) |
| P3-18 | m/z = 802.31($C_{59}H_{38}N_4$ = 802.96) |
| P3-19 | m/z = 562.24($C_{42}H_{30}N_2$ = 562.70) |
| P3-20 | m/z = 668.23($C_{48}H_{32}N_2S$ = 668.85) |
| P3-21 | m/z = 728.28($C_{54}H_{36}N_2O$ = 728.88 |
| P3-22 | m/z = 754.33($C_{57}H_{42}N_2$ = 754.96) |
| P3-23 | m/z = 802.33($C_{61}H_{42}N_2$ = 803.00) |
| P3-24 | m/z = 800.32($C_{61}H_{40}N_2$ = 800.98) |
| P3-25 | m/z = 612.26($C_{46}H_{32}N_2$ = 612.76) |
| P3-26 | m/z = 718.24($C_{52}H_{34}N_2S$ = 718.90) |
| P3-27 | m/z =804.31($C_{60}H_{40}N_2O$ = 804.97) |
| P3-28 | m/z = 754.33($C_{57}H_{42}N_2$ = 754.96) |
| P3-29 | m/z = 928.38($C_{71}H_{48}N_2$ = 929.15) |
| P3-30 | m/z = 926.37($C_{71}H_{46}N_2$ = 927.14) |
| P3-31 | m/z = 688.29($C_{52}H_{36}N_2$ = 688.86) |
| P3-32 | m/z = 794.28($C_{58}H_{38}N_2S$ = 795.00) |
| P3-33 | m/z = 729.28($C_{53}H_{35}N_3O$ = 729.86) |
| P3-34 | m/z = 805.35($C_{60}H_{43}N_3$ = 806.00) |
| P3-35 | m/z = 854.34($C_{63}H_{42}N_4$ = 855.03) |
| P3-36 | m/z = 802.31($C_{59}H_{38}N_4$ = 802.96) |
| P3-37 | m/z = 714.30($C_{54}H_{38}N_2$ = 714.89) |
| P3-38 | m/z = 714.30($C_{54}H_{38}N_2$ = 714.89) |
| P4-1 | m/z = 816.33($C_{60}H_{40}N_4$ =816.99) |
| P4-2 | m/z = 727.30($C_{54}H_{37}N_3$ =727.89) |
| P4-3 | m/z = 741.28($C_{54}H_{35}N_3O$ = 741.88) |
| P4-4 | m/z = 757.26($C_{54}H_{35}N_3S$ = 757.94) |
| P4-5 | m/z = 701.28($C_{52}H_{35}N_3$ = 701.85) |
| P4-6 | m/z = 803.33($C_{60}H_{41}N_3$ = 803.99) |
| P4-7 | m/z = 757.26($C_{54}H_{35}N_3S$ = 757.94) |
| P4-8 | m/z = 909.32($C_{66}H_{43}N_3S$ = 910.13) |
| P4-9 | m/z = 767.33($C_{57}H_{41}N_3$ = 767.96) |

TABLE 3-continued

| Compound | FD-MS |
|---|---|
| P4-10 | m/z = 833.29($C_{60}H_{39}N_3S$ = 834.04) |
| P4-11 | m/z = 701.28($C_{52}H_{35}N_3$ = 701.85) |
| P4-12 | m/z = 807.27($C_{58}H_{37}N_3S$ = 808.00) |
| P4-13 | m/z = 803.33($C_{60}H_{41}N_3$ =803.99) |
| P4-14 | m/z = 727.30($C_{54}H_{37}N_3$ =727.89) |
| P4-15 | m/z = 833.29($C_{60}H_{39}N_3S$ = 834.04) |
| P4-16 | m/z = 777.31($C_{58}H_{39}N_3$ =777.95) |
| P4-17 | m/z = 727.30($C_{54}H_{37}N_3$ = 727.89) |
| P4-18 | m/z = 777.31($C_{58}H_{39}N_3$ = 777.95) |
| P4-19 | m/z = 757.26($C_{54}H_{35}N_3S$ = 757.94) |
| P4-20 | m/z = 767.33($C_{57}H_{41}N_3$ =767.96) |
| P4-21 | m/z = 817.35($C_{61}H_{43}N_3$ = 818.01) |
| P4-22 | m/z = 727.30($C_{54}H_{37}N_3$ =827.89) |
| P4-23 | m/z = 892.36($C_{66}H_{44}N_4$ = 893.08) |
| P4-24 | m/z = 891.36($C_{67}H_{45}N_3$ =892.09) |
| P4-25 | m/z = 777.31($C_{58}H_{39}N_3$ = 777.95) |
| P4-26 | m/z = 817.35($C_{61}H_{43}N_3$ = 818.01) |
| P4-27 | m/z = 803.33($C_{60}H_{41}N_3$ = 803.99) |
| P4-28 | m/z = 777.31($C_{58}H_{39}N_3$ = 777.95) |
| P4-29 | m/z = 777.31($C_{58}H_{39}N_3$ = 777.95) |
| P4-30 | m/z = 777.31($C_{58}H_{39}N_3$ = 777.95) |
| P4-31 | m/z = 778.31($C_{57}H_{38}N_4$ = 778.94) |
| P4-32 | m/z = 943.39($C_{71}H_{49}N_3$ = 944.17) |
| P4-33 | m/z = 882.35($C_{63}H_{42}N_6$ = 883.05) |
| P4-34 | m/z = 732.33($C_{54}H_{32}D_5N_3$ = 732.92) |
| P4-35 | m/z = 833.29($C_{60}H_{39}N_3S$ = 834.04) |
| P4-36 | m/z = 732.33($C_{54}H_{32}D_5N_3$ = 732.92) |

Fabrication and Evaluation of Organic Electronic Element

[Example 1] Green OLEDs (A Hole Transport Layer)

Organic light emitting diodes (OLEDs) were fabricated according to a conventional method by using a compound of the present invention as a hole transport layer material.

First, an ITO layer (anode) was formed on a glass substrate, and a film of 4,4',4''-Tris[2-naphthyl(phenyl)amino]triphenylamine ("2-TNATA") was vacuum-deposited on the ITO layer to form a hole injection layer with a thickness of 60 nm. Subsequently, P1-1 of the present invention was vacuum-deposited with a thickness of 60 nm on the hole injection layer to form a hole transport layer.

Subsequently, a light emitting layer with a thickness of 30 nm was deposited on the hole transport layer by doping the hole transport layer with 4,4'-N,N'-dicarbazole-biphenyl ("CBP") as a host material and tris(2-phenylpyridine)-iridium ("$Ir(ppy)_3$") as a dopant material in a weight ratio of 90:10.

Next, a film of ((1,1'-bisphenyl)-4-olato)bis(2-methyl-8-quinolinolato)aluminum ("BAlq") was vacuum-deposited with a thickness of 10 nm on the light emitting layer to form a hole blocking layer, and a film of tris(8-quinolinolato)aluminum ("$Alq_3$") was formed with a thickness of 40 nm to form an electron transport layer.

Next, LiF as halogenated alkali metal was deposited with a thickness of 0.2 nm on the electron transport layer to form an electron injection layer, and then Al was deposited with a thickness of 150 nm on the electron injection layer to form a cathode. In this way, the OLED was completed.

[Example 2] to [Example 256] Green OLEDs (A Hole Transport Layer)

The OLEDs were manufactured in the same manner as described in Example 1, except that any one of the compounds P1-2 to P1-112, P2-1 to P2-112, P3-1 to P3-6, P3-19 to P3-24, P3-37 and P3-38 of the present invention in the Table 4 below was used as the hole transport layer material, instead of the inventive compound P1-1.

Comparative Example 1

An OLED was manufactured in the same manner as described in Example 1, except that the following Comparative Compound 1 was used as the hole transport layer material, instead of the inventive compound P1-1.

<Comparative compound 1>

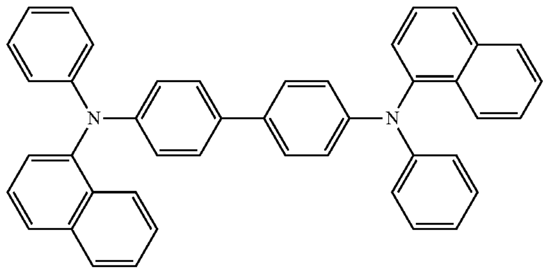

Comparative Example 2

An OLED was manufactured in the same manner as described in Example 1, except that the following Comparative Compound 2 was used as the hole transport layer material, instead of the inventive compound P1-1.

<Comparative compound 2>

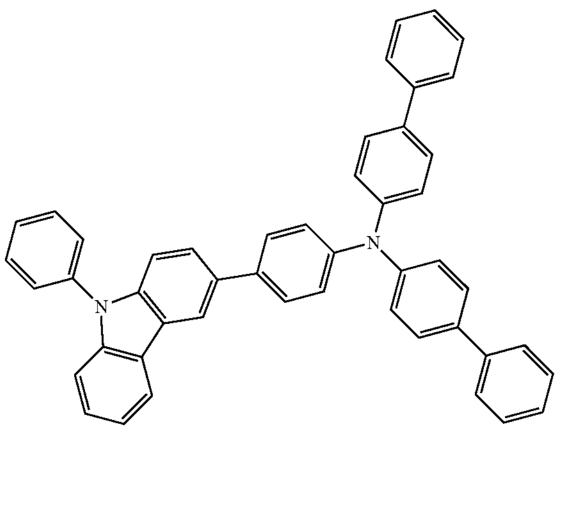

Comparative Example 3

An OLED was manufactured in the same manner as described in Example 1, except that the following Comparative Compound 3 was used as the hole transport layer material, instead of the inventive compound P1-1.

<Comparative compound 3>

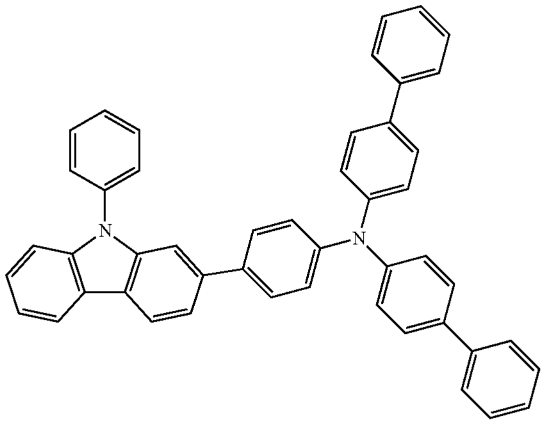

Comparative Example 4

An OLED was manufactured in the same manner as described in Example 1, except that the following Comparative Compound 4 was used as the hole transport layer material, instead of the inventive compound P1-1.

<Comparative compound 4>

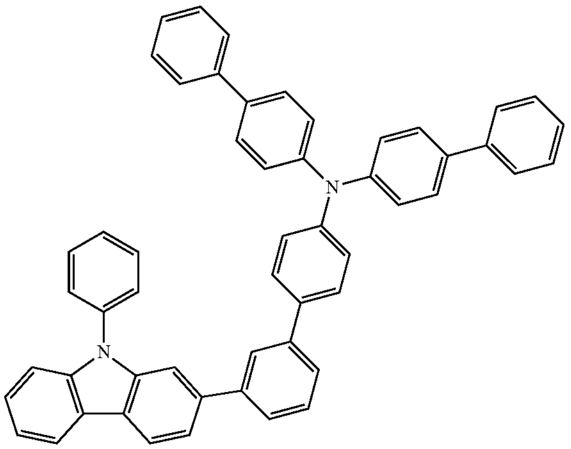

A forward bias DC voltage was applied to each of the OLEDs manufactured through the Examples 1 to 238 and the Comparative Examples 1 to 4, and electroluminescence (EL) characteristics of the OLED were measured by PR-650 (Photoresearch). Also, T90 life span was measured by life span measuring equipment (Mcscience) at the reference brightness of 5000 cd/$m^2$. Evaluation results are in the Table 4 below.

TABLE 4

| | Compound | Voltage (V) | Current Density (mA/$cm^2$) | Brightness (cd/$m^2$) | Efficiency (cd/A) | Lifetime T(95) | CIE x | CIE y |
|---|---|---|---|---|---|---|---|---|
| Com. Ex (1) | Com. Com (1) | 5.6 | 17.9 | 5000.0 | 27.9 | 68.2 | 0.33 | 0.62 |
| Com. Ex (2) | Com. Com (2) | 5.1 | 15.2 | 5000.0 | 33.0 | 115.9 | 0.33 | 0.61 |
| Com. Ex (3) | Com. Com (3) | 5.3 | 13.0 | 5000.0 | 38.6 | 101.4 | 0.33 | 0.61 |
| Com. Ex (4) | Com. Com (4) | 5.5 | 14.2 | 5000.0 | 35.1 | 100.9 | 0.33 | 0.61 |
| Ex. (1) | P1-1 | 5.3 | 10.2 | 5000.0 | 49.1 | 125.1 | 0.33 | 0.62 |
| Ex. (2) | P1-2 | 5.4 | 10.0 | 5000.0 | 49.8 | 138.4 | 0.33 | 0.61 |
| Ex. (3) | P1-3 | 5.5 | 10.8 | 5000.0 | 46.4 | 121.2 | 0.33 | 0.61 |
| Ex. (4) | P1-4 | 5.4 | 11.0 | 5000.0 | 45.4 | 149.6 | 0.33 | 0.61 |
| Ex. (5) | P1-5 | 5.4 | 10.2 | 5000.0 | 49.2 | 143.2 | 0.33 | 0.62 |
| Ex. (6) | P1-6 | 5.3 | 10.4 | 5000.0 | 48.3 | 134.7 | 0.33 | 0.62 |
| Ex. (7) | P1-7 | 5.3 | 10.5 | 5000.0 | 47.6 | 114.8 | 0.33 | 0.61 |
| Ex. (8) | P1-8 | 5.5 | 10.9 | 5000.0 | 45.9 | 140.2 | 0.33 | 0.62 |
| Ex. (9) | P1-9 | 5.3 | 10.2 | 5000.0 | 49.0 | 104.7 | 0.33 | 0.61 |
| Ex. (10) | P1-10 | 5.5 | 10.4 | 5000.0 | 48.1 | 107.3 | 0.33 | 0.62 |
| Ex. (11) | P1-11 | 5.4 | 10.1 | 5000.0 | 49.4 | 140.6 | 0.33 | 0.61 |
| Ex. (12) | P1-12 | 5.3 | 10.0 | 5000.0 | 49.9 | 136.9 | 0.33 | 0.61 |
| Ex. (13) | P1-13 | 5.4 | 10.5 | 5000.0 | 47.5 | 125.9 | 0.33 | 0.61 |
| Ex. (14) | P1-14 | 5.4 | 10.3 | 5000.0 | 48.5 | 129.6 | 0.33 | 0.62 |
| Ex. (15) | P1-15 | 5.4 | 10.3 | 5000.0 | 48.7 | 117.2 | 0.33 | 0.61 |
| Ex. (16) | P1-16 | 5.4 | 11.0 | 5000.0 | 45.5 | 134.9 | 0.33 | 0.61 |
| Ex. (17) | P1-17 | 5.5 | 10.8 | 5000.0 | 46.3 | 124.6 | 0.33 | 0.62 |
| Ex. (18) | P1-18 | 5.4 | 10.2 | 5000.0 | 48.9 | 117.8 | 0.33 | 0.61 |
| Ex. (19) | P1-19 | 5.5 | 11.0 | 5000.0 | 45.4 | 116.0 | 0.33 | 0.62 |
| Ex. (20) | P1-20 | 5.3 | 10.9 | 5000.0 | 45.9 | 118.4 | 0.33 | 0.62 |
| Ex. (21) | P1-21 | 5.5 | 10.7 | 5000.0 | 46.6 | 103.5 | 0.33 | 0.61 |
| Ex. (22) | P1-22 | 5.4 | 10.3 | 5000.0 | 48.7 | 126.5 | 0.33 | 0.62 |
| Ex. (23) | P1-23 | 5.5 | 11.0 | 5000.0 | 45.5 | 131.3 | 0.33 | 0.62 |
| Ex. (24) | P1-24 | 5.5 | 10.3 | 5000.0 | 48.4 | 139.0 | 0.33 | 0.62 |
| Ex. (25) | P1-25 | 5.5 | 10.8 | 5000.0 | 46.3 | 142.0 | 0.33 | 0.62 |
| Ex. (26) | P1-26 | 5.4 | 10.4 | 5000.0 | 48.2 | 112.5 | 0.33 | 0.61 |
| Ex. (27) | P1-27 | 5.4 | 10.1 | 5000.0 | 49.4 | 125.0 | 0.33 | 0.61 |
| Ex. (28) | P1-28 | 5.3 | 10.7 | 5000.0 | 46.7 | 109.0 | 0.33 | 0.61 |
| Ex. (29) | P1-29 | 5.5 | 10.9 | 5000.0 | 45.8 | 116.8 | 0.33 | 0.62 |
| Ex. (30) | P1-30 | 5.3 | 10.6 | 5000.0 | 47.1 | 108.8 | 0.33 | 0.62 |
| Ex. (31) | P1-31 | 5.5 | 11.0 | 5000.0 | 45.4 | 122.0 | 0.33 | 0.62 |
| Ex. (32) | P1-32 | 5.3 | 11.1 | 5000.0 | 45.1 | 104.5 | 0.33 | 0.61 |
| Ex. (33) | P1-33 | 5.4 | 10.1 | 5000.0 | 49.4 | 113.6 | 0.33 | 0.61 |
| Ex. (34) | P1-34 | 5.4 | 10.9 | 5000.0 | 45.8 | 104.9 | 0.33 | 0.62 |
| Ex. (35) | P1-35 | 5.4 | 10.7 | 5000.0 | 46.8 | 112.4 | 0.33 | 0.62 |

TABLE 4-continued

| | Compound | Voltage (V) | Current Density (mA/cm²) | Brightness (cd/m²) | Efficiency (cd/A) | Lifetime T(95) | CIE x | CIE y |
|---|---|---|---|---|---|---|---|---|
| Ex. (36) | P1-36 | 5.4 | 10.3 | 5000.0 | 48.6 | 140.7 | 0.33 | 0.61 |
| Ex. (37) | P1-37 | 5.3 | 10.1 | 5000.0 | 49.3 | 148.9 | 0.33 | 0.62 |
| Ex. (38) | P1-38 | 5.5 | 10.5 | 5000.0 | 47.6 | 141.1 | 0.33 | 0.61 |
| Ex. (39) | P1-39 | 5.5 | 10.1 | 5000.0 | 49.4 | 119.2 | 0.33 | 0.62 |
| Ex. (40) | P1-40 | 5.4 | 10.2 | 5000.0 | 49.1 | 140.0 | 0.33 | 0.61 |
| Ex. (41) | P1-41 | 5.4 | 10.6 | 5000.0 | 47.2 | 127.7 | 0.33 | 0.62 |
| Ex. (42) | P1-42 | 5.4 | 10.6 | 5000.0 | 47.3 | 126.2 | 0.33 | 0.61 |
| Ex. (43) | P1-43 | 5.3 | 11.1 | 5000.0 | 45.2 | 129.9 | 0.33 | 0.62 |
| Ex. (44) | P1-44 | 5.4 | 10.7 | 5000.0 | 46.6 | 146.3 | 0.33 | 0.62 |
| Ex. (45) | P1-45 | 5.3 | 11.0 | 5000.0 | 45.6 | 116.5 | 0.33 | 0.62 |
| Ex. (46) | P1-46 | 5.4 | 10.2 | 5000.0 | 49.1 | 133.9 | 0.33 | 0.61 |
| Ex. (47) | P1-47 | 5.5 | 10.8 | 5000.0 | 46.2 | 124.9 | 0.33 | 0.62 |
| Ex. (48) | P1-48 | 5.5 | 10.2 | 5000.0 | 48.8 | 144.4 | 0.33 | 0.61 |
| Ex. (49) | P1-49 | 5.4 | 10.3 | 5000.0 | 48.3 | 148.9 | 0.33 | 0.61 |
| Ex. (50) | P1-50 | 5.5 | 10.3 | 5000.0 | 48.4 | 139.4 | 0.33 | 0.61 |
| Ex. (51) | P1-51 | 5.4 | 10.3 | 5000.0 | 48.4 | 112.3 | 0.33 | 0.61 |
| Ex. (52) | P1-52 | 5.3 | 10.5 | 5000.0 | 47.6 | 116.9 | 0.33 | 0.62 |
| Ex. (53) | P1-53 | 5.5 | 10.2 | 5000.0 | 49.1 | 132.5 | 0.33 | 0.61 |
| Ex. (54) | P1-54 | 5.4 | 11.0 | 5000.0 | 45.6 | 115.2 | 0.33 | 0.62 |
| Ex. (55) | P1-55 | 5.5 | 10.5 | 5000.0 | 47.8 | 130.9 | 0.33 | 0.61 |
| Ex. (56) | P1-56 | 5.5 | 10.6 | 5000.0 | 47.0 | 101.8 | 0.33 | 0.61 |
| Ex. (57) | P1-57 | 5.3 | 10.3 | 5000.0 | 48.4 | 129.2 | 0.33 | 0.62 |
| Ex. (58) | P1-58 | 5.3 | 11.0 | 5000.0 | 45.6 | 138.7 | 0.33 | 0.61 |
| Ex. (59) | P1-59 | 5.5 | 10.5 | 5000.0 | 47.4 | 103.0 | 0.33 | 0.61 |
| Ex. (60) | P1-60 | 5.5 | 10.6 | 5000.0 | 47.2 | 144.0 | 0.33 | 0.61 |
| Ex. (61) | P1-61 | 5.3 | 10.8 | 5000.0 | 46.5 | 144.6 | 0.33 | 0.62 |
| Ex. (62) | P1-62 | 5.4 | 10.7 | 5000.0 | 46.9 | 136.5 | 0.33 | 0.61 |
| Ex. (63) | P1-63 | 5.3 | 10.9 | 5000.0 | 45.8 | 136.9 | 0.33 | 0.62 |
| Ex. (64) | P1-64 | 5.4 | 10.9 | 5000.0 | 45.9 | 148.7 | 0.33 | 0.62 |
| Ex. (65) | P1-65 | 5.5 | 10.5 | 5000.0 | 47.6 | 102.2 | 0.33 | 0.61 |
| Ex. (66) | P1-66 | 5.4 | 10.0 | 5000.0 | 49.8 | 116.5 | 0.33 | 0.62 |
| Ex. (67) | P1-67 | 5.4 | 10.6 | 5000.0 | 47.1 | 108.9 | 0.33 | 0.61 |
| Ex. (68) | P1-68 | 5.4 | 10.4 | 5000.0 | 47.9 | 129.8 | 0.33 | 0.62 |
| Ex. (69) | P1-69 | 5.4 | 11.1 | 5000.0 | 45.1 | 138.5 | 0.33 | 0.62 |
| Ex. (70) | P1-70 | 5.4 | 10.6 | 5000.0 | 47.0 | 144.4 | 0.33 | 0.62 |
| Ex. (71) | P1-71 | 5.3 | 10.4 | 5000.0 | 48.2 | 137.4 | 0.33 | 0.61 |
| Ex. (72) | P1-72 | 5.3 | 10.9 | 5000.0 | 45.7 | 127.3 | 0.33 | 0.62 |
| Ex. (73) | P1-73 | 5.3 | 10.3 | 5000.0 | 48.7 | 112.1 | 0.33 | 0.61 |
| Ex. (74) | P1-74 | 5.3 | 11.1 | 5000.0 | 45.0 | 140.8 | 0.33 | 0.61 |
| Ex. (75) | P1-75 | 5.3 | 10.1 | 5000.0 | 49.5 | 119.1 | 0.33 | 0.61 |
| Ex. (76) | P1-76 | 5.3 | 10.2 | 5000.0 | 49.2 | 127.2 | 0.33 | 0.62 |
| Ex. (77) | P1-77 | 5.5 | 10.1 | 5000.0 | 49.4 | 115.6 | 0.33 | 0.62 |
| Ex. (78) | P1-78 | 5.4 | 10.2 | 5000.0 | 48.8 | 121.9 | 0.33 | 0.61 |
| Ex. (79) | P1-79 | 5.4 | 10.3 | 5000.0 | 48.5 | 128.4 | 0.33 | 0.62 |
| Ex. (80) | P1-80 | 5.3 | 10.8 | 5000.0 | 46.3 | 142.9 | 0.33 | 0.61 |
| Ex. (81) | P1-81 | 5.4 | 10.1 | 5000.0 | 49.7 | 126.1 | 0.33 | 0.61 |
| Ex. (82) | P1-82 | 5.4 | 10.7 | 5000.0 | 46.5 | 130.2 | 0.33 | 0.62 |
| Ex. (83) | P1-83 | 5.5 | 10.2 | 5000.0 | 48.9 | 128.7 | 0.33 | 0.61 |
| Ex. (84) | P1-84 | 5.4 | 10.3 | 5000.0 | 48.7 | 114.1 | 0.33 | 0.61 |
| Ex. (85) | P1-85 | 5.4 | 10.5 | 5000.0 | 47.8 | 119.6 | 0.33 | 0.61 |
| Ex. (86) | P1-86 | 5.3 | 10.9 | 5000.0 | 45.8 | 142.8 | 0.33 | 0.62 |
| Ex. (87) | P1-87 | 5.4 | 10.6 | 5000.0 | 47.0 | 114.0 | 0.33 | 0.61 |
| Ex. (88) | P1-88 | 5.5 | 10.6 | 5000.0 | 47.3 | 120.6 | 0.33 | 0.62 |
| Ex. (89) | P1-89 | 5.5 | 11.0 | 5000.0 | 45.4 | 121.9 | 0.33 | 0.62 |
| Ex. (90) | P1-90 | 5.4 | 10.9 | 5000.0 | 45.8 | 108.0 | 0.33 | 0.61 |
| Ex. (91) | P1-91 | 5.3 | 10.8 | 5000.0 | 46.1 | 139.9 | 0.33 | 0.62 |
| Ex. (92) | P1-92 | 5.4 | 10.3 | 5000.0 | 48.7 | 111.4 | 0.33 | 0.61 |
| Ex. (93) | P1-93 | 5.5 | 10.0 | 5000.0 | 50.0 | 122.0 | 0.33 | 0.62 |
| Ex. (94) | P1-94 | 5.3 | 10.7 | 5000.0 | 46.8 | 109.5 | 0.33 | 0.61 |
| Ex. (95) | P1-95 | 5.5 | 10.3 | 5000.0 | 48.6 | 144.9 | 0.33 | 0.61 |
| Ex. (96) | P1-96 | 5.4 | 11.1 | 5000.0 | 45.1 | 137.9 | 0.33 | 0.62 |
| Ex. (97) | P1-97 | 5.4 | 10.1 | 5000.0 | 49.6 | 143.9 | 0.33 | 0.61 |
| Ex. (98) | P1-98 | 5.5 | 10.6 | 5000.0 | 47.1 | 130.9 | 0.33 | 0.62 |
| Ex. (99) | P1-99 | 5.3 | 10.7 | 5000.0 | 46.5 | 147.2 | 0.33 | 0.62 |
| Ex. (100) | P1-100 | 5.3 | 10.8 | 5000.0 | 46.3 | 108.6 | 0.33 | 0.61 |
| Ex. (101) | P1-101 | 5.3 | 10.1 | 5000.0 | 49.3 | 124.4 | 0.33 | 0.61 |
| Ex. (102) | P1-102 | 5.3 | 10.3 | 5000.0 | 48.5 | 132.0 | 0.33 | 0.61 |
| Ex. (103) | P1-103 | 5.3 | 11.0 | 5000.0 | 45.6 | 142.0 | 0.33 | 0.62 |
| Ex. (104) | P1-104 | 5.4 | 10.6 | 5000.0 | 47.3 | 131.6 | 0.33 | 0.62 |
| Ex. (105) | P1-105 | 5.3 | 10.9 | 5000.0 | 46.0 | 126.8 | 0.33 | 0.62 |
| Ex. (106) | P1-106 | 5.4 | 10.5 | 5000.0 | 47.7 | 131.9 | 0.33 | 0.61 |
| Ex. (107) | P1-107 | 5.4 | 10.2 | 5000.0 | 49.0 | 138.4 | 0.33 | 0.61 |
| Ex. (108) | P1-108 | 5.5 | 10.6 | 5000.0 | 47.2 | 130.5 | 0.33 | 0.62 |
| Ex. (109) | P1-109 | 5.4 | 11.0 | 5000.0 | 45.4 | 104.3 | 0.33 | 0.62 |
| Ex. (110) | P1-110 | 5.5 | 10.4 | 5000.0 | 48.3 | 105.0 | 0.33 | 0.62 |

TABLE 4-continued

| | Compound | Voltage (V) | Current Density (mA/cm²) | Brightness (cd/m²) | Efficiency (cd/A) | Lifetime T(95) | CIE x | CIE y |
|---|---|---|---|---|---|---|---|---|
| Ex. (111) | P1-111 | 5.5 | 10.2 | 5000.0 | 48.9 | 127.1 | 0.33 | 0.61 |
| Ex. (112) | P1-112 | 5.4 | 10.5 | 5000.0 | 47.8 | 121.9 | 0.33 | 0.61 |
| Ex. (113) | P2-1 | 5.4 | 12.0 | 5000.0 | 41.7 | 128.7 | 0.33 | 0.61 |
| Ex. (114) | P2-2 | 5.4 | 11.2 | 5000.0 | 44.6 | 139.5 | 0.33 | 0.61 |
| Ex. (115) | P2-3 | 5.3 | 12.3 | 5000.0 | 40.6 | 137.4 | 0.33 | 0.61 |
| Ex. (116) | P2-4 | 5.4 | 11.6 | 5000.0 | 43.2 | 143.3 | 0.33 | 0.62 |
| Ex. (117) | P2-5 | 5.4 | 11.8 | 5000.0 | 42.3 | 126.1 | 0.33 | 0.61 |
| Ex. (118) | P2-6 | 5.4 | 11.4 | 5000.0 | 44.0 | 117.9 | 0.33 | 0.62 |
| Ex. (119) | P2-7 | 5.4 | 11.3 | 5000.0 | 44.1 | 137.9 | 0.33 | 0.61 |
| Ex. (120) | P2-8 | 5.5 | 11.1 | 5000.0 | 45.0 | 113.7 | 0.33 | 0.62 |
| Ex. (121) | P2-9 | 5.4 | 11.7 | 5000.0 | 42.6 | 136.6 | 0.33 | 0.61 |
| Ex. (122) | P2-10 | 5.4 | 11.3 | 5000.0 | 44.4 | 111.7 | 0.33 | 0.62 |
| Ex. (123) | P2-11 | 5.3 | 11.8 | 5000.0 | 42.3 | 147.2 | 0.33 | 0.61 |
| Ex. (124) | P2-12 | 5.4 | 11.3 | 5000.0 | 44.2 | 100.4 | 0.33 | 0.61 |
| Ex. (125) | P2-13 | 5.4 | 12.3 | 5000.0 | 40.6 | 128.7 | 0.33 | 0.61 |
| Ex. (126) | P2-14 | 5.5 | 11.6 | 5000.0 | 43.0 | 125.4 | 0.33 | 0.62 |
| Ex. (127) | P2-15 | 5.4 | 11.6 | 5000.0 | 43.2 | 132.3 | 0.33 | 0.61 |
| Ex. (128) | P2-16 | 5.5 | 11.6 | 5000.0 | 43.0 | 120.3 | 0.33 | 0.62 |
| Ex. (129) | P2-17 | 5.3 | 12.2 | 5000.0 | 41.1 | 141.2 | 0.33 | 0.62 |
| Ex. (130) | P2-18 | 5.4 | 12.3 | 5000.0 | 40.6 | 129.3 | 0.33 | 0.62 |
| Ex. (131) | P2-19 | 5.4 | 12.2 | 5000.0 | 41.0 | 126.2 | 0.33 | 0.61 |
| Ex. (132) | P2-20 | 5.3 | 11.7 | 5000.0 | 42.6 | 132.3 | 0.33 | 0.62 |
| Ex. (133) | P2-21 | 5.4 | 12.0 | 5000.0 | 41.8 | 127.9 | 0.33 | 0.62 |
| Ex. (134) | P2-22 | 5.5 | 11.3 | 5000.0 | 44.2 | 141.8 | 0.33 | 0.61 |
| Ex. (135) | P2-23 | 5.4 | 11.6 | 5000.0 | 43.0 | 116.7 | 0.33 | 0.62 |
| Ex. (136) | P2-24 | 5.4 | 12.5 | 5000.0 | 40.1 | 113.0 | 0.33 | 0.61 |
| Ex. (137) | P2-25 | 5.3 | 12.3 | 5000.0 | 40.5 | 107.7 | 0.33 | 0.61 |
| Ex. (138) | P2-26 | 5.5 | 12.4 | 5000.0 | 40.4 | 107.7 | 0.33 | 0.61 |
| Ex. (139) | P2-27 | 5.3 | 12.5 | 5000.0 | 40.1 | 147.2 | 0.33 | 0.61 |
| Ex. (140) | P2-28 | 5.4 | 11.4 | 5000.0 | 43.7 | 143.1 | 0.33 | 0.61 |
| Ex. (141) | P2-29 | 5.4 | 11.5 | 5000.0 | 43.6 | 104.9 | 0.33 | 0.62 |
| Ex. (142) | P2-30 | 5.4 | 11.9 | 5000.0 | 41.9 | 129.5 | 0.33 | 0.62 |
| Ex. (143) | P2-31 | 5.5 | 12.2 | 5000.0 | 41.1 | 129.9 | 0.33 | 0.62 |
| Ex. (144) | P2-32 | 5.5 | 12.3 | 5000.0 | 40.8 | 137.8 | 0.33 | 0.61 |
| Ex. (145) | P2-33 | 5.4 | 11.2 | 5000.0 | 44.6 | 126.9 | 0.33 | 0.61 |
| Ex. (146) | P2-34 | 5.4 | 12.5 | 5000.0 | 40.1 | 108.1 | 0.33 | 0.62 |
| Ex. (147) | P2-35 | 5.4 | 11.9 | 5000.0 | 42.1 | 135.4 | 0.33 | 0.62 |
| Ex. (148) | P2-36 | 5.3 | 12.2 | 5000.0 | 40.9 | 106.3 | 0.33 | 0.62 |
| Ex. (149) | P2-37 | 5.5 | 11.9 | 5000.0 | 42.1 | 102.7 | 0.33 | 0.62 |
| Ex. (150) | P2-38 | 5.3 | 11.3 | 5000.0 | 44.3 | 137.2 | 0.33 | 0.62 |
| Ex. (151) | P2-39 | 5.4 | 12.2 | 5000.0 | 41.0 | 132.0 | 0.33 | 0.61 |
| Ex. (152) | P2-40 | 5.4 | 11.7 | 5000.0 | 42.6 | 135.3 | 0.33 | 0.61 |
| Ex. (153) | P2-41 | 5.4 | 11.7 | 5000.0 | 42.9 | 130.5 | 0.33 | 0.62 |
| Ex. (154) | P2-42 | 5.5 | 11.4 | 5000.0 | 43.9 | 126.1 | 0.33 | 0.62 |
| Ex. (155) | P2-43 | 5.3 | 11.9 | 5000.0 | 42.0 | 111.7 | 0.33 | 0.62 |
| Ex. (156) | P2-44 | 5.4 | 11.5 | 5000.0 | 43.4 | 121.9 | 0.33 | 0.61 |
| Ex. (157) | P2-45 | 5.4 | 11.7 | 5000.0 | 42.9 | 142.8 | 0.33 | 0.61 |
| Ex. (158) | P2-46 | 5.4 | 12.4 | 5000.0 | 40.2 | 121.0 | 0.33 | 0.61 |
| Ex. (159) | P2-47 | 5.5 | 12.1 | 5000.0 | 41.4 | 134.9 | 0.33 | 0.61 |
| Ex. (160) | P2-48 | 5.5 | 12.0 | 5000.0 | 41.8 | 107.9 | 0.33 | 0.62 |
| Ex. (161) | P2-49 | 5.4 | 11.5 | 5000.0 | 43.3 | 109.4 | 0.33 | 0.62 |
| Ex. (162) | P2-50 | 5.4 | 11.4 | 5000.0 | 43.8 | 116.0 | 0.33 | 0.62 |
| Ex. (163) | P2-51 | 5.4 | 12.4 | 5000.0 | 40.2 | 128.9 | 0.33 | 0.62 |
| Ex. (164) | P2-52 | 5.4 | 11.8 | 5000.0 | 42.4 | 139.9 | 0.33 | 0.62 |
| Ex. (165) | P2-53 | 5.5 | 11.2 | 5000.0 | 44.5 | 148.4 | 0.33 | 0.62 |
| Ex. (166) | P2-54 | 5.5 | 12.4 | 5000.0 | 40.4 | 108.1 | 0.33 | 0.62 |
| Ex. (167) | P2-55 | 5.5 | 11.2 | 5000.0 | 44.6 | 145.4 | 0.33 | 0.62 |
| Ex. (168) | P2-56 | 5.4 | 11.4 | 5000.0 | 44.0 | 108.7 | 0.33 | 0.61 |
| Ex. (169) | P2-57 | 5.4 | 12.1 | 5000.0 | 41.2 | 135.0 | 0.33 | 0.61 |
| Ex. (170) | P2-58 | 5.5 | 12.3 | 5000.0 | 40.6 | 110.6 | 0.33 | 0.62 |
| Ex. (171) | P2-59 | 5.4 | 11.4 | 5000.0 | 43.9 | 147.2 | 0.33 | 0.61 |
| Ex. (172) | P2-60 | 5.4 | 12.5 | 5000.0 | 40.1 | 113.1 | 0.33 | 0.62 |
| Ex. (173) | P2-61 | 5.4 | 11.3 | 5000.0 | 44.2 | 143.9 | 0.33 | 0.62 |
| Ex. (174) | P2-62 | 5.4 | 11.7 | 5000.0 | 42.6 | 138.2 | 0.33 | 0.61 |
| Ex. (175) | P2-63 | 5.5 | 11.4 | 5000.0 | 43.9 | 138.4 | 0.33 | 0.62 |
| Ex. (176) | P2-64 | 5.5 | 11.7 | 5000.0 | 42.8 | 102.3 | 0.33 | 0.61 |
| Ex. (177) | P2-65 | 5.4 | 12.3 | 5000.0 | 40.7 | 143.3 | 0.33 | 0.61 |
| Ex. (178) | P2-66 | 5.4 | 11.5 | 5000.0 | 43.5 | 105.8 | 0.33 | 0.62 |
| Ex. (179) | P2-67 | 5.4 | 11.7 | 5000.0 | 42.7 | 142.8 | 0.33 | 0.62 |
| Ex. (180) | P2-68 | 5.4 | 11.4 | 5000.0 | 43.9 | 141.9 | 0.33 | 0.61 |
| Ex. (181) | P2-69 | 5.4 | 11.2 | 5000.0 | 44.7 | 146.5 | 0.33 | 0.62 |
| Ex. (182) | P2-70 | 5.5 | 11.3 | 5000.0 | 44.2 | 147.3 | 0.33 | 0.62 |
| Ex. (183) | P2-71 | 5.4 | 11.6 | 5000.0 | 43.1 | 142.0 | 0.33 | 0.61 |
| Ex. (184) | P2-72 | 5.4 | 11.6 | 5000.0 | 43.2 | 136.0 | 0.33 | 0.62 |
| Ex. (185) | P2-73 | 5.4 | 12.1 | 5000.0 | 41.2 | 137.8 | 0.33 | 0.61 |

TABLE 4-continued

| | Compound | Voltage (V) | Current Density (mA/cm²) | Brightness (cd/m²) | Efficiency (cd/A) | Lifetime T(95) | CIE x | CIE y |
|---|---|---|---|---|---|---|---|---|
| Ex. (186) | P2-74 | 5.4 | 11.5 | 5000.0 | 43.3 | 111.1 | 0.33 | 0.62 |
| Ex. (187) | P2-75 | 5.3 | 11.8 | 5000.0 | 42.4 | 129.3 | 0.33 | 0.62 |
| Ex. (188) | P2-76 | 5.4 | 11.4 | 5000.0 | 43.9 | 100.8 | 0.33 | 0.61 |
| Ex. (189) | P2-77 | 5.4 | 11.4 | 5000.0 | 43.8 | 131.5 | 0.33 | 0.61 |
| Ex. (190) | P2-78 | 5.3 | 11.2 | 5000.0 | 44.8 | 114.3 | 0.33 | 0.62 |
| Ex. (191) | P2-79 | 5.4 | 11.4 | 5000.0 | 44.0 | 116.1 | 0.33 | 0.61 |
| Ex. (192) | P2-80 | 5.5 | 11.6 | 5000.0 | 43.2 | 116.1 | 0.33 | 0.61 |
| Ex. (193) | P2-81 | 5.4 | 11.2 | 5000.0 | 44.7 | 123.3 | 0.33 | 0.62 |
| Ex. (194) | P2-82 | 5.4 | 11.4 | 5000.0 | 43.8 | 148.3 | 0.33 | 0.61 |
| Ex. (195) | P2-83 | 5.5 | 11.3 | 5000.0 | 44.1 | 135.3 | 0.33 | 0.61 |
| Ex. (196) | P2-84 | 5.5 | 12.2 | 5000.0 | 40.9 | 128.0 | 0.33 | 0.61 |
| Ex. (197) | P2-85 | 5.5 | 11.6 | 5000.0 | 43.0 | 139.1 | 0.33 | 0.61 |
| Ex. (198) | P2-86 | 5.4 | 11.7 | 5000.0 | 42.7 | 125.3 | 0.33 | 0.62 |
| Ex. (199) | P2-87 | 5.3 | 11.1 | 5000.0 | 45.0 | 140.8 | 0.33 | 0.62 |
| Ex. (200) | P2-88 | 5.5 | 11.6 | 5000.0 | 43.0 | 101.5 | 0.33 | 0.61 |
| Ex. (201) | P2-89 | 5.4 | 11.1 | 5000.0 | 45.0 | 133.6 | 0.33 | 0.61 |
| Ex. (202) | P2-90 | 5.5 | 11.2 | 5000.0 | 44.6 | 141.8 | 0.33 | 0.62 |
| Ex. (203) | P2-91 | 5.3 | 11.9 | 5000.0 | 42.0 | 149.2 | 0.33 | 0.62 |
| Ex. (204) | P2-92 | 5.3 | 11.5 | 5000.0 | 43.4 | 120.3 | 0.33 | 0.62 |
| Ex. (205) | P2-93 | 5.4 | 11.6 | 5000.0 | 43.2 | 121.9 | 0.33 | 0.62 |
| Ex. (206) | P2-94 | 5.5 | 11.3 | 5000.0 | 44.4 | 145.6 | 0.33 | 0.61 |
| Ex. (207) | P2-95 | 5.5 | 11.8 | 5000.0 | 42.2 | 122.0 | 0.33 | 0.61 |
| Ex. (208) | P2-96 | 5.4 | 11.5 | 5000.0 | 43.5 | 134.2 | 0.33 | 0.61 |
| Ex. (209) | P2-97 | 5.3 | 11.7 | 5000.0 | 42.9 | 114.2 | 0.33 | 0.62 |
| Ex. (210) | P2-98 | 5.4 | 11.7 | 5000.0 | 42.7 | 142.4 | 0.33 | 0.62 |
| Ex. (211) | P2-99 | 5.5 | 12.2 | 5000.0 | 40.9 | 112.8 | 0.33 | 0.62 |
| Ex. (212) | P2-100 | 5.4 | 11.7 | 5000.0 | 42.6 | 142.0 | 0.33 | 0.61 |
| Ex. (213) | P2-101 | 5.3 | 11.6 | 5000.0 | 43.1 | 127.1 | 0.33 | 0.61 |
| Ex. (214) | P2-102 | 5.5 | 11.7 | 5000.0 | 42.9 | 143.4 | 0.33 | 0.61 |
| Ex. (215) | P2-103 | 5.5 | 12.2 | 5000.0 | 40.8 | 106.6 | 0.33 | 0.62 |
| Ex. (216) | P2-104 | 5.5 | 11.9 | 5000.0 | 42.0 | 100.8 | 0.33 | 0.61 |
| Ex. (217) | P2-105 | 5.4 | 11.7 | 5000.0 | 42.6 | 108.6 | 0.33 | 0.62 |
| Ex. (218) | P2-106 | 5.4 | 12.4 | 5000.0 | 40.2 | 138.3 | 0.33 | 0.62 |
| Ex. (219) | P2-107 | 5.5 | 12.1 | 5000.0 | 41.3 | 130.2 | 0.33 | 0.61 |
| Ex. (220) | P2-108 | 5.5 | 11.6 | 5000.0 | 43.0 | 111.0 | 0.33 | 0.62 |
| Ex. (221) | P2-109 | 5.5 | 12.2 | 5000.0 | 41.0 | 126.4 | 0.33 | 0.62 |
| Ex. (222) | P2-110 | 5.4 | 11.6 | 5000.0 | 43.1 | 120.7 | 0.33 | 0.61 |
| Ex. (223) | P2-111 | 5.4 | 12.2 | 5000.0 | 41.0 | 107.3 | 0.33 | 0.61 |
| Ex. (224) | P2-112 | 5.5 | 12.4 | 5000.0 | 40.2 | 138.3 | 0.33 | 0.61 |
| Ex. (225) | P3-1 | 5.5 | 11.5 | 5000.0 | 43.3 | 128.1 | 0.33 | 0.62 |
| Ex. (226) | P3-2 | 5.5 | 12.1 | 5000.0 | 41.3 | 143.0 | 0.33 | 0.62 |
| Ex. (227) | P3-3 | 5.3 | 11.4 | 5000.0 | 43.9 | 96.3 | 0.33 | 0.61 |
| Ex. (228) | P3-4 | 5.4 | 12.2 | 5000.0 | 41.0 | 105.8 | 0.33 | 0.62 |
| Ex. (229) | P3-5 | 5.4 | 12.0 | 5000.0 | 41.7 | 145.1 | 0.33 | 0.62 |
| Ex. (230) | P3-6 | 5.5 | 11.6 | 5000.0 | 42.9 | 124.4 | 0.33 | 0.61 |
| Ex. (231) | P3-19 | 5.5 | 10.1 | 5000.0 | 49.4 | 148.0 | 0.33 | 0.61 |
| Ex. (232) | P3-20 | 5.3 | 10.4 | 5000.0 | 48.1 | 94.6 | 0.33 | 0.61 |
| Ex. (233) | P3-21 | 5.4 | 10.4 | 5000.0 | 48.1 | 107.8 | 0.33 | 0.62 |
| Ex. (234) | P3-22 | 5.4 | 10.6 | 5000.0 | 47.3 | 104.9 | 0.33 | 0.62 |
| Ex. (235) | P3-23 | 5.4 | 10.9 | 5000.0 | 45.7 | 112.1 | 0.33 | 0.61 |
| Ex. (236) | P3-24 | 5.5 | 10.2 | 5000.0 | 48.9 | 144.6 | 0.33 | 0.62 |
| Ex. (237) | P3-37 | 5.5 | 10.4 | 5000.0 | 48.1 | 99.5 | 0.33 | 0.62 |
| Ex. (238) | P3-38 | 5.4 | 11.4 | 5000.0 | 44.0 | 110.6 | 0.33 | 0.61 |

It can be seen from the results in Table 4 above, that the OLEDs employing the inventive compounds as a hole transport layer materials showed predominantly improved efficiency and lifespan, compared to the OLEDs employing comparative compounds 1 to 4 as a hole transport layer materials. Especially, it can be seen that the OLEDs employing the inventive compounds showed predominantly improved efficiency and lifespan, compared to the Comparative Example 1 employing comparative compound 1 of which structure is different from the inventive compound.

Further, referring to the Comparative Example 2 to 4 employing comparative compounds 2 to 4 that have carbazole as core as the structure in the present invention, the OLED employing comparative compound 2 where a linker is linked to 2-position of the carbazole moiety (Com. Ex (3) and Com. Ex (4)) showed higher drive voltage and shorter life span yet higher efficiency, compared to the OLED employing comparative compounds 2 where a linker is linked to 3-position of the carbazole moiety (Com. Ex (2)). Comparing OLEDs employing the inventive compounds having a non-linear phenyl linker and the OLED of Com. Ex (4) having a non-linear biphenyl linker, the efficiency of OLEDs employing the inventive compounds is higher than the OLED of Com. Ex (4).

From the result in Table 4, it is seen that the OLEDs employing as a hole transport layer material, the compound of the present invention wherein the linker phenyl is linked to 2-position of carbazole derivative and an amine group is linked on ortho- or meta-position of the phenyl, showed high efficiency, compared to the OLED of Com. Ex (4) wherein the linker biphenyl is linked to 2-position of carbazole derivative and the amine group is linked to biphenyl on meta position.

These results are believed to come from that in a compound where the linker is linked on 2-position of the carbazole core, the conjugation length gets shorter than in a compound where the linker is linked on 3-position of the carbazole core, and the band gap gets widened and the HOMO value gets deepen.

Further, it is seen that where an amine group is linked on ortho- or meta-position of a linker and the linker is not biphenyl but phenyl as the inventive subject matter, the bonding angle gets decreased than in a case where the amine group is linked linear to the linker on para-position, and the T1 values get higher, and as a result the electron blocking abilities are improved.

Therefore, the OLED employing the inventive compound as a hole transport layer material has deep HOMO values and the improved electron blocking abilities, and as a result the exciton is more easily produced to improve efficiency and lengthen lifespan.

Considering the characteristics (deep HOMO energy level, high T1 value, heat-stability) described above together, it can be seen that the band gap and electrical properties, as well as the surface properties can change much depending on the linking position of the carbazole core and the amine, and which the linker is phenyl or biphenyl, which can be main factors in improving performance of the organic electric elements.

Furthermore, properties from the hole transport layer should be considered in relation with the light emitting layer (host), and one skilled in the art, even using a similar core compound, would have difficulty in inferring the characteristics shown by the hole transport layer using the compound of the present invention.

[Example 239] An Emission-Auxiliary Layer (Red)

Organic light emitting diodes (OLEDs) were fabricated according to a conventional method by using a compound of the present invention as an emission-auxiliary layer material.

First, an ITO layer (anode) was formed on a glass substrate, and a film of 2-TNATA was vacuum-deposited on the ITO layer to form a hole injection layer with a thickness of 60 nm. Subsequently, N,N'-Bis(1-naphthalenyl)-N,N'-bis-phenyl-(1,1'-biphenyl)-4,4'-diamine ("NPD") was vacuum-deposited with a thickness of 60 nm on the hole injection layer to form a hole transport layer.

Subsequently, a film of the compound P1-1 of the present invention was vacuum-deposited on the hole transport layer to form a emission-auxiliary layer with a thickness of 20 nm.

A light emitting layer with a thickness of 30 nm was deposited on the emission-auxiliary layer by using the CBP as a host material and bis-(1-phenylisoquinolyl)iridium(III) acetylacetonate ("$(piq)_2Ir(acac)$") as a dopant material in a weight ratio of 95:5.

Next, a film of BAlq was vacuum-deposited with a thickness of 10 nm on the light emitting layer to form a hole blocking layer, and a film of $Alq_3$ was formed with a thickness of 40 nm to form an electron transport layer.

Next, LiF as halogenated alkali metal was deposited with a thickness of 0.2 nm on the electron transport layer to form an electron injection layer, and then Al was deposited with a thickness of 150 nm on the electron injection layer to form a cathode. In this way, the OLED was completed.

[Example 240] to [Example 365] An Emission-Auxiliary Layer (Red)

The OLED was manufactured in the same manner as described in Test Example 239, except that any one of the compounds P1-2 to P1-20, P1-45 to P1-52, P1-61 to P1-64, P1-101 to P1-108, P2-1 to P2-20, P2-45 to P2-52, P2-61 to P2-64, P2-101 to P2-108, P3-1 to P3-38, P4-2, P4-5, P4-8 to P4-10, P4-17, P4-20, P4-22 and P4-24 of the present invention in the Table 5 below was used as the emission-auxiliary layer material, instead of the inventive compound P1-1.

Comparative Example 5

An OLED was manufactured in the same manner as described in Test Example 239, except that Comparative Compound 2 above was used as the emission-auxiliary layer material, instead of the inventive compound P1-1.

Comparative Example 6

An OLED was manufactured in the same manner as described in Test Example 239, except that Comparative Compound 3 above was used as the emission-auxiliary layer material, instead of the inventive compound P1-1.

Comparative Example 7

An OLED was manufactured in the same manner as described in Test Example 239, except that Comparative Compound 4 above was used as the emission-auxiliary layer material, instead of the inventive compound P1-1.

Comparative Example 8

An OLED was manufactured in the same manner as described in Test Example 239, except not to form the emission-auxiliary layer.

A forward bias DC voltage was applied to each of the OLEDs manufactured through Test Examples 239 to 365 and Comparative Examples 5 to 8, and electroluminescence (EL) characteristics of the OLED were measured by PR-650 (Photoresearch). Also, T95 life span was measured by life span measuring equipment (Mcscience) at the reference brightness of 2500 cd/$m^2$. Table 5 below shows evaluation results of OLEDs manufactured Test Examples and Comparative Examples.

TABLE 5

| | Compound | Voltage (V) | Current Density (mA/cm$^2$) | Brightness (cd/m$^2$) | Efficiency (cd/A) | Lifetime T(95) | CIE x | CIE y |
|---|---|---|---|---|---|---|---|---|
| Com. Ex (5) | Com. Com (2) | 5.9 | 26.5 | 2500.0 | 9.5 | 95.4 | 0.65 | 0.31 |
| Com. Ex (6) | Com. Com (3) | 6.0 | 27.7 | 2500.0 | 9.0 | 96.1 | 0.64 | 0.34 |
| Com. Ex (7) | Com. Com (4) | 6.1 | 26.4 | 2500.0 | 9.5 | 91.4 | 0.66 | 0.33 |
| Com. Ex (8) | — | 5.7 | 33.3 | 2500.0 | 7.5 | 71.3 | 0.64 | 0.31 |
| Ex. (239) | P1-1 | 5.7 | 23.5 | 2500.0 | 10.7 | 117.6 | 0.64 | 0.32 |
| Ex. (240) | P1-2 | 5.6 | 22.7 | 2500.0 | 11.0 | 116.9 | 0.65 | 0.31 |

TABLE 5-continued

| | Compound | Voltage (V) | Current Density (mA/cm²) | Brightness (cd/m²) | Efficiency (cd/A) | Lifetime T(95) | CIE x | CIE y |
|---|---|---|---|---|---|---|---|---|
| Ex. (241) | P1-3 | 5.6 | 19.5 | 2500.0 | 12.8 | 117.1 | 0.66 | 0.32 |
| Ex. (242) | P1-4 | 5.6 | 19.4 | 2500.0 | 12.9 | 115.1 | 0.66 | 0.30 |
| Ex. (243) | P1-5 | 5.7 | 24.7 | 2500.0 | 10.1 | 116.9 | 0.66 | 0.32 |
| Ex. (244) | P1-6 | 5.6 | 19.7 | 2500.0 | 12.7 | 119.8 | 0.64 | 0.30 |
| Ex. (245) | P1-7 | 5.6 | 21.1 | 2500.0 | 11.8 | 116.2 | 0.66 | 0.33 |
| Ex. (246) | P1-8 | 5.6 | 19.8 | 2500.0 | 12.6 | 115.1 | 0.65 | 0.30 |
| Ex. (247) | P1-9 | 5.7 | 24.7 | 2500.0 | 10.1 | 110.0 | 0.65 | 0.31 |
| Ex. (248) | P1-10 | 5.7 | 24.4 | 2500.0 | 10.2 | 117.0 | 0.66 | 0.33 |
| Ex. (249) | P1-11 | 5.7 | 20.7 | 2500.0 | 12.1 | 115.9 | 0.65 | 0.32 |
| Ex. (250) | P1-12 | 5.6 | 21.9 | 2500.0 | 11.4 | 116.2 | 0.65 | 0.30 |
| Ex. (251) | P1-13 | 5.6 | 24.0 | 2500.0 | 10.4 | 114.4 | 0.65 | 0.34 |
| Ex. (252) | P1-14 | 5.7 | 23.7 | 2500.0 | 10.6 | 112.4 | 0.64 | 0.34 |
| Ex. (253) | P1-15 | 5.7 | 19.4 | 2500.0 | 12.9 | 111.6 | 0.64 | 0.31 |
| Ex. (254) | P1-16 | 5.7 | 22.1 | 2500.0 | 11.3 | 114.8 | 0.65 | 0.32 |
| Ex. (255) | P1-17 | 5.6 | 22.1 | 2500.0 | 11.3 | 111.2 | 0.65 | 0.30 |
| Ex. (256) | P1-18 | 5.7 | 20.6 | 2500.0 | 12.2 | 112.2 | 0.66 | 0.32 |
| Ex. (257) | P1-19 | 5.6 | 22.0 | 2500.0 | 11.3 | 112.4 | 0.64 | 0.31 |
| Ex. (258) | P1-20 | 5.6 | 22.3 | 2500.0 | 11.2 | 112.0 | 0.66 | 0.31 |
| Ex. (259) | P1-45 | 5.7 | 21.6 | 2500.0 | 11.6 | 111.0 | 0.65 | 0.30 |
| Ex. (260) | P1-46 | 5.6 | 20.0 | 2500.0 | 12.5 | 113.9 | 0.64 | 0.31 |
| Ex. (261) | P1-47 | 5.6 | 20.9 | 2500.0 | 12.0 | 110.8 | 0.64 | 0.31 |
| Ex. (262) | P1-48 | 5.6 | 19.3 | 2500.0 | 13.0 | 117.2 | 0.65 | 0.33 |
| Ex. (263) | P1-49 | 5.6 | 25.0 | 2500.0 | 10.0 | 110.2 | 0.65 | 0.34 |
| Ex. (264) | P1-50 | 5.7 | 20.7 | 2500.0 | 12.1 | 118.1 | 0.64 | 0.31 |
| Ex. (265) | P1-51 | 5.6 | 19.8 | 2500.0 | 12.6 | 113.1 | 0.65 | 0.31 |
| Ex. (266) | P1-52 | 5.7 | 22.4 | 2500.0 | 11.1 | 116.0 | 0.65 | 0.31 |
| Ex. (267) | P1-61 | 5.7 | 24.2 | 2500.0 | 10.3 | 116.4 | 0.65 | 0.33 |
| Ex. (268) | P1-62 | 5.6 | 23.8 | 2500.0 | 10.5 | 116.2 | 0.66 | 0.31 |
| Ex. (269) | P1-63 | 5.6 | 23.1 | 2500.0 | 10.8 | 115.0 | 0.64 | 0.33 |
| Ex. (270) | P1-64 | 5.7 | 20.5 | 2500.0 | 12.2 | 111.3 | 0.64 | 0.31 |
| Ex. (271) | P1-101 | 5.6 | 20.9 | 2500.0 | 12.0 | 119.3 | 0.64 | 0.31 |
| Ex. (272) | P1-102 | 5.7 | 19.7 | 2500.0 | 12.7 | 113.9 | 0.65 | 0.30 |
| Ex. (273) | P1-103 | 5.7 | 23.8 | 2500.0 | 10.5 | 116.8 | 0.65 | 0.34 |
| Ex. (274) | P1-104 | 5.7 | 19.5 | 2500.0 | 12.8 | 116.2 | 0.66 | 0.33 |
| Ex. (275) | P1-105 | 5.6 | 20.3 | 2500.0 | 12.3 | 116.7 | 0.66 | 0.31 |
| Ex. (276) | P1-106 | 5.7 | 22.9 | 2500.0 | 10.9 | 119.3 | 0.65 | 0.31 |
| Ex. (277) | P1-107 | 5.7 | 21.1 | 2500.0 | 11.9 | 115.2 | 0.66 | 0.32 |
| Ex. (278) | P1-108 | 5.6 | 23.9 | 2500.0 | 10.5 | 116.1 | 0.65 | 0.33 |
| Ex. (279) | P2-1 | 5.7 | 24.4 | 2500.0 | 10.3 | 118.8 | 0.65 | 0.33 |
| Ex. (280) | P2-2 | 5.6 | 22.4 | 2500.0 | 11.1 | 117.7 | 0.65 | 0.32 |
| Ex. (281) | P2-3 | 5.6 | 20.6 | 2500.0 | 12.1 | 119.9 | 0.65 | 0.31 |
| Ex. (282) | P2-4 | 5.7 | 20.5 | 2500.0 | 12.2 | 111.9 | 0.64 | 0.30 |
| Ex. (283) | P2-5 | 5.7 | 22.2 | 2500.0 | 11.3 | 115.8 | 0.65 | 0.33 |
| Ex. (284) | P2-6 | 5.6 | 19.7 | 2500.0 | 12.7 | 113.5 | 0.66 | 0.31 |
| Ex. (285) | P2-7 | 5.6 | 19.3 | 2500.0 | 12.9 | 112.6 | 0.64 | 0.31 |
| Ex. (286) | P2-8 | 5.6 | 21.0 | 2500.0 | 11.9 | 111.7 | 0.66 | 0.30 |
| Ex. (287) | P2-9 | 5.7 | 23.2 | 2500.0 | 10.8 | 118.4 | 0.65 | 0.31 |
| Ex. (288) | P2-10 | 5.6 | 20.9 | 2500.0 | 12.0 | 117.3 | 0.66 | 0.30 |
| Ex. (289) | P2-11 | 5.7 | 24.9 | 2500.0 | 10.0 | 111.8 | 0.65 | 0.33 |
| Ex. (290) | P2-12 | 5.6 | 19.4 | 2500.0 | 12.9 | 116.1 | 0.66 | 0.34 |
| Ex. (291) | P2-13 | 5.6 | 20.6 | 2500.0 | 12.1 | 119.4 | 0.66 | 0.31 |
| Ex. (292) | P2-14 | 5.6 | 20.6 | 2500.0 | 12.1 | 114.0 | 0.65 | 0.34 |
| Ex. (293) | P2-15 | 5.6 | 20.6 | 2500.0 | 12.1 | 116.0 | 0.65 | 0.32 |
| Ex. (294) | P2-16 | 5.6 | 23.2 | 2500.0 | 10.8 | 114.7 | 0.65 | 0.32 |
| Ex. (295) | P2-17 | 5.6 | 22.6 | 2500.0 | 11.0 | 114.2 | 0.64 | 0.30 |
| Ex. (296) | P2-18 | 5.6 | 24.5 | 2500.0 | 10.2 | 114.1 | 0.66 | 0.32 |
| Ex. (297) | P2-19 | 5.7 | 21.5 | 2500.0 | 11.6 | 113.9 | 0.66 | 0.30 |
| Ex. (298) | P2-20 | 5.6 | 20.1 | 2500.0 | 12.5 | 112.6 | 0.64 | 0.31 |
| Ex. (299) | P2-45 | 5.7 | 23.5 | 2500.0 | 10.6 | 116.1 | 0.66 | 0.30 |
| Ex. (300) | P2-46 | 5.6 | 23.3 | 2500.0 | 10.7 | 115.0 | 0.64 | 0.33 |
| Ex. (301) | P2-47 | 5.6 | 21.1 | 2500.0 | 11.9 | 112.1 | 0.66 | 0.33 |
| Ex. (302) | P2-48 | 5.6 | 21.8 | 2500.0 | 11.5 | 118.8 | 0.65 | 0.32 |
| Ex. (303) | P2-49 | 5.6 | 20.2 | 2500.0 | 12.4 | 114.8 | 0.65 | 0.32 |
| Ex. (304) | P2-50 | 5.7 | 22.9 | 2500.0 | 10.9 | 119.3 | 0.64 | 0.31 |
| Ex. (305) | P2-51 | 5.7 | 19.8 | 2500.0 | 12.6 | 119.3 | 0.65 | 0.33 |
| Ex. (306) | P2-52 | 5.7 | 21.5 | 2500.0 | 11.6 | 115.3 | 0.65 | 0.33 |
| Ex. (307) | P2-61 | 5.7 | 19.9 | 2500.0 | 12.6 | 115.2 | 0.66 | 0.32 |
| Ex. (308) | P2-62 | 5.7 | 22.0 | 2500.0 | 11.3 | 111.6 | 0.66 | 0.31 |
| Ex. (309) | P2-63 | 5.6 | 20.0 | 2500.0 | 12.5 | 111.5 | 0.65 | 0.31 |
| Ex. (310) | P2-64 | 5.7 | 24.9 | 2500.0 | 10.0 | 113.3 | 0.64 | 0.32 |
| Ex. (311) | P2-101 | 5.7 | 23.7 | 2500.0 | 10.5 | 115.6 | 0.65 | 0.31 |
| Ex. (312) | P2-102 | 5.7 | 23.6 | 2500.0 | 10.6 | 118.9 | 0.65 | 0.32 |
| Ex. (313) | P2-103 | 5.7 | 20.4 | 2500.0 | 12.3 | 113.0 | 0.65 | 0.31 |
| Ex. (314) | P2-104 | 5.7 | 22.3 | 2500.0 | 11.2 | 116.4 | 0.66 | 0.33 |
| Ex. (315) | P2-105 | 5.7 | 23.7 | 2500.0 | 10.6 | 110.5 | 0.66 | 0.34 |

TABLE 5-continued

| | Compound | Voltage (V) | Current Density (mA/cm$^2$) | Brightness (cd/m$^2$) | Efficiency (cd/A) | Lifetime T(95) | CIE x | CIE y |
|---|---|---|---|---|---|---|---|---|
| Ex. (316) | P2-106 | 5.7 | 24.3 | 2500.0 | 10.3 | 115.3 | 0.66 | 0.31 |
| Ex. (317) | P2-107 | 5.7 | 21.6 | 2500.0 | 11.6 | 110.9 | 0.65 | 0.33 |
| Ex. (318) | P2-108 | 5.6 | 21.6 | 2500.0 | 11.6 | 111.9 | 0.66 | 0.34 |
| Ex. (319) | P3-1 | 5.5 | 17.5 | 2500.0 | 14.3 | 128.9 | 0.65 | 0.32 |
| Ex. (320) | P3-2 | 5.6 | 17.6 | 2500.0 | 14.2 | 129.4 | 0.65 | 0.32 |
| Ex. (321) | P3-3 | 5.6 | 16.8 | 2500.0 | 14.9 | 127.3 | 0.66 | 0.32 |
| Ex. (322) | P3-4 | 5.6 | 17.5 | 2500.0 | 14.3 | 123.5 | 0.66 | 0.31 |
| Ex. (323) | P3-5 | 5.5 | 17.1 | 2500.0 | 14.7 | 127.8 | 0.66 | 0.32 |
| Ex. (324) | P3-6 | 5.5 | 17.3 | 2500.0 | 14.4 | 123.9 | 0.65 | 0.34 |
| Ex. (325) | P3-7 | 5.5 | 17.6 | 2500.0 | 14.2 | 128.1 | 0.66 | 0.33 |
| Ex. (326) | P3-8 | 5.6 | 17.4 | 2500.0 | 14.3 | 126.5 | 0.65 | 0.30 |
| Ex. (327) | P3-9 | 5.6 | 17.4 | 2500.0 | 14.4 | 123.9 | 0.65 | 0.32 |
| Ex. (328) | P3-10 | 5.6 | 16.8 | 2500.0 | 14.9 | 126.3 | 0.65 | 0.30 |
| Ex. (329) | P3-11 | 5.5 | 17.6 | 2500.0 | 14.2 | 129.8 | 0.64 | 0.32 |
| Ex. (330) | P3-12 | 5.6 | 17.4 | 2500.0 | 14.3 | 123.4 | 0.65 | 0.32 |
| Ex. (331) | P3-13 | 5.5 | 17.1 | 2500.0 | 14.7 | 127.5 | 0.65 | 0.34 |
| Ex. (332) | P3-14 | 5.6 | 17.5 | 2500.0 | 14.3 | 125.8 | 0.66 | 0.34 |
| Ex. (333) | P3-15 | 5.6 | 17.4 | 2500.0 | 14.4 | 120.3 | 0.65 | 0.32 |
| Ex. (334) | P3-16 | 5.6 | 17.5 | 2500.0 | 14.3 | 124.3 | 0.65 | 0.31 |
| Ex. (335) | P3-17 | 5.6 | 17.2 | 2500.0 | 14.6 | 121.3 | 0.65 | 0.34 |
| Ex. (336) | P3-18 | 5.6 | 17.6 | 2500.0 | 14.2 | 124.6 | 0.66 | 0.31 |
| Ex. (337) | P3-19 | 5.6 | 17.1 | 2500.0 | 14.6 | 129.0 | 0.64 | 0.30 |
| Ex. (338) | P3-20 | 5.6 | 17.1 | 2500.0 | 14.6 | 125.9 | 0.65 | 0.33 |
| Ex. (339) | P3-21 | 5.5 | 17.5 | 2500.0 | 14.3 | 123.6 | 0.65 | 0.34 |
| Ex. (340) | P3-22 | 5.6 | 17.0 | 2500.0 | 14.7 | 122.6 | 0.65 | 0.31 |
| Ex. (341) | P3-23 | 5.5 | 17.3 | 2500.0 | 14.5 | 124.0 | 0.65 | 0.32 |
| Ex. (342) | P3-24 | 5.5 | 16.7 | 2500.0 | 14.9 | 127.4 | 0.65 | 0.32 |
| Ex. (343) | P3-25 | 5.5 | 17.6 | 2500.0 | 14.2 | 121.1 | 0.65 | 0.31 |
| Ex. (344) | P3-26 | 5.5 | 17.7 | 2500.0 | 14.1 | 127.2 | 0.66 | 0.34 |
| Ex. (345) | P3-27 | 5.6 | 17.7 | 2500.0 | 14.1 | 124.5 | 0.66 | 0.32 |
| Ex. (346) | P3-28 | 5.6 | 17.0 | 2500.0 | 14.7 | 121.5 | 0.65 | 0.31 |
| Ex. (347) | P3-29 | 5.5 | 17.1 | 2500.0 | 14.6 | 126.6 | 0.65 | 0.32 |
| Ex. (348) | P3-30 | 5.6 | 16.7 | 2500.0 | 14.9 | 128.7 | 0.65 | 0.32 |
| Ex. (349) | P3-31 | 5.6 | 17.3 | 2500.0 | 14.4 | 129.9 | 0.65 | 0.34 |
| Ex. (350) | P3-32 | 5.6 | 17.3 | 2500.0 | 14.5 | 124.3 | 0.64 | 0.32 |
| Ex. (351) | P3-33 | 5.6 | 16.8 | 2500.0 | 14.9 | 127.0 | 0.65 | 0.30 |
| Ex. (352) | P3-34 | 5.5 | 17.2 | 2500.0 | 14.6 | 125.5 | 0.66 | 0.32 |
| Ex. (353) | P3-35 | 5.6 | 16.9 | 2500.0 | 14.7 | 123.8 | 0.64 | 0.33 |
| Ex. (354) | P3-36 | 5.5 | 16.9 | 2500.0 | 14.8 | 127.7 | 0.66 | 0.31 |
| Ex. (355) | P3-37 | 5.5 | 16.7 | 2500.0 | 15.0 | 126.7 | 0.66 | 0.30 |
| Ex. (356) | P3-38 | 5.6 | 16.7 | 2500.0 | 15.0 | 125.3 | 0.65 | 0.31 |
| Ex. (357) | P4-2 | 5.0 | 12.8 | 2500.0 | 19.5 | 138.7 | 0.65 | 0.31 |
| Ex. (358) | P4-5 | 5.0 | 12.9 | 2500.0 | 19.4 | 132.7 | 0.65 | 0.32 |
| Ex. (359) | P4-8 | 5.1 | 13.2 | 2500.0 | 18.9 | 131.6 | 0.65 | 0.32 |
| Ex. (360) | P4-9 | 5.0 | 13.4 | 2500.0 | 18.6 | 132.7 | 0.65 | 0.31 |
| Ex. (361) | P4-10 | 5.0 | 13.8 | 2500.0 | 18.2 | 139.3 | 0.66 | 0.34 |
| Ex. (362) | P4-17 | 5.2 | 14.9 | 2500.0 | 16.8 | 132.5 | 0.66 | 0.32 |
| Ex. (363) | P4-20 | 5.2 | 14.2 | 2500.0 | 17.6 | 131.0 | 0.65 | 0.31 |
| Ex. (364) | P4-22 | 5.3 | 14.6 | 2500.0 | 17.1 | 130.8 | 0.65 | 0.32 |
| Ex. (365) | P4-24 | 5.2 | 14.0 | 2500.0 | 17.8 | 136.4 | 0.65 | 0.32 |

[Example 366] An Emission-Auxiliary Layer (Green)

Organic light emitting diodes (OLEDs) were fabricated according to a conventional method by using a compound of the present invention as an emission-auxiliary layer material First, an ITO layer (anode) was formed on a glass substrate, and a film of 2-TNATA was vacuum-deposited on the ITO layer to form a hole injection layer with a thickness of 60 nm. Subsequently, NPD was vacuum-deposited with a thickness of 60 nm on the hole injection layer to form a hole transport layer.

Subsequently, a film of the compound P1-21 of the present invention was vacuum-deposited on the hole transport layer to form a emission-auxiliary layer with a thickness of 20 nm. A light emitting layer with a thickness of 30 nm was deposited on the emission-auxiliary layer by using the CBP as a host material and $Ir(ppy)_3$ as a dopant material in a weight ratio of 95:5.

Next, a film of BAlq was vacuum-deposited with a thickness of 10 nm on the light emitting layer to form a hole blocking layer, and a film of $Alq_3$ was formed with a thickness of 40 nm to form an electron transport layer.

Next, LiF as halogenated alkali metal was deposited with a thickness of 0.2 nm on the electron transport layer to form an electron injection layer, and then Al was deposited with a thickness of 150 nm on the electron injection layer to form a cathode. In this way, the OLED was completed.

[Example 367] to [Example 485] An Emission-Auxiliary Layer (Green)

The OLED was manufactured in the same manner as described in Test Example 366, except that any one of the compounds P1-22 to P1-44, P1-77 to P1-112, P2-21 to P2-44, and P2-77 to P2-112 of the present invention in the Table 6 below was used as the emission-auxiliary layer material, instead of the inventive compound P1-21.

Comparative Example 9

An OLED was manufactured in the same manner as described in Test Example 366, except that Comparative Compound 2 above was used as the emission-auxiliary layer material, instead of the inventive compound P1-21.

Comparative Example 10

An OLED was manufactured in the same manner as described in Test Example 366, except that Comparative Compound 3 above was used as the emission-auxiliary layer material, instead of the inventive compound P1-21.

Comparative Example 11

An OLED was manufactured in the same manner as described in Test Example 366, except that Comparative Compound 4 above was used as the emission-auxiliary layer material, instead of the inventive compound P1-21.

Comparative Example 12

An OLED was manufactured in the same manner as described in Test Example 366, except not to form the emission-auxiliary layer.

A forward bias DC voltage was applied to each of the OLEDs manufactured through Test Examples 366 to 485 and Comparative Example 9 to 12, and electroluminescence (EL) characteristics of the OLED were measured by PR-650 (Photoresearch). Also, T95 life span was measured by life span measuring equipment (Mcscience) at the reference brightness of 5000 cd/$m^2$. Table 6 below shows evaluation results of OLEDs manufactured Test Examples and Comparative Examples.

TABLE 6

| | Compound | Voltage (V) | Current Density (mA/$cm^2$) | Brightness (cd/$m^2$) | Efficiency (cd/A) | Lifetime T(95) | CIE x | CIE y |
|---|---|---|---|---|---|---|---|---|
| Com .Ex (9) | Com. Com (2) | 5.6 | 13.6 | 5000.0 | 36.8 | 116.9 | 0.33 | 0.61 |
| Com. Ex (10) | Com. Com (3) | 5.9 | 12.1 | 5000.0 | 41.2 | 116.5 | 0.33 | 0.61 |
| Com. Ex (11) | Com. Com (4) | 6.2 | 11.4 | 5000.0 | 44.0 | 110.1 | 0.33 | 0.61 |
| Com. Ex (12) | — | 5.6 | 21.7 | 5000.0 | 23.0 | 65.7 | 0.33 | 0.61 |
| Ex. (366) | P1-21 | 6.1 | 10.4 | 5000.0 | 48.2 | 147.9 | 0.33 | 0.62 |
| Ex. (367) | P1-22 | 5.8 | 10.2 | 5000.0 | 49.0 | 114.2 | 0.33 | 0.62 |
| Ex. (368) | P1-23 | 5.8 | 10.1 | 5000.0 | 49.3 | 104.8 | 0.33 | 0.61 |
| Ex. (369) | P1-24 | 5.8 | 10.1 | 5000.0 | 49.4 | 143.6 | 0.33 | 0.61 |
| Ex. (370) | P1-25 | 6.0 | 10.0 | 5000.0 | 49.8 | 126.5 | 0.33 | 0.62 |
| Ex. (371) | P1-26 | 5.9 | 10.1 | 5000.0 | 49.5 | 118.2 | 0.33 | 0.61 |
| Ex. (372) | P1-27 | 5.9 | 10.3 | 5000.0 | 48.4 | 109.7 | 0.33 | 0.62 |
| Ex. (373) | P1-28 | 6.0 | 10.4 | 5000.0 | 48.3 | 131.0 | 0.33 | 0.62 |
| Ex. (374) | P1-29 | 5.8 | 10.4 | 5000.0 | 48.3 | 103.4 | 0.33 | 0.62 |
| Ex. (375) | P1-30 | 6.0 | 10.3 | 5000.0 | 48.8 | 116.9 | 0.33 | 0.61 |
| Ex. (376) | P1-31 | 6.1 | 10.4 | 5000.0 | 47.9 | 112.7 | 0.33 | 0.62 |
| Ex. (377) | P1-32 | 6.1 | 10.1 | 5000.0 | 49.5 | 106.9 | 0.33 | 0.61 |
| Ex. (378) | P1-33 | 5.9 | 10.3 | 5000.0 | 48.6 | 104.9 | 0.33 | 0.62 |
| Ex. (379) | P1-34 | 5.7 | 10.5 | 5000.0 | 47.6 | 127.4 | 0.33 | 0.61 |
| Ex. (380) | P1-35 | 6.0 | 10.5 | 5000.0 | 47.4 | 126.6 | 0.33 | 0.61 |
| Ex. (381) | P1-36 | 5.8 | 10.1 | 5000.0 | 49.7 | 140.1 | 0.33 | 0.62 |
| Ex. (382) | P1-37 | 5.7 | 10.3 | 5000.0 | 48.6 | 134.4 | 0.33 | 0.61 |
| Ex. (383) | P1-38 | 5.9 | 10.3 | 5000.0 | 48.4 | 142.4 | 0.33 | 0.61 |
| Ex. (384) | P1-39 | 6.1 | 10.2 | 5000.0 | 49.2 | 129.9 | 0.33 | 0.62 |
| Ex. (385) | P1-40 | 6.0 | 10.5 | 5000.0 | 47.6 | 140.4 | 0.33 | 0.61 |
| Ex. (386) | P1-41 | 6.0 | 10.4 | 5000.0 | 48.1 | 145.4 | 0.33 | 0.61 |
| Ex. (387) | P1-42 | 5.9 | 10.3 | 5000.0 | 48.5 | 129.9 | 0.33 | 0.62 |
| Ex. (388) | P1-43 | 6.0 | 10.6 | 5000.0 | 47.1 | 118.9 | 0.33 | 0.61 |
| Ex. (389) | P1-44 | 6.1 | 10.6 | 5000.0 | 47.2 | 114.1 | 0.33 | 0.62 |
| Ex. (390) | P1-77 | 5.9 | 10.4 | 5000.0 | 48.1 | 126.6 | 0.33 | 0.62 |
| Ex. (391) | P1-78 | 6.0 | 10.2 | 5000.0 | 48.8 | 140.4 | 0.33 | 0.61 |
| Ex. (392) | P1-79 | 6.2 | 10.2 | 5000.0 | 49.1 | 131.8 | 0.33 | 0.61 |
| Ex. (393) | P1-80 | 5.8 | 10.3 | 5000.0 | 48.4 | 130.1 | 0.33 | 0.61 |
| Ex. (394) | P1-81 | 6.2 | 10.4 | 5000.0 | 48.1 | 115.5 | 0.33 | 0.62 |
| Ex. (395) | P1-82 | 6.1 | 10.2 | 5000.0 | 48.9 | 143.7 | 0.33 | 0.62 |
| Ex. (396) | P1-83 | 6.2 | 10.5 | 5000.0 | 47.5 | 119.2 | 0.33 | 0.61 |
| Ex. (397) | P1-84 | 5.9 | 10.0 | 5000.0 | 50.0 | 128.0 | 0.33 | 0.62 |
| Ex. (398) | P1-85 | 5.9 | 10.6 | 5000.0 | 47.1 | 132.9 | 0.33 | 0.61 |
| Ex. (399) | P1-86 | 5.8 | 10.1 | 5000.0 | 49.6 | 115.8 | 0.33 | 0.61 |
| Ex. (400) | P1-87 | 5.8 | 10.1 | 5000.0 | 49.6 | 137.4 | 0.33 | 0.61 |
| Ex. (401) | P1-88 | 5.8 | 10.4 | 5000.0 | 48.2 | 105.4 | 0.33 | 0.62 |
| Ex. (402) | P1-89 | 5.8 | 10.5 | 5000.0 | 47.5 | 109.9 | 0.33 | 0.62 |
| Ex. (403) | P1-90 | 5.8 | 10.2 | 5000.0 | 49.0 | 104.9 | 0.33 | 0.61 |
| Ex. (404) | P1-91 | 6.1 | 10.1 | 5000.0 | 49.3 | 125.1 | 0.33 | 0.61 |
| Ex. (405) | P1-92 | 6.2 | 10.0 | 5000.0 | 49.8 | 109.0 | 0.33 | 0.61 |
| Ex. (406) | P1-93 | 6.0 | 10.6 | 5000.0 | 47.3 | 139.3 | 0.33 | 0.62 |
| Ex. (407) | P1-94 | 6.1 | 10.1 | 5000.0 | 49.3 | 143.5 | 0.33 | 0.62 |
| Ex. (408) | P1-95 | 5.8 | 10.3 | 5000.0 | 48.3 | 148.4 | 0.33 | 0.62 |
| Ex. (409) | P1-96 | 6.2 | 10.2 | 5000.0 | 49.0 | 129.1 | 0.33 | 0.62 |
| Ex. (410) | P1-97 | 6.0 | 10.3 | 5000.0 | 48.5 | 120.9 | 0.33 | 0.62 |
| Ex. (411) | P1-98 | 5.8 | 10.6 | 5000.0 | 47.3 | 118.2 | 0.33 | 0.62 |
| Ex. (412) | P1-99 | 6.0 | 10.4 | 5000.0 | 48.2 | 100.5 | 0.33 | 0.62 |
| Ex. (413) | P1-100 | 6.1 | 10.2 | 5000.0 | 49.0 | 110.1 | 0.33 | 0.61 |

TABLE 6-continued

| | Compound | Voltage (V) | Current Density (mA/cm$^2$) | Brightness (cd/m$^2$) | Efficiency (cd/A) | Lifetime T(95) | CIE x | CIE y |
|---|---|---|---|---|---|---|---|---|
| Ex. (414) | P1-101 | 5.8 | 10.6 | 5000.0 | 47.3 | 103.9 | 0.33 | 0.62 |
| Ex. (415) | P1-102 | 5.9 | 10.6 | 5000.0 | 47.4 | 118.9 | 0.33 | 0.62 |
| Ex. (416) | P1-103 | 5.9 | 10.3 | 5000.0 | 48.7 | 107.0 | 0.33 | 0.61 |
| Ex. (417) | P1-104 | 6.2 | 10.6 | 5000.0 | 47.2 | 112.5 | 0.33 | 0.62 |
| Ex. (418) | P1-105 | 6.2 | 10.0 | 5000.0 | 49.9 | 110.3 | 0.33 | 0.62 |
| Ex. (419) | P1-106 | 5.9 | 10.2 | 5000.0 | 49.0 | 141.6 | 0.33 | 0.61 |
| Ex. (420) | P1-107 | 6.0 | 10.4 | 5000.0 | 47.9 | 108.6 | 0.33 | 0.62 |
| Ex. (421) | P1-108 | 5.8 | 10.2 | 5000.0 | 48.9 | 130.0 | 0.33 | 0.62 |
| Ex. (422) | P1-109 | 5.9 | 10.6 | 5000.0 | 47.4 | 132.4 | 0.33 | 0.62 |
| Ex. (423) | P1-110 | 5.7 | 10.4 | 5000.0 | 48.3 | 132.7 | 0.33 | 0.61 |
| Ex. (424) | P1-111 | 5.9 | 10.0 | 5000.0 | 49.8 | 140.1 | 0.33 | 0.61 |
| Ex. (425) | P1-112 | 6.2 | 10.1 | 5000.0 | 49.7 | 124.7 | 0.33 | 0.62 |
| Ex. (426) | P2-21 | 5.7 | 9.5 | 5000.0 | 52.4 | 149.6 | 0.33 | 0.61 |
| Ex. (427) | P2-22 | 6.0 | 9.1 | 5000.0 | 54.7 | 101.9 | 0.33 | 0.61 |
| Ex. (428) | P2-23 | 6.0 | 9.1 | 5000.0 | 54.8 | 103.2 | 0.33 | 0.61 |
| Ex. (429) | P2-24 | 6.1 | 9.4 | 5000.0 | 53.4 | 125.4 | 0.33 | 0.61 |
| Ex. (430) | P2-25 | 6.0 | 9.2 | 5000.0 | 54.2 | 141.2 | 0.33 | 0.62 |
| Ex. (431) | P2-26 | 6.0 | 9.3 | 5000.0 | 54.0 | 116.4 | 0.33 | 0.61 |
| Ex. (432) | P2-27 | 6.1 | 9.5 | 5000.0 | 52.6 | 138.5 | 0.33 | 0.61 |
| Ex. (433) | P2-28 | 6.0 | 9.4 | 5000.0 | 53.1 | 132.0 | 0.33 | 0.61 |
| Ex. (434) | P2-29 | 6.0 | 9.9 | 5000.0 | 50.4 | 133.6 | 0.33 | 0.61 |
| Ex. (435) | P2-30 | 6.0 | 9.6 | 5000.0 | 52.2 | 117.4 | 0.33 | 0.61 |
| Ex. (436) | P2-31 | 6.0 | 9.2 | 5000.0 | 54.2 | 149.9 | 0.33 | 0.61 |
| Ex. (437) | P2-32 | 6.0 | 9.7 | 5000.0 | 51.4 | 105.8 | 0.33 | 0.62 |
| Ex. (438) | P2-33 | 5.7 | 9.7 | 5000.0 | 51.8 | 135.1 | 0.33 | 0.62 |
| Ex. (439) | P2-34 | 6.1 | 9.5 | 5000.0 | 52.7 | 127.6 | 0.33 | 0.62 |
| Ex. (440) | P2-35 | 5.9 | 9.3 | 5000.0 | 54.0 | 137.8 | 0.33 | 0.62 |
| Ex. (441) | P2-36 | 5.8 | 9.7 | 5000.0 | 51.7 | 115.8 | 0.33 | 0.61 |
| Ex. (442) | P2-37 | 6.0 | 9.4 | 5000.0 | 53.4 | 142.9 | 0.33 | 0.61 |
| Ex. (443) | P2-38 | 6.0 | 9.6 | 5000.0 | 52.1 | 144.4 | 0.33 | 0.61 |
| Ex. (444) | P2-39 | 6.0 | 9.5 | 5000.0 | 52.4 | 126.3 | 0.33 | 0.62 |
| Ex. (445) | P2-40 | 5.8 | 9.5 | 5000.0 | 52.6 | 128.5 | 0.33 | 0.61 |
| Ex. (446) | P2-41 | 5.8 | 9.6 | 5000.0 | 52.3 | 109.2 | 0.33 | 0.61 |
| Ex. (447) | P2-42 | 5.7 | 9.9 | 5000.0 | 50.7 | 129.7 | 0.33 | 0.62 |
| Ex. (448) | P2-43 | 6.0 | 9.5 | 5000.0 | 52.7 | 110.0 | 0.33 | 0.61 |
| Ex. (449) | P2-44 | 6.0 | 9.9 | 5000.0 | 50.5 | 141.9 | 0.33 | 0.62 |
| Ex. (450) | P2-77 | 6.0 | 9.1 | 5000.0 | 54.7 | 128.6 | 0.33 | 0.62 |
| Ex. (451) | P2-78 | 5.7 | 9.9 | 5000.0 | 50.5 | 109.1 | 0.33 | 0.61 |
| Ex. (452) | P2-79 | 6.1 | 9.1 | 5000.0 | 54.9 | 100.5 | 0.33 | 0.62 |
| Ex. (453) | P2-80 | 6.0 | 9.9 | 5000.0 | 50.6 | 132.8 | 0.33 | 0.62 |
| Ex. (454) | P2-81 | 5.8 | 9.7 | 5000.0 | 51.3 | 141.8 | 0.33 | 0.61 |
| Ex. (455) | P2-82 | 5.9 | 9.7 | 5000.0 | 51.3 | 148.1 | 0.33 | 0.61 |
| Ex. (456) | P2-83 | 5.9 | 9.2 | 5000.0 | 54.1 | 141.2 | 0.33 | 0.61 |
| Ex. (457) | P2-84 | 5.8 | 9.3 | 5000.0 | 53.6 | 142.6 | 0.33 | 0.61 |
| Ex. (458) | P2-85 | 5.8 | 9.6 | 5000.0 | 52.3 | 129.5 | 0.33 | 0.61 |
| Ex. (459) | P2-86 | 6.0 | 9.2 | 5000.0 | 54.5 | 127.9 | 0.33 | 0.62 |
| Ex. (460) | P2-87 | 6.1 | 9.6 | 5000.0 | 52.3 | 112.8 | 0.33 | 0.61 |
| Ex. (461) | P2-88 | 5.8 | 9.4 | 5000.0 | 53.4 | 119.6 | 0.33 | 0.62 |
| Ex. (462) | P2-89 | 6.0 | 9.4 | 5000.0 | 53.2 | 101.3 | 0.33 | 0.62 |
| Ex. (463) | P2-90 | 5.9 | 9.6 | 5000.0 | 52.3 | 148.0 | 0.33 | 0.62 |
| Ex. (464) | P2-91 | 5.7 | 9.8 | 5000.0 | 50.9 | 136.2 | 0.33 | 0.62 |
| Ex. (465) | P2-92 | 5.8 | 9.2 | 5000.0 | 54.2 | 103.4 | 0.33 | 0.61 |
| Ex. (466) | P2-93 | 6.0 | 9.1 | 5000.0 | 54.8 | 137.7 | 0.33 | 0.62 |
| Ex. (467) | P2-94 | 5.8 | 9.8 | 5000.0 | 51.1 | 131.6 | 0.33 | 0.62 |
| Ex. (468) | P2-95 | 6.0 | 9.7 | 5000.0 | 51.7 | 144.1 | 0.33 | 0.62 |
| Ex. (469) | P2-96 | 5.7 | 9.3 | 5000.0 | 53.6 | 109.9 | 0.33 | 0.62 |
| Ex. (470) | P2-97 | 6.0 | 9.8 | 5000.0 | 50.9 | 120.6 | 0.33 | 0.62 |
| Ex. (471) | P2-98 | 6.0 | 9.1 | 5000.0 | 54.8 | 139.7 | 0.33 | 0.62 |
| Ex. (472) | P2-99 | 5.9 | 9.3 | 5000.0 | 53.9 | 125.5 | 0.33 | 0.62 |
| Ex. (473) | P2-100 | 6.0 | 9.3 | 5000.0 | 53.7 | 127.2 | 0.33 | 0.61 |
| Ex. (474) | P2-101 | 6.1 | 9.4 | 5000.0 | 53.3 | 137.4 | 0.33 | 0.62 |
| Ex. (475) | P2-102 | 6.2 | 9.9 | 5000.0 | 50.7 | 136.5 | 0.33 | 0.61 |
| Ex. (476) | P2-103 | 6.2 | 9.3 | 5000.0 | 53.5 | 115.7 | 0.33 | 0.62 |
| Ex. (477) | P2-104 | 6.1 | 9.8 | 5000.0 | 51.2 | 119.4 | 0.33 | 0.61 |
| Ex. (478) | P2-105 | 5.7 | 10.0 | 5000.0 | 50.0 | 125.9 | 0.33 | 0.61 |
| Ex. (479) | P2-106 | 6.1 | 9.2 | 5000.0 | 54.3 | 143.8 | 0.33 | 0.62 |
| Ex. (480) | P2-107 | 5.8 | 9.9 | 5000.0 | 50.4 | 105.0 | 0.33 | 0.62 |
| Ex. (481) | P2-108 | 5.8 | 9.7 | 5000.0 | 51.5 | 107.6 | 0.33 | 0.61 |
| Ex. (482) | P2-109 | 5.8 | 9.2 | 5000.0 | 54.3 | 136.8 | 0.33 | 0.62 |
| Ex. (483) | P2-110 | 5.9 | 9.4 | 5000.0 | 53.3 | 121.4 | 0.33 | 0.62 |
| Ex. (484) | P2-111 | 5.7 | 9.6 | 5000.0 | 52.0 | 134.9 | 0.33 | 0.62 |
| Ex. (485) | P2-112 | 5.9 | 9.7 | 5000.0 | 51.6 | 136.1 | 0.33 | 0.62 |

It can be seen from the results in Tables 5 and 6 above, that the OLEDs using the inventive compounds as the auxiliary emission layer material showed predominantly improved efficiency and lifespan, compared to the OLEDs using comparative compounds 2 to 4 as the auxiliary emission layer material and the OLEDs not having the auxiliary emission layer.

That is, the OLEDs using the present invention compounds showed predominantly improved efficiency and long life span, compared to the OLEDs not forming the auxiliary emission layer, and the OLEDs using comparative compounds 2 to 4 as the auxiliary emission layer material.

Especially, comparing the case that OLEDs employ comparative compounds 3 and 4 and the case that OLEDs employ the inventive compounds, it can be seen that significant difference in efficiency and life span was shown between the compounds having a linker equally linked to the same 2-position of the carbazole cores yet the substituent amine group is linked on a different position of the linker. This is believed because different bonding angle occurs depending on to which position of the linker the amine group is linked, so does the different T1 values, which causes different electron blocking abilities.

In addition, referring to Table 5 showing the result in OLEDs comprising red auxiliary emission layer, it can be seen that although efficiency and driving voltage are similar or slightly increased, life span is improved where compounds (P3-1 to P3-38) of the present invention having $R^3$ being a substituent other than hydrogen are used as a red auxiliary emission layer, compared to the compounds having $R^3$ being hydrogen. It is inferred that this result is caused because when the layer of OLED is formed, packing density, hole injection and mobility are dependent on the kinds of substituent $R^3$.

Further, the case that the inventive compounds (P4-2~24) of which $Ar^2$ is carabzole derivatives among the inventive compounds are employed as red auxiliary emission layer materials showed the best results, especially, showed predominantly improved efficiency and driving voltage. These results are believed to come from that heat-degradation in the interfacial between ITO and a hole transport layer is decreased and heat the life span of the organic elements is improved because the abilities of a hole injection and a hole mobility are improved by comprising another carabzole derivatives in the inventive compound, and the driving voltage, efficiency and life span are optimized because charge balance between a hole and an electron in a light emitting layer is increased and the light emitting is well made in the light emitting layer not the interfacial of the hole transport layer by transferring more holes to the light emitting layer.

Furthermore, in compounds (P4-2~10) where $Ar^2$ is a carbazole derivatives and $Ar^2$ is linked to L (linker) on ortho position, the driving voltage of the organic element gets lower than in compounds (P4-17~24) where $Ar^2$ is a carbazole derivatives and $Ar^2$ is linked to L (linker) on meta position, because packing density of the compound where $Ar^2$ is linked to L (linker) on ortho position gets well during deposition.

As described above, it was shown that the linking position of between the carbazole core and the linker substituted with a amine group, between the linker and the amine group, and the kind of the linker is important factor because the performance ability of the organic elements in an auxiliary emission layer as well as a hole transport layer changes depending on the linking position and the kind of the linker.

Although exemplary embodiments of the present invention have been described for illustrative purposes, those skilled in the art will appreciate that various modifications, additions and substitutions are possible, without departing from the scope and spirit of the invention as disclosed in the accompanying claims. Therefore, the embodiment disclosed in the present invention is intended to illustrate the scope of the technical idea of the present invention, and the scope of the present invention is not limited by the embodiment. The scope of the present invention shall be construed on the basis of the accompanying claims, and it shall be construed that all of the technical ideas included within the scope equivalent to the claims belong to the present invention.

The invention claimed is:

1. A compound of Formula 1:

[Formula 1]

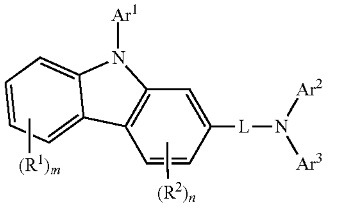

wherein, $Ar^1$ to $Ar^3$ are each independently selected from the group consisting of a $C_6$-$C_{60}$ aryl group; a fluorenyl group; a $C_2$-$C_{60}$ heterocyclic group containing at least one heteroatom selected from the group consisting of O, N, S, Si, and P; a fused ring formed by a $C_3$-$C_{60}$ aliphatic ring and a $C_6$-$C_{60}$ aromatic ring; a $C_1$-$C_{50}$ alkyl group; a $C_2$-$C_{20}$ alkenyl group; a $C_2$-$C_{20}$ alkynyl group; a $C_1$-$C_{30}$ alkoxy group; and a $C_6$-$C_{30}$ aryloxy group, with the proviso that the compound of Formula 1 wherein $Ar^1$ is a $C_6$-$C_{60}$ aryl group and at least one of $Ar^2$ and $Ar^3$ is a fluorenyl group or one of $Ar^2$ and $Ar^3$ is a N-containing $C_2$-$C_9$ heterocyclic group, is excluded, L is

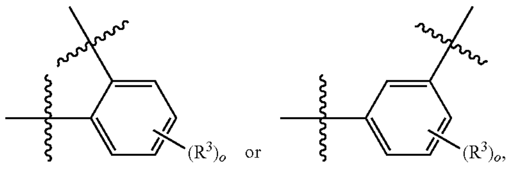

m and o are each an integer of 0 to 4, n is an integer of 0 to 3, $R^1$, $R^2$ and $R^3$ are each independently selected from the group consisting of deuterium;

halogen; a $C_6$-$C_{60}$ aryl group; a fluorenyl group; a $C_2$-$C_{60}$ heterocyclic group containing at least one heteroatom selected from the group consisting of O, N, S, Si, and P; a fused ring formed by a $C_3$-$C_{60}$ aliphatic ring and a $C_6$-$C_{60}$ aromatic ring; a $C_1$-$C_{50}$ alkyl group; a $C_2$-$C_{20}$ alkenyl group; a $C_2$-$C_{20}$ alkynyl group; a $C_1$-$C_{30}$ alkoxy group; a $C_6$-$C_{30}$ aryloxy group; -L'-N($R^a$)($R^b$); and a combination thereof, with the proviso that $R^3$ is not -L'-N($R^a$)($R^b$), L' is selected from the group consisting of single bond; a $C_6$-$C_{60}$ arylene group; a fluorenylene group; a fused ring formed by a $C_3$-$C_{60}$ aliphatic ring and a $C_6$-$C_{60}$ aromatic ring; and a $C_2$-$C_{60}$ heterocyclic group containing at least one heteroatom selected from the group consisting of O, N, S, Si, and P, $R^a$ and $R^b$ are each independently selected from the group consisting of $C_6$-$C_{60}$ aryl group; a fluorenyl group; a fused ring formed by a $C_3$-$C_{60}$ aliphatic ring and a $C_6$-$C_{60}$ aromatic ring; and a $C_2$-$C_{60}$ heterocyclic group containing at least one heteroatom selected from the group consisting of O, N, S, Si, and P, and each of the above aryl group, fluorenyl group, heterocyclic group, fused ring group, alkyl group, alkenyl group, alkynyl group, alkoxy group, aryloxy group, arylene group and fluorenylene group may be substituted with one or more substituents selected from the group consisting of deuterium; halogen; a silane group; a siloxane group; a boron group; a germanium group; a cyano group; a nitro group; a $C_1$-$C_{20}$ alkylthio group; a $C_1$-$C_{20}$ alkoxy group; a $C_1$-$C_{20}$ alkyl group; a $C_2$-$C_{20}$ alkenyl group; a $C_2$-$C_{20}$ alkynyl group; a $C_6$-$C_{20}$ aryl group; a $C_6$-$C_{20}$ aryl group substituted with deuterium; a fluorenyl group; a $C_2$-$C_{20}$ heterocyclic group containing at least one heteroatom selected from the group consisting of O, N, S, Si, and P; a $C_3$-$C_{20}$ cycloalkyl group; a $C_7$-$C_{20}$ arylalkyl group; and a $C_8$-$C_{20}$ arylalkenyl group.

2. The compound of claim 1, wherein $Ar^1$ is represented by one of Formulas below:

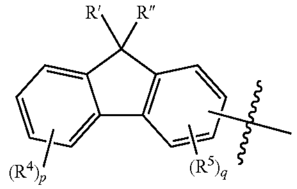

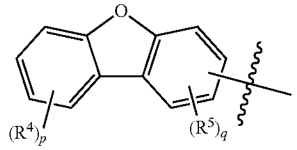

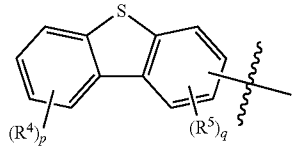

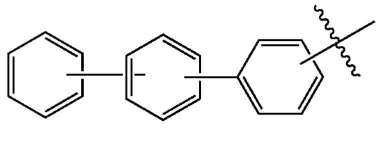

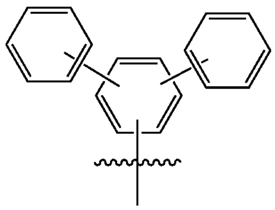

, wherein,

R' and R" are each independently selected from the group consisting of hydrogen; deuterium; tritium; a $C_6$-$C_{20}$ aryl group; a $C_1$-$C_{20}$ alkyl group; and a $C_2$-$C_{20}$ alkenyl group, and R' and R" may be linked together to form a spiro compound with the carbon to which they are attached, p is an integer of 0 to 4, q is an integer of 0 to 3, $R^4$ and $R^5$ are each independently selected from the group consisting of i) deuterium; tritium; halogen; a $C_6$-$C_{60}$ aryl group; a fluorenyl group; a $C_2$-$C_{60}$ heterocyclic group containing at least one heteroatom selected from the group consisting of O, N, S, Si, and P; a fused ring formed by a $C_3$-$C_{60}$ aliphatic ring and a $C_6$-$C_{60}$ aromatic ring; a $C_1$-$C_{50}$ alkyl group; a $C_2$-$C_{20}$ alkenyl group; a $C_2$-$C_{20}$ alkynyl group; a $C_1$-$C_{30}$ alkoxyl group; and a $C_6$-$C_{30}$ aryloxy group, and ii) any two adjacent groups of $R^4$ and $R^5$ may be optionally linked together to form at least one ring, and the groups of $R^4$s and $R^5$s not forming a ring may be the same as defined in the above i).

3. The compound of claim 1, wherein $Ar^2$ to $Ar^3$ are each independently selected from the following structures:

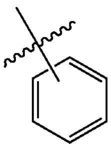

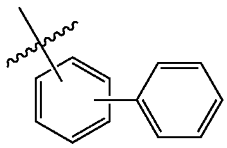

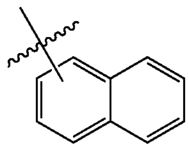

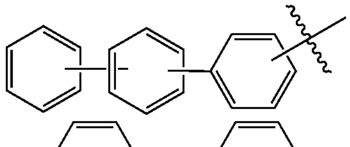

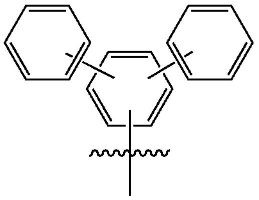

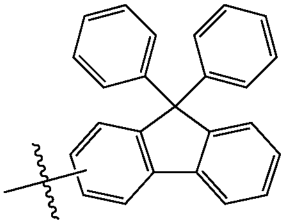

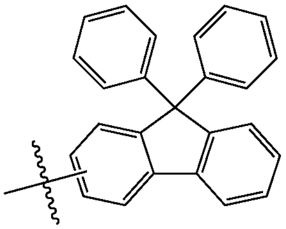

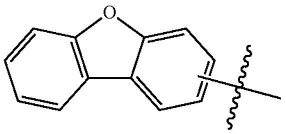

-continued

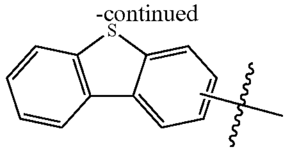

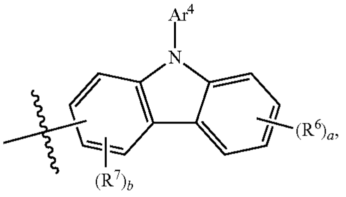

wherein, $Ar^4$ is selected from the group consisting of a $C_6$-$C_{60}$ aryl group; a fluorenyl group; and a $C_2$-$C_{60}$ heterocyclic group containing at least one heteroatom selected from the group consisting of O, N, S, Si, and P, $R^6$ and $R^7$ are each independently selected from the group consisting of i) deuterium; halogen; a $C_6$-$C_{60}$ aryl group; a fluorenyl group; a $C_2$-$C_{60}$ heterocyclic group containing at least one heteroatom selected from the group consisting of O, N, S, Si, and P; a fused ring formed by a $C_3$-$C_{60}$ aliphatic ring and a $C_6$-$C_{60}$ aromatic ring; a $C_1$-$C_{50}$ alkyl group; a $C_2$-$C_{20}$ alkenyl group; a $C_2$-$C_{20}$ alkynyl group; a $C_1$-$C_{30}$ alkoxy group; a $C_6$-$C_{30}$ aryloxy group; and -L'-N($R^a$)($R^b$), wherein, L' is selected from the group consisting of single bond; a $C_6$-$C_{60}$ arylene group; a fluorenylene group; a fused ring formed by a $C_3$-$C_{60}$ aliphatic ring and a $C_6$-$C_{60}$ aromatic ring; and a $C_2$-$C_{60}$ heterocyclic group containing at least one heteroatom selected from the group consisting of O, N, S, Si, and P, and $R^a$ and $R^b$ are each independently selected from the group consisting of $C_6$-$C_{60}$ aryl group; a fluorenyl group; a fused ring formed by a $C_3$-$C_{60}$ aliphatic ring and a $C_6$-$C_{60}$ aromatic ring; and a $C_2$-$C_{60}$ heterocyclic group containing at least one heteroatom selected from the group consisting of O, N, S, Si, and P, or ii) any two adjacent groups of $R^6$ and $R^7$ may be independently linked together to form at least one ring, and the groups of $R^6$s and $R^7$s not forming a ring may be the same as defined in the above i), a is an integer of 0 to 4, wherein plural $R^6$s may be same or different each other when a is each 2 or more, b is an integer of 0 to 3, wherein plural $R^7$s may be same or different each other when b is each 2 or more.

4. The compound of claim 1, wherein o is 0 (zero).

5. The compound of claim 1, wherein $R^3$ is selected from the following structures:

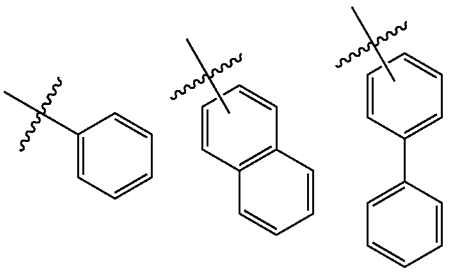

-continued

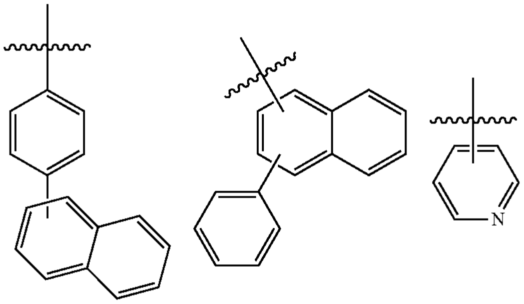

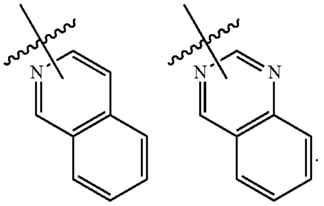

6. The compound of claim 1 represented by Formula 11:

[Formula 11]

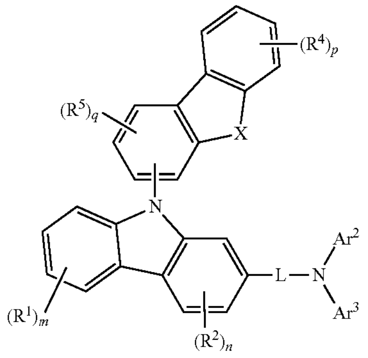

wherein $Ar^2$, $Ar^3$, L, $R^1$, $R^2$, m and n are the same as defined in claim 1, X is O, S or C(R')(R"), R' and R" are each independently selected from the group consisting of hydrogen; deuterium; tritium; a $C_6$-$C_{20}$ aryl group; a $C_1$-$C_{20}$ alkyl group; and a $C_2$-$C_{20}$ alkenyl group, and R' and R" may be linked together to form a spiro compound with the carbon to which they are attached, p is an integer of 0 to 4, q is an integer of 0 to 3, $R^4$ and $R^5$ are each independently selected from the group consisting of i) deuterium; tritium; halogen; a $C_6$-$C_{60}$ aryl group; a fluorenyl group; a $C_2$-$C_{60}$ heterocyclic group containing at least one heteroatom selected from the group consisting of O, N, S, Si, and P; a fused ring formed by a $C_3$-$C_{60}$ aliphatic ring and a $C_6$-$C_{60}$ aromatic ring; a $C_1$-$C_{50}$ alkyl group; a $C_2$-$C_{20}$ alkenyl group; a $C_2$-$C_{20}$ alkynyl group; a $C_1$-$C_{30}$ alkoxyl group; and a $C_6$-$C_{30}$ aryloxy group, and ii) any two adjacent groups of $R^4$ and $R^5$ may be optionally linked together to form at least one ring, and the groups of $R^4$s and $R^5$s not forming a ring may be the same as defined in the above i).

7. The compound of claim 1 represented by the following Formula:

[Formula 21]

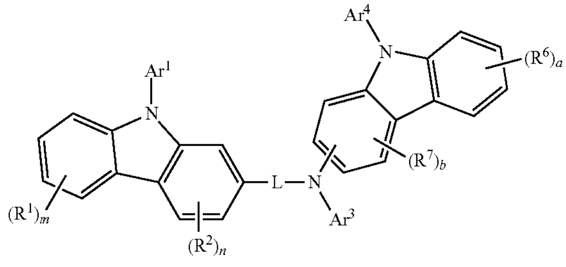

wherein $R^1$, $R^2$, m, n, $Ar^1$, $Ar^3$ and L are the same as defined in Formula 1, $Ar^4$ is selected from the group consisting of a $C_6$-$C_{60}$ aryl group; a fluorenyl group; and a $C_2$-$C_{60}$ heterocyclic group containing at least one heteroatom selected from the group consisting of O, N, S, Si, and P, $R^6$ and $R^7$ are each independently selected from the group consisting of i) deuterium; halogen; a $C_6$-$C_{60}$ aryl group; a fluorenyl group; a $C_2$-$C_{60}$ heterocyclic group containing at least one heteroatom selected from the group consisting of O, N, S, Si, and P; a fused ring formed by a $C_3$-$C_{60}$ aliphatic ring and a $C_6$-$C_{60}$ aromatic ring; a $C_1$-$C_{50}$ alkyl group; a $C_2$-$C_{20}$ alkenyl group; a $C_2$-$C_{20}$ alkynyl group; a $C_1$-$C_{30}$ alkoxy group; a $C_6$-$C_{60}$ aryloxy group; and -L'-N($R^a$)($R^b$), wherein, L' is selected from the group consisting of single bond; a $C_6$-$C_{60}$ arylene group; a fluorenylene group; a fused ring formed by a $C_3$-$C_{60}$ aliphatic ring and a $C_6$-$C_{60}$ aromatic ring; and a $C_2$-$C_{60}$ heterocyclic group containing at least one heteroatom selected from the group consisting of O, N, S, Si, and P, and $R^a$ and $R^b$ are each independently selected from the group consisting of $C_6$-$C_{60}$ aryl group; a fluorenyl group; a fused ring formed by a $C_3$-$C_{60}$ aliphatic ring and a $C_6$-$C_{60}$ aromatic ring; and a $C_2$-$C_{60}$ heterocyclic group containing at least one heteroatom selected from the group consisting of O, N, S, Si, and P, or ii) any two adjacent groups may be independently linked together to form at least one ring, and the groups of $R^6$s and $R^7$s not forming a ring may be the same as defined in the above i), a is an integer of 0 to 4, wherein plural $R^6$s may be same or different each other when a is each 2 or more, b is an integer of 0 to 3, wherein plural $R^7$s may be same or different each other when b is each 2 or more.

8. The compound of claim 7 represented by the following Formulas:

[Formula 22]

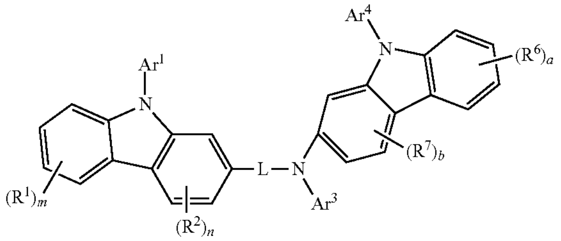

[Formula 23]

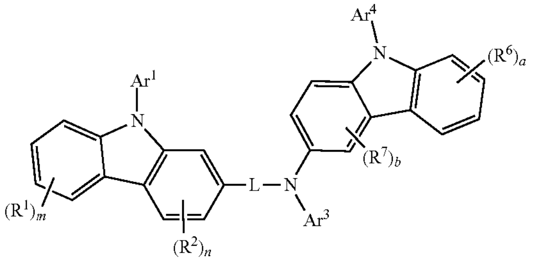

wherein, $R^1$, $R^2$, $R^6$, $R^7$, a, b, m, n, $Ar^1$, $Ar^3$, $Ar^4$ and L are the same as defined in claim 7.

9. A compound selected from the group consisting of the following compounds:

P1-1

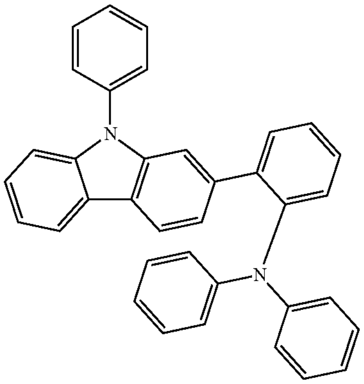

P1-2

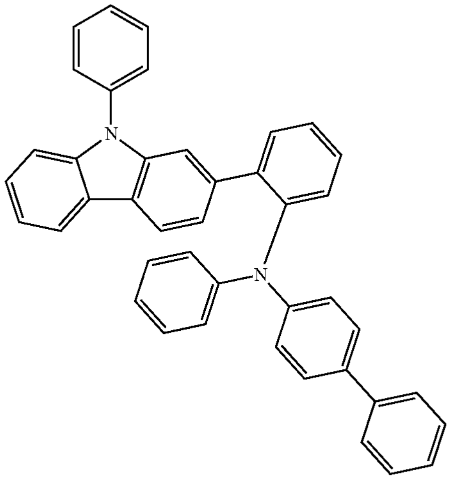

-continued
P1-3
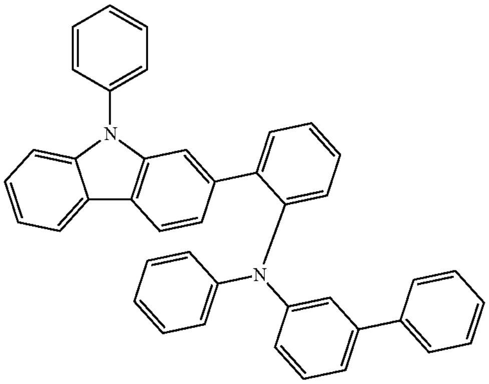
P1-4
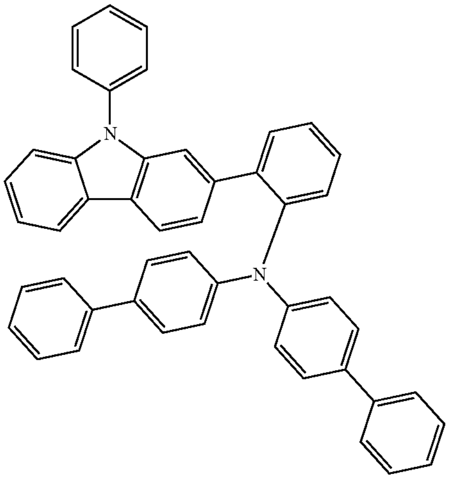
P1-5
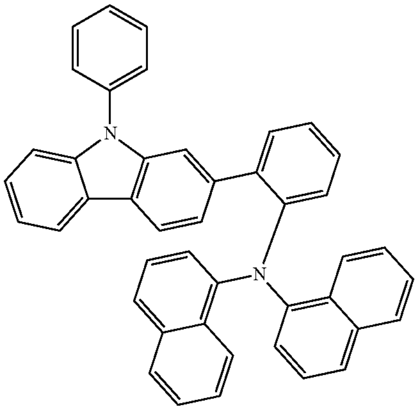
P1-6
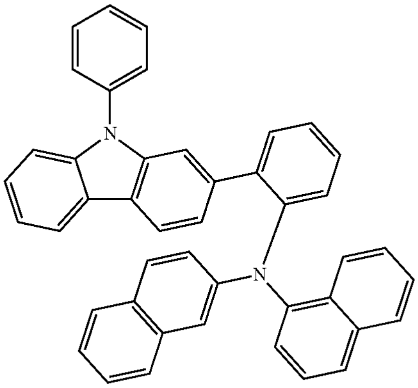
P1-7
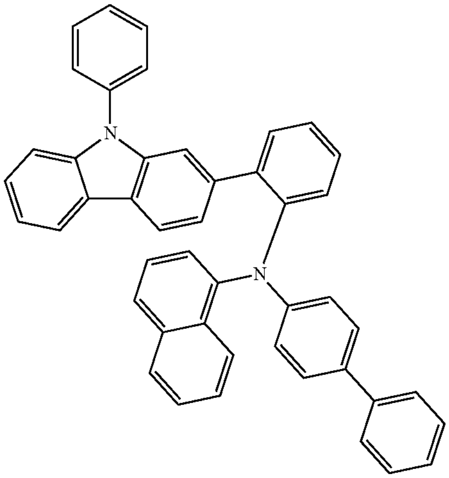
P1-8
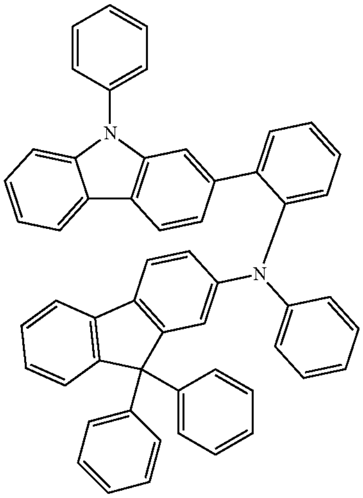

-continued
P1-9
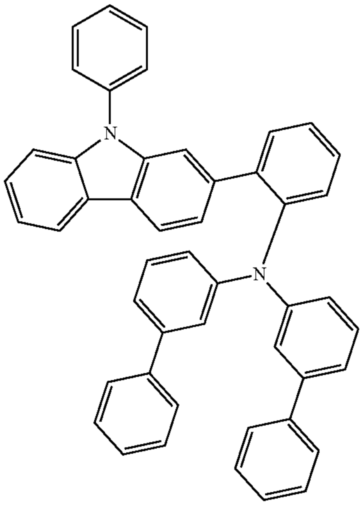
P1-10
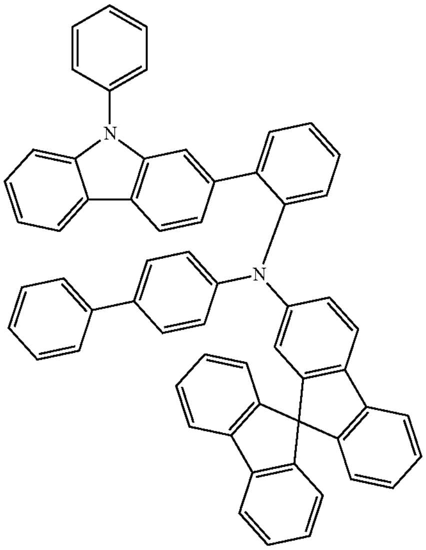
P1-11
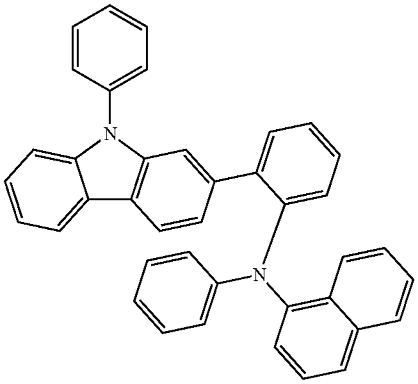
P1-12
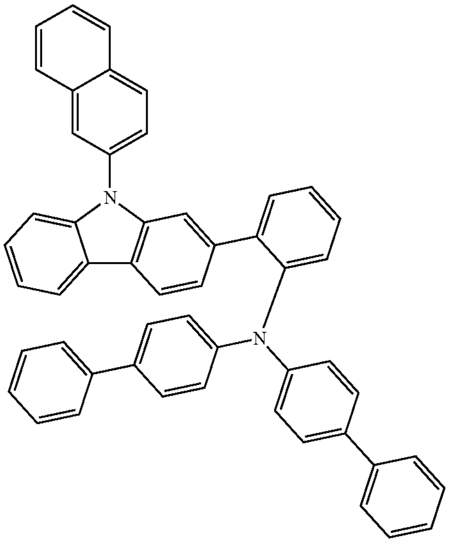

-continued
P1-13
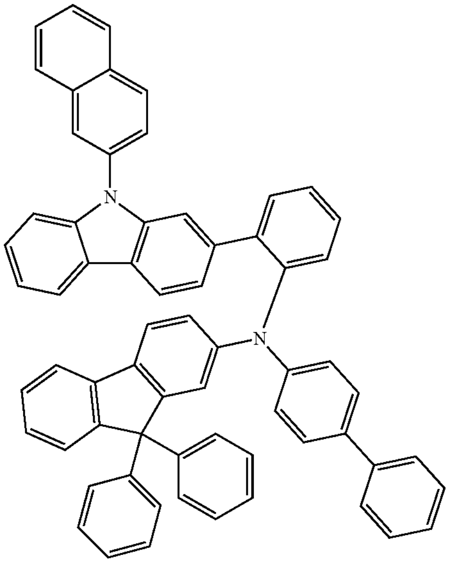
P1-14
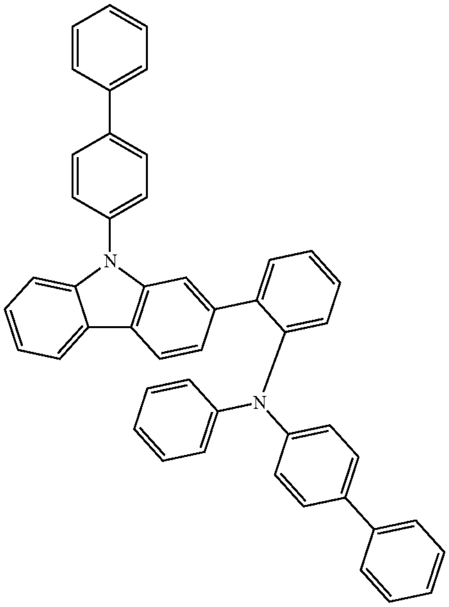
P1-15
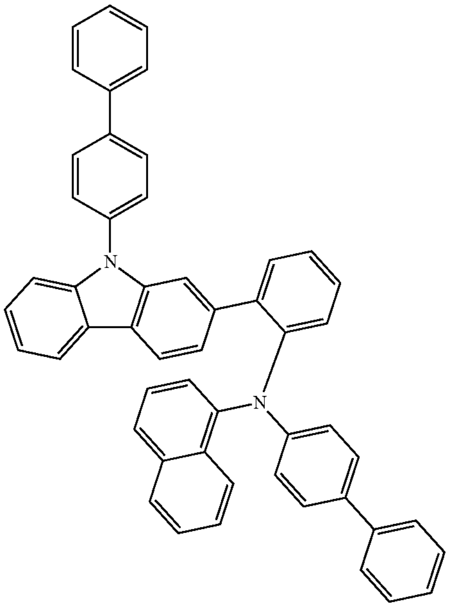
P1-16
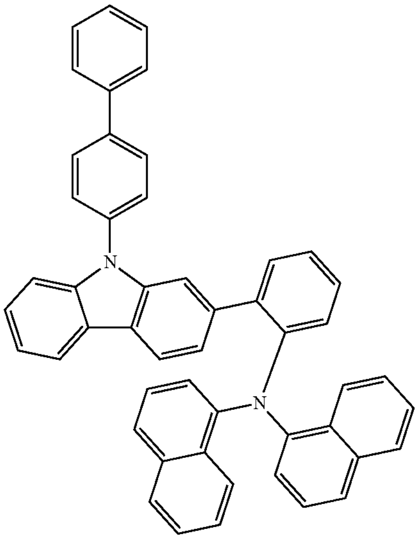
P1-17
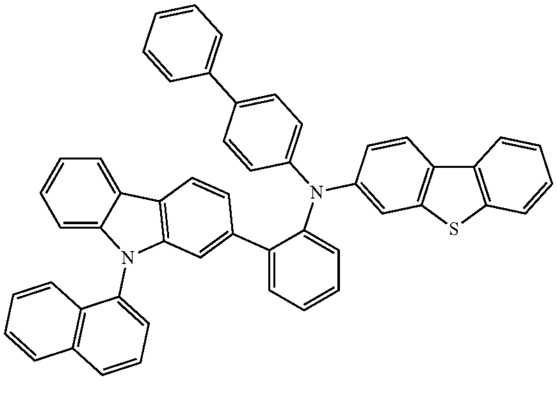
P1-18
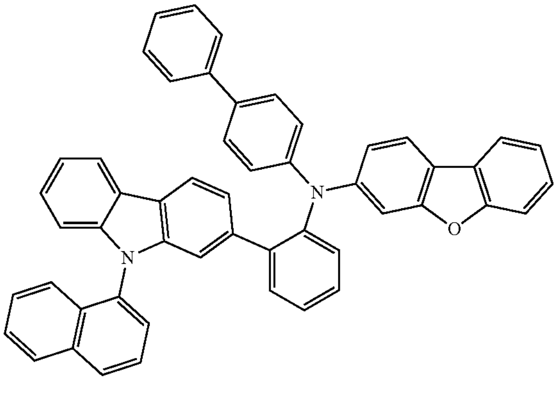

-continued
P1-19
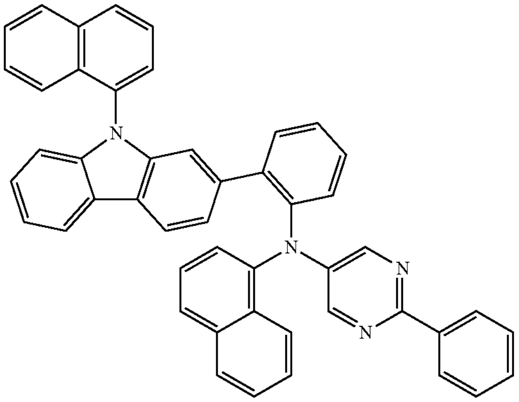
P1-20
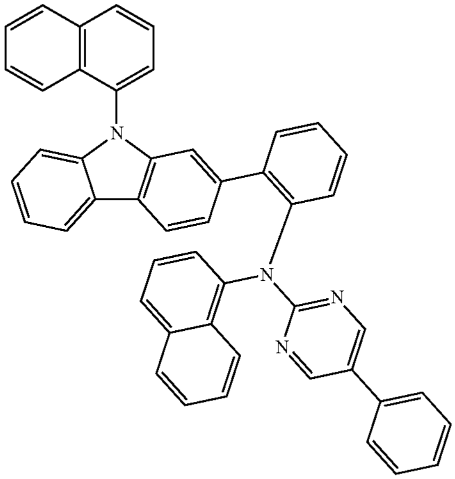
P1-21
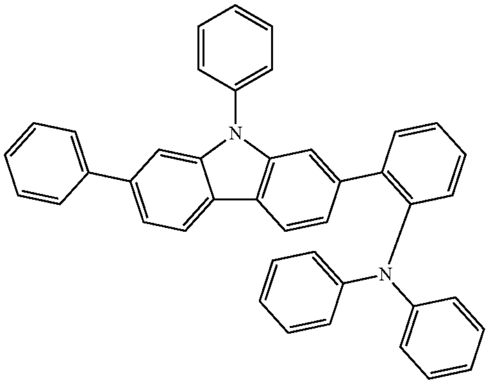
P1-22
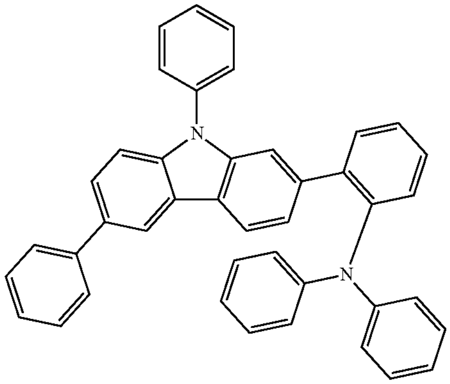
P1-23
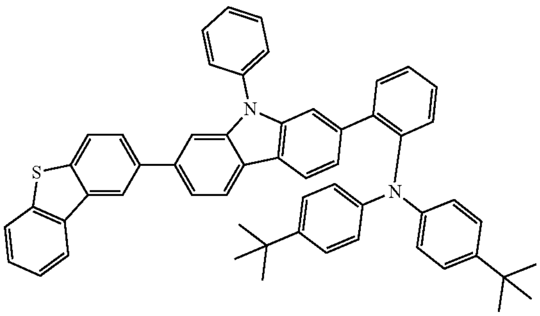
P1-24
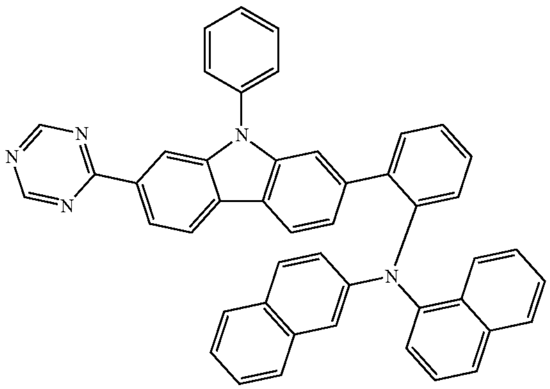

-continued
P1-25
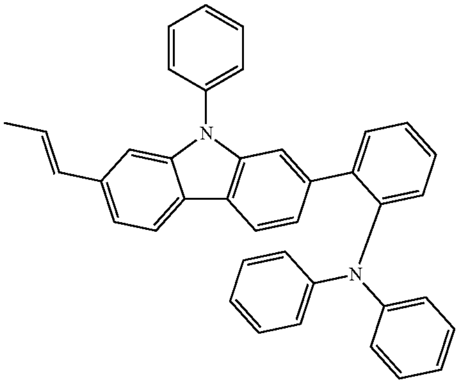
P1-26
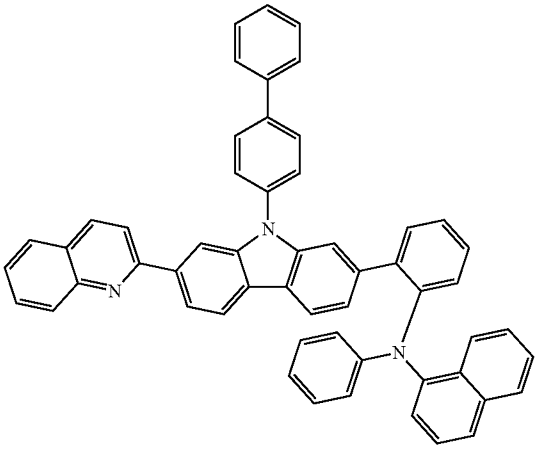
P1-27
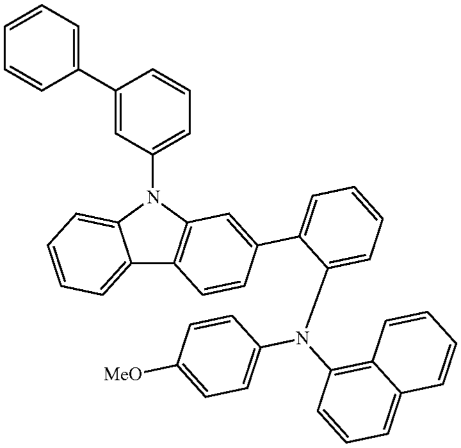
P1-28
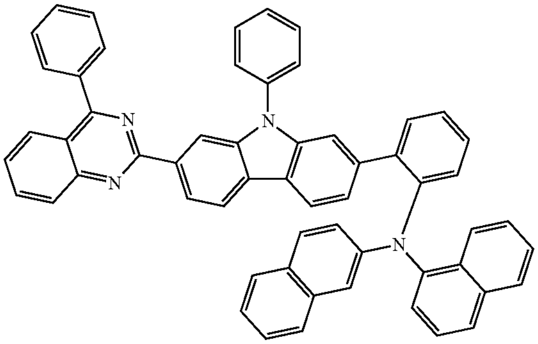
P1-29
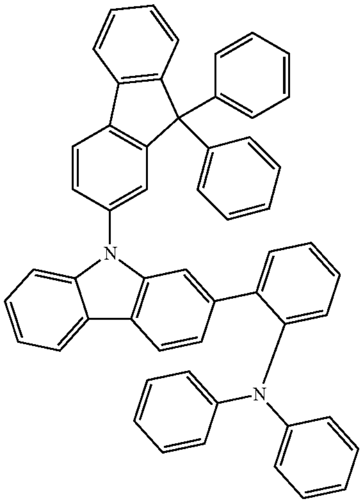
P1-30
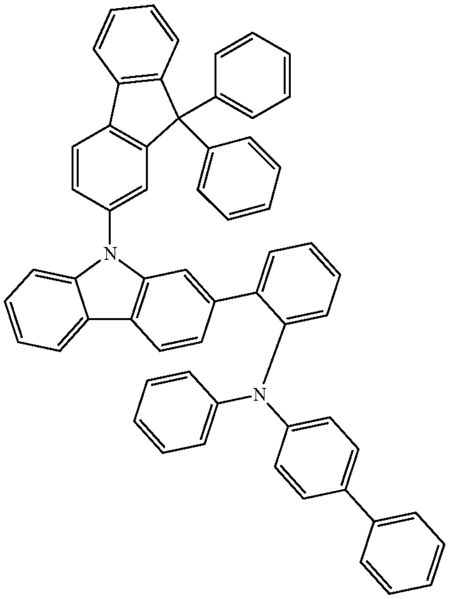

-continued
P1-31
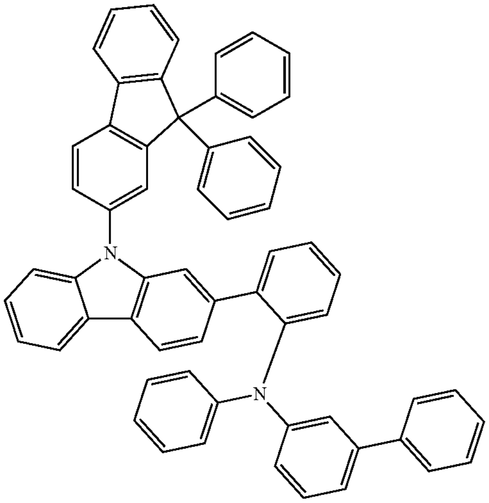
P1-32
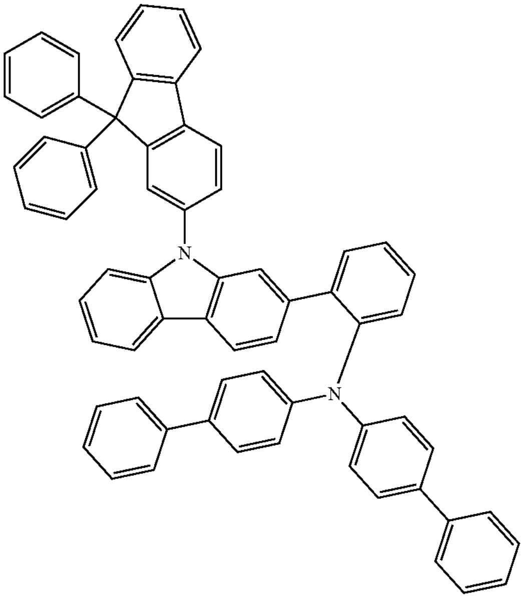
P1-33
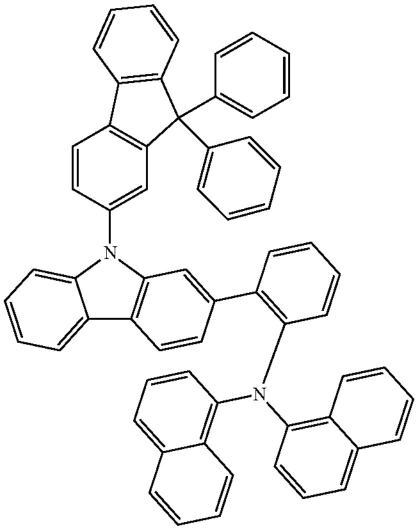
P1-34
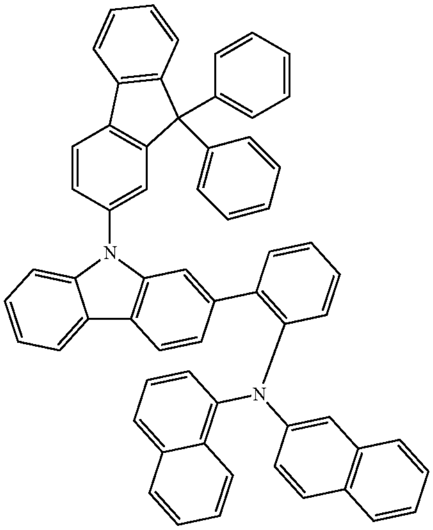

-continued
P1-35
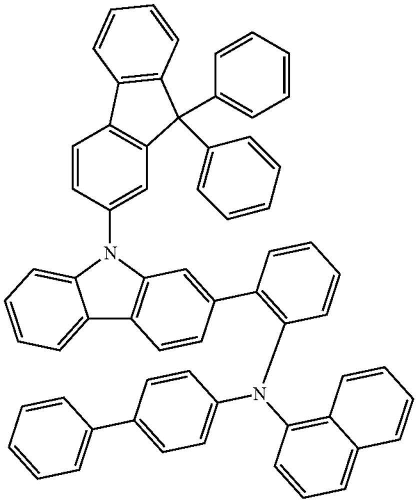
P1-36
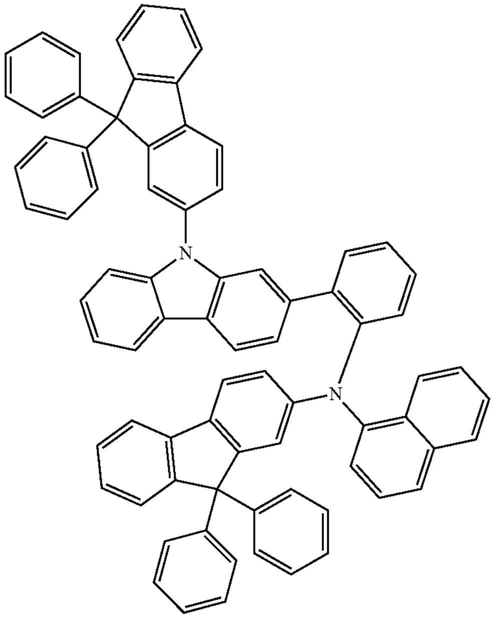
P1-37
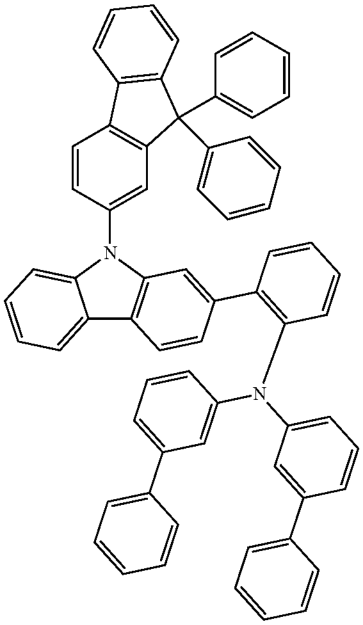
P1-38
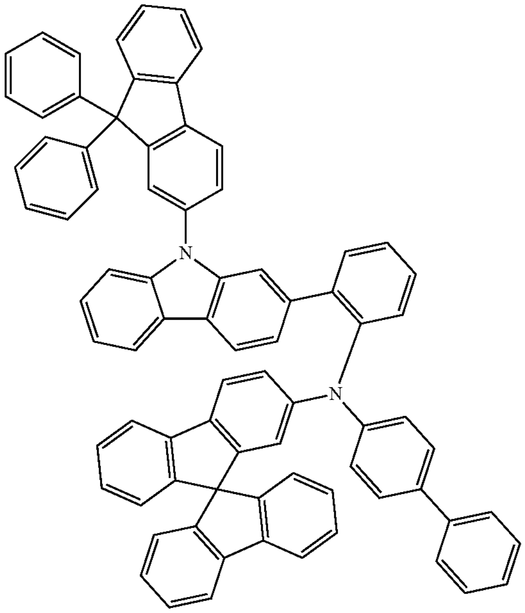

-continued
P1-39
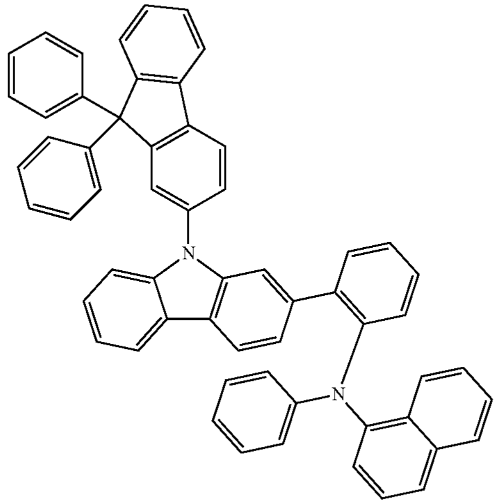
P1-40
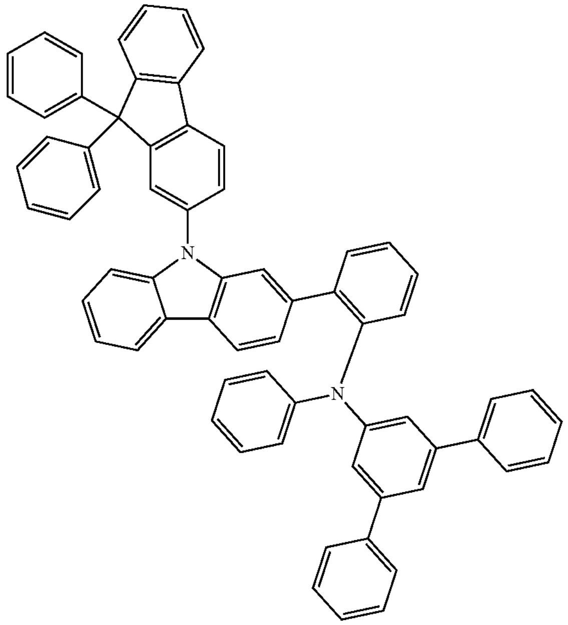
P1-41
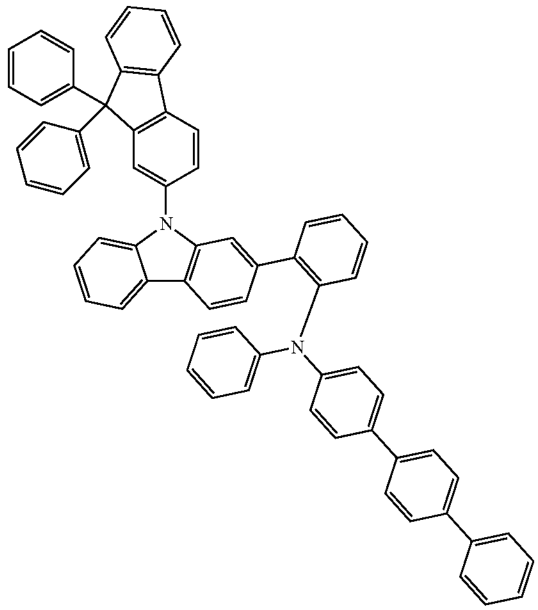
P1-42
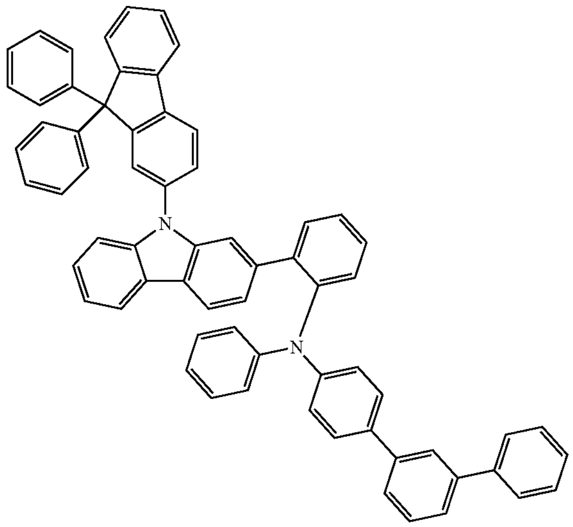

-continued
P1-43
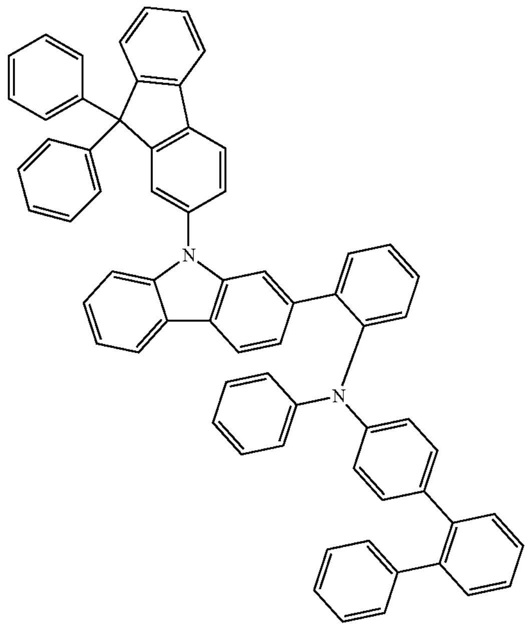
P1-44
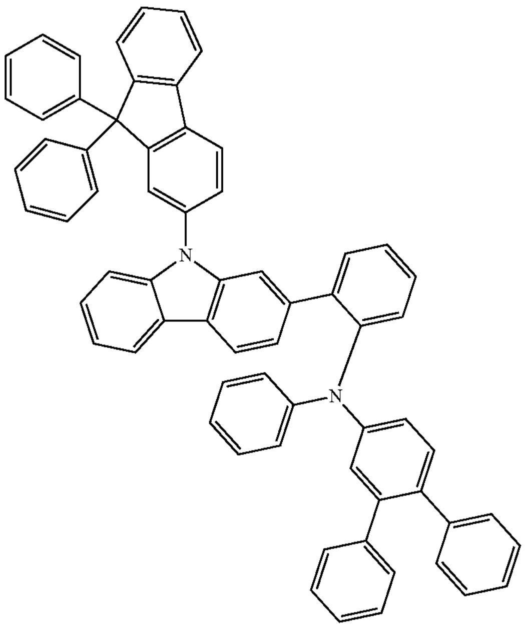
P1-45
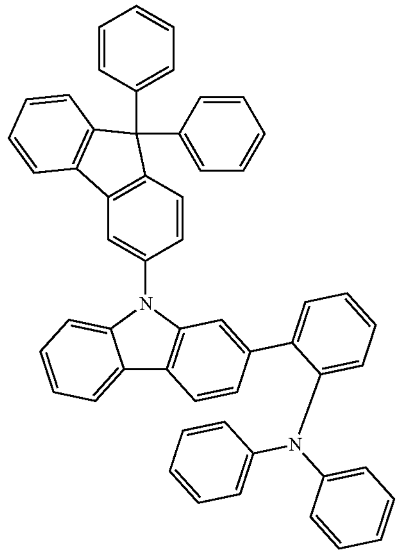
P1-46
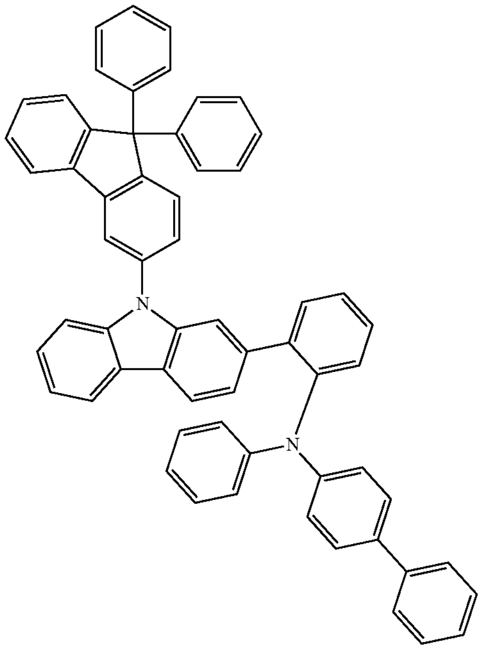

-continued
P1-47
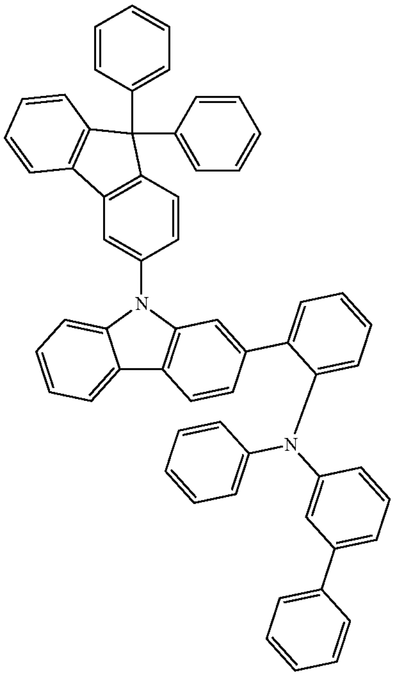
P1-48
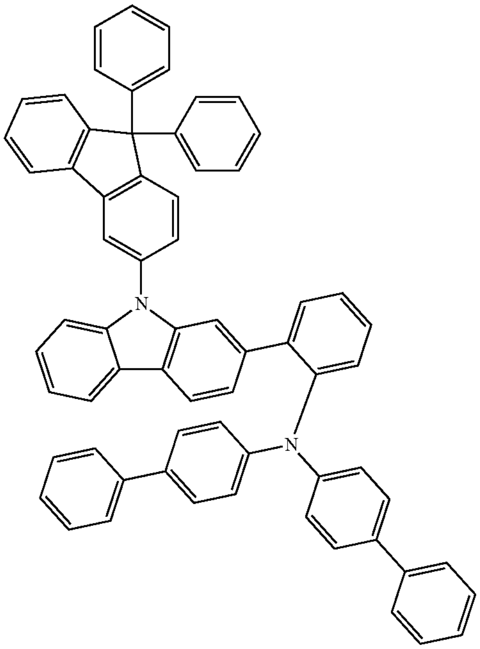
P1-49
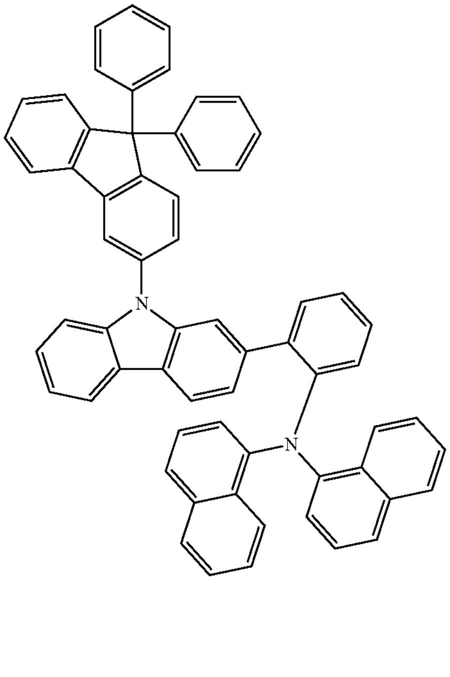
P1-50
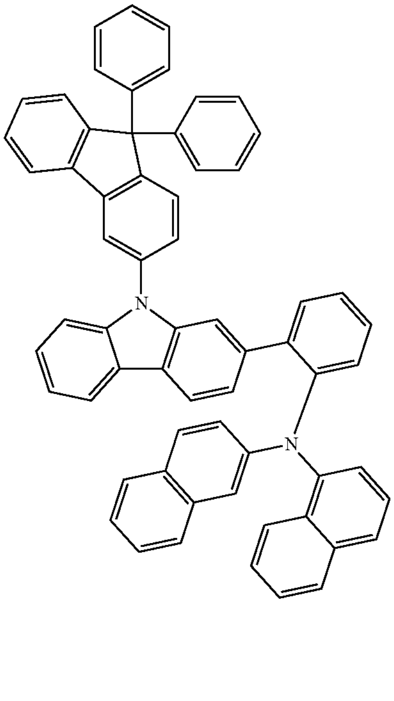

-continued
P1-51
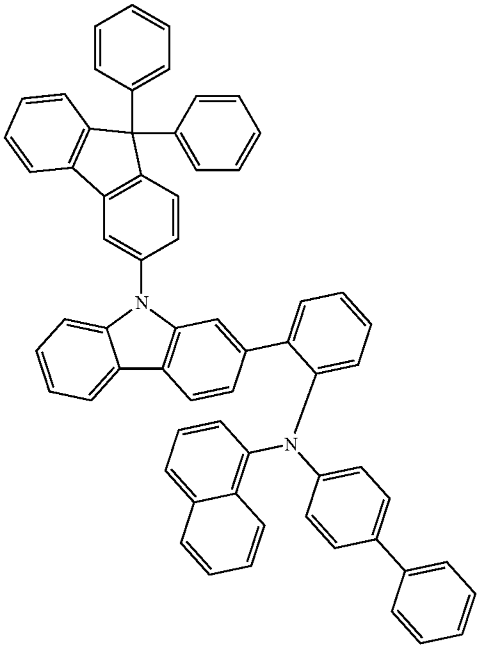
P1-52
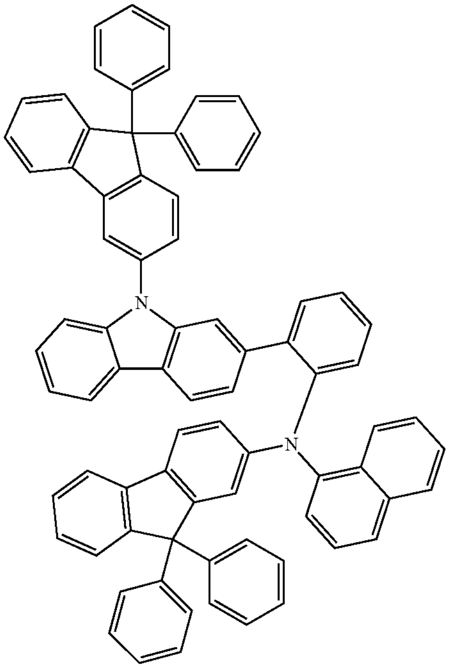
P1-53
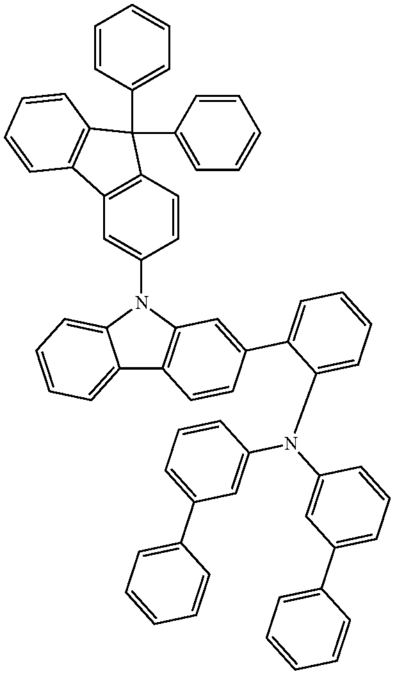
P1-54
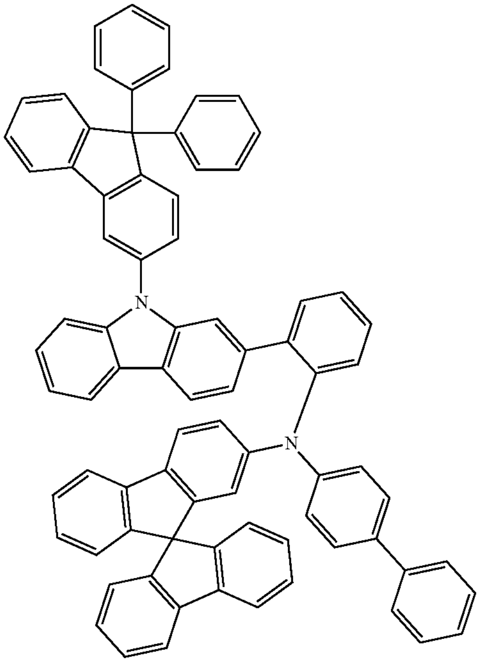

-continued
P1-55
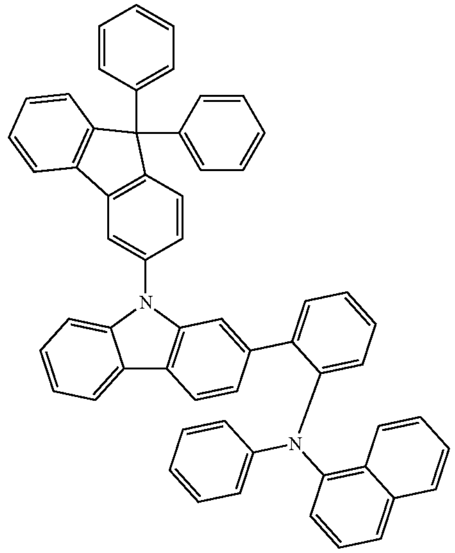
P1-56
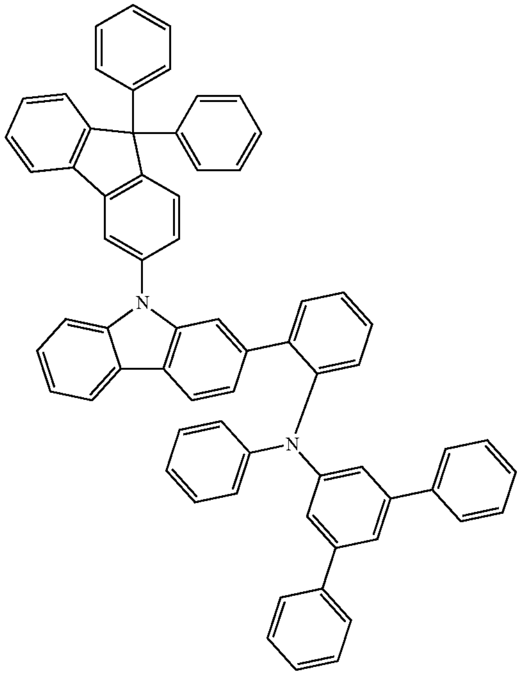
P1-57
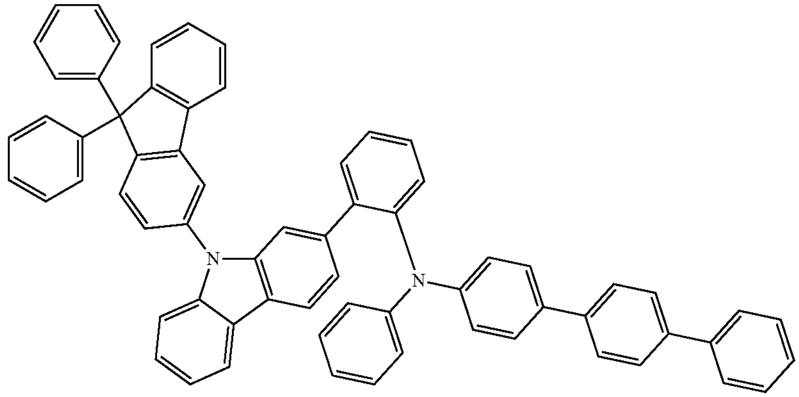
P1-58
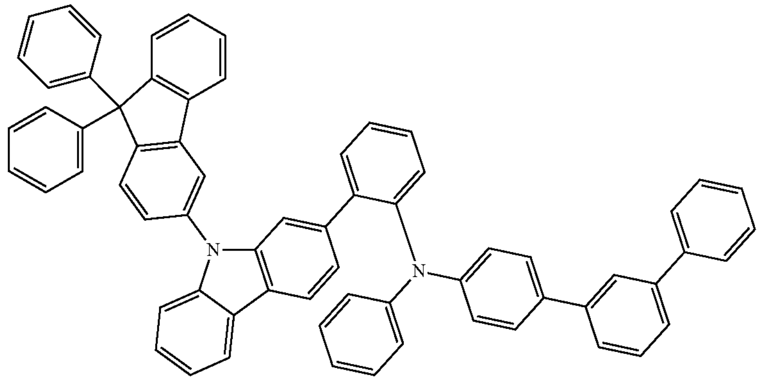

-continued
P1-59
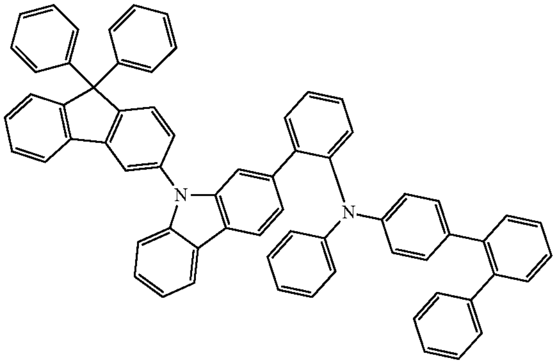
P1-60
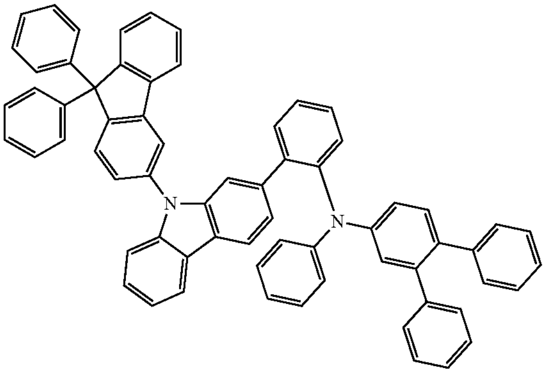
P1-61
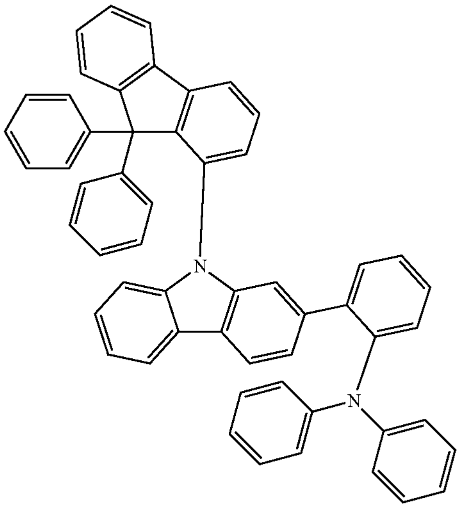
P1-62
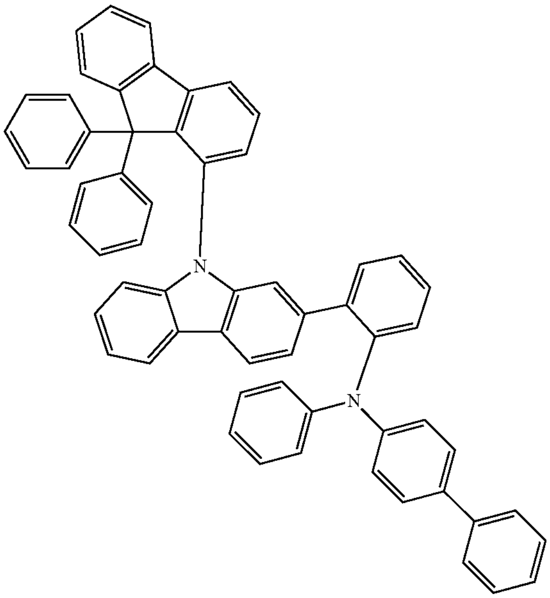
P1-63
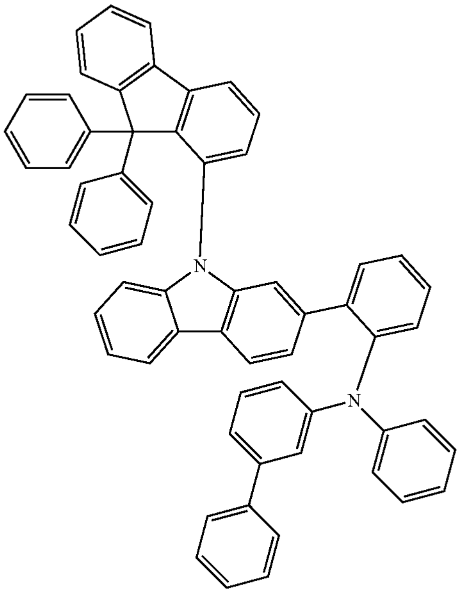
P1-64
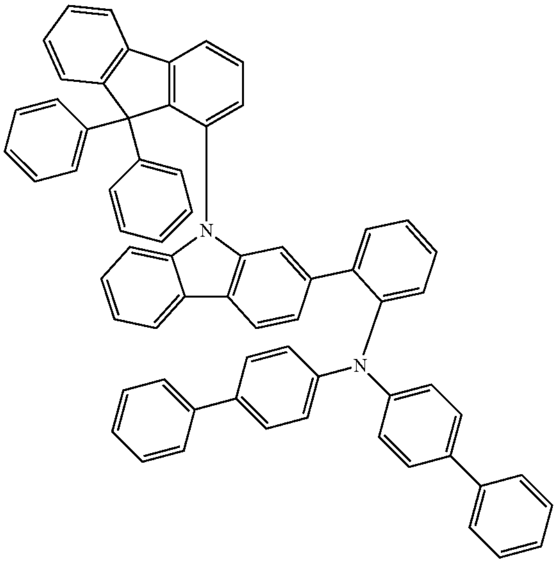

-continued
P1-65
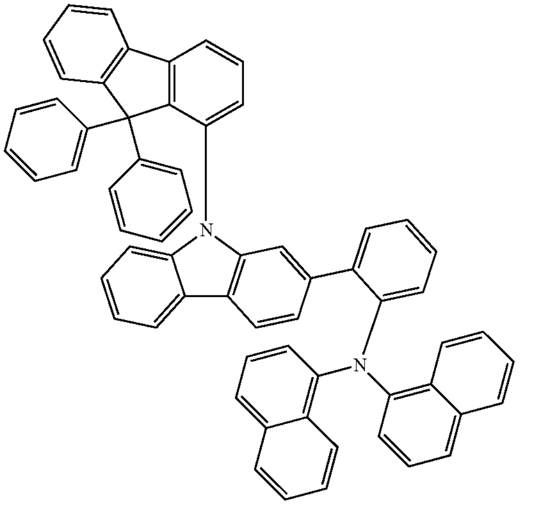
P1-66
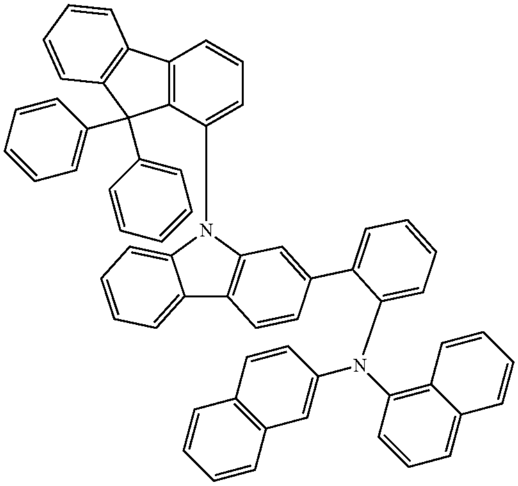
P1-67
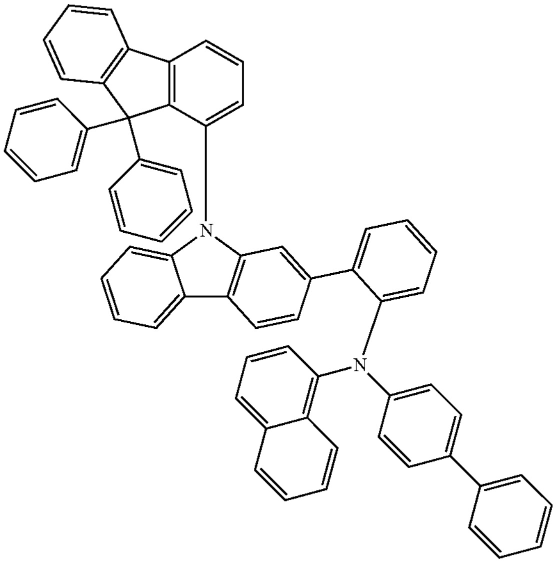
P1-68
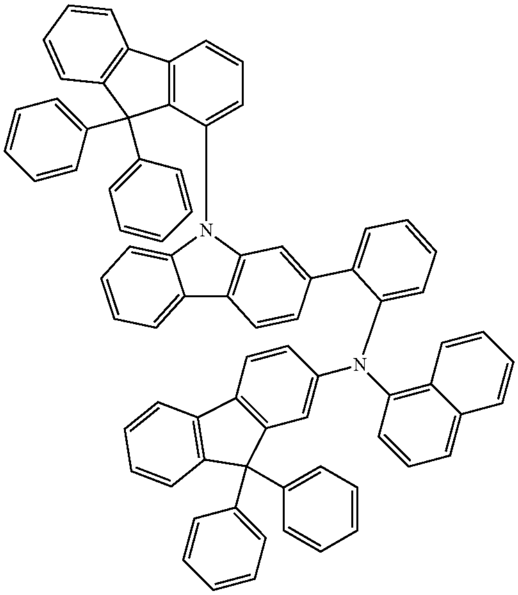

-continued
P1-69
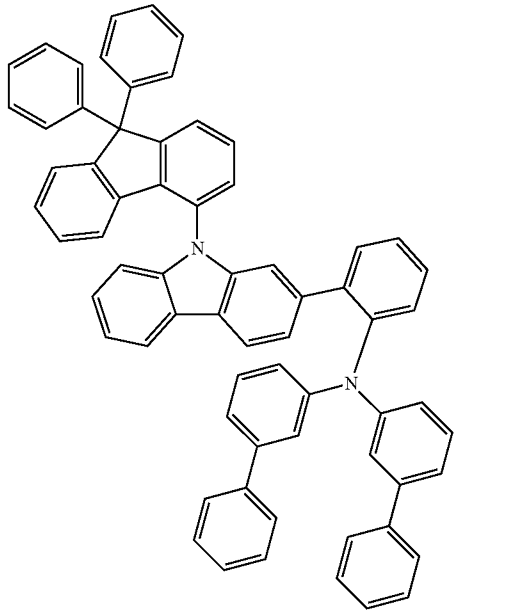
P1-70
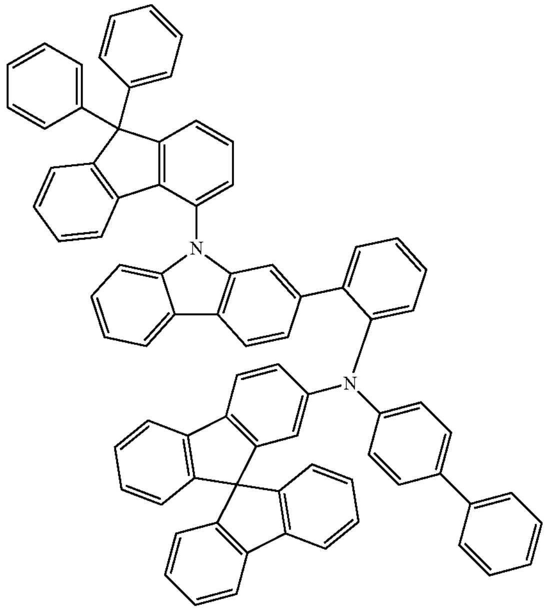
P1-71
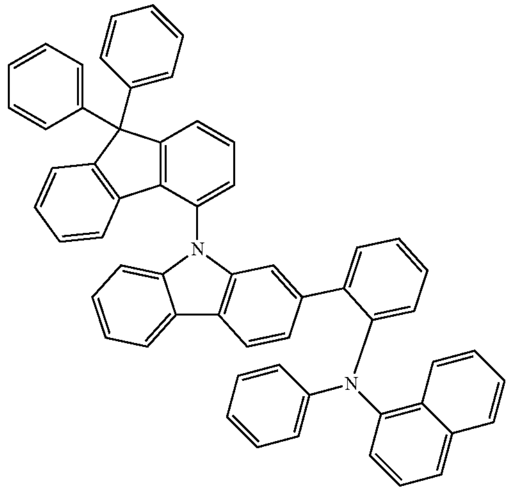
P1-72
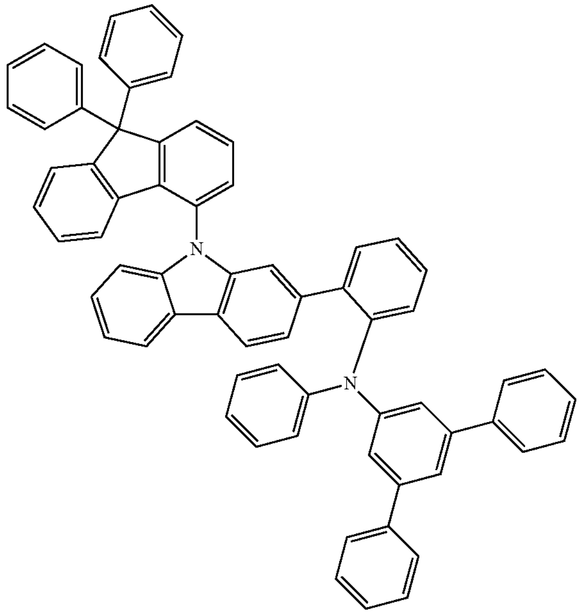
P1-73
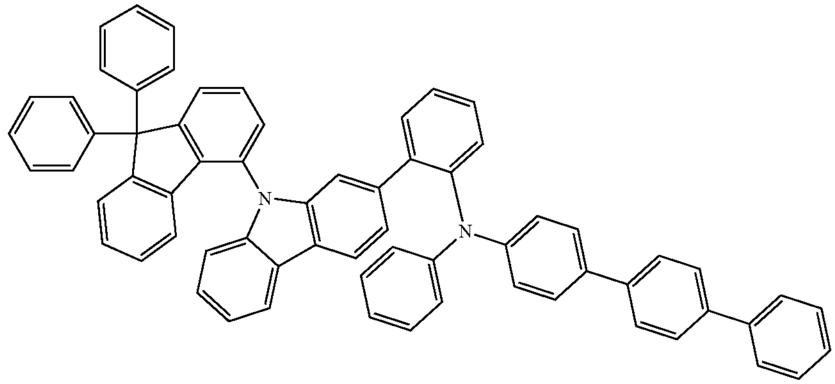

-continued
P1-74
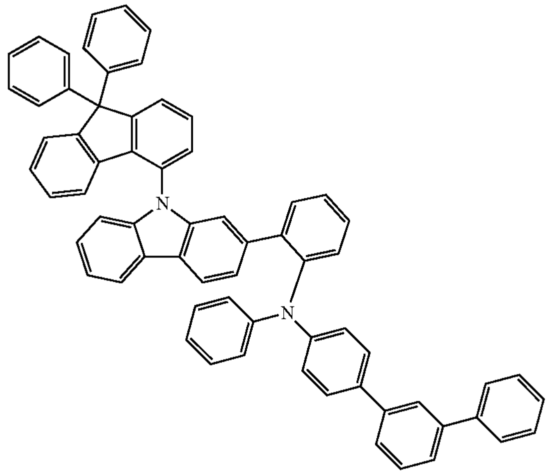
P1-75
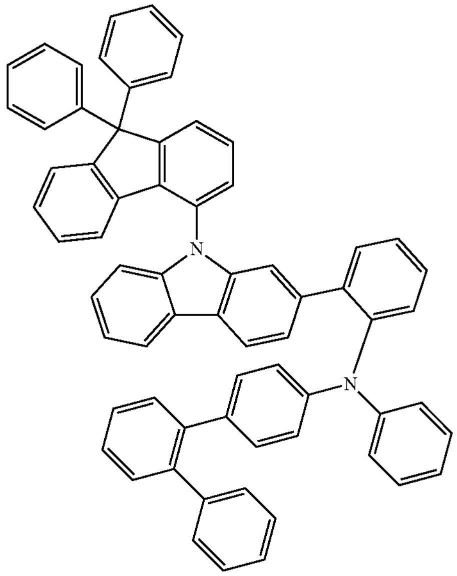
P1-76
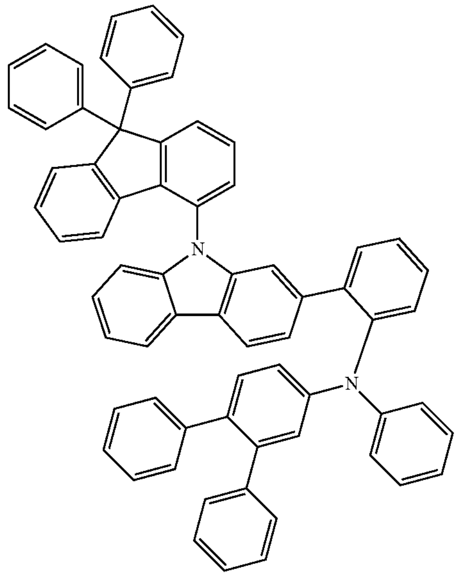
P1-77
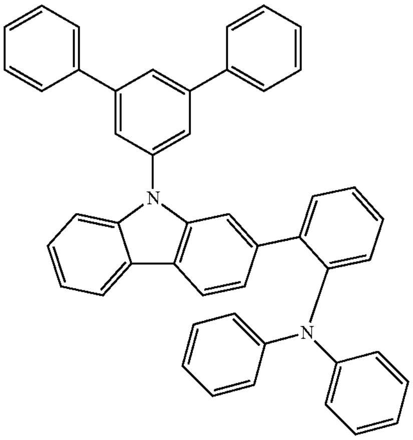

-continued
P1-78
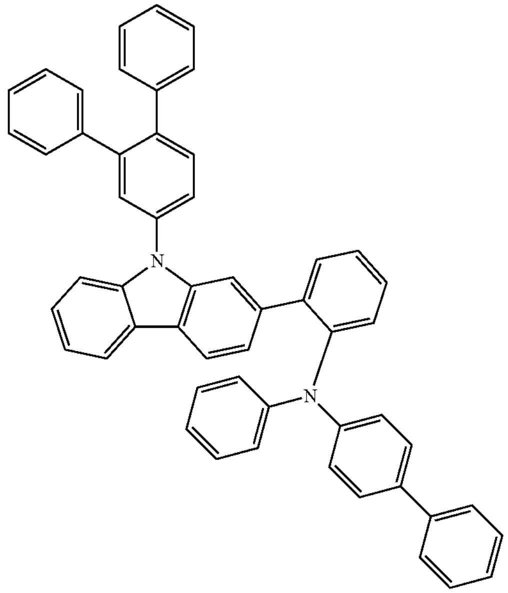
P1-79
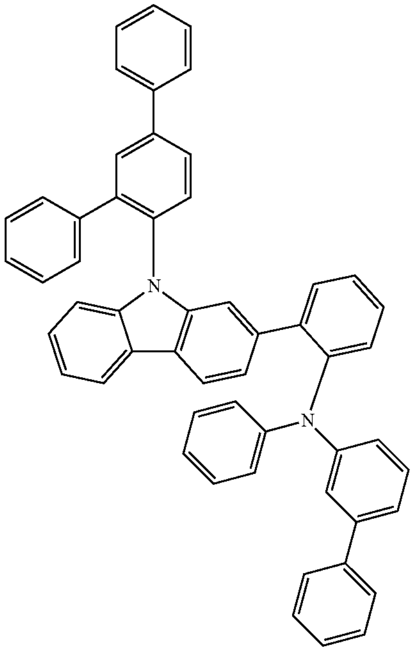
P1-80
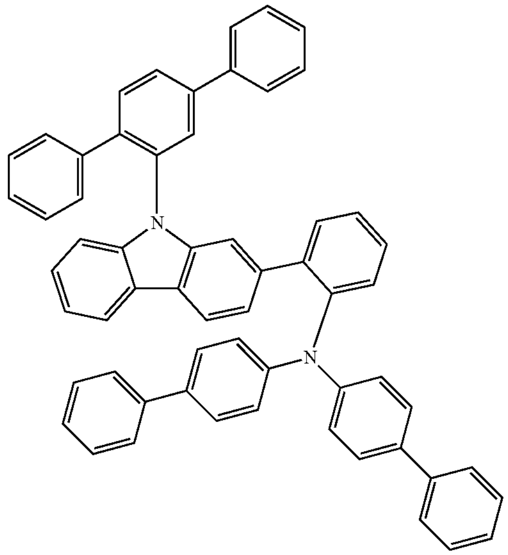
P1-81
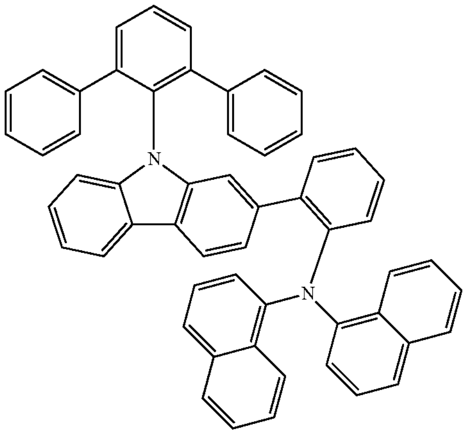

-continued
P1-82
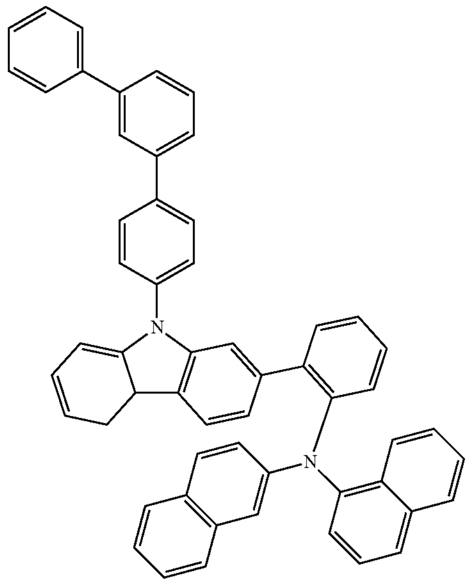
P1-83
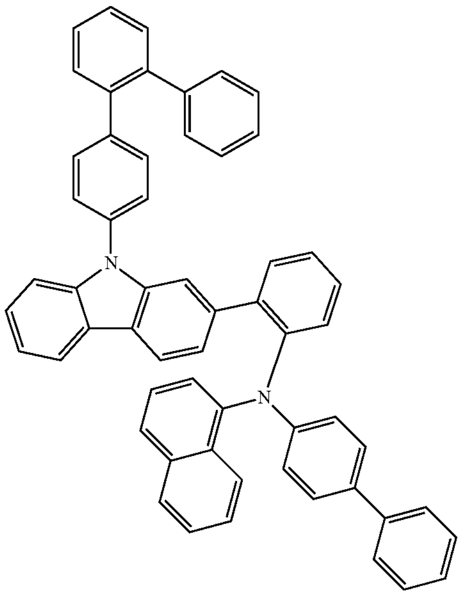
P1-84
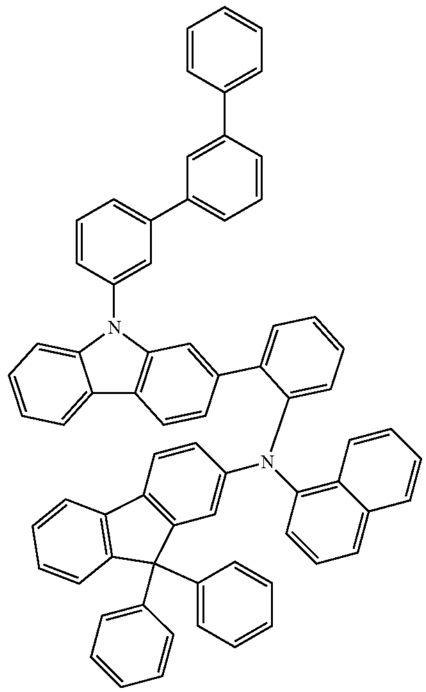
P1-85
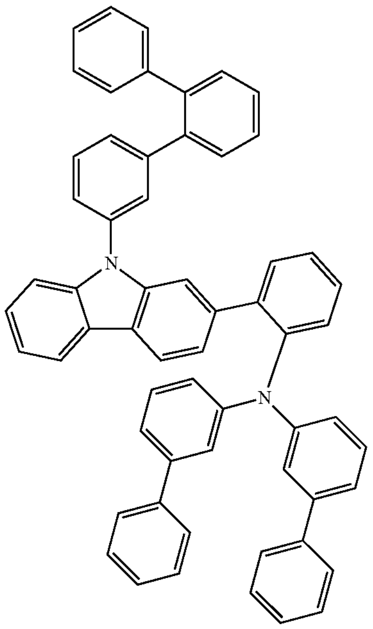

-continued
P1-86
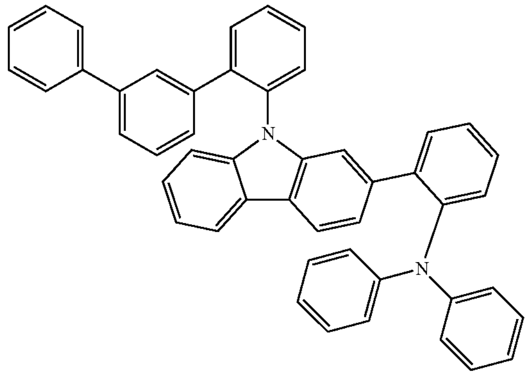
P1-87
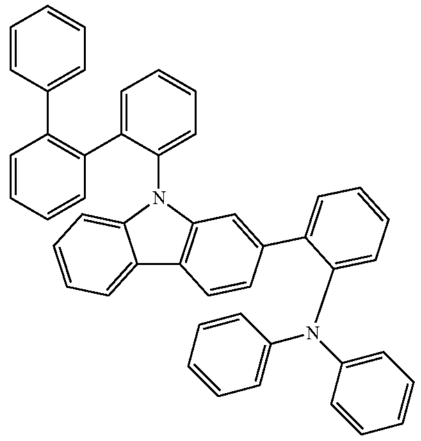
P1-88
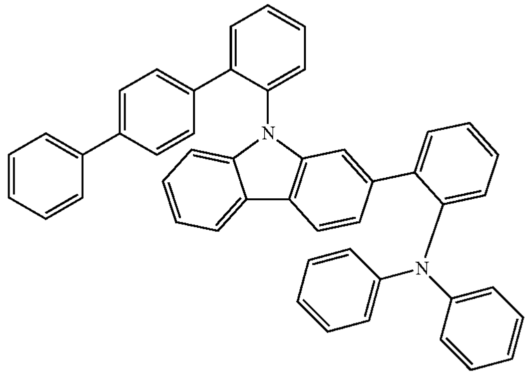
P1-89
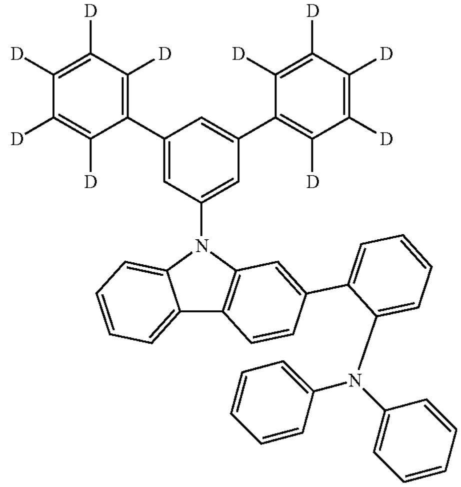
P1-90
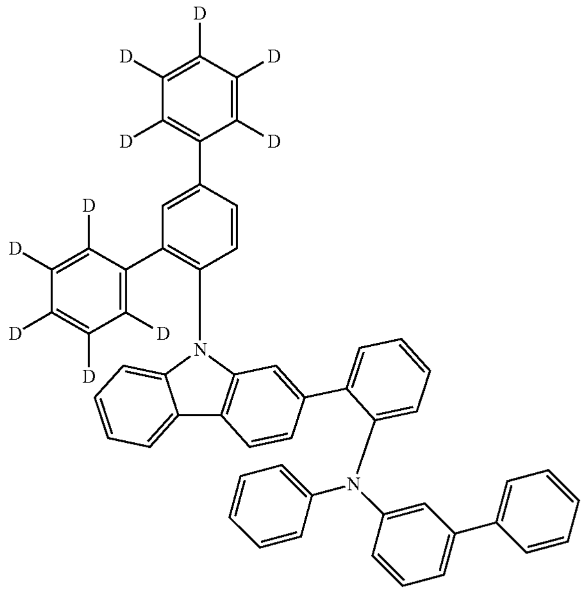
P1-91
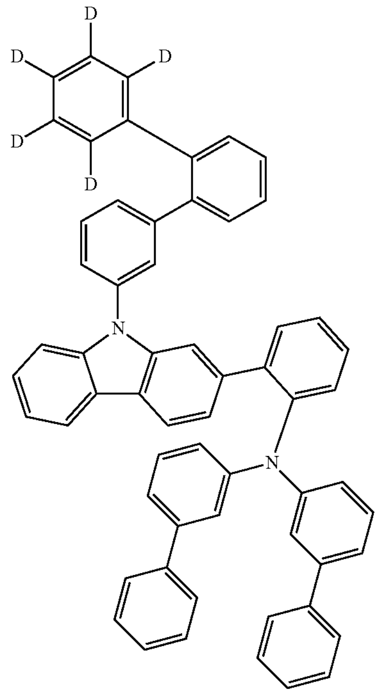

-continued
P1-92
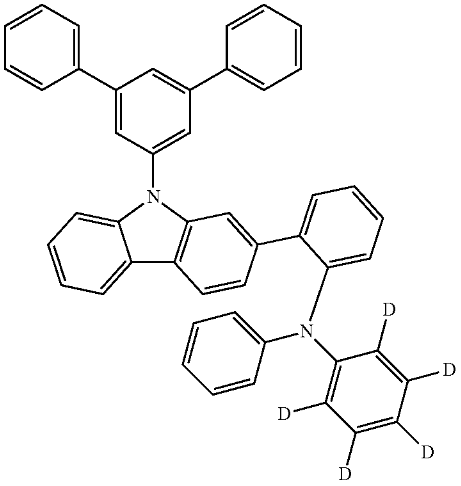
P1-101
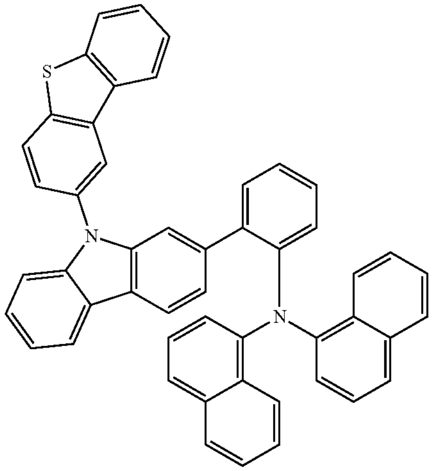
P1-102
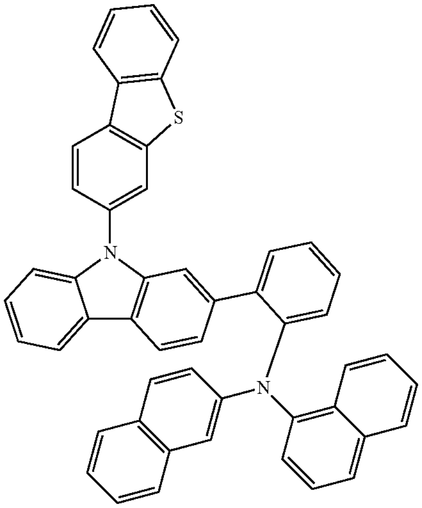
P1-103
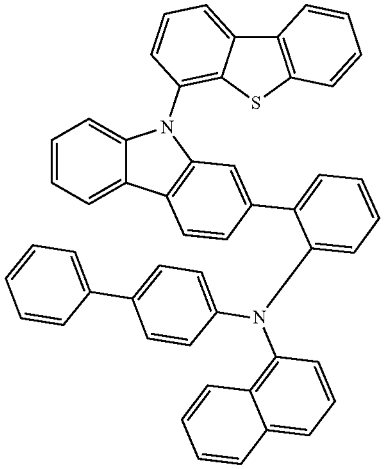
P1-104
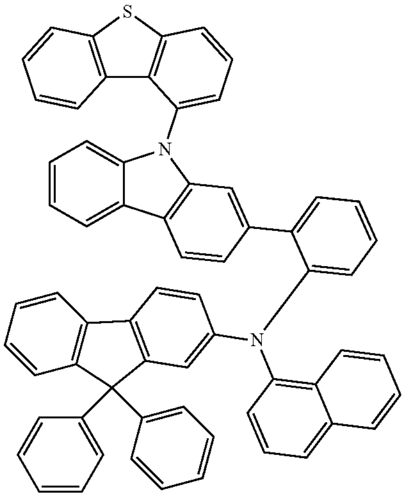
P1-105
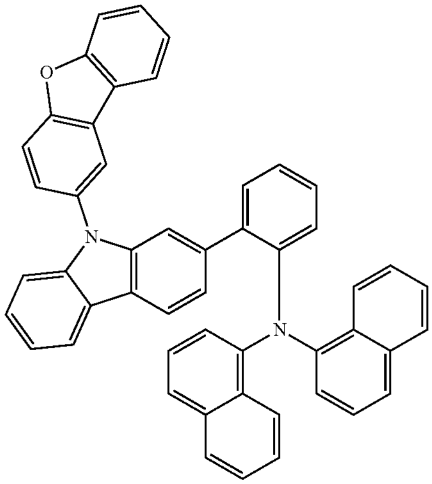

-continued
P1-106
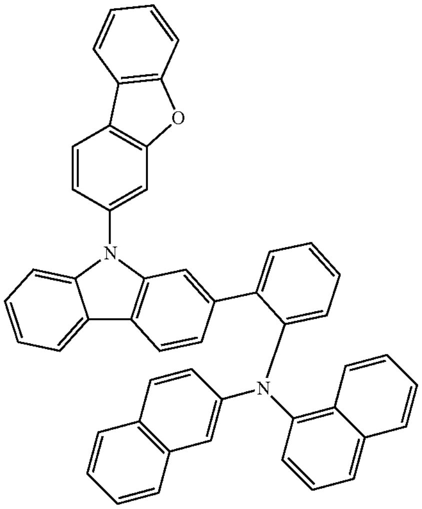
P1-107
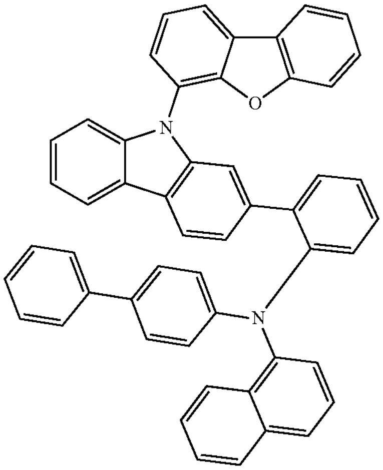
P1-108
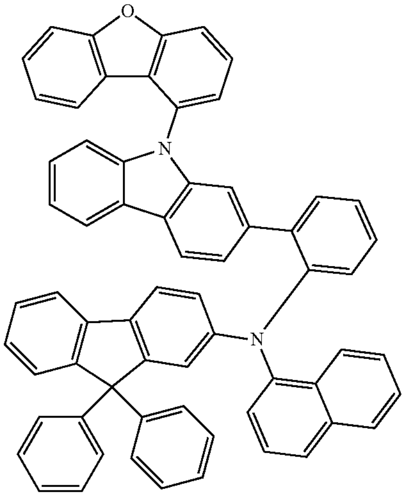
P1-111
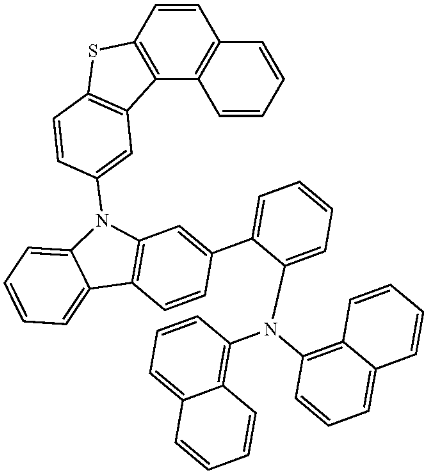
P1-112
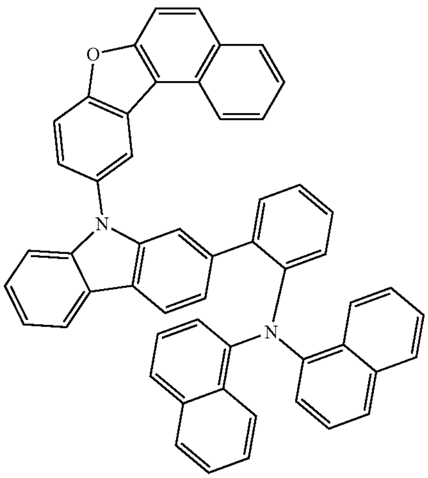
P2-1
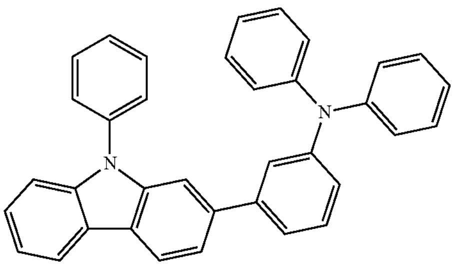

-continued
P2-2
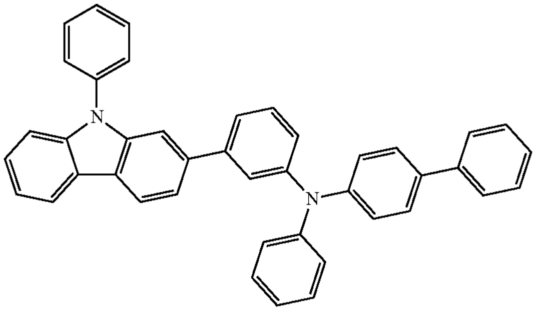
P2-3
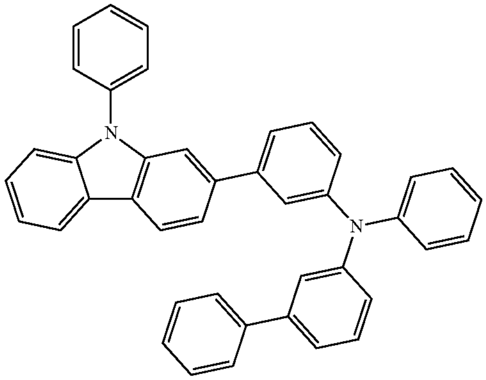
P2-4
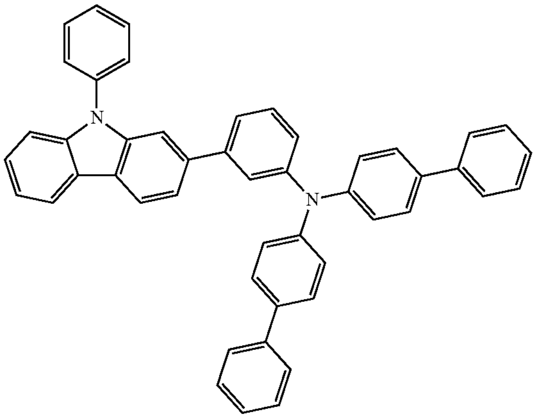
P2-5
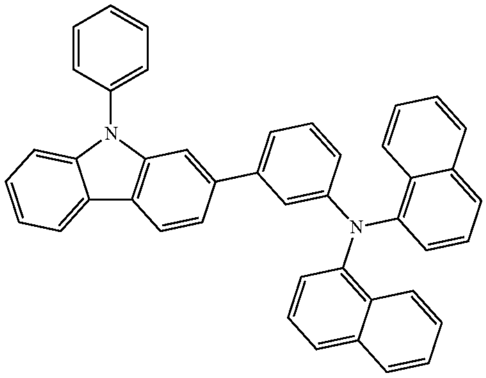
P2-6
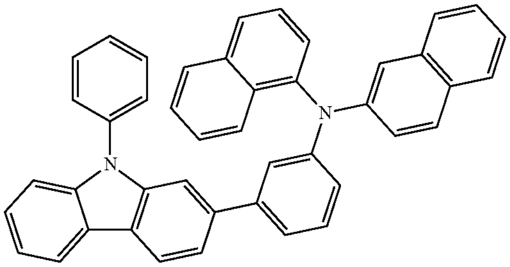
P2-7
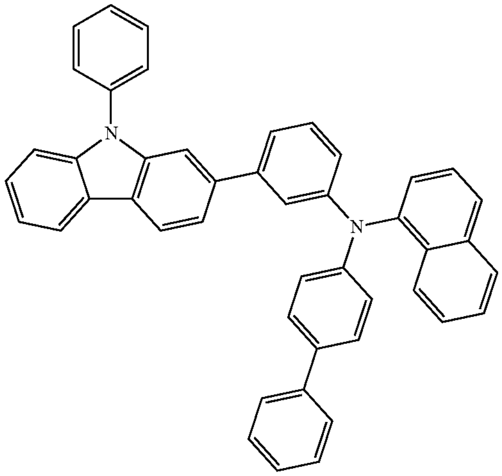

-continued
P2-8
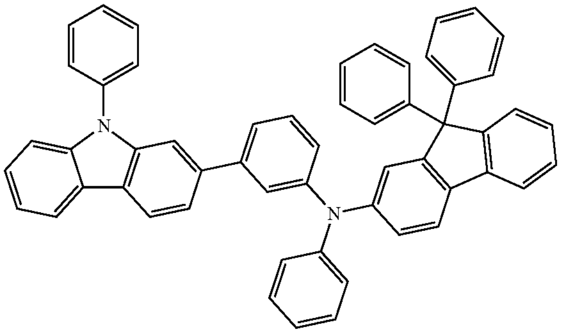
P2-9
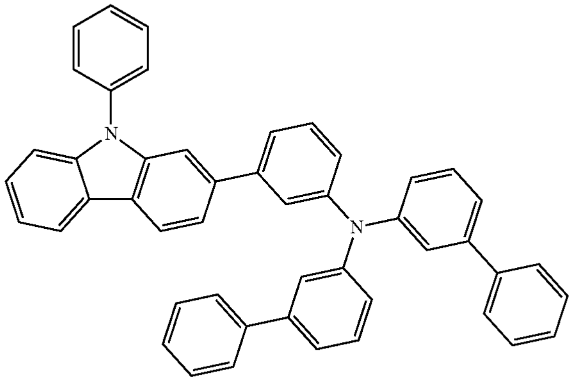
P2-10
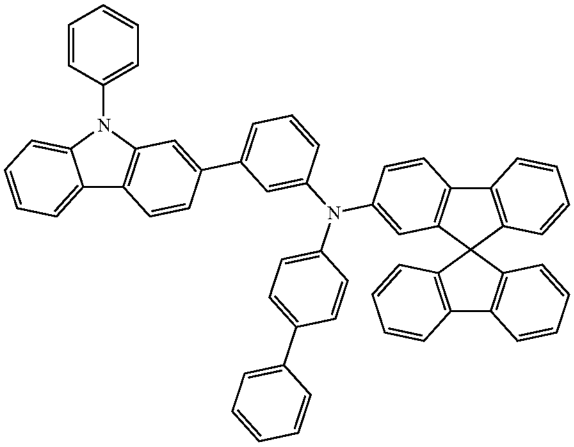
P2-11
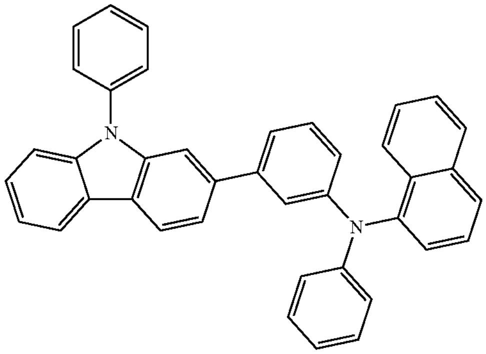
P2-12
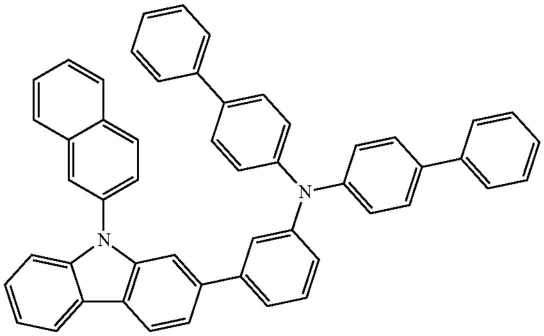
P2-13
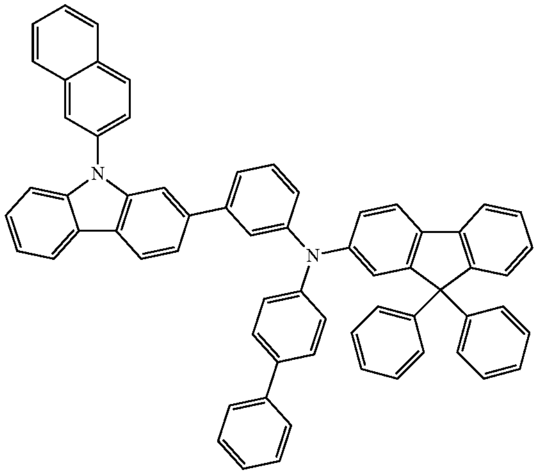

-continued
P2-14
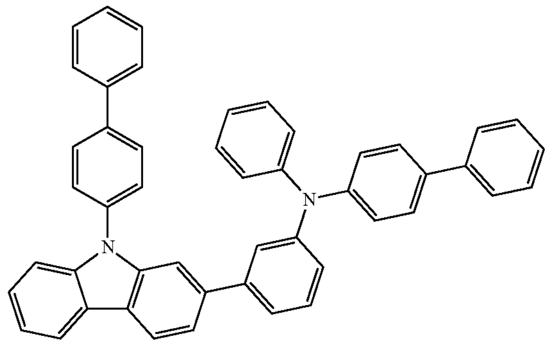
P2-15
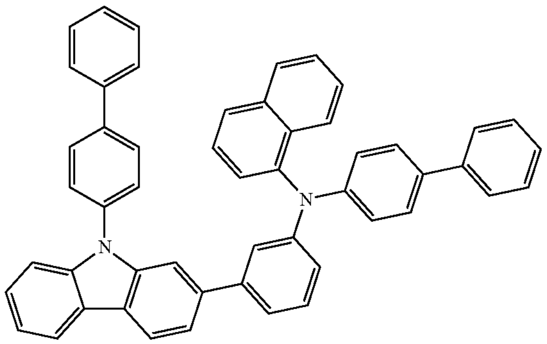
P2-16
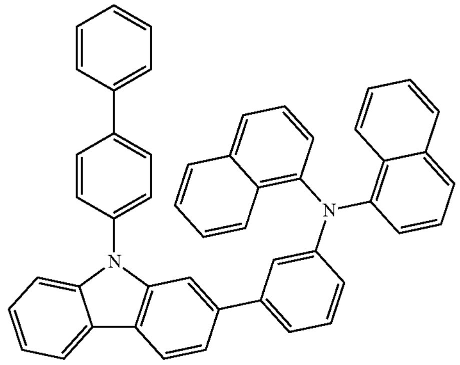
P2-17
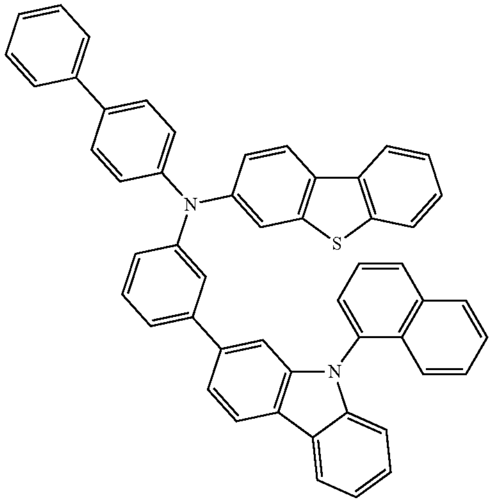
P2-18
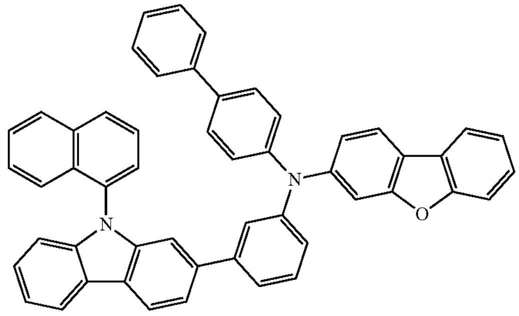
P2-19
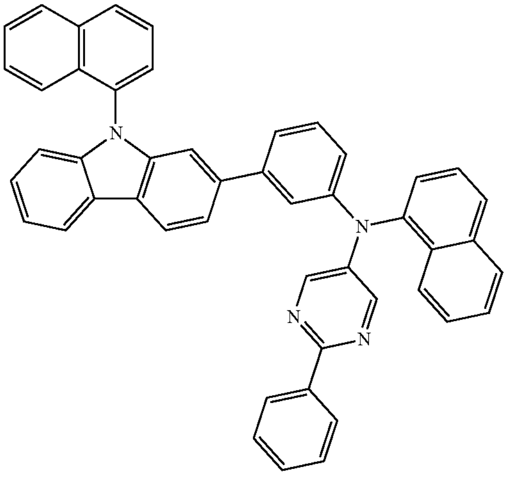

-continued
P2-20
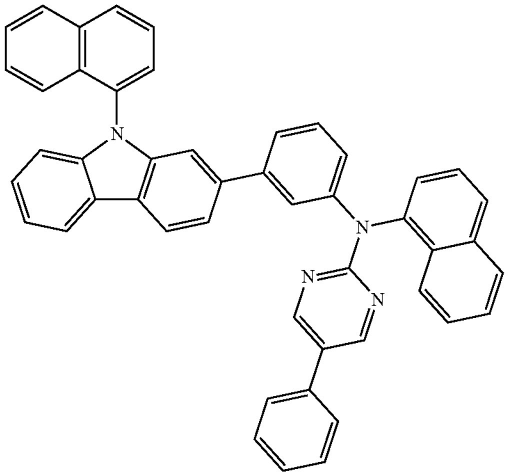
P2-21
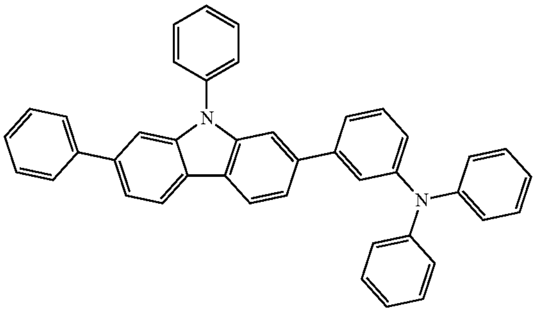
P2-22
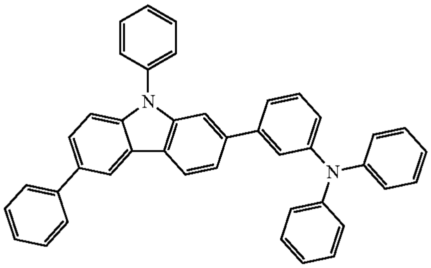
P2-23
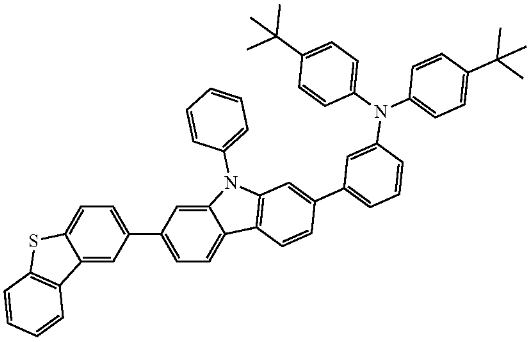
P2-24
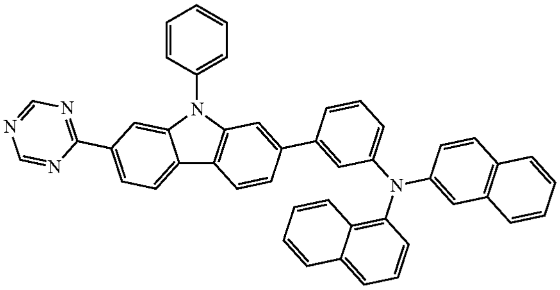
P2-25
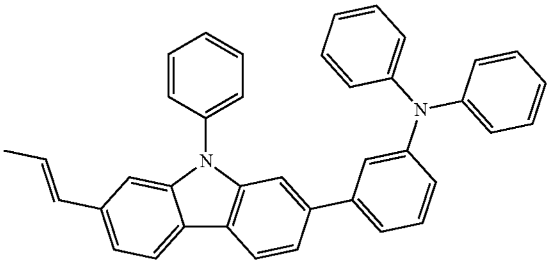
P2-26
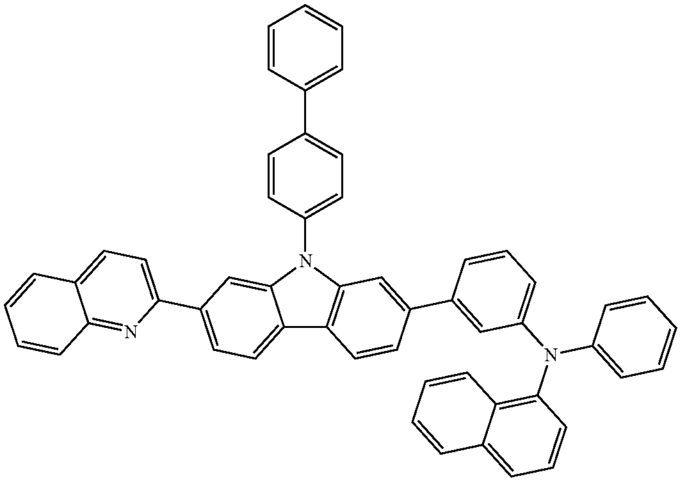

-continued
P2-27
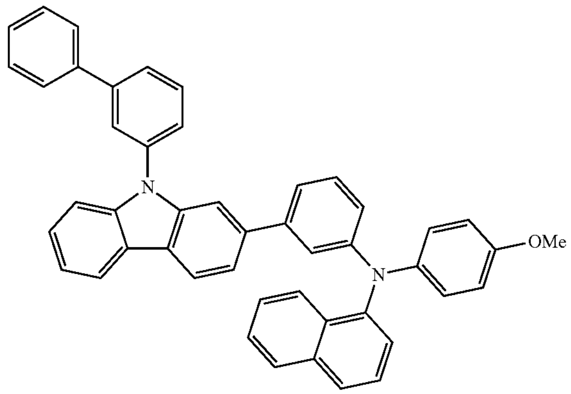
P2-28
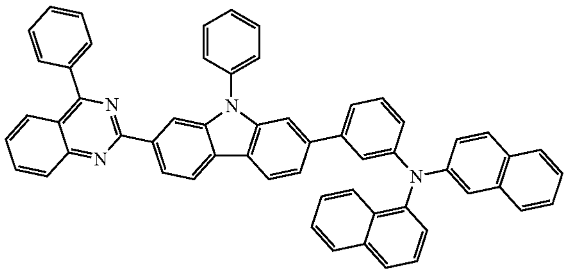
P2-29
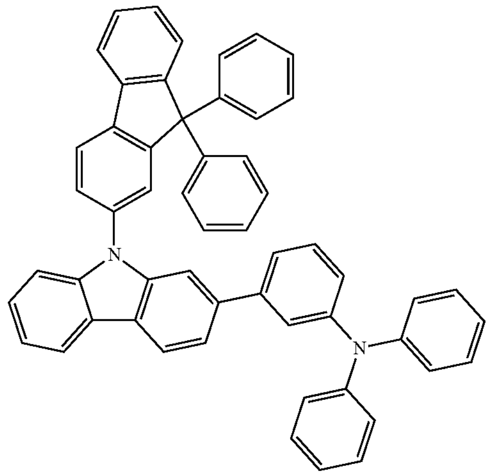
P2-30
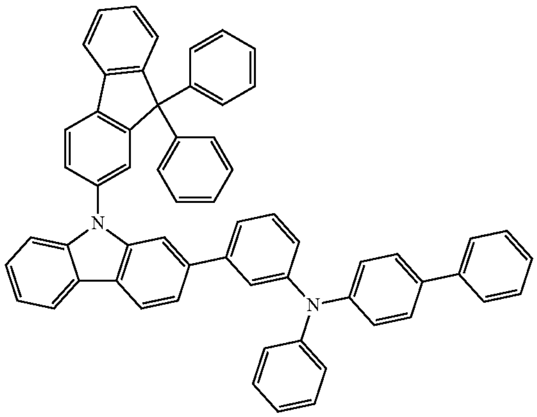
P2-31
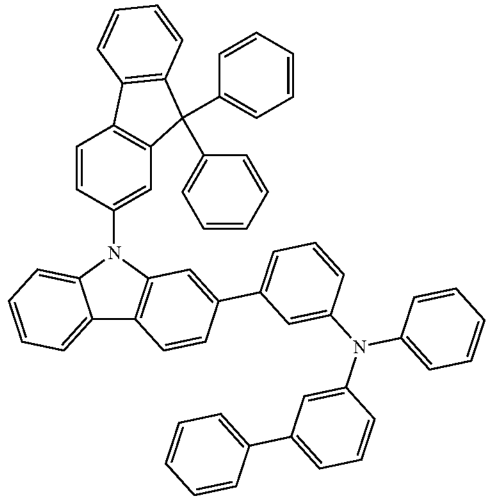
P2-32
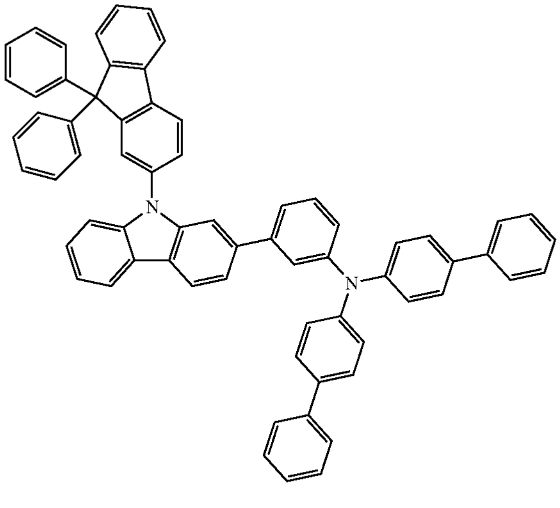

-continued
P2-33
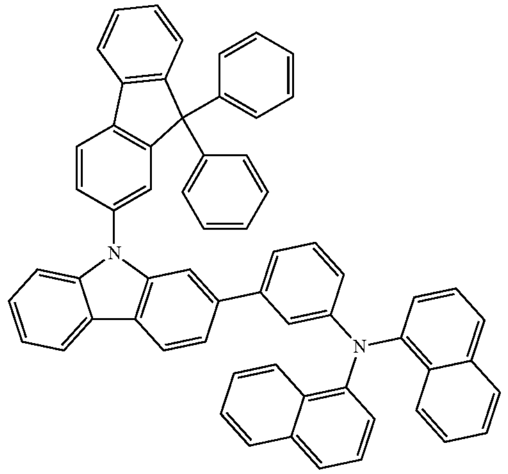
P2-34
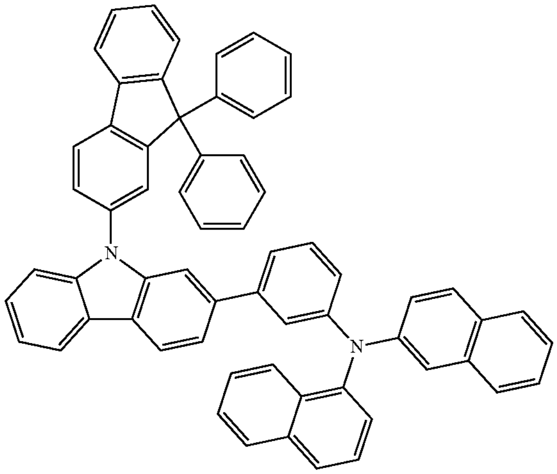
P2-35
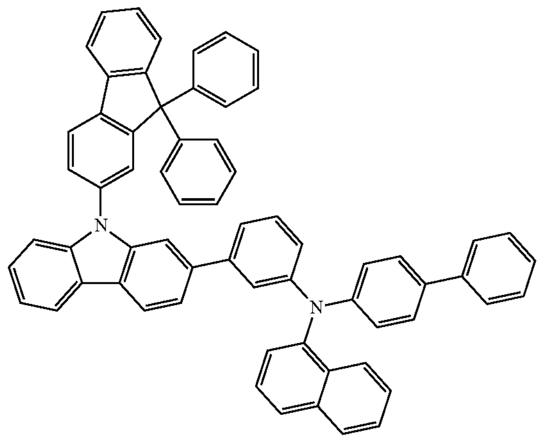
P2-36
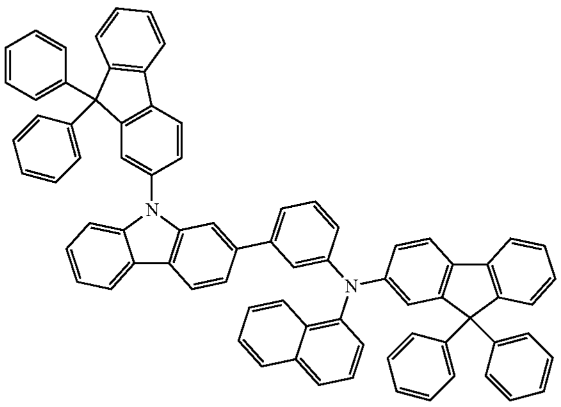
P2-37
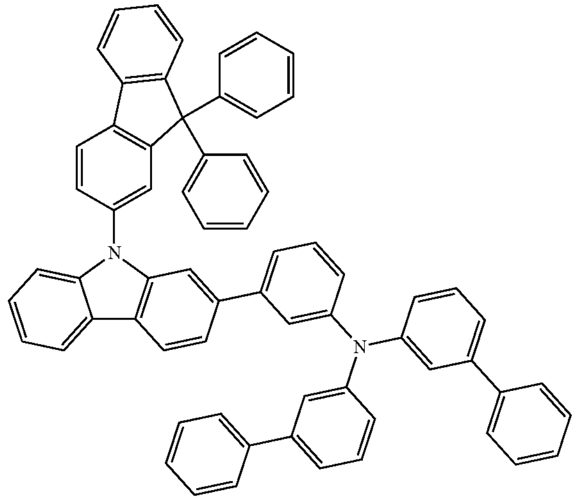
P2-38
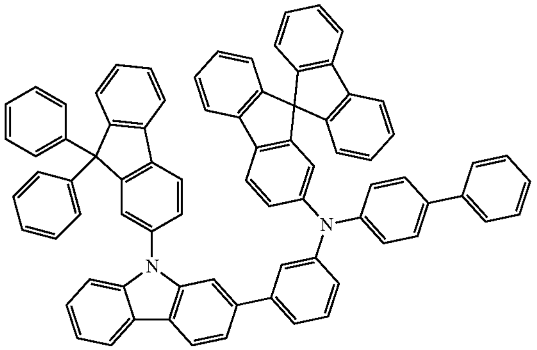

-continued
P2-39
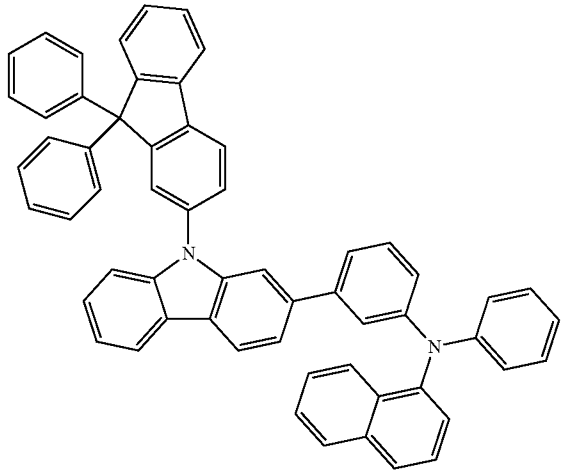
P2-40
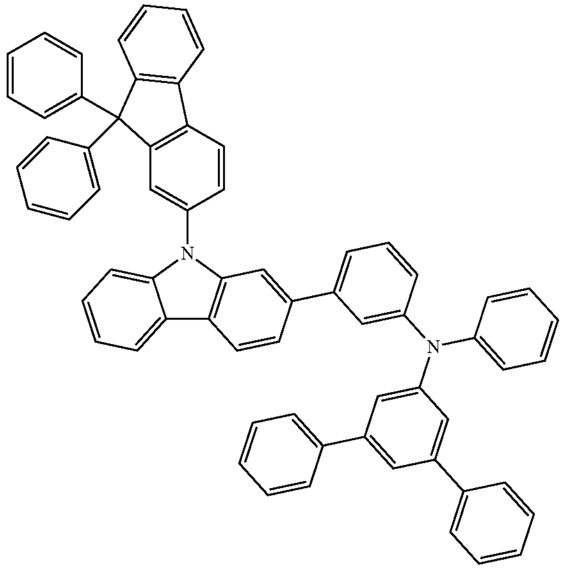
P2-41
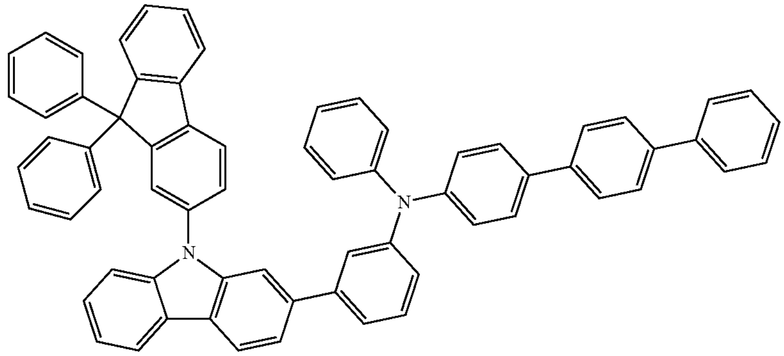
P2-42
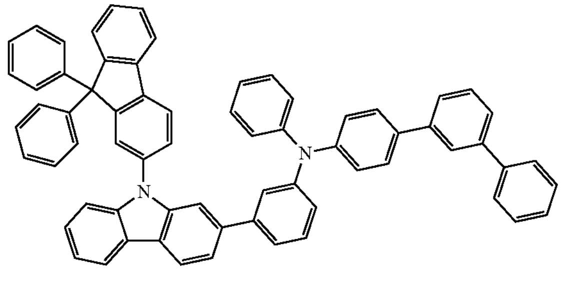
P2-43
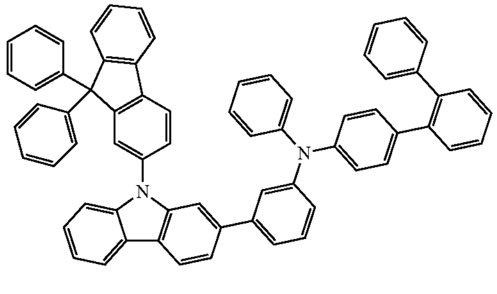
P2-44
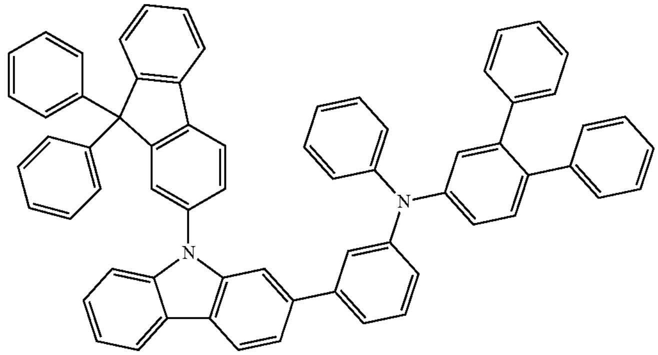

P2-49
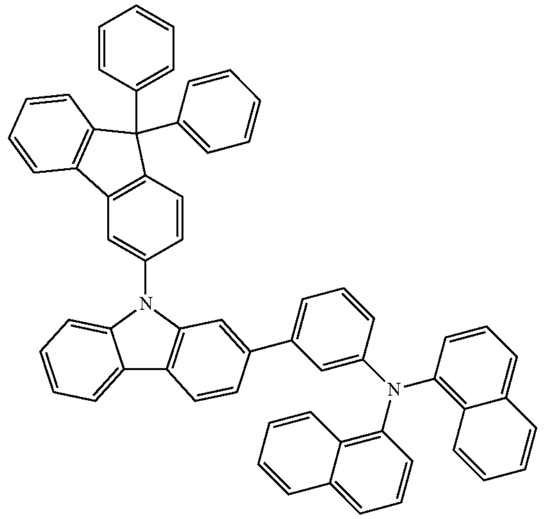
P2-50
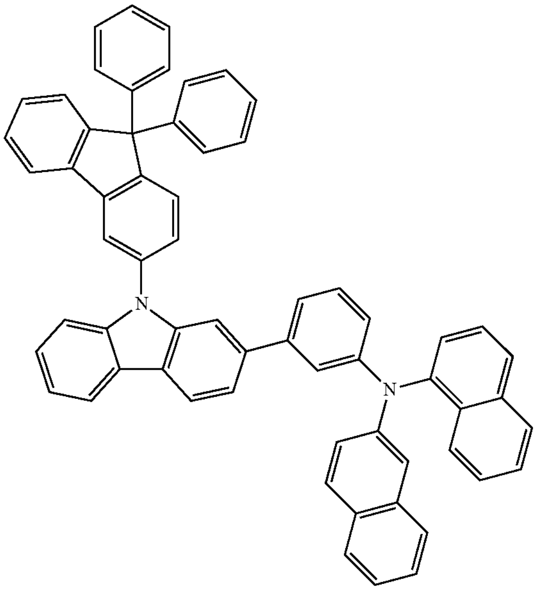
P2-51
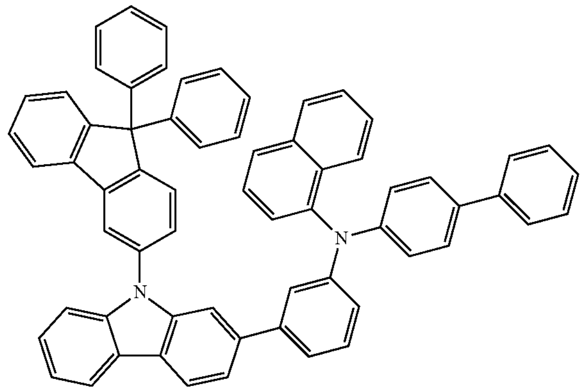
P2-52
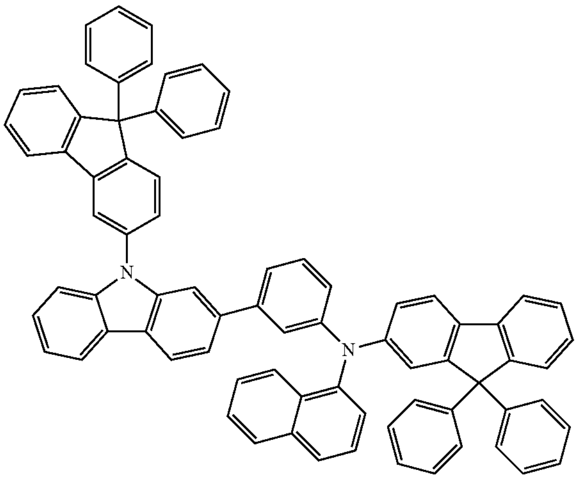

-continued
P2-53
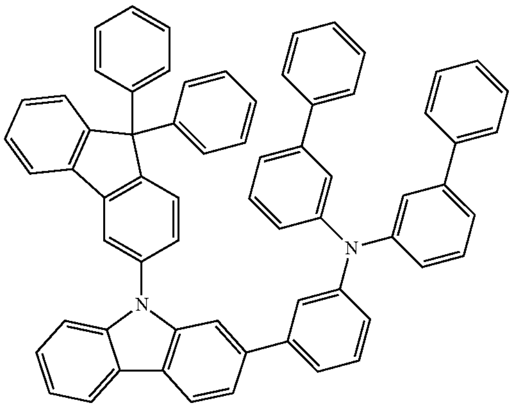
P2-54
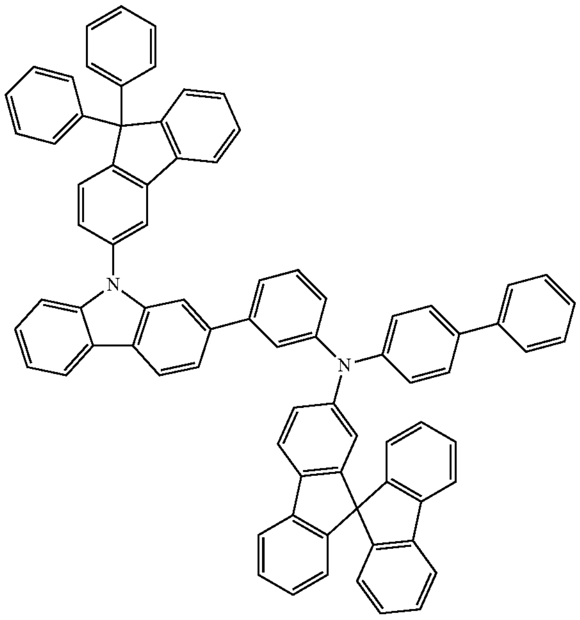
P2-55
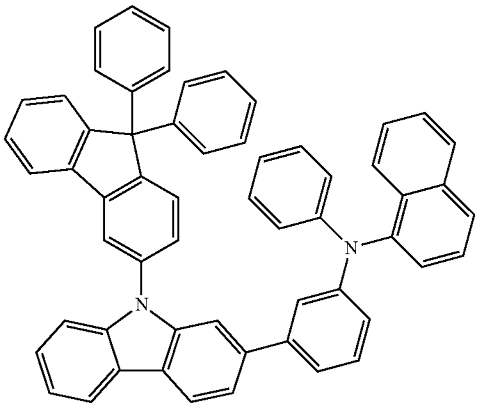
P2-56
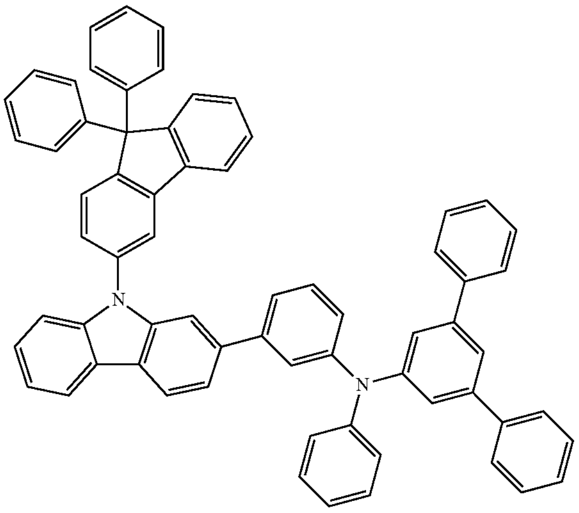
P2-57
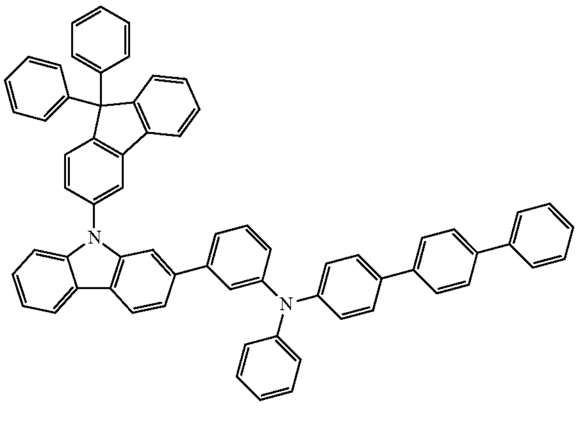
P2-58
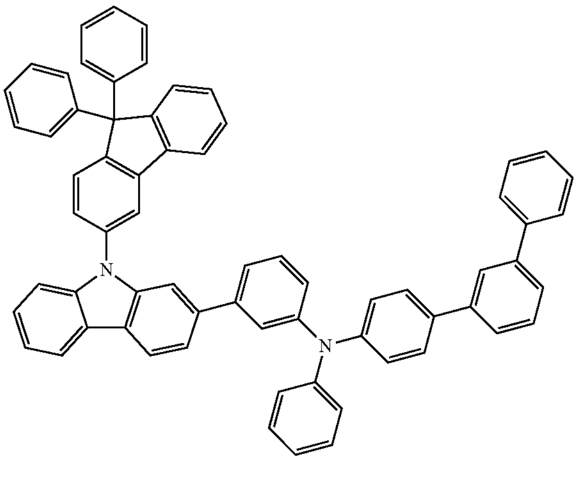

-continued
P2-59
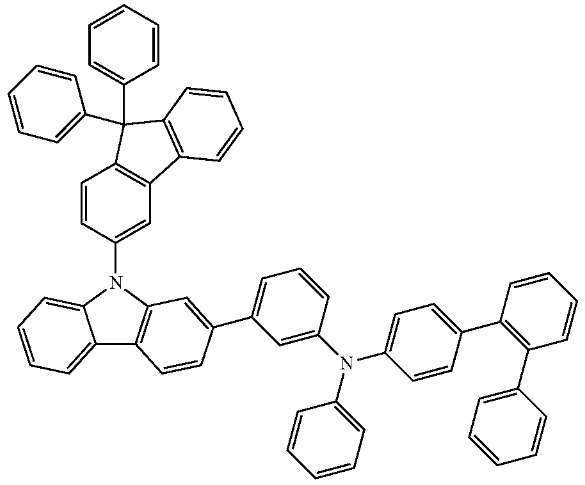
P2-60
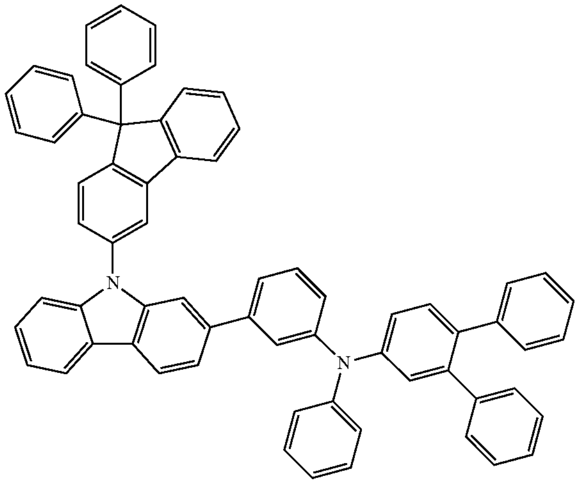
P2-61
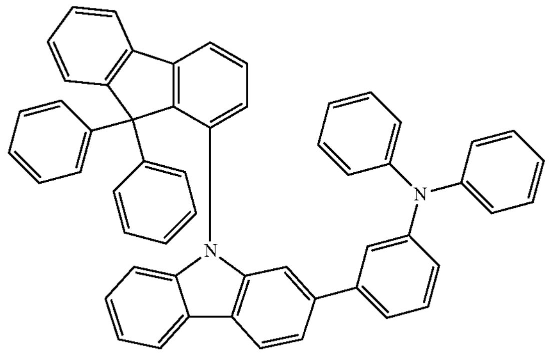
P2-62
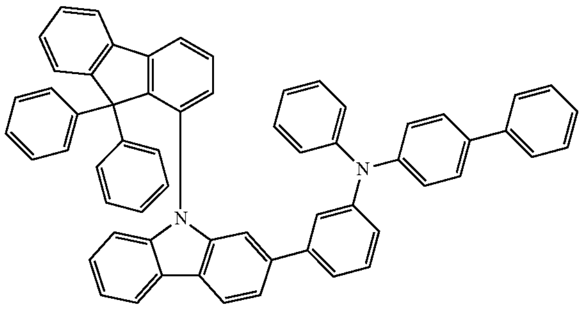
P2-63
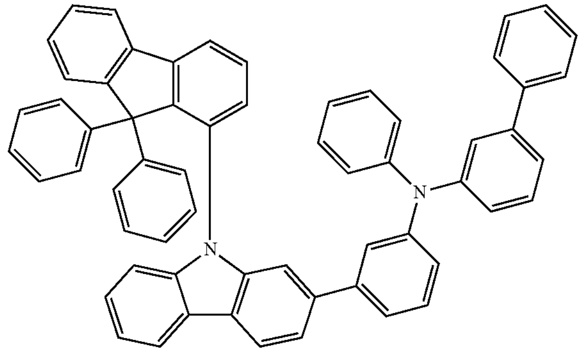
P2-64
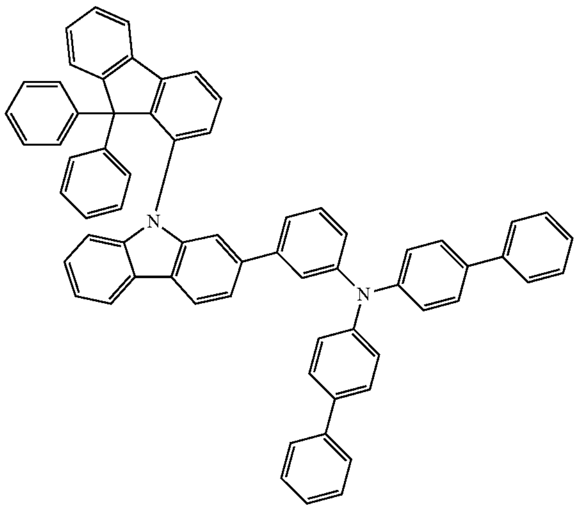

-continued
P2-65
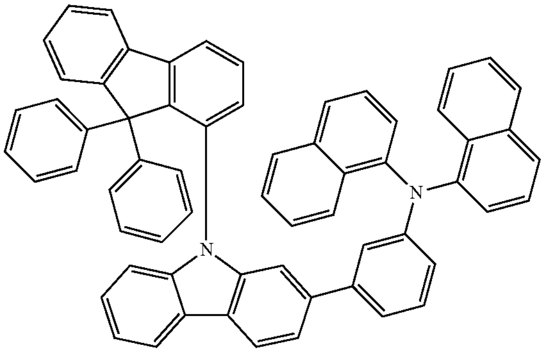
P2-66
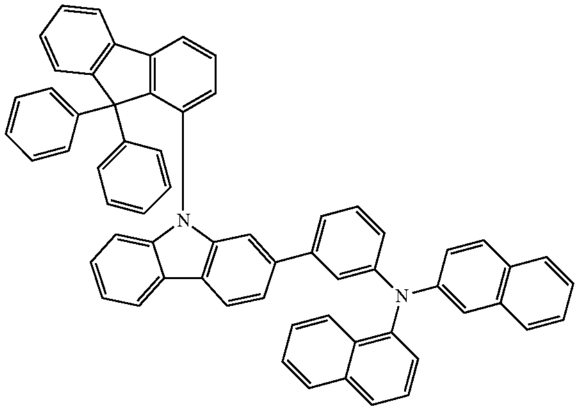
P2-67
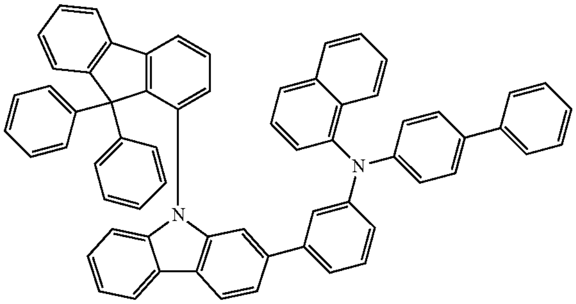
P2-68
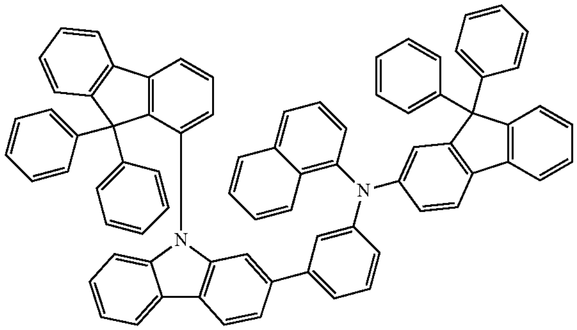
P2-69
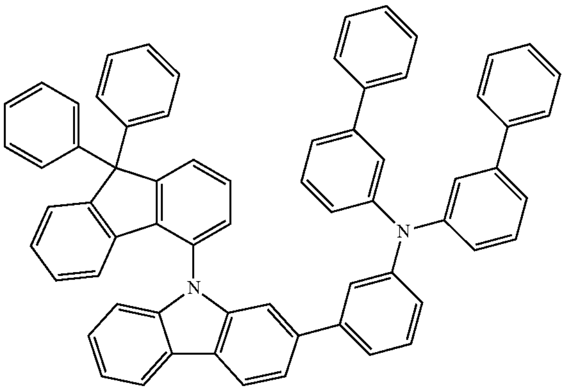
P2-70
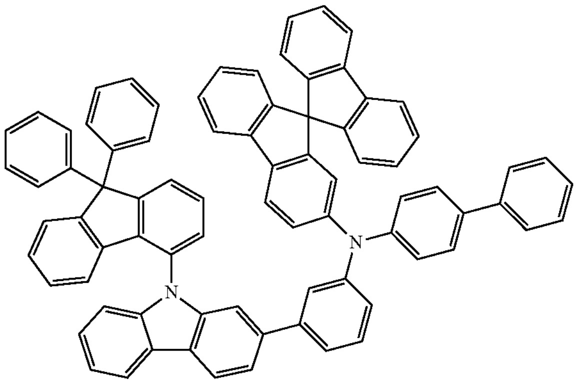

-continued
P2-71
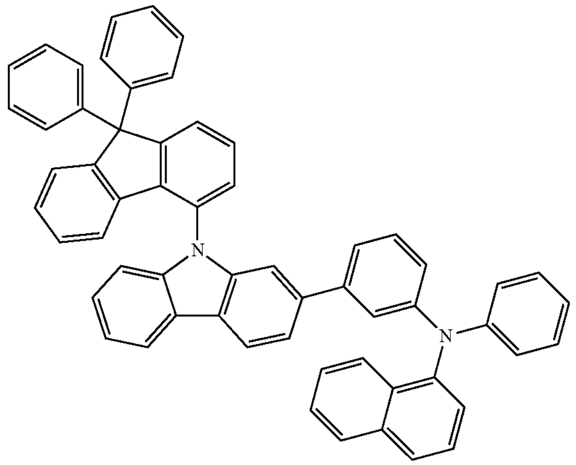
P2-72
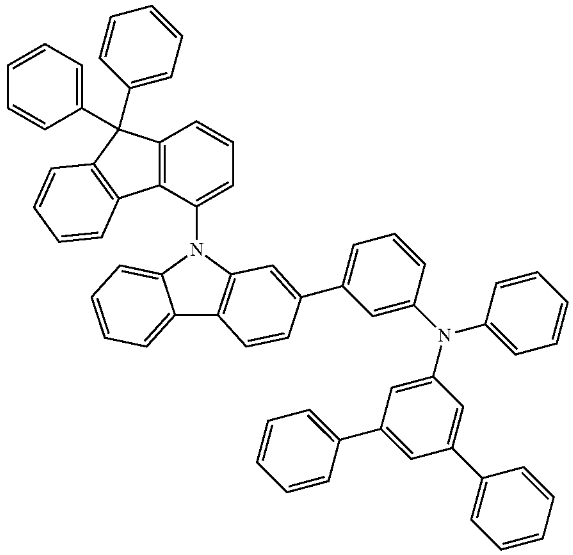
P2-73
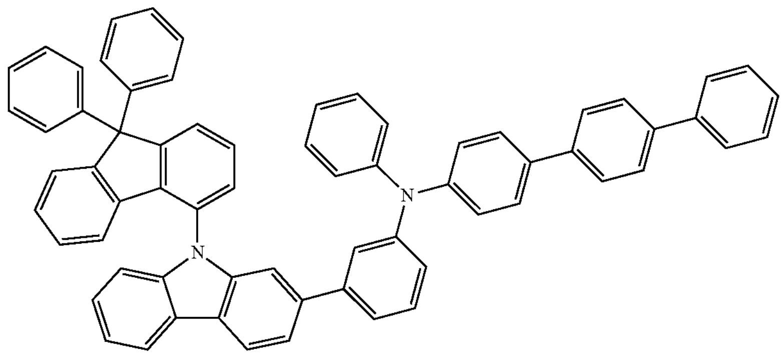
P2-74
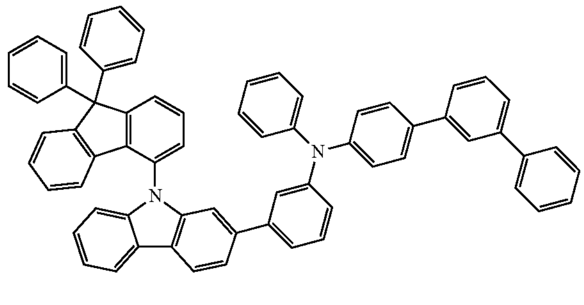
P2-75
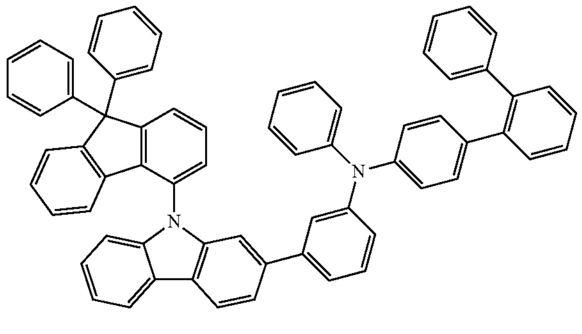

-continued
P2-76
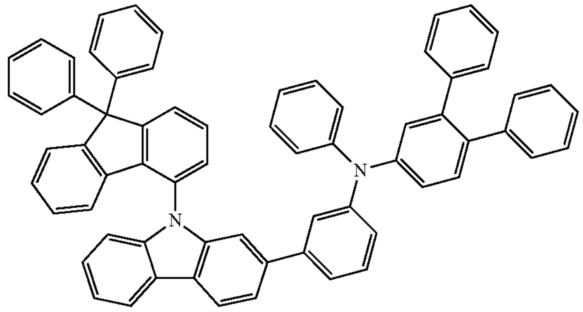
P2-77
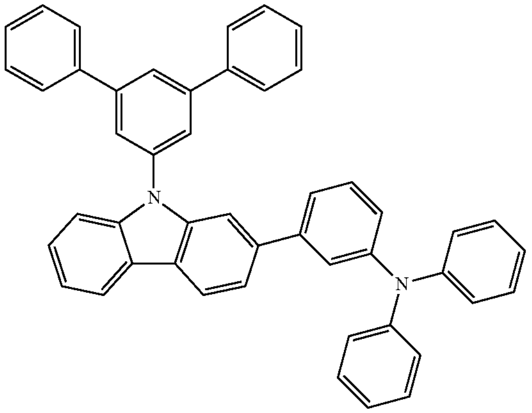
P2-78
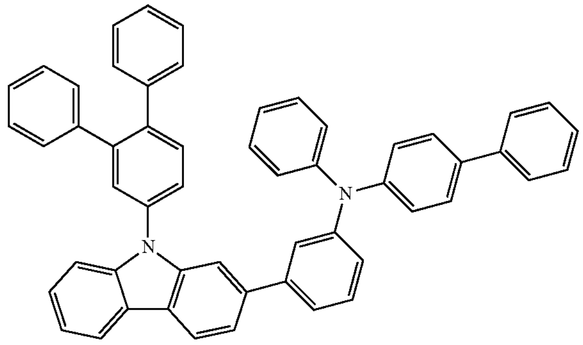
P2-79
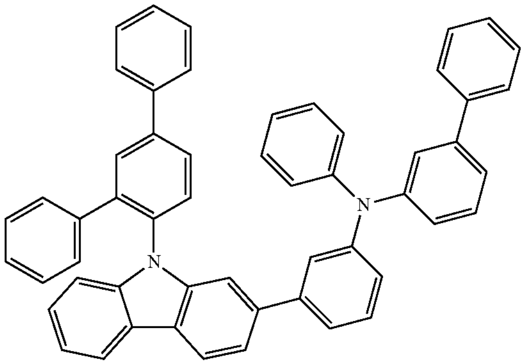
P2-80
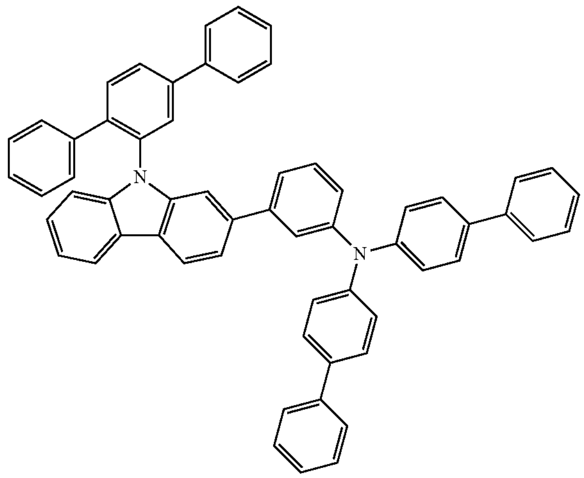
P2-81
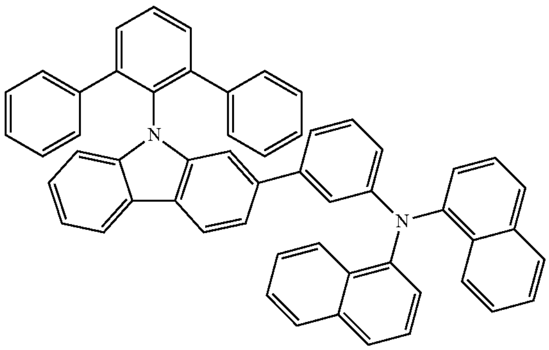

-continued
P2-82
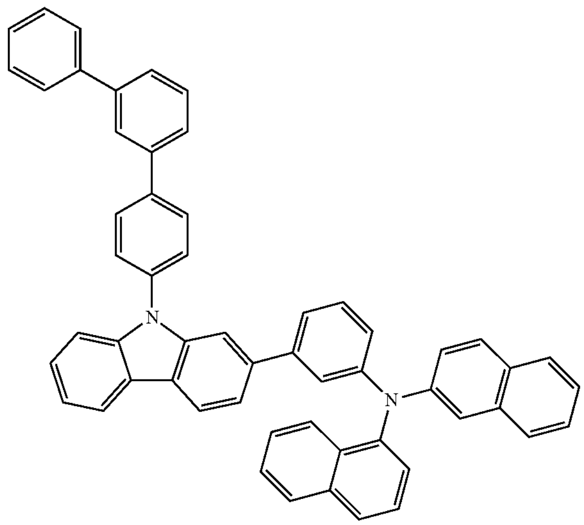
P2-83
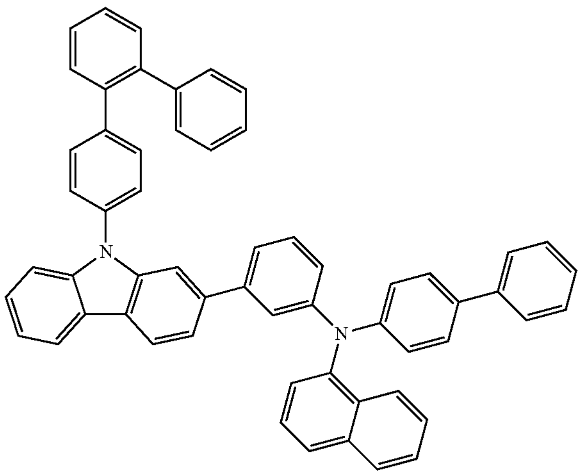
P2-84
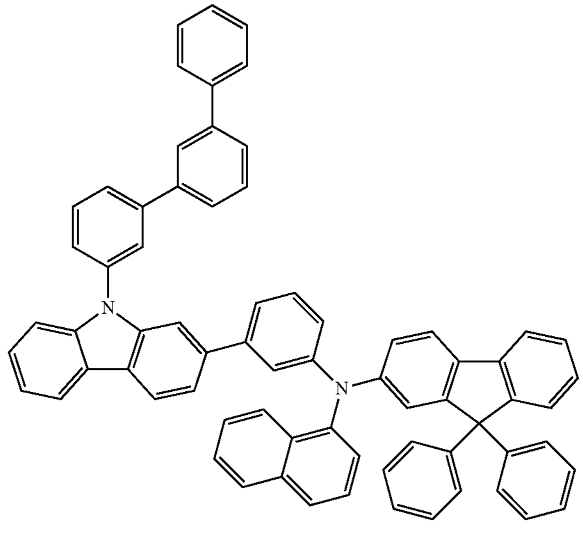

P2-85
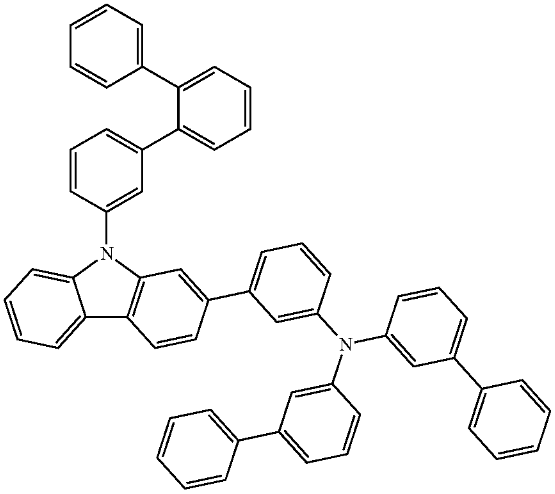
P2-86
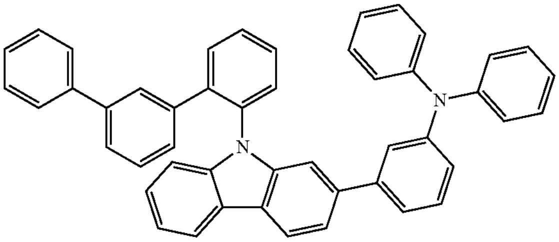
P2-87
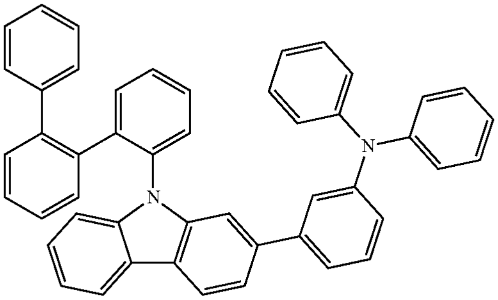
P2-88
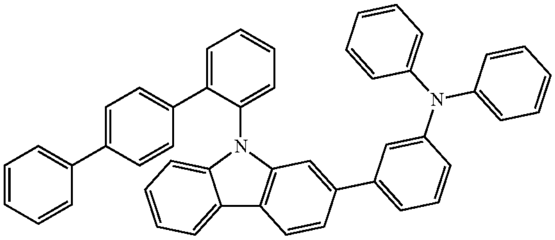
P2-65
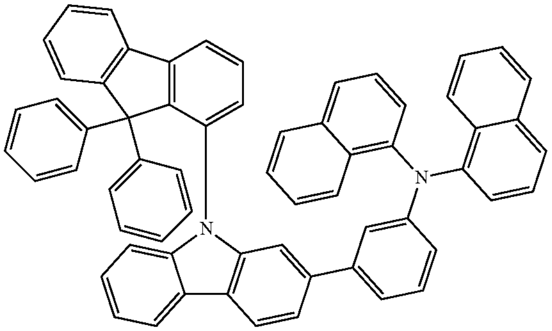
P2-66
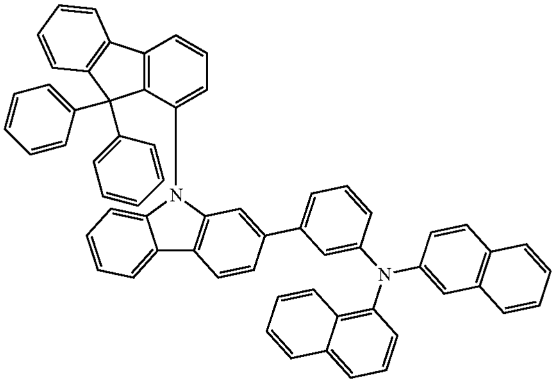
P2-67
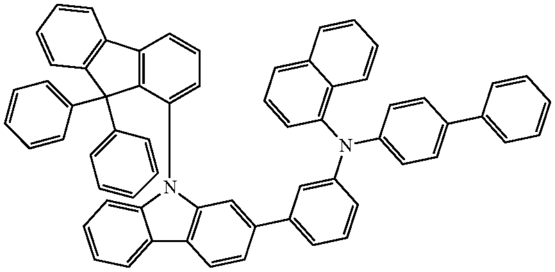
P2-68
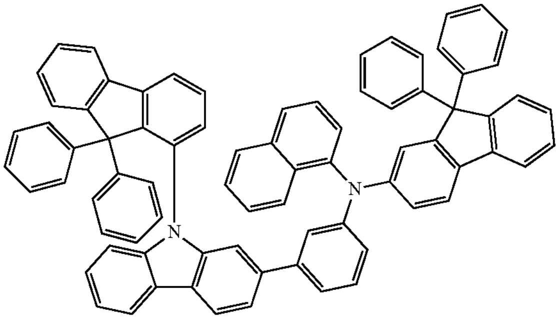

-continued
P2-69
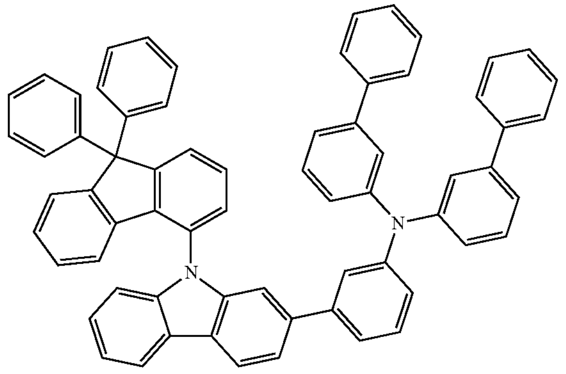
P2-70
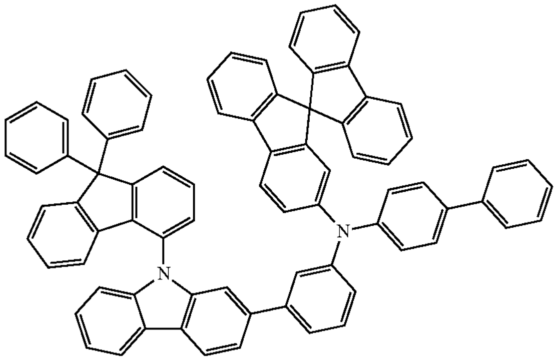
P2-71
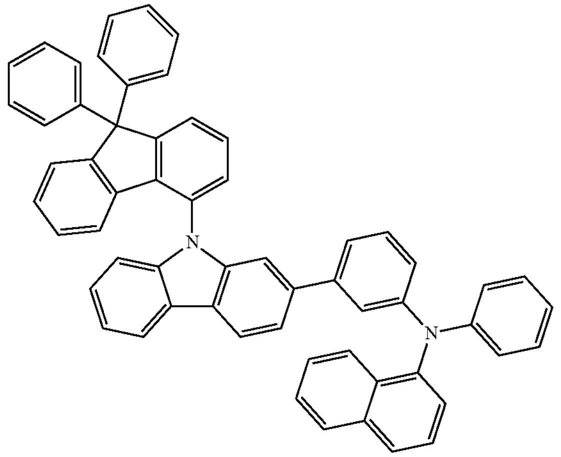
P2-72
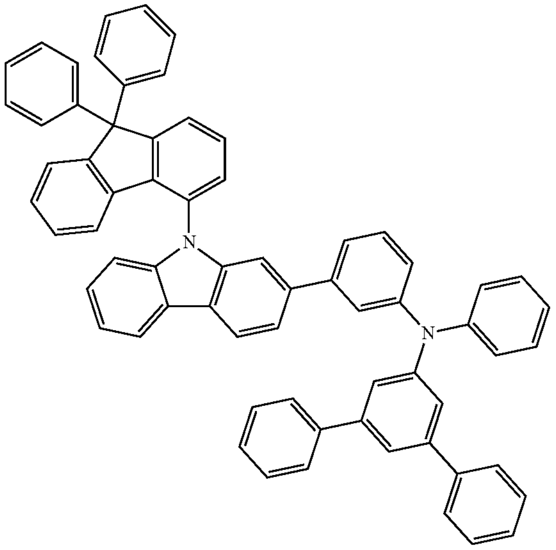
P2-73
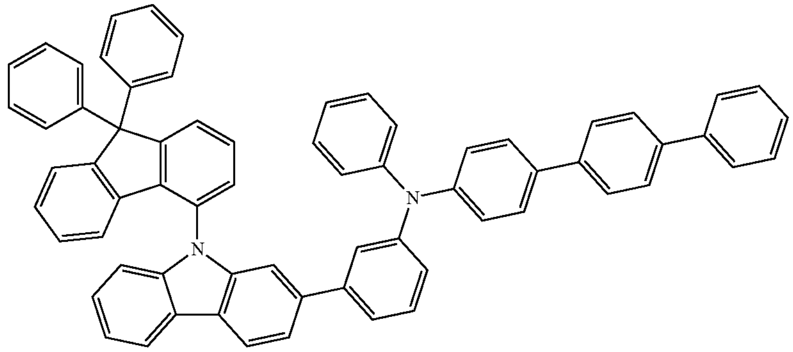
P2-74
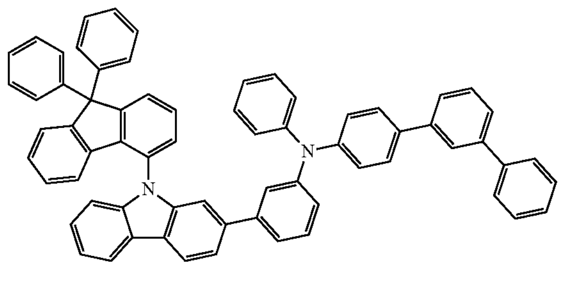
P2-75
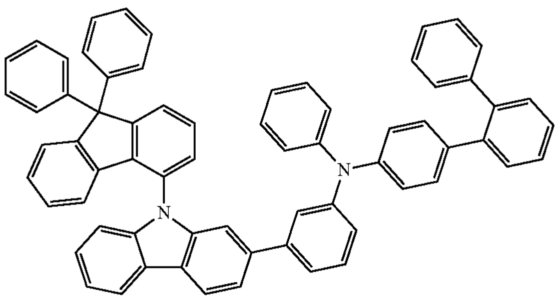

-continued
P2-76
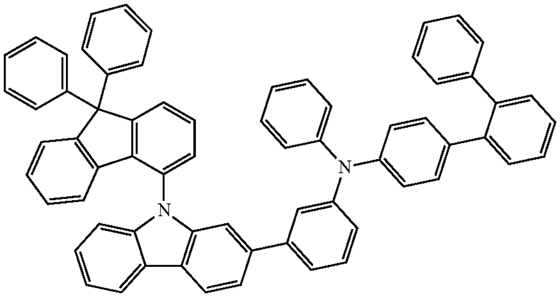
P2-77
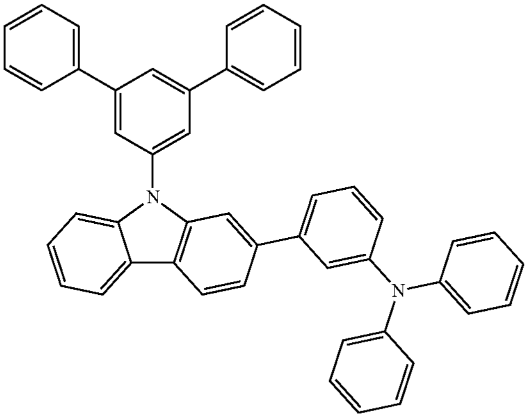
P2-78
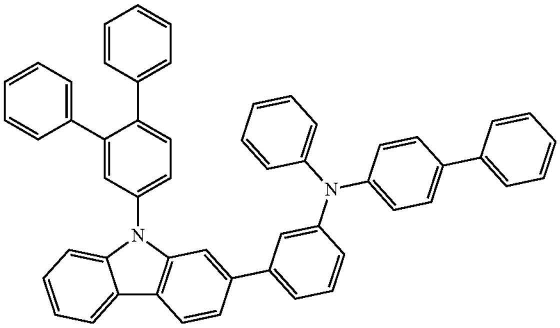
P2-79
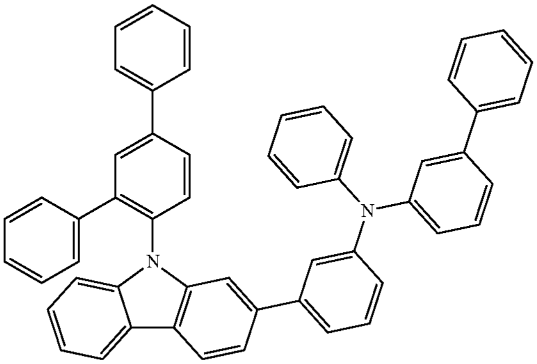
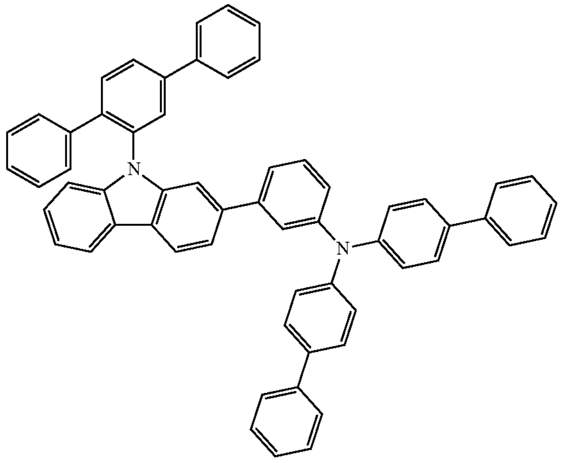
P2-81
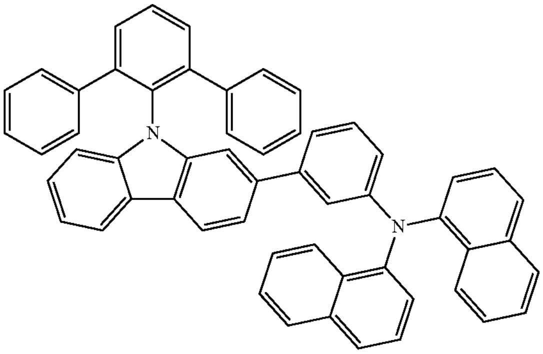

-continued
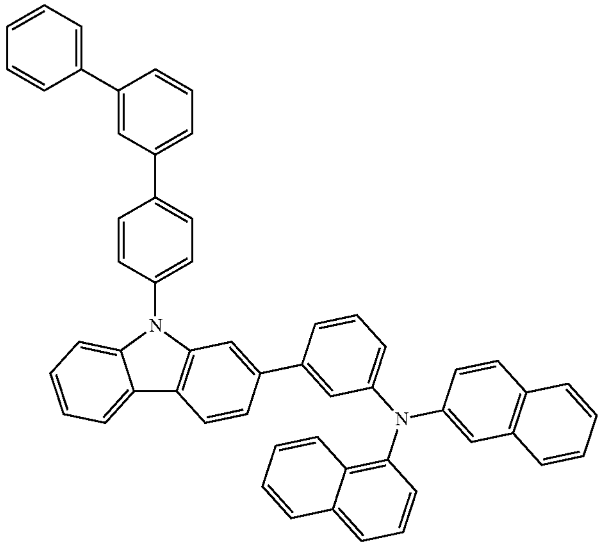
P2-83
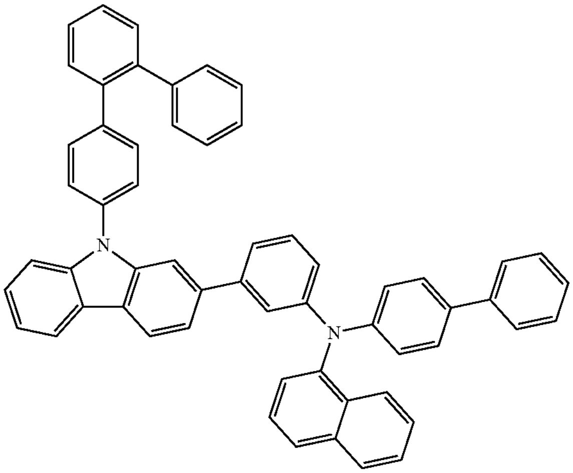
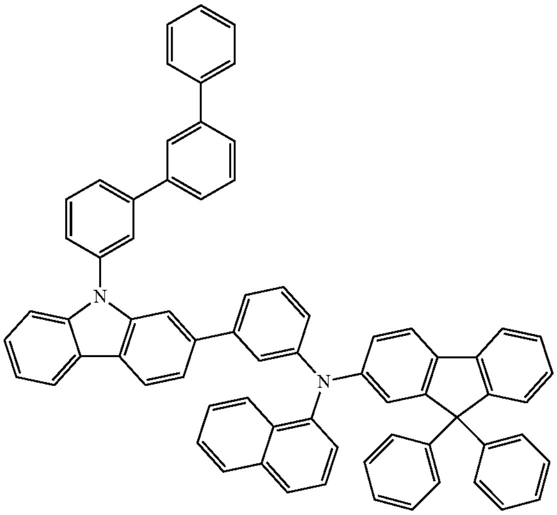
P2-85
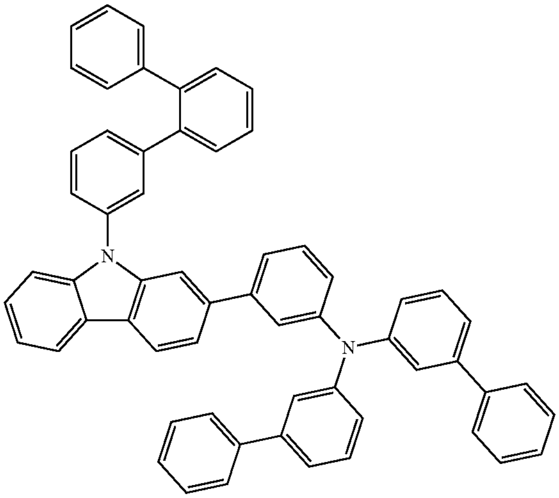
P2-86
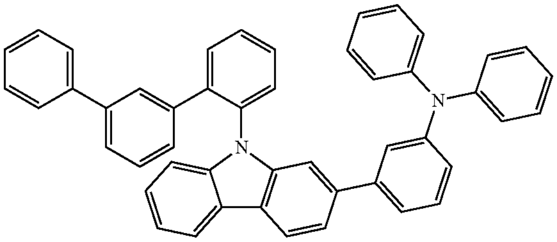
P2-87
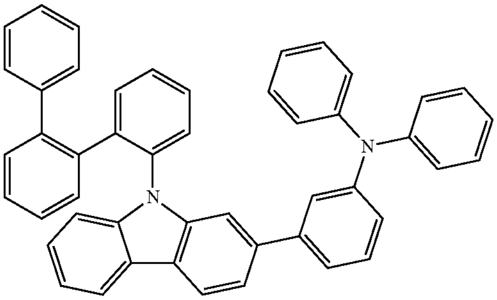

-continued
P2-88
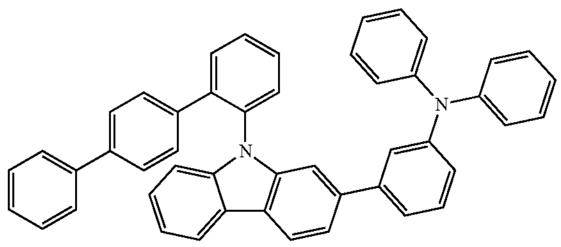
P2-89
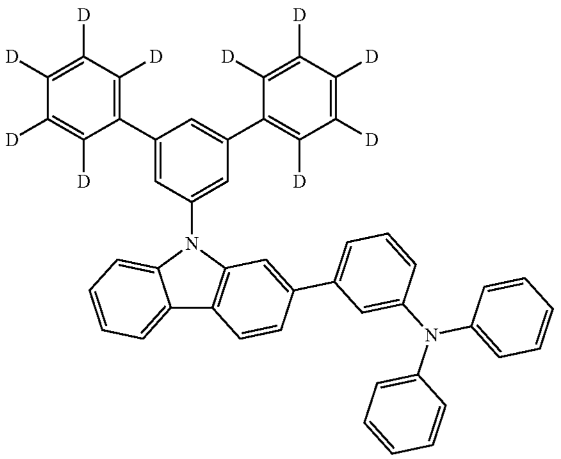
P2-90
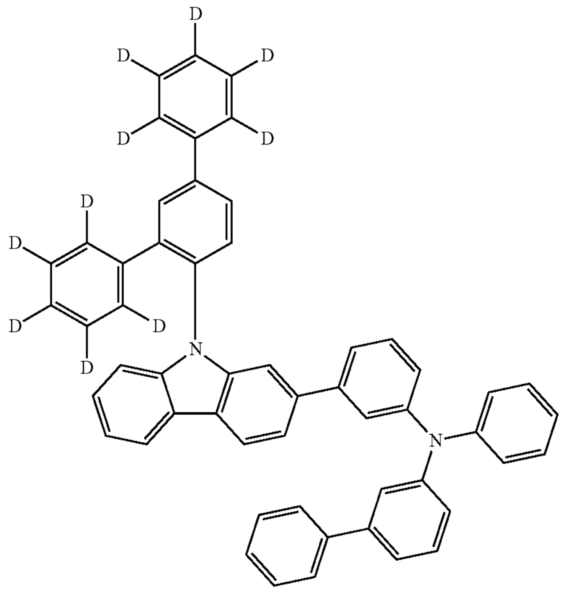
P2-91
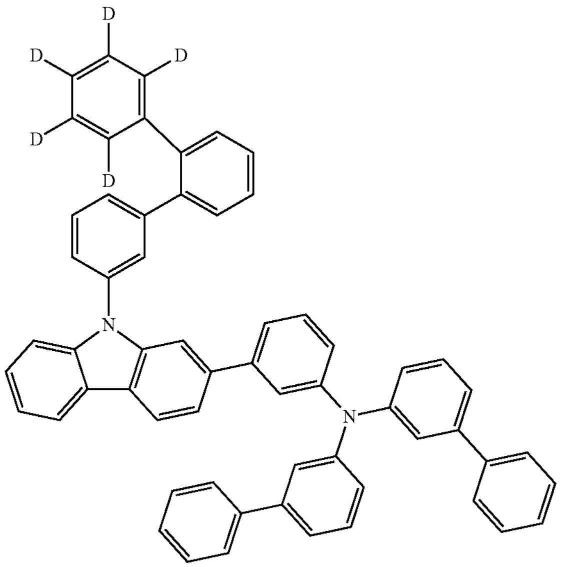
P2-92
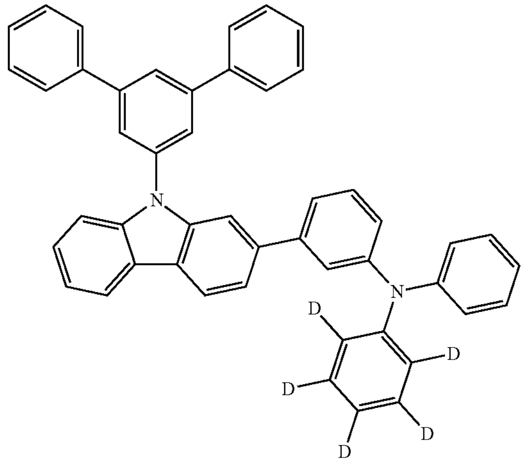
P2-101
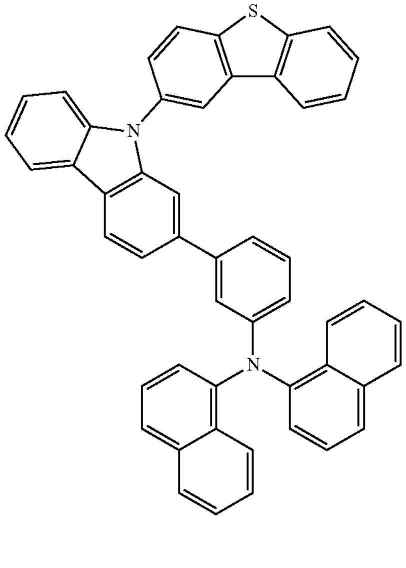

-continued
P2-102
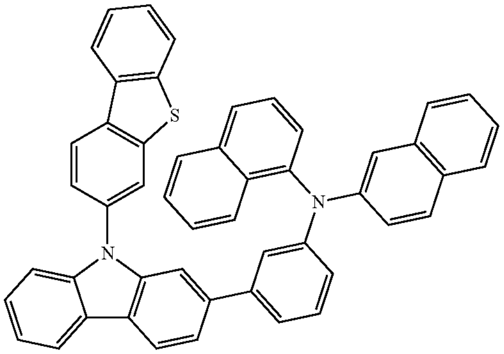
P2-103
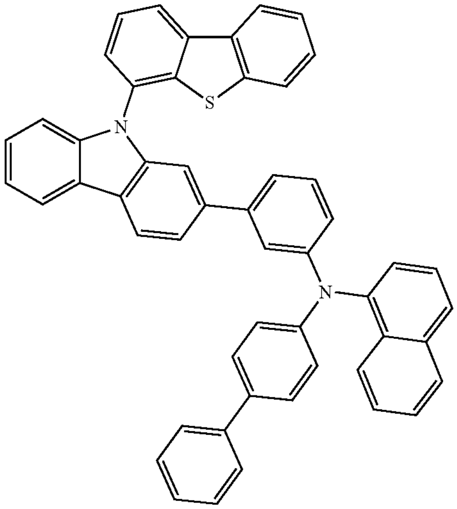
P2-104
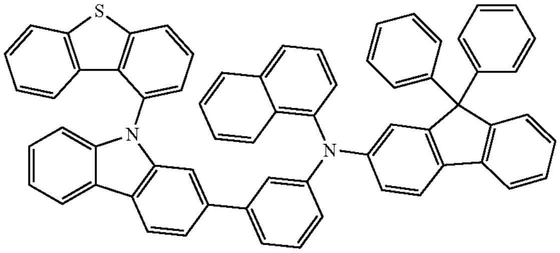
P2-105
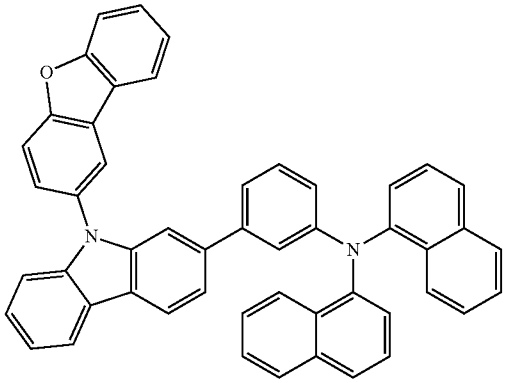
P2-106
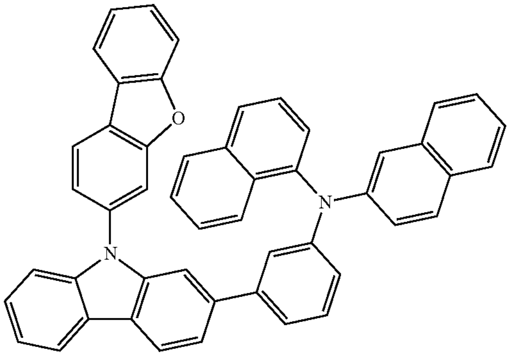
P2-107
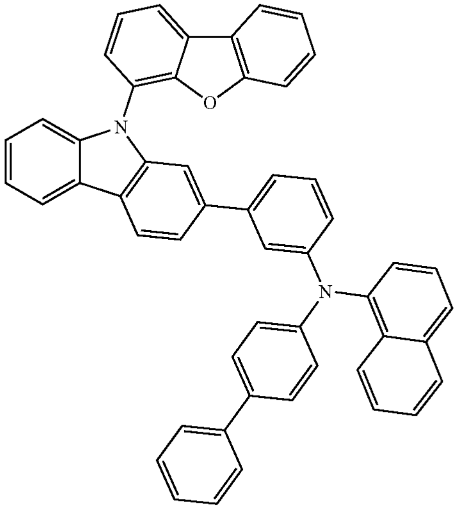

-continued
P2-108
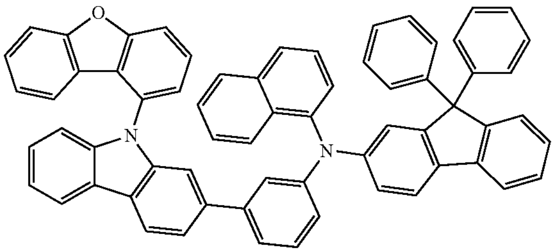
P2-111
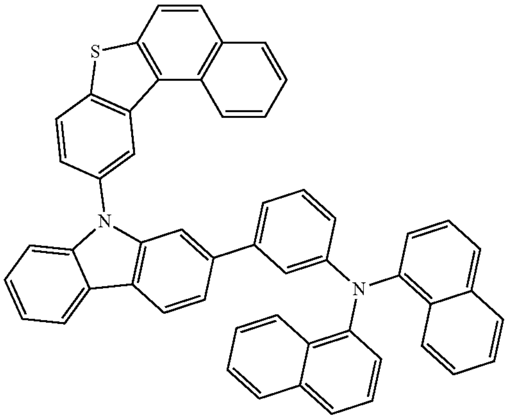
P2-112
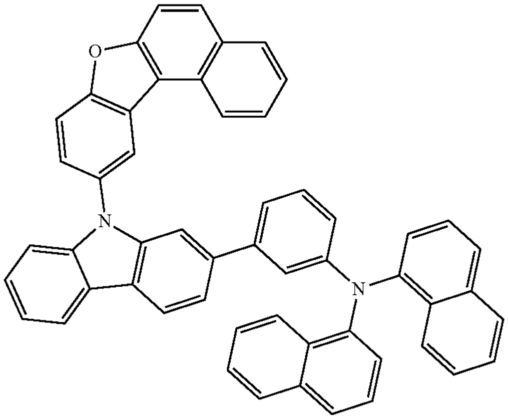
-continued
P3-1
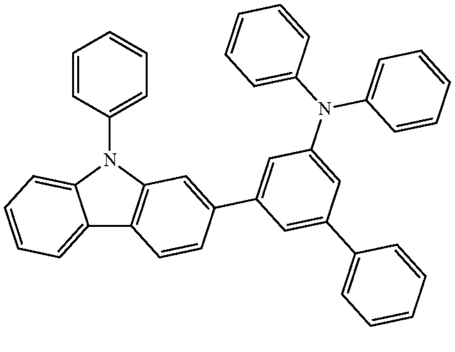
P3-2
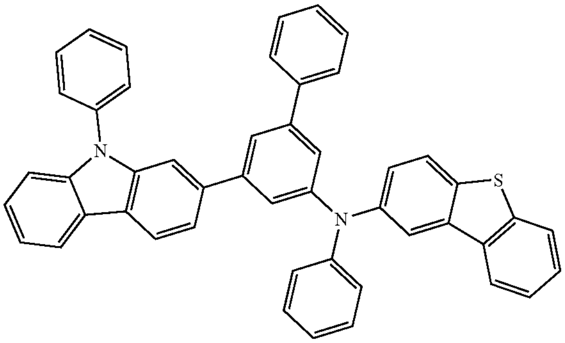

-continued
P3-3
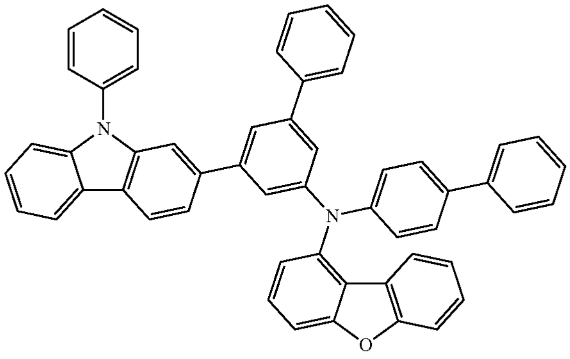
P3-4
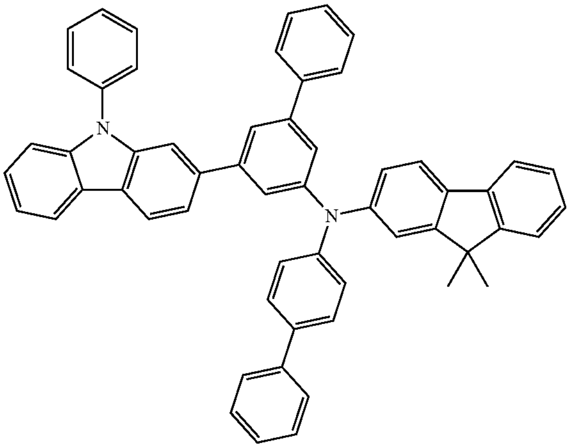
P3-5
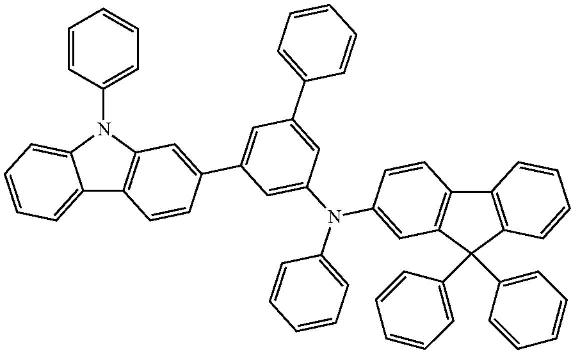
P3-6
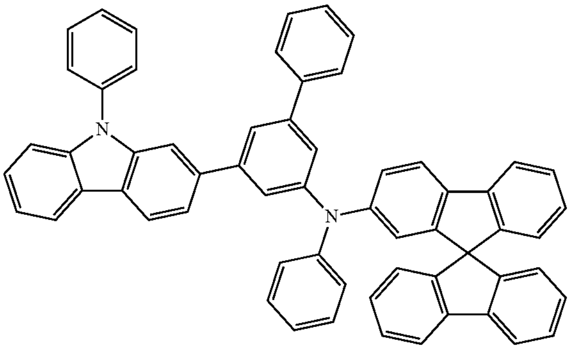
-continued
P3-7
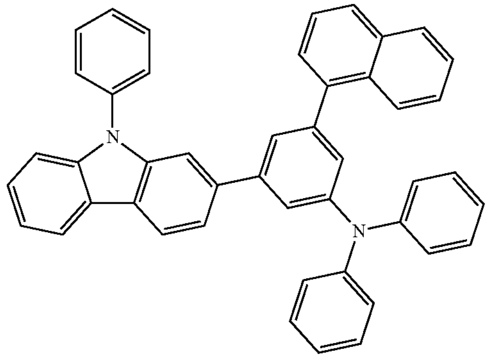
P3-8
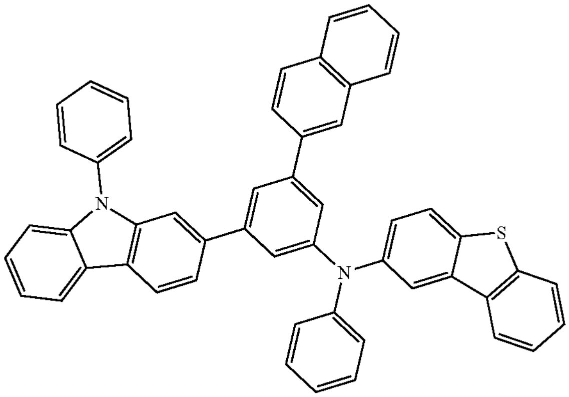
P3-9
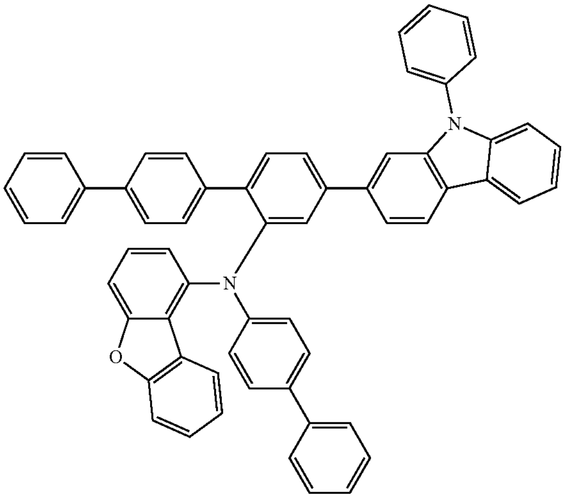

-continued
P3-10
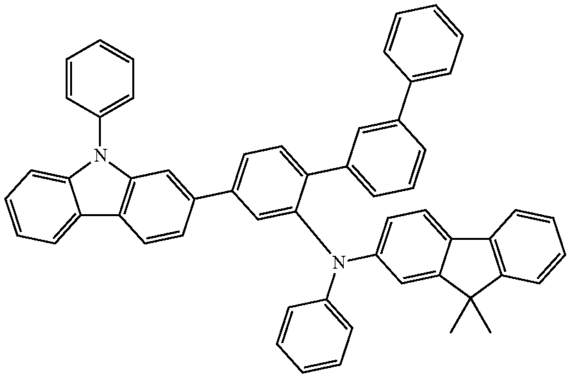
P3-11
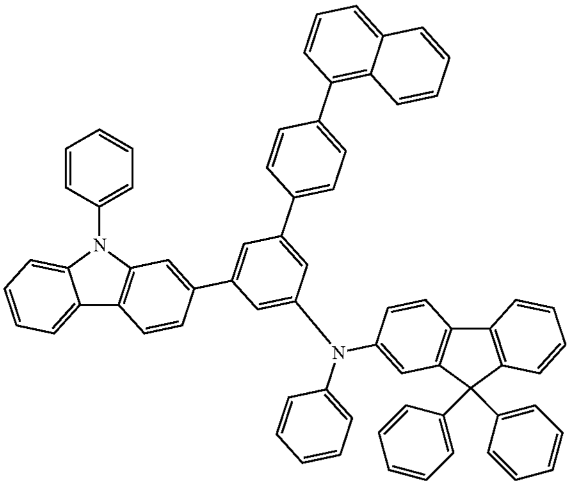
P3-12
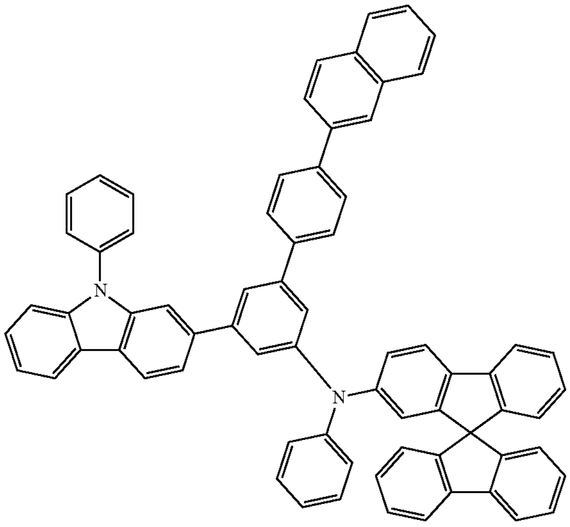
-continued
P3-13
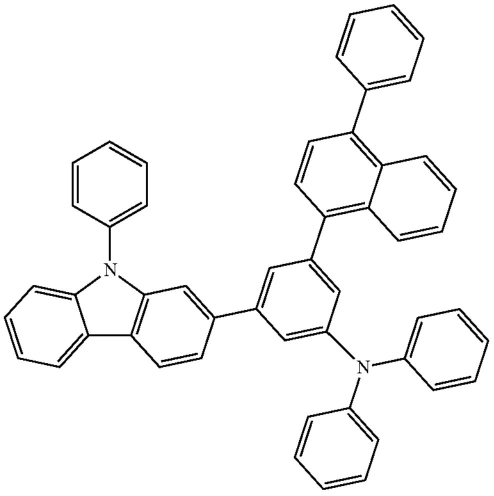
P3-14
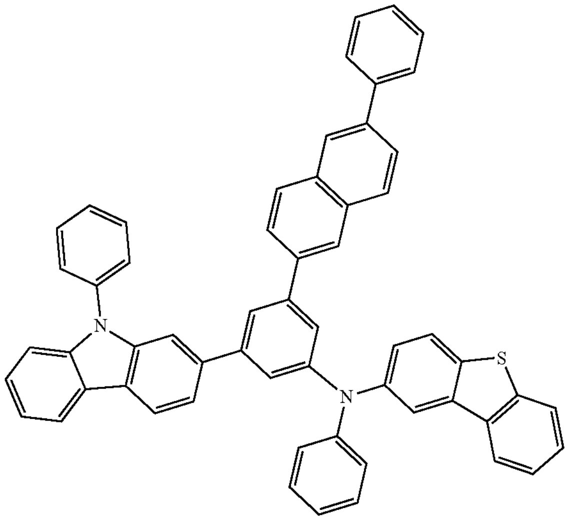
P3-15
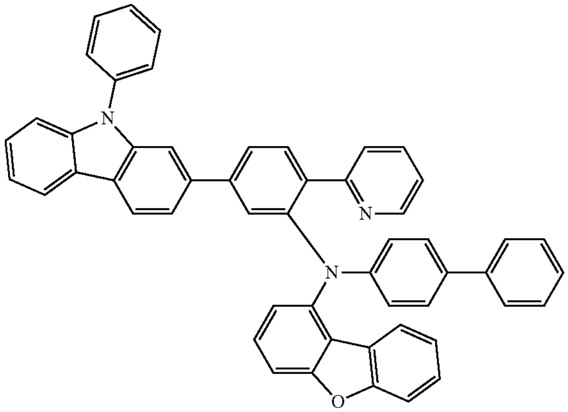

-continued
P3-16
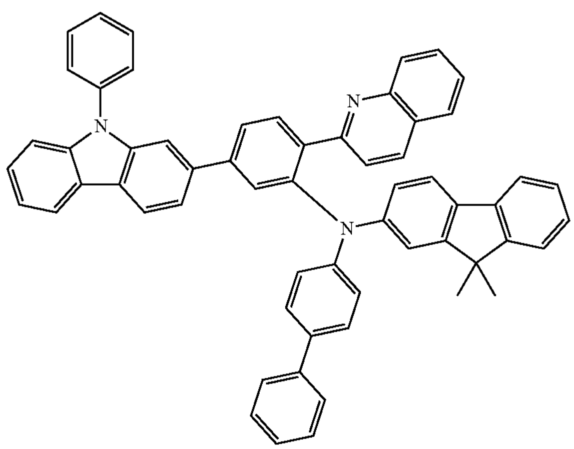
P3-17
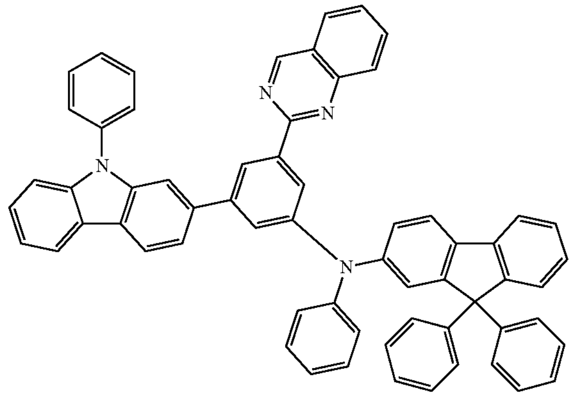
P3-18
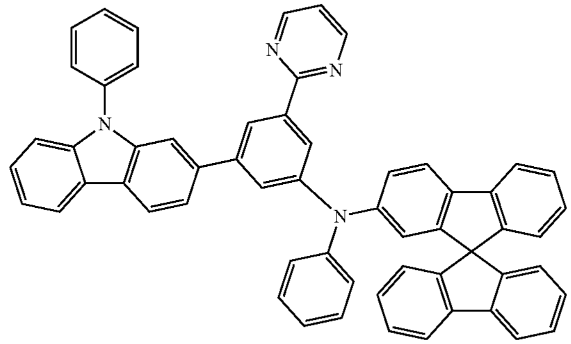
P3-19
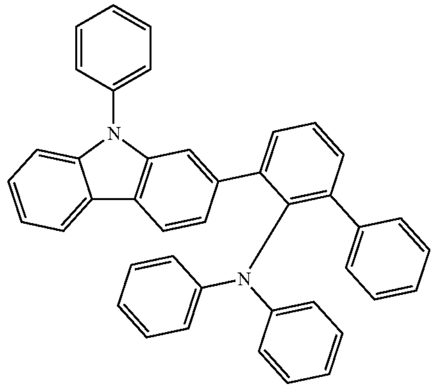
-continued
P3-20
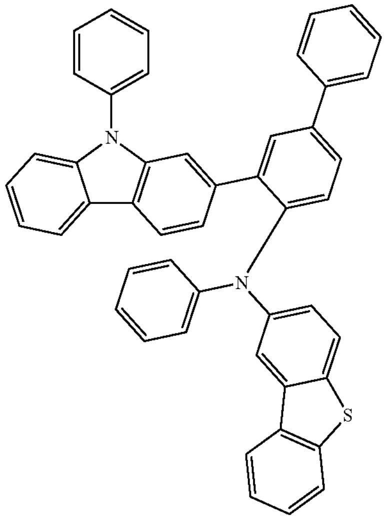
P3-21
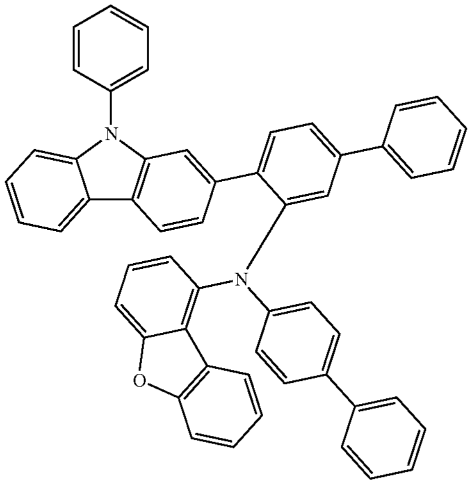
P3-22
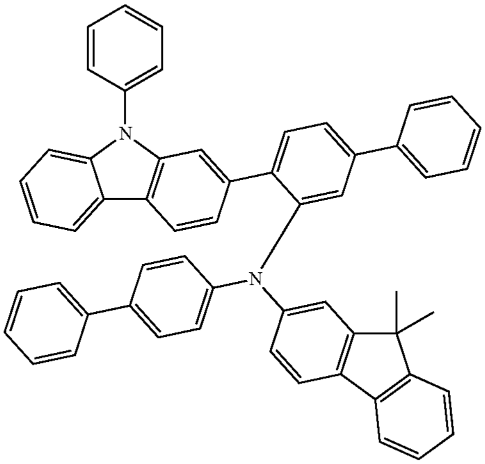

-continued
P3-23
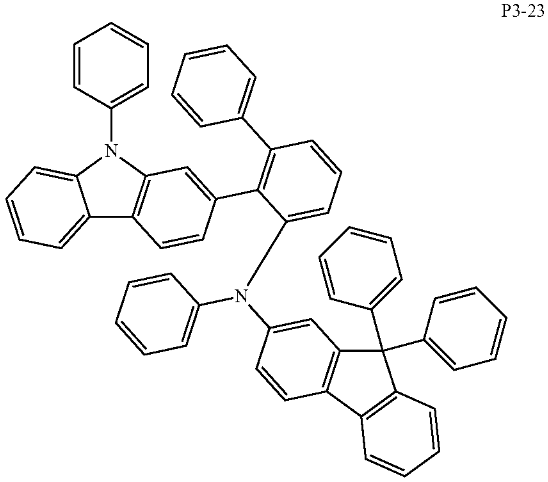
P3-24
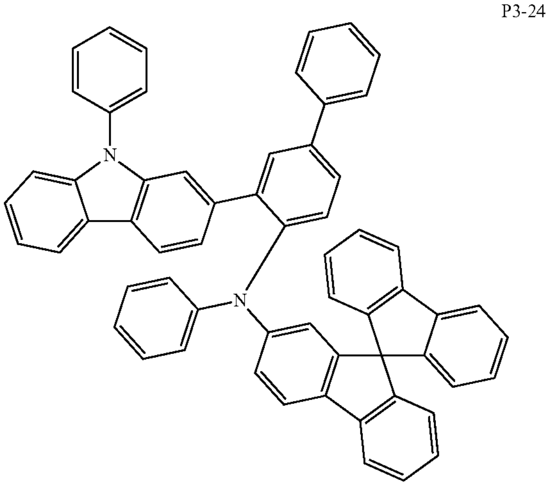
P3-25
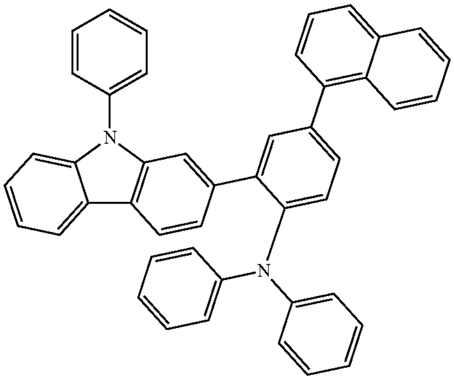
-continued
P3-26
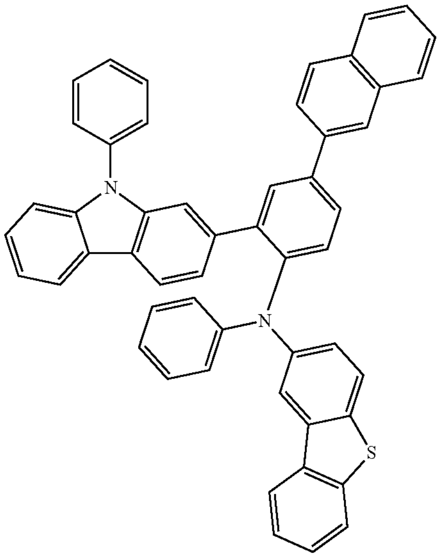
P3-27
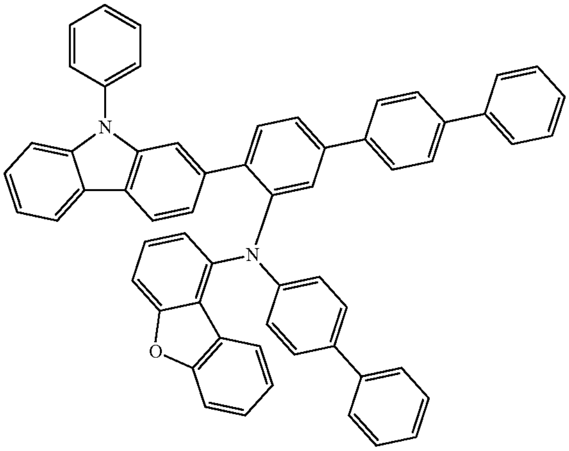
P3-28
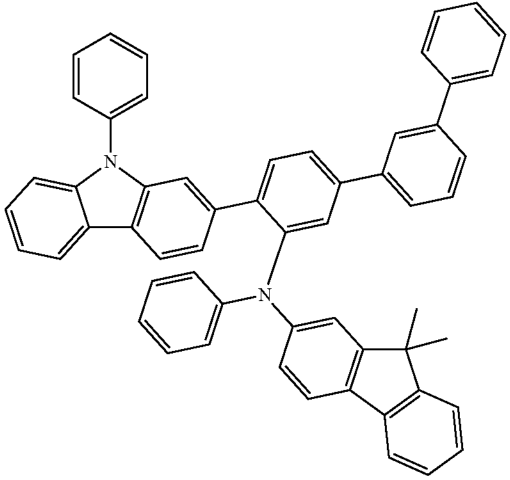

-continued
P3-29
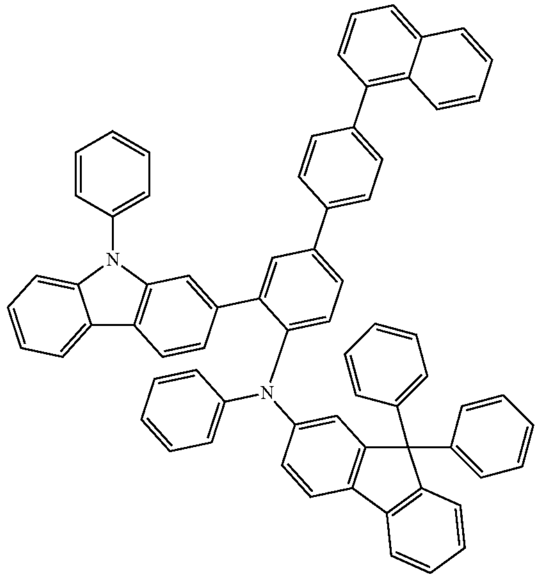
P3-30
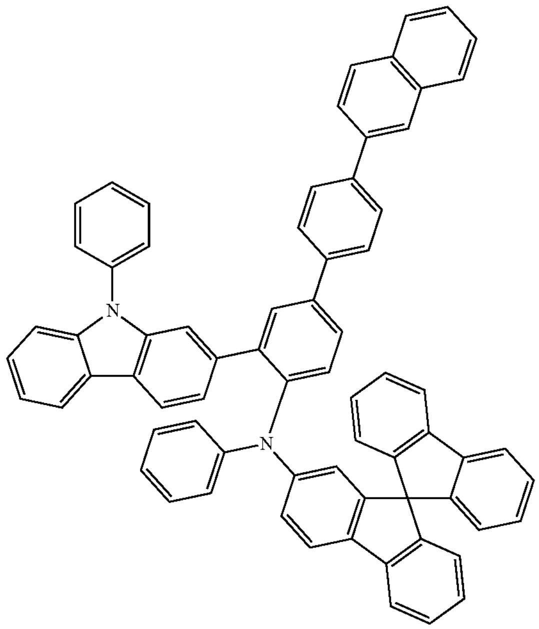
-continued
P3-31
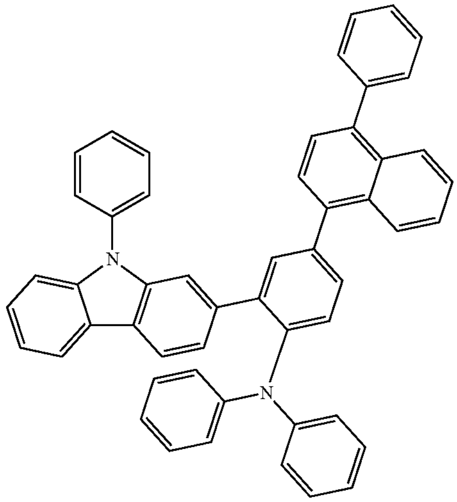
P3-32
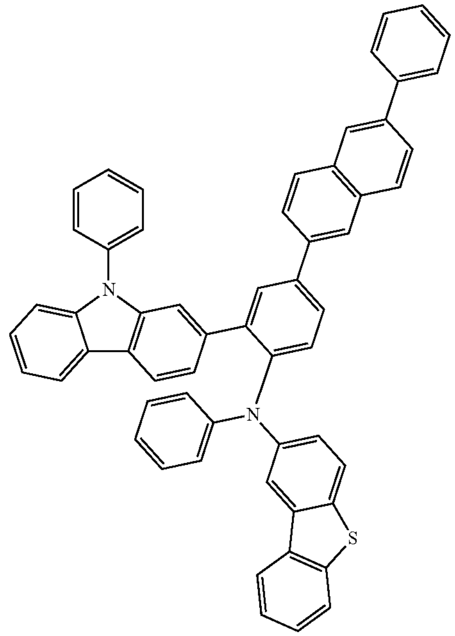
P3-33
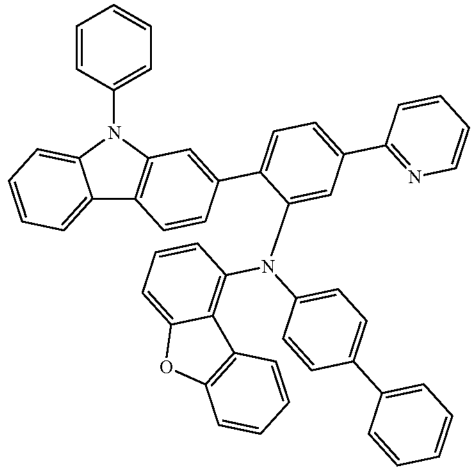

-continued
P3-34
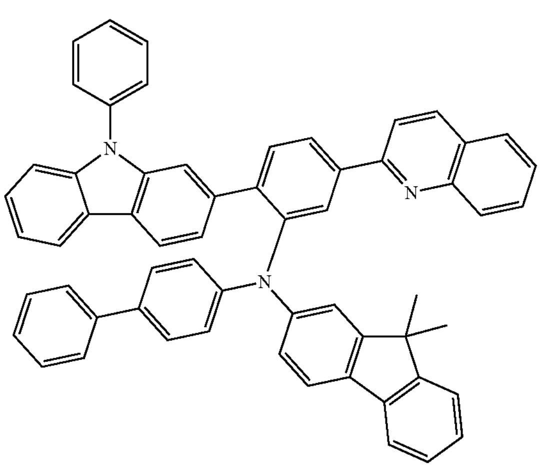
P3-35
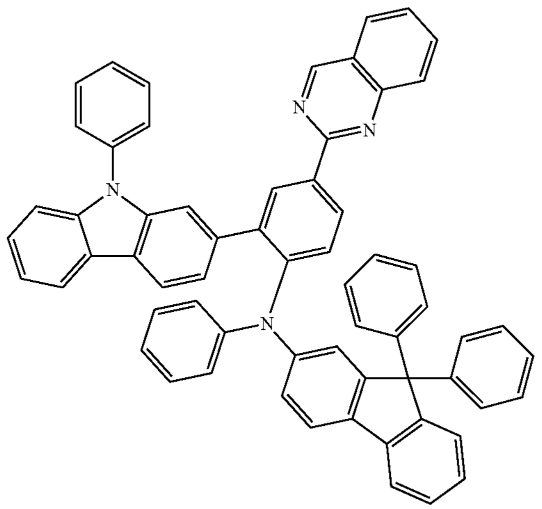
P3-36
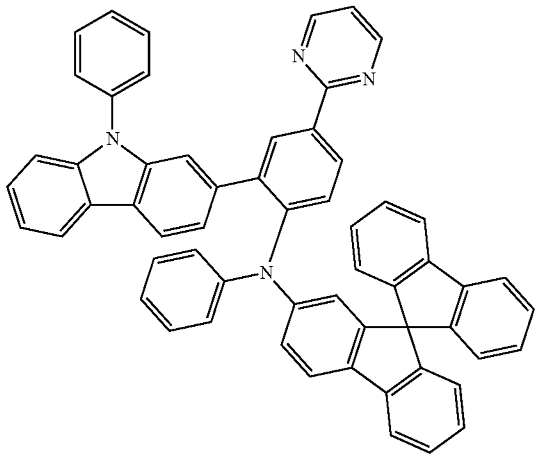
-continued
P3-37
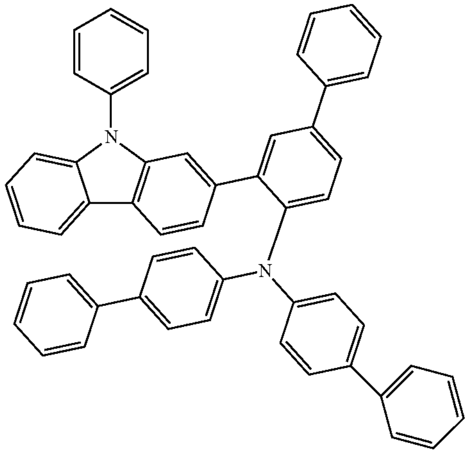
P3-38
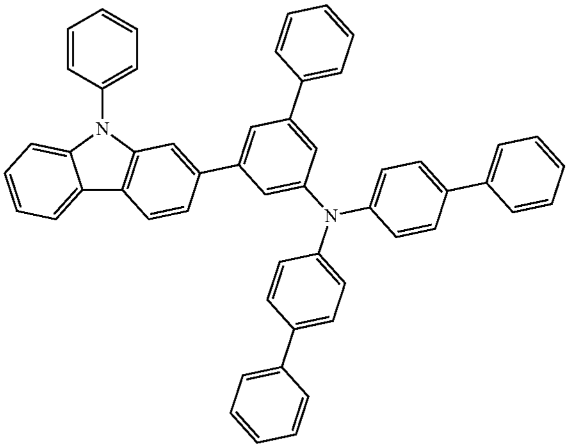
P4-1
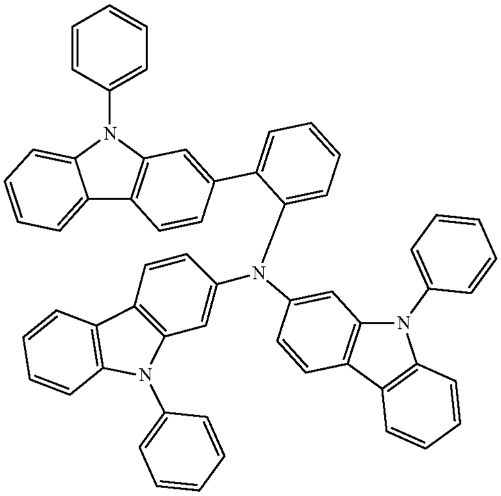

-continued
P4-2
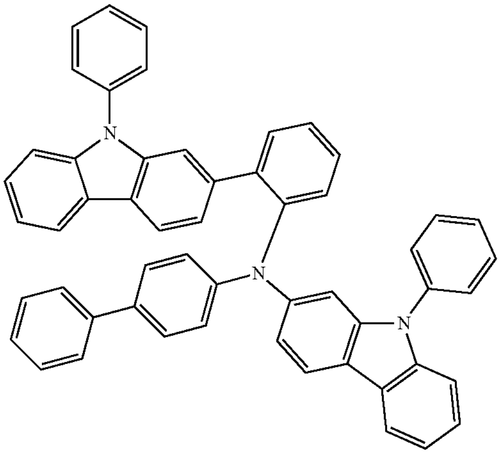
P4-3
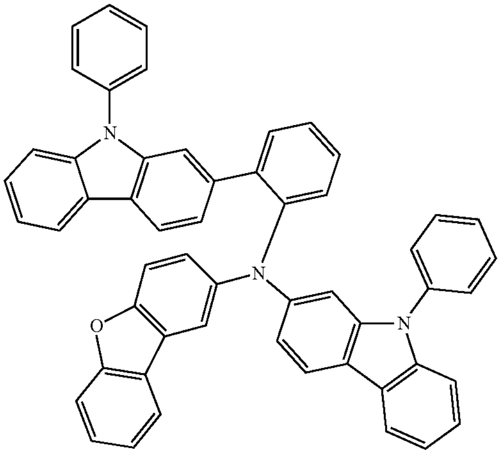
P4-4
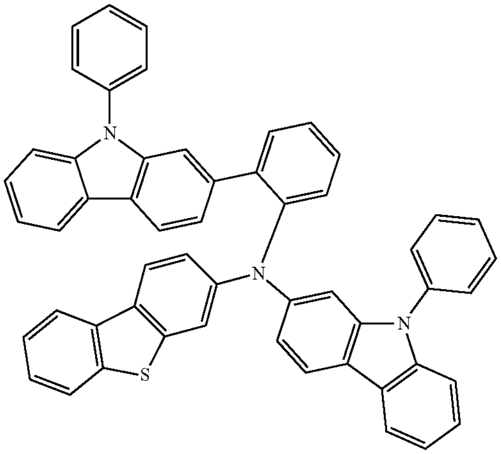
-continued
P4-5
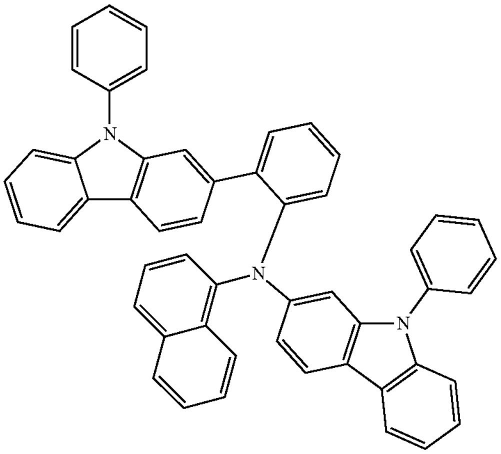
P4-6
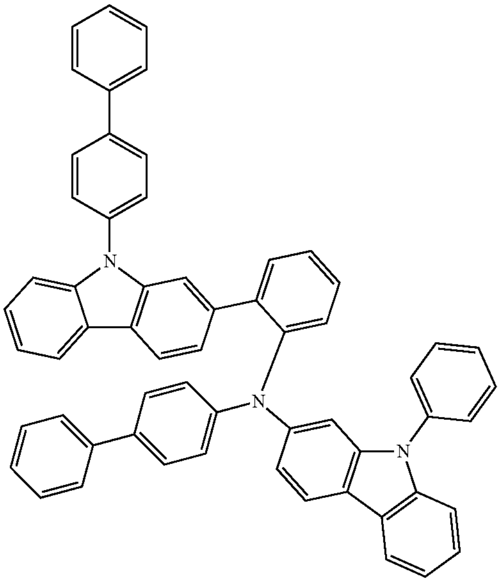
P4-7
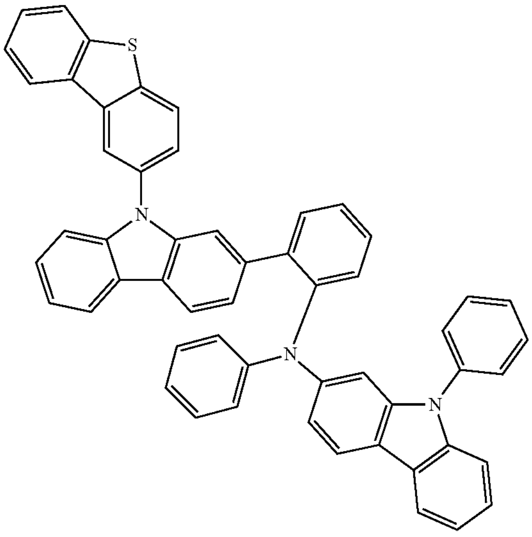

-continued
P4-8
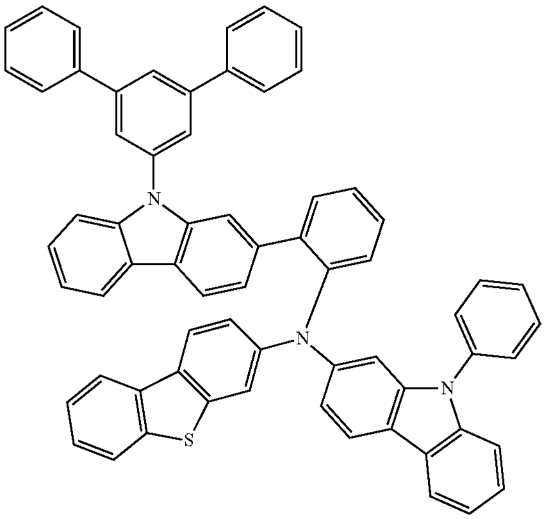
P4-9
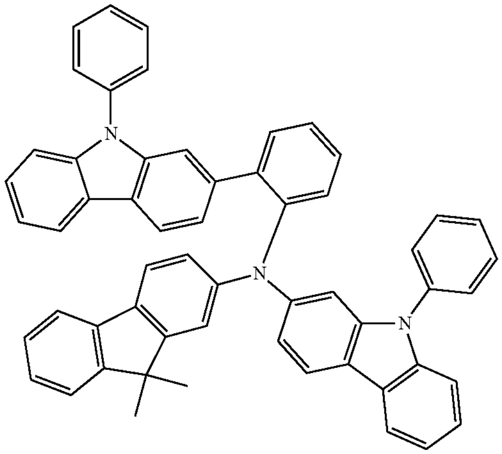
P4-10
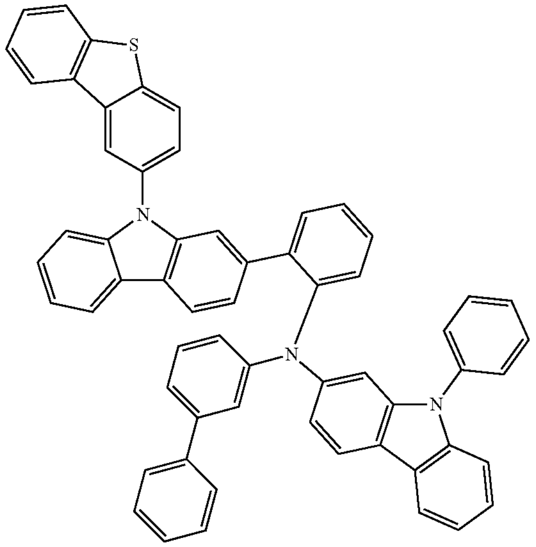
-continued
P4-12
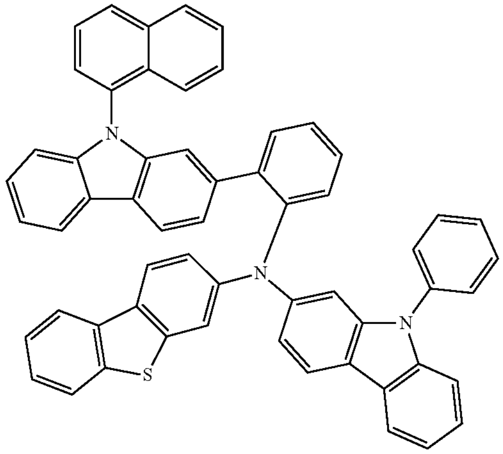
P4-13
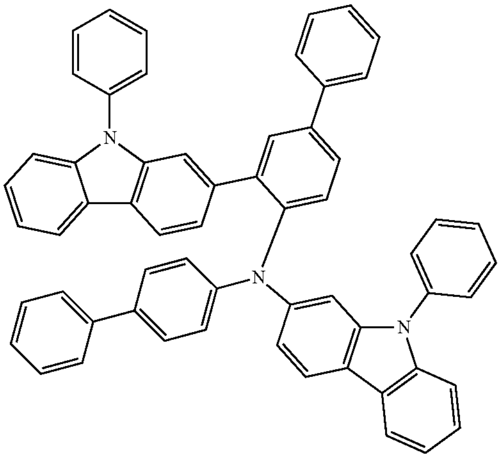
P4-14
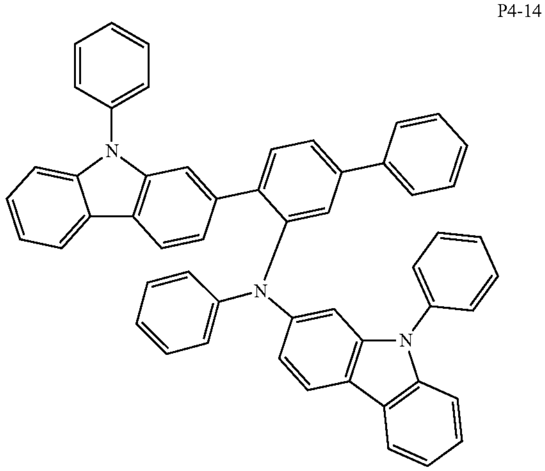

-continued
P4-15
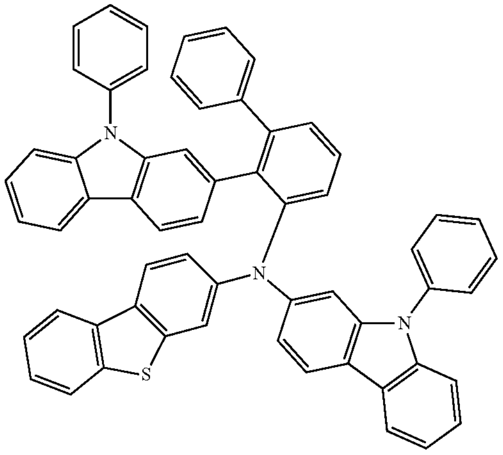
P4-17
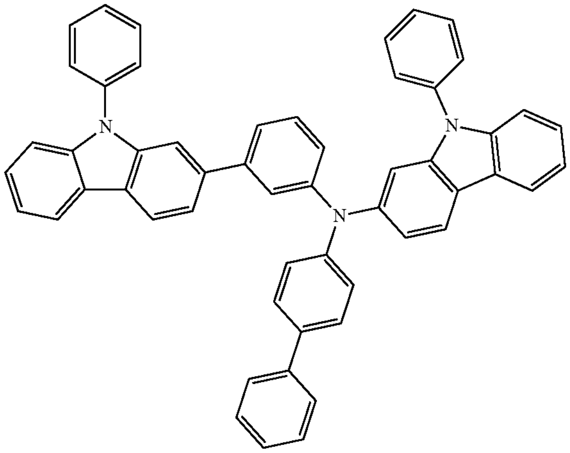
P4-18
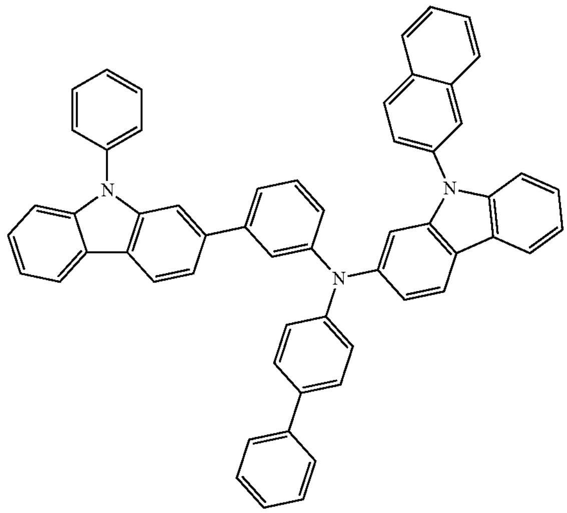
-continued
P4-19
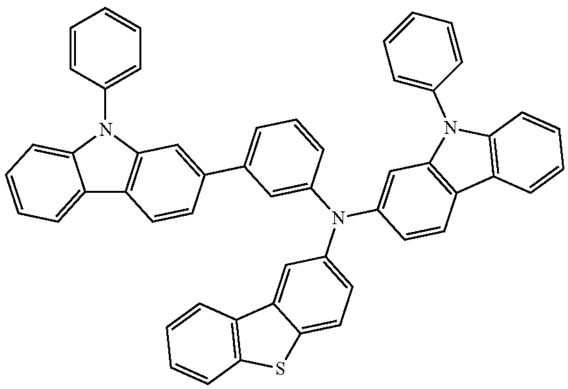
P4-20
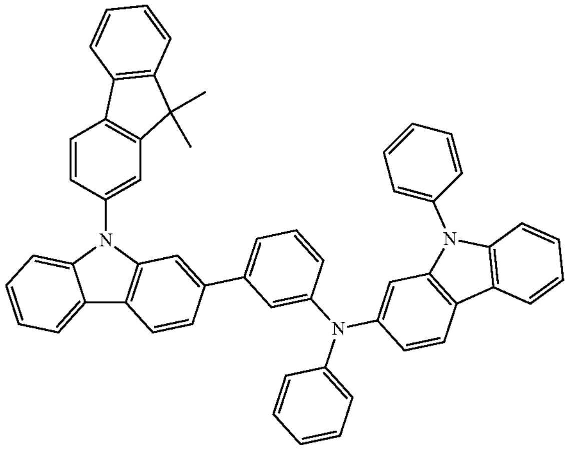
P4-21
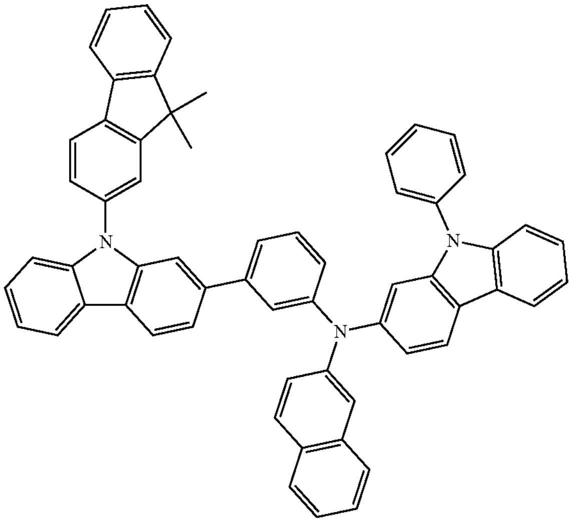

-continued
P4-22
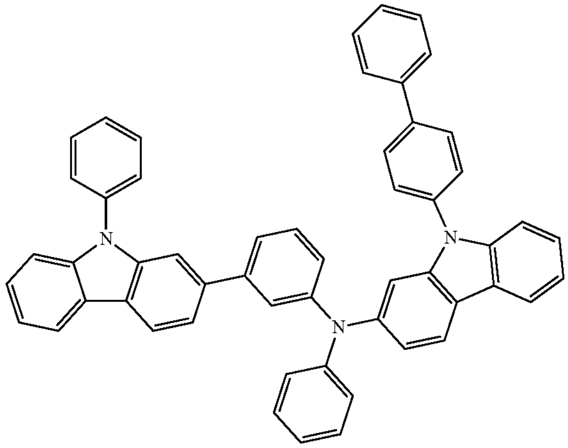
P4-23
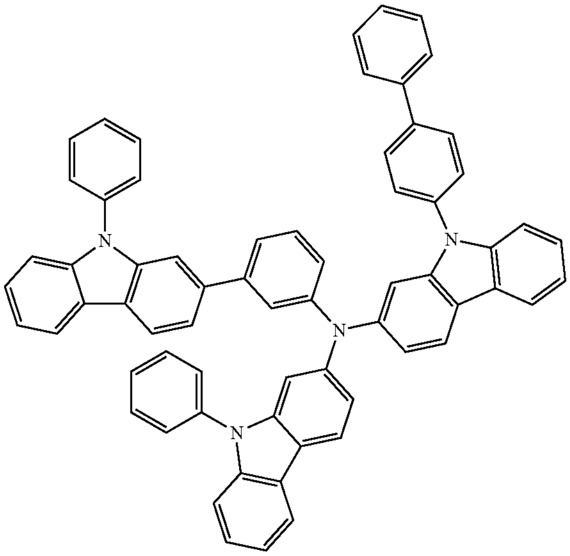
P4-24
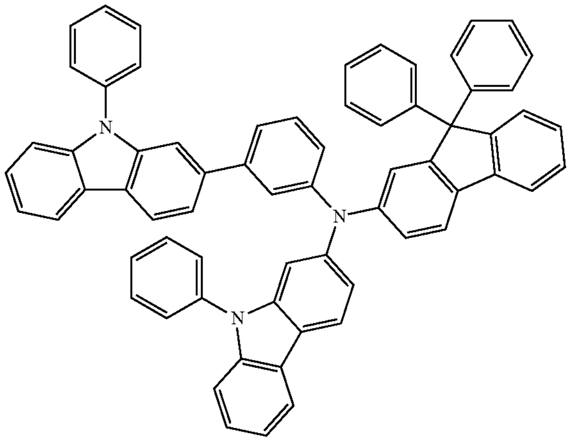
-continued
P4-27
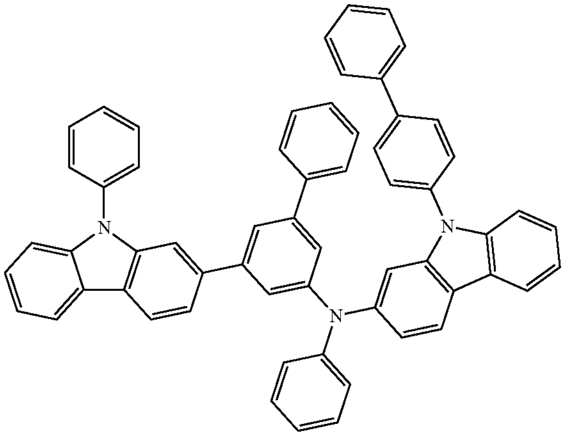
P4-28
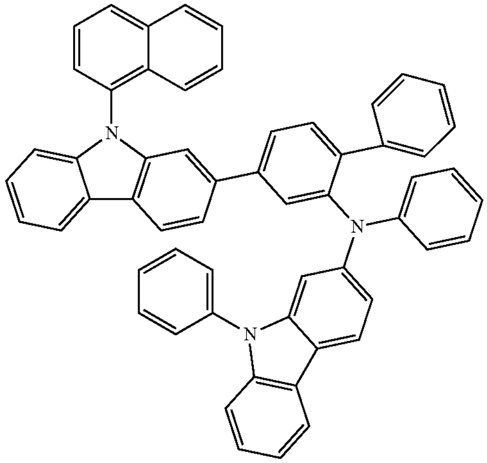
P4-29
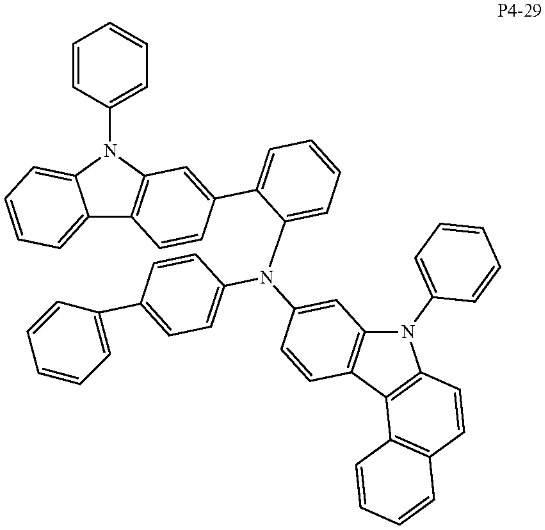

-continued
P4-30
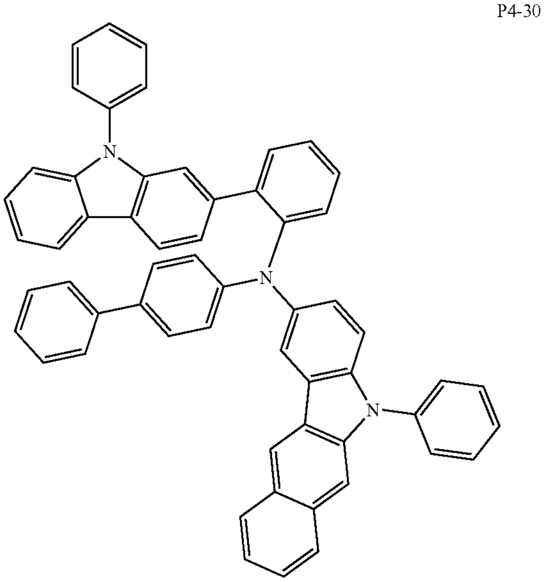
P4-31
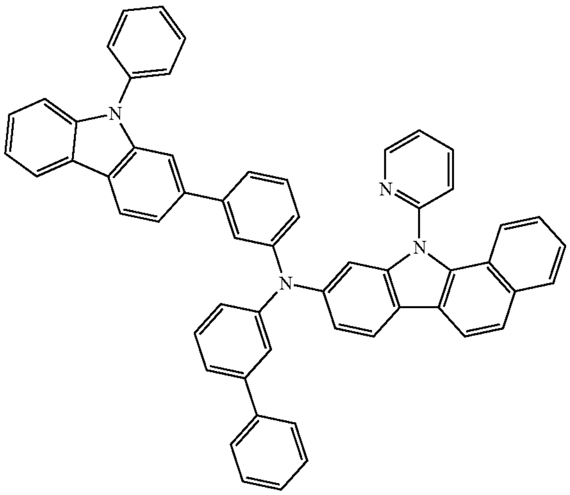
P4-32
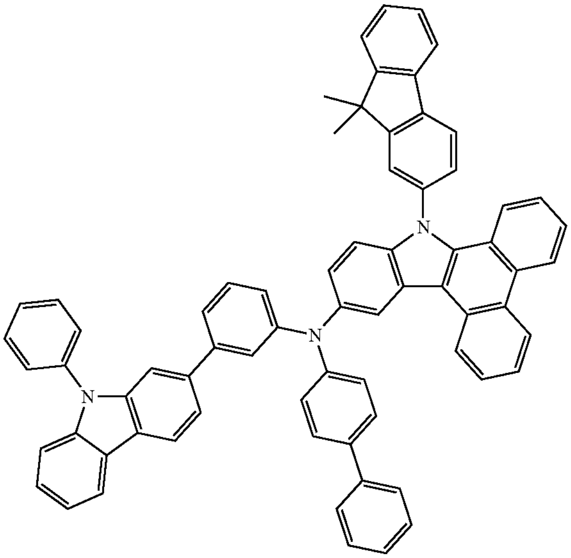
-continued
P4-33
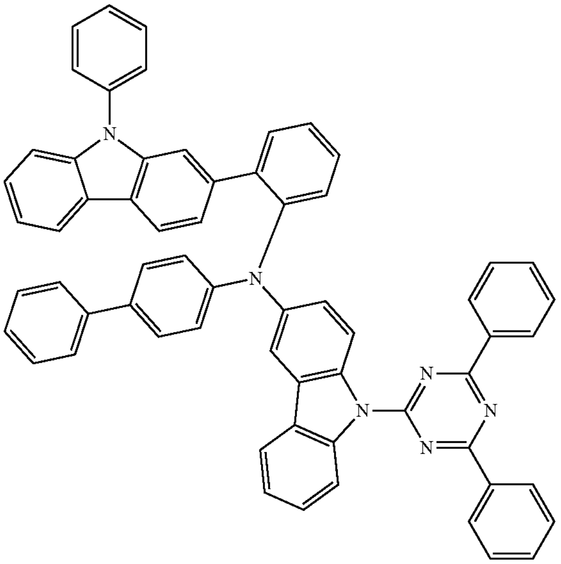
P4-34
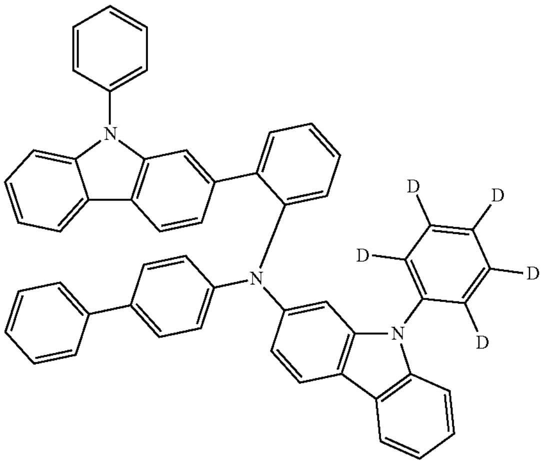
P4-35
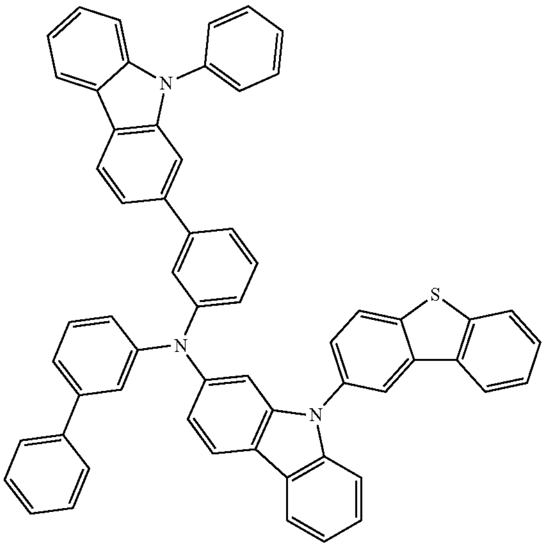

-continued

P4-36

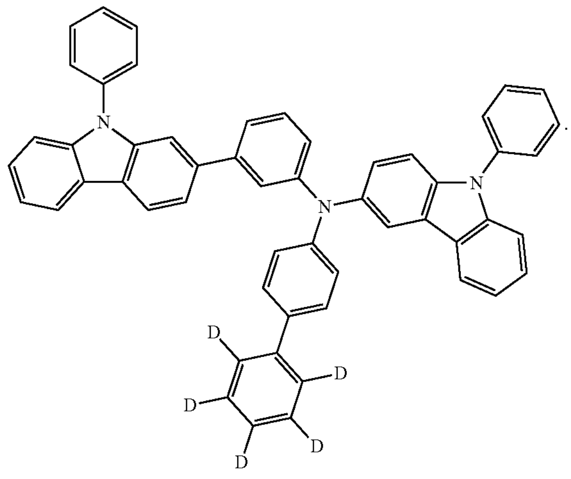

10. An organic electric element comprising a first electrode, a second electrode, and an organic material layer disposed between the first electrode and the second electrode, wherein the organic material layer comprises the compound of claim 1.

11. The organic electric element of claim 10, wherein the organic material layer comprises at least one of a hole injection layer, a hole transport layer, an emission-auxiliary layer and an emitting layer, and the at least one of the layers comprises the compound.

12. The organic electric element of claim 10, wherein the organic electric element further comprises at least one layer to improve luminescence efficiency, formed on at least one of the sides of the first and second electrodes opposite to the organic material layer.

13. The organic electric element of claim 10, wherein the organic material layer is formed by any one of the processes of spin coating, nozzle printing, inkjet printing, slot coating, dip coating and roll-to-roll.

14. An electronic device comprising a display device, which comprises the organic electric element of claim 10, and a control unit for driving the display device.

15. The electronic device of claim 14, wherein the organic electric element comprises at least one of an organic light emitting diode, an organic solar cell, an organic photo conductor, an organic transistor, and an element for monochromatic or white illumination.

16. An organic electric element comprising a first electrode, a second electrode, and an organic material layer disposed between the first electrode and the second electrode, wherein the organic material layer comprises the compound of claim 9.

17. The organic electric element of claim 16, wherein the organic material layer comprises at least one of a hole injection layer, a hole transport layer, an emission-auxiliary layer and an emitting layer, and the at least one of the layers comprises the compound.

18. An electronic device comprising a display device, which comprises the organic electric element of claim 16, and a control unit for driving the display device.

* * * * *